US007767689B2

(12) United States Patent
Moon et al.

(10) Patent No.: US 7,767,689 B2

(45) **Date of Patent: *Aug. 3, 2010**

(54) CARBOLINE DERIVATIVES USEFUL IN THE TREATMENT OF CANCER

(75) Inventors: Young-Choon Moon, Belle Mead, NJ (US); Liangxian Cao, Parlin, NJ (US); Nadarajan Tamilarasu, Edison, NJ (US); Hongyan Qi, Plainsboro, NJ (US); Soongyu Choi, Skillman, NJ (US); William Joseph Lennox, South Plainfield, NJ (US); Donald Thomas Corson, Annandale, NJ (US); Seongwoo Hwang, Edison, NJ (US); Thomas Davis, South Orange, NJ (US)

(73) Assignee: PTC Therapeutics, Inc., South Planfield, NJ (US)

( * ) Notice: Subject to any disclaimer, the term of this patent is extended or adjusted under 35 U.S.C. 154(b) by 1256 days.

This patent is subject to a terminal disclaimer.

(21) Appl. No.: 11/107,783

(22) Filed: Apr. 18, 2005

(65) Prior Publication Data

US 2005/0282849 A1 Dec. 22, 2005

Related U.S. Application Data

(63) Continuation-in-part of application No. 11/079,420, filed on Mar. 15, 2005, now Pat. No. 7,601,840.

(60) Provisional application No. 60/552,725, filed on Mar. 15, 2004.

(51) Int. Cl.

*A61K 31/437* (2006.01)

*C07D 487/04* (2006.01)

(52) U.S. Cl. ....................................... 514/292; 546/117

(58) Field of Classification Search ....................... None

See application file for complete search history.

(56) References Cited

U.S. PATENT DOCUMENTS

| | | | |
|---|---|---|---|
| 3,492,304 | A | 1/1970 | Shavel et al. |
| 4,014,890 | A | 3/1977 | Welch, Jr. et al. |
| 4,720,484 | A | 1/1988 | Vincent et al. |
| 4,754,038 | A | 6/1988 | Abou-Gharbia |
| 5,039,801 | A | 8/1991 | Brossi et al. |
| 5,120,543 | A | 6/1992 | Hagin et al. |
| 5,166,204 | A | 11/1992 | Nagai et al. |
| 5,206,377 | A | 4/1993 | McAfee |
| 5,382,569 | A | 1/1995 | Cody et al. |
| 5,403,851 | A | 4/1995 | D'Orlando et al. |
| 5,451,600 | A | 9/1995 | Banner et al. |
| 5,580,878 | A | 12/1996 | D'Orlando et al. |
| 5,622,960 | A | 4/1997 | Pommier et al. |
| 5,633,388 | A | 5/1997 | Diana et al. |
| 6,043,252 | A | 3/2000 | Bombrun |
| 6,048,868 | A | 4/2000 | Fourtillan et al. |
| 6,175,015 | B1 | 1/2001 | Yuan et al. |
| 6,235,718 | B1 | 5/2001 | Balasubramanium et al. |
| 6,306,870 | B1 | 10/2001 | Bombrun |
| 6,331,543 | B1 | 12/2001 | Garvey et al. |
| 6,350,757 | B1 | 2/2002 | Goldstein et al. |
| 6,376,529 | B1 | 4/2002 | Tang et al. |
| 6,514,981 | B1 | 2/2003 | Tang et al. |
| 6,552,017 | B1 | 4/2003 | Robichaud et al. |
| 6,630,589 | B1 | 10/2003 | Giodano et al. |
| 6,635,638 | B2 | 10/2003 | Sui et al. |
| 6,653,132 | B1 | 11/2003 | Keshet et al. |
| 6,667,152 | B2 | 12/2003 | Miles et al. |
| 6,706,750 | B1 | 3/2004 | Bentley et al. |
| 6,890,933 | B1 | 5/2005 | Feng et al. |
| 2002/0016298 | A1 | 2/2002 | Hay et al. |
| 2002/0091125 | A1 | 7/2002 | Hay et al. |
| 2002/0128206 | A1 | 9/2002 | Hay et al. |
| 2002/0173503 | A1 | 11/2002 | Robichaud et al. |
| 2003/0023087 | A1 | 1/2003 | Garvey et al. |
| 2003/0040527 | A1 | 2/2003 | Yeh et al. |
| 2003/0130171 | A1 | 7/2003 | Schoenhard |
| 2003/0220377 | A1 | 11/2003 | Chesworth |
| 2004/0023947 | A1 | 2/2004 | Martin et al. |

(Continued)

FOREIGN PATENT DOCUMENTS

| | | | |
|---|---|---|---|
| CA | 2099060 | A1 | 12/1993 |
| EP | 0008249 | B1 | 8/1981 |
| EP | 0 357 122 | A2 | 3/1990 |
| EP | 0406734 | A2 | 1/1991 |
| EP | 0468789 | A2 | 1/1992 |

(Continued)

OTHER PUBLICATIONS

Akiri et al., "Regulation of Vascular Endothelial Growth Factor (VEGF) Expression is Mediated by Internal Initiation of Translation and Alternative Initiation of Transcription", *Oncogene*, 17:227-236 (1998).

(Continued)

*Primary Examiner*—Rita J Desai

(74) *Attorney, Agent, or Firm*—Jones Day

(57) ABSTRACT

In accordance with the present invention, compounds that inhibit the expression of VEGF post-transcriptionally have been identified, and methods for their use provided. In one aspect of the invention, compounds useful in the inhibition of VEGF production, in the treatment of solid tumor cancer, and in reducing plasma and/or tumor VEGF levels, are provided. In another aspect of the invention, methods are provided for the inhibition of VEGF production, the treatment of cancer, and the reduction of plasma and/or tumor VEGF levels, using the compounds of the invention.

12 Claims, 13 Drawing Sheets

U.S. PATENT DOCUMENTS

| | | | |
|---|---|---|---|
| 2004/0058877 | A1 | 3/2004 | Hay et al. |
| 2004/0116458 | A1 | 6/2004 | Sawyer et al. |
| 2004/0127482 | A1 | 7/2004 | Robichaud et al. |
| 2004/0157834 | A1 | 8/2004 | Hay et al. |
| 2004/0186094 | A1 | 9/2004 | Robichaud et al. |
| 2004/0209864 | A1 | 10/2004 | Robichaud et al. |
| 2004/0214223 | A1 | 10/2004 | Cao |
| 2004/0214848 | A1 | 10/2004 | Schoenhard |
| 2004/0229864 | A1 | 11/2004 | Bourrain et al. |
| 2005/0004156 | A1 | 1/2005 | Feng et al. |
| 2005/0054568 | A1 | 3/2005 | Ling et al. |
| 2005/0054634 | A1 | 3/2005 | Busch et al. |
| 2005/0267018 | A1 | 12/2005 | Blatt et al. |
| 2005/0272759 | A1 | 12/2005 | Moon et al. |

FOREIGN PATENT DOCUMENTS

| | | | |
|---|---|---|---|
| EP | 0491943 | A1 | 7/1992 |
| EP | 0 549 916 | A2 | 7/1993 |
| EP | 0 549 916 | A3 | 8/1993 |
| EP | 0719837 | A2 | 12/1995 |
| EP | 0300541 | B1 | 3/1996 |
| EP | 1512397 | A1 | 3/2005 |
| EP | 1383765 | B1 | 12/2006 |
| FR | 2432025 | B1 | 2/1980 |
| FR | 2 662 940 | A1 | 12/1991 |
| JP | 3-287586 | A | 12/1991 |
| JP | 4-275221 | | 9/1992 |
| WO | 94/10175 | A1 | 5/1994 |
| WO | 94/11378 | A1 | 5/1994 |
| WO | WO 94/10175 | A1 | 5/1994 |
| WO | 96/26207 | A1 | 8/1996 |
| WO | 96/32003 | A2 | 10/1996 |
| WO | 97/37658 | | 10/1997 |
| WO | 97/43287 | A1 | 11/1997 |
| WO | 99/06390 | A1 | 2/1999 |
| WO | 00/39314 | A1 | 7/2000 |
| WO | 01/21584 | A1 | 3/2001 |
| WO | 01/21589 | A2 | 3/2001 |
| WO | 01/47887 | A1 | 7/2001 |
| WO | 01/87038 | A2 | 11/2001 |
| WO | 01/87038 | A3 | 11/2001 |
| WO | 02/051805 | A1 | 7/2002 |
| WO | 02/088123 | A1 | 11/2002 |
| WO | 03/033496 | A1 | 4/2003 |
| WO | 03/051841 | A2 | 6/2003 |
| WO | 03/087815 | A2 | 10/2003 |
| WO | 03/099821 | A1 | 12/2003 |
| WO | 03/103656 | A1 | 12/2003 |
| WO | 2004/035047 | A1 | 4/2004 |
| WO | WO 2004/069831 | | 8/2004 |
| WO | WO 2004/096766 | | 11/2004 |
| WO | 2004/110999 | A1 | 12/2004 |
| WO | WO 2004/113336 | A1 | 12/2004 |
| WO | 2005/000246 | A2 | 1/2005 |
| WO | 2005/005386 | A1 | 1/2005 |
| WO | WO 2005/007672 | A2 | 1/2005 |
| WO | 2005/014543 | A1 | 2/2005 |
| WO | WO 2005/009370 | A2 | 2/2005 |
| WO | 2005/037791 | A1 | 4/2005 |
| WO | WO 2005/070930 | A2 | 8/2005 |
| WO | WO 2005/089764 | A1 | 9/2005 |
| WO | 2005/097162 | A2 | 10/2005 |
| WO | 2005/113003 | A2 | 12/2005 |
| WO | WO 2006/015035 | A1 | 2/2006 |
| WO | WO 2006/058088 | A2 | 6/2006 |
| WO | 2006/113703 | A2 | 10/2006 |

OTHER PUBLICATIONS

Asano et al., "Wide Spectrum of Antitumor Activity of a Neutralizing Monoclonal Antibody to Human Vascular Endothelial Growth Factor", *Jpn. J. Cancer Res.*, 90:93-100 (1999).

Bergsland et al., "A Randomized Phase II Trial Comparing rhuMAb VEGF (Recombinant Humanized Monoclonal Antibody to Vascular Endothelial Cell Growth Factor) Plus 5-Fluorouracil/Leucovorin (FU/LV) to FU/LV Alone in Patients with Metastatic Colorectal Cancer", American Society of Clinical Oncology 36$^{th}$ Annual Meeting, May 2000, New Orleans, LA, USA, Abstract No. 939.

Borgström et al., "Neutralizing Anti-Vascular Endothelial Growth Factor Antibody Completely Inhibits Angiogenesis and Growth of Human Prostate Carcinoma Micro Tumors In Vivo", *Prostate*, 35:1-10 (1998).

Boyer, S. J., "Small Molecule Inhibitors of KDR (VEGFR-2) Kinase: An Overview of Structure Activity Relationships", *Current Topics in Medicinal Chemistry*, 2:973-1000 (2002).

Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice", *Cancer Res.*, 60:5117-5124 (2000).

Carmeliet, Peter, "Angiogenesis in Health and Disease", *Nature Medicine*, 9(6):653-660 (2003).

Carmeliet et al., "Abnormal Blood Vessel Development and Lethality in Embryos Lacking a Single VEGF Allele" *Nature*, 380:435-439 (1996).

Carmeliet et al., "Angiogenesis in Cancer and Other Diseases", *Nature*, 407:249-257 (2000).

Clark et al., "Ophthalmic Drug Discovery", *Nat. Rev. Drug Discovery*, 2:448-459 (2003).

Connolly et al., "Human Vascular Permeability Factor", *J. Biol. Chem.*, 264(33):20017-20024 (1989).

DeVore et al., "A Randomized Phase II Trial Comparing Rhumab VEGF (Recombinant Humanized Monoclonal Antibody to Vascular Endothelial Cell Growth Factor) Plus Carboplatin/Paclitaxel (CP) to CP Alone in Patients with Stage IIIB/IV NSCLC", American Society of Clinical Oncology 36$^{th}$ Annual Meeting, May 2000, New Orleans, LA, USA, Abstract No. 1896.

Dirix et al., "Elevated Levels of the Angiogenic Cytokines Basic Fibroblast Growth Factor and Vascular Endothelial Growth Factor in Sera of Cancer Patients", *Br. J. Cancer*, 76(2):238-243 (1997).

Ellis et al., "Down-Regulation of Vascular Endothelial Growth Factor in Human Colon Carcinoma Cell Lines by Antisense Transfection Decreases Endothelial Cell Proliferation", *Surgery*, 120(5):871-878 (1996).

Eyetech Study Group, "Preclinical and Phase 1A Clinical Evaluation of an Anti-VEGF Pegylated Aptamer (EYE001) for the Treatment of Exudative Age-Related Macular Degeneration", 22(2):143-52 (2002).

Ferrara et al., "The Biology of Vascular Endothelial Growth Factor", *Endocr. Rev.*, 18(1):4-25 (1997).

Ferrara et al., "Vascular Endothelial Growth Factor is Essential for Corpus Luteum Angiogenesis", *Nat. Med.*, 4(3):336-340 (1998).

Ferrara et al., "Clinical Applications of Angiogenic Growth Factors and Their Inhibitors", *Nat. Med.*, 5(12):1359-64 (1999).

Ferrara, Napoleone, "Role of Vascular Endothelial Growth Factor in Physiologic and Pathologic Angiogenesis: Therapeutic Implications", *Semin. Oncol.*, 29(6 Suppl 16):10-14 (2002).

Filleur et al., "SiRNA-Mediated Inhibition of Vascular Endothelial Growth Factor Severely Limits Tumor Resistance to Antiangiogenic Thrombospondin-1 and Slows Tumor Vascularization and Growth", *Cancer Res.*, 63:3919-22 (2003).

Folkman, Judah, "Tumor Angiogenesis: Therapeutic Implications", *N. Engl. J. Med.*, 285(21):1182-6 (1971).

Fong et al., "SU5416 is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", *Cancer Res.*, 59:99-106 (1999).

Fong et al., "Role of the Flt-1 Receptor Tyrosine Kinase in Regulating the Assembly of Vascular Endothelium", *Nature*, 376:66-70 (1995).

Funatsu et al., "Angiotensin II and Vascular Endothelial Growth Factor in the Vitreous Fluid of Patients with Diabetic Macular Edema and Other Retinal Disorders", *Am. J. Ophthalmol.*, 133(4):537-43 (2002).
Gasparini et al., "Prognostic Significance of Vascular Endothelial Growth Factor Protein in Node-Negative Breast Carcinoma", *J. Natl. Cancer Inst.*, 89(2):139-147 (1997).
Geng et al., "Inhibition of Vascular Endothelial Growth Factor Receptor Signaling Leads to Reversal of Tumor Resistance to Radiotherapy", *Cancer Res.*, 61:2413-2419 (2001).
Giles et al., "Phase II Study of SU5416-a Small-Molecule, Vascular Endothelial Growth Factor Tyrosine-Kinase Receptor Inhibitor-in Patients with Refractory Myeloproliferative Diseases", *Cancer*, 97(8):1920-8 (2003).
Goldberg et al., "A 40-bp RNA Element that Mediates Stabilization of Vascular Endothelial Growth Factor mRNA by HuR", *J. Biol. Cell. J. Biol. Chem.*, 277(16):13635-40 (2002).
Hanahan et al., "Patterns and Emerging Mechanisms of the Angiogenic Switch During Tumorigenesis" *Cell*, 86:353-364 (1996).
Hicklin et al., "Monoclonal Antibody Strategies to Block Angiogenesis", *Drug Discovery Today*, 6(10):517-528 (2001).
Holash et al., "Vessel Cooption, Regression, and Growth in Tumors Mediated by Angiopoietins and VEGF", *Science*, 284:1994-1998 (1999).
Honda et al., "Experimental Subretinal Neovascularization is Inhibited by Adenovirus-Mediated Soluble VEGF/flt-1 Receptor Gene Trasfection: A Role of VEGF and Possible Treatment for SRN in Age-Related Macular Degeneration", *Gene Ther.*, 7:978-85 (2000).
Huez et al., "Two Independent Internal Ribosome Entry Sites Are Involved in Translation Initiation of Vascular Endothelial Growth Factor mRNA" *Mol. Cell. Biol.*, 18(11):6178-6190 (1998).
Ikeda et al., "Hypoxia-Induced Transcriptional Activation and Increased mRNA Stability of Vascular Endothelial Growth Factor in C6 Glioma Cells", *J. Biol. Chem.* 270(34):19761-19766 (1995).
International Search Report PCT/US2005/008481 (mailed Mar. 8, 2005).
Ishida et al., "Antitumor Agents 201. Cytotoxicity of Harmine and β-Carboline Analogs", *Bioorganic & Medicinal Chemistry Letters*, 9:3319-3324 (1999).
Kerbel et al., "Clinical Translation of Angiogenesis Inhibitors", *Nat. Rev. Cancer*, 2:727-39 (2002).
Kim et al., "Inhibition of Vascular Endothelial Growth Factor-Induced Angiogenesis Suppresses Tumor Growth in vivo", *Nature*, 362:841-844 (1993).
Kraggerud et al., "Regulation of Protein Synthesis in Human Cells Exposed to Extreme Hypoxia", *Anticancer Res.*, 15:683-686 (1995).
Krzystolik et al., "Prevention of Experimental Choroidal Neovascularization with Intravitreal Anti-Vascular Endothelial Growth Factor Antibody Fragment", *Arch. Ophthalmol.*, 120:338-46 (2002).
Laird et al., "SU6668 is a Potent Antiangiogenic and Antitumor Agent that Induces Regression of Established Tumors", *Cancer Res.*, 60:4152-60 (2000).
Leung et al., "Vascular Endothelial Growth Factor is a Secreted Angiogenic Mitogen", *Science*, 246:1306-1309 (1989).
Levy et al., "Post-Transcriptional Regulation of Vascular Endothelial Growth Factor by Hypoxia", *J. Biol. Chem.* 271(5):2746-2753 (1996).
Lin et al., "Inhibition of Tumor Growth by Targeting Tumor Endothelium Using a Soluble Vascular Endothelial Growth Factor Receptor", *Cell Growth Differ.*, 9:49-58 (1998).
Lip et al., "Age-Related Macular Degeneration is Associated with Increased Vascular Endothelial Growth Factor, Hemorheology and Endothelial Dysfunction", *Ophthalmology*, 108(4):705-10 (2001).
Liu et al., "Hypoxia Regulates Vascular Endothelial Growth Factor Gene Expression in Endothelial Cells Identification of a 5' Enhancer", *Circ. Res.*, 77(3):638-643 (1995).
Abou-Gharbia et al., "Antipsychotic Activity of Substituted γ-Carbolines", *J. Med. Chem.* 30:1818-1823 (1987).
Matter, "Tumor Angiogenesis as a Therapeutic Target", *Drug Discovery Today*, 6(19):1005-1024 (2001).
Maxwell et al., "The Tumour Suppressor Protein VHL Targets Hypoxia-Inducible Factors for Oxygen-Dependent Proteolysis", *Nature*, 399:271-275 (1999).
Millauer et al., "Glioblastoma Growth Inhibited in vivo by a Dominant-Negative Flk-1 Mutant", *Nature*, 367:576-579 (1994).
Moulder et al., "Epidermal Growth Factor Receptor (HER1) Tyrosine Kinase Inhibitor ZD1839 (Iressa) Inhibits HER2/*neu* (*erb*B2)-Overexpressing Breast Cancer Cells in Vitro and in Vivo", *Cancer Res.* 61:8887-95 (2001).
Ohno-Matsui et al., "Inducible Expression of Vascular Endothelial Growth Factor in Adult Mice Causes Severe Proliferative Retinopathy and Retinal Detachment", *Am. J. Pathol.*, 160(2):711-719 (2002).
Ortega et al., "Signal Relays in the VEGF System", *Front. Biosci.*, 4:d141-152 (1999).
Ozaki et al., "Blockage of Vascular Endothelial Cell Growth Factor Receptor Signaling is Sufficient to Completely Prevent Retinal Neovascularization", *Am. J. Pathol.*, 156(2):697-707 (2000).
Parry et al., "Bioactivity of Anti-Angiogenic Ribozymes Targeting Flt-1 and KDR mRNA", *Nucleic Acids Res.*, 27(13):2569-2577 (1999).
Plouet et al., "Isolation and Characterization of a Newly Identified Endothelial Cell Mitogen Produced by AtT-20 Cells", *EMBO J.*, 8(12):3801-3806 (1989).
Rak et al., "Oncogenes and Tumor Angiogenesis: Differential Modes of Vascular Endothelial Growth Factor Up-Regulation in *ras*-Transformed Epithelial Cells and Fibroblasts", *Cancer Res.*, 60:490-498 (2000).
Reich et al., "Small Interfering RNA (siRNA) Targeting *VEGF* Effectively Inhibits Ocular Neovascularization in a Mouse Model", *Mol. Vis.* 9:210-216 (2003).
Rofstad et al., "Vascular Endothelial Growth Factor, Interleukin 8, Platelet-Derived Endothelial Cell Growth Factor, and Basic Fibroblast Growth Factor Promote Angiogenesis and Metastasis in Human Melanoma Xenografts", *Cancer Res.*, 60:4932-4938 (2000).
Ryan et al., "Toxicologic Pathology of Unique Biotechnology Agents and Biotherapies", *Toxicol. Pathol.*, 27(1)78-86 (1999).
Saishin et al., "VEGF-TRAP$_{R1R2}$ Suppresses Choroidal Neovascularization and VEGF-Induced Breakdown of the Blood-Retinal Barrier", *J. Cell Physiol.*, 195:241-8 (2003).
Sato et al., "Properties of Two VEGF Receptors, Flt-1 and KDR, in Signal Transduction", *Annals of New York Academy of Sciences*, 902:201-207, (2000).
Schwesinger et al., "Intrachoroidal Neovascularization in Transgenic Mice Overexpressing Vascular Endothelial Growth Factor in the Retinal Pigment Epithelium", *Am. J. Pathol.*, 158(3):1161-1172 (2001).
Semenza, "Regulation of Mammalian $O_2$ Homeostasis by Hypoxia-Inducible Factor 1", *Annu. Rev. Cell. Dev. Biol.*, 15:551-578 (1999).
Shalaby et al., "Failure of Blood-Island Formation and Vasculogenesis in Flk-1-Deficient Mice", *Nature*, 376:62-66, (1995).
Shen et al., "Preclinical Evaluation of a Phosphorothioate Oligonucleotide in the Retina of Rhesus Monkey", *Lab Invest.*, 82(2):167-82 (2002).
Stein et al., "Translation of Vascular Endothelial Growth Factor mRNA by Internal Ribosome Entry: Implications for Translation Under Hypoxia", *Mol. Cell. Biol.* 18(6):3112-3119 (1998).
Sugimoto et al., "Neutralization of Circulating Vascular Endothelial Growth Factor (VEGF) by Anti-VEGF Antibodies and Soluble VEGF Receptor 1 (sFlt-1) Induces Proteinuria", *J. Biol. Chem.*, 278(15):12605-8 (2003).
Tischer et al., "The Human Gene for Vascular Endothelial Growth Factor", *J. Biol. Chem.*, 266(18):11947-11954 (1991).
Verheul et al., "Platelet and Coagulation Activation with Vascular Endothelial Growth Factor Generation in Soft Tissue Sarcomas", *Clin. Cancer Res.*, 6:166-171 (2000).
Wedge et al., "ZD4190: An Orally Active Inhibitor of Vascular Endothelial Growth Factor Signaling with Broad-Spectrum Antitumor Efficacy", *Cancer Res.*, 60:970-5 (2000).
Witmer et al., "Vascular Endothelial Growth Factors and Angiogenesis in Eye Disease", *Prog. Retin Eye Res.*, 22:1-29 (2003).
Yoshida et al., "Oxidation of Cycloalkan[*b*]indoles with Iodine Pentoxide ($I_2O_5$)", *Chem. Pharm. Bull.*, 35(12):4700-4704 (1987).

Yuan et al., "Time-Dependent Vascular Regression and Permeability Changes in Established Human Tumor Xenografts Induced by an Anti-Vascular Endothelial Growth Factor/Vascular Permeability Factor Antibody", *Proc. Natl. Acad. Sci. USA*, 93:14765-14770 (1996).
Zhu et al., "Inhibition of Tumor Growth and Metastasis by Targeting Tumor-Associated Angiogenesis with Antagonists to the Receptors of Vascular Endothelial Growth Factor", *Invest. New Drugs*, 17:195-212 (1999).
International Search Report issued in PCT/US2005/042484 on Oct. 4, 2006.
Shanmugasundaram et al., "Synthesis and biological activity of pyrazino[3,2,1-*j,k*]carbazoles", *Indian Journal of Chemistry*, 37b:1133-1136 (1998).
Shanmugasundaram et al., "Synthesis of 3-Phenylisoxazolo[3,4-a]carbazoles", *Zeitschrift Für Naturforschung*, 54b:1202-1204 (1999).
R. Cao et al., "Synthesis and in vitro Cytotoxic Evaluation of 1,3-Bisubstituted and 1,3,9-Trisubstituted β-Carboline Derivatives," *European Journal of Medicinal Chemistry*, 40:249-257 (2005).
E. Fuhrmann-Benzakein et al., "Elevated Levels of Angiogenic Cytokines in the Plasma of Cancer Patients," *Int. J. Cancer*, 85:40-45 (2000).
T. Ichihara et al., "Enhancer for Carcinostatic Effect," Derwent AN—1992-376264 (Sep. 30, 1992).
B.J.R. Nicolaus, "Symbiotic Approach to Drug Design," *Decision Making in Drug Research* (F. Gross, ed., Raven Press, New York, NY), pp. 173-186 (1983).
International Search Report issued on Feb. 26, 2007 in corresponding International Application PCT/US2006/014547.
Chomczynski et al., "Single-Step Method of RNA Isolation by Acid Guanidinium Thiocyanate-Phenol-Chloroform Exstraction", *Anal. Biochem*. 162:156-159 (1987).
Gordon et al., "Phase I Safety and Pharmacokinetic Study of Recombinant Human Anti-Vascular Endothelial Growth Factor in Patients With Advanced Cancer", *Journal of Clinical Oncology*, 19(3):843-850 (2001).
Leclerc et al., "Folypoly-γ-glutamate Synthetase Gene mRNA Splice Variants and Protein Expression in Primary Human Leukemia Cells, Cell Lines, and Normal Human Tissues", *Clin. Cancer Res*. 7:942-951 (2001).
Bornes et al., "Control of the Vascular Endothelial Growth Factor Internal Ribosome Entry Side (IRES) Activity and Translation Initiation by Alternatively Spliced Coding Sequences," J. Biol. Chem., 279(18):18717-18726 (2004).
Claffey et al., "Identification of a Human VPF/VEGF 3' Untranslated Region Mediating Hypoxia-Induced mRNA Stability," Molecular Biology of the Cell, 9:469-481 (1998).
DeJong et al., "RNA and RNA-Protein Complexes as Targets for Therapeutic Intervention," Current Topics in Medicinal Chemistry, 2(3):289-302 (2002).
Daugan et al., "The Discovery of Tadalafil: A Novel and Highly Selective PDE5 Inhibitor. 2: 2,3,6,7,12,12a-Hexahydropyrazino[1',2':1,6]pyrido[3,4-b]Indole-1,4-Dione Analogues," J. Med. Chem., 46(21):4533-4542 (2003).
Daugan et al., "The Discovery of Tadalafil: A Novel and Highly Selective PDE5 Inhibitor. 1: 5,6,11,11a-Tetrahydro-1H-imidazo[1',5':1,6]Pyrido[3,4-b]Indole-1,3(2H)-dione Analogues," J. Med. Chem., 46:4525-4532 (2003).
Dreyfuss et al., "Messenger-RNA-Binding Proteins and the Messages They Carry," Nature Reviews Molecular Cell Biology, 3:195-205 (2002).
Ge et al., "Regulation of Promoter Activity of the APP Gene by Cytokines and Growth Factors," Ann. N.Y. Acad. Sci., 973:463-467 (2002).
Henry et al., "Aromatic Isocyanates as Reagents for the Identification of Some Heterocyclic Compounds," J. Am. Chem. Soc., pp. 2297-3000 (1949).
Kedersha et al., "Stress Granules: Sites of mRNA Triage that Regulate mRNA Stability and Translatability," Biochemical Society Transactions, 30(6):963-969 (2002).
Kozak, "Influences of mRNA Secondary Structure on Initiation by Eukaryotic Ribosomes," PNAS, 83:2850-2854 (1986).
Lai et al., "Evidence that Tristetraprolin Binds to AU-Rich Elements and Promotes the Deadenylation and Destabilization of Tumor Necrosis Factor Alpha mRNA," Molecular and Cellular Biology, 19(6):4311-4323 (1999).
Miller et al., "The Vascular Endothelial Growth Factor mRNA Contains an Internal Ribosome Entry Site," FEBS Letters, 434:417-420 (1998).
Stoecklin et al., "A Constitutive Decay Element Promotes Tumor Necrosis Factor Alpha mRNA Degradation via an AU-Rich Element-Independent Pathway," Molecular and Cellular Biology, 23(10):3506-3515 (2003).
Sun et al., "4-(2-Pyridyl)piperazine-1-carboxamides: Potent Vanilloid Receptor 1 Antagonists," Bioorganic & Medicinal Chem. Lett., 13:3611-3616 (2003).
Trotta et al., "BCR/ABL Activates mdm2 mRNA Translation via the La Antigen," Cancer Cell, 3:145-160 (2003).
International Search Report mailed Jun. 16, 2006, issued in International Application No. PCT/US05/042483.
International Search Report mailed Jun. 16, 2006, issued in International Application No. PCT/US05/042482.
International Search Report mailed Oct. 24, 2005, issued in International Application No. PCT/US05/008452.
Unpublished U.S. Appl. No. 10/592,761, filed Sep. 14, 2006.
Unpublished U.S. Appl. No. 11/735,069, filed Apr. 13, 2007.
Unpublished U.S. Appl. No. 11/720,057, filed May 23, 2007.
Unpublished U.S. Appl. No. 11/720,055, filed May 23, 2007.
Unpublished U.S. Appl. No. 11/720,061, filed May 23, 2007.
Unpublished U.S. Appl. No. 11/765,871, filed Jun. 20, 2007.
Registry Copyright 2006 ACS on STN, Registry No. 337318-01-1.
Registry Copyright 2006 ACS on STN, Registry No. 337318-07-7.
Registry Copyright 2006 ACS on STN, Registry No. 337318-10-2.
Registry Copyright 2006 ACS on STN, Registry No. 337318-13-5.
Registry Copyright 2006 ACS on STN, Registry No. 337318-16-8.
Registry Copyright 2006 ACS on STN, Registry No. 337318-22-6.
Registry Copyright 2006 ACS on STN, Registry No. 337318-25-9.
Registry Copyright 2006 ACS on STN, Registry No. 337318-28-2.
Registry Copyright 2006 ACS on STN, Registry No. 337318-31-7.
Registry Copyright 2006 ACS on STN, Registry No. 337318-34-0.
Registry Copyright 2006 ACS on STN, Registry No. 337318-37-3.
Registry Copyright 2006 ACS on STN, Registry No. 337318-43-1.
Registry Copyright 2006 ACS on STN, Registry No. 337318-46-4.
Registry Copyright 2006 ACS on STN, Registry No. 337318-49-7.
Registry Copyright 2006 ACS on STN, Registry No. 337318-55-5.
Registry Copyright 2006 ACS on STN, Registry No. 337318-58-8.
Registry Copyright 2006 ACS on STN, Registry No. 337318-64-6.
Registry Copyright 2006 ACS on STN, Registry No. 337318-67-9.
Registry Copyright 2006 ACS on STN, Registry No. 337318-70-4.
Registry Copyright 2006 ACS on STN, Registry No. 337318-85-1.
Registry Copyright 2006 ACS on STN, Registry No. 337318-88-4.
Registry Copyright 2006 ACS on STN, Registry No. 337318-91-9.
Registry Copyright 2006 ACS on STN, Registry No. 337318-94-2.
Registry Copyright 2006 ACS on STN, Registry No. 337318-97-5.
Registry Copyright 2006 ACS on STN, Registry No. 337319-03-6.
Registry Copyright 2006 ACS on STN, Registry No. 337319-09-2.
Registry Copyright 2006 ACS on STN, Registry No. 337319-12-7.
Registry Copyright 2006 ACS on STN, Registry No. 337319-21-8.
Registry Copyright 2006 ACS on STN, Registry No. 337319-24-1.
Registry Copyright 2006 ACS on STN, Registry No. 337319-30-9.
Registry Copyright 2006 ACS on STN, Registry No. 337319-33-2.
Registry Copyright 2006 ACS on STN, Registry No. 337319-36-5.
Registry Copyright 2006 ACS on STN, Registry No. 337319-42-3.
Registry Copyright 2006 ACS on STN, Registry No. 337319-48-9.
Registry Copyright 2006 ACS on STN, Registry No. 337331-00-7.
Registry Copyright 2006 ACS on STN, Registry No. 337332-12-4.
Registry Copyright 2006 ACS on STN, Registry No. 337333-42-3.
Registry Copyright 2006 ACS on STN, Registry No. 337334-25-5.
Registry Copyright 2006 ACS on STN, Registry No. 337338-22-4.
Registry Copyright 2006 ACS on STN, Registry No. 337338-52-0.
Registry Copyright 2006 ACS on STN, Registry No. 400867-22-3.
Taylor et al., "Highly enantioselective catalytic acyl-Pictet-Spengler reactions", Journal of the American Chemical Society, 126(34): 10558-10559 (2004).

WPINDEX Copyright 2006 The Thomson Corp on STN, Accession No. 1995-275237, Abstract of WO 1995/019978 A1, (Icos-N) ICOS Corp, et. al. (Jul. 27, 1995).
WPINDEX Copyright 2006 The Thomson Corp on STN, Acession No. 1997-528820, Abstract of EP 0 803 505 A1, (Adir) Adir & Cie, et. al. (Oct. 29, 1997).
WPINDEX Copyright 2006 The Thomson Corp on STN, AN 1990-068877, Abstract of EP 357122 A, (Duin) Duphar Int Res BV, (Sep. 28, 1993).
Yamanaka et al., "A development of Pictet-Spengler reaction in aprotic media using chloroflormates; a short synthesis of borrerine", Heterocycles, 22(2): 371-4 (1984).
Zhang et al., "Concise Enantioselective Syntheses of Quinolactacins A2 and B through Alternative Winterfeldt Oxidation", Journal of Organic Chemistry, 68(11): 4523-4526 (2003).
Davis, T. et. al., Abstract 3870 Post-transcriptional control as a novel approach to anti-angiogenesis: development of a small molecule that reduces the production of tumor vascular endothelial growth factor A (VEGF), Abstract presented at 96th annual meeting of American Association for Cancer Research, Apr. 16-20, 2005.
Davis, T. et. al. Post-transcriptional control as a novel approach to anti-angiogenesis: development of a small molecule that reduces the production of tumor vascular endothelial growth factor A (VEGF), Poster presented at 96th annual meeting of American Association for Cancer Research, Apr. 16-20, 2005.
Ullner, P. et. al., Abstract 3857 Post-transcriptional inhibition of vascular endothelial growth factor (VEGF) expression arrests tumor growth at a prevascular stage, Abstract presented at American Association for Cancer Research, Apr. 16-20, 2005.
Hirawat, S., et. al. PTC299: A Novel Post-transcriptional VEGF Expression Inhibitor, Poster presented at 5th International Colorectal Cancer Congress, Oct. 2006.
Hirawat, S., et. al. Phase 1 Single-dose Safety, PK, and Food-effect Study of PTC299, a Novel VEGF Expression Inhibitor for Treatment of Solid Tumors, Poster presented at EORTC in 2006.
David, T. et. al., Preclinical Development of PTC299: An Orally Bioavailable Small Molecule Drug That Selectively Inhibits VEGF Protein Production, Tumor Growth, and Microvessel Density, Poster submitted at EORTC in 2006.
Cao, L. et. al., PTC299 Inhibits VEGF Expression Through Its 5' UTR, Poster submitted at EORTC in 2006.
Hirawat, S., et. al., A Phase 1 Multiple-Dose Safety, Pharmacokinetic, and Pharmacodynamic Study of PTC299, a Novel VEGF Expression Inhibitor for Treatment of Solid Tumors, Abstract submitted Nov. 28, 2006 for 2007 meeting of American Association for Cancer Research, Tracking No. 07-AB-4295-AACR.
Hirawat, S., Phase 1 single-dose safety, PK, and food-effect study of PTC299, a novel VEGF expression inhibitor for treatment of solid tumors, Abstract submitted for 19th Meeting of the European Association for Cancer Research on Jun. 12, 2006.
Hirawat, S. et. al., Phase 1 Multiple Dose Safety, Pharmacokinetic, Pharmacodynamic Study of PTC299, a Novel VEGF Expression Inhibitor for the Treatment of Solid Tumors, Poster presented at American Association for Cancer Research, Apr. 14-18, 2007.
Hirawat, S. et. al., Phase 1 studies assessing the safety, PK, and VEGF-modulating effects of PTC299, a novel VEGF expression inhibitor, submitted to American Society of Clinical Oncology on Jan. 9, 2007, Tracking No. 07-AB-33792-ASCO.
PTC299 Phase 1 Study in Healthy Volunteers (Study 002) Power Point Presentation presented at American Association for Cancer Research meeting 2007.
Davis, T., et. al., Discovery and preclinical efficacy of PTC299, an antiangiogenic candidate in clinical development for the treatment of cancer, presented at 10th International Symposium on Anti-Angiogenic Agents in 2008.
Miao, H. et. al., Preclinical and Phase 1 Study Results of PTC 299, an Oral Inhibitor of VEGF Expression, Poster presented Feb. 7-9, 2008.
Trotta C. et. al., PTC299 Inhibits Expression of VEGF Through the 5' Untranslated Region of its mRNA, Poster presented at 10th International Symposium on Anti-Angiogenic Agents, Feb. 2008.
International Search Report issued on Jul. 25, 2008, in corresponding International Application No. PCT/US2008/004810.
HCAPLUS Copyright 2006 ACS on STN, AN 1965:480584, Abstract of Freter et al., "Reactions of 1-aryl-1,2,3,4-tetrahydro-β-carbolines in acid solution", Justus Liebigs Annalen der Chemie, 684: 159-87 (1965).
BABS Copyright 2006 Beilstein MDL on STN, AN 5523540, Abstract of Massiot, G., "Synthesis of Indole Alkaloids and Related Molecules Along Non Biogenetic Routes", Bull. Soc. Chem. Belg., 99(9): 717-728 (1990).
BABS Copyright 2006 Beilstein MDL on STN, AN 5669242, Abstract of Piper et al., "Pictet-Spengler reaction of biogenic amines with carbohydrates. Synthesis of novel C-nucleosides", Can. J. Chem., 61: 2721-2728 (1983).
BABS Copyright 2006 Beilstein MDL on STN, AN 5702218, Abstract of Pogosyan et al., "Synthesis and Biological Activity of 3-R-1,2,3,4-Tetrahydro-4β-Carboline Derivatives", Pharm. Chem. J. (Engl. Transl.), 21(6): 414-417 (1987).
BABS Copyright 2006 Beilstein MDL on STN, AN 5776298, Abstract of Moehrle et al., "Fused Dihydro-1,2,4-triazines", Arch. Pharm. (Weinheim Ger.), 320(3): 198-202 (1987).
BABS Copyright 2006 Beilstein MDL on STN, AN 6010011, Abstract of Waldmann et al., "Asymmetrische Pictet-Spengler-Reaktionen mit N,N-Phthaloyl-Aminosaeuren als chiralen Hilfsgruppen", Angew.Chem. (1995), 107(21), 2608-2610.
BABS Copyright 2006 Beilstein MDL on STN, AN 6236596, Abstract of Lu et al., "Stereoselective Synthesis of Phosphorothioate and Alkylphosphinate Analogs Using a L-Tryptophan Derived Chiral Auxiliary", Tetrahedron, 56(26): 4355-4366 (2000).
Beilstein Copyright 2006 Beilstein MDL on STN, Beilstein Records (BRN): 9976380.
Beilstein Copyright 2006 Beilstein MDL on STN, Beilstein Records (BRN): 9975229.
Beilstein Copyright 2006 Beilstein MDL on STN, Beilstein Records (BRN): 9974267.
Beilstein Copyright 2006 Beilstein MDL on STN, Beilstein Records (BRN): 9973640.
Beilstein Copyright 2006 Beilstein MDL on STN, Beilstein Records (BRN): 9817157.
Beilstein Copyright 2006 Beilstein MDL on STN, Beilstein Records (BRN): 9802212.
Beilstein Copyright 2006 Beilstein MDL on STN, Beilstein Records (BRN): 9793124.
Beilstein Copyright 2006 Beilstein MDL on STN, Beilstein Records (BRN): 9792788.
Beilstein Copyright 2006 Beilstein MDL on STN, Beilstein Records (BRN): 9790084.
Beilstein Copyright 2006 Beilstein MDL on STN, Beilstein Records (BRN): 9784177.
Beilstein Copyright 2006 Beilstein MDL on STN, Beilstein Records (BRN): 9781935.
Beilstein Copyright 2006 Beilstein MDL on STN, Beilstein Records (BRN): 9778052.
Beilstein Copyright 2006 Beilstein MDL on STN, Beilstein Records (BRN): 9715971.
Beilstein Copyright 2006 Beilstein MDL on STN, Beilstein Records (BRN): 9713454.
Beilstein Copyright 2006 Beilstein MDL on STN, Beilstein Records (BRN): 9666272.
Beilstein Copyright 2006 Beilstein MDL on STN, Beilstein Records (BRN): 9664783.
Beilstein Copyright 2006 Beilstein MDL on STN, Beilstein Records (BRN): 9664782.
Beilstein Copyright 2006 Beilstein MDL on STN, Beilstein Records (BRN): 9662877.
Beilstein Copyright 2006 Beilstein MDL on STN, Beilstein Records (BRN): 9662875.
Beilstein Copyright 2006 Beilstein MDL on STN, Beilstein Records (BRN): 9656936.
Beilstein Copyright 2006 Beilstein MDL on STN, Beilstein Records (BRN): 9530614.
Beilstein Copyright 2006 Beilstein MDL on STN, Beilstein Records (BRN): 9529248.
Beilstein Copyright 2006 Beilstein MDL on STN, Beilstein Records (BRN): 9526693.

Beilstein Copyright 2006 Beilstein MDL on STN, Beilstein Records (BRN): 9525620.
Beilstein Copyright 2006 Beilstein MDL on STN, Beilstein Records (BRN): 9525619.
Beilstein Copyright 2006 Beilstein MDL on STN, Beilstein Records (BRN): 9525032.
Beilstein Copyright 2006 Beilstein MDL on STN, Beilstein Records (BRN): 9523521.
Beilstein Copyright 2006 Beilstein MDL on STN, Beilstein Records (BRN): 9520875.
Beilstein Copyright 2006 Beilstein MDL on STN, Beilstein Records (BRN): 9520142.
Beilstein Copyright 2006 Beilstein MDL on STN, Beilstein Records (BRN): 9517212.
Beilstein Copyright 2006 Beilstein MDL on STN, Beilstein Records (BRN): 9504026.
Beilstein Copyright 2006 Beilstein MDL on STN, Beilstein Records (BRN): 9446639.
Beilstein Copyright 2006 Beilstein MDL on STN, Beilstein Records (BRN): 9374742.
Beilstein Copyright 2006 Beilstein MDL on STN, Beilstein Records (BRN): 9371916.
Beilstein Copyright 2006 Beilstein MDL on STN, Beilstein Records (BRN): 9370648.
Beilstein Copyright 2006 Beilstein MDL on STN, Beilstein Records (BRN): 9370647.
Beilstein Copyright 2006 Beilstein MDL on STN, Beilstein Records (BRN): 9370056.
Beilstein Copyright 2006 Beilstein MDL on STN, Beilstein Records (BRN): 9370055.
Beilstein Copyright 2006 Beilstein MDL on STN, Beilstein Records (BRN): 9367542.
Beilstein Copyright 2006 Beilstein MDL on STN, Beilstein Records (BRN): 9364536.
Beilstein Copyright 2006 Beilstein MDL on STN, Beilstein Records (BRN): 9364535.
Beilstein Copyright 2006 Beilstein MDL on STN, Beilstein Records (BRN): 9363589.
Beilstein Copyright 2006 Beilstein MDL on STN, Beilstein Records (BRN): 9362270.
Beilstein Copyright 2006 Beilstein MDL on STN, Beilstein Records (BRN): 9361560.
HCAPLUS Copyright 2006 ACS on STN, Accession No. 2000:772630, Abstract of WO 2000/064897 A1, Macef et al. (Nov. 2, 2000).
HCAPLUS Copyright 2006 ACS on STN, Accession No. 2001:12443, Abstract of WO 2001/000610 A1, Aventis Pharma Deutschland GmbH (Jan. 4, 2001).
HCAPLUS Copyright 2006 ACS on STN, Accession No. 2001:338479, Abstract of WO 2001/032604 A1, University College London (May 10, 2001).
HCAPLUS Copyright 2006 ACS on STN, Accession No. 2001:62384, Abstract of EP 1 070 716 A1, Adir et Compagnie (Jan. 24, 2001).
HCAPLUS Copyright 2006 ACS on STN, Accession No. 2001:851157, Abstract of WO 2001/087882, Ortho-McNeil Pharmaceutical, Inc. (Nov. 22, 2001).
HCAPLUS Copyright 2006 ACS on STN, Accession No. 2002:275987, Abstract of WO 2002/028858 A2, Lilly Icos LLC (Apr. 11, 2002).
HCAPLUS Copyright 2006 ACS on STN, Accession No. 2002:408517, Abstract of WO 2002/041884, Pain Therapeutics, Inc. (May 30, 2002).
HCAPLUS Copyright 2006 ACS on STN, Accession No. 2002:615404, Abstract of WO 2002/062339 A1, Smithkline Beecham Corporation (Aug. 15, 2002).
HCAPLUS Copyright 2006 ACS on STN, Accession No. 2002:637677, Abstract of WO 2002/064591, Lilly Icos LLC, USA (Aug. 22, 2002).
HCAPLUS Copyright 2006 ACS on STN, Accession No. 2002:946116, Abstract of WO 2002/098428 A1, Lilly Icos LLC (Dec. 12, 2002).
HCAPLUS Copyright 2006 ACS on STN, Accession No. 2003:356232, Abstract of WO 2003/037310 A2, Pain Therapeutics, Inc. (May 8, 2003).
HCAPLUS Copyright 2006 ACS on STN, Accession No. 2003:356260, Abstract of WO 2003/037340 A1, Pain Therapeutics, Inc. (May 8, 2003).
HCAPLUS Copyright 2006 ACS on STN, Accession No. 2003:5960, Abstract of WO 2003/000691 A1, Lilly Icos Llc (Jan. 3, 2003).
HCAPLUS Copyright 2006 ACS on STN, Accession No. 2003:76556, Abstract of WO 2003/007888 A2, Adipogenix, Inc. (Jan. 30, 2003).
HCAPLUS Copyright 2006 ACS on STN, Accession No. 2004:1154677, Abstract of WO 2004/113300 A1, Ono Pharmaceutical Co., Ltd. (Dec. 29, 2004).
HCAPLUS Copyright 2006 ACS on STN, Accession No. 2004:41506, Abstract of WO 2004/005328 A2, Sigma-Tau Industrie Farmaceutiche Riunite S.p.A. (Jan. 15, 2004).
HCAPLUS Copyright 2006 ACS on STN, Accession No. 2004:965248, Abstract of WO 2004/096802, Oscient Pharmaceuticals et al. (Nov. 11, 2004).
HCAPLUS Copyright 2006 ACS on STN, Accession No. 2005:1106860, Abstract of WO 2005/095403, Intermune, Inc. (Oct. 13, 2005).
HCAPLUS Copyright 2006 ACS on STN, Accession No. 2005:371064, Abstract of WO 2005/037214, Intermune, Inc. et al. (Apr. 28, 2005).
HCAPLUS Copyright 2006 ACS on STN, Accession No. 2005:696910, Abstract of WO 2005/070930 A2, Chiron Corporation (Aug. 4, 2005).
HCAPLUS Copyright 2006 ACS on STN, Accession No. 2005:902862, Abstract of WO 2005/077912 A1, Mitsubishi Pharma Corporation (Aug. 25, 2005).
Jiang et al., "Potassium Superoxide as an Alternative Reagent for Winterfeldt Oxidation of β-Carbolines", Organic Letters, 5(1): 43-46 (2003).
List of Compounds from Registry Copyright 2006 ACS on STN.
MARPAT Copyright 2006 ACS on STN, Accession No. 109:129416, Abstract of EP 0 272 056 A1, Harbor Branch Oceanographic Institution, Inc. (Jun. 22, 1988).
MARPAT Copyright 2006 ACS on STN, Accession No. 116:235610, Abstract of EP 0 466 548 A1, Adir et Cie. Jan. 15, 1992).
MARPAT Copyright 2006 ACS on STN, Accession No. 116:256054, Abstract of WO 1992/000295 A1, Rorer International (Holdings), Inc. (Jan. 9, 1992).
MARPAT Copyright 2006 ACS on STN, Accession No. 117:212969, Abstract of WO 1992/006108 A1, Polifarma S.p.A. (Apr. 16, 1992).
MARPAT Copyright 2006 ACS on STN, Accession No. 117:234001, Abstract of JP 04173786 A2, Kawaken Fine Chemicals Co., Ltd. (Jun. 22, 1992).
MARPAT Copyright 2006 ACS on STN, Accession No. 121:179566, Abstract of WO 1994/010175 A1, United States Dept. of Health and Human Services et al. (May 11, 1994).
MARPAT Copyright 2006 ACS on STN, Accession No. 121:301326, Abstract of DE 42 43 496 A1, Boehringer Ingelheim KG (Mar. 10, 1994).
MARPAT Copyright 2006 ACS on STN, Accession No. 122:106542, Abstract of WO 1994/014843 A1, Warner-Lambert Co. (Jul. 7, 1994).
MARPAT Copyright 2006 ACS on STN, Accession No. 124:117997, Abstract of EP 0 675 112 A1, Bristol-Myers Squibb Co. (Oct. 4, 1995).
MARPAT Copyright 2006 ACS on STN, Accession No. 124:203106, Abstract of WO 1995/030687, Boehringer Ingelheim KG et al. (Nov. 16, 1995).
MARPAT Copyright 2006 ACS on STN, Accession No. 124:233150, Abstract of DE 44 45 939 A1, Boehringer Ingelheim KG (Nov. 9, 1995).
MARPAT Copyright 2006 ACS on STN, Accession No. 124:290283, Abstract of CA 2143588, Bhide et al. (Sep. 25, 1995).
MARPAT Copyright 2006 ACS on STN, Accession No. 124:344109, Abstract of EP 0 696 593 A2, Bristol-Myers Squibb Company (Feb. 14, 1996).
MARPAT Copyright 2006 ACS on STN, Accession No. 125:33473, Abstract of WO 1996/003377 A1, Sankyo Co., Ltd. (Feb. 8, 1996).

MARPAT Copyright 2006 ACS on STN, Accession No. 125:33651, Abstract of CA 2157998, Lilly Industries Ltd. (Mar. 13, 1996).
MARPAT Copyright 2006 ACS on STN, Accession No. 129:260346, Abstract of WO 1998/040385 A1, Novo Nordisk A/S (Sep. 17, 1998).
MARPAT Copyright 2006 ACS on STN, Accession No. 132:35702, Abstract of WO 1999/064420 A1, Societe De Conseils De Recherches Et D'applications Scientifiques S. A. (Dec. 16, 1999).
MARPAT Copyright 2006 ACS on STN, Accession No. 132:88209, Abstract of WO 2000/002878 A1, University of Bristol (Jan. 20, 2000).
MARPAT Copyright 2006 ACS on STN, Accession No. 133:247280, Abstract of WO 2000/056304, Harbor Branch Oceanographic Institution, Inc. et al. (Sep. 28, 2000).
MARPAT Copyright 2006 ACS on STN, Accession No. 134:252660, Abstract of EP 1 086 947 A1, Pfizer Products Inc. (Mar. 28, 2001).
MARPAT Copyright 2006 ACS on STN, Accession No. 134:56654, Abstract of WO 2000/077001 A1, Du Pont Pharmaceuticals Company (Dec. 21, 2000).
MARPAT Copyright 2006 ACS on STN, Accession No. 134:56655, Abstract of WO 2000/077002 A1, Du Pont Pharmaceuticals Company (Dec. 21, 2000).
MARPAT Copyright 2006 ACS on STN, Accession No. 134:56657, Abstract of WO 2000/077010 A2, Du Pont Pharmaceuticals Company (Dec. 21, 2000).
MARPAT Copyright 2006 ACS on STN, Accession No. 135:371735, Abstract of WO 2001/087038, Ortho-McNeil Pharmaceutical, Inc. (Nov. 22, 2001).
MARPAT Copyright 2006 ACS on STN, Accession No. 137:140432, Abstract of WO 2002/059129 A2, Bristol-Myers Squibb Company (Aug. 1, 2002).
MARPAT Copyright 2006 ACS on STN, Accession No. 137:353008, Abstract of WO 2002/088123 A1, Lilly Icos LLC (Nov. 7, 2002).
MARPAT Copyright 2006 ACS on STN, Accession No. 137:78864, Abstract of WO 2002/051842 A1, F. Hoffmann-La Roche A.-G. (Jul. 4, 2002).
HCAPLUS Copyright 2006 ACS on STN, AN 1996:512657, Abstract of Legseir et al., "Synthesis of optically active tetrahydro-β-carbolines by the Pictet-Spengler reaction", Journal de la Societe Algerienne de Chimie, 6(1): 17-27 (1996).
HCAPLUS Copyright 2006 ACS on STN, AN 1997:55320, Abstract of Schmidt et al., "Asymmetric control in the Pictet-Spengler reaction by means of N-protected amino acids as chiral auxiliary groups", Chemistry—A European Journal, 2(12): 1566-1571 (1996) Published in: Angew. Chem., Int. Ed. Engl., 35 (23/24).
HCAPLUS Copyright 2006 ACS on STN, AN 1998:355721, Abstract of Bienayme, H., ""Reagent Explosion": an efficient method to increase library size and diversity", Tetrahedron Letters, 39(24): 4255-4258 (1998).
HCAPLUS Copyright 2006 ACS on STN, AN 1999:767765, Abstract of Zhao et al., "Easy generation of an enantiopure general indol alkaloid building block by kinetic resolution", Tetrahedron: Asymmetry, 10(20): 3899-3905 (1999).
HCAPLUS Copyright 2006 ACS on STN, AN 1999:799056, Abstract of Boumendjel et al., "Synthesis of ajmalicine derivatives using Wittig-Horner and Knoevenagel reactions", Tetrahedron Letters, 40(51): 9033-9036 (1999).
HCAPLUS Copyright 2006 ACS on STN, AN 2000:337953, Abstract of You et al., "Application of DDQ in the synthesis of β-carboline alkaloid", Hecheng Huaxue, 8(1): 83-86 (2000). Only English STN Abstract Provided.
HCAPLUS Copyright 2006 ACS on STN, AN 2002:637676, Abstract of WO 2002/064590, Lilly Icos LLC (Aug. 22, 2002).
HCAPLUS Copyright 2006 ACS on STN, AN 2002:659480, Abstract of Bonnefont-Rousselot et al., "Melatonin related compounds inhibit lipid peroxidation during copper or free radical-induced LDL oxidation", Journal of Pineal Research, 33(2): 109-117 (2002).
HCAPLUS Copyright 2006 ACS on STN, AN 2002:861062, Abstract of Joule, J.A., "Product Class 13: indole and its derivatives", Science of Synthesis, 10: 361-652 (2001).
HCAPLUS Copyright 2006 ACS on STN, AN 2003:431047, Abstract of Cheve et al., "Antioxidant activity of pinoline analogues in the LDL oxidation model", Medicinal Chemistry Research, 11(7): 361-379 (2002).
HCAPLUS Copyright 2006 ACS on STN, AN 2004:611809, Abstract of Donova et al., "N-Acyliminium reagents of 3,4-dihydro-β-carboline and acyl chlorides in the reaction of intermolecular α-amidoalkylation toward heteroarormatics", Synthetic Communications, 34(15): 2813-2821(2004).
HCAPLUS Copyright 2006 ACS on STN, AN 2005:580707, Abstract of Zhuang et al., "Enantioselective Friedel-Crafts type addition of indoles to nitro-olefins using a chiral hydrogen-bonding catalyst—a synthesis of optically active tetrahydro-β-carbolines", Organic & Biomolecular Chemistry, 3(14): 2566-2571 (2005).
HCAPLUS Copyright 2006 ACS on STN, AN 2005:643328, Abstract of Mekhloufi et al., "Antioxidant activity of melatonin and a pinoline derivative on linoleate model system", Journal of Pineal Research, 39(1): 27-33 (2005).
HCAPLUS Copyright 2006 ACS on STN, AN 2005:886847, Abstract of Tailleux et al., "Increased Susceptibility of Low-Density Lipoprotein to Ex Vivo Oxidation in Mice Transgenic for Human Apolipoprotein B Treated with 1 Melatonin-Related Compound Is Not Associated with Atherosclerosis Progression", Journal of Cardiovascular Pharmacology, 46(3): 241-249 (2005).
HCAPLUS Copyright 2006 ACS on STN, AN 1980:22200, Abstract of Kluge et al., "Phosphate reagents for the synthesis of enol ethers and one-carbon homologation to aldehydes", Journal of Organic Chemistry, 44(26): 4847-52 (1979).
HCAPLUS Copyright 2006 ACS on STN, AN 1982:143144, Abstract of Cloudsdale et al., "Synthetic studies in the ajmaline series", Journal of Organic Chemistry, 47(6): 919-28 (1982).
HCAPLUS Copyright 2006 ACS on STN, Accession No. 1965:498671, Abstract of NL 6413518, Omnium Chimique, Societe Anon. (May 24, 1965).
HCAPLUS Copyright 2006 ACS on STN, Accession No. 1966:420748, Abstract of NL 6512087, Imperial Chemical Industries Ltd. (Mar. 17, 1966).
HCAPLUS Copyright 2006 ACS on STN, Accession No. 1972:501562, Abstract of DE 20 61 359 A, Badische Anilin- & Soda-Fabrik AG (Jun. 22, 1972).
HCAPLUS Copyright 2006 ACS on STN, Accession No. 1972:526602, Abstract of DE 20 62 828 A, Boehringer, C. H. (Jun. 22, 1972).
HCAPLUS Copyright 2006 ACS on STN, Accession No. 1977:423246, Abstract of DE 26 37 503 A1, Endo Laboratories Inc. (Mar. 3, 1977).
HCAPLUS Copyright 2006 ACS on STN, Accession No. 1977:468520, Abstract of JP 52031097 A1, Oki et al. (Mar. 9, 1977).
HCAPLUS Copyright 2006 ACS on STN, Accession No. 1980:471821, Abstract of EP 0 008 249, Synthelabo S. A. (Feb. 20, 1980).
HCAPLUS Copyright 2006 ACS on STN, Accession No. 1981:121318, Abstract of JP 55145687 A2, Synthelabo S. A. (Nov. 13, 1980).
HCAPLUS Copyright 2006 ACS on STN, Accession No. 1981:139775, Abstract of EP 0 017 727 A1, Ciba-Geigy A.-G. (Oct. 29, 1980).
HCAPLUS Copyright 2006 ACS on STN, Accession No. 1981:175153, Abstract of EP 0 018 857 A1, Synthelabo S. A. (Nov. 12, 1980).
HCAPLUS Copyright 2006 ACS on STN, Accession No. 1981:497842, Abstract of FR 2456743 A1, Synthelabo S. A. (Dec. 12, 1980).
HCAPLUS Copyright 2006 ACS on STN, Accession No. 1982:35284, Abstract of FR 2460301 A2, Synthelabo S. A. (Jan. 23, 1981).
HCAPLUS Copyright 2006 ACS on STN, Accession No. 1982:550721, Abstract of FR 2486801 A1, Synthelabo S. A. (Jan. 22, 1982).
HCAPLUS Copyright 2006 ACS on STN, Accession No. 1984:490905, Abstract of EP 0 101 574 A1, BASF A.-G. (Feb. 29, 1984).

HCAPLUS Copyright 2006 ACS on STN, Accession No. 1985:24611, Abstract of DE 33 02 126 A1, Boehringer Ingelheim K.-G. (Jul. 26, 1984).
HCAPLUS Copyright 2006 ACS on STN, Accession No. 1986:207248, Abstract of JP 60246385 A2, Sankyo Co., Ltd. (Dec. 6, 1985).
HCAPLUS Copyright 2006 ACS on STN, Accession No. 1988:630991, Abstract of EP 0 273 321 A1, Kawaken Fine Chemicals Co., Ltd. (Jul. 6, 1988).
HCAPLUS Copyright 2006 ACS on STN, Accession No. 1989:205701, Abstract of DE 37 05 220 A1, Boehringer Ingelheim K.-G. (Sep. 1, 1988).
HCAPLUS Copyright 2006 ACS on STN, Accession No. 1989:407060, Abstract of WO 1989/000159 A1, Richter, Gedeon, Vegyeszeti Gyar Rt (Jan. 12, 1989).
HCAPLUS Copyright 2006 ACS on STN, Accession No. 1989:477986, Abstract of EP 0 300 541 A1, Duphar International Research B. V. (Jan. 25, 1989).
HCAPLUS Copyright 2006 ACS on STN, Accession No. 1989:554290, Abstract of HU 46032 A2, Gyogynoveny Kutato Intezet (Sep. 28, 1988).
HCAPLUS Copyright 2006 ACS on STN, Accession No. 1990:235665, Abstract of JP 01319482 A2, Kawaken Fine Chemicals Co., Ltd. (Dec. 25, 1989).
HCAPLUS Copyright 2006 ACS on STN, Accession No. 1990:441332, Abstract of EP 0 346 847 A2, Hoffmann-La Roche, F., und Co. A.-G. (Dec. 20, 1989).
HCAPLUS Copyright 2006 ACS on STN, Accession No. 1992:235613, Abstract of JP 03287586, Taisho Pharmaceutical Co., Ltd. (Dec. 18, 1991).
HCAPLUS Copyright 2006 ACS on STN, Accession No. 1993:175782, Abstract of JP 04275221 A2, Taisho Pharmaceutical Co., Ltd. (Sep. 30, 1992).
HCAPLUS Copyright 2006 ACS on STN, Accession No. 1994:54535, Abstract of HU 63164 A2, Richter, Gedeon, Vegyeszeti Gyar Rt. (Jul. 28, 1993).
HCAPLUS Copyright 2006 ACS on STN, Accession No. 1995:861292, Abstract of JP 07179467, Nippon Shoji Kk (Jul. 18, 1995).
HCAPLUS Copyright 2006 ACS on STN, Accession No. 1996:311402, Abstract of DE 44 36 190 A1, Bringmann et al. Apr. 11, 1996).
HCAPLUS Copyright 2006 ACS on STN, Accession No. 1996:425286, Abstract of WO 1996/008490 A1, Cemaf et al. (Mar. 21, 1996).
HCAPLUS Copyright 2006 ACS on STN, Accession No. 1997:244196, Abstract of EP 0 758 021 A2, Polifarma S.P.A. (Feb. 12, 1997).
HCAPLUS Copyright 2006 ACS on STN, Accession No. 1997:618080, Abstract of WO 1997/032860 A1, James Black Foundation Ltd. et al. (Sep. 12, 1997).
HCAPLUS Copyright 2006 ACS on STN, Accession No. 1997:752957, Abstract of WO 1997/043287 A1, Icos Corporation et al. (Nov. 20, 1997).
HCAPLUS Copyright 2006 ACS on STN, Accession No. 2000:191086, Abstract of WO 2000/015639 A1, Icos Corp. (Mar. 23, 2000).
HCAPLUS Copyright 2006 ACS on STN, Accession No. 2000:755247, Abstract of EP 1 046 627 A2, Solvay (Societe Anonyme) (Oct. 25, 2000).
Registry Copyright 2006 ACS on STN, Registry No. 335120-76-8.
Registry Copyright 2006 ACS on STN, Registry No. 335120-78-0.
Registry Copyright 2006 ACS on STN, Registry No. 335120-82-6.
Registry Copyright 2006 ACS on STN, Registry No. 335120-84-8.
Registry Copyright 2006 ACS on STN, Registry No. 335120-87-1.
Registry Copyright 2006 ACS on STN, Registry No. 335120-89-3.
Registry Copyright 2006 ACS on STN, Registry No. 335120-91-7.
Registry Copyright 2006 ACS on STN, Registry No. 335120-93-9.
Registry Copyright 2006 ACS on STN, Registry No. 335120-95-1.
Registry Copyright 2006 ACS on STN, Registry No. 335120-97-3.
Registry Copyright 2006 ACS on STN, Registry No. 335120-99-5.
Registry Copyright 2006 ACS on STN, Registry No. 335121-01-2.
Registry Copyright 2006 ACS on STN, Registry No. 335121-03-4.
Registry Copyright 2006 ACS on STN, Registry No. 335121-05-6.
Registry Copyright 2006 ACS on STN, Registry No. 335121-07-8.
Registry Copyright 2006 ACS on STN, Registry No. 335121-11-4.
Registry Copyright 2006 ACS on STN, Registry No. 335121-13-6.
Registry Copyright 2006 ACS on STN, Registry No. 335121-23-8.
Registry Copyright 2006 ACS on STN, Registry No. 335121-25-0.
Registry Copyright 2006 ACS on STN, Registry No. 335121-27-2.
Registry Copyright 2006 ACS on STN, Registry No. 335121-31-8.
Registry Copyright 2006 ACS on STN, Registry No. 335121-33-0.
Registry Copyright 2006 ACS on STN, Registry No. 335121-35-2.
Registry Copyright 2006 ACS on STN, Registry No. 335121-39-6.
Registry Copyright 2006 ACS on STN, Registry No. 335121-41-0.
Registry Copyright 2006 ACS on STN, Registry No. 335121-43-2.
Registry Copyright 2006 ACS on STN, Registry No. 335121-45-4.
Registry Copyright 2006 ACS on STN, Registry No. 335121-49-8.
Registry Copyright 2006 ACS on STN, Registry No. 336120-14-0.
Registry Copyright 2006 ACS on STN, Registry No. 336120-15-1.
Registry Copyright 2006 ACS on STN, Registry No. 336120-16-2.
Registry Copyright 2006 ACS on STN, Registry No. 336120-17-3.
Registry Copyright 2006 ACS on STN, Registry No. 336120-19-5.
Registry Copyright 2006 ACS on STN, Registry No. 336120-20-8.
Registry Copyright 2006 ACS on STN, Registry No. 336120-21-9.
Registry Copyright 2006 ACS on STN, Registry No. 336120-22-0.
Registry Copyright 2006 ACS on STN, Registry No. 336120-23-1.
Registry Copyright 2006 ACS on STN, Registry No. 336120-24-2.
Registry Copyright 2006 ACS on STN, Registry No. 336120-25-3.
Registry Copyright 2006 ACS on STN, Registry No. 336120-26-4.
Registry Copyright 2006 ACS on STN, Registry No. 336120-27-5.
Registry Copyright 2006 ACS on STN, Registry No. 336120-28-6.
Registry Copyright 2006 ACS on STN, Registry No. 336120-29-7.
Registry Copyright 2006 ACS on STN, Registry No. 336120-30-0.
Registry Copyright 2006 ACS on STN, Registry No. 336120-31-1.
Registry Copyright 2006 ACS on STN, Registry No. 336120-33-3.
Registry Copyright 2006 ACS on STN, Registry No. 337317-89-2.
Registry Copyright 2006 ACS on STN, Registry No. 337317-92-7.
Registry Copyright 2006 ACS on STN, Registry No. 337317-95-0.
Registry Copyright 2006 ACS on STN, Registry No. 337317-98-3.
MARPAT Copyright 2006 ACS on STN, Accession No. 138:11447, Abstract of WO 2002/098875 A1, Lilly Icos LLC (Dec. 12, 2002).
MARPAT Copyright 2006 ACS on STN, Accession No. 138:338490, Abstract of WO 2003/033496 A1, Transtech Pharma, Inc. (Apr. 24, 2003).
MARPAT Copyright 2006 ACS on STN, Accession No. 139:395821, Abstract of WO 2003/095427 A1, Taisho Pharmaceutical Co., Ltd. (Nov. 20, 2003).
MARPAT Copyright 2006 ACS on STN, Accession No. 141:379919, Abstract of WO 2004/092123, Microbia, Inc. (Oct. 28, 2004).
MARPAT Copyright 2006 ACS on STN, Accession No. 142:162053, Abstract of FR 2857581 A1, Institut Europeen Biologie Cellulaire (Jan. 21, 2005).
MARPAT Copyright 2006 ACS on STN, Accession No. 142:411220, Abstract of CN 1472209, Fuda University (Feb. 4, 2004).
MARPAT Copyright 2006 ACS on STN, Accession No. 94:139825, Abstract of JP 55104282 A2, Synthelabo S. A. (Aug. 9, 1980).
Mohan et al., "Pictet-Spengler reaction of solid support: synthesis of 1,2,3,4-tetrahydro-β-carboline libraries", Tetrahedron Letters, 37(23): 3963-3966 (1996).
Neipp et al., "Synthesis of Bridged Azabicyclic Structures via Ring-Closing Olefin Metathesis," J. Org. Chem., 68:8867-8878 (2003).
Registry Copyright 2006 ACS on STN, Registry No. 97405-15-7.
Registry Copyright 2006 ACS on STN, Registry No. 865678-67-7.
Registry Copyright 2006 ACS on STN, Registry No. 289656-58-2.
Registry Copyright 2006 ACS on STN, Registry No. 289656-60-6.
Registry Copyright 2006 ACS on STN, Registry No. 334490-33-4.
Registry Copyright 2006 ACS on STN, Registry No. 334490-34-5.
Registry Copyright 2006 ACS on STN, Registry No. 334490-35-6.
Registry Copyright 2006 ACS on STN, Registry No. 335094-02-5.
Registry Copyright 2006 ACS on STN, Registry No. 335094-03-6.
Registry Copyright 2006 ACS on STN, Registry No. 335094-04-7.
Registry Copyright 2006 ACS on STN, Registry No. 335094-06-9.
Registry Copyright 2006 ACS on STN, Registry No. 335094-07-0.
Registry Copyright 2006 ACS on STN, Registry No. 335094-08-1.
Registry Copyright 2006 ACS on STN, Registry No. 335094-09-2.

Registry Copyright 2006 ACS on STN, Registry No. 335094-11-6.
Registry Copyright 2006 ACS on STN, Registry No. 335094-12-7.
Registry Copyright 2006 ACS on STN, Registry No. 335094-13-8.
Registry Copyright 2006 ACS on STN, Registry No. 335094-14-9.
Registry Copyright 2006 ACS on STN, Registry No. 335094-15-0.
Registry Copyright 2006 ACS on STN, Registry No. 335094-17-2.
Registry Copyright 2006 ACS on STN, Registry No. 335094-20-7.
Registry Copyright 2006 ACS on STN, Registry No. 335094-21-8.
Registry Copyright 2006 ACS on STN, Registry No. 335094-22-9.
Registry Copyright 2006 ACS on STN, Registry No. 335094-23-0.
Registry Copyright 2006 ACS on STN, Registry No. 335094-24-1.
Registry Copyright 2006 ACS on STN, Registry No. 335094-25-2.
Registry Copyright 2006 ACS on STN, Registry No. 335094-26-3.
Registry Copyright 2006 ACS on STN, Registry No. 335094-27-4.
Registry Copyright 2006 ACS on STN, Registry No. 335094-29-6.
Registry Copyright 2006 ACS on STN, Registry No. 335094-31-0.
Registry Copyright 2006 ACS on STN, Registry No. 335120-54-2.
Registry Copyright 2006 ACS on STN, Registry No. 335120-56-4.
Registry Copyright 2006 ACS on STN, Registry No. 335120-58-6.
Registry Copyright 2006 ACS on STN, Registry No. 335120-60-0.
Registry Copyright 2006 ACS on STN, Registry No. 335120-62-2.
Registry Copyright 2006 ACS on STN, Registry No. 335120-64-4.
Registry Copyright 2006 ACS on STN, Registry No. 335120-66-6.
Registry Copyright 2006 ACS on STN, Registry No. 335120-68-8.
Registry Copyright 2006 ACS on STN, Registry No. 335120-72-4.
Registry Copyright 2006 ACS on STN, Registry No. 335120-74-6.
Beilstein Copyright 2006 Beilstein MDL on STN, Beilstein Records (BRN): 9359112.
Beilstein Copyright 2006 Beilstein MDL on STN, Beilstein Records (BRN): 9345640.
Beilstein Copyright 2006 Beilstein MDL on STN, Beilstein Records (BRN): 9344461.
Beilstein Copyright 2006 Beilstein MDL on STN, Beilstein Records (BRN): 9342433.
Beilstein Copyright 2006 Beilstein MDL on STN, Beilstein Records (BRN): 9230699.
Beilstein Copyright 2006 Beilstein MDL on STN, Beilstein Records (BRN): 9162855.
Beilstein Copyright 2006 Beilstein MDL on STN, Beilstein Records (BRN): 9147336.
Beilstein Copyright 2006 Beilstein MDL on STN, Beilstein Records (BRN): 9145027.
Beilstein Copyright 2006 Beilstein MDL on STN, Beilstein Records (BRN): 9102751.
Beilstein Copyright 2006 Beilstein MDL on STN, Beilstein Records (BRN): 9101976.
Beilstein Copyright 2006 Beilstein MDL on STN, Beilstein Records (BRN): 9100379.
Beilstein Copyright 2006 Beilstein MDL on STN, Beilstein Records (BRN): 9100313.
Beilstein Copyright 2006 Beilstein MDL on STN, Beilstein Records (BRN): 9099224.
Beilstein Copyright 2006 Beilstein MDL on STN, Beilstein Records (BRN): 9097021.
Beilstein Copyright 2006 Beilstein MDL on STN, Beilstein Records (BRN): 9096422.
Beilstein Copyright 2006 Beilstein MDL on STN, Beilstein Records (BRN): 9093081.
Beilstein Copyright 2006 Beilstein MDL on STN, Beilstein Records (BRN): 8871444.
Beilstein Copyright 2006 Beilstein MDL on STN, Beilstein Records (BRN): 8870325.
Beilstein Copyright 2006 Beilstein MDL on STN, Beilstein Records (BRN): 8866741.
Beilstein Copyright 2006 Beilstein MDL on STN, Beilstein Records (BRN): 8817881.
Beilstein Copyright 2006 Beilstein MDL on STN, Beilstein Records (BRN): 8816950.
Beilstein Copyright 2006 Beilstein MDL on STN, Beilstein Records (BRN): 8816625.
Beilstein Copyright 2006 Beilstein MDL on STN, Beilstein Records (BRN): 8816426.
Beilstein Copyright 2006 Beilstein MDL on STN, Beilstein Records (BRN): 8816097.
Beilstein Copyright 2006 Beilstein MDL on STN, Beilstein Records (BRN): 8816032.
Beilstein Copyright 2006 Beilstein MDL on STN, Beilstein Records (BRN): 8816007.
Beilstein Copyright 2006 Beilstein MDL on STN, Beilstein Records (BRN): 8815946.
Beilstein Copyright 2006 Beilstein MDL on STN, Beilstein Records (BRN): 8815858.
Beilstein Copyright 2006 Beilstein MDL on STN, Beilstein Records (BRN): 8815758.
Beilstein Copyright 2006 Beilstein MDL on STN, Beilstein Records (BRN): 8815143.
Beilstein Copyright 2006 Beilstein MDL on STN, Beilstein Records (BRN): 8813808.
Beilstein Copyright 2006 Beilstein MDL on STN, Beilstein Records (BRN): 8813211.
Beilstein Copyright 2006 Beilstein MDL on STN, Beilstein Records (BRN): 8813188.
Beilstein Copyright 2006 Beilstein MDL on STN, Beilstein Records (BRN): 8813024.
Beilstein Copyright 2006 Beilstein MDL on STN, Beilstein Records (BRN): 8813017.
Beilstein Copyright 2006 Beilstein MDL on STN, Beilstein Records (BRN): 8812495.
Beilstein Copyright 2006 Beilstein MDL on STN, Beilstein Records (BRN): 8812493.
Beilstein Copyright 2006 Beilstein MDL on STN, Beilstein Records (BRN): 8811818.
Beilstein Copyright 2006 Beilstein MDL on STN, Beilstein Records (BRN): 8811580.
Beilstein Copyright 2006 Beilstein MDL on STN, Beilstein Records (BRN): 8811014.
Beilstein Copyright 2006 Beilstein MDL on STN, Beilstein Records (BRN): 8808882.
Beilstein Copyright 2006 Beilstein MDL on STN, Beilstein Records (BRN): 8808569.
Beilstein Copyright 2006 Beilstein MDL on STN, Beilstein Records (BRN): 8807751.
Beilstein Copyright 2006 Beilstein MDL on STN, Beilstein Records (BRN): 8806692.
Beilstein Copyright 2006 Beilstein MDL on STN, Beilstein Records (BRN): 8800981.
Beilstein Copyright 2006 Beilstein MDL on STN, Beilstein Records (BRN): 8665535.
Beilstein Copyright 2006 Beilstein MDL on STN, Beilstein Records (BRN): 8665534.
Beilstein Copyright 2006 Beilstein MDL on STN, Beilstein Records (BRN): 8644848.
Beilstein Copyright 2006 Beilstein MDL on STN, Beilstein Records (BRN): 8626861.
Beilstein Copyright 2006 Beilstein MDL on STN, Beilstein Records (BRN): 8462875.
Beilstein Copyright 2006 Beilstein MDL on STN, Beilstein Records (BRN): 720845.
Beilstein Copyright 2006 Beilstein MDL on STN, Beilstein Records (BRN): 697548.
Beilstein Copyright 2006 Beilstein MDL on STN, Beilstein Records (BRN): 264050.
Beilstein Copyright 2006 Beilstein MDL on STN, Beilstein Records (BRN): 264804.
Beilstein Copyright 2006 Beilstein MDL on STN, Beilstein Records (BRN): 297782.
Beilstein Copyright 2006 Beilstein MDL on STN, Beilstein Records (BRN): 315587.
Beilstein Copyright 2006 Beilstein MDL on STN, Beilstein Records (BRN): 356831.
Beilstein Copyright 2006 Beilstein MDL on STN, Beilstein Records (BRN): 368153.
Beilstein Copyright 2006 Beilstein MDL on STN, Beilstein Records (BRN): 678238.

Beilstein Copyright 2006 Beilstein MDL on STN, Beilstein Records (BRN): 689657.
Beilstein Copyright 2006 Beilstein MDL on STN, Beilstein Records (BRN): 694521.
Beilstein Copyright 2006 Beilstein MDL on STN, Beilstein Records (BRN): 723806.
Beilstein Copyright 2006 Beilstein MDL on STN, Beilstein Records (BRN): 730528.
Beilstein Copyright 2006 Beilstein MDL on STN, Beilstein Records (BRN): 941361.
Birman et al., "A novel route to the geissoschizine skeleton: the influence of ligands on the diastereoselectivity of the Heck cyclization", Tetrahedron Letters, 39(40): 7219-7222 (1998).
CAPLUS Copyright 2006 ACS on STN, Accession No. 1964:404361, Abstract of Antonaccio et al., "Recent progress in Aspidosperma alkaloids", Anais da Associacao Brasileira de Quimica, 21: 31-7 (1962).
CAPLUS Copyright 2006 ACS on STN, Accession No. 1964:52704, Abstract of Taborsky et al., "Synthesis and preliminary pharmacology of some 9H-pyrido [3,4-b] indoles (β-carbolines) and tryptamines related to serotonin and melatonin", Journal of Medicinal Chemistry, 7(2): 135-41 (1964).
CAPLUS Copyright 2006 ACS on STN, Accession No. 1981:84336, Abstract of Afza et al., "Some new derivatives of tetrahydroharmine", Pakistan Journal of Scientific and Industrial Research, 22(6): 290-2 (1979).
CAPLUS Copyright 2006 ACS on STN, Accession No. 1988:5744, Abstract of O'Malley et al., "Tremorgenic mycotoxins. Synthesis of 6-demethoxyfumitremorgin B", Tetrahedron Letters, 28(11): 1131-4 (1987).
CAPLUS Copyright 2006 ACS on STN, Accession No. 1991:471974, Abstract of Jean et al., "Heteroyohimbine-type indole alkaloids: synthesis of a key intermediate of (+)-ajmalicine from carbohydrates and tryptamine", Discovery and Innovation, 2(3): 42-50 (1990).
CAPLUS Copyright 2006 ACS on STN, Accession No. 1994:481198, Abstract of Herraiz et al., "Separation and characterization of 1,2,3,4-tetrahydro-β-carboline-3-carboxylic acids by HPLC and GC-MS. Identification in wine samples", American Journal of Enology and Viticulture, 45(1): 92-101 (1994).
CAPLUS Copyright 2006 ACS on STN, Accession No. 1995:957085, Abstract of Peters et al., "Endogenous alkaloids in man. Part 24. 2-Trifluoroacetyl-1-methyl-1,2,3,4-tetrahydro-β-carboline, a gas chromatographically useful derivative of the mammalian alkaloid eleagnine", Zeitschrift fuer Naturforschung, B: Chemical Sciences, 50(10): 1564-5 (1995).
CAPLUS Copyright 2006 ACS on STN, Accession No. 1996:127543, Abstract of Pellegrini et al., "Total synthesis of (+)-elacomine and (−) -isoelacomine, two hitherto unnamed oxindole alkaloids from *Elaeagnus commutata*", Helvetica Chimica Acta, 79(1): 151-68 (1996).
CAPLUS Copyright 2006 ACS on STN, Accession No. 1997:311459, Abstract of Herraiz, T., "Analysis of tetrahydro-β-carbolines and their precursors by electron ionization mass spectrometry. Identification in foodstuffs by gas chromatography/mass spectrometry", Rapid Communications in Mass Spectrometry, 11(7): 762-768 (1997).
CAPLUS Copyright 2006 ACS on STN, Accession No. 1997:303146, Abstract of Tietze et al., "Efficient biomimetic synthesis of indole alkaloids of the vallesiachotamine group by domino Knoevenagel hetero Diels-Alder hydrogenation sequence", Liebigs Annalen/Recueil, (5): 881-886 (1997).
CAPLUS Copyright 2006 ACS on STN, Accession No. 1998:229659, Abstract of Madrigal et al., "Stererocontrolled Synthesis of 3,6-Dimethyl-2,3,6,7,12,12a-hexahydropyrazino[1,2-b]β-carboline-1,4-diones", Journal of Organic Chemistry, 63(8): 2724-2727 (1998).
CAPLUS Copyright 2006 ACS on STN, Accession No. 1999:726418, Abstract of Itoh et al., "A novel synthesis of chiral 1-allyl-1,2,3,4-tetrahydro-β-carboline employing allyltributyltin and chiral acyl chlorides", Synlett, (11): 1799-1801 (1999).
CAPLUS Copyright 2006 ACS on STN, Accession No. 2003:829870, Abstract of Itoh et al., "Proline-Catalyzed Asymmetric Addition Reaction of 9-Tosyl-3,4-dihydro-β-carboline with Ketones", Organic Letters, 5(23): 4301-4304 (2003).
CAPLUS Copyright 2006 ACS on STN, Accession No. 2003:689601, Abstract of Santos et al., "A novel asymmetric reduction of dihydro-β-carboline derivatives using calix[6]arene/chiral amine as a host complex", Tetrahedron: Asymmetry, 14(17): 2515-2519 (2003).
CAPLUS Copyright 2006 ACS on STN, Accession No. 2003:545316, Abstract of Takayama et al., "First Asymmetric Total Synthesis of Us-7 and -8, Novel D-seco Corynanthe-Type Oxindole Alkaloids from *Uncaria attenuata*: Structure Revision of Us-7 and Determination of Absolute Stereochemistry", Organic Letters, 5(16): 2967-2970 (2003).
CAPLUS Copyright 2006 ACS on STN, Accession No. 2004:164526, Abstract of Itoh et al., "Syntheses of 1,2,3,4,6,7,12,12b-octahydroindolo [2,3-a]quinolizine and harmicine using a chiral 1-allyl-1,2,3,4-tetrahydro-β-carboline as the starting material", Heterocycles, 63(3): 655-661 (2004).
CAPLUS Copyright 2006 ACS on STN, Accession No. 2004:752104, Abstract of Toscano et al., "Alkaloids and Diterpenes From *Croton moritibensis*", Pharmaceutical Biology (Lisse, Netherlands), 42(1): 62-67 (2004).
CAPLUS Copyright 2006 ACS on STN, Accession No. 2005:208078, Abstract of Milen et al., "Studies on stereoselective approaches to β-carboline derivatives", Central European Journal of Chemistry, 3(1): 118-136 (2005).
CAPLUS Copyright 2006 ACS on STN, Accession No. 1960:103442, Abstract of Kanaok, Yuichi, "Applications of the Robinson dehydrogenation reaction. IV. Oxidation of some tetrahydro-β-carboline derivs", Chemical & Pharmaceutical Bulletin, 7: 597-601 (1959).
CAPLUS Copyright 2006 ACS on STN, Accession No. 1980:586630, Abstract of Campos et al., "Selenium dioxide oxidations in the β-carboline area", Heterocycles, 14(7): 975-84 (1980).
CAPLUS Copyright 2006 ACS on STN, Accession No. 1981:567018 Beck et al., "Analysis of 1-methyl-1,2,3,4-tetrahydro-β-carboline in alcoholic beverages", Food and Cosmetics Toxicology, 19(2): 173-7 (1981).
CAPLUS Copyright 2006 ACS on STN, Accession No. 1982:523372, Abstract of Allen et al., "Analysis of 1-methyl-1,2,3,4-tetrahydro-β-carboline by GC/MS using deuterium-labeled internal standards", Analytical Chemistry Symposia Series, 11(Stable Isot.): 611-16 (1982).
CAPLUS Copyright 2006 ACS on STN, Accession No. 1982:598438, Abstract of Cain et al., "Dichlorodicyanoquinone oxidations in the indole area. Synthesis of crenatine", Journal of Organic Chemistry, 47(25): 4933-6 (1982).
CAPLUS Copyright 2006 ACS on STN, Accession No. 1983:160991, Abstract of Cain et al., "Selenium dioxide oxidations in the indole area. Synthesis of β-carboline alkaloids", Journal of the American Chemical Society, 105(4): 907-13 (1983).
CAPLUS Copyright 2006 ACS on STN, Accession No. 1983:198514, Abstract of Siddiqui et al., "Studies in harmine series of alkaloids. Part 1. Derivatives of tetrahydroharmine", Pakistan Journal of Scientific and Industrial Research, 25(5): 147-52 (1982).
CAPLUS Copyright 2006 ACS on STN, Accession No. 1996:494549, Abstract of Nakamura et al., "Enantioselective Allylzincation of Cyclic Aldimines in the Presence of Anionic Bis-oxazoline Ligand", Journal of the American Chemical Society, 118(35): 8489-8490 (1996).
CAPLUS Copyright 2006 ACS on STN, Accession No. 2005:240075, Abstract of Roszkowski et al., "Enantioselective synthesis of 1-substituted tetrahydro-β-carboline derivatives via asymmetric transfer hydrogenation", Journal of Molecular Catalysis A: Chemical, 232(1-2): 143-149 (2005).
CAPLUS Copyright 2006 ACS on STN, Accession No. 1930:788, Abstract of Tatsui, G., "Synthesis of carboline derivatives. II", Yakugaku Zasshi, 49: 749-58 (1929).
CAPLUS Copyright 2006 ACS on STN, Accession No. 1930:789, Abstract of Zelinskii et al., "Decomposition of cholesterylene and of cholesteryl ether with aluminum chloride", Ber. 62b: 2199-2202 (1929).

CAPLUS Copyright 2006 ACS on STN, Accession No. 1964:16683, deStevens et al., "Heterocycles. XIV. 2-and3-Azaoctahydroindolo [2,3-a]quinolizines", Journal of Organic Chemistry, 28(11): 3210-12 (1963).
CAPLUS Copyright 2006 ACS on STN, Accession No. 1964:404362Abdusalamov et al., "Some derivatives of tetrahydroharman", Uzbekskii Khimicheskii Zhurnal, 8(1): 48-50 (1964).
CAPLUS Copyright 2006 ACS on STN, Accession No. 1965:23665, Abstract of Lefer et al., "Potentiation of the cardiovascular effects of norepinephrine by a tetrahydro-β-carboline", Archives Internationales de Pharmacodynamie et de Therapie, 151(3-4): 383-93 (1964).
CAPLUS Copyright 2006 ACS on STN, Accession No. 1965:446445, Abstract of Trojanek et al., "Absolute configuration of vincamine and some other alkaloids of the eburnamine type", Chemistry & Industry (London, United Kingdom), (28): 1261 (1965).
CAPLUS Copyright 2006 ACS on STN, Accession No. 1966:499526, Abstract of Potier et al., "Alkaloids of *Cinchona ledgeriana* leaves. II. Structure of cinschophyllamine and isocinchophyllamine", Bulletin de la Societe Chimique de France, (7): 2309-15 (1966).
CAPLUS Copyright 2006 ACS on STN, Accession No. 1967:473734, Abstract of Abdusalamov et al., "Some tetrahydroharman derivatives", Nauchnye Trudy-Tashkentskii Gosudarstvennyi Universitet im. V. I. Lenina, 286: 76-9 (1966).
HCAPLUS Copyright 2006 ACS on STN, AN 1961:112225, Abstract of Vejdelek et al., "Synthetic experiments in the group of hypotensive alkaloids. XXI. Chemistry of 1,2,3,4-tetrahydronorharman-1-carboxylic acid and derivatives", Journal of Medicinal & Pharmaceutical Chemistry, 3: 427-40 (1961).
HCAPLUS Copyright 2006 ACS on STN, AN 1961:99570, Abstract of Mndzhoyan et al., "Syntheses based on harmine and tetrahydroharmine. III. Cyanoethylation of harmine and tetrahydroharmine", Izvest. Akad. Nauk Armyan. S.S.R., Khim. Nauki, 13(No. 14): 297-304 (1960).
HCAPLUS Copyright 2006 ACS on STN, AN 1962:45986, Abstract of Agbalyan, S. G., "Decyanoethylation in 1,2,3,4-tetrahydro-β-carbolines", Izvest. Akad. Nauk Armyan. S.S.R., Khim. Nauki, 14: 277-82 (1961).
HCAPLUS Copyright 2006 ACS on STN, AN 1963:27125, Abstract of Agbalyan, S. G., "Cyanoethylation of harmine and tetrahydroharmine", Izvestiya Akademii Nauk Armyanskoi SSR, Khimicheskie Nauki, 14: 611-16 (1961).
HCAPLUS Copyright 2006 ACS on STN, AN 1963:415546, Walls et al., "Synthesis of 1,2,3,4,6,7-hexahydroindolo [2,3-a]-1,3-trimethylenequinolizine and its intermediates", Bol. Inst. Quim. Univ. Nal. Auton. Mex., 14: 32-47 (1962).
HCAPLUS Copyright 2006 ACS on STN, AN 1964:30874, Abstract of Henecka et a., "Synthesis in the β-carboline series", Med. Chem., Abhandl. Med.-Chem. Forschungsstaetten Farbenfabriken Bayer A.-G., 7: 277-86 (1963).
HCAPLUS Copyright 2006 ACS on STN, AN 1967:115626, Abstract of Elliott et al., "New synthetic approaches to the benz [h] indolo [2,3-a] quinolizine ring system", Journal of Heterocyclic Chemistry, 4(1): 127-9 (1967).
HCAPLUS Copyright 2006 ACS on STN, AN 1967:65442, Abstract of Szantay et al., "Synthesis of substituted octahydroindolo [2,3-a]-quinolizines. The formation of a new type of ring system", Journal of Organic Chemistry, 32(2): 423-7 (1967).
HCAPLUS Copyright 2006 ACS on STN, AN 1969:11546, Abstract of Von Strandtmann et al., "Azecino [2,1-α] tetrahydroisoquinolines and related compounds. I. Reaction of 3,4-dihydroisoquinolines with nonenolizable β-diketones", Journal of Organic Chemistry, 33(11): 4010-15 (1968).
HCAPLUS Copyright 2006 ACS on STN, AN 1971:53396, Abstract of Mukerdzhi et al., "Indole derivatives. LX. Synthesis of β-lactams of the indole series", Khimiya Geterotsiklicheskikh Soedinenii, (12): 1626-30 (1970).
HCAPLUS Copyright 2006 ACS on STN, AN 1971:551703, Abstract of Novak et al., "Synthesis of an analog of Quantril containing the indoloquinolizidine ring", Acta Chimica Academiae Scientiarum Hungaricae, 70(1-2): 91-6 (1971).
HCAPLUS Copyright 2006 ACS on STN, AN 1973:438449, Abstract of Velichkova, St., "MAO [monoamine oxidase] -inhibiting effect of some simplified structural analogs of reserpine", Trudove na Nauchnoizsledovatelskiya Khimikofarmatsevtichen Institut, 8: 321-6 (1972).
HCAPLUS Copyright 2006 ACS on STN, AN 1975:479451, Abstract of Bikova et al., "Synthesis and pharmacological study of new pyridine-N-(acetylamido)-β-carboline derivatives", Trudove na Nauchnoizsledovatelskiya Khimikofarmatsevtichen Institut, 9: 141-53 (1974).
HCAPLUS Copyright 2006 ACS on STN, AN 1978:540332, Abstract of Rehse et al., "Neuropsychotropic activity of reserpine analogs, 1,2,3,4-tetreahydro-β-carbolines", Archly der Pharmazie (Weinheim, Germany), 311(3): 228-35 (1978).
HCAPLUS Copyright 2006 ACS on STN, AN 1981:30596, Abstract of Bikova et al., "Synthesis and pharmacological testing of β-carbolines with basic substitutes", Trudove na Nauchnoizsledovatelskiya Khimikofarmatsevtichen Institut, 10: 65-84 (1978).
HCAPLUS Copyright 2006 ACS on STN, AN 1983:16659, Abstract of Kumar et al., "Agents acting on CNS. Part XXIX. Synthesis of seco analogs of centbutindole, a potent neuroleptic", European Journal of Medicinal Chemistry, 17(4): 312-16 (1982).
HCAPLUS Copyright 2006 ACS on STN, AN 1983:53150, Abstract of Massiot et al., "α, α'-Bis(phenylthio)carbonyls in organic synthesis", Bulletin de la Societe Chimique de France, (7-8, Pt. 2): 241-8 (1982).
HCAPLUS Copyright 2006 ACS on STN, AN 1985:184894, Abstract of Flecker et al., "Reactions with indole derivatives. LI. Seco-aldehydes from didrovaltratum", Tetrahedron, 40(23): 4843-52 (1984).
HCAPLUS Copyright 2006 ACS on STN, AN 1985:406574, Abstract of Mandal et al., "Synthesis of 3-acetyl-1,4,6,7,12,12b-hexahydroindolo [2,3-a] quinolizine", Heterocycles, 23(4): 931-4 (1985).
HCAPLUS Copyright 2006 ACS on STN, AN 1985:6903, Abstract of Massiot et al., "Synthesis of (−)-ajmalicine from (−)-tryptophan", Journal of the Chemical Society, Chemical Communications, (11): 715-16 (1984).
HCAPLUS Copyright 2006 ACS on STN, AN 1987:138281, Abstract of Bobowski et al., "1, 1-Disubsituted-2,3,4,9-tetrahydro-1H-pyrido [3,4-b] indolecarboxylic acid esters and ketones. The base catalyzed transformation of 1-(2', 3', 4', 9'-tetrahydrospiro [cyclohexane-1, 1'- [1H] pyrido [3,4-b] indol]-2-yl) alkanones into 2-(4,9-dihydro-3H-pyrido[3,4-b]indol-1-yl)-1-alkylcyclohexanols", Journal of Heterocyclic Chemistry, 22(6): 1679-88 (1985).
HCAPLUS Copyright 2006 ACS on STN, AN 1987:509062, Abstract of Blasko et al., "Octahydroindolo [2,3-a] quinolizines and 3,4-dihydro-β-carbolines as new inhibitors of human platelet aggregation", Arzneimittel-Forschung, 37(6): 667-9 (1987).
HCAPLUS Copyright 2006 ACS on STN, AN 1987:568626, Misztal et al., "Synthesis and pharmacological properties of some 2-substituted 1-(3-pyridyl)-1,2,3,4-tetrahydro-β-carbolines", Polish Journal of Pharmacology and Pharmacy, 39(1): 97-103 (1987).
HCAPLUS Copyright 2006 ACS on STN, AN 1987:590347, Abstract of Pogosyan et al., "Synthesis and biological activity of 3-substituted-1,2,3,4-tetrahydro-β-carboline derivatives", Khimiko-Farmatsevticheskii Zhurnal, 21(6): 678-81 (1987).
HCAPLUS Copyright 2006 ACS on STN, AN 1988:131668, Abstract of Moehrle et al., "Tetracyclic imidazoles", Monatshefte fuer Chemie, 118(4): 477-83 (1987).
HCAPLUS Copyright 2006 ACS on STN, AN 1988:21850, Abstract of Moehrle et al., "Methylhydrazone function as a neighboring group in amine dehydrogenations", Archiv der Pharmazie (Weinheim, Germany), 320(3): 258-63 (1987).
HCAPLUS Copyright 2006 ACS on STN, AN 1988:400244, Abstract of Hulinska et al., "1-Methyl-, 1-phenyl-, and 1-[2-(2-dimethylaminoethoxy)phenyl]-2,3,4,9- tetrahydro-1H-pyrido[3,4-b] indole and their 2-substituted derivatives. Synthesis and pharmacological screening", Collection of Czechoslovak Chemical Communications, 53(2): 373-80 (1988).
HCAPLUS Copyright 2006 ACS on STN, AN 1989:107998, Abstract of Misztal et al., "Synthesis and pharmacological properties of some 2-(3-aminopropionyl)-and 2-(3-aminopropyl)-1-(3-pyridyl)-1,2,3,4-tetrahydro-β-carbolines", Polish Journal of Pharmacology and Pharmacy, 40(4): 413-22 (1988).
HCAPLUS Copyright 2006 ACS on STN, AN 1989:477876, Abstract of Grigg et al., "A dehydration route to azomethine ylides and isoindoles", Journal of the Chemical Society, Perkin Transactions 1: Organic and Bio-Organic Chemistry (1972-1999), (1): 198-200 (1989).
HCAPLUS Copyright 2006 ACS on STN, AN 1989:595214, Abstract of Wasserman et al.,; "The chemistry of vicinal tricarbonyl compounds. Applications in the synthesis of vincamine-related alkaloids", Tetrahedron Letters, 30(7): 873-6 (1989).
HCAPLUS Copyright 2006 ACS on STN, AN 1990:440504, Abstract of Fujii et al., "Synthesis of 1-(pentafluorophenyl)-β-carboline", Journal of Fluorine Chemistry, 46(3): 479-89 (1990).
HCAPLUS Copyright 2006 ACS on STN, AN 1990:552798, Abstract of Rosenmund et al., "Stereoselective synthesis of rac-yohimb-15-enone", Liebigs Annalen der Chemie, (9): 857-62 (1990).
HCAPLUS Copyright 2006 ACS on STN, AN 1991:492679, Abstract of Huizenga et al., "Models of folate cofactors. 22. Lewis acid catalyzed cyclization of carbon-fragment transfer products of folate cofactor models. Synthesis of enantiomerically pure tetracyclic (ABCE) ring system of Aspidosperma alkaloids", Tetrahedron, 47(24): 4155-64 (1991).
HCAPLUS Copyright 2006 ACS on STN, AN 1991:558999, Abstract of Zhang et al., "Stereoselective synthesis of enantiomerically pure 3-acetyl-1,4,6,7,12,12b-hexahydroindolo-2, 3-quinolizine", Huaxue Tongbao, (6): 31-3 (1991).
HCAPLUS Copyright 2006 ACS on STN, AN 1991:583240, Abstract of Misztal et al., "Structure and spectral properties of β-carbolines. Part 4. Synthesis of the new ring system: 9,10,15,15b-tetrahydroindolo [1', 2': 4,3] pyrazino [2,1-a] carbolin-7 (6H)-one", Journal of the Chemical Society, Perkin Transactions 1: Organic and Bio-Organic Chemistry (1972-1999), (8): 1871-4 (1991).
HCAPLUS Copyright 2006 ACS on STN, AN 1991:62055, Abstract of Misztal et al., "Structure and spectral properties of β-carbolines. Part 3. Synthesis and stereochemistry of 1,2,3,4,6,7,9,10,15b,15c-decahydropyrido [1", 2": 1', 2'] pyrazino [4', 3': 1,2] pyrido [3, 4-b] indoles", Journal of the Chemical Society, Perkin Transactions 1: Organic and Bio-Organic Chemistry (1972-1999), (8): 2311-15 (1990).
HCAPLUS Copyright 2006 ACS on STN, AN 1992:448375, Abstract of Kawate et al., "New evidence for the presence of a spiroindolenium species in the Pictet-Spengler reaction", Heterocycles, 33(2): 801-11 (1992).
HCAPLUS Copyright 2006 ACS on STN, AN 1992:470107, Abstract of Qais et al., "Asymmetric syntheses of 1-alkyltetrahydro-β-carbolines and a 9-thio analog", Chemical & Pharmaceutical Bulletin, 39(12): 3338-40 (1991).
HCAPLUS Copyright 2006 ACS on STN, AN 1992:634323, Abstract of Wasserman et al., "Oxidation of Ylide Precursors to Vicinal Tricarbonyls. Applications in Vincamine Alkaloid Synthesis", Tetrahedron, 48(34): 7071-7082 (1992).
HCAPLUS Copyright 2006 ACS on STN, AN 1992:83990, Abstract of McNulty et al., "Diastereoselective Pictet-Spengler reactions of L-(Boc) prolinal: a biomimetic synthesis of eudistomins H and I, and woodinine", Tetrahedron Letters, 32(37): 4875-8 (1991).
HCAPLUS Copyright 2006 ACS on STN, AN 1993:409022, Abstract of Peng et al., "Synthesis of enantiomerically pure indoloquinolizine derivatives", Liebigs Annalen der Chemie, (2): 141-6 (1993).
HCAPLUS Copyright 2006 ACS on STN, AN 1993:603331, Abstract of Kawate et al., "Alkylation of 3,4-dihydro-β-carboline", Chemical & Pharmaceutical Bulletin, 41(2): 287-91 (1993).
HCAPLUS Copyright 2006 ACS on STN, AN 1994:135090, Abstract of Waldmann, et al., "Asymmetric Pictet-Spengler reactions employing amino acid esters as mediators of selectivity", Tetrahedron Letters, 34(37): 5867-70 (1993).
HCAPLUS Copyright 2006 ACS on STN, AN 1994:298503, Abstract of Lehmann et al., "Indoles. X. Synthesis, structure and D2-affinity of the β-carboline analog of flutroline", Archly der Pharmazie (Weinheim, Germany), 326(12): 947-51 (1993).
HCAPLUS Copyright 2006 ACS on STN, AN 1994:557928, Abstract of McNulty et al., "Diastereoselective Pictet-Spengler reactions of L- (Boc) phenylalaninal and L- (Boc) prolinal: biomimetic syntheses of eudistomin T and (−) -woodinine", Journal of Chemical Society, Perkin Transactions 1: Organic and Bio-Organic Chemistry (1972-1999), (10): 1329-37 (1994).
HCAPLUS Copyright 2006 ACS on STN, AN 1995:202652, Abstract of Lehnert et al., "DNA topoisomerase II inhibition by substituted 1,2,3,4-tetrahydro-β-carboline derivatives", Bioorganic & Medicinal Chemistry Letters, 4(20): 2411-16 (1994).
HCAPLUS Copyright 2006 ACS on STN, AN 1995:347689, Abstract of Zhao et al., "Proton NMR and stereochemistry of synthetic indole alkaloids", Bopuxue Zazhi, 12(1): 71-8 (1995).
HCAPLUS Copyright 2006 ACS on STN, AN 1995:764144, Abstract of Loegers et al., "Mannich Biscyclizations. Total Synthesis of (−)-Ajmalicine", Journal of the American Chemical Society, 117(36): 9139-50 (1995).
HCAPLUS Copyright 2006 ACS on STN, AN 1995:957191, Abstract of Waldmann et al., "Asymmetric Pictet-Spengler reactions employing N, N-phthaloyl amino acids as chiral auxiliary groups", Angewandte Chemie, International Edition in English, 34(21): 2402-3 (1995).
HCAPLUS Copyright 2006 ACS on STN, AN 1996:268475, Abstract of Uematsu et al., "Asymmetric Transfer Hydrogenation of Imines", Journal of the American Chemical Society, 118(20): 4916-17 (1996).
Beilstein Copyright 2006 Beilstein MDL on STN, Beilstein Records (BRN): 8455070.
Beilstein Copyright 2006 Beilstein MDL on STN, Beilstein Records (BRN): 8454267.
Beilstein Copyright 2006 Beilstein MDL on STN, Beilstein Records (BRN): 8454265.
Beilstein Copyright 2006 Beilstein MDL on STN, Beilstein Records (BRN): 8454264.
Beilstein Copyright 2006 Beilstein MDL on STN, Beilstein Records (BRN): 8453888.
Beilstein Copyright 2006 Beilstein MDL on STN, Beilstein Records (BRN): 8453887.
Beilstein Copyright 2006 Beilstein MDL on STN, Beilstein Records (BRN): 8453886.
Beilstein Copyright 2006 Beilstein MDL on STN, Beilstein Records (BRN): 8453110.
Beilstein Copyright 2006 Beilstein MDL on STN, Beilstein Records (BRN): 8450993.
Beilstein Copyright 2006 Beilstein MDL on STN, Beilstein Records (BRN): 8448477.
Beilstein Copyright 2006 Beilstein MDL on STN, Beilstein Records (BRN): 8448341.
Beilstein Copyright 2006 Beilstein MDL on STN, Beilstein Records (BRN): 8445916.
Beilstein Copyright 2006 Beilstein MDL on STN, Beilstein Records (BRN): 8442395.
Beilstein Copyright 2006 Beilstein MDL on STN, Beilstein Records (BRN): 8439487.
Beilstein Copyright 2006 Beilstein MDL on STN, Beilstein Records (BRN): 8437234.
Beilstein Copyright 2006 Beilstein MDL on STN, Beilstein Records (BRN): 8434528.
Beilstein Copyright 2006 Beilstein MDL on STN, Beilstein Records (BRN): 8432032.
Beilstein Copyright 2006 Beilstein MDL on STN, Beilstein Records (BRN): 8372543.
Beilstein Copyright 2006 Beilstein MDL on STN, Beilstein Records (BRN): 8372542.
Beilstein Copyright 2006 Beilstein MDL on STN, Beilstein Records (BRN): 8360332.
Beilstein Copyright 2006 Beilstein MDL on STN, Beilstein Records (BRN): 8355677.
Beilstein Copyright 2006 Beilstein MDL on STN, Beilstein Records (BRN): 8228273.
Beilstein Copyright 2006 Beilstein MDL on STN, Beilstein Records (BRN): 8222993.

Beilstein Copyright 2006 Beilstein MDL on STN, Beilstein Records (BRN): 8081712.
Beilstein Copyright 2006 Beilstein MDL on STN, Beilstein Records (BRN): 8079036.
Beilstein Copyright 2006 Beilstein MDL on STN, Beilstein Records (BRN): 8075760.
Beilstein Copyright 2006 Beilstein MDL on STN, Beilstein Records (BRN): 8021716.
Beilstein Copyright 2006 Beilstein MDL on STN, Beilstein Records (BRN): 8019500.
Beilstein Copyright 2006 Beilstein MDL on STN, Beilstein Records (BRN): 8016588.
Beilstein Copyright 2006 Beilstein MDL on STN, Beilstein Records (BRN): 8011654.
Beilstein Copyright 2006 Beilstein MDL on STN, Beilstein Records (BRN): 7866702.
Beilstein Copyright 2006 Beilstein MDL on STN, Beilstein Records (BRN): 7866701.
Beilstein Copyright 2006 Beilstein MDL on STN, Beilstein Records (BRN): 7755570.
Beilstein Copyright 2006 Beilstein MDL on STN, Beilstein Records (BRN): 7742795.
Beilstein Copyright 2006 Beilstein MDL on STN, Beilstein Records (BRN): 7742792.
Beilstein Copyright 2006 Beilstein MDL on STN, Beilstein Records (BRN): 7742791.
Beilstein Copyright 2006 Beilstein MDL on STN, Beilstein Records (BRN): 7679040.
Beilstein Copyright 2006 Beilstein MDL on STN, Beilstein Records (BRN): 7676206.
Beilstein Copyright 2006 Beilstein MDL on STN, Beilstein Records (BRN): 7675004.
Beilstein Copyright 2006 Beilstein MDL on STN, Beilstein Records (BRN): 7674764.
Beilstein Copyright 2006 Beilstein MDL on STN, Beilstein Records (BRN): 7671562.
Beilstein Copyright 2006 Beilstein MDL on STN, Beilstein Records (BRN): 7662538.
Beilstein Copyright 2006 Beilstein MDL on STN, Beilstein Records (BRN): 7659004.
Beilstein Copyright 2006 Beilstein MDL on STN, Beilstein Records (BRN): 7652157.
Beilstein Copyright 2006 Beilstein MDL on STN, Beilstein Records (BRN): 7470167.
Beilstein Copyright 2006 Beilstein MDL on STN, Beilstein Records (BRN): 7470143.
Beilstein Copyright 2006 Beilstein MDL on STN, Beilstein Records (BRN): 7470039.
Beilstein Copyright 2006 Beilstein MDL on STN, Beilstein Records (BRN): 7469940.
Beilstein Copyright 2006 Beilstein MDL on STN, Beilstein Records (BRN): 7402634.
Beilstein Copyright 2006 Beilstein MDL on STN, Beilstein Records (BRN): 7398947.
CAPLUS Copyright 2006 ACS on STN, Accession No. 1968:95725McIsaac et al., "Chromatography of β-carbolines", Journal of Chromatography, 31(2): 446-54 (1967).
CAPLUS Copyright 2006 ACS on STN, Accession No. 1979:152436, Abstract of Oikawa et al., "Synthesis of oxidized diketopiperazine alkaloids by the selective oxidation of C-3 side chains of indoles", Tennen Yuki Kagobutsu Toronkai Koen Yoshishu, 21st, 22-7 (1978).
CAPLUS Copyright 2006 ACS on STN, Accession No. 1988:56414, Abstract of Bailey et al., "Synthesis of 3-(2-indolyl)propenoate derivatives of tryptamine, valuable intermediates for the preparation of indole alkaloids", Tetrahedron Letters, 28(25): 2879-82 (1987).
CAPLUS Copyright 2006 ACS on STN, Accession No. 1989:173526, Abstract of Somei et al., "The chemistry of indoles. XLV. A convenient synthetic method of 2-substituted indoles and its application for the synthesis of natural alkaloid, borrerine", Heterocycles, 27(7): 1585-7 (1988).
CAPLUS Copyright 2006 ACS on STN, Accession No. 1998:710496, Abstract of Ottoni et al., "Efficient and simple methods for the introduction of the sulfonyl, acyl, and alkyl protecting groups on the nitrogen of indole and its derivatives", Tetrahedron, 54(46): 13915-13928 (1998).
CAPLUS Copyright 2006 ACS on STN, Accession No. 1999:655036, Abstract of Zhao et al., "Synthesis of 6-amino-acid-substituted 4,6,7,12-tetrahydro-4-oxoindolo [2,3-α]quinolizines", Journal fuer Praktische Chemie (Weinheim, Germany), 341(7): 691-694 (1999).
CAPLUS Copyright 2006 ACS on STN, Accession No. 2000:659238, Abstract of Bringmann et al., "Endogenous alkaloids in man Part 36, chemical modification of the mitochondrial complex I inhibitor 1-trichloromethyl-1,2,3,4-tetrahydro-β-carboline: synthesis and evaluation of N-alkanoyl derivatives", Zeitschriff fuer Naturforschung, C: Journal of Biosciences, 55(7/8): 620-630 (2000).
CAPLUS Copyright 2006 ACS on STN, Accession No. 2001:615283, Abstract of Itoh et al., "Preparation of both enantiomers of 1-allyl-1,2,3,4-tetrahydro-β-carboline using allyltin reagents and a chiral auxiliary derived from L-proline", Tetrahedron, 57(34): 7277-7289 (2001).
CAPLUS Copyright 2006 ACS on STN, Accession No. 2002:928751, Abstract of Itoh et al., "Concise syntheses of harmicine and a pyrrolidino-isoquinoline derivative using chiral 1-allyl adducts of β-carboline and isoquinoline as starting materials", Heterocycles, 58: 115-118 (2002).
CAPLUS Copyright 2006 ACS on STN, Accession No. 2003:190790, Abstract of Fekete et al., "Comparative study on separation of diastereomers by HPLC", Chromatographia, 57(3/4): 147-153 (2003).
CAPLUS Copyright 2006 ACS on STN, Accession No. 2004:1128008, Abstract of Ohba et al., "Synthesis of Na-demthyl-20-deethylsuaveoline, the structure proposed for sellowiine", Heterocycles, 63(12): 2845-2850 (2004).
CAPLUS Copyright 2006 ACS on STN, Accession No. 2005:226859, Abstract of Danieli et al., "Combinatorial Solid-Phase Synthesis of 6-Hydroxy-1,2,3,4-tetrahydro-β-carbolines from L-5-Hydroxytroptophan", Journal of Combinatorial Chemistry, 7(3): 458-462 (2005).
CAPLUS Copyright 2006 ACS on STN, Accession No. 2005:443867, Abstract of Kinderman et al., "Catalytic N-Sulfonyliminium Ion-Mediated Cyclizations to a α-Vinyl-Substituted Isoquinolines and β-Carbolines and Applications in Metathesis", Journal of Organic Chemistry, 70(14): 5519-5527 (2005).
CAPLUS Copyright 2006 ACS on STN, Accession No. 2005:502638, Abstract of Nagata et al., "Cross-metathesis of 1-allylated β-carboline and isoquinoline derivatives", Heterocycles, 65(6):1283-1287.
CAPLUS Copyright 2006 ACS on STN, Accession No. 2005:640103, Abstract of Takasu et al., "Synthesis and evaluation of β-carbolinium cations as new antimalarial agents based on pi-delocalized lipophilic cation (DLC) hypothesis", Chemical & Pharmaceutical Bulletin, 53(6): 653-661 (2005).
Chemcats Copyright 2006 ACS on STN, Accession No. 2006:455990.
Chemcats Copyright 2006 ACS on STN, Accession No. 1999: 170837.
Chemcats Copyright 2006 ACS on STN, Accession No. 2004: 1704901.
Chemcats Copyright 2006 ACS on STN, Accession No. 2004: 2860460.
Chemcats Copyright 2006 ACS on STN, Accession No. 2004: 3826780.
Chemcats Copyright 2006 ACS on STN, Accession No. 2005: 1150844.
Chemcats Copyright 2006 ACS on STN, Accession No. 2005: 1418898.
Chemcats Copyright 2006 ACS on STN, Accession No. 2005: 1937218.
Chemcats Copyright 2006 ACS on STN, Accession No. 2005: 2670194.
Chemcats Copyright 2006 ACS on STN, Accession No. 2005: 3598258.

Chemcats Copyright 2006 ACS on STN, Accession No. 2005: 464357.
Chemcats Copyright 2006 ACS on STN, Accession No. 2005: 691695.
Song et al., "β-Carbolines as Specific Inhibitors of Cyclin-Dependent Kinases," Bioorg. Med. Chem. Lett., 12:1129-1132 (2002).
Cleaveland et al., "Identification of a novel inhibitor (NSC 665564) of dihydroorotate dehydrogenase with a potency equivalent to brequinar", Biochemical and Biophysical Research Communications, 223(3): 654-659 (1996).
Freter et al., "Reactions of 1-aryl-1,2,3,4-tetrahydro-β-carbolines in acid solution", Justus Liebigs Annalen der Chemie, 684: 159-87 (1965).
HCA Copyright 2006 ACS on STN, Accession No. 114:42770, Abstract of EP 0 380 155 A1, Duphar International Research B. V. (Aug. 1, 1990).
HCA Copyright 2006 ACS on STN, Accession No. 116:207832, Abstract of EP 0 468 789 A2, Merck Frosst Canada Inc. (Jan. 29, 1992).
HCA Copyright 2006 ACS on STN, Accession No. 127:149080, Abstract of WO 1997/023458 A1, Warner-Lambert Company et al. (Jul. 3, 1997).
HCA Copyright 2006 ACS on STN, Accession No. 136:325823, Abstract of WO 2002/030421, Curls, Inc. (Apr. 18, 2002).
HCA Copyright 2006 ACS on STN, Accession No. 136:64122, Abstract of WO 2001/098344 A2, Biogen, Inc. (Dec. 27, 2001).
HCAPLUS Copyright 2006 ACS on STN, Accession No. 1995:188469, Abstract of Waldmann et al., "Asymmetric steering of the Pictet-Spengler reaction by means of amino acid esters as chiral auxiliary groups", Tetrahedron, 50(41): 11865-84 (1994).
HCAPLUS Copyright 2006 ACS on STN, Accession No. 1995:470885, Abstract of Soe et al., "Asymmetric Pictet-Spengler reaction with a chiral N- (β-3-indolyl) ethyl-1-methylbenzylamine", Tetrahedron Letters, 36(11): 1857-60 (1995).
HCAPLUS Copyright 2006 ACS on STN, Accession No. 1995:741637, Abstract of Kawashima et al., "Synthesis and pharmacological evaluation of 1,2,3,4-tetrahydro-β-carboline derivatives", Chemical & Pharmaceutical Bulletin, 43(5): 783-7 (1995).
HCAPLUS Copyright 2006 ACS on STN, Accession No. 1996:94639, Abstract of Soe et al., "Asymmetric Pictet-Spengler reaction using α-methylbenzylamine as a chiral auxiliary group", Heterocycles, 42(1): 347-58 (1996).
HCAPLUS Copyright 2006 ACS on STN, Accession No. 1999:241413, Abstract of Kawate et al., "Chiral auxiliary approach to the asymmetric Pictet-Spengler reaction of tryptamines", Heterocycles, 50(2): 1033-1039 (1999).
HCAPLUS Copyright 2006 ACS on STN, Accession No. 2002:862393, Abstract of Jiang et al., "Synthesis of optically pure pyrroloquinolones via Pictet-Spengler and Winterfeldt reactions", Tetrahedron Letters, 43(49): 8941-8945 (2002).
HCAPLUS Copyright 2006 ACS on STN, Accession No. 2003:67259, Abstract of Tsuji et al., "An efficient synthetic approach to optically active β-carboline derivatives via Pictet-Spengler reaction promoted by trimethylchlorosilane", Tetrahedron: Asymmetry, 14(2): 177-180 (2003).
HCAPLUS Copyright 2006 ACS on STN, Accession No. 1990:198356, Abstract of CZ 261296 B1, Protiva, et. al. (Jan. 12, 1989).
HCAPLUS Copyright 2006 ACS on STN, Accession No. 1990:77229, Abstract of CZ 262100 B1, Protiva, et. al. (Feb. 10, 1989).
HCAPLUS Copyright 2006 ACS on STN, Accesssion No. 1999:131592, Abstract of Venkov et al., "Synthesis of 2-acyltetrahydro-β-carbolines by an intramolecular α-amidoalkylation reaction", Synthetic Communications, 29(3): 487-494 (1999).
HCAPLUS Copyright 2006 ACS on STN, AN 1928:29116, Abstract of Tatsui, G., "Synthesis of carboline derivatives", Yakugaku Zasshi, 48: 453-9 (1928).
HCAPLUS Copyright 2006 ACS on STN, AN 1952:57257, Abstract of Groves et al., "Constitution of yohimbine and related alkaloids. VI. The synthesis of 1,2,3,4,6,7,12,12b-octahydro-2-ketoindolo-[2,3-a]pyridocoline and 1,2,3,4-tetrahydro [2, 3-a] pyridocoline", Journal of the Chemical Society, 650-61 (1952).
HCAPLUS Copyright 2006 ACS on STN, AN 1958:98075, Abstract of Prasad et al., "Constitution of yohimbine and related alkaloids. XII. Unsuccessful synthetic approaches to yohimbine and alstoniline", Journal of the Chemical Society, 2045-51 (1958).
HCAPLUS Copyright 2006 ACS on STN, AN 1959:122350, Abstract of Bartlett et al., "The alkaloids of Tabernanthe iboga. VIII", Journal of the American Chemical Society, 81: 1932-5 (1959).
HCAPLUS Copyright 2006 ACS on STN, AN 1959:122351, Abstract of Kline, G. Bruce, "Indole alkaloids. A study of the Dieckmann condensation of 1-carbethoxymethyl-2-(2-carbethoxyethyl)-1,2,3,4-tetrahydro-β-carboline. A synthesis of 20-carbethoxy-15(16)-yohinnben-17-one", Journal of the American Chemical Society, 81, 2251-5 (1959).
Beilstein Copyright 2006 Beilstein MDL on STN, Beilstein Records (BRN): 7148211.
Beilstein Copyright 2006 Beilstein MDL on STN, Beilstein Records (BRN): 7145754.
Beilstein Copyright 2006 Beilstein MDL on STN, Beilstein Records (BRN): 7071896.
Beilstein Copyright 2006 Beilstein MDL on STN, Beilstein Records (BRN): 7071895.
Beilstein Copyright 2006 Beilstein MDL on STN, Beilstein Records (BRN): 7071528.
Beilstein Copyright 2006 Beilstein MDL on STN, Beilstein Records (BRN): 7066532.
Beilstein Copyright 2006 Beilstein MDL on STN, Beilstein Records (BRN): 7066215.
Beilstein Copyright 2006 Beilstein MDL on STN, Beilstein Records (BRN): 7065599.
Beilstein Copyright 2006 Beilstein MDL on STN, Beilstein Records (BRN): 7062671.
Beilstein Copyright 2006 Beilstein MDL on STN, Beilstein Records (BRN): 7061800.
Beilstein Copyright 2006 Beilstein MDL on STN, Beilstein Records (BRN): 6885612.
Beilstein Copyright 2006 Beilstein MDL on STN, Beilstein Records (BRN): 6490207.
Beilstein Copyright 2006 Beilstein MDL on STN, Beilstein Records (BRN): 5915066.
Beilstein Copyright 2006 Beilstein MDL on STN, Beilstein Records (BRN): 5914990.
Beilstein Copyright 2006 Beilstein MDL on STN, Beilstein Records (BRN): 5897211.
Beilstein Copyright 2006 Beilstein MDL on STN, Beilstein Records (BRN): 5891878.
Beilstein Copyright 2006 Beilstein MDL on STN, Beilstein Records (BRN): 5679522.
Beilstein Copyright 2006 Beilstein MDL on STN, Beilstein Records (BRN): 5176764.
Beilstein Copyright 2006 Beilstein MDL on STN, Beilstein Records (BRN): 5140134.
Beilstein Copyright 2006 Beilstein MDL on STN, Beilstein Records (BRN): 5134348.
Beilstein Copyright 2006 Beilstein MDL on STN, Beilstein Records (BRN): 4895148.
Beilstein Copyright 2006 Beilstein MDL on STN, Beilstein Records (BRN): 4762626.
Beilstein Copyright 2006 Beilstein MDL on STN, Beilstein Records (BRN): 4635034.
Beilstein Copyright 2006 Beilstein MDL on STN, Beilstein Records (BRN): 4620668.
Beilstein Copyright 2006 Beilstein MDL on STN, Beilstein Records (BRN): 4617494.
Beilstein Copyright 2006 Beilstein MDL on STN, Beilstein Records (BRN): 4604797.
Beilstein Copyright 2006 Beilstein MDL on STN, Beilstein Records (BRN): 4213069.
Beilstein Copyright 2006 Beilstein MDL on STN, Beilstein Records (BRN): 1206456.
Beilstein Copyright 2006 Beilstein MDL on STN, Beilstein Records (BRN): 1206372.
Beilstein Copyright 2006 Beilstein MDL on STN, Beilstein Records (BRN): 942566.

Beilstein Copyright 2006 Beilstein MDL on STN, Beilstein Records (BRN): 850369.
Beilstein Copyright 2006 Beilstein MDL on STN, Beilstein Records (BRN): 845560.
Beilstein Copyright 2006 Beilstein MDL on STN, Beilstein Records (BRN): 843324.
Beilstein Copyright 2006 Beilstein MDL on STN, Beilstein Records (BRN): 592929.
Beilstein Copyright 2006 Beilstein MDL on STN, Beilstein Records (BRN): 382858.
Beilstein Copyright 2006 Beilstein MDL on STN, Beilstein Records (BRN): 382697.
Beilstein Copyright 2006 Beilstein MDL on STN, Beilstein Records (BRN): 382603.
Beilstein Copyright 2006 Beilstein MDL on STN, Beilstein Records (BRN): 382449.
Beilstein Copyright 2006 Beilstein MDL on STN, Beilstein Records (BRN): 360771.
Beilstein Copyright 2006 Beilstein MDL on STN, Beilstein Records (BRN): 356831.
Beilstein Copyright 2006 Beilstein MDL on STN, Beilstein Records (BRN): 326903.
Beilstein Copyright 2006 Beilstein MDL on STN, Beilstein Records (BRN): 309045.
Beilstein Copyright 2006 Beilstein MDL on STN, Beilstein Records (BRN): 297782.
Beilstein Copyright 2006 Beilstein MDL on STN, Beilstein Records (BRN): 264050.
Beilstein Copyright 2006 Beilstein MDL on STN, Beilstein Records (BRN): 263250.
Beilstein Copyright 2006 Beilstein MDL on STN, Beilstein Records (BRN): 9977461.
Beilstein Copyright 2006 Beilstein MDL on STN, Beilstein Records (BRN): 9977460.
Beilstein Copyright 2006 Beilstein MDL on STN, Beilstein Records (BRN): 930285.
Beilstein Copyright 2006 Beilstein MDL on STN, Beilstein Records (BRN): 927125.
Beilstein Copyright 2006 Beilstein MDL on STN, Beilstein Records (BRN): 900708.
International Search Report issued on Aug. 4, 2008, in corresponding International Application No. PCT/US2008/004809.
Hirawat et al., "51 Poster Phase 1 single-dose safety, PK, and food-effect study of PTC299, a novel VEGF expression inhibitor for treatment of solid tumors," European Journal of Cancer. Supplement, Pergamon (Oxford, Great Britain), vol. 4, No. 12, pp. 19-20 (Nov. 1, 2006).
Hirawat et al., "Phase 1 studies assessing the safety, PK, and VEGF-modulating effects of PTC299, a novel Vegf expression inhibitor," Journal of Clinical Oncology, ASCO Annual Meeting Proceedings, Part I, vol. 25, No. 18S (Jun. 20, 2007) (URL: http://www.asco.org/ASCO/Abstracts+%26+Virtual+Meeting/Abstracts?&vmview=abst_detail_view&confID=47&abstractID=33792>) (abstract 3562).
HCAPLUS Copyright 2006 ACS on STN, AN 1982:143144, Abstract of Cloudsdale et al., "Synthetic Studies in the Ajmaline Series," J. Org. Chem., 47(6):919-928 (1982).
HCAPLUS Copyright 2006 ACS on STN, AN 1980:22200, Abstract of Kluge et al., "Phosphonate reagents for the synthesis of enol ethers and one-carbon homologation to aldehydes," J. Org. Chem., 44(26):4847-4852 (1979).
HCA Copyright 2006 ACS on STN, Accession No. 134:311102, Abstract of WO 2001/026644, Curis, Inc. (Apr. 19, 2001).
Registry Copyright 2006 ACS on STN, Registry No. 335120-70-2.
MARPAT Accession No. 114:37805, Abstract of US 5120543, Hagin, et.al. (Jun. 9, 1992).
CAPLUS printout for CAS Reg. No. 252916-29-3, 2009.
CAPLUS printout for CAS Reg. No. 341031-54-7, 2009.
CAPLUS printout for CAS Reg. No. 259188-38-0, 2009.
CAPLUS printout for CAS Reg. No. 15866-90-7, 2009.
CAPLUS printout for CAS Reg. No. 862124-26-3, 2009.
CAPLUS printout for CAS Reg. No. 365253-37-8, 2009.
CAPLUS printout for CAS Reg. No. 443913-73-3, 2009.
Hanahan and Folkman, 1996, "Patterns and Emerging Mechanisms of the Angiogenic Switch during Tumorogencsis," *Cell* 86:353-364.
Ikeda et al., 1995, "Hypoxia-indcued Transcriptional Activation and Increased mRNA Stability of Vascular Endothelial Growth Factor in C6 Glioma Cells,"*J. Biol. Chem.* 270(34):19761-19766.
Stein et al., 1998, "Translation of Vascular Endothelial Growth Factor mRNA by Internal Ribosome Entry: Implication for Translation Under Hypoxia," *Mol. Cell. Biol.* 18(6):3112-3119.
Levy et al., 1996, "Post-transcriptional Regulation of Vascular Endothelial Growth Factor by Hypoxia," *J. Biol. Chem.* 271(5):2746-2753.
Claffey et al., 1998, "Identification of Human VPF/Vegf3' Untranslated Region Mediating Hypoxia-Induced mRNA Stability," *Mol. Cell. Biol.* 9():469-481.
Folkman, 1996, "Fighting Cancer by Attacking Its Blood Supply," *Scientific American* 275(3):150-154.
Gasparini et al., 1997, "Prognostic Significance of Vascular Endothelial Growth Factor Protein in Node-Negative Breast Carcinoma," *J. Natl. Cancer Inst.* 89(2):139-147.
Ferrara et al., 1997, "The Biology of Vascular Endothelial Growth Factor," *Endocr. Rev.* 18(1):4-25.
Avastin® Product Insert (2008).
Sutent® Product Insert (2006).
Nexavar® Product Insert (2005).

Calu-6 (lung cancer cells) Xenograft

Wilms and Neuroblastoma Orthotopic Xenograft Models

* p<0.05 vs. 0.9% saline: Holm-Sidak ANOVA analysis
* p<0.05 vs PO vehicle: Holm-Sidak ANOVA analysis
* p < 0.05 vs. Compound E only)

Figure 11
SK-NEP-1
SY5Y
NGP
Control
Compound E

CARBOLINE DERIVATIVES USEFUL IN THE TREATMENT OF CANCER

CROSS REFERENCE TO RELATED APPLICATION

This application is a continuation-in-part of U.S. application Ser. No. 11/079,420, filed Mar. 15, 2005, now U.S. Pat. No. 7,601,840 and having the title "Carboline Derivatives Useful in the Inhibition of Angiogenesis," which claims the benefit of and priority to U.S. Provisional Application No. 60/552,725, filed Mar. 15, 2004, which applications are incorporated herein by reference. This application also claims priority to International Application No. PCT/US2005/08481, filed Mar. 15, 2005, and having the title "Carboline Derivatives Useful in the Inhibition of Angiogenesis," which application is incorporated herein by reference.

STATEMENT REGARDING FEDERALLY SPONSORED RESEARCH OR DEVELOPMENT

This invention was made with government support under Federal Award ID 1R43CA108330-01 awarded by the National Institutes of Health. The government has certain rights in the invention.

FIELD OF THE INVENTION

The present invention relates to methods and compounds for inhibiting angiogenesis. More particularly, the present invention relates to methods and compounds for treating solid tumor cancers.

BACKGROUND OF THE INVENTION

Aberrant angiogenesis plays a critical role in the pathogenesis of numerous diseases, including malignant, ischemic, inflammatory and immune disorders (Carmeliet, *Nat. Med.*, 9(6):653-60 (2003), Ferrara, *Semin. Oncol.*, 29(6 Suppl 16): 10-4 (2002)). The best-known of these disorders are cancer, exudative macular degeneration and diabetic retinopathy (DR), the last two of which are leading cause of blindness in the United States (Witmer et al., *Prog. Retin Eye Res.*, 22(1): 1-29 (2003), Clark et al., *Nat. Rev. Drug Discovery*, 2:448-459 (2003)). During the last decade our understanding of the molecular basis of angiogenesis has grown considerably. Numerous cytokines and growth factors that stimulate angiogenesis, such as VEGF, FGF-2, PDGF, IGF-1, TGF, TNF-α, G-CSF have been identified (Ferrara et al., *Nat. Med.*, 5(12): 1359-64 (1999), Kerbel et al., *Nat. Rev. Cancer*, 2(10):727-39 (2002), Rofstad et al., *Cancer Res.*, 60(17):4932-8 (2000)). Among these growth factors, Vascular Endothelial Growth Factor (VEGF) plays a central role in angiogenesis (Ferrara, *Semin. Oncol.*, 29(6 Suppl 16):10-4 (2002)).

VEGF, also known as VEGF-A, was initially identified for its ability to induce vascular permeability and to promote vascular endothelial cell proliferation (Leung et al., *Science*, 246:1306-1309 (1989), Plouet et al., *EMBO J.*, 8:3801-3806 (1989), Connolly et al., *J. Biol. Chem.*, 264:20017-20024 (1989)). VEGF is encoded by a single gene that gives rise to four isoforms by alternative splicing (Tischer et al., *J. Biol. Chem.*, 266:11947-11954 (1991)). All four isoforms share the same unusually long and GC rich 5'-UTR, as well as a 3'-UTR that includes multiple RNA stability determinants. The receptors VEGFR-2 (also known as KERN or Flk-1) and VEGFR-1 (previously known as Flt1) recognize the dimeric form of VEGF (Ortega et al., *Front. Biosci.*, 4:D141-52 (1999), Sato et al., *Annals of New York Academy of Science*, 902:201-207, (2000)). The highly specific VEGFR-2 receptor is expressed on endothelial cells. VEGF binding to the VEGFR-2 receptor activates the receptor's tyrosine kinase activity, leading to endothelial cell proliferation, differentiation and primitive vessel formation (Shalaby et al., *Nature*, 376:62-66, (1995)). VEGFR-1 inhibits endothelial cell growth either by acting as a decoy or by suppressing signaling pathways through VEGFR-2 (Fong et al., *Nature*, 376:66-70 (1995)).

Over 30 years ago, it was proposed that inhibition of tumor angiogenesis could be an effective approach for the treatment of cancer (Folkman, *N. Engl. J. Med.*, 285(21):1182-6 (1971)). VEGF and its receptor have been demonstrated to have a central role in tumor angiogenesis, especially in the early stages of tumor growth (Hanahan et al., *Cell*, 86:353-364, 1996)). Indeed, increased levels of VEGF expression have been correlated with microvessel density in primary tumor tissues (Gasparini et al., *J. Natl. Cancer Inst.*, 89:139-147 (1997)). Moreover, increased levels of the VEGF transcript are found in virtually all of the common solid tumors (Ferrara et al., *Endocr. Rev.*, 18:4-25, 1997)). In general, tumor-bearing patients have higher levels of VEGF compared to those in tumor-free individuals, and high VEGF levels in serum/plasma are associated with poor prognosis (Dirix et al., *Br. J. Cancer*, 76:238-243 (1997)). Consistent with the role of VEGF in tumor angiogenesis, VEGF null embryonic stem cells showed a dramatically reduced ability to form tumors in nude mice (Carmeliet et al., *Nature*, 380:435-439 (1996)). Direct evidence for the involvement of VEGF in tumorgenesis was demonstrated by using specific antibodies against VEGF in human xenografts implanted in nude mice (Kim et al., *Nature*, 362:841-844 (1993), Hichlin et al., *Drug Discovery Today*, 6:517-528 (2001)). In these studies, the inhibition of tumor growth correlated positively with decreased vessel formation in the antibody-treated tumors. Subsequent experiments using the soluble receptors substantiated the importance of VEGF activity in tumor growth (Lin et al., *Cell Growth Differ.*, 9(1):49-58 (1998)), and demonstrated that inactivation of VEGF by specific antibody treatment directly resulted in a nearly complete suppression of tumor-associated neovascularization (Borgstrom et al., *Prostate*, 35:1-10 (1998), Yuan et al. *Proc. Natl. Acad. Sci. USA*, 93:14765-14770 (1996)).

In exudative macular degeneration and diabetic retinopathy, pre-clinical experiments and clinical trials have demonstrated that over production of VEGF is critical for aberrant retinal or choroidal neovascularization (reviewed in Witmer et al., *Prog. Retin Eye Res.*, 22(1):1-29 (2003)). Evidence has been obtained that intra-ocular VEGF levels are strongly correlated with active retinal/choroidal neovascularization (CNV) in patients with diseases such as diabetic retinopathy and wet form macular degeneration (Funatsu et al., *Am. J. Ophthalmol.*, 133(4):537-43 (2002), Lip et al., *Ophthalmology*, 108(4):705-10 (2001)). In addition, studies using transgenic mice demonstrated that overexpression of VEGF in retinal pigment epithelial cells or photoreceptor cells results in choroidal or retinal neovasucularization (Schwesinger et al., *Am. J. Pathol.*, 158(3):1161-72 (2001), Ohno-Matsui et al., *Am. J. Pathol.*, 160(2):711-9 (2002)). In recent studies neutralizing antibodies, soluble receptor, receptor antagonists, or siRNA have proven efficacious in reducing VEGF-mediated blood vessel formation in animal models and in the clinic. (Eyetech Study Group, 22(2):143-52 (2002), Krzystolik et al., *Arch. Ophthalmol.*, 120(3):338-46 (2002), Shen et al., *Lab Invest.*, 82(2):167-82 (2002), Honda et al., *Gene Ther.*, 7(11):978-85 (2000), Saishin et al., *J Cell Physiol.*, 195(2):241-8 (2003)).

VEGF expression is regulated by a number of factors and agents including cytokines, growth factors, steroid hormones and chemicals, and mutations that modulate the activity of oncogenes such as ras or the tumor suppressor gene VHL (Maxwell et al., *Nature,* 399:271-275 (1999), Rak et al., *Cancer Res.,* 60:490-498 (2000)). Nevertheless, hypoxia is the most significant physiologic signal for regulating VEGF expression. Hypoxia results in enhanced VEGF expression by increasing both the transcription rate and stability of the VEGF transcript (Ikeda et al., *J. Biol. Chem.* 270:19761-19766 (1995), Stein et al., *Mol. Cell. Biol.* 18:3112-3119 (1998), Levy et al., *J. Biol. Chem.* 271:2746-2753 (1996)). Hypoxia-inducible factor lax (HIF-1α) is a transcription factor that increases VEGF gene expression in cells undergoing hypoxia by binding to the hypoxia response element (HRE) located in the VEGF promoter (Liu et al., *Circ. Res.,* 77:638-643 (1995), Semenza, *Annu. Rev. Cell. Dev. Biol.,* 5:551-578 (1999)). Both the stability and translation efficiency of the VEGF transcript is influenced by sequences in the 5'- and 3'-untranslated regions (UTRs). The 5'-UTR contains an internal ribosomal entry site (IRES) and mediates cap-independent translation initiation while the 3'-UTR harbors multiple AU-rich (AUR) stability determinants that have been previously shown to regulate turnover of VEGF mRNA. In addition, the translation initiation of the VEGF transcript is uniquely regulated. Under hypoxic conditions, translation of most cellular transcripts mediated by cap-dependent translation initiation process is greatly impaired (Kraggerud et al., *Anticancer Res.,* 15:683-686 (1995)). Initiation of translation of the VEGF mRNA, however, is unique under hypoxic conditions in that it is mediated via an internal ribosome entry site (IRES) within the VEGF 5'UTR (Stein et al., *Mol. Cell. Biol.* 18:3112-3119 (1998), Levy et al., *J. Biol. Chem.* 271:2746-2753 (1996), Huez et al., *Mol. Cell. Biol.,* 18:6178-6190 (1998), Akiri et al., *Oncogene,* 17:227-236 (1998)). Thus, this form of post-transciptional regulation permits cells to produce large amounts of VEGF protein to support either further tumor growth or aberrant neovascularization in ocular diseases under hypoxic conditions. The stability of VEGF mRNA is also greatly enhanced as a consequence of the binding of factors to elements in the 3'-UTR (Goldberg et al., *J. Biol. Cell. J. Biol. Chem.,* 277(16): 13635-40 (2002)).

There is a large body of experimental evidence indicating that tumor growth can be inhibited by the prevention of neovascularization (Lin et al., *Cell Growth Differ.,* 9(1):49-58 (1998), Zhu et al., *Invest. New Drugs,* 17:195-212 (1999)). Tumor vessels are generally immature and constantly undergo remodeling (Carmeliet, *Nat. Med.,* 9(6):653-60 (2003), Carmeliet et al., *Nature,* 407:249-257 (2000)). Active and aberrant angiogenesis is the result of a disruption in the normal balance of proangiogenic and anti-angiogenic factors, including various cytokines, growth factors and steroid hormones. Despite the complexity of the regulation of tumor angiogenesis, accumulated evidence indicates that targeting a single proangiogenic factor might be sufficient to inhibit tumor angiogenesis and suppress tumor growth (Kim et al., *Nature,* 362:841-844 (1993), Millauer et al., *Nature,* 367:576-579 (1994), Fong et al., *Cancer Res.,* 59:99-106 (1999)). Among many angiogenesis targets, VEGF and its receptor are most attractive (Carmeliet, *Nat. Med.,* 9(6):653-60 (2003), Ortega et al., *Front. Biosci.,* 4:D141-52 (1999)). As noted above, treatment with a monoclonal antibody specifically targeting VEGF inhibited the growth of tumors in human xenografts implanted in nude mice. Subsequently, various approaches designed to inactivate VEGF signaling have been tested in tumor models and have proven to be highly effective in a broad range of tumor cell lines including carcinomas, sarcomas and gliomas (Ferrara et al., *Endocr. Rev.,* 18:4-25, 1997), Kim et al., *Nature,* 362:841-844 (1993), Millauer et al., *Nature,* 367:576-579 (1994), Fong et al., *Cancer Res.,* 59:99-106 (1999), Geng et al., *Cancer Res.,* 61:2413-2419 (2001)). In addition, inhibition of VEGF by anti-VEGF antibody did not result in significant side effects in fully developed rodents or primates (Ryan et al, *Toxicol. Pathol.,* 27:78-86 (1999), Ferrara et al., *Nat. Med.,* 4:336-340 (1998)). Taken together, these results indicate that VEGF is a valid target for the development of tumor therapy. Indeed, a number of clinical trials are underway using VEGF inhibitors (Matter, *Drug Discovery Today,* 6:1005-1024 (2001), Hichlin et al., *Drug Discovery Today,* 6:517-528 (2001)).

Although several pro-angiogenic factors are implicated in the pathology of exudative age-related macular degeneration, VEGF appears to be the most critical in the pathogenesis and development of this disease (Witmer et al., *Prog. Retin Eye Res.,* 22(1):1-29 (2003), Holash et al., *Science,* 284:1994-1998 (1999)). Data from preclinical experiments and clinical trials have demonstrated that blockade of VEGF alone is sufficient to alleviate or stabilize disease progression (Eyetech Study Group, 22(2):143-52 (2002), Krzystolik et al., *Arch. Ophthalmol.,* 120(3):338-46 (2002), Shen et al., *Lab Invest.,* 82(2):167-82 (2002), Honda et al., *Gene Ther.,* 7(11):978-85 (2000), Saishin et al., *J Cell Physiol.,* 195(2):241-8 (2003)). For example, inhibition of VEGFR signaling by a specific tyrosine kinase inhibitor is sufficient to completely prevent retinal neovascularization in a murine retinopathy of prematurity model (Ozaki H, Seo M S, Ozaki et al., *Am. J. Pathol.,* 156(2):697-707 (2000)). Furthermore, it has recently been demonstrated that small interfering RNAs (siRNA) directed against murine VEGF significantly inhibited ocular neovascularization after laser photocoagulation in a mouse model (Reich et al., *Mol. Vis.* 30;9:210-6 (2003)). These results indicate that selective inhibition of VEGF expression is achievable and offers validation of this approach for the treatment of ocular neovascular diseases such as exudative macular degeneration and diabetic retinopathy.

Three approaches have been used to inhibit VEGF activity, including (1) neutralization of VEGF activity by using a specific antibody, soluble VEGF receptor or aptamer oligos against the VEGF/VEGFR interaction (Kim et al., *Nature,* 362:841-844 (1993), Lin et al., *Cell Growth Differ.,* 9(1):49-58 (1998), Borgstrom et al., *Prostate,* 35:1-10 (1998), Zhu et al., *Invest. New Drugs,* 17:195-212 (1999), Millauer et al., *Nature,* 367:576-579 (1994), Asano et al., *Jpn. J. Cancer Res.,* 90(1):93-100 (1999), Brekken et al., *Cancer Res.,* 60(18):5117-24 (2000)); (2) inhibition of VEGFR mediated signal transduction by specific small molecule tyrosine kinase inhibitors (Fong et al., *Cancer Res.,* 59:99-106 (1999), Wedge et al., *Cancer Res.,* 60(4):970-5 (2000), Laird et al., *Cancer Res.,* 60(15):4152-60 (2000)); and (3) inhibition of VEGF/VEGFR expression by using antisense, siRNA or ribozyme (Reich et al., *Mol. Vis.* 30;9:210-6 (2003), Parry et al., *Nucleic Acids Res.,* 27:2569-2577 (1999), Ellis et al., *Surgery,* 120:871-878 (1996), Filleur et al., *Cancer Res.,* 63(14):3919-22 (2003)). Although all of these approaches show significant inhibition of angiogenesis in vivo, they all possess significant limitations. For example, therapeutic proteins (antibody and soluble receptors) or oligos (antisense, siRNA and ribozyme) are large molecules with poor permeability that usually require parenteral administration and are costly to produce. For treatment of chronic ocular neovascularization, multiple injections may be impractical due to potential complications such as retinal detachment and procedure related infection. Moreover, tyrosine kinase inhibitors have the potential for limited specificity. VEGF is constitutively expressed at a low level in normal eyes and other tissues and thus it may be harmful to completely suppress VEGF function by administration of antibody or tyrosine kinase inhibitors systemically, especially for patients with AMD and RD many of whom are also hypertensive (Giles et al., *Cancer,* 97(8):1920-8 (2003), Sugimoto et al., *J. Biol. Chem.,* 278 (15):12605-8 (2003), Bergsland et al., American Society of Clinical Oncology $36^{th}$ Annual Meeting, 20-23 May, 2000, New Orleans, La., USA, Abstract 939), DeVore et al., American Society of Clinical Oncology $36^{th}$ Annual Meeting, 20-23 May, 2000, New Orleans, La., USA, Abstract 1896).

Thus, there remains a need to develop, characterize and optimize lead molecules for the development of novel anti-angiogenesis drugs. Accordingly, it is an object of the present invention to provide such compounds.

All documents referred to herein are incorporated by reference into the present application as though fully set forth herein.

SUMMARY OF THE INVENTION

In accordance with the present invention, compounds that inhibit the expression of VEGF post-transcriptionally have been identified, and methods for their use provided.

In one aspect of the invention, compounds of Formulas (I), (II) and (III), including Formulas (I-a) to (I-l), are provided which are useful in the inhibition of VEGF production, in the inhibition of angiogenesis, and/or in the treatment of cancer, diabetic retinopathy or exudative macular degeneration.

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

The present invention also provides methods for treating a solid tumor cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating a Wilms tumor comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating a neuroblastoma comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of treating a malignant melanoma comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods for treating cervical cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating lung cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating colon cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods for treating a solid tumor cancer by post-transcriptionally modifying VEGF expression comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods for treating a solid tumor cancer by slowing tumorigenesis at a pre-vascular stage comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating a solid tumor cancer by reducing tumor VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods for treating a solid tumor cancer by reducing perivascularly sequestered VEGF comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of inhibiting VEGF mRNA translation comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of slowing tumorigenesis at a pre-vascular stage comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods of reducing tumor VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of reducing plasma VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of reducing perivascularly sequestered VEGF comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods of treating a solid tumor cancer comprising measuring plasma levels of VEGF, tumor levels of VEGF, or both, and administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of diagnosing solid tumor cancers comprising measuring plasma levels of VEGF.

The present invention further provides methods of diagnosing solid tumor cancers comprising measuring tumor levels of VEGF.

The present invention yet further provides methods of treating a solid tumor cancer comprising administering a therapeutically effective amount of a compound of Formula (I), or a pharmaceutically acceptable salt, hydrate, solvate, clathrate, polymorph, racemate or stereoisomer thereof, together with one or more additional agents useful for treating cancer to a subject in need thereof.

These and other aspects of the invention will be more clearly understood with reference to the following preferred embodiments and detailed description.

BRIEF DESCRIPTION OF THE DRAWINGS

FIG. 1 illustrates inhibition of VEGF expression in a cervical cancer tumor by a certain compound of the invention.

FIG. 2 illustrates inhibition of lung cancer tumor growth by a certain compound of the invention.

FIG. 3 illustrates inhibition of Wilms and neuroblastoma tumor growth by a certain compound of the invention.

FIG. 4 illustrates inhibition of fibrosarcoma tumor growth by a certain compound of the invention.

FIG. 5 illustrates inhibition of malignant melanoma tumor growth by a certain compound of the invention.

FIG. 6 illustrates inhibition of VEGF expression in a fibrosarcoma tumor by a certain compound of the invention.

FIG. 7 illustrates inhibition of colon cancer tumor growth by a certain compound of the invention, either alone or in combination with 5-FU (fluorouracil).

FIG. 8 illustrates inhibition of cervical cancer tumor growth by a certain compound of the invention, either alone or in combination with Taxol (paclitaxel).

FIG. 9 illustrates inhibition of tumor growth by a certain compound of the invention, either alone or in combination with Avastin (bevacizumab, an antibody to VEGF).

FIG. 10 illustrates inhibition of tumor and plasma VEGF expression by a certain compound of the invention, either alone or in combination with Avastin.

FIG. 11 illustrates inhibition of angiogenesis by a certain compound of the invention.

FIG. 12 illustrates that a certain compound of the invention does not affect VEGF mRNA levels under hypoxic conditions.

FIG. 13 illustrates that the activity of phosphdiesterase 5 (PDE-5) is not affected by certain compounds of the invention.

DETAILED DESCRIPTION OF THE INVENTION

Figure 1:
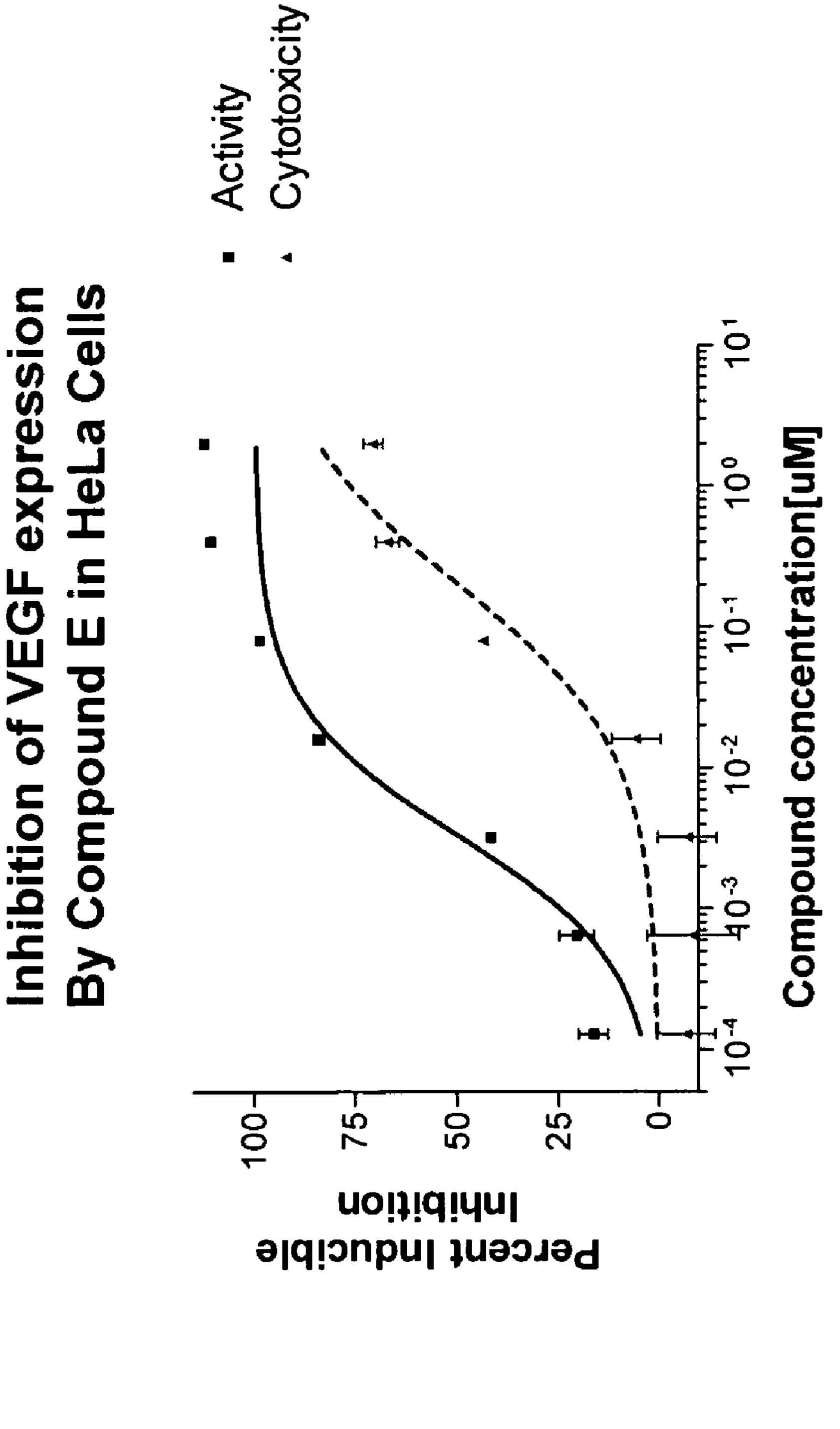
FIG. 1.

Aberrant up-regulation of Vascular Endothelial Growth Factor (VEGF), a key factor for angiogenesis, is an important contributor to the pathogenesis of disease states such as cancer, diabetic retinopathy, rheumatoid arthritis, psoriasis, atherosclerosis, chronic inflammation, other chronic inflammation-related diseases and disorders, obesity, or exudative macular degeneration. In accordance with the present invention, compounds that inhibit the expression of VEGF post-transcriptionally have been identified, and methods for their use provided. The compounds of the invention have nanomolar to sub-nanomolar activity for the inhibition of VEGF expression.

A. Compounds of the Invention

In one aspect of the invention, compounds are provided which are useful in the inhibition of VEGF production, in the inhibition of angiogenesis, and/or in the treatment of cancer, diabetic retinopathy or exudative macular degeneration. In certain embodiments, the compounds of the invention specifically inhibit VEGF production, while in other embodiments, the compounds of the invention inhibit VEGF expression as well as that of other angiogenesis factors such as FGF-2. In this regard, pan-angiogenic inhibitor may be preferred in methods of inhibiting tumor growth, while VEGF specific inhibitors may be preferred for the treatment of ocular neovascular disorders (Eyetech Study Group, 22(2):143-52 (2002)).

The compounds of the invention generally include one or more chiral centers, and as such may exist as racemic mixtures (R/S) or as enantiomerically pure compositions. The compounds may exist as (R) or (S) isomers (when one chiral center is present) in enantiomerically pure compositions. In a preferred embodiment, the compounds of the invention are the (S) isomers and may exist as enantiomerically pure compositions comprising only the (S) isomer. As one of skill will recognize, when more than one chiral center is present, the compounds of the invention may exist as (R,R), (R,S), (S,R), (S,S), etc. isomer. Preferred compounds included (S,S) and (S,R) isomers.

As used herein, "enantiomerically pure" refers to compositions consisting substantially of a single isomer, preferably consisting of greater than or equal to 90%, 92%, 95%, 98%, 99%, or equal to 100% of a single isomer.

As used herein, a "racemic mixture" is any mixture of isometric forms that are not "enantiomerically pure," including, without limitation, about 50/50, about 60/40, and about 70/30 mixtures.

Preferred compounds of the present invention useful in the inhibition of VEGF production include those of Formula (I) as shown below.

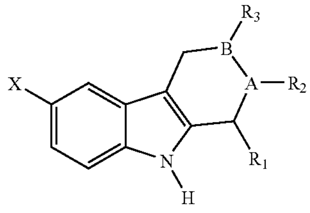

(I)

wherein,

X is hydrogen; a $C_1$ to $C_6$ alkyl, optionally substituted with one or more halogens; a hydroxyl group; a halogen; a $C_1$ to $C_5$ alkoxy, optionally substituted with a $C_6$ to $C_{10}$ aryl group;

A is C or N;

B is C or N, with the proviso that at least one of A or B is N, and that when A is N, B is C;

$R_1$ is a hydroxyl group; a $C_1$ to $C_8$ alkyl group, optionally substituted with an alkylthio group, a 5 to 10 membered heteroaryl, a $C_6$ to $C_{10}$ aryl group optionally substituted with at least one independently selected $R_0$ group; a $C_2$ to $C_8$ alkyenyl group; a $C_2$ to $C_8$ alkynyl group; a 3 to 12 membered heterocycle group, wherein the heterocycle group is optionally substituted with at least one independently selected halogen, oxo, amino, alkylamino, acetamino, thio, or alkylthio group; a 5 to 12 membered heteroaryl group, wherein the heteroaryl group is optionally substituted with at least one independently selected halogen, oxo, amino, alkylamino, acetamino, thio, or alkylthio group; or a $C_6$ to $C_{10}$ aryl group, optionally substituted with at least one independently selected $R_0$ group;

$R_0$ is a halogen; a cyano; a nitro; a sulfonyl, wherein the sulfonyl is optionally substituted with a $C_1$ to $C_6$ alkyl or a 3 to 10 membered heterocycle; an amino group, wherein the amino group is optionally substituted with a $C_1$ to $C_6$ alkyl, —C(O)—$R_b$, —C(O)O—$R_b$, a sulfonyl, an alkylsulfonyl, a 3 to 10 membered heterocycle group optionally substituted with a —C(O)O—$R_n$; —C(O)—NH—$R_b$; a 5 to 6 membered heterocycle; a 5 to 6 membered heteroaryl; a $C_1$ to $C_6$ alkyl group, wherein the alkyl group is optionally substituted with at least one independently selected hydroxyl, halogen, amino, or 3 to 12 membered heterocycle group, wherein the amino group and heterocycle group are optionally substituted with at least one independently selected $C_1$ to $C_4$ alkyl group, which $C_1$ to $C_4$ alkyl group is optionally substituted with at least one independently selected $C_1$ to $C_4$ alkoxy group, amino group, alkylamino group, or 5 to 10 membered heterocycle group; a —C(O)—$R_n$ group; or an —$OR_a$ group;

$R_a$ is hydrogen; $C_2$ to $C_8$ alkylene; a —C(O)O—$R_b$ group; a —C(O)—NH—$R_b$; a $C_1$ to $C_8$ alkyl, wherein the alkyl group is optionally substituted with at least one independently selected hydroxyl, halogen, $C_1$ to $C_4$ alkoxy, amino, alkylamino, acetamide, —C(O)—$R_b$, —C(O)O—$R_b$, $C_6$ to $C_{10}$ aryl, 3 to 12 membered heterocycle, or 5 to 12 heteroaryl group, further wherein the alkylamino is optionally substituted with a hydroxyl, a $C_1$ to $C_4$ alkoxy, or a 5 to 12 membered heteroaryl optionally substituted with a $C_1$ to $C_4$ alkyl, further wherein the acetamide is optionally substituted with a $C_1$ to $C_4$ alkoxy, sulfonyl, or alkylsulfonyl, further wherein and the heterocycle group is optionally substituted with a $C_1$ to $C_4$ alkyl optionally substituted with a hydroxyl group, —C(O)—$R_n$, —C(O)O—$R_n$, or an oxo group;

$R_b$ is hydroxyl; an amino; an alkylamino, wherein the alkylamino is optionally substituted with a hydroxyl, an amino, an alkylamino, a $C_1$ to $C_4$ alkoxy, a 3 to 12 membered heterocycle optionally substituted with at least one independently selected $C_1$ to $C_6$ alkyl, oxo, —C(O)O—$R_n$, or a 5 to 12 membered heteroaryl optionally substituted with a $C_1$ to $C_4$ alkyl; a $C_1$ to $C_4$ alkoxy; a $C_2$ to $C_8$ alkenyl; a $C_2$ to $C_8$ alkynyl; a $C_6$ to $C_{10}$ aryl, wherein the aryl is optionally substituted with at least one independently selected halogen or $C_1$ to $C_4$ alkoxy; a 5 to 12 membered heteroaryl; 3 to 12 membered heterocycle group, wherein the heterocycle is optionally substituted with at least one independently selected acetamide, —C(O)O—$R_n$, 5 to 6 membered heterocycle, or $C_1$ to $C_6$ alkyl optionally substituted with a hydroxyl, $C_1$ to $C_4$ alkoxy, amino group, or alkylamino group; or a $C_1$ to $C_8$ alkyl, wherein the alkyl is optionally substituted with at least one independently selected $C_1$ to $C_4$ alkoxy, $C_6$ to $C_{10}$ aryl, amino, or 3 to 12 membered heterocycle group, wherein the amino and heterocycle groups are optionally substituted with at least one independently selected $C_1$ to $C_6$ alkyl, oxo, or —C(O)O—$R_n$ group;

$R_2$ is a hydrogen; a hydroxyl; a 5 to 10 membered heteroaryl group; a $C_1$ to $C_8$ alkyl group, wherein the alkyl group is optionally substituted with a hydroxyl, a $C_1$ to $C_4$ alkoxy, a 3 to 10 membered heterocycle, a 5 to 10 membered heteroaryl, or $C_6$ to $C_{10}$ aryl group; a —C(O)—$R_c$ group; a —C(O)O—$R_d$ group; a —C(O)—N($R_d R_d$) group; a —C(S)—N($R_d R_d$) group; a —C(S)—O—$R_e$ group; a —S($O_2$)—$R_e$ group; a —C($NR_e$)—S—$R_e$ group; or a —C(S)—S—$R_f$ group;

$R_c$ is hydrogen; an amino, wherein the amino is optionally substituted with at least one independently selected $C_1$ to $C_6$ alkyl or $C_6$ to $C_{10}$ aryl group; a $C_6$ to $C_{10}$ aryl, wherein the aryl is optionally substituted with at least one independently selected halogen, haloalkyl, hydroxyl, $C_1$ to $C_4$ alkoxy, or $C_1$ to $C_6$ alkyl group; —C(O)—$R_n$; a 5 to 6 membered heterocycle, wherein the heterocycle is optionally substituted with a —C(O)—$R_n$ group; a 5 to 6 membered heteroaryl; a thiazoleamino group; a $C_1$ to $C_8$ alkyl group, wherein the alkyl group is optionally substituted with at least one independently selected halogen, a $C_1$ to $C_4$ alkoxy, a phenyloxy, a $C_6$ to $C_{10}$ aryl, —C(O)—$R_n$, —O—C(O)—$R_n$, hydroxyl, or amino group, optionally substituted with a —C(O)O—$R_n$ group;

$R_d$ is independently hydrogen; a $C_2$ to $C_8$ alkenyl group; a $C_2$ to $C_8$ alkynyl group; a $C_6$ to $C_{10}$ aryl group, wherein the aryl is optionally substituted with at least one independently selected halogen, nitro, $C_1$ to $C_6$ alkyl, —C(O)O—$R_e$, or —$OR_e$; or a $C_1$ to $C_8$ alkyl group, wherein the alkyl group is optionally substituted with at least one independently selected halogen, $C_1$ to $C_4$ alkyl, $C_1$ to $C_4$ alkoxy, phenyloxy, $C_6$ to $C_{10}$ aryl, 5 to 6 membered heteroaryl, —C(O)—$R_n$, —O—C(O)—$R_n$, or hydroxyl group, wherein the $C_6$ to $C_{10}$ aryl group is optionally substituted with at least one independently selected halogen or haloalkyl group;

$R_e$ is a hydrogen; a $C_1$ to $C_6$ alkyl group, wherein the alkyl group is optionally substituted with at least one independently selected halogen or alkoxy group; or a $C_6$ to $C_{10}$ aryl group, wherein the aryl group is optionally substituted with at least one independently selected halogen or alkoxy group;

$R_f$ is a $C_1$ to $C_6$ alkyl group, optionally substituted with at least one independently selected halogen, hydroxyl, $C_1$ to $C_4$ alkoxy, cyano, $C_6$ to $C_{10}$ aryl, or —C(O)—$R_n$ group, wherein the alkoxy group may be optionally substituted with at least one $C_1$ to $C_4$ alkoxy group and the aryl group may be optionally substituted with at least one independently selected halogen, hydroxyl, $C_1$ to $C_4$ alkoxy, cyano, or $C_1$ to $C_6$ alkyl group;

$R_n$ is a hydroxyl, $C_1$ to $C_4$ alkoxy, amino, or $C_1$ to $C_6$ alkyl group;

$R_3$ is hydrogen or —C(O)—$R_g$;

$R_g$ is a hydroxyl group; an amino group, wherein the amino is optionally substituted with a $C_6$ to $C_{10}$ cycloalkyl group or a 5 to 10 membered heteroaryl group; or a 5 to 10 membered heterocycle group, wherein the heterocycle group is optionally substituted with a —C(O)—$R_n$ group; and n is 0, 1, 2, or 3.

As will be evident to one of skill in the art, the compounds of Formula (I) comprise at least one stereocenter (e.g., at the $R_1$ substituent), and may exist as a racemic mixture or as an enantiomerically pure composition. In a preferred embodiment, the compounds of Formula (I) are the (S) isomer, in an enantiomerically pure composition.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be include $C_1$ to $C_8$, $C_1$ to $C_6$, or $C_1$ to $C_4$ alkyl groups. The alkyl group may be optionally substituted with one or more halogen or alkoxy groups. For instance, the alkyl group may be a haloalkyl, dihaloalkyl, or trihaloalkyl.

As used herein, "alkenyl" generally refers to linear, branched or cyclic alkene radicals having one or more carbon-carbon double bonds, such as $C_2$ to $C_8$ and $C_2$ to $C_6$ alkenyl groups, including 3-propenyl.

As used herein, "alkynyl" generally refers to linear, branched or cyclic alkyne radicals having one or more carbon-carbon triple bonds, such as $C_2$ to $C_8$ and $C_2$ to $C_6$ alkynyl groups, including hex-3-yne.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain one or more heteroatoms, two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, dihydro-chromen-4-only, 1,3-diazine, 1,2-diazine, 1,2-diazole, 1,4-diazanaphthalene, furan, furazan, imidazole, indole, isoxazole, isoquinoline, isothiazole, isoindolyl, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline. In certain embodiments, the heteroaryl may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. In some embodiments, the heterocycle groups may be selected from heterocycle groups that contain one or more heteroatoms, two or more heteroatoms, three or more heteroatoms, or four or more heteroatoms. Example of heterocycle groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkanoyl" generally refers to a group with the structure —C(O)—R. In certain embodiments, R may be a hydrogen, an alkyl, an 4-morpholinyl group, or a thiazoleamino group.

As used herein, "alkoxy" generally refers to a group with the structure —O—R. In certain embodiments, R may be an alkyl group, such as a $C_1$ to $C_5$ alkyl group.

For the purposes of this invention, halo substituents may be independently selected from the halogens such as fluorine, chlorine, bromine, iodine, and astatine.

In certain preferred embodiments, X may be hydrogen, methoxy, hydroxyl, benzoxy, or a halogen, preferably bromide or chloride. In other embodiments, X may preferably be a $C_1$ to $C_4$ alkyl or a haloalkyl.

$R_1$ may preferably be a $C_6$ to $C_8$ aryl group, optionally substituted with at least one $R_0$ group. $R_0$ may then preferably be methoxy, benzoxy, a $C_1$ to $C_6$ alkyl, a 5 to 6 membered heteroaryl (such as furyl or imidazole), cyano, nitro, tri-fluro methyl, or a halogen, more preferably methoxy, benzoxy, iso-butyl or a halogen, and more preferably methoxy, iso-butyl, bromide or chloride. Alternatively, $R_1$ may be a 5 to 10 membered heteroaryl or 3 to 12 membered heterocycle, such as a pyridinyl group, a thiophene group, a furyl group, a tetrahydro furyl group, and a thiazole group dihydro-chromen-4-onyl group, a 1H-isoindolyl group, or a benzo-dioxole group.

$R_2$ may preferably be a —$CH_2$-furyl group, a pyrimidyl group, or a —C(O)O—$R_d$ group. $R_d$ may preferably then be a $C_1$ to $C_6$ alkyl, optionally substituted with at least one halogen; or a $C_5$ to $C_6$ aryl, optionally substituted with at least one methyl, methoxy, or halogen.

Preferred $R_1$ substituents also include the following, where the * indicates the bond of attachment to the carboline scaffold molecule.

——OH -ethyl -pentyl

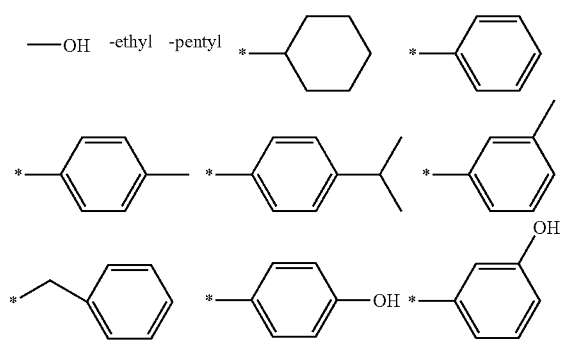

-continued
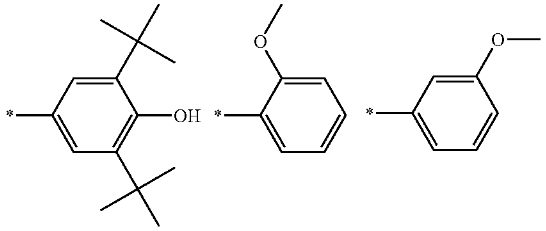
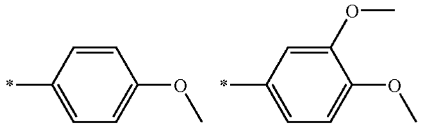
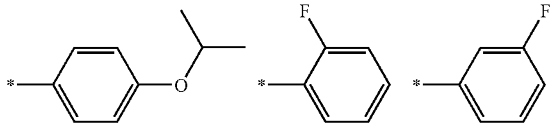
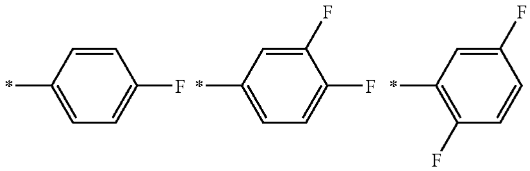
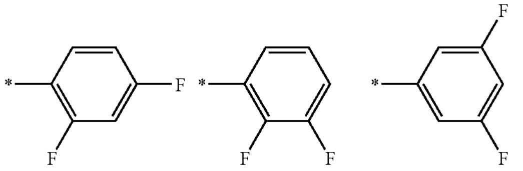
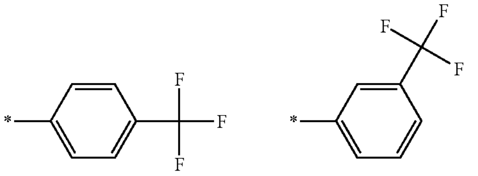
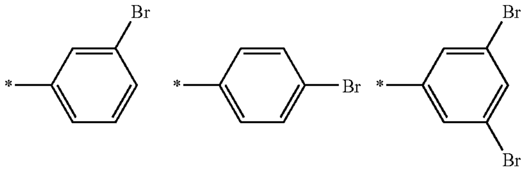
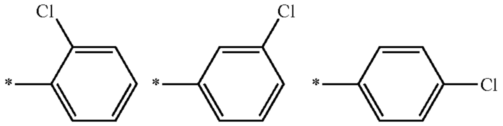
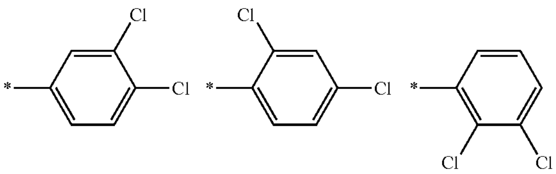
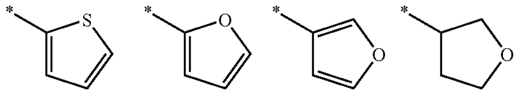
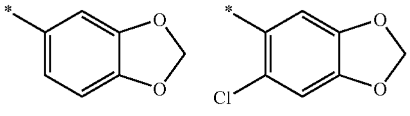
-continued
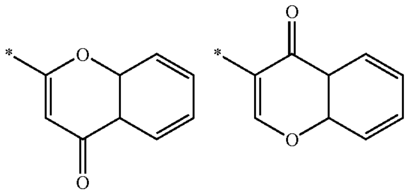
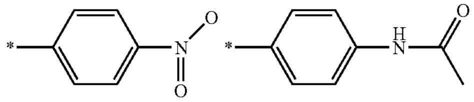
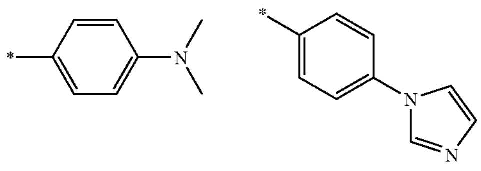
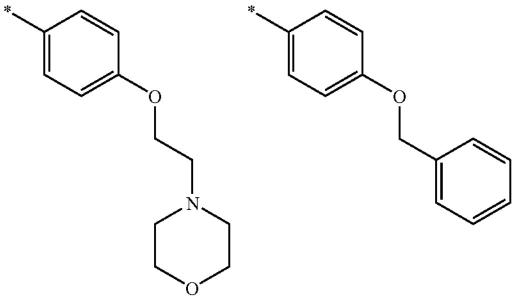
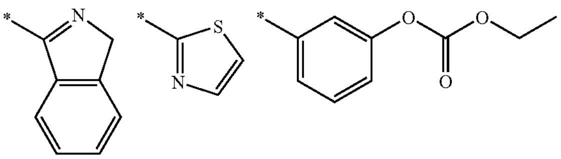
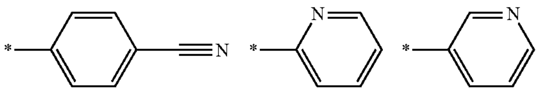
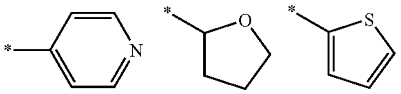
Other preferred $R_1$ substituents include the following, where the * indicates the bond of attachment to the carboline scaffold molecule.
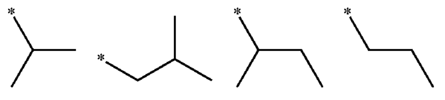
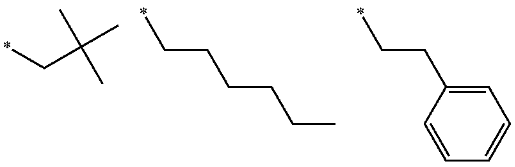

-continued
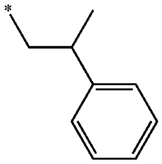
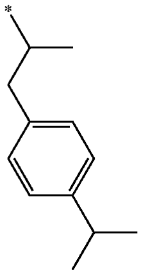
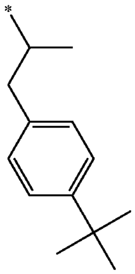
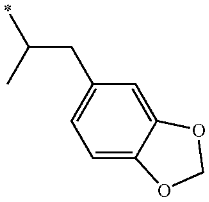
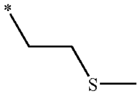
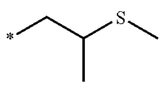
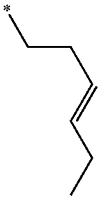
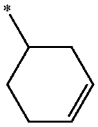
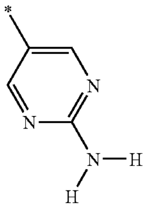
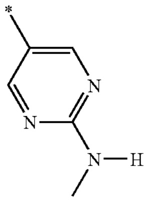
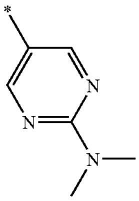
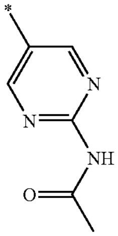
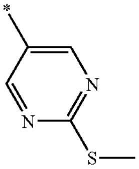
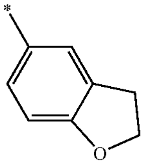
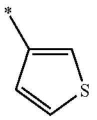
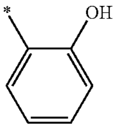
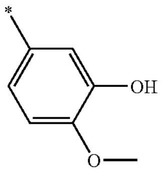
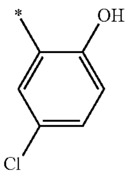
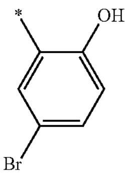
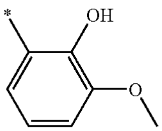
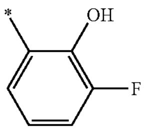
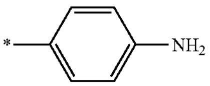
-continued
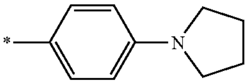
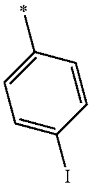
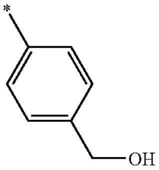
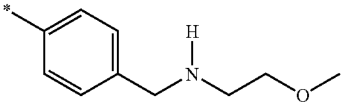
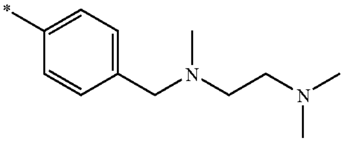
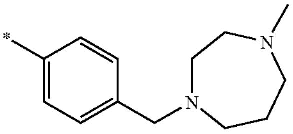
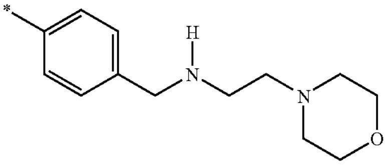
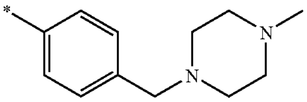
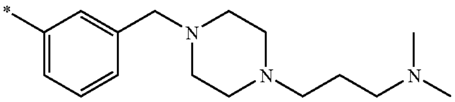
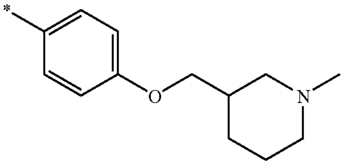
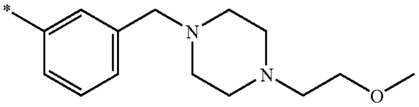
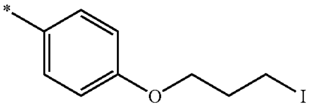
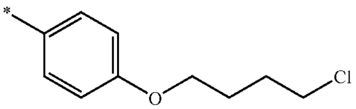
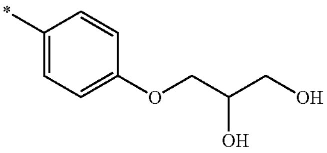
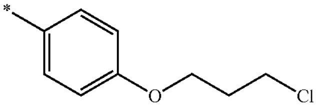

-continued
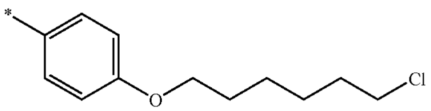
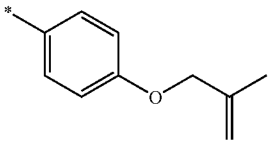
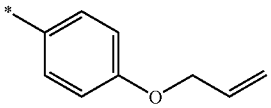
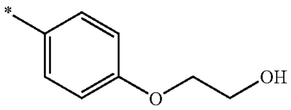
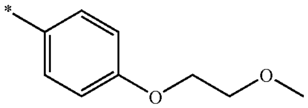
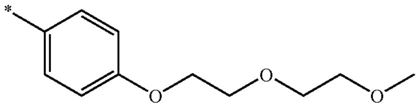
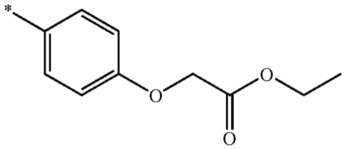
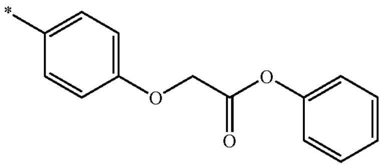
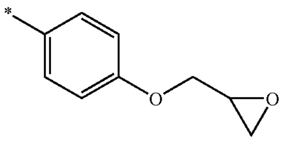
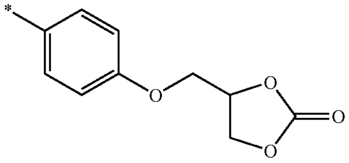
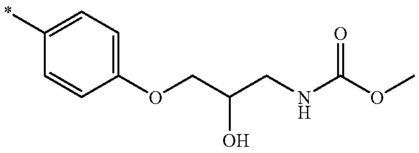
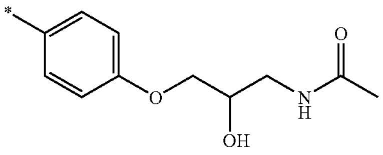
-continued
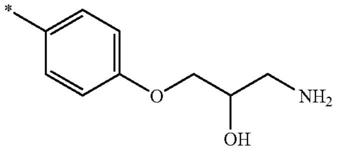
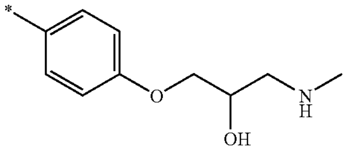
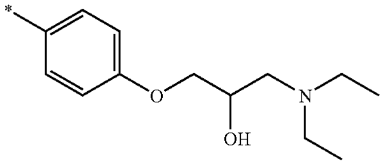
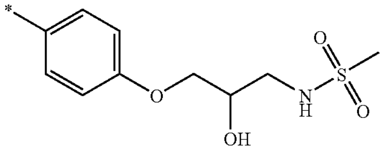
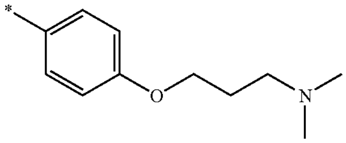
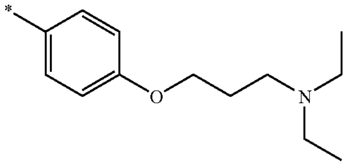
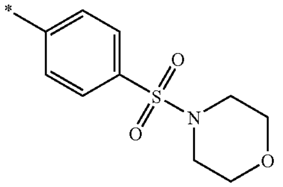
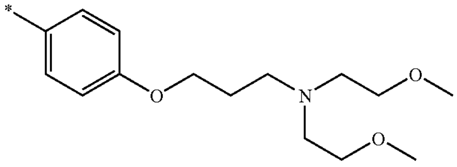
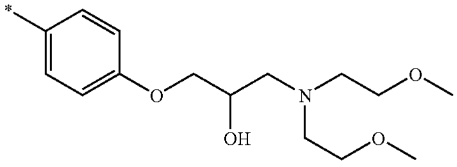
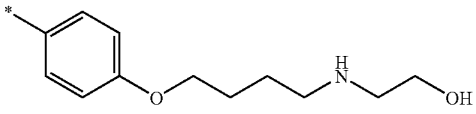
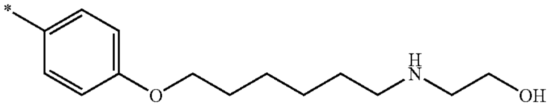

-continued
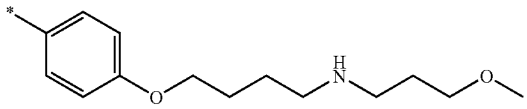
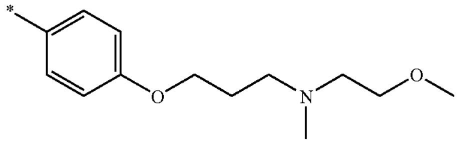
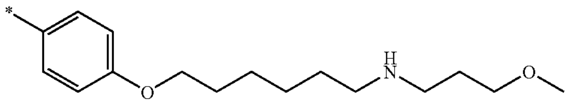
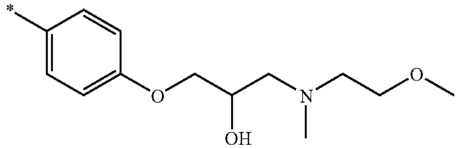
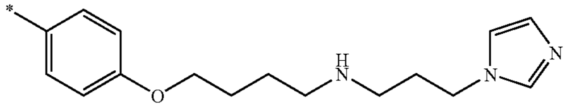
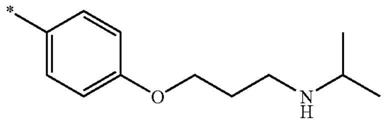
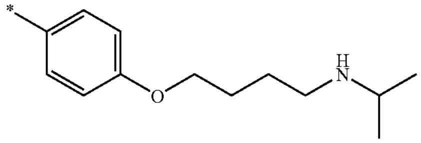
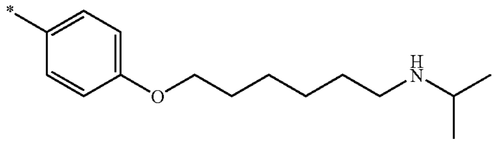
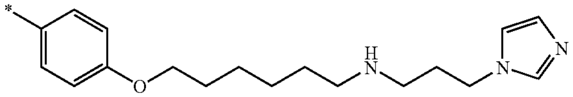
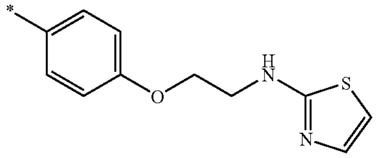
and regioisomers thereof
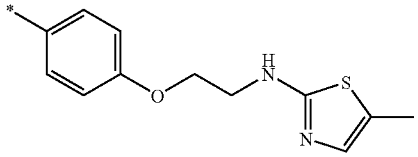
and regioisomers thereof
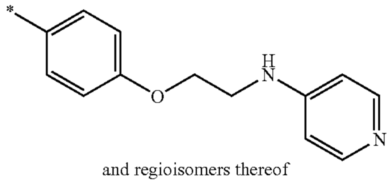
and regioisomers thereof
-continued
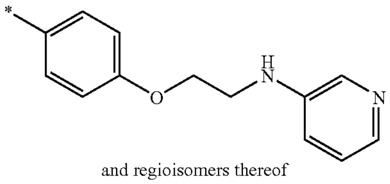
and regioisomers thereof
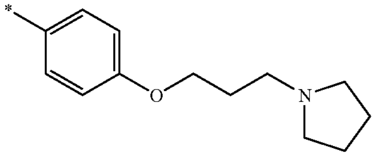
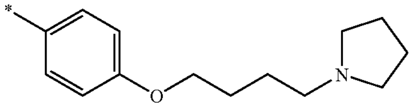
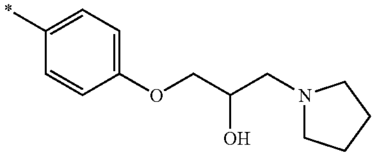
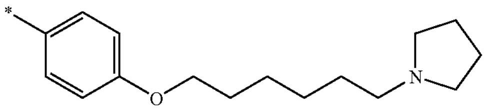
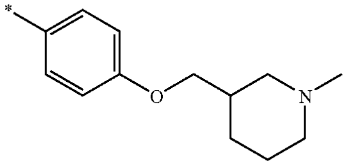
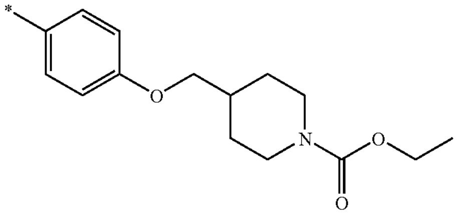
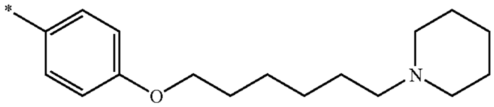
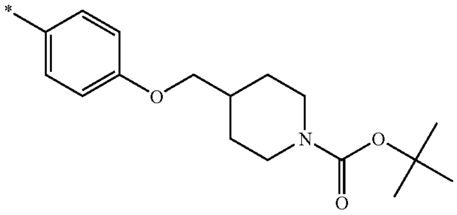
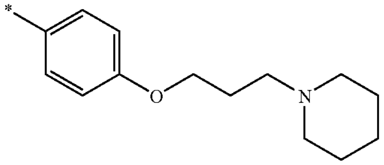
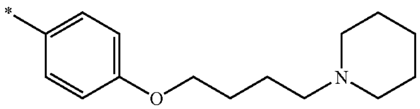

-continued
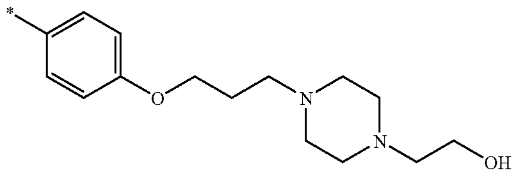
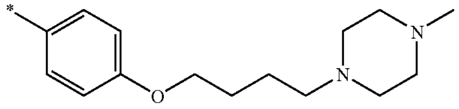
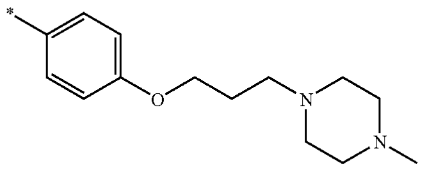
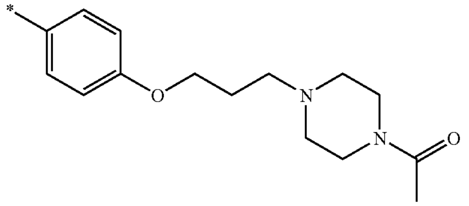
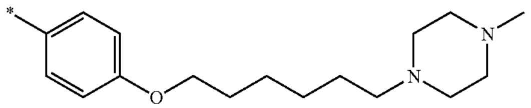
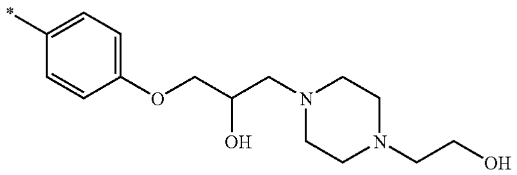
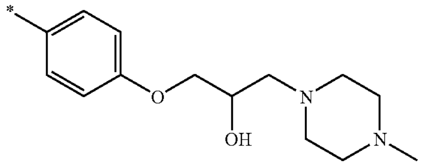
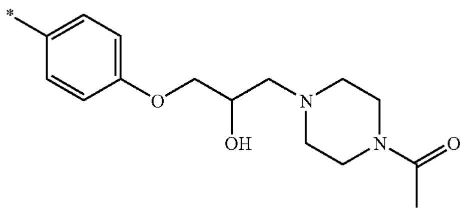
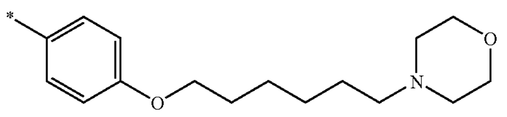
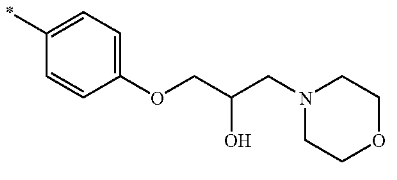
-continued
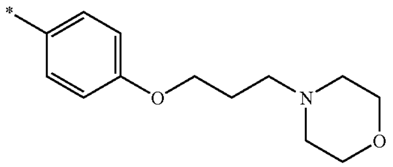
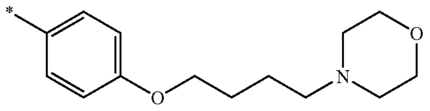
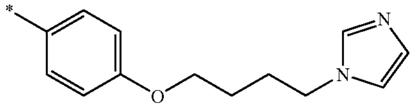
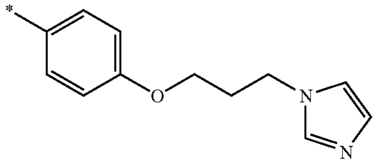
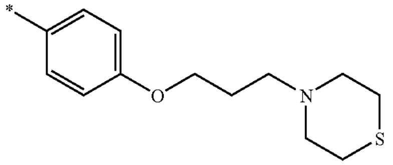
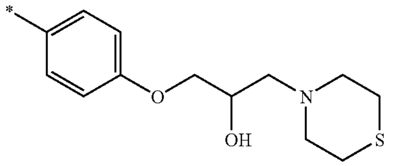
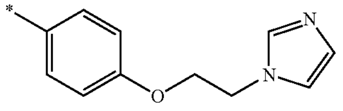
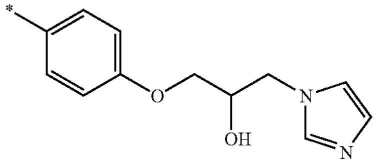
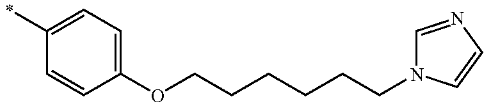
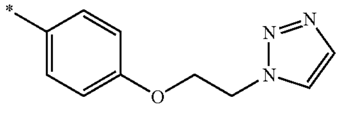
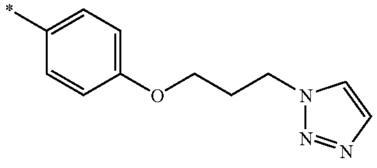
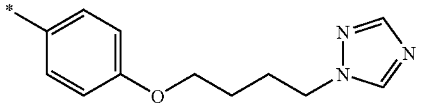

-continued
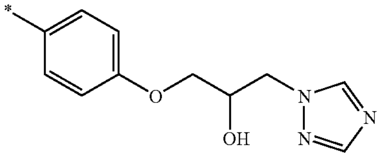
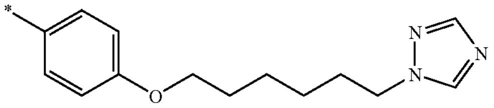
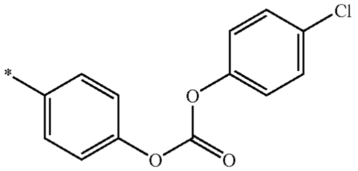
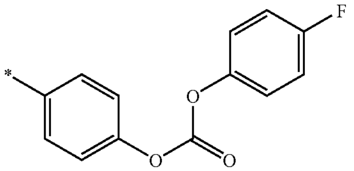
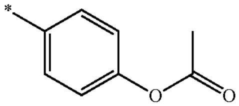
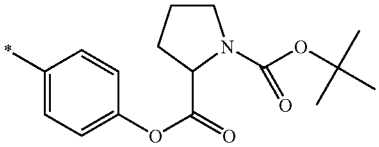
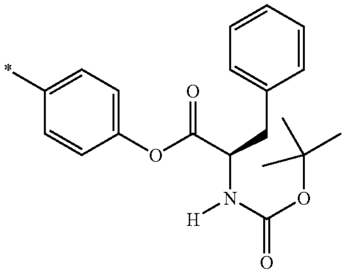
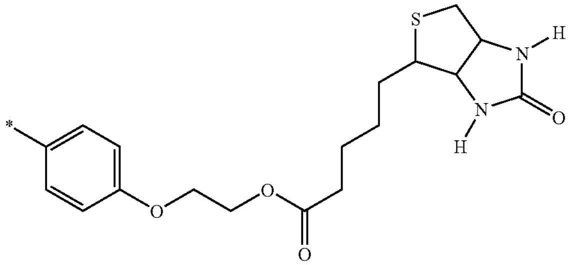
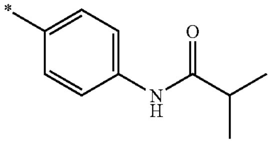
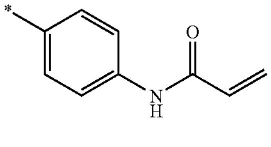
-continued
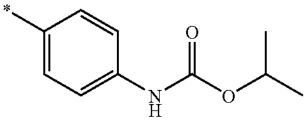
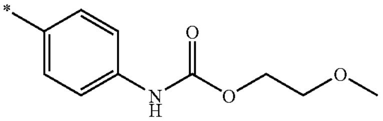
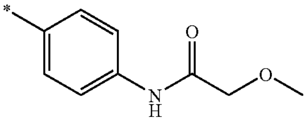
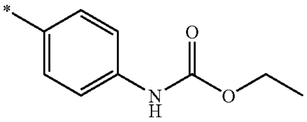
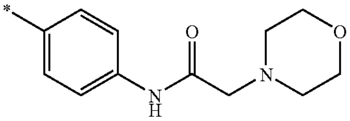
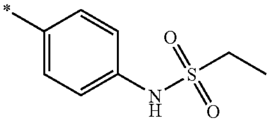
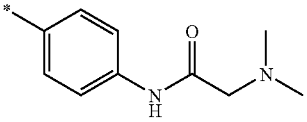
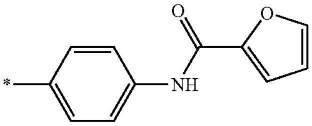
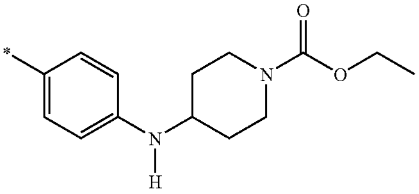
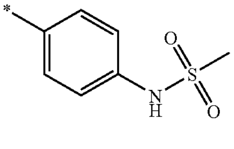
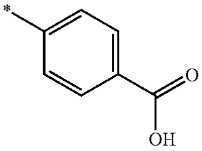
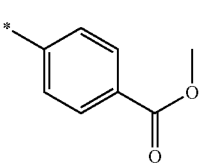
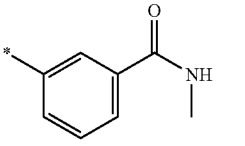
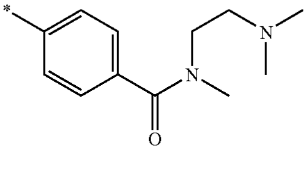

-continued
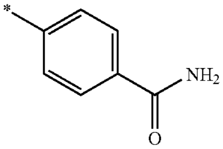
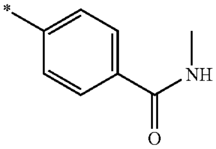
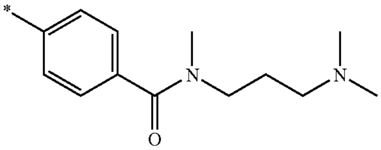
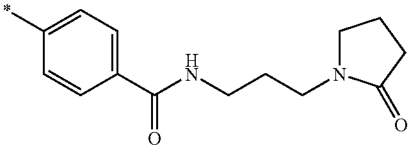
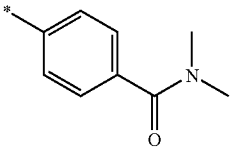
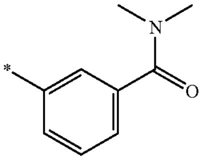
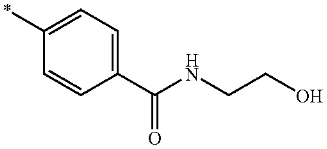
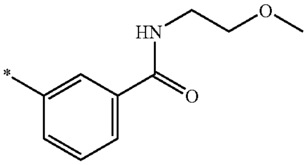
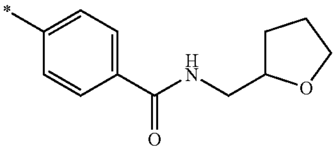
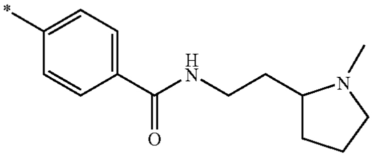
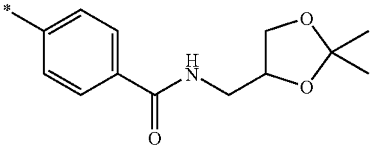
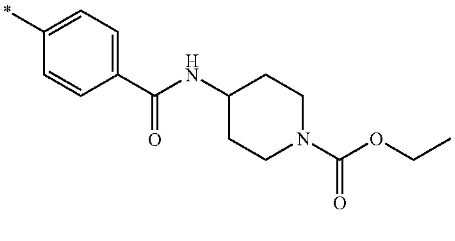
-continued
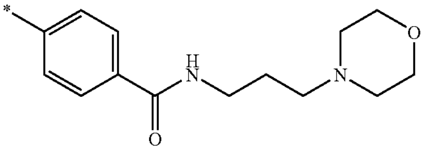
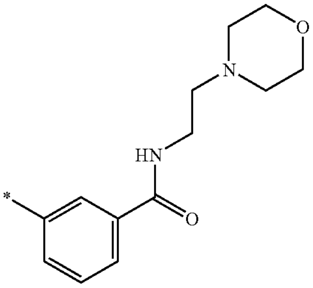
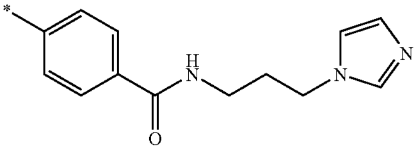
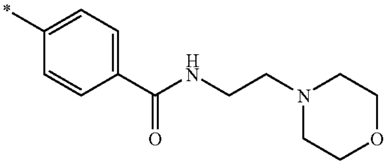
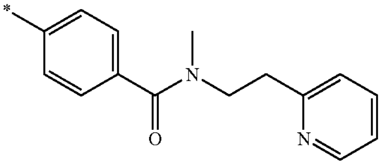
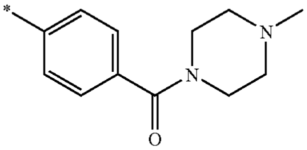
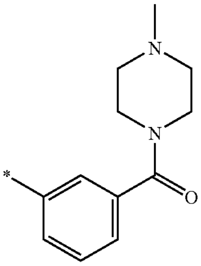
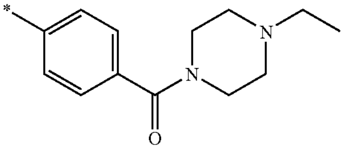
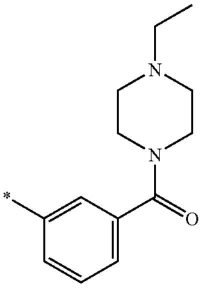

-continued
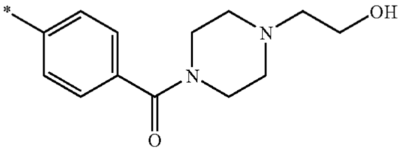
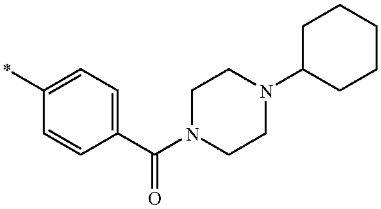
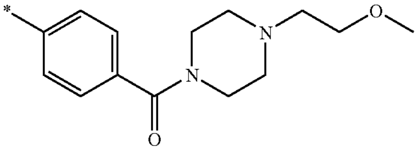
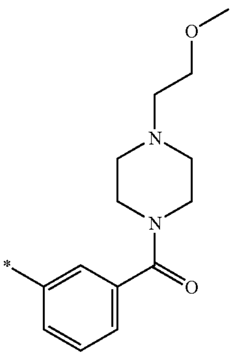
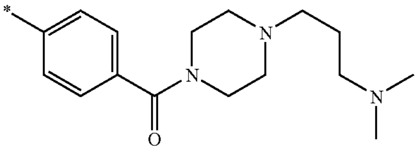
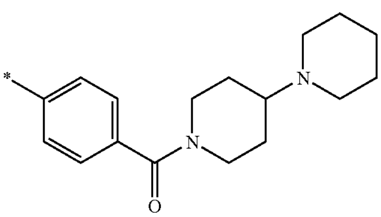
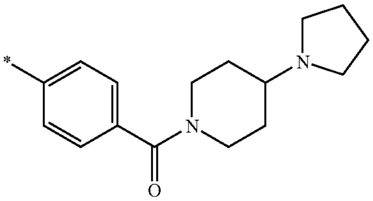
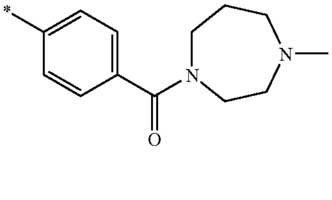
-continued
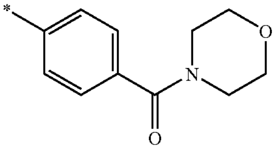
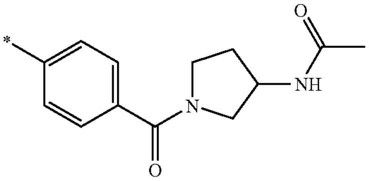
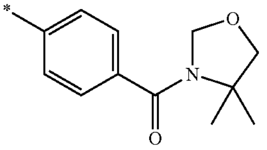
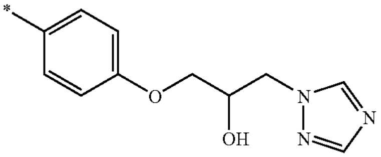
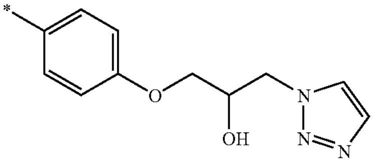
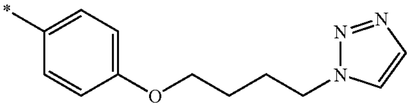
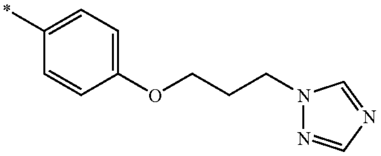
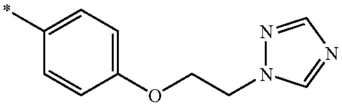
Preferred $R_2$ substituents also include the following, where the * indicates the bond of attachment to the carboline scaffold molecule.
  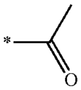 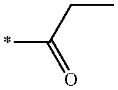 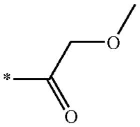
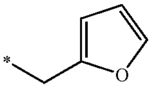 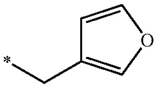 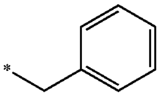

-continued
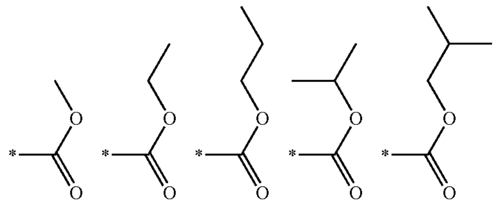
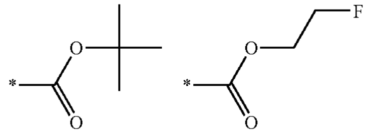
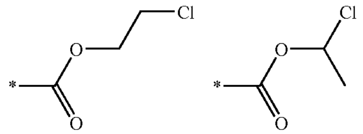
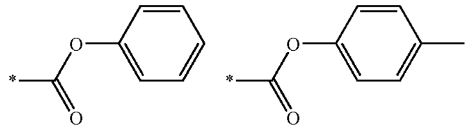
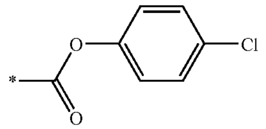
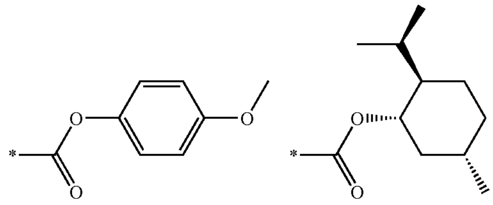
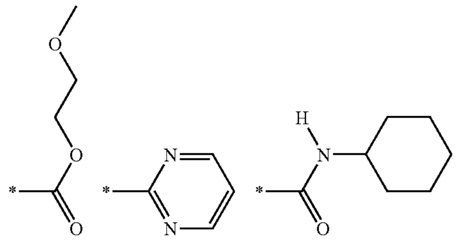
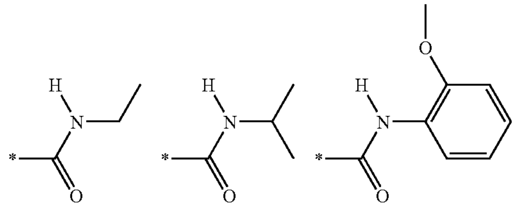
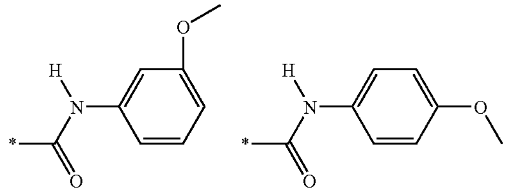
-continued
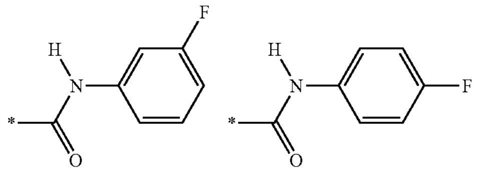
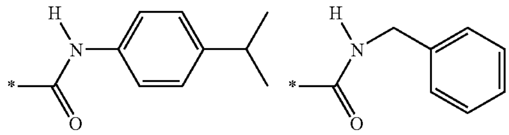
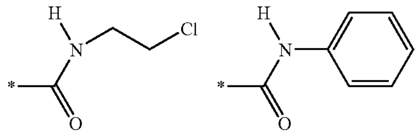
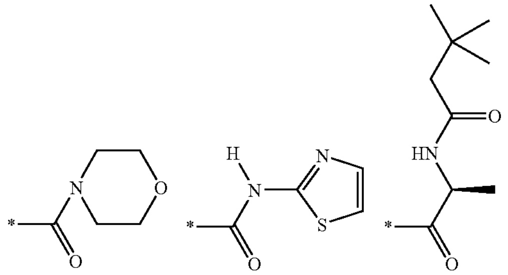
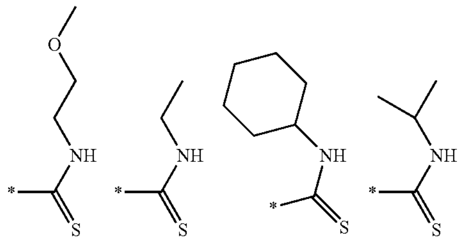
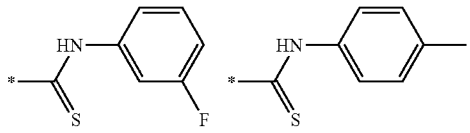
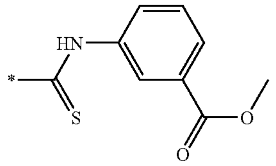
Other preferred $R_2$ substituents include the following, where the * indicates the bond of attachment to the carboline scaffold molecule.
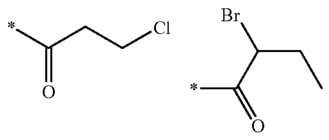

-continued
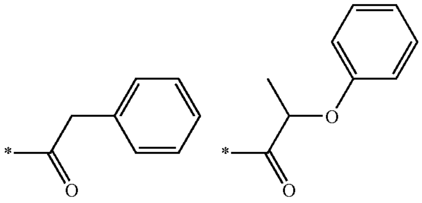
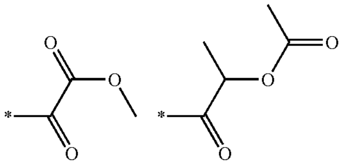
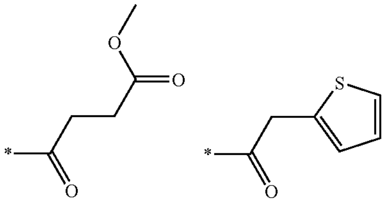
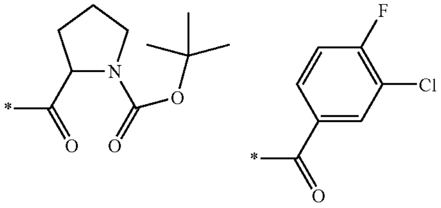
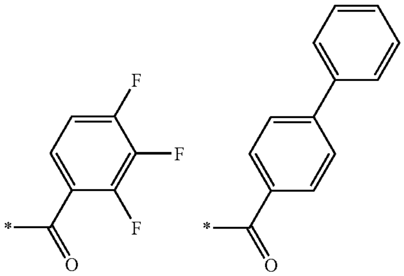
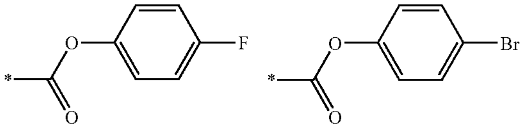
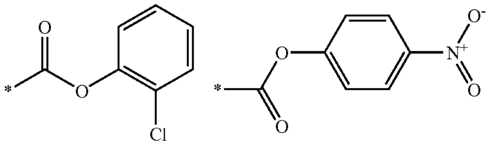
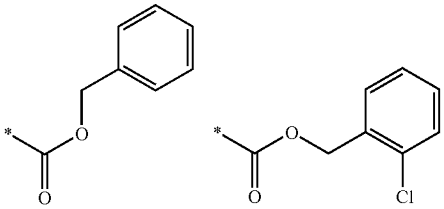
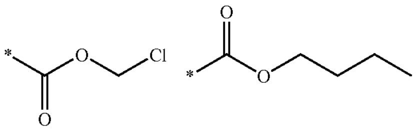
-continued
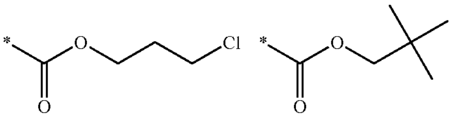
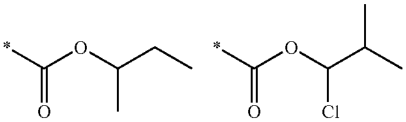
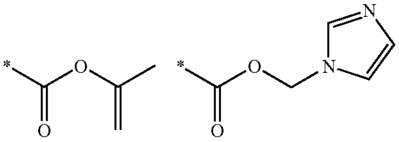
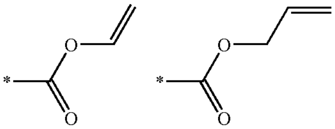
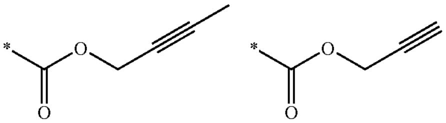
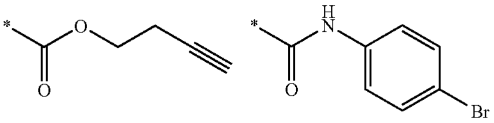
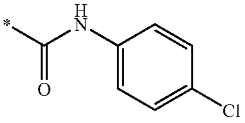
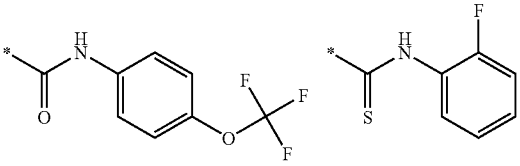
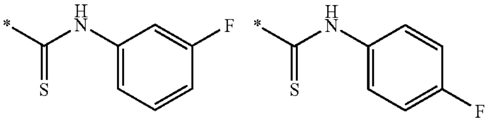
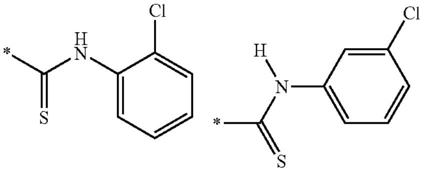
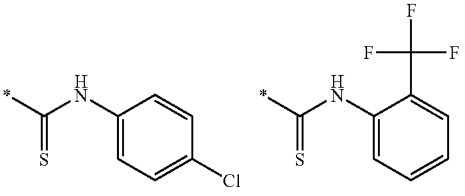
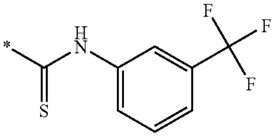

-continued
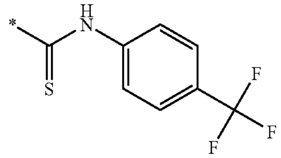
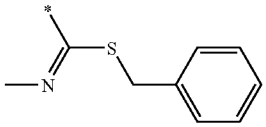
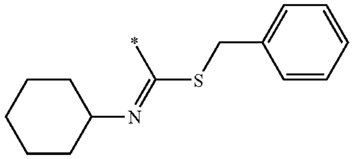
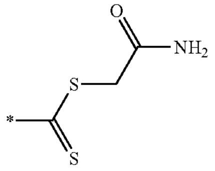
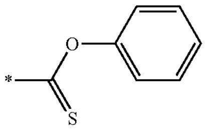
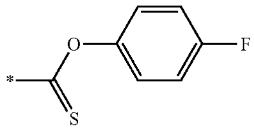
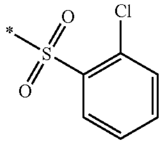
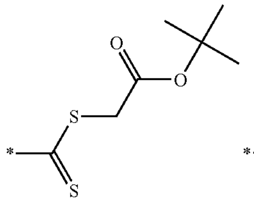
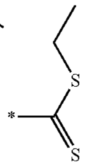
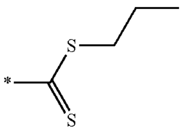
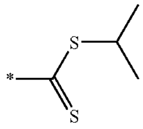
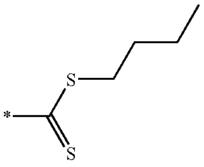
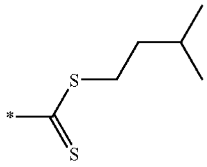
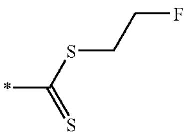
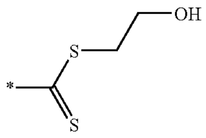
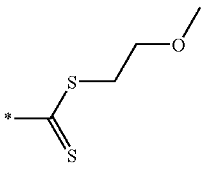
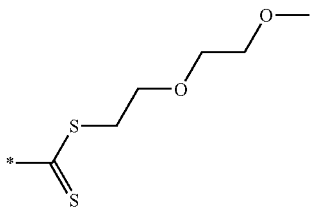
-continued
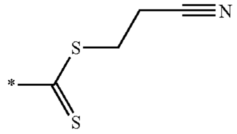
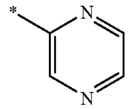
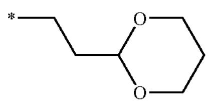
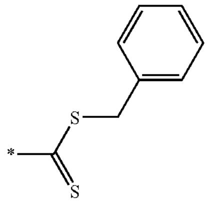
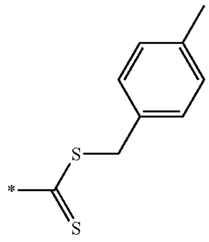
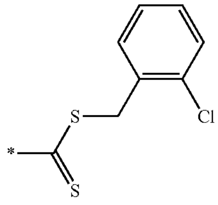
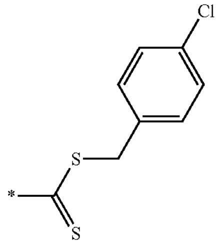
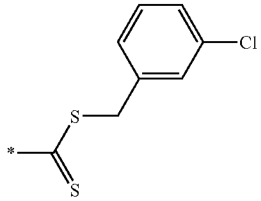
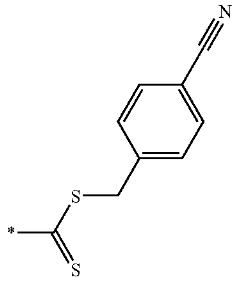
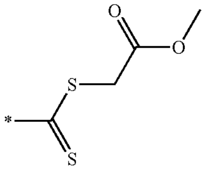
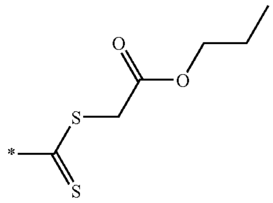
Preferred $R_3$ substituents include the following, where the * indicates the bond of attachment to the carboline scaffold molecule.
*—OH
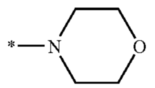
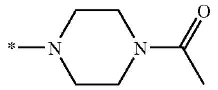

-continued

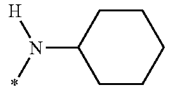

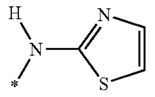

A preferred class of compounds within Formula (I) include those compounds of Formula (I-a) as shown below.

(I-a)

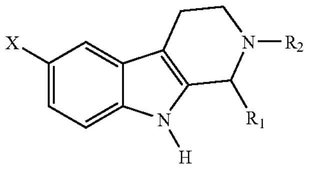

wherein X, $R_1$ and $R_2$ are defined as described with regard to Formula (I) and the preferred embodiments described above.

Another preferred class of compounds within Formula (I) include those compounds of Formula (I-b) as shown below.

(I-b)

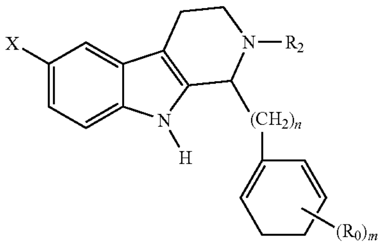

wherein:

X is a halogen;

$R_2$ is as described above with regard to Formula (I);

$R_0$ is as described above with regard to Formula (I);

m is 0, 1, 2, or 3; and n is 0, 1, 2, or 3.

Other preferred classes of compounds within Formula (I) include the following.

(I-c)

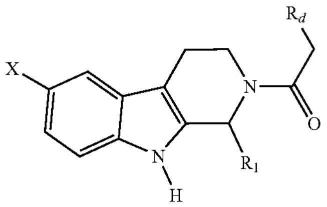

-continued (I-d)

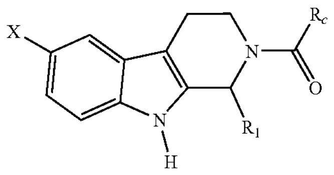

(I-e)

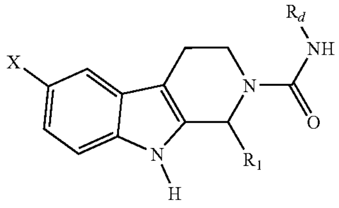

(I-f)

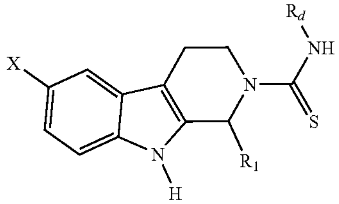

(I-g)

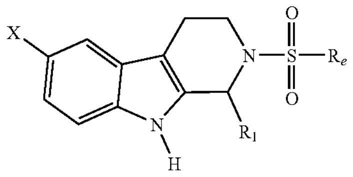

(I-h)

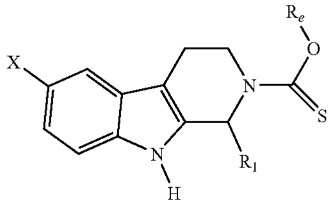

(I-i)

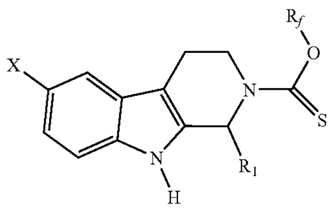

It is understood that substituents X and $R_1$, $R_c$, $R_d$, and $R_e$ of the compounds of Formulas (I-c) to (I-i) are defined as in Formula (I).

In other embodiments, preferred compounds of the present invention useful in the inhibition of VEGF production include those of Formulas (I-i) through (I-l), as shown below. In the embodiments of Formulas (I-j) through (I-l), substituents X, $R_1$, $R_2$, $R_3$, etc. are defined as in Formula (I), as well as Formulas (I-a) to (I-i).

(I-j)

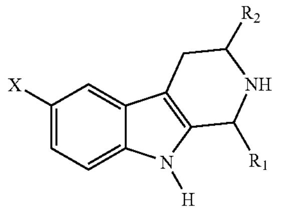

(I-k)

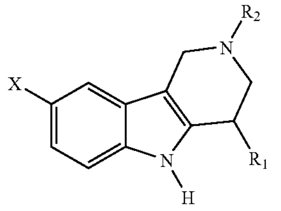

Also included within the scope of the invention are pharmaceutically acceptable salts, hydrates, solvates, calthrates, polymorphs, racemates and stereoisomers of the compounds described herein.

In another aspect of the invention, preferred compounds of the present invention useful in the inhibition of VEGF production include those of Formula (I-l) as shown below.

(I-l)

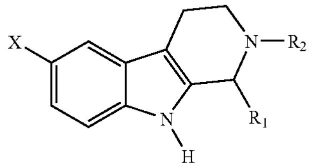

wherein,

X is hydrogen; a hydroxyl group; a halogen; a $C_1$-$C_4$ alkyl; a $C_1$ to $C_5$ alkoxy, optionally substituted with a $C_6$ to $C_8$ aryl group;

$R_1$ is a hydroxyl group; a $C_1$ to $C_8$ alkyl group, optionally substituted with a $C_6$ to $C_8$ aryl group, wherein the $C_6$ to $C_8$ aryl group is optionally substituted with at least one $R_0$ group; a heterocycle group; a heteroaryl group; and a $C_6$ to $C_8$ aryl group, optionally substituted with at least one $R_0$ group;

$R_0$ is a halogen; a $C_1$ to $C_6$ alkyl, optionally substituted with one or more halogen groups; a cyano group; a nitro group; an amino group; an aminoalkyl group; an acetamide group; an imidazole group; or $OR_a$;

$R_a$ is hydrogen; a $C_1$ to $C_6$ alkyl, optionally substituted with a heterocycle group or a $C_6$ to $C_8$ aryl group; or a —C(O)O—$R_b$;

$R_b$ is $C_1$ to $C_4$ alkyl group;

$R_2$ is a hydrogen; a hydroxyl; a heteroaryl group; a $C_1$ to $C_8$ alkyl group, optionally substituted with an alkoxy, hydroxyl, heteroaryl, or $C_6$ to $C_8$ aryl group; a —C(O)—$R_c$ group; a —C(O)O—$R_d$ group; a —C(O)NH—$R_d$ group; a —C(S)NH—$R_d$ group; a —S($O_2$)—$R_e$ group; or (1S)-isopropyl-carbamic acid tert-butyl ester;

$R_c$ is hydrogen; a 4-morpholinyl group; a thiazoleamino group; a piperazinyl group, optionally substituted with a —C(O)$CH_3$ group; a $C_1$ to $C_6$ alkyl group, optionally substituted with a halogen, an alkoxy, or hydroxyl group;

$R_d$ is hydrogen; a benzyl group; a $C_1$ to $C_8$ alkyl group, optionally substituted with a halogen or an alkoxy group; a $C_6$ to $C_8$ aryl group, optionally substituted with at least one halogen, $C_1$ to $C_5$ alkyl, —C(O)$OR_e$, or $OR_e$;

$R_e$ is a hydrogen; a $C_1$ to $C_6$ alkyl group, optionally substituted with at least one halogen or alkoxy group; or a $C_6$ to $C_8$ aryl group; and n is 0, 1, 2, or 3.

In another embodiment, compounds of Formulas (II), (III) and (IV) are provided, which are useful for inhibiting VEGF production, and treating cancer.

(II)

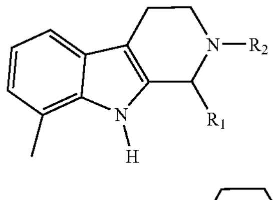

(III)

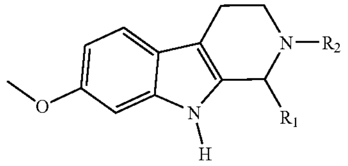

(IV)

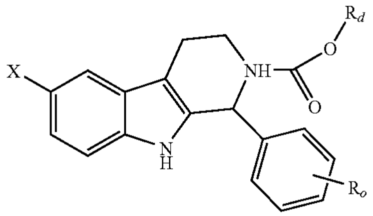

Wherein X, $R_1$, $R_2$, $R_0$ and $R_d$ are defined as described above with regard with Formula (I).

For the purposes of this invention, where one or more functionalities encompassing X $R_1$, $R_2$, $R_0$, $R_a$, $R_b$, $R_c$, $R_d$, and $R_e$, are incorporated into a molecule of Formulas (I), (II), and (III), including Formulas (I-a) to (I-k), each of the functionalities appearing at any location within the disclosed may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

Preferred compounds of the invention include the following.

1

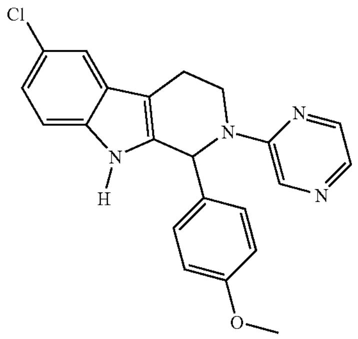

-continued
2
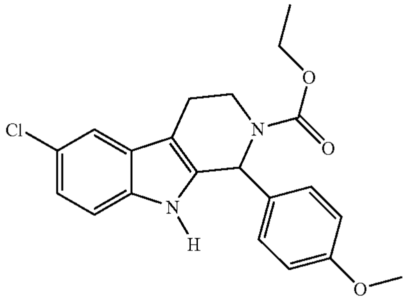
3
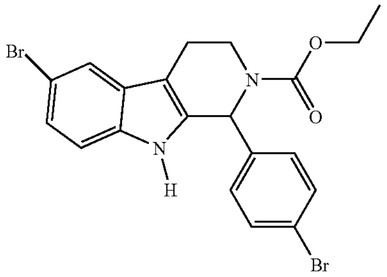
4
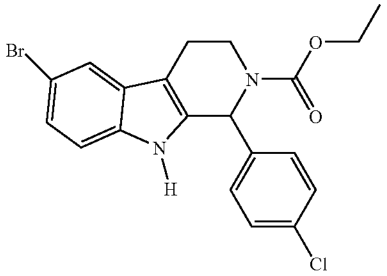
5
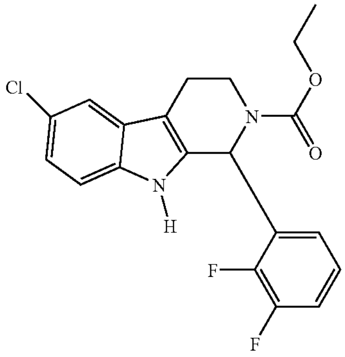
6
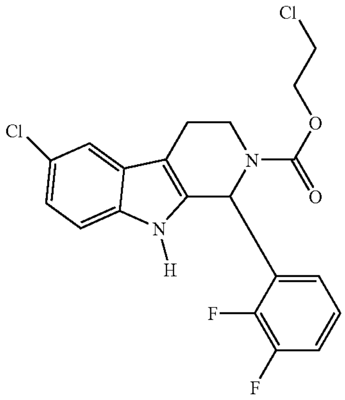
-continued
7
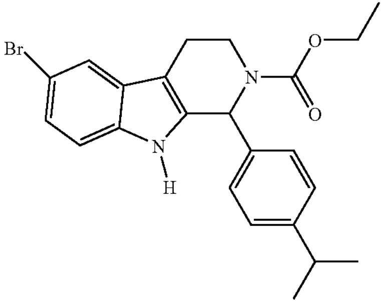
8
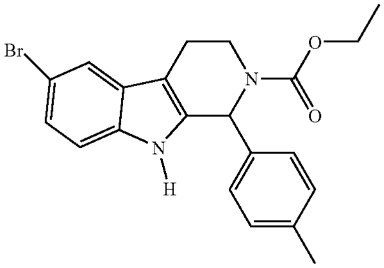
9
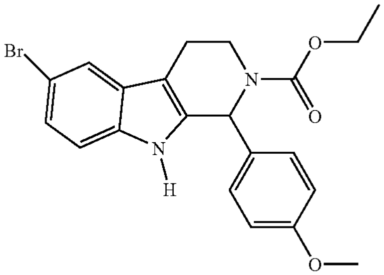
10
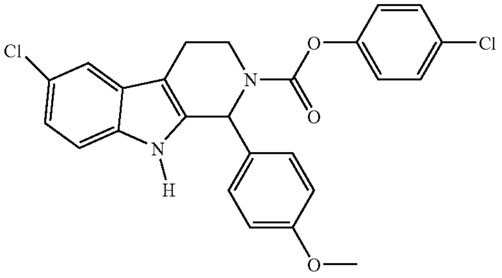
11
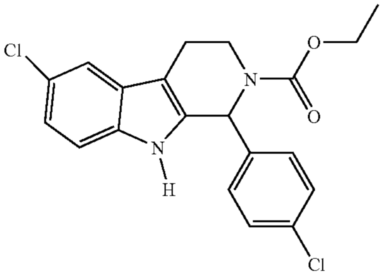

-continued
12
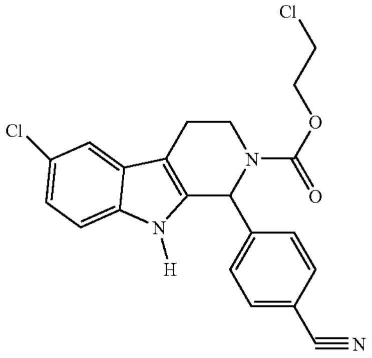
13
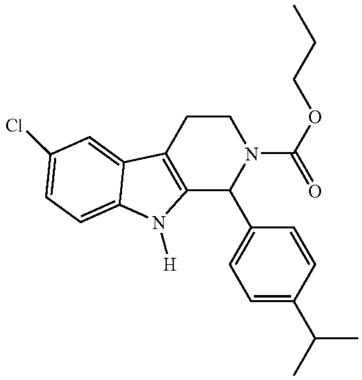
14
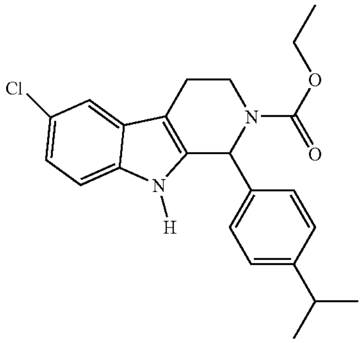
15
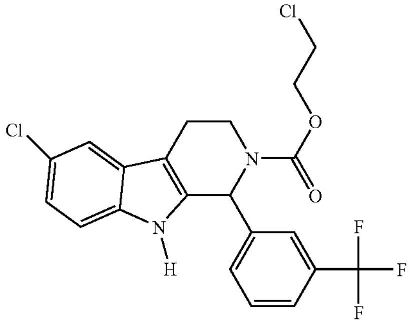
-continued
16
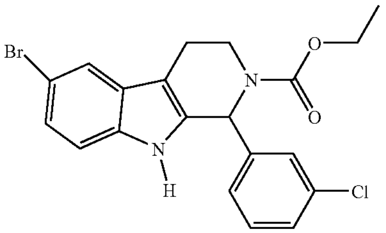
17
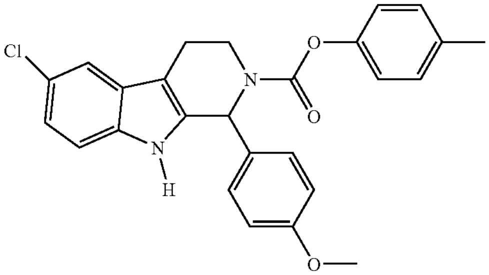
18
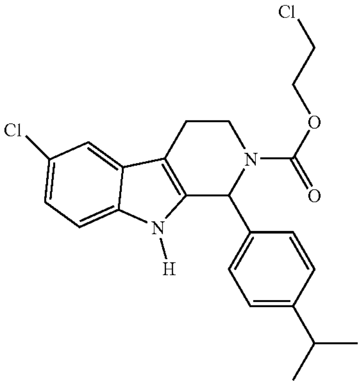
19
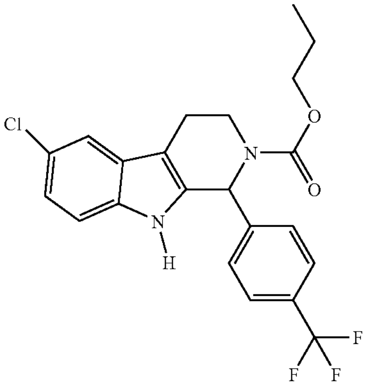
20
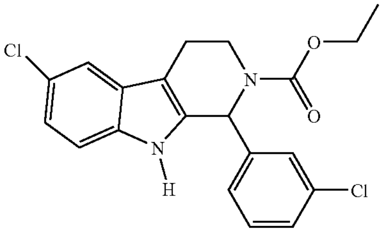

-continued
21
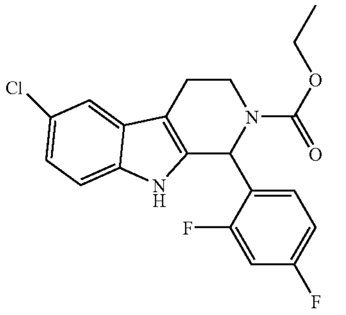
22
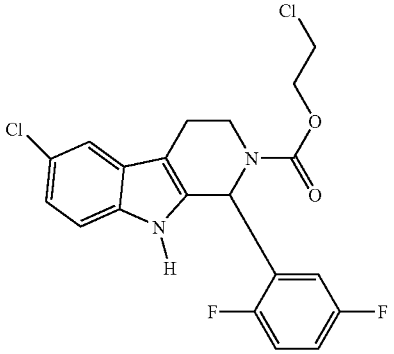
23
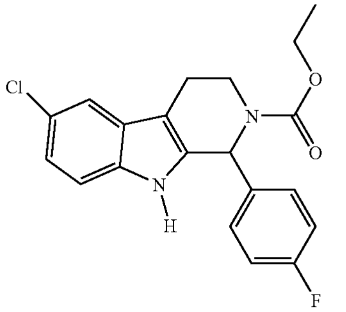
24
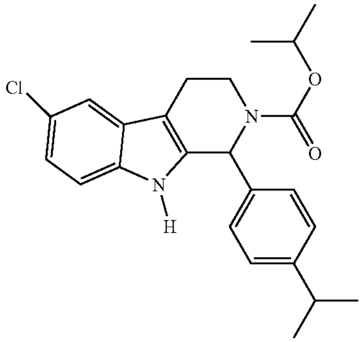
25
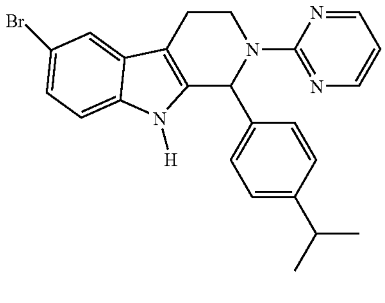
-continued
26
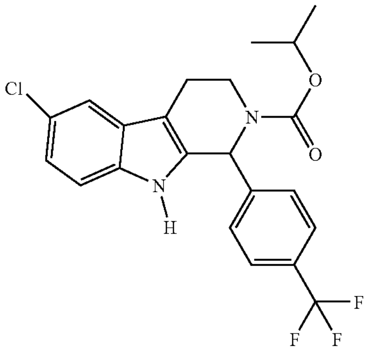
27
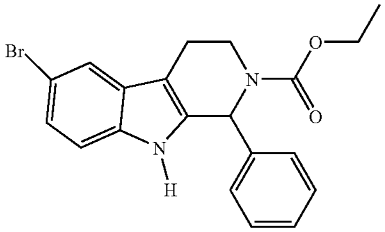
28
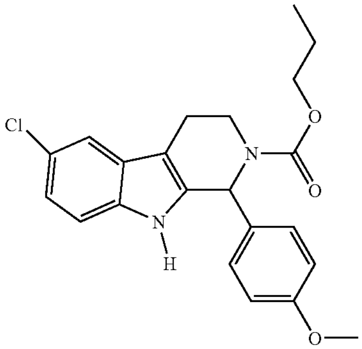
29
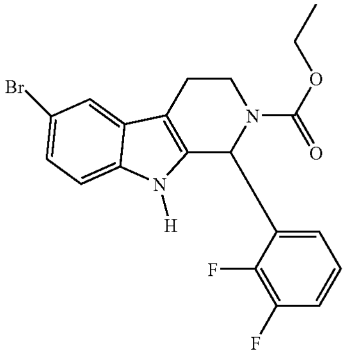
30
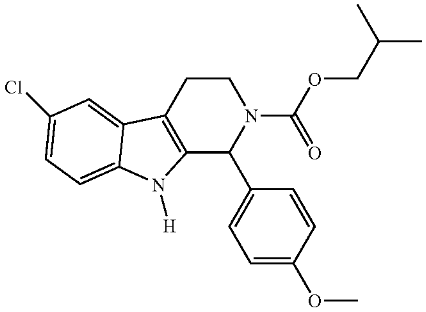

-continued
31
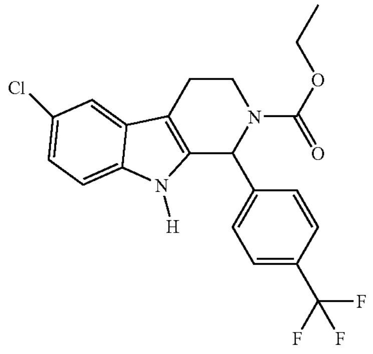
32
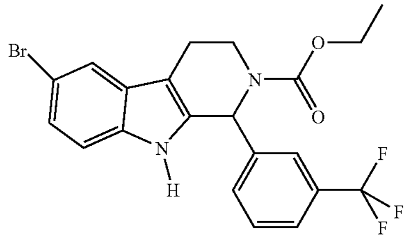
33
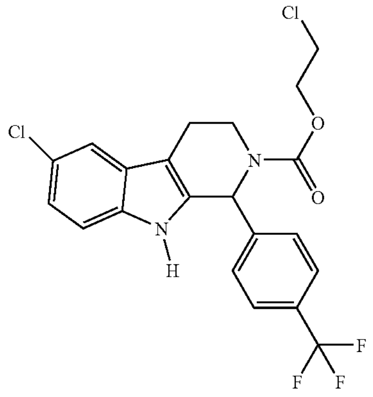
34
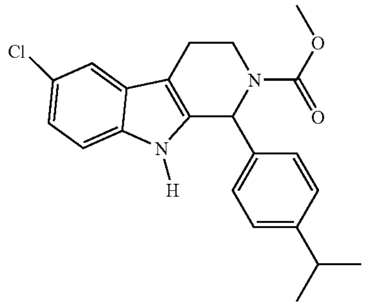
-continued
35
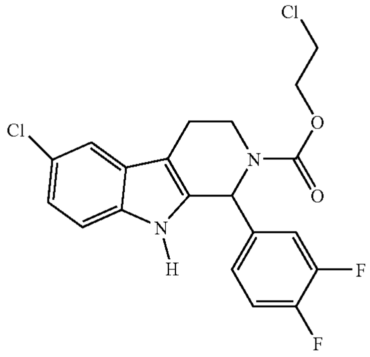
36
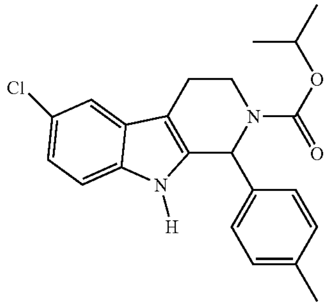
37
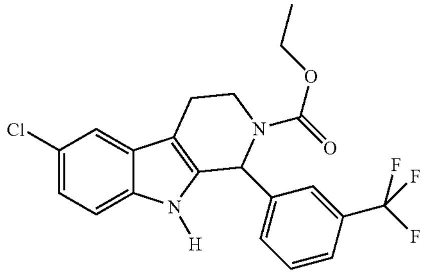
38
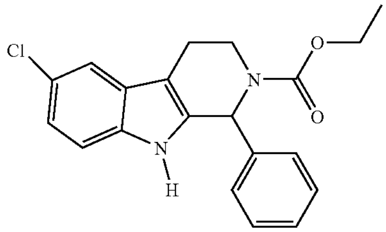
39
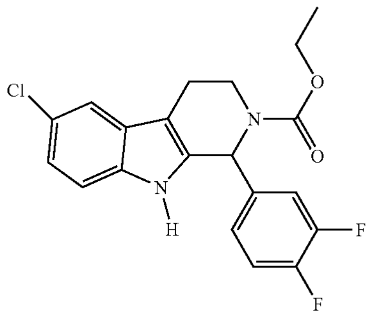

-continued
40
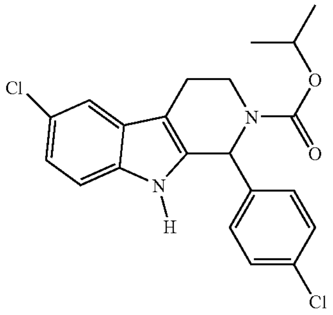
41
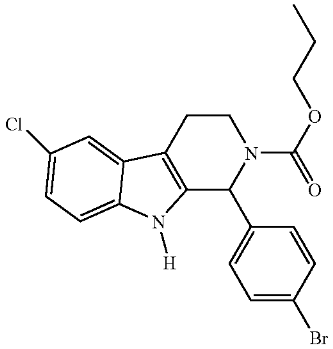
42
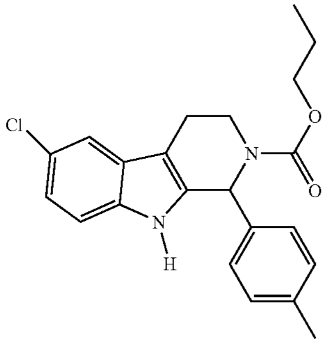
43
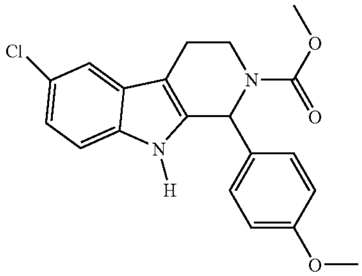
44
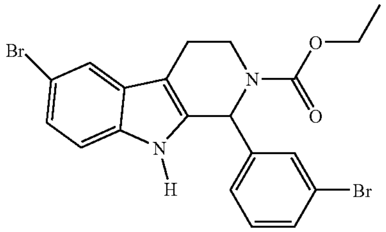
-continued
45
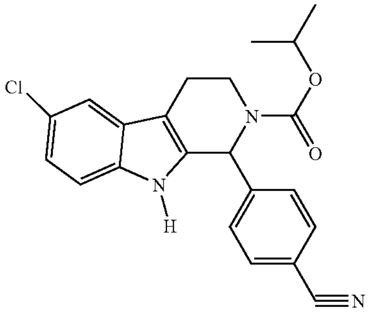
46
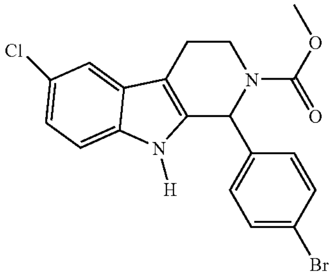
47
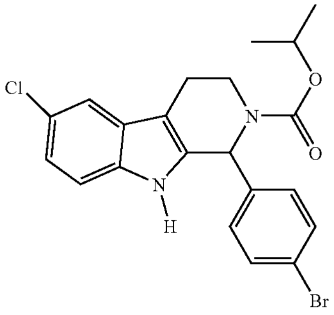
48
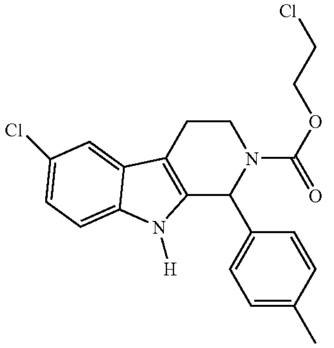
49
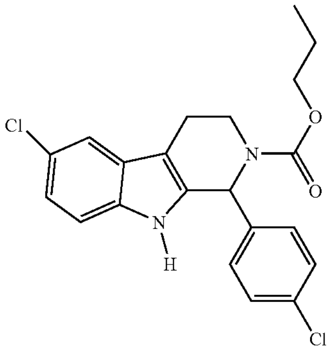

-continued
50
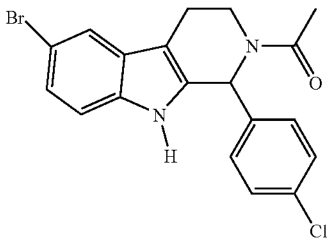
51
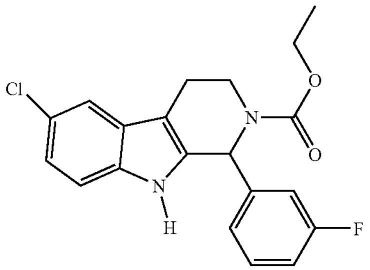
52
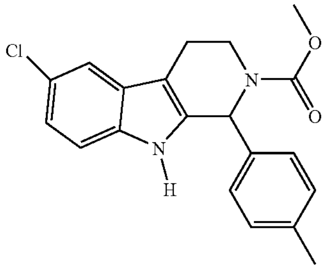
53
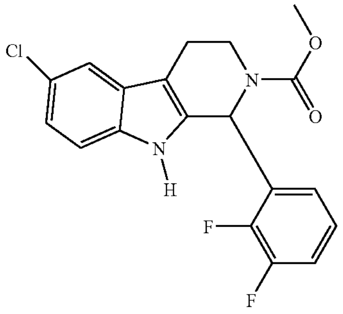
54
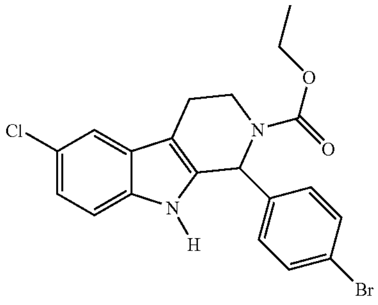
-continued
55
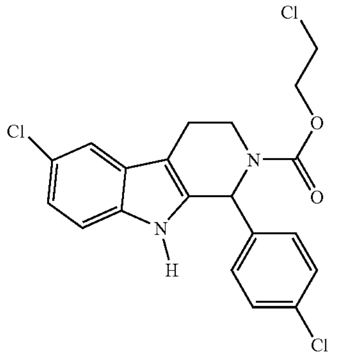
56
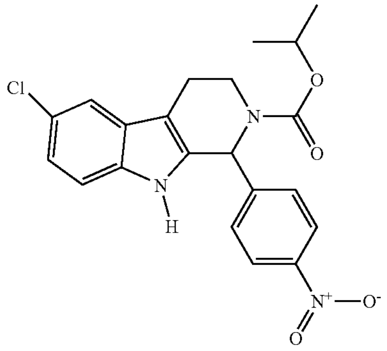
57
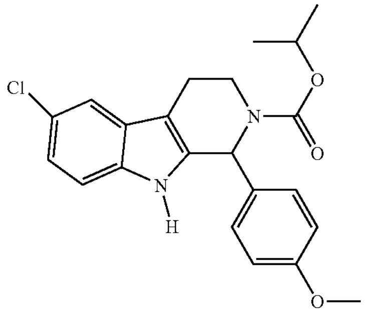
58
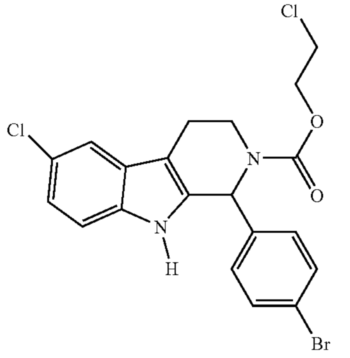

-continued
59
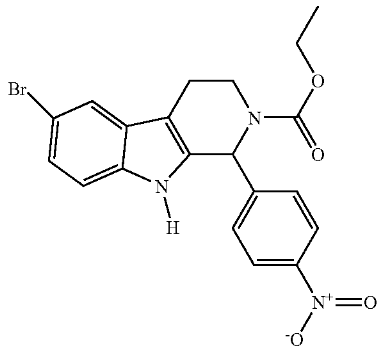
60
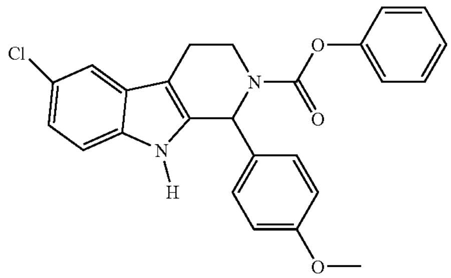
61
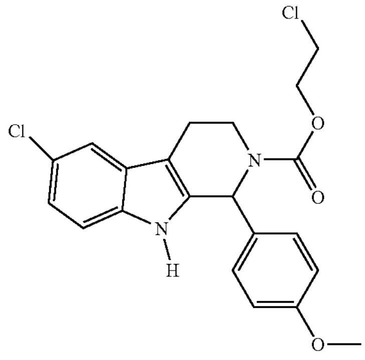
62
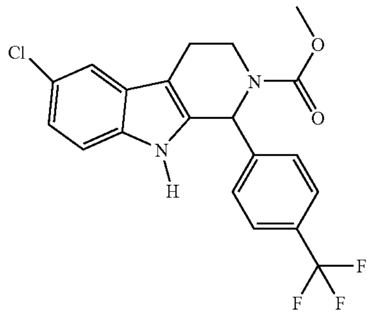
-continued
63
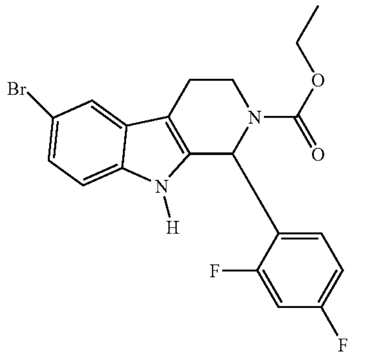
64
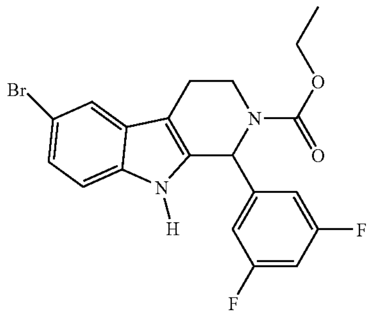
65
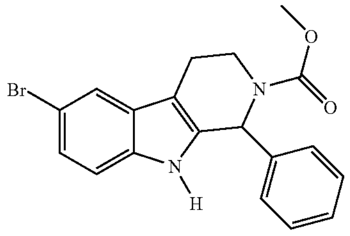
66
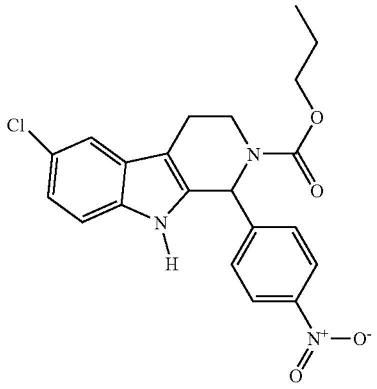
67
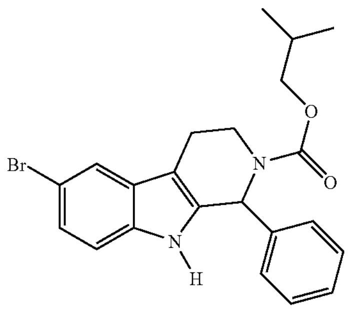

-continued
68
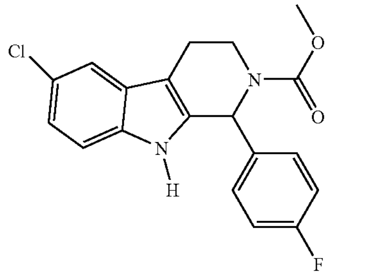
69
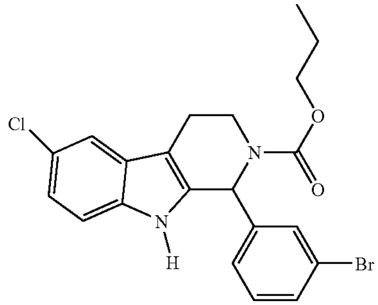
70
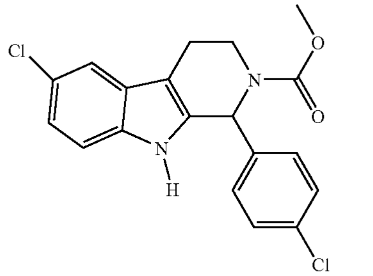
71
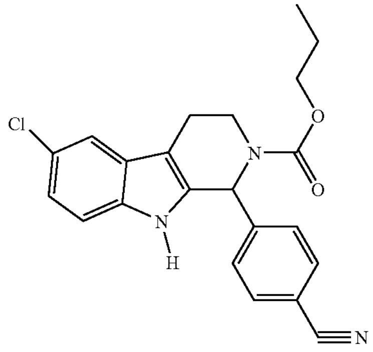
72
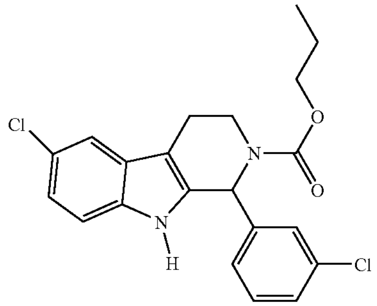
-continued
73
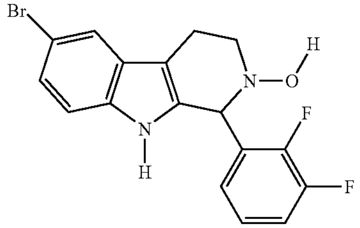
74
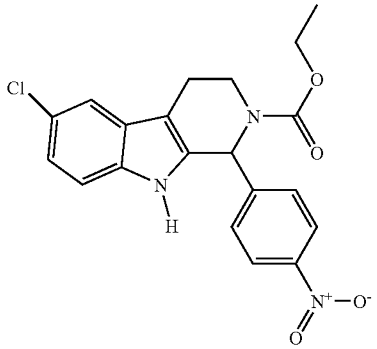
75
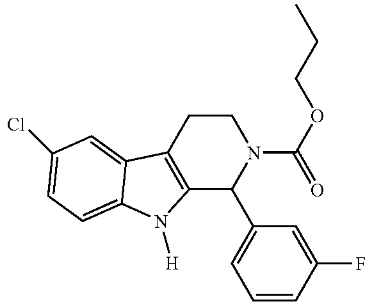
76
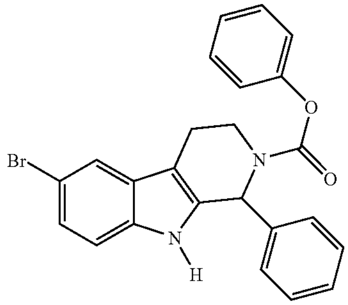
77
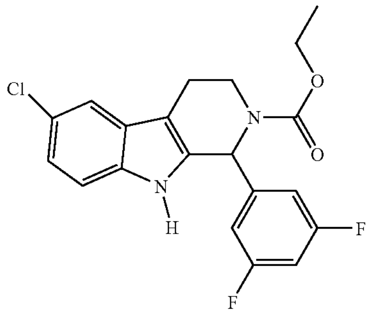

-continued
78
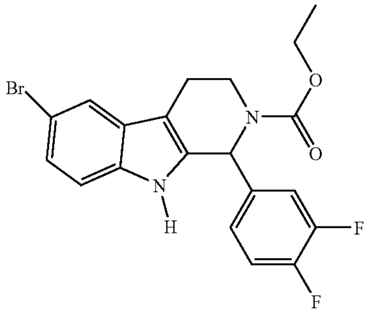
79
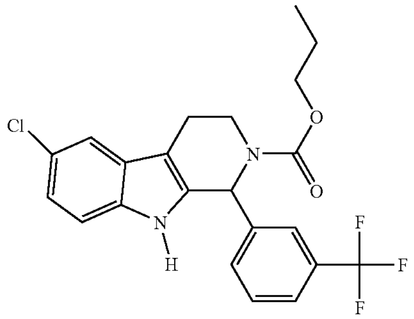
80
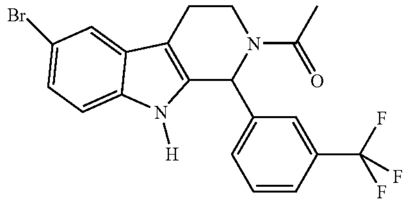
81
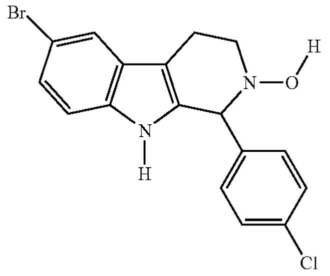
82
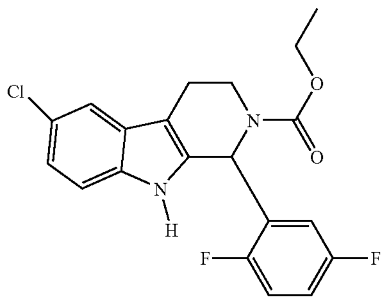
-continued
83
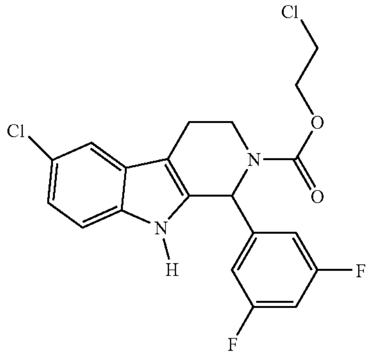
84
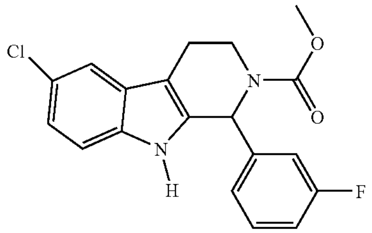
85
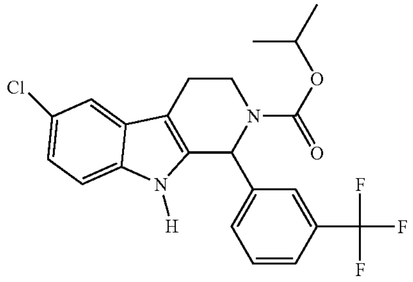
86
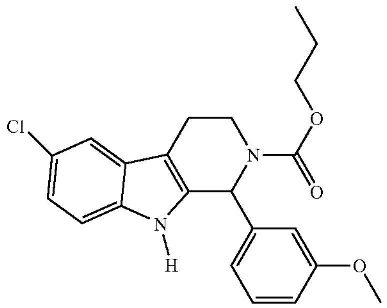
87
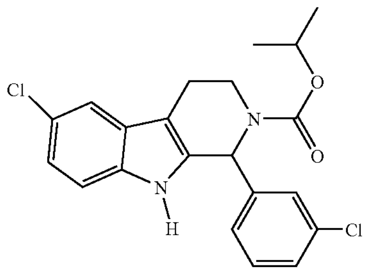

-continued
88
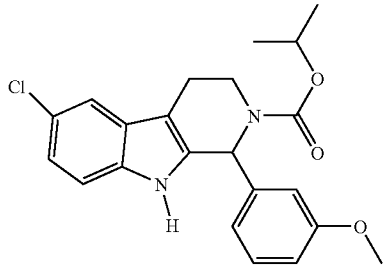
89
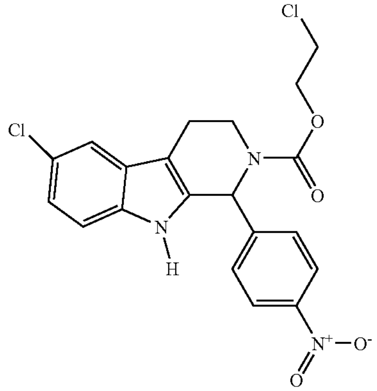
90
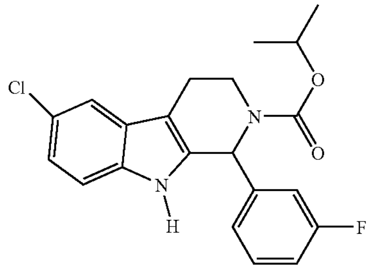
91
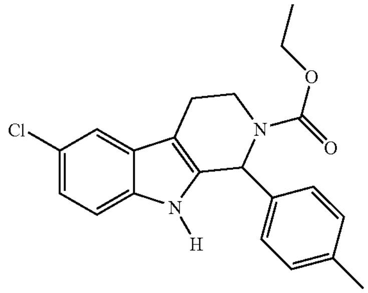
92
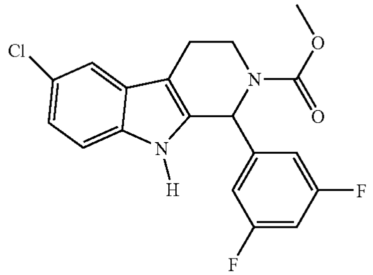
-continued
93
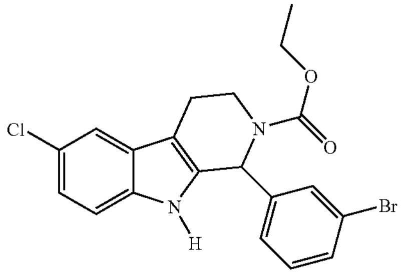
94
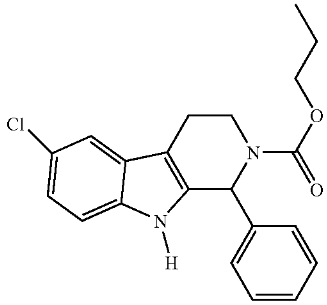
95
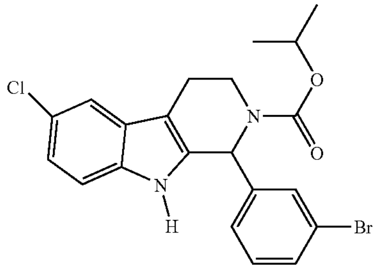
96
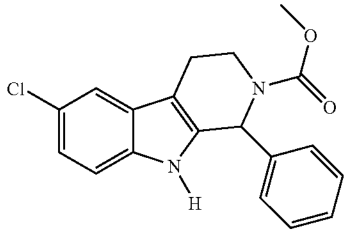
97
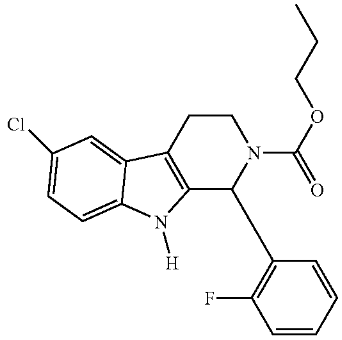

-continued
98
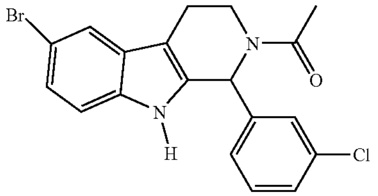
99
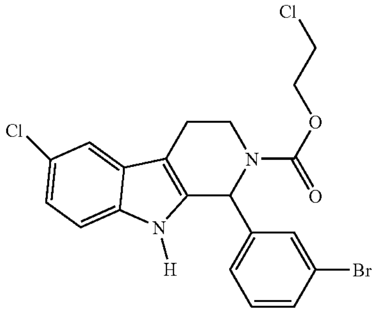
100
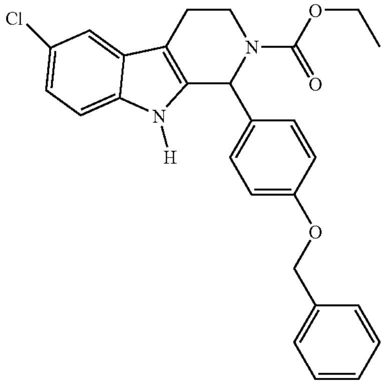
101
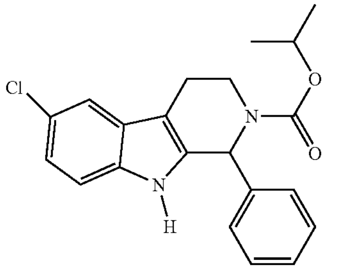
102
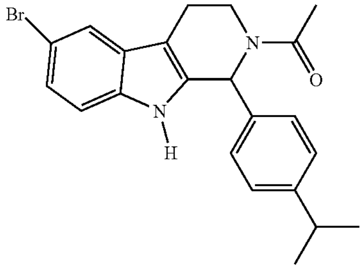
-continued
103
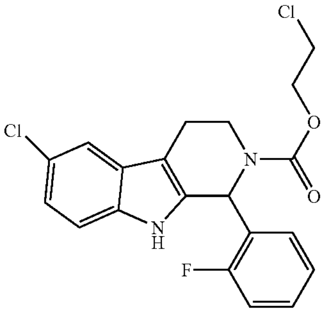
104
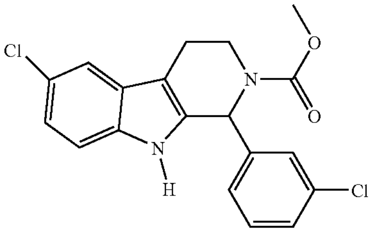
105
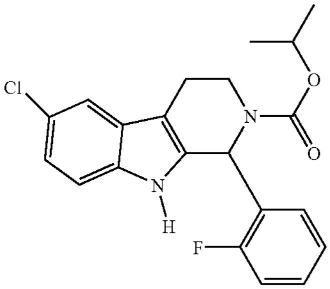
106
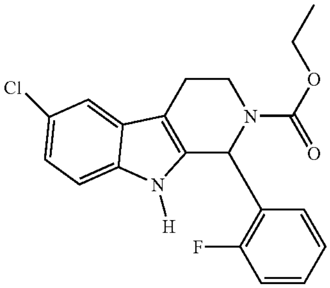
107
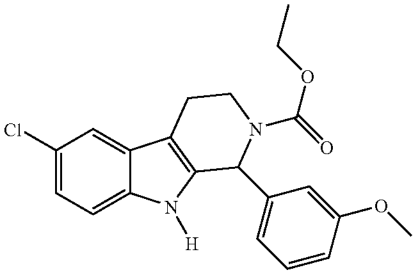

-continued
108
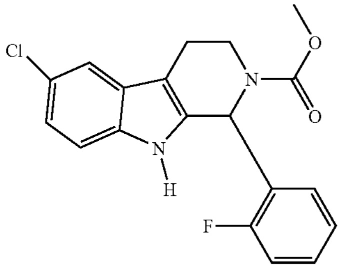
109
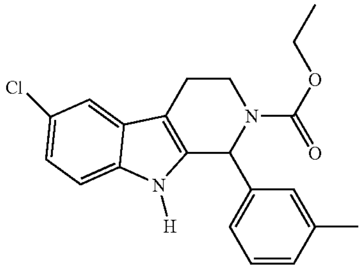
110
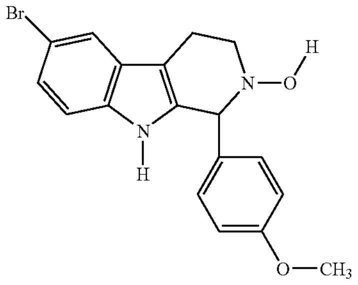
111
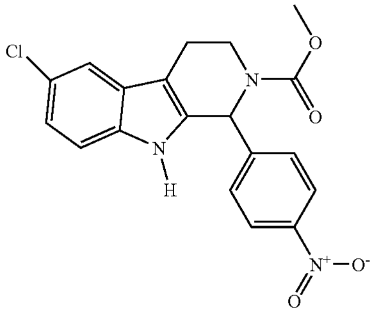
112
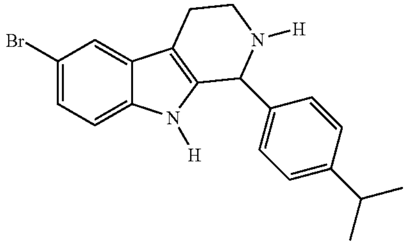
-continued
113
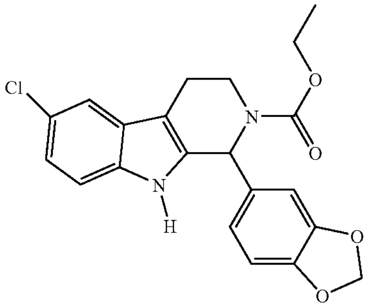
114
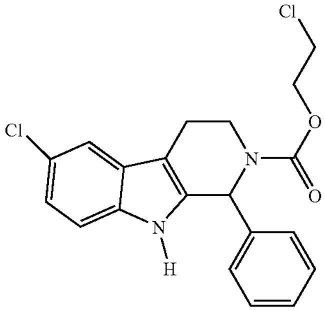
115
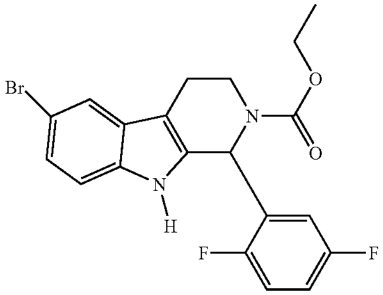
116
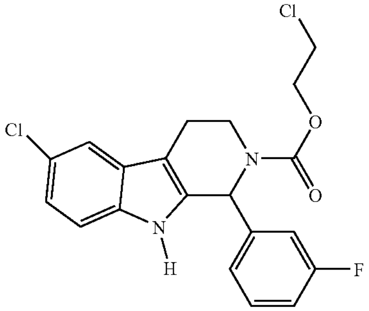
117
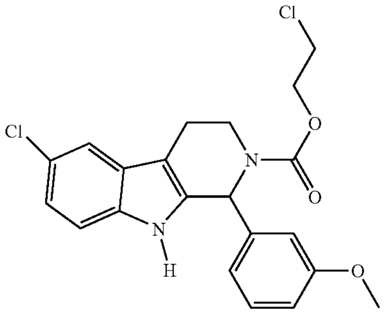

-continued
118
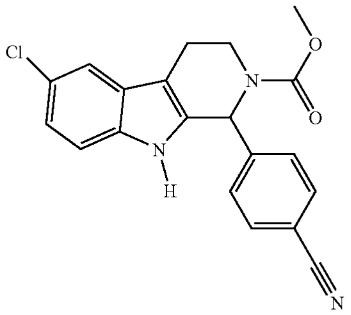
119
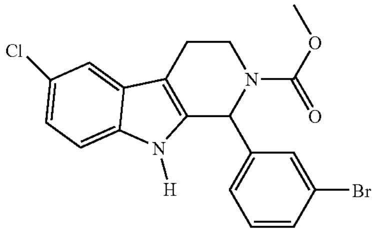
120
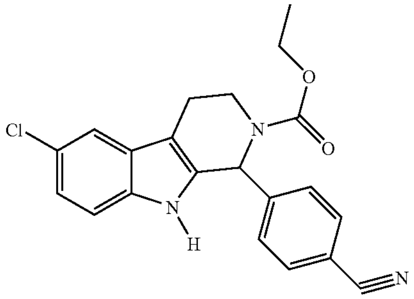
121
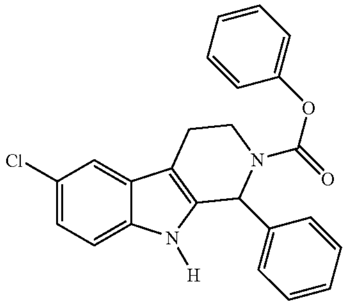
122
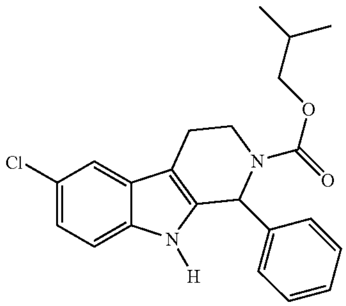
-continued
123
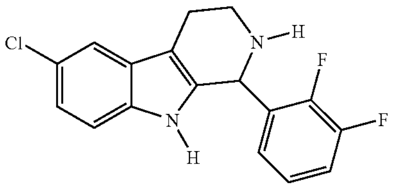
124
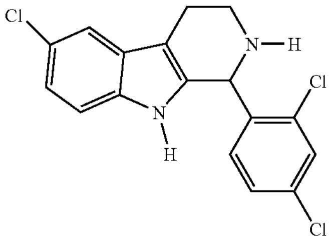
125
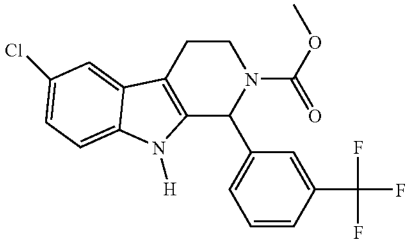
126
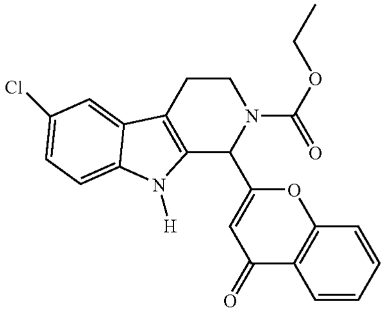
127
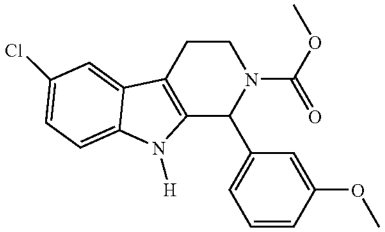
128
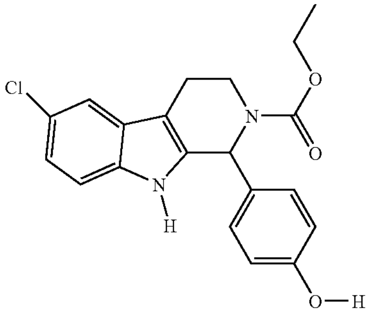

-continued
129
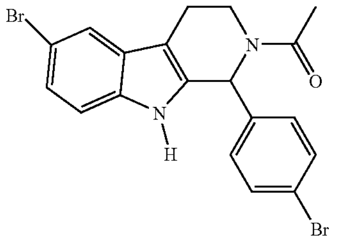
130
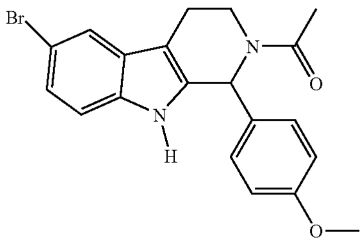
131
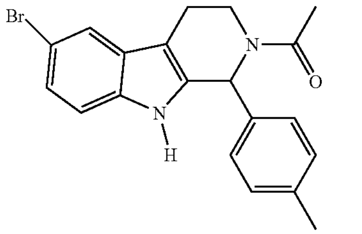
132
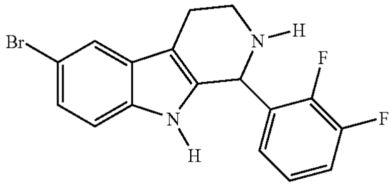
133
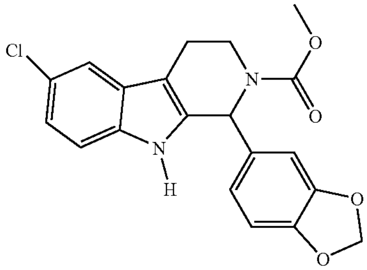
134
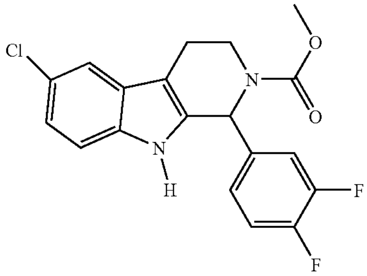
-continued
135
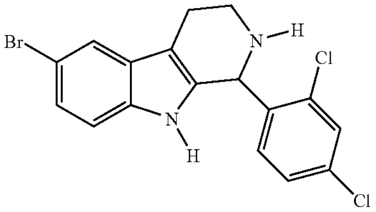
136
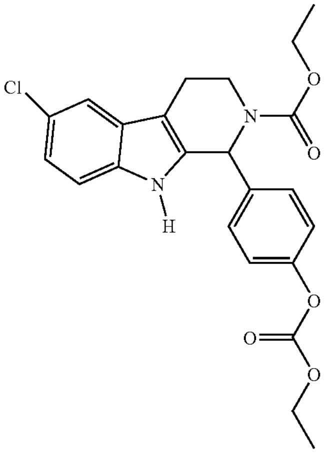
137
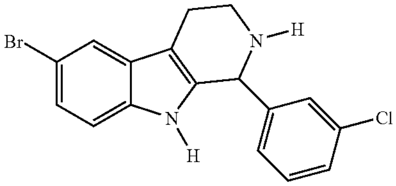
138
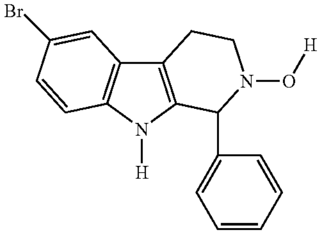
139
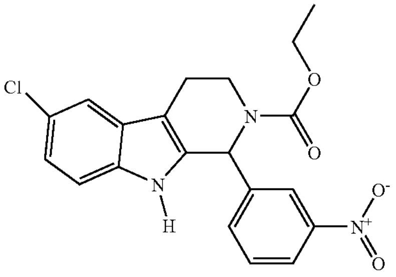
140
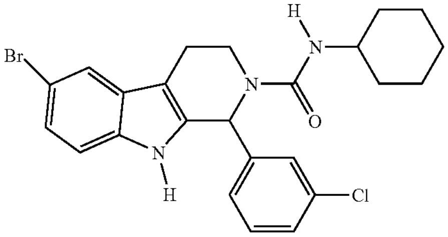

-continued
141
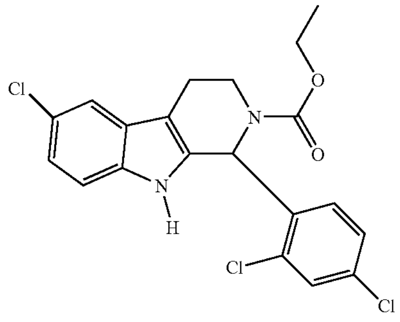
142
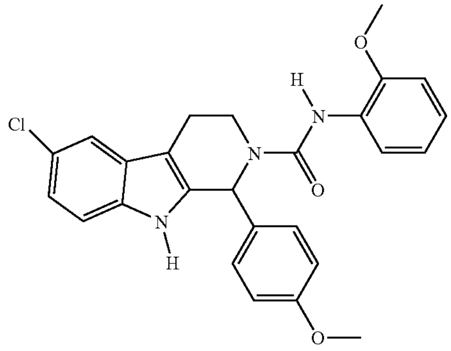
143
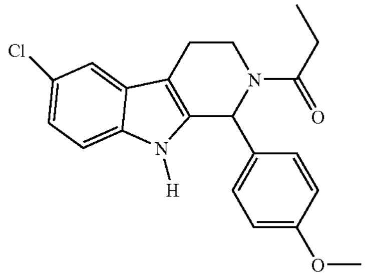
144
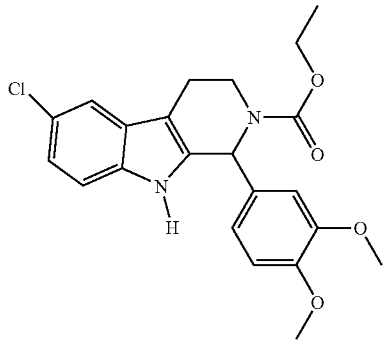
145
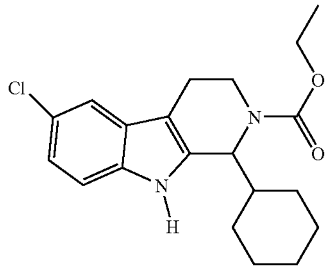
-continued
146
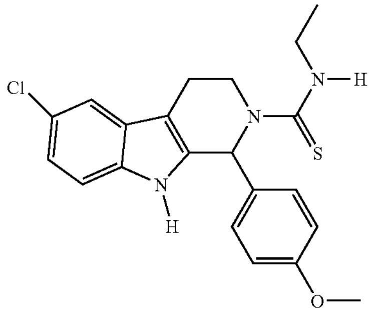
147
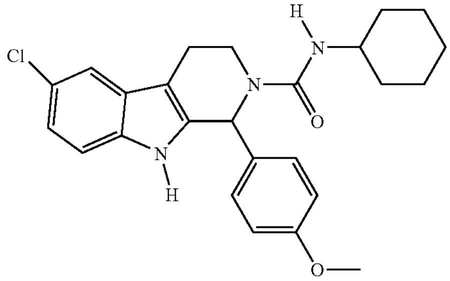
148
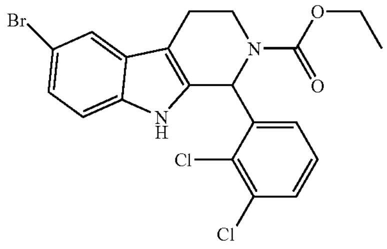
149
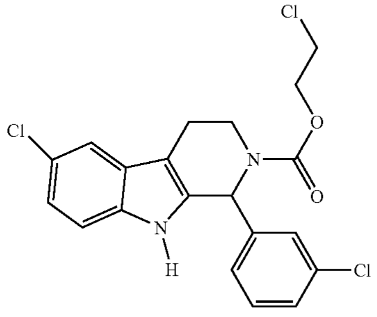
150
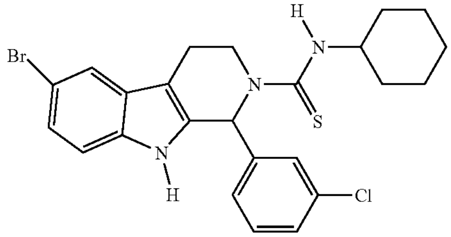
151
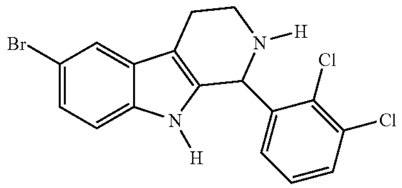

-continued
152
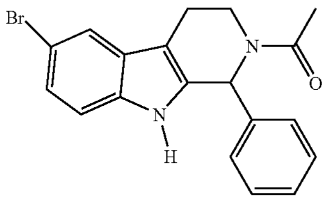
153
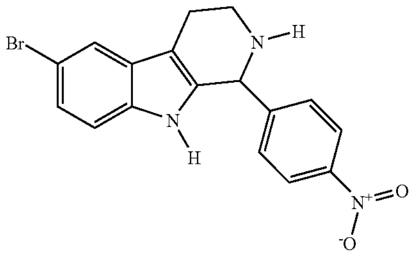
154
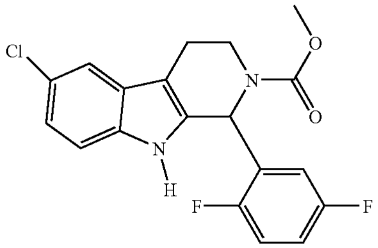
155
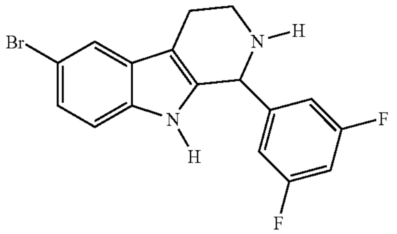
156
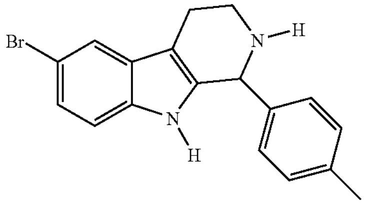
157
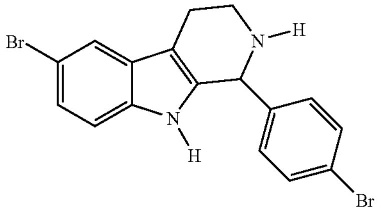
158
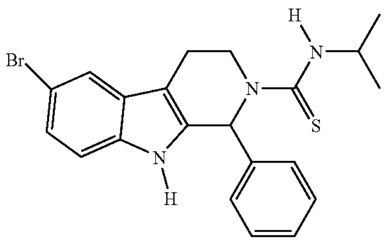
-continued
159
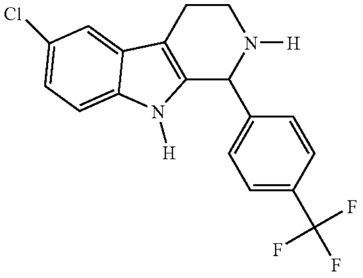
160
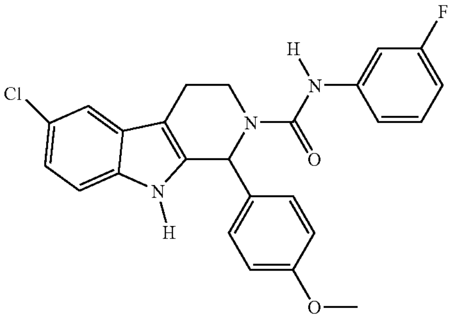
161
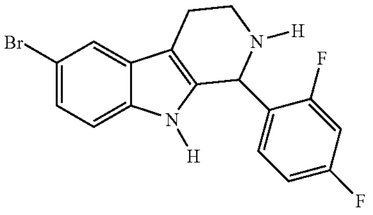
162
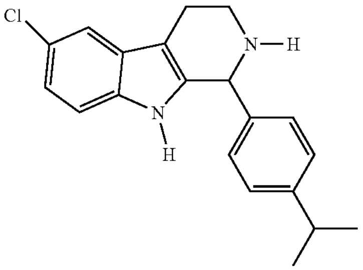
163
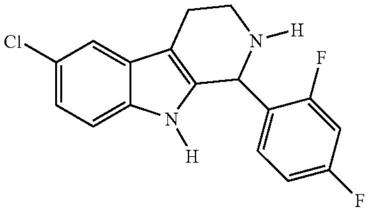

-continued
164
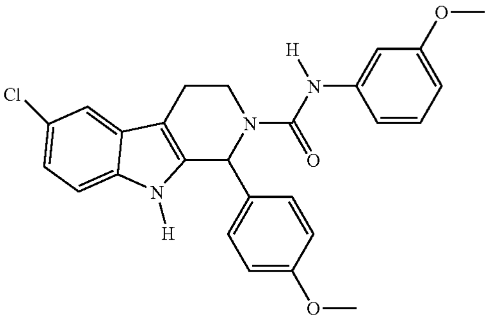
165
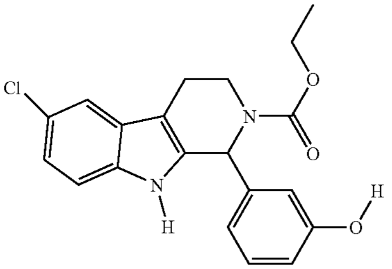
166
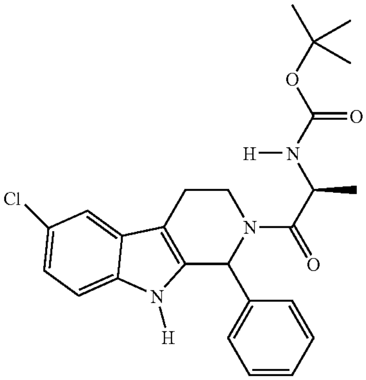
167
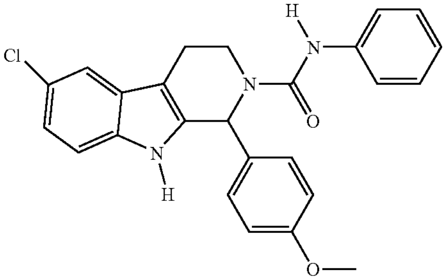
168
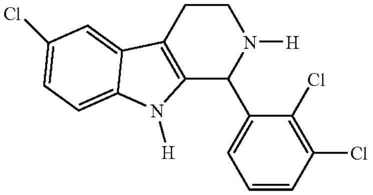
-continued
169
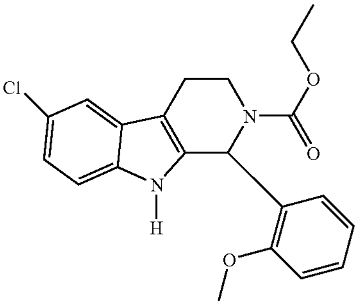
170
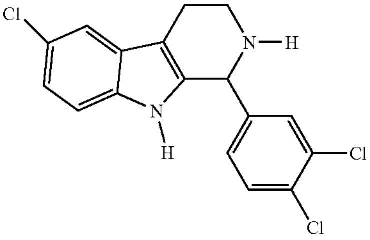
171
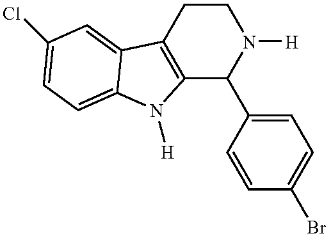
172
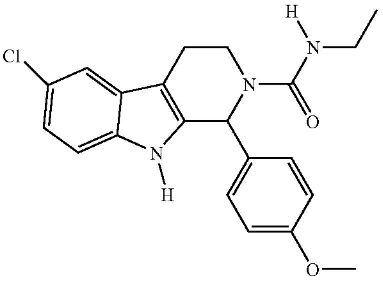
173
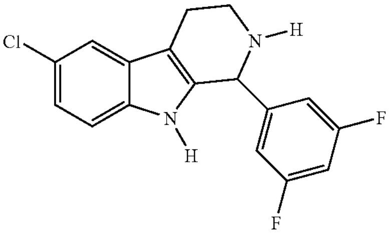
174
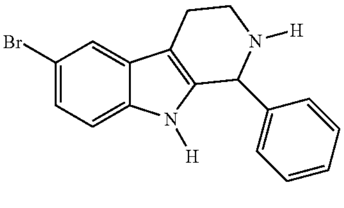

-continued
175
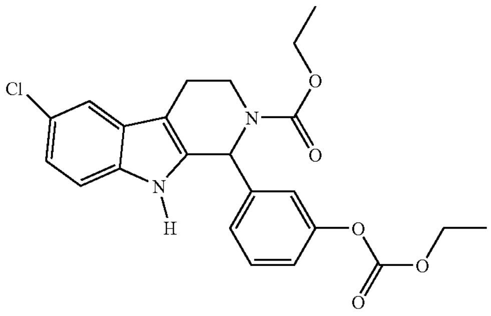
176
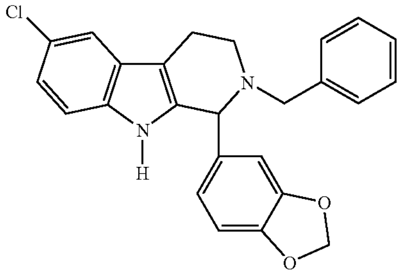
177
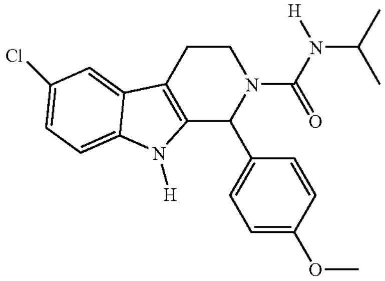
178
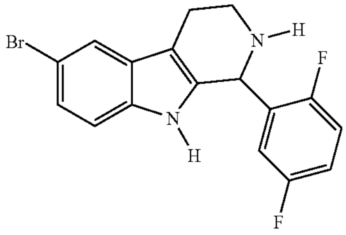
179
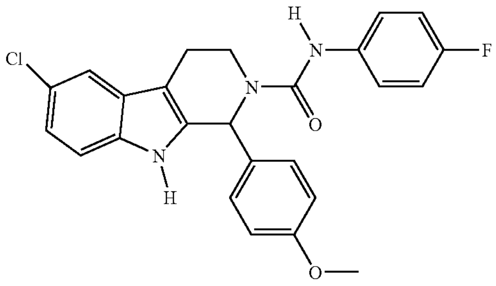
-continued
180
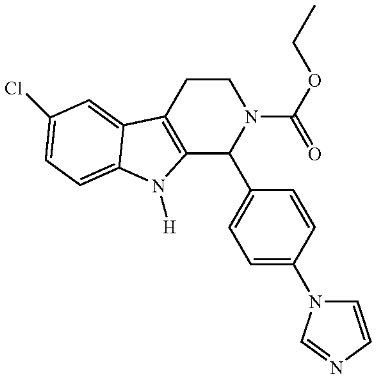
181
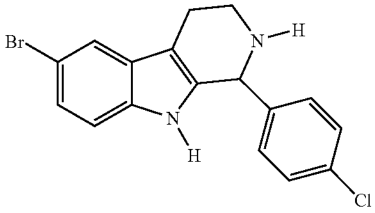
182
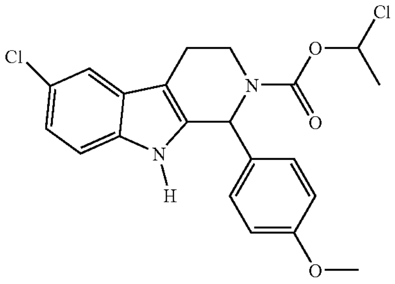
183
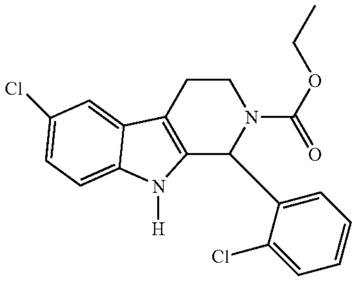
184
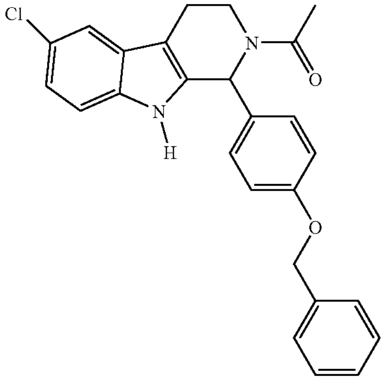

-continued
185
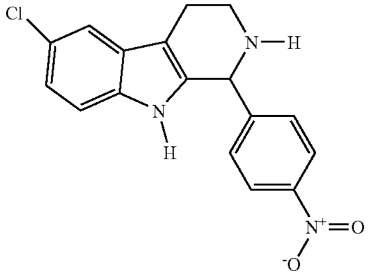
186
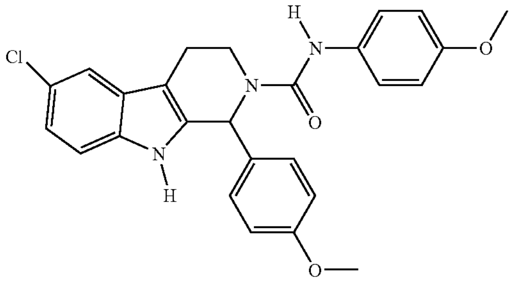
187
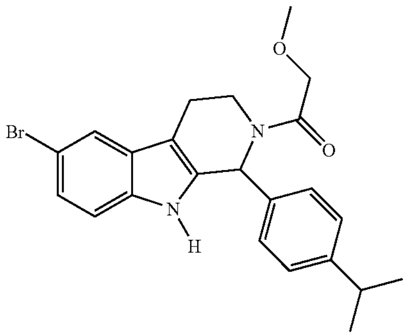
188
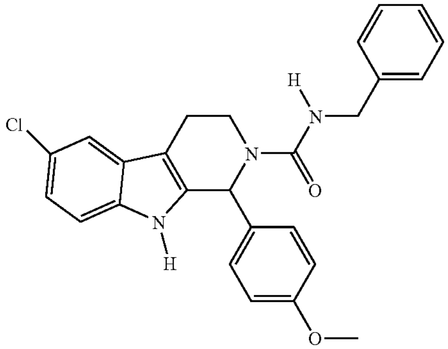
189
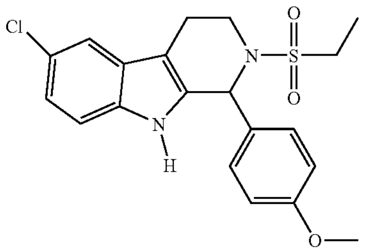
-continued
190
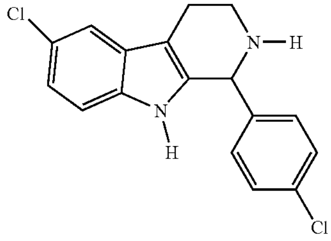
191
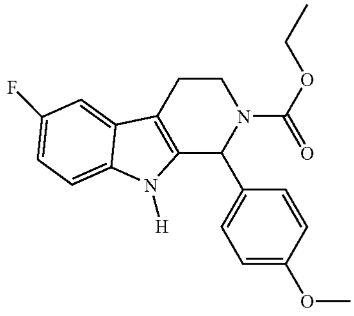
192
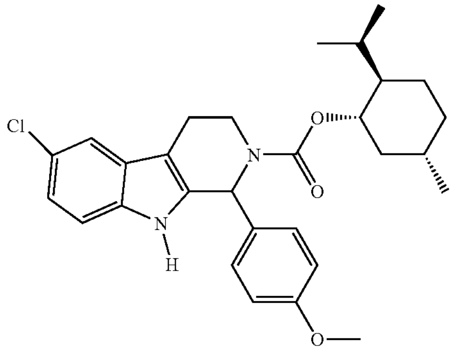
193
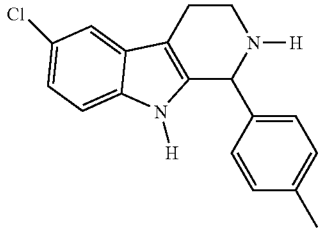
194
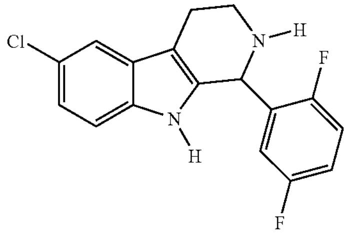

-continued
195
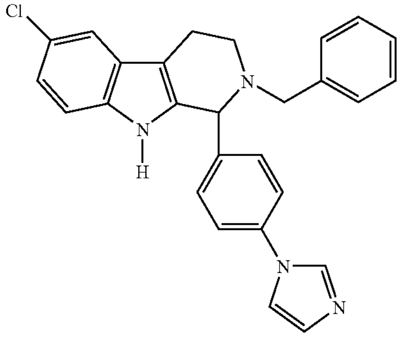
196
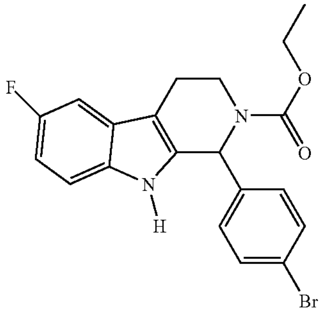
197
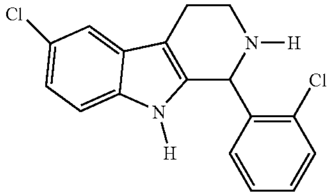
198
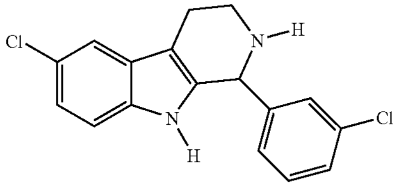
199
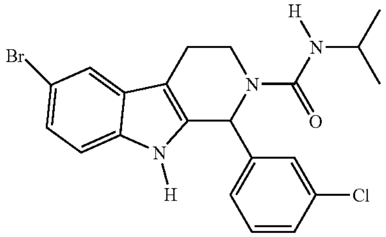
200
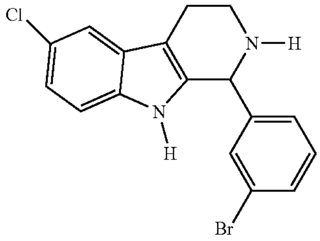
-continued
201
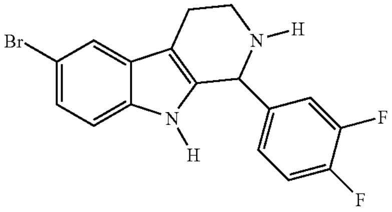
202
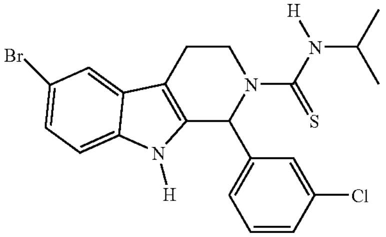
203
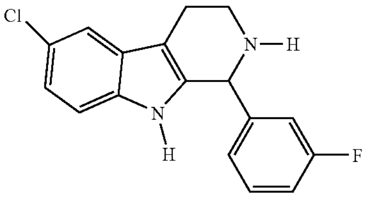
204
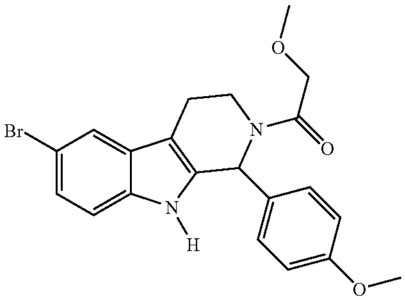
205
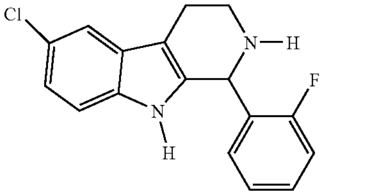
206
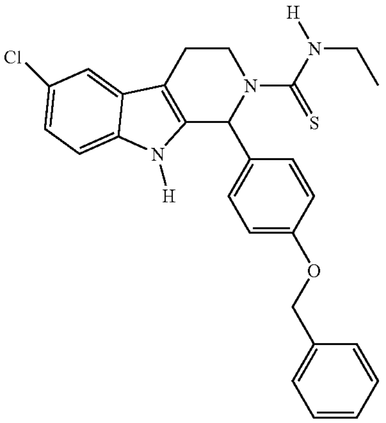

-continued
207
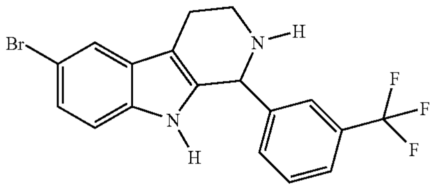
208
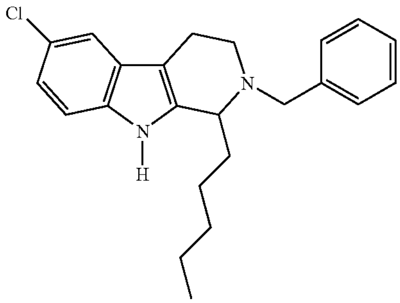
209
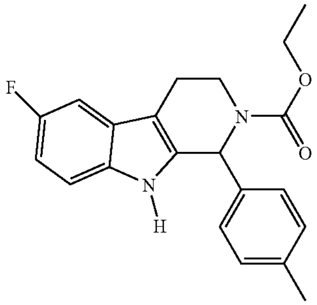
210
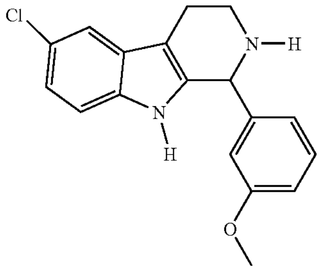
211
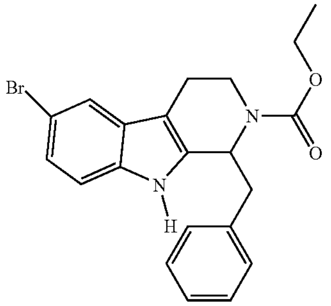
-continued
212
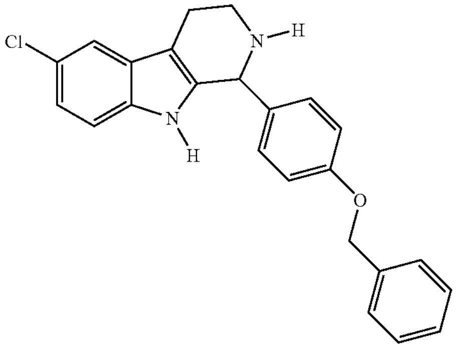
213
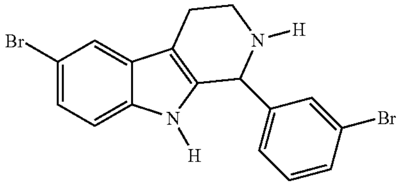
214
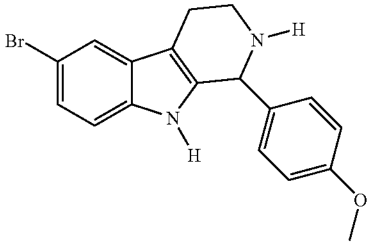
215
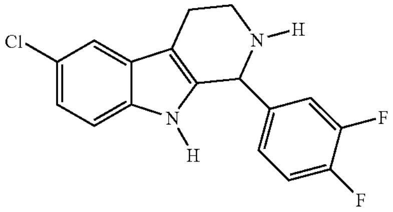
216
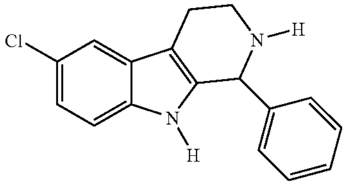
217
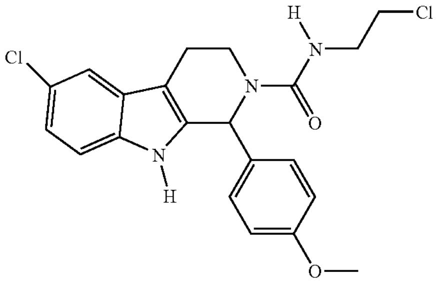

-continued
218
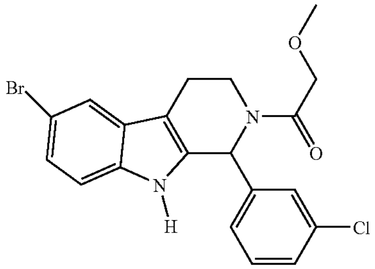
220
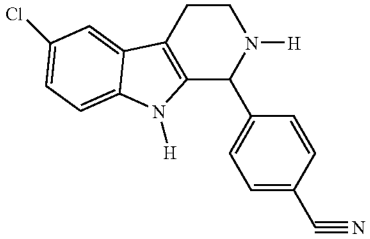
221
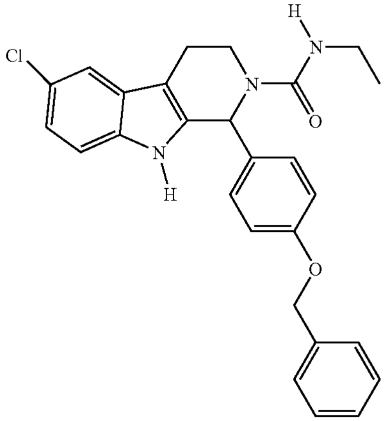
222
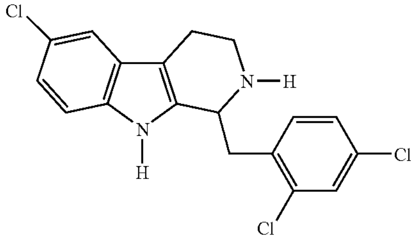
223
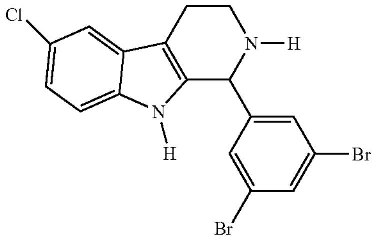
-continued
224
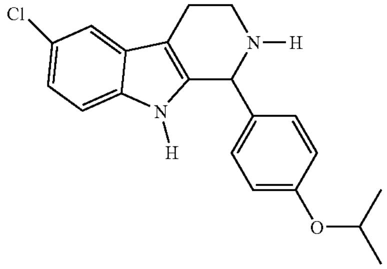
225
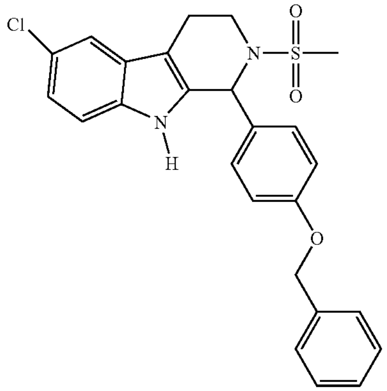
226
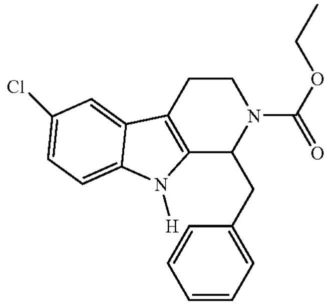
227
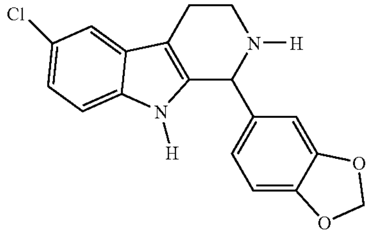
228
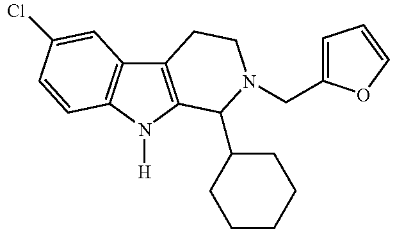

-continued
229
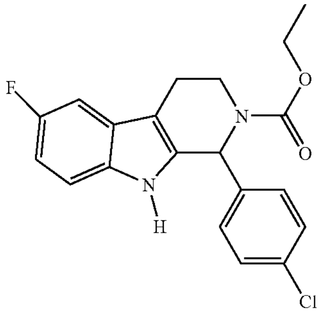
230
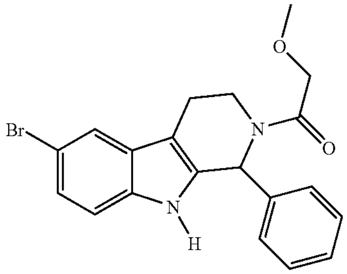
231
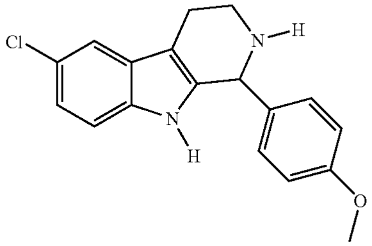
232
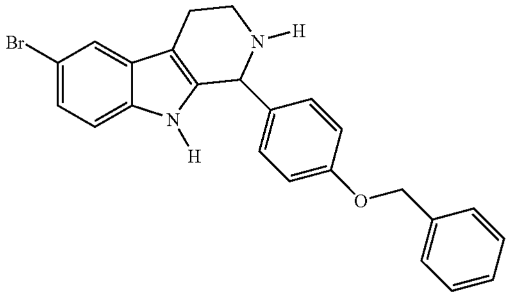
233
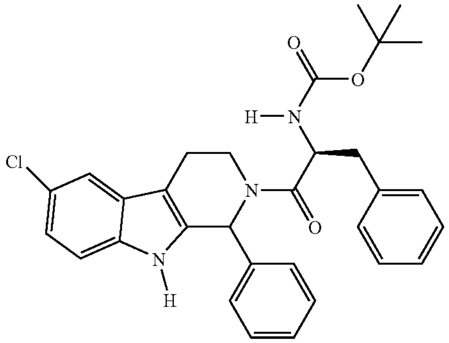
-continued
234
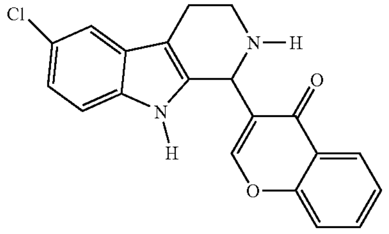
235
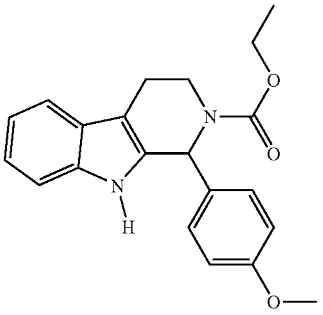
236
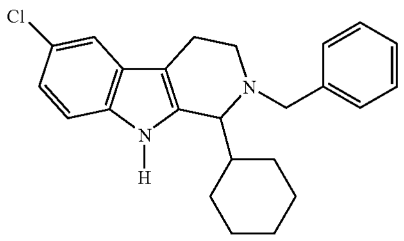
237
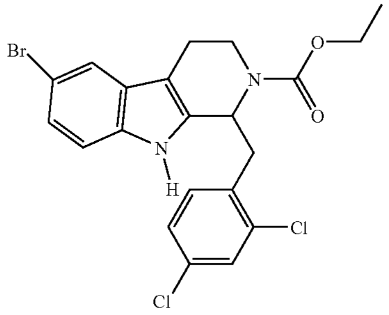
238
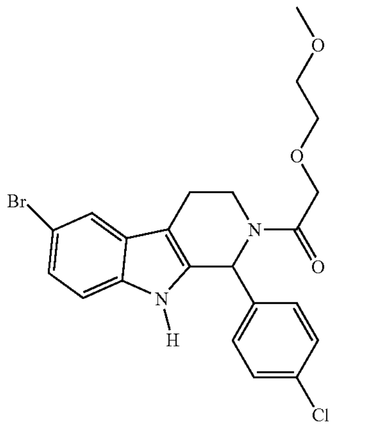

-continued
239
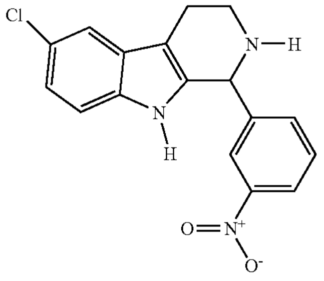
240
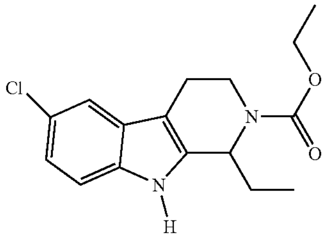
241
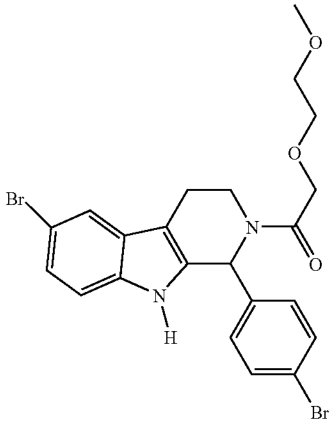
242
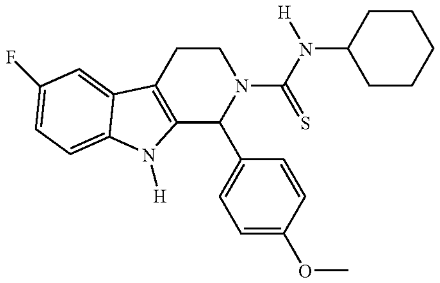
243
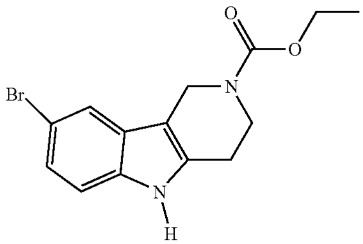
-continued
244
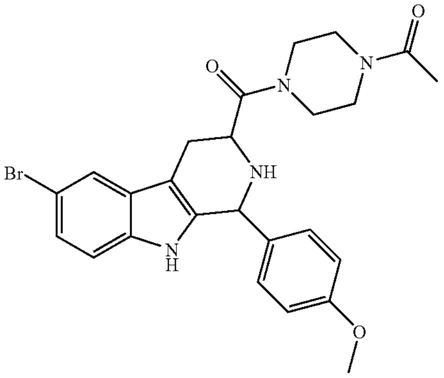
245
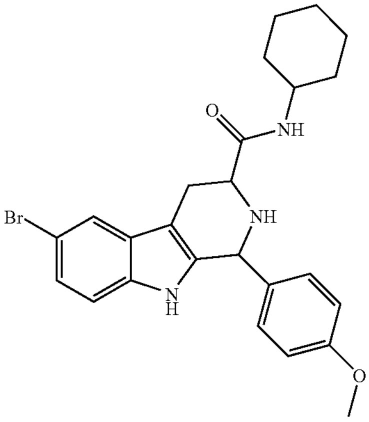
246
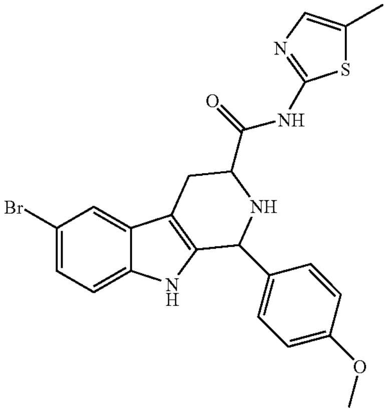
247
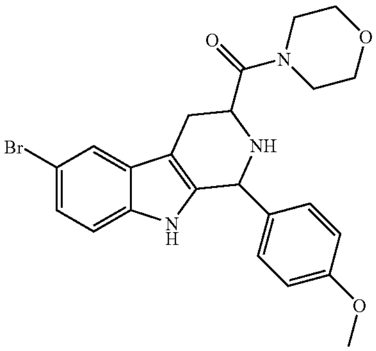

-continued
248
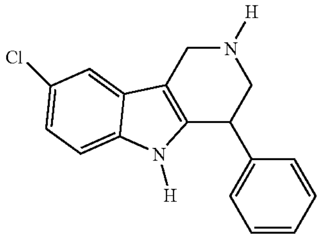
249
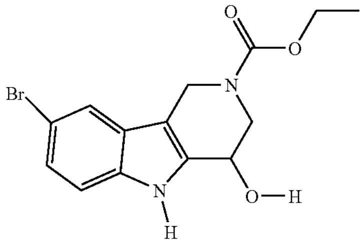
250
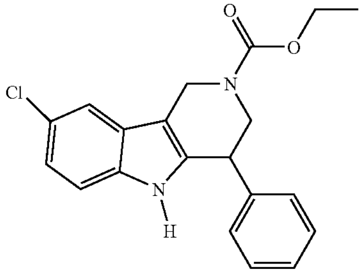
251
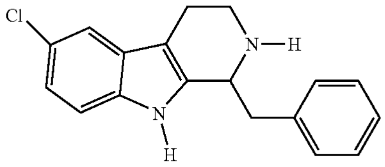
252
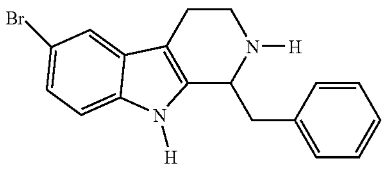
253
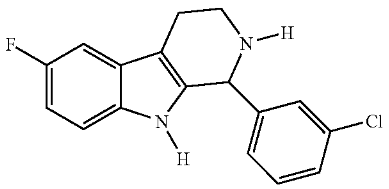
254
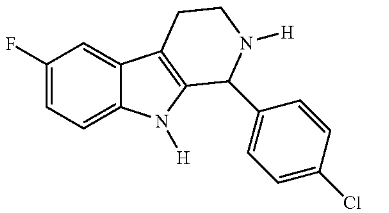
-continued
255
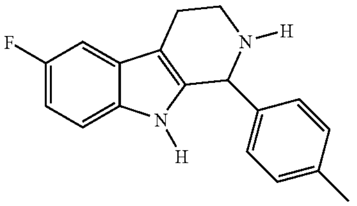
256
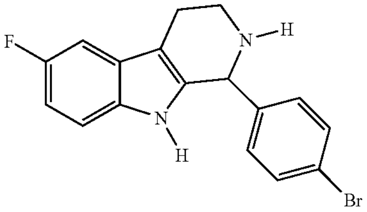
257
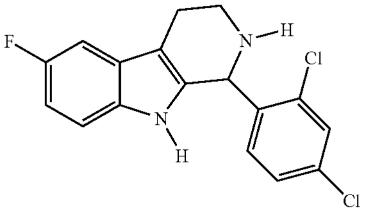
258
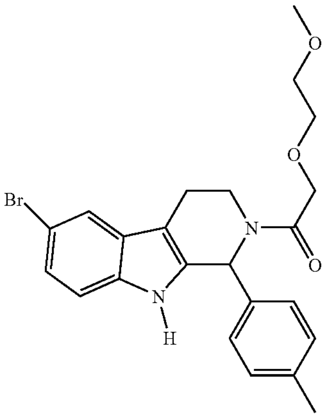
259
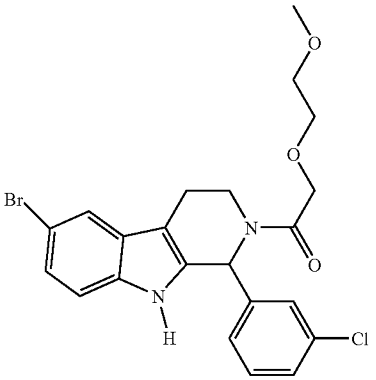

-continued
260
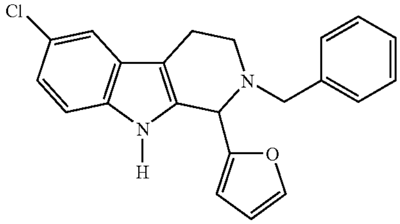
261
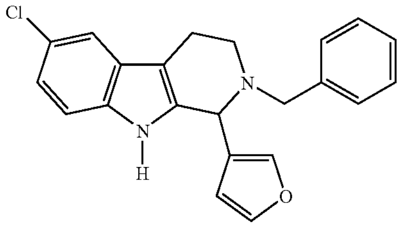
262
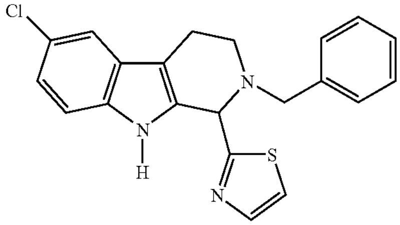
263
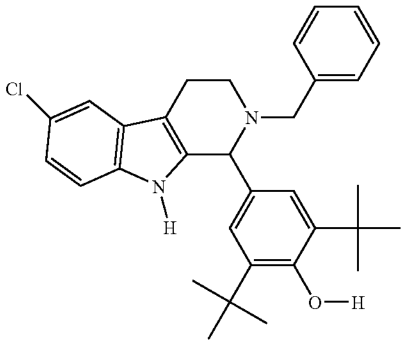
264
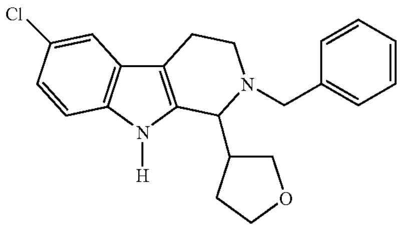
265
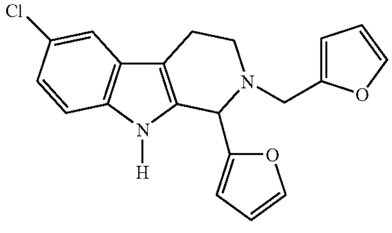
-continued
266
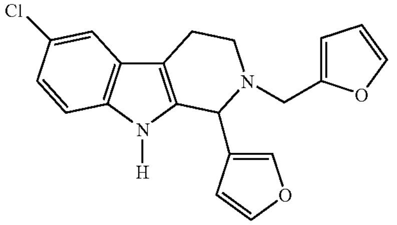
267
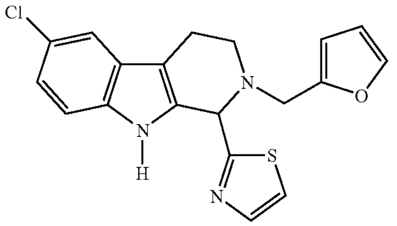
268
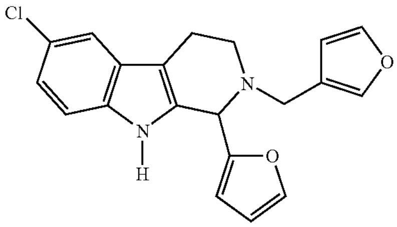
269
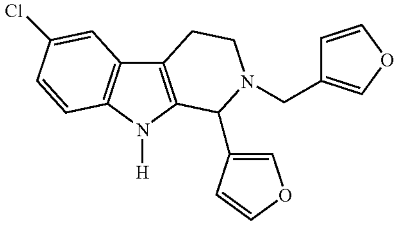
270
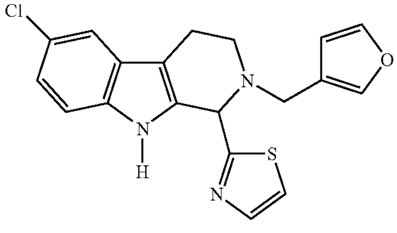
271
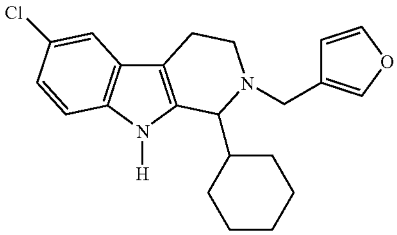

-continued
272
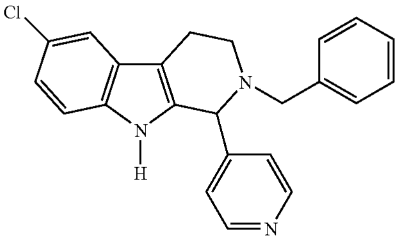
273
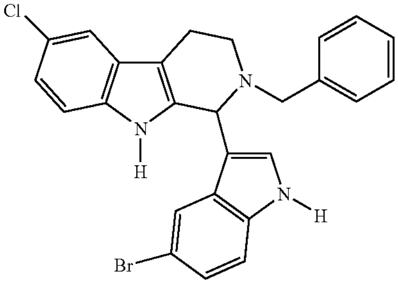
274
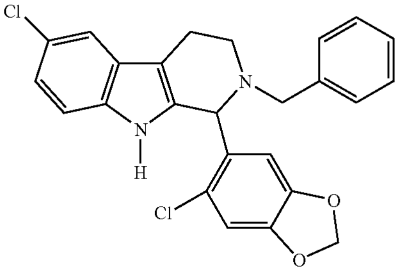
275
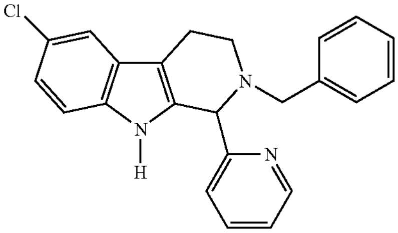
276
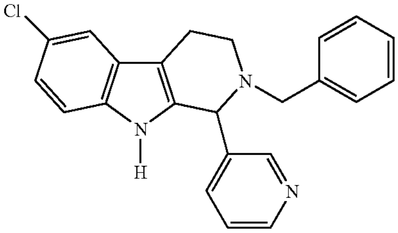
277
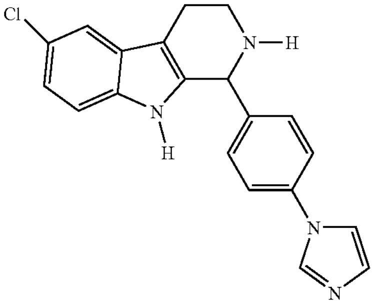
-continued
278
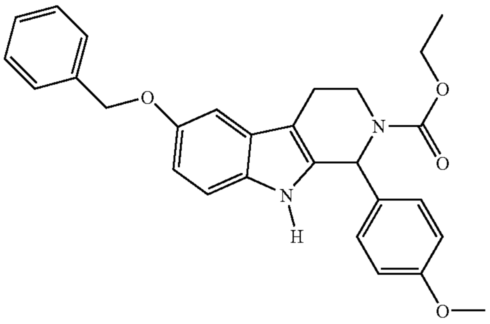
279
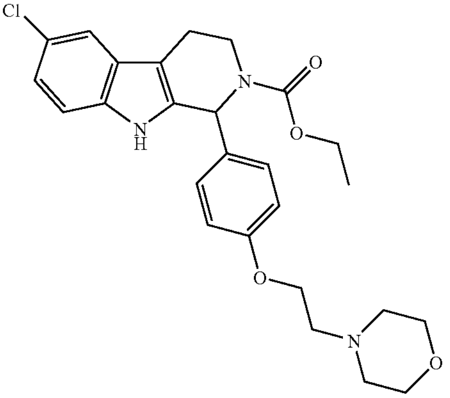
280
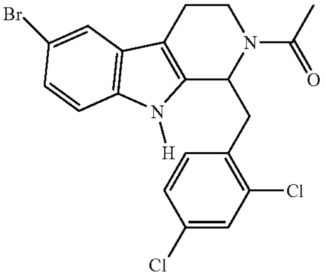
281
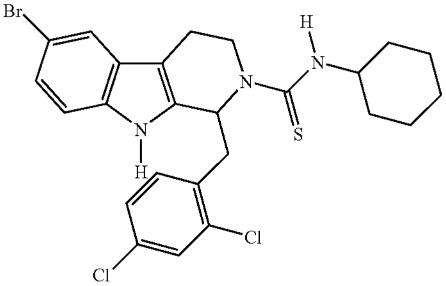
282
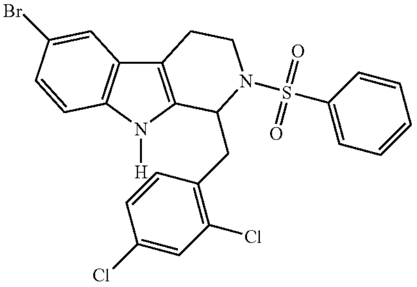

-continued
283
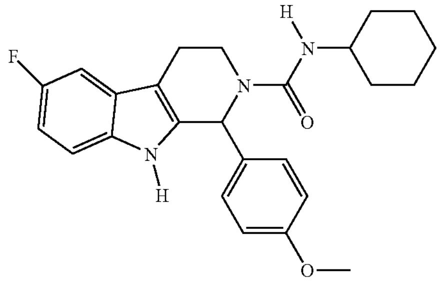
284
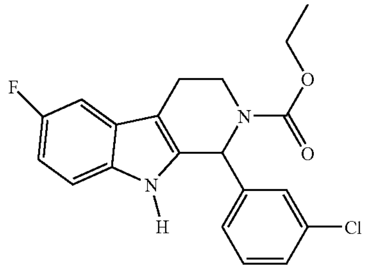
285
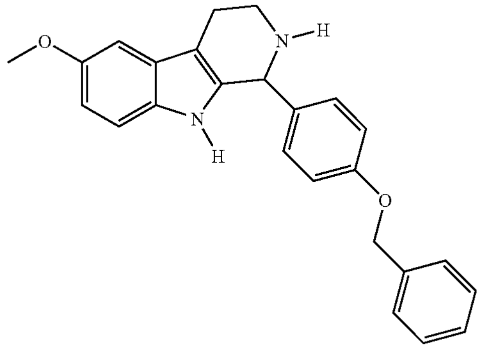
286
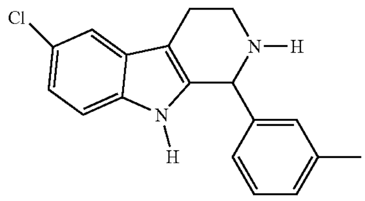
287
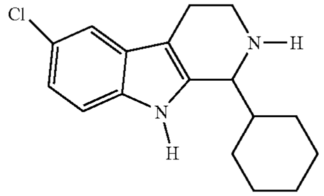
-continued
288
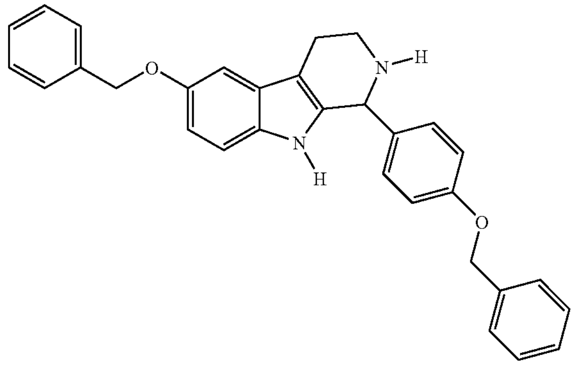
289
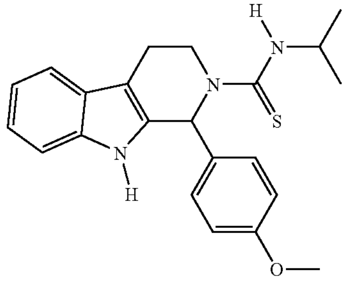
290
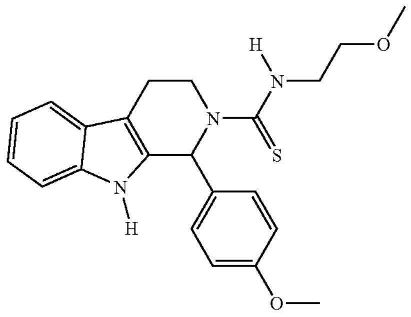
291
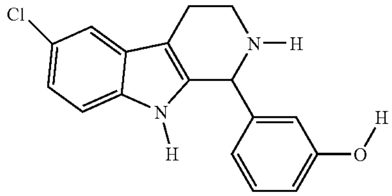
292
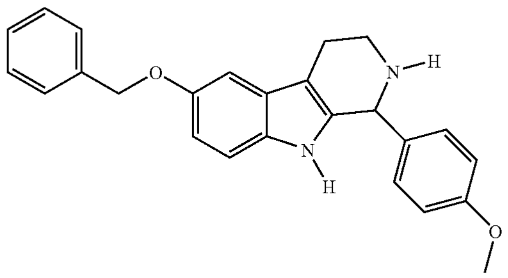

-continued
293
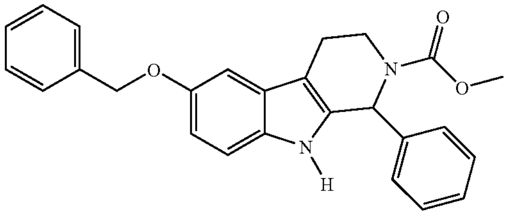
294
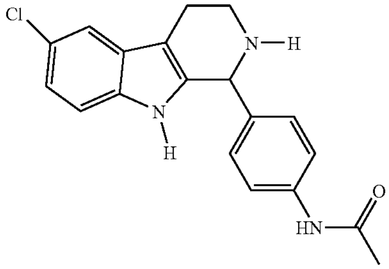
295
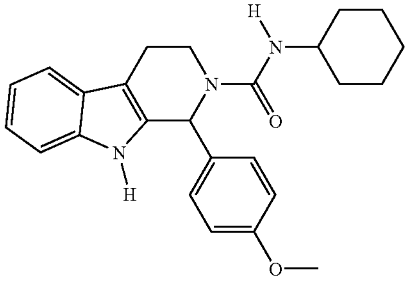
296
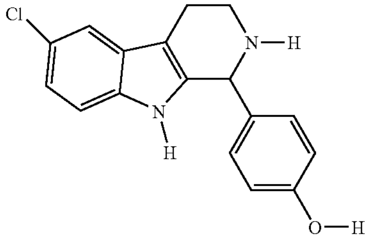
297
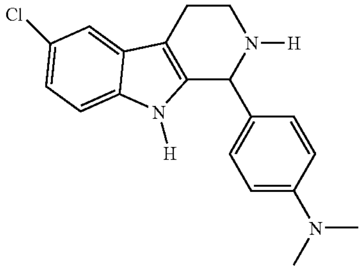
298
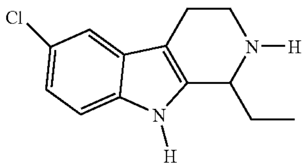
-continued
299
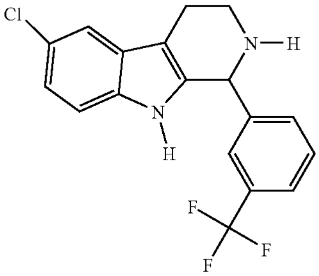
300
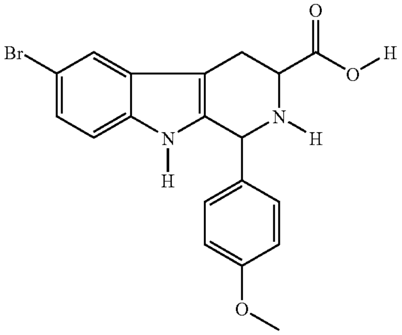
301
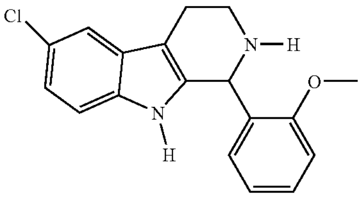
302
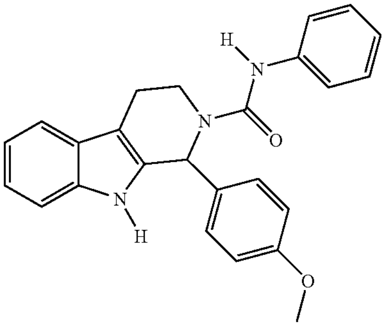
303
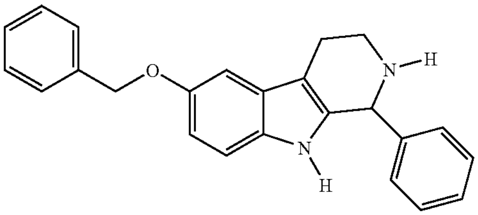

-continued
304
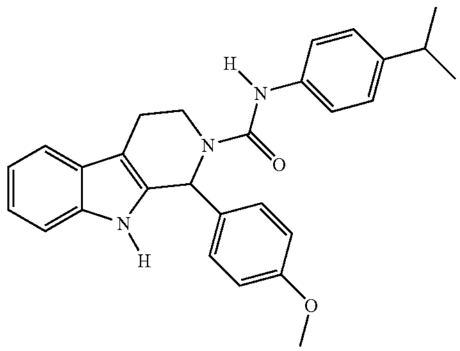
305
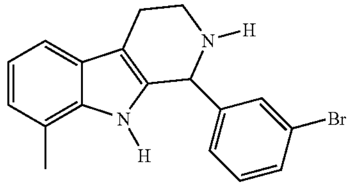
306
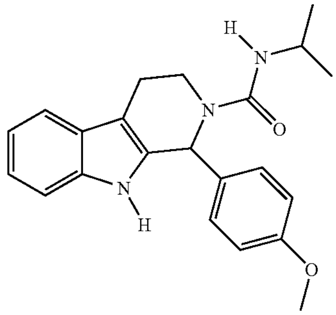
307
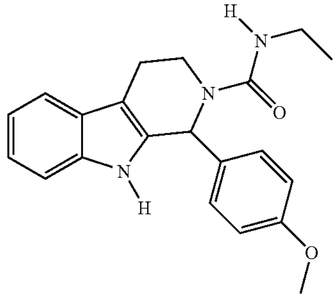
308
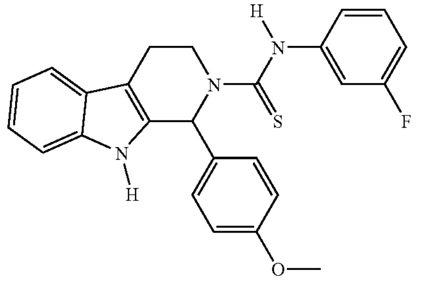
-continued
309
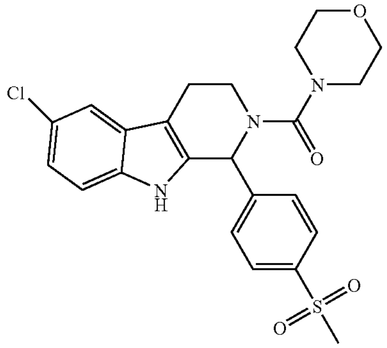
310
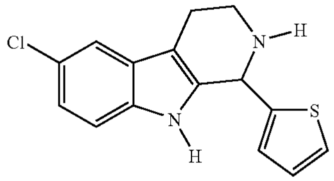
311
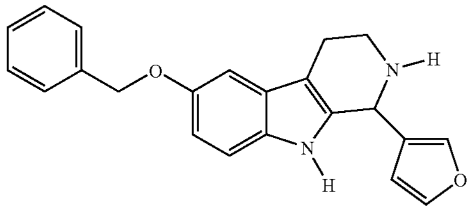
312
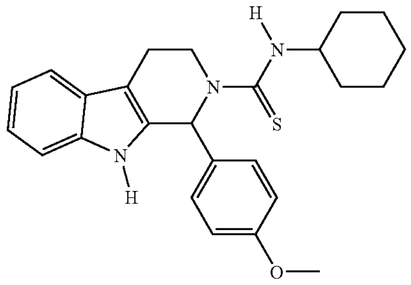
313
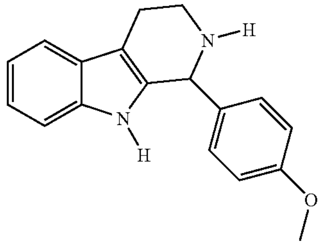
314
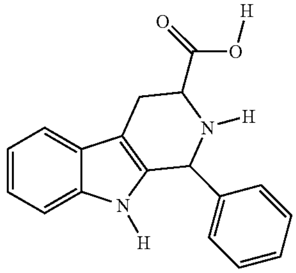

-continued
315
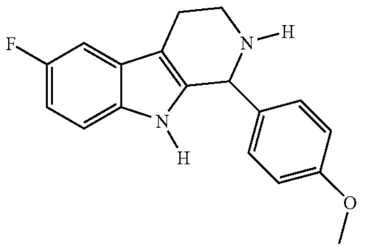
316
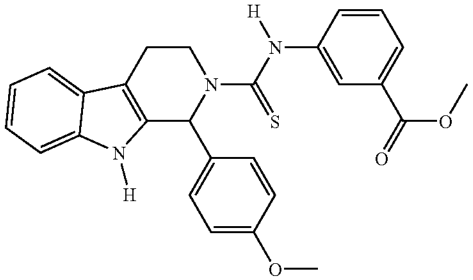
317
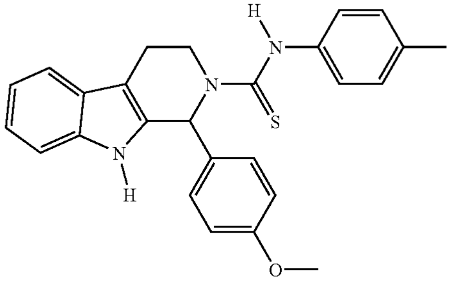
318
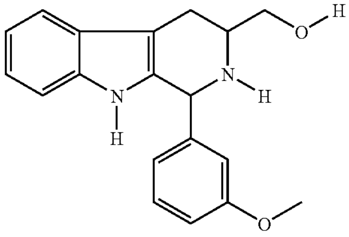
319
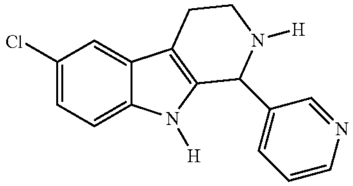
320
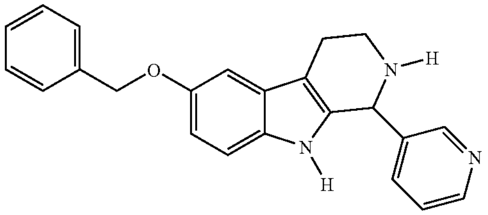
-continued
321
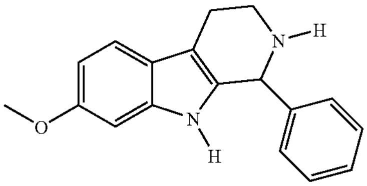
322
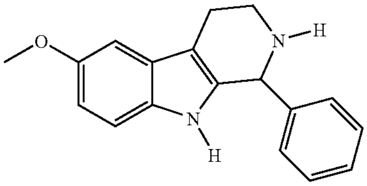
323
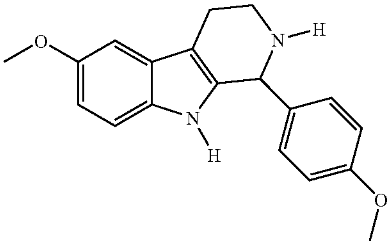
324
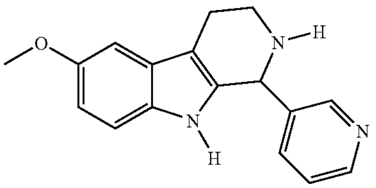
325
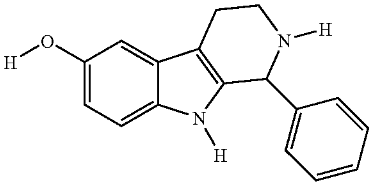
326
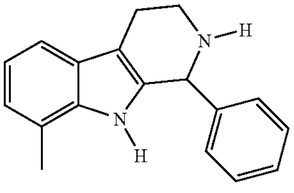
327
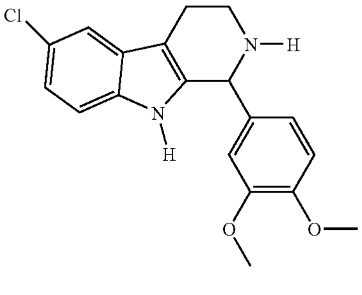

-continued
328
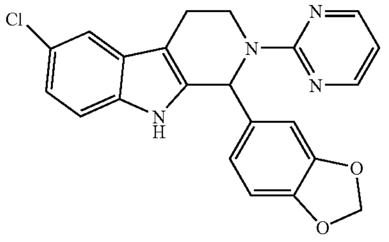
329
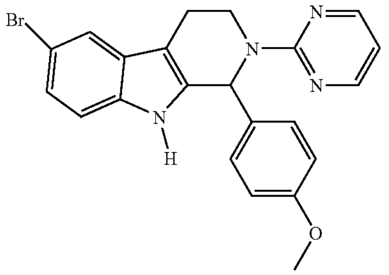
330
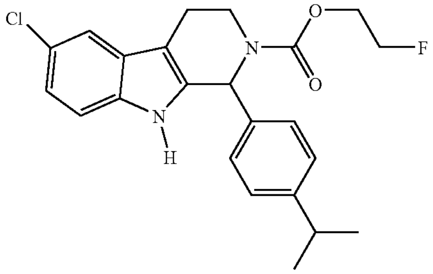
331
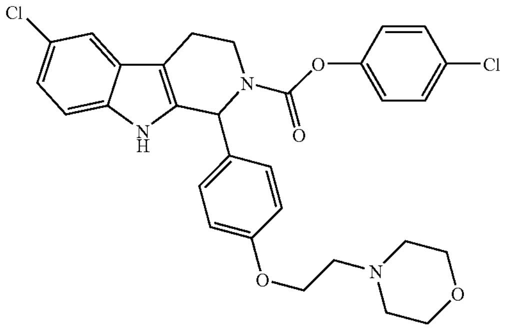
332
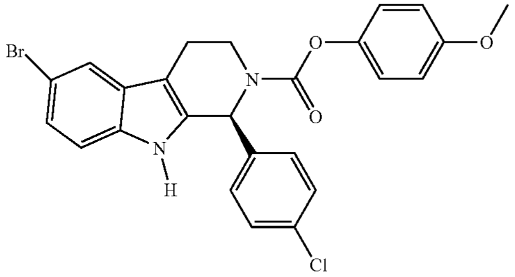
-continued
333
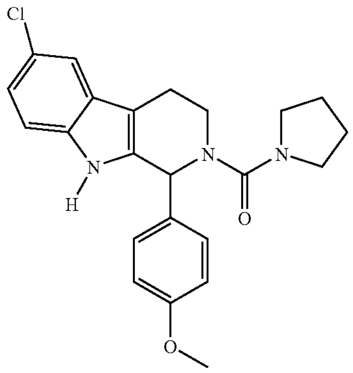
334
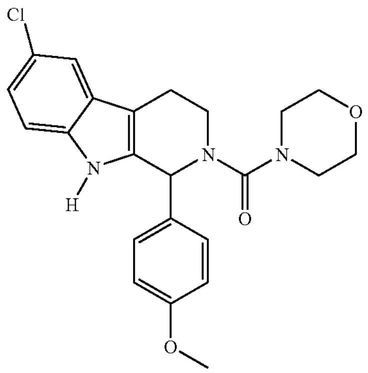
335
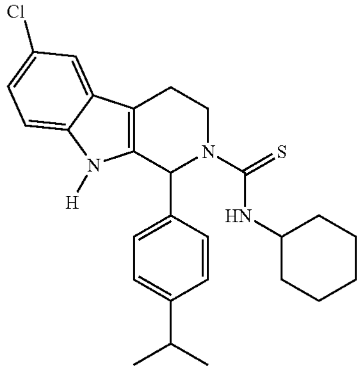
336
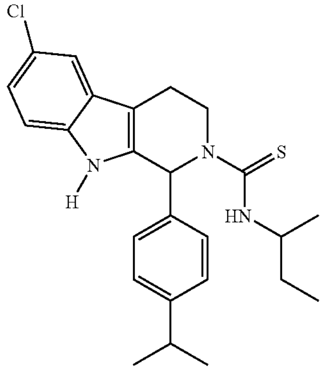

-continued
337
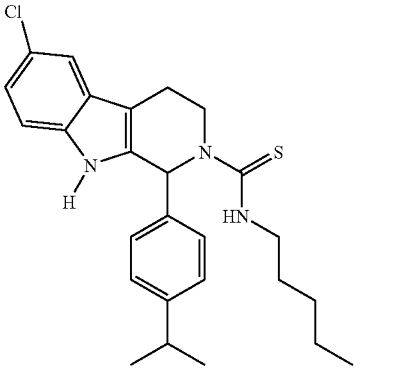
338
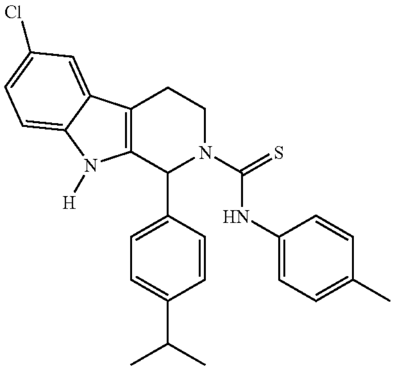
339
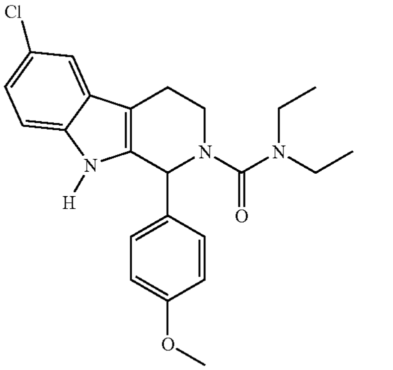
340
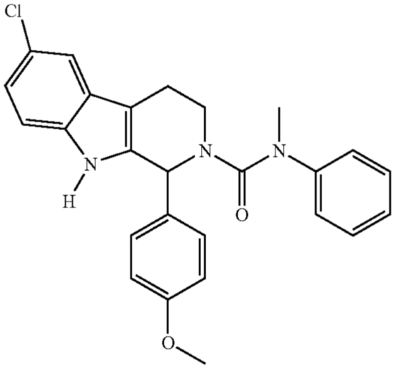
-continued
341
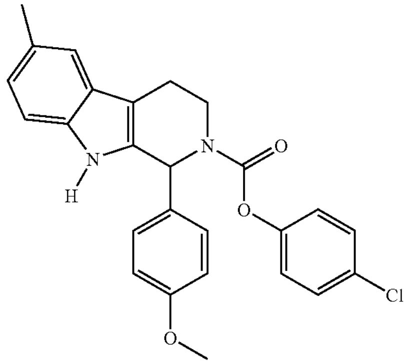
342
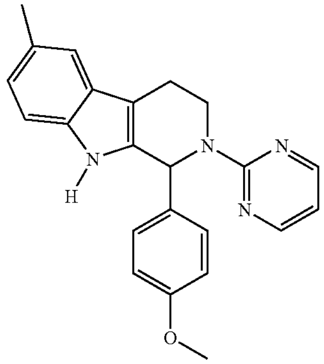
343
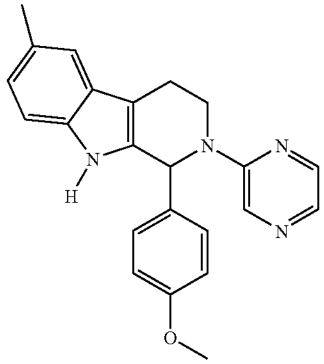
344
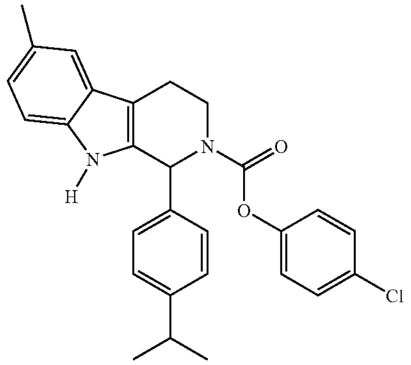

-continued
345
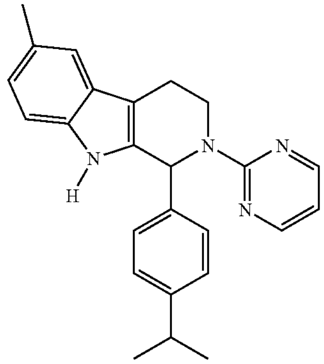
346
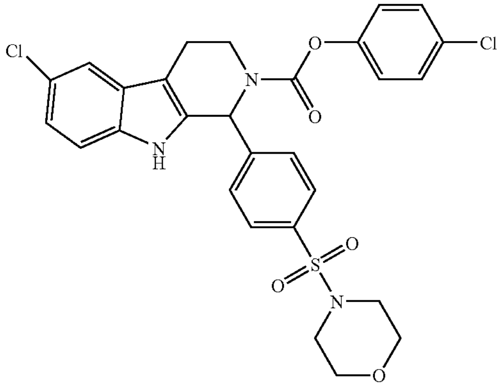
347
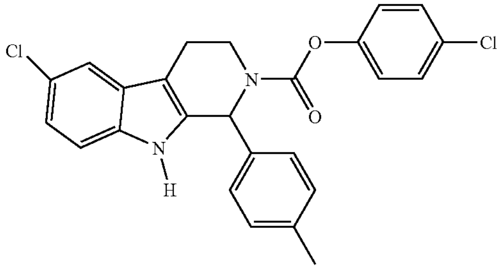
348
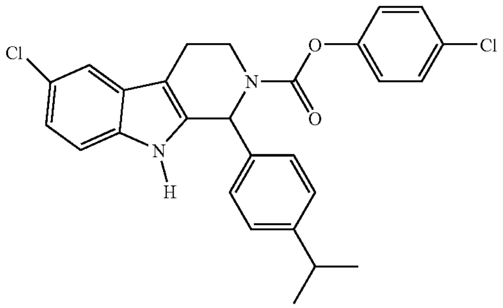
-continued
349
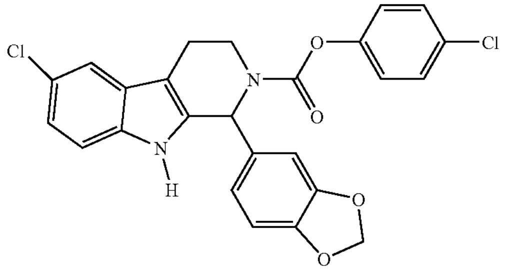
350
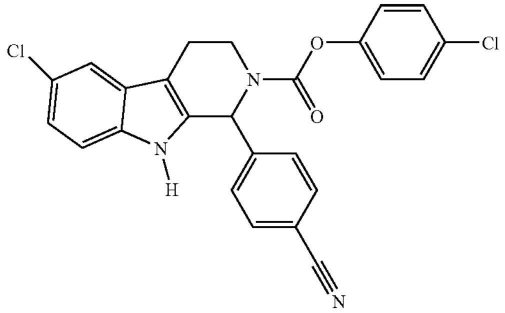
351
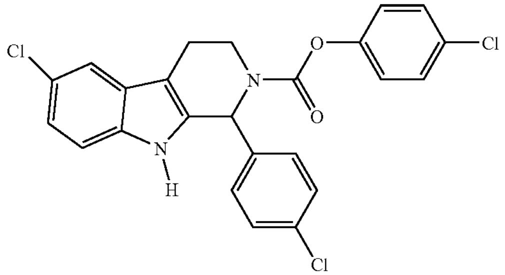
352
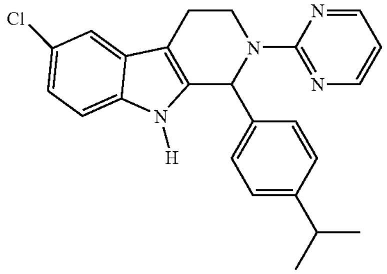
353
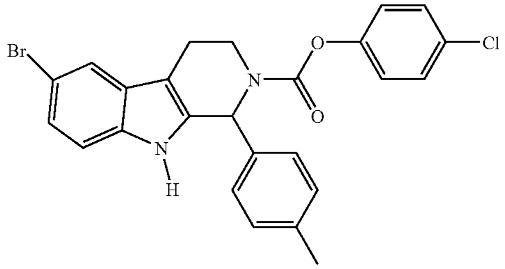

-continued
354
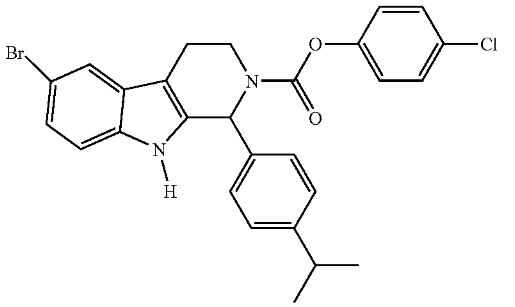
355
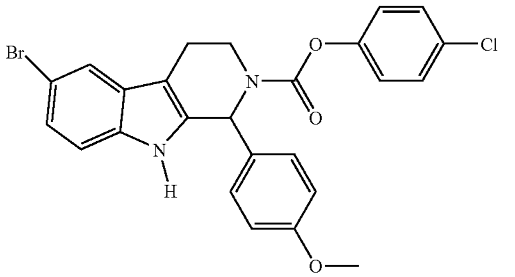
356
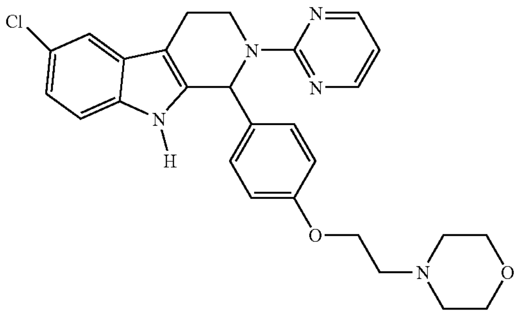
357
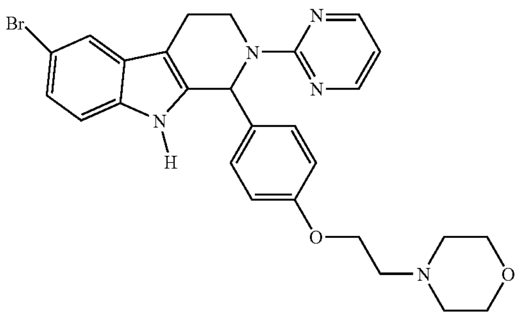
-continued
358
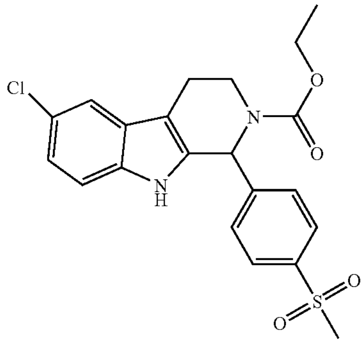
359
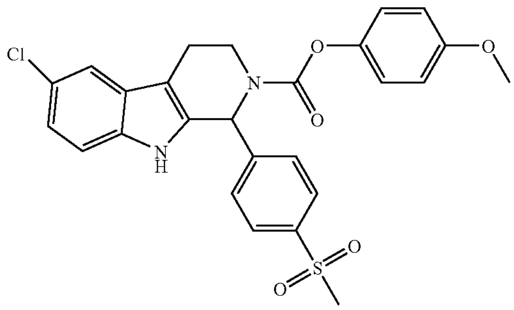
360
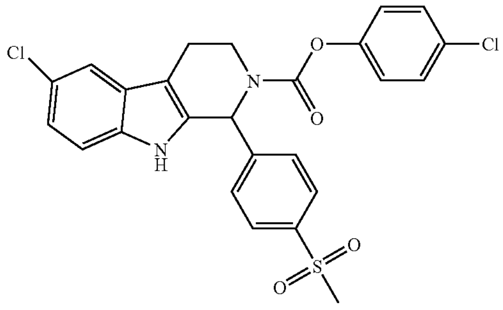
361
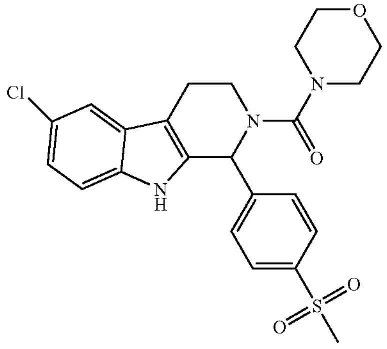
362
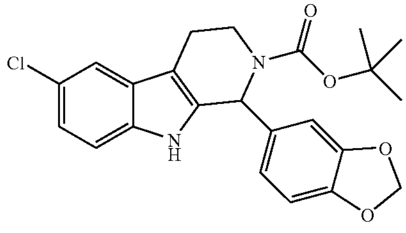

-continued
363
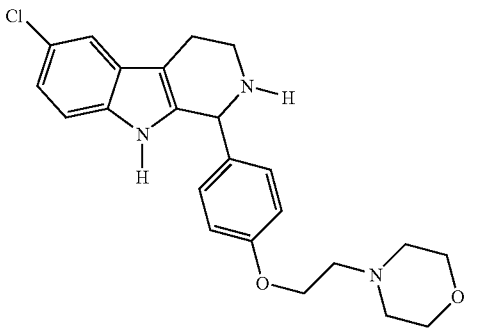
364
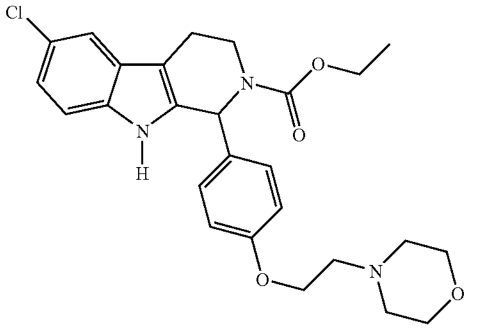
365
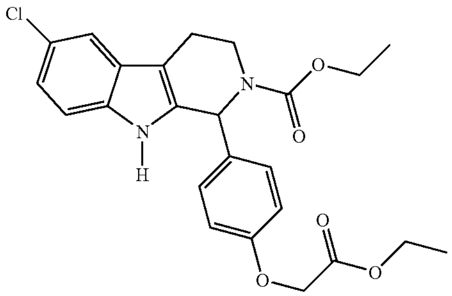
366
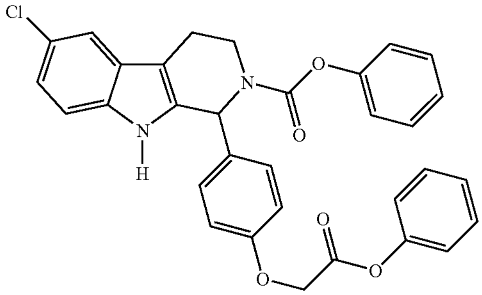
367
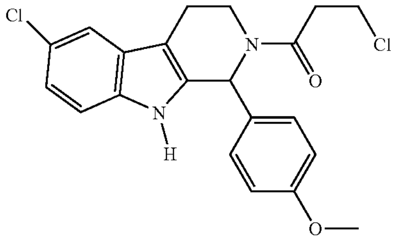
-continued
368
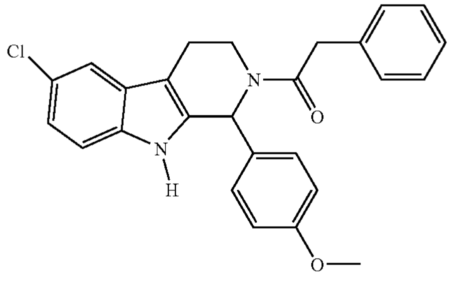
369
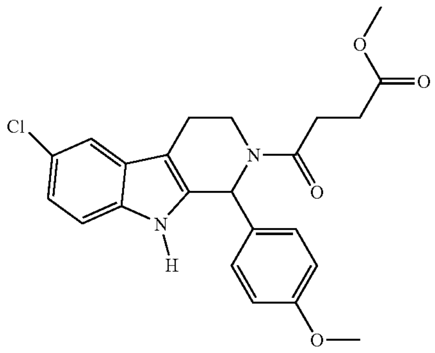
370
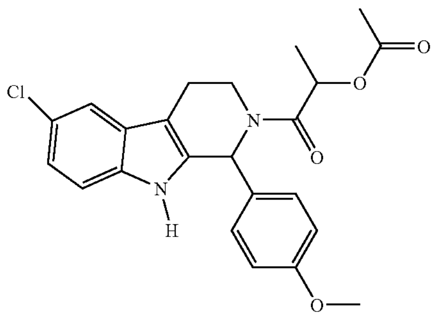
371
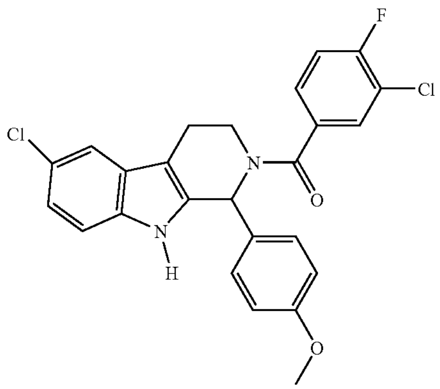

-continued
372
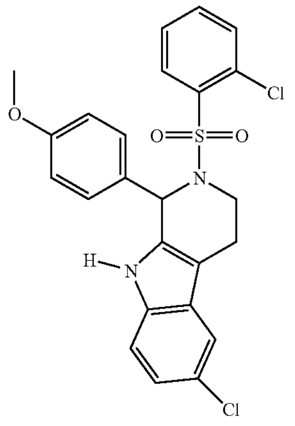
373
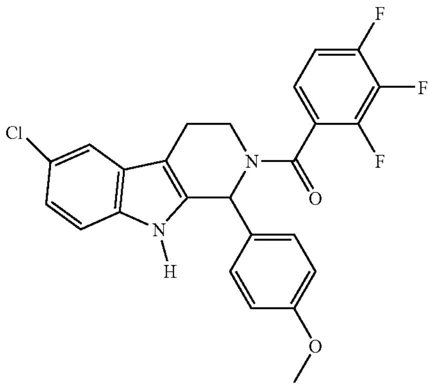
374
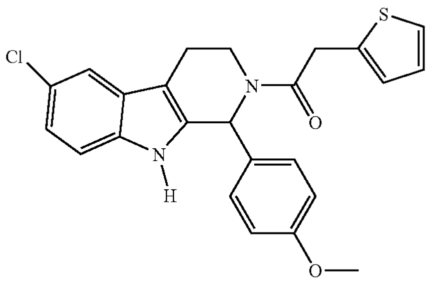
375
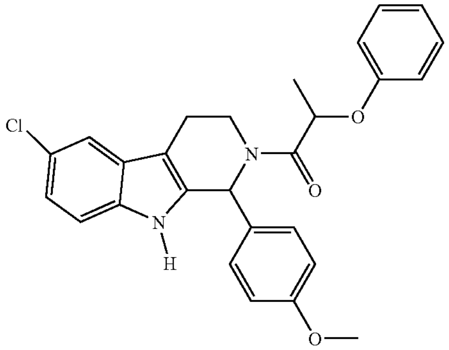
-continued
376
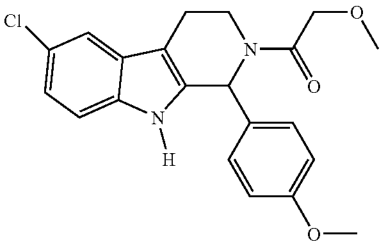
377
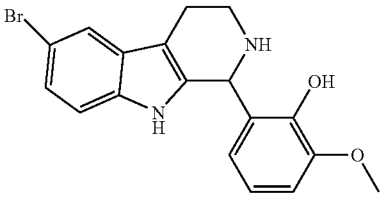
378
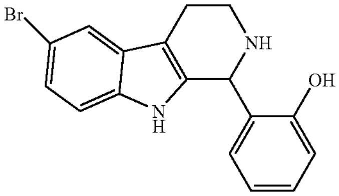
379
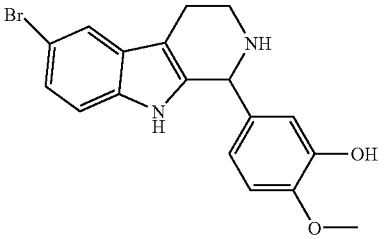
380
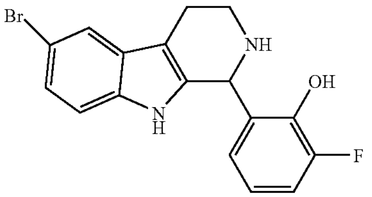
381
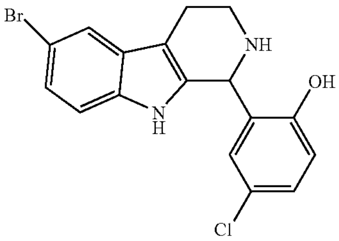
382
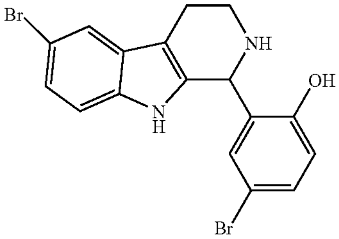

-continued
383
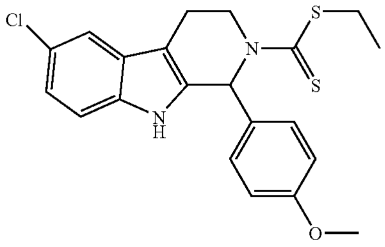
384
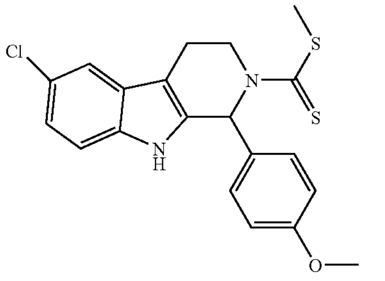
385
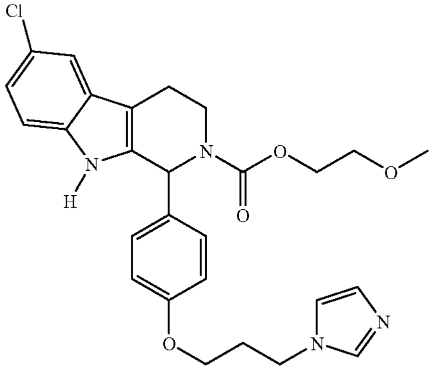
386
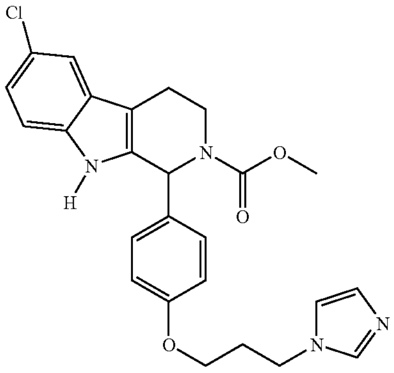
-continued
387
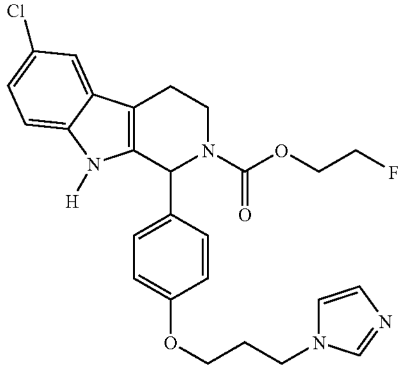
388
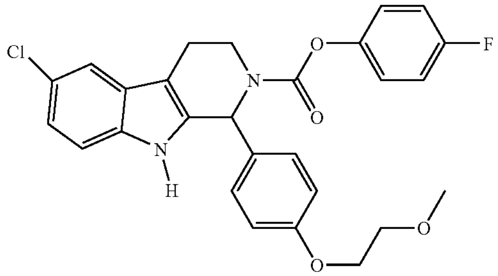
389
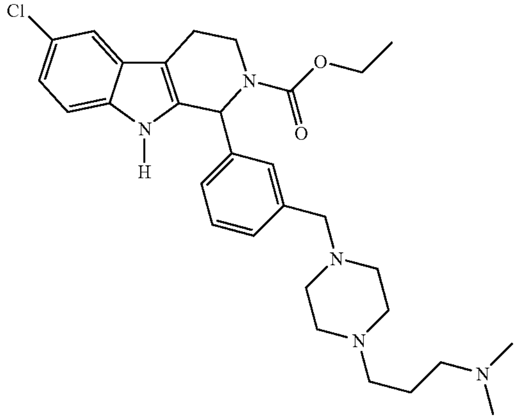
390
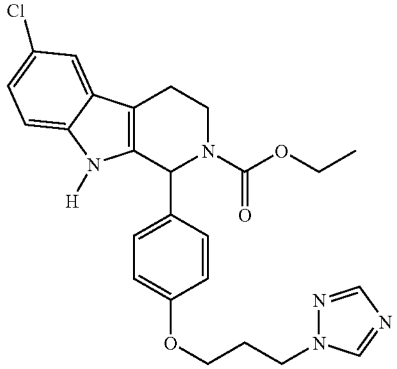

-continued
391
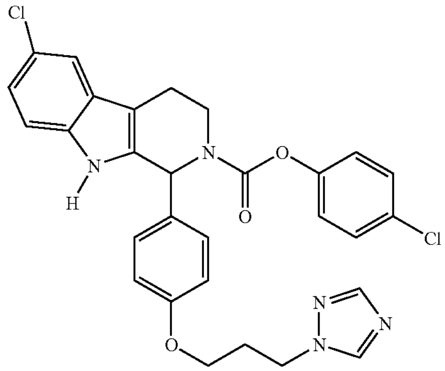
392
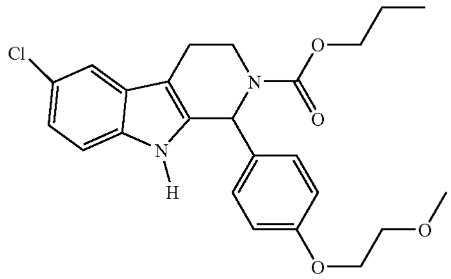
393
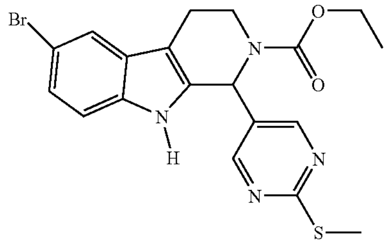
394
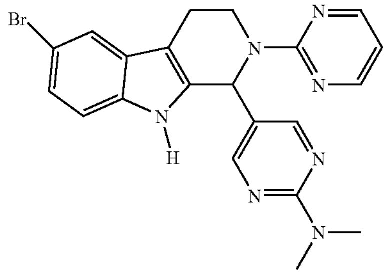
395
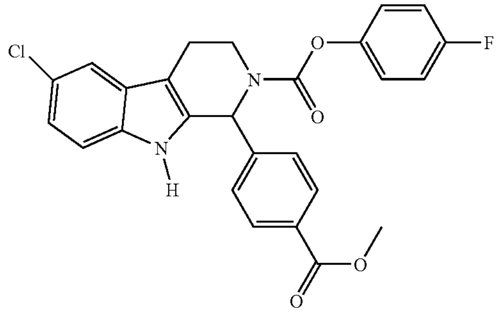
-continued
396
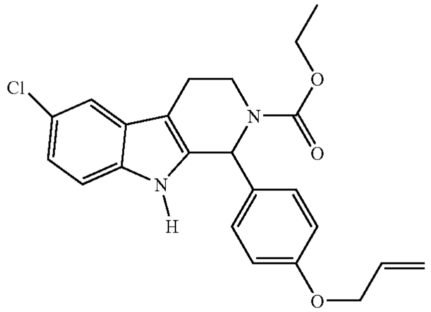
397
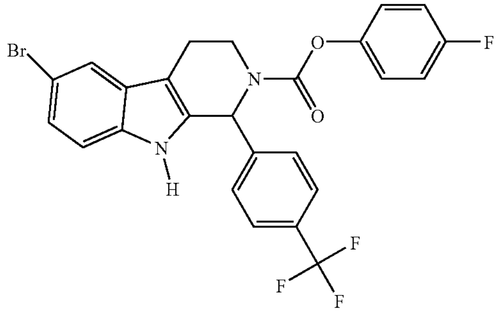
398
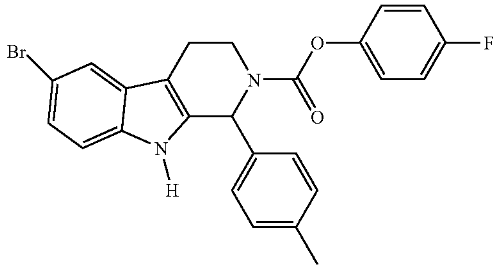
399
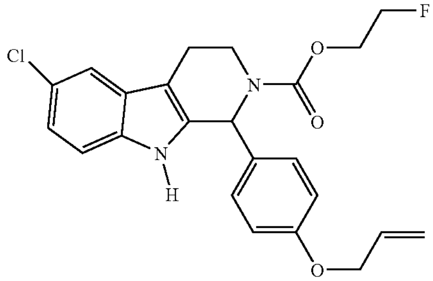
400
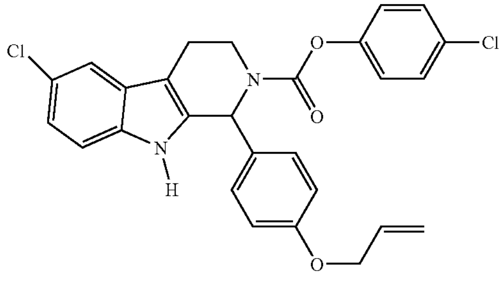

-continued
401
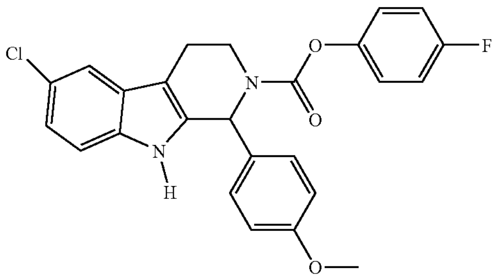
402
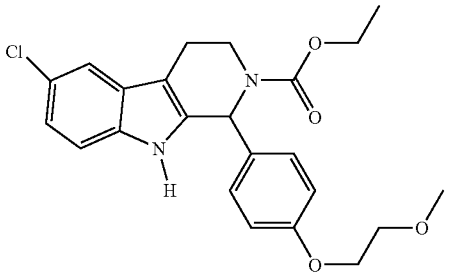
403
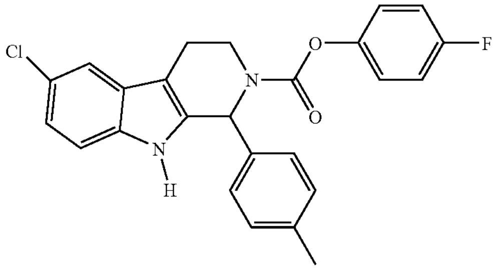
404
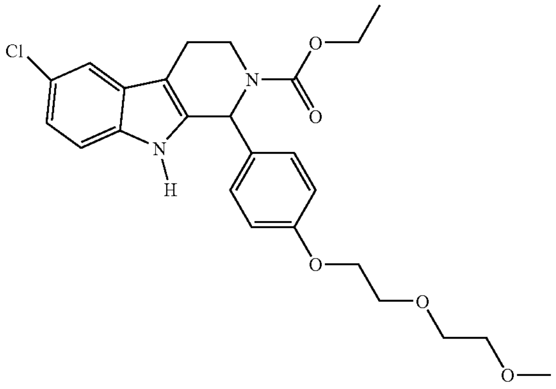
405
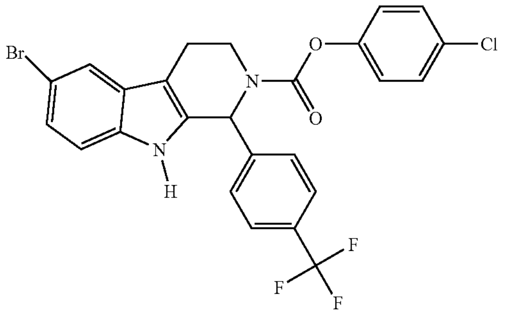
-continued
406
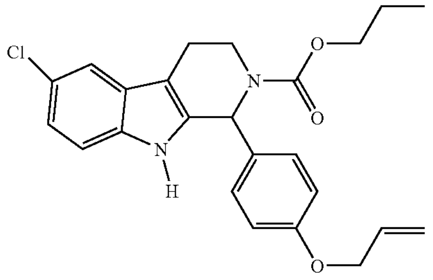
407
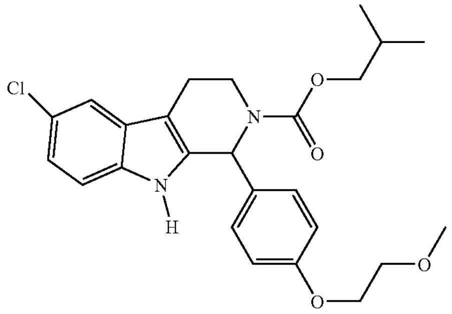
408
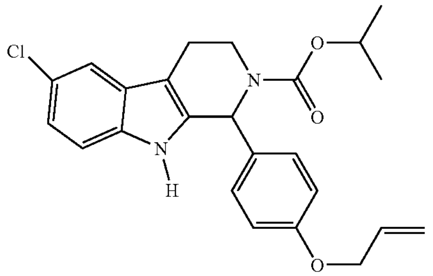
409
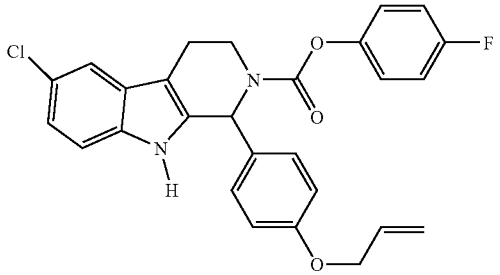
410
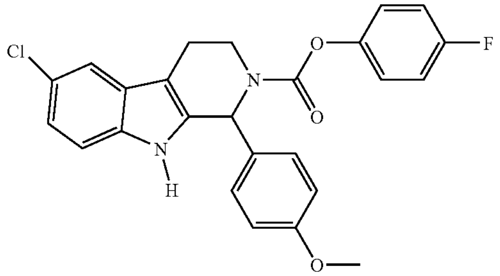

-continued
411
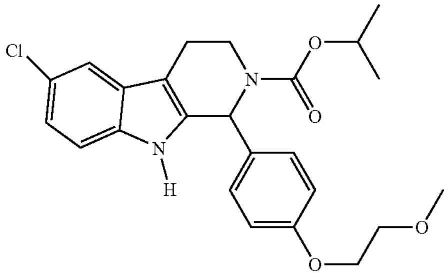
412
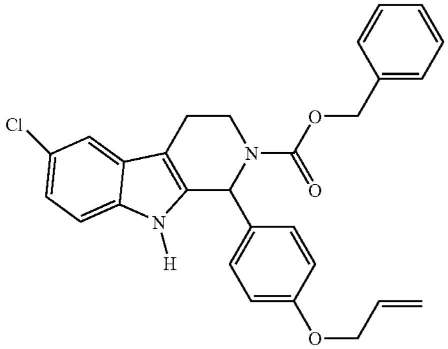
413
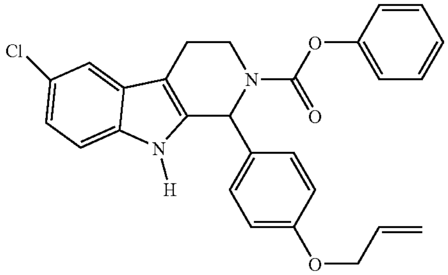
414
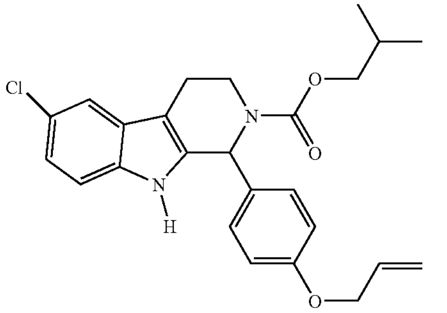
415
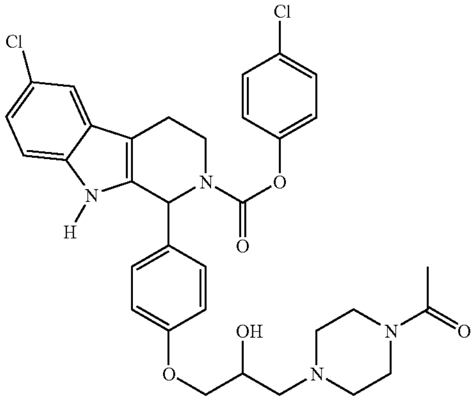
-continued
416
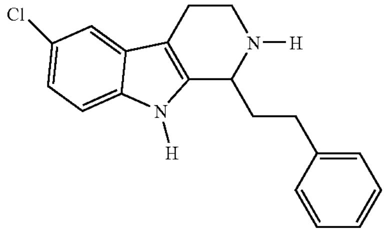
417
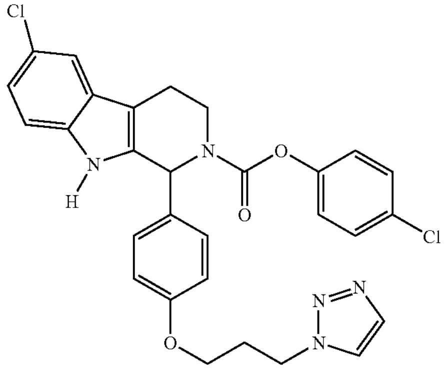
418
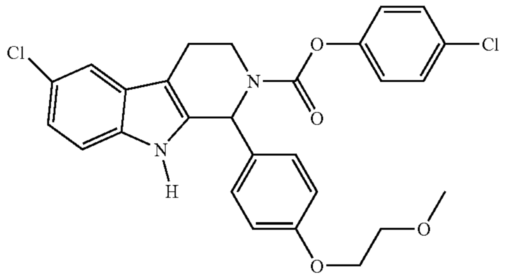
419
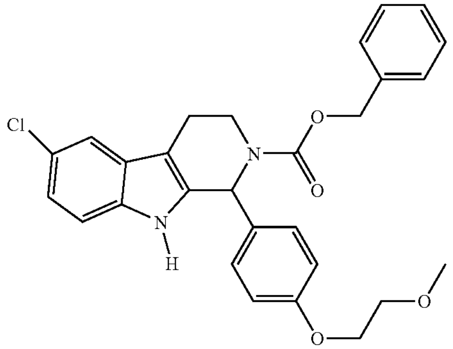
420
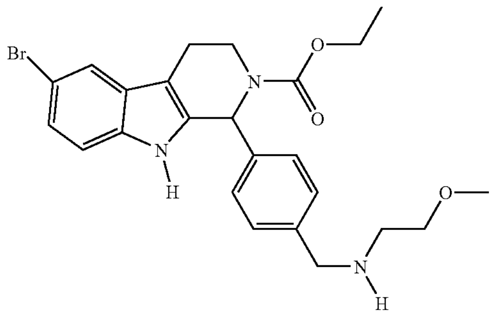

-continued
421
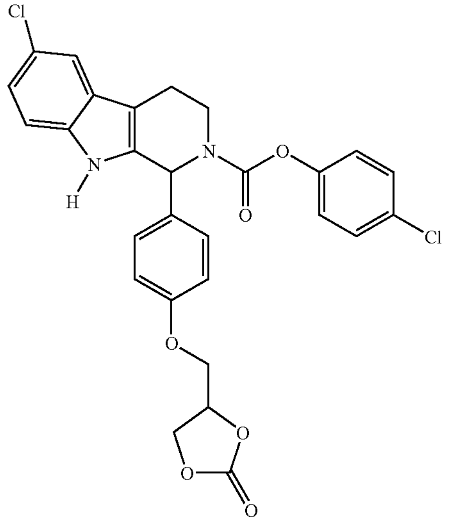
422
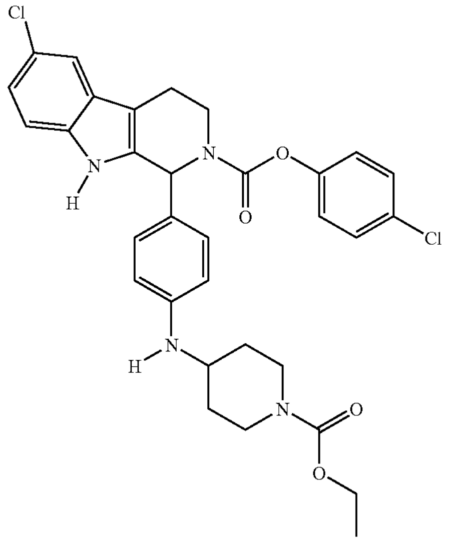
423
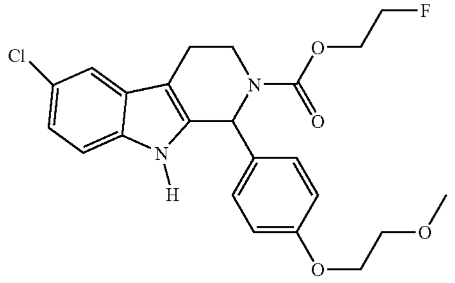
-continued
424
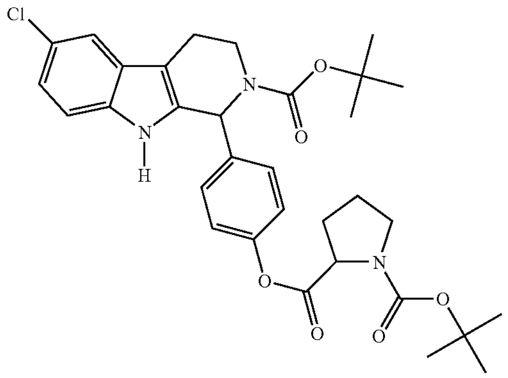
425
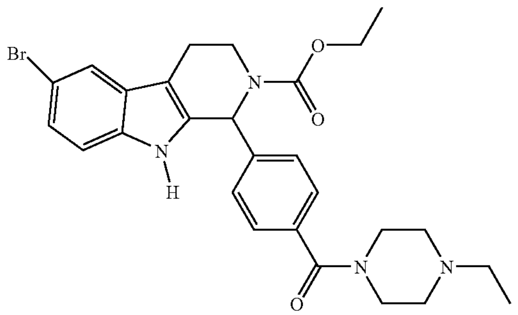
426
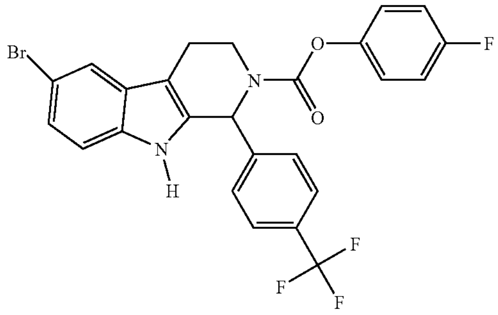
427
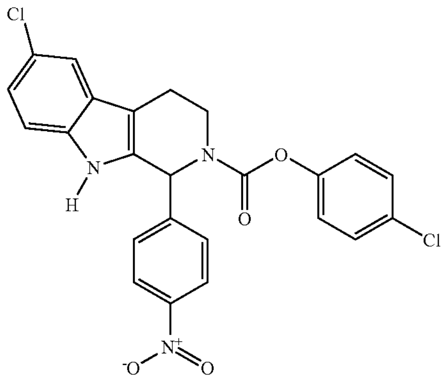

-continued
428
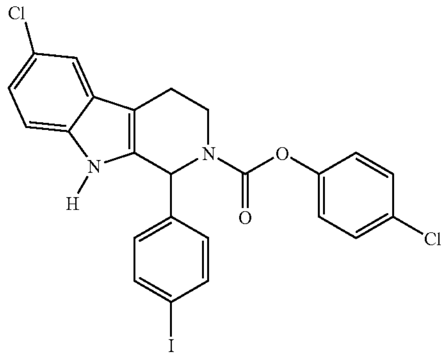
429
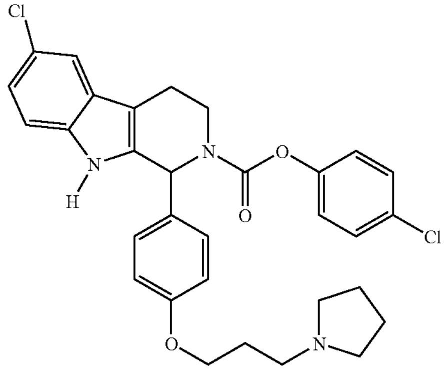
430
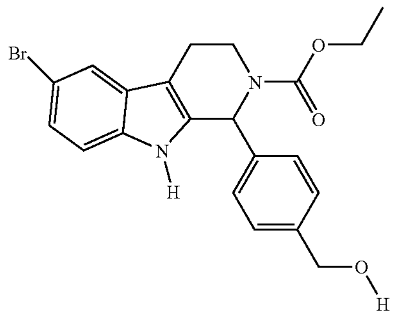
431
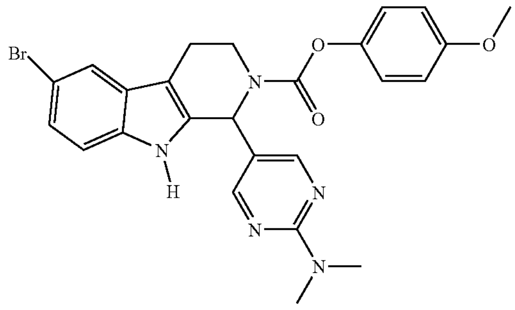
-continued
432
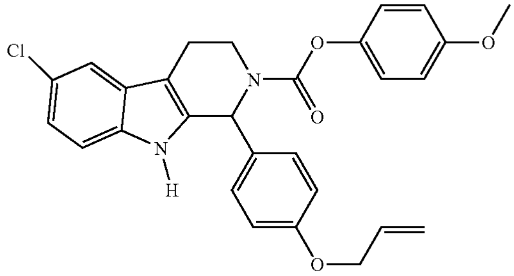
433
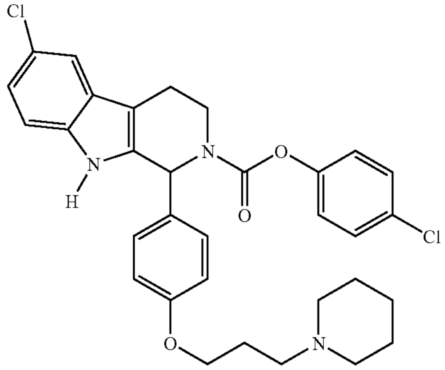
434
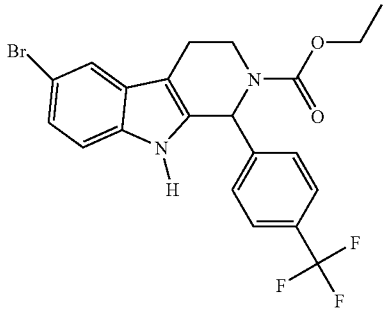
435
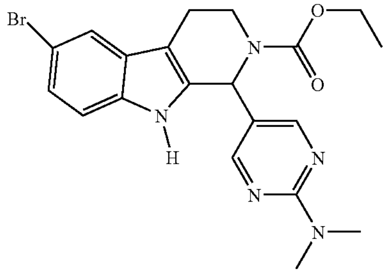
436
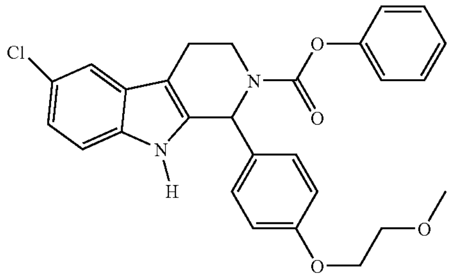

-continued
437
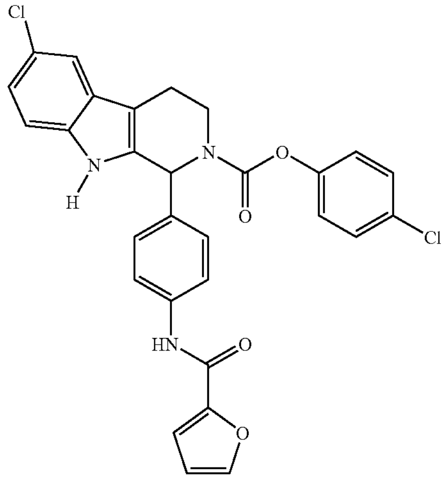
438
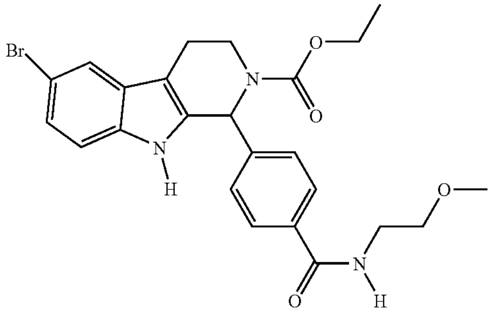
439
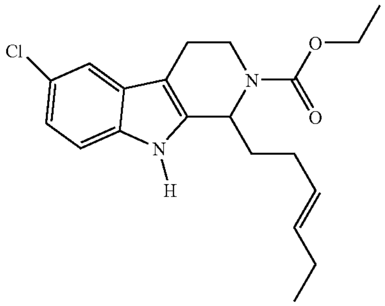
440
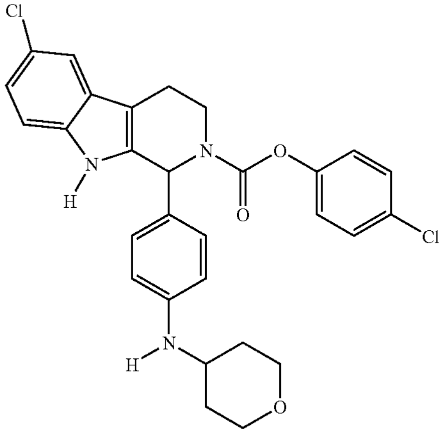
-continued
441
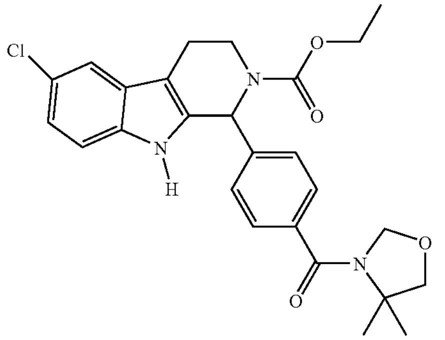
442
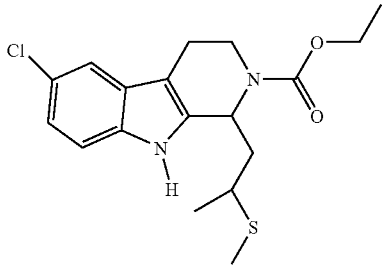
443
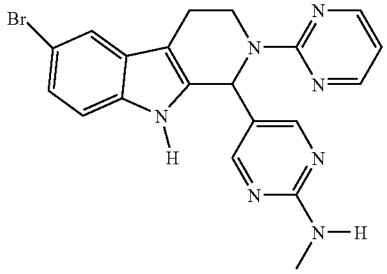
444
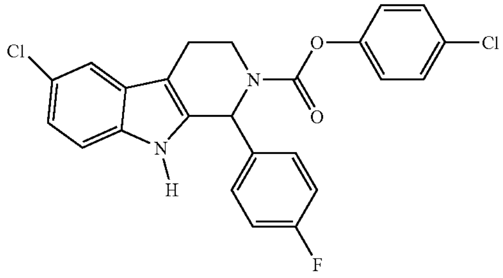
445
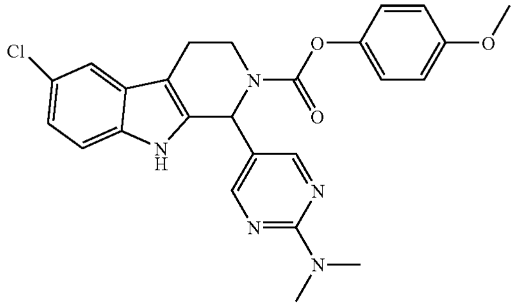

-continued
446
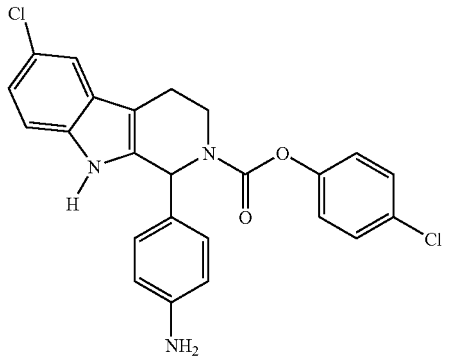
447
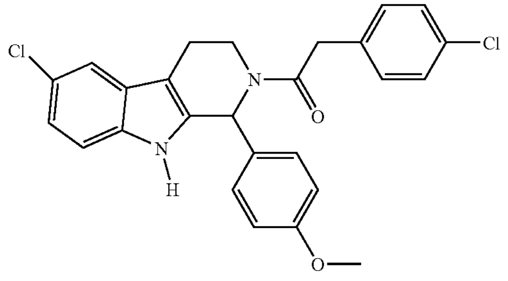
448
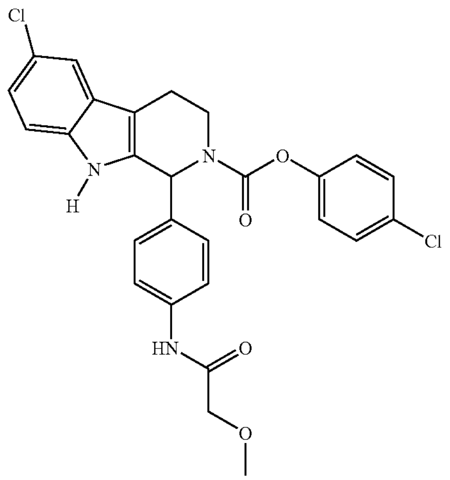
449
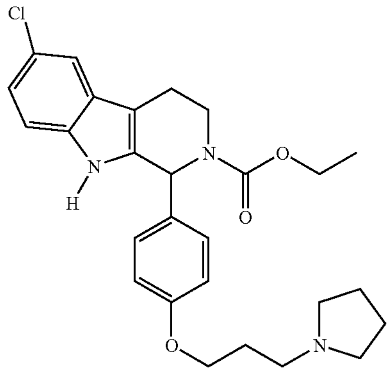
-continued
450
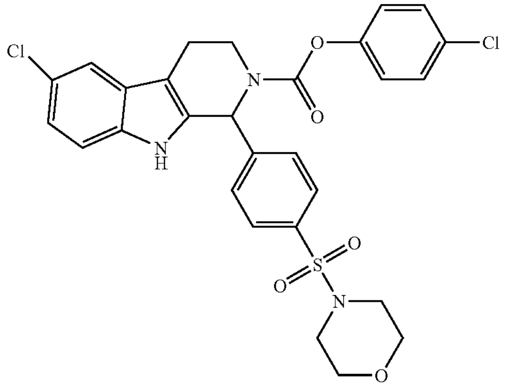
451
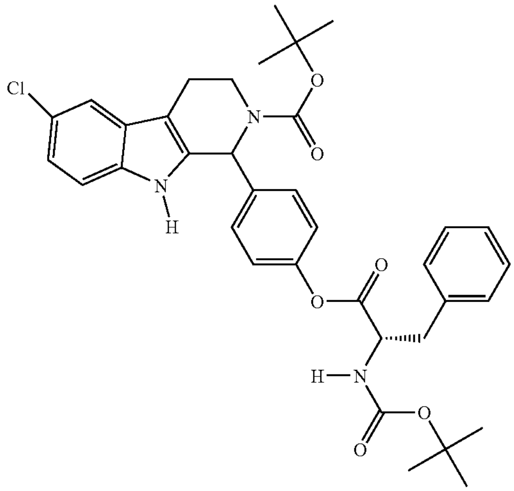
452
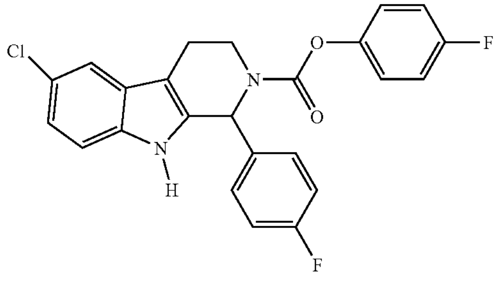

-continued
453
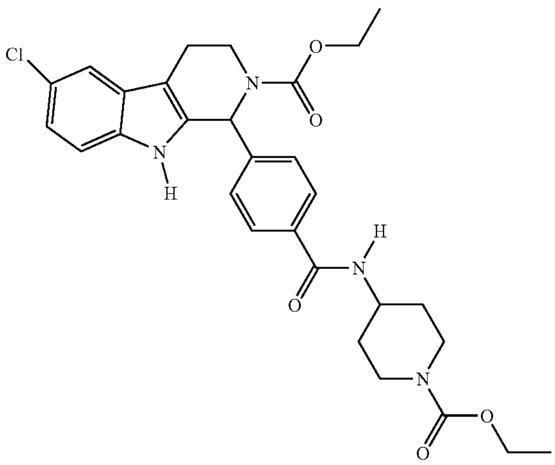
454
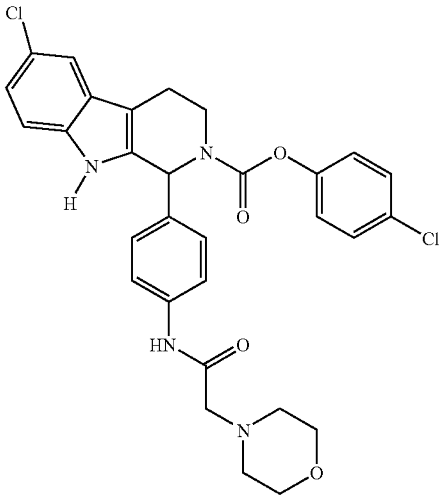
455
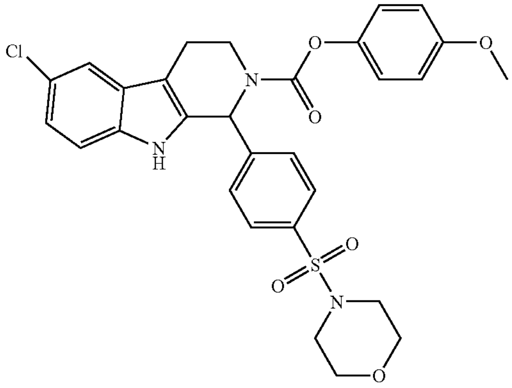
-continued
456
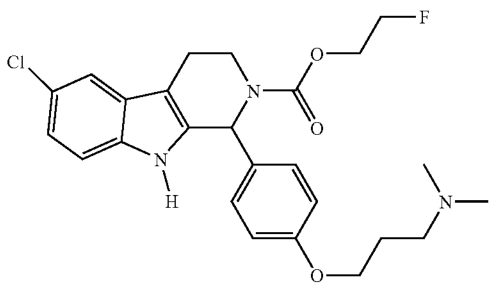
457
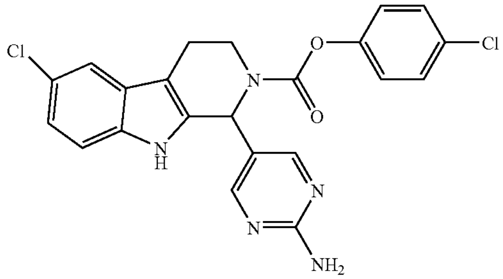
458
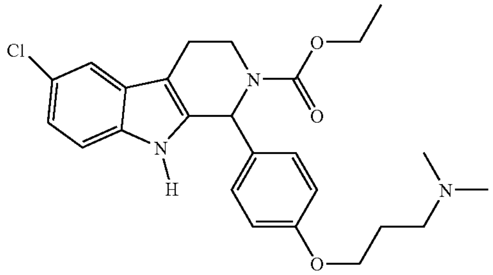
459
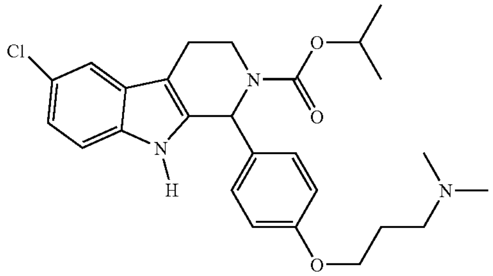

-continued
460
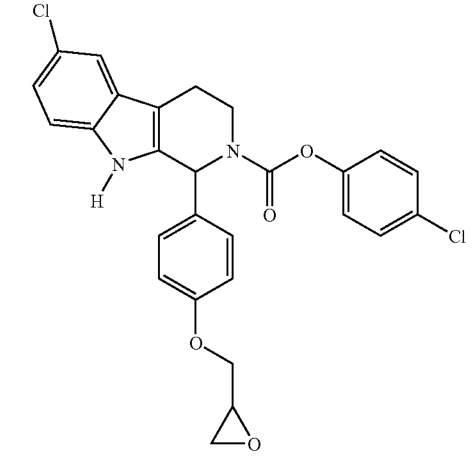
461
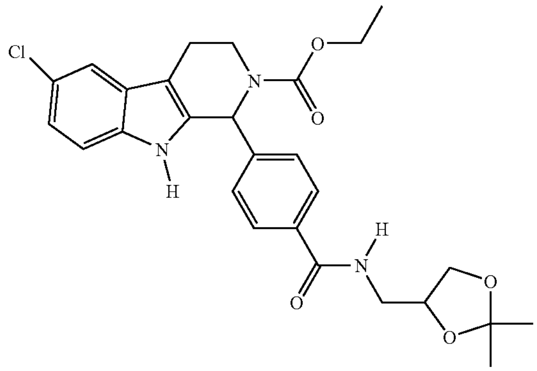
462
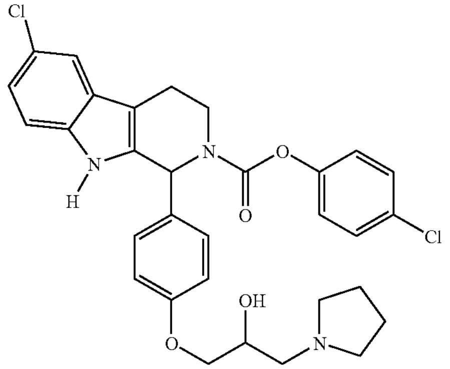
463
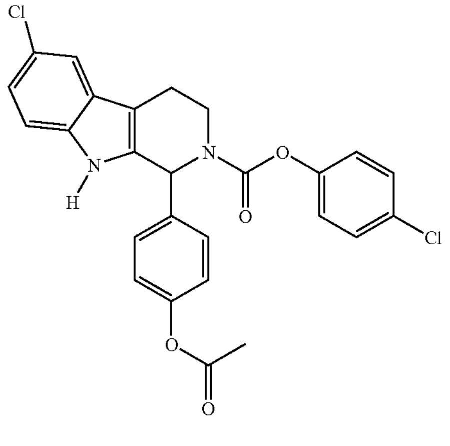
-continued
464
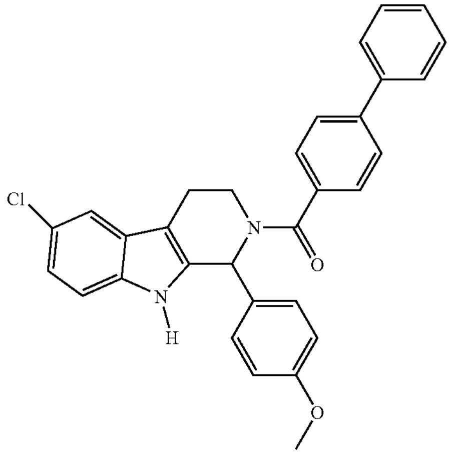
465
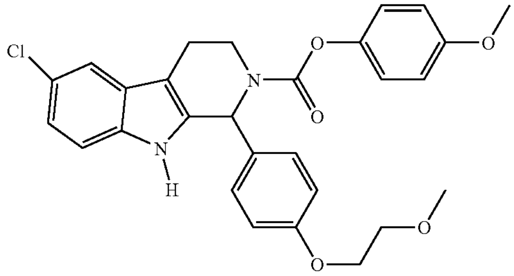
466
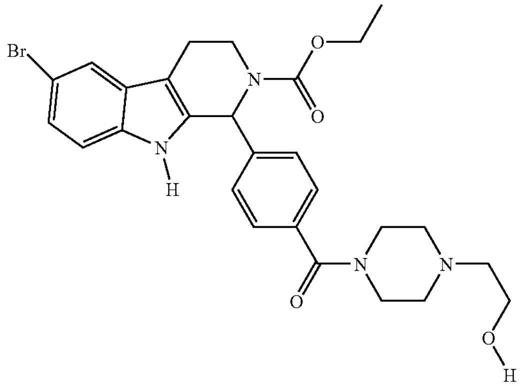
467
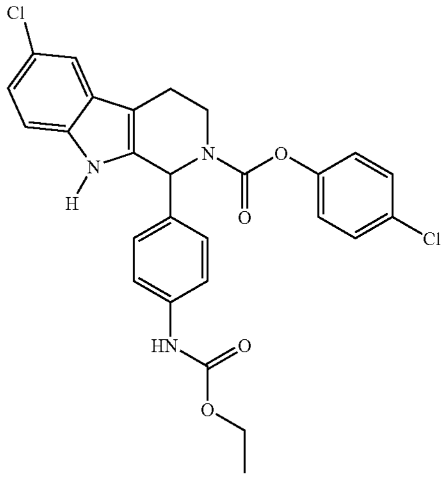

-continued
468
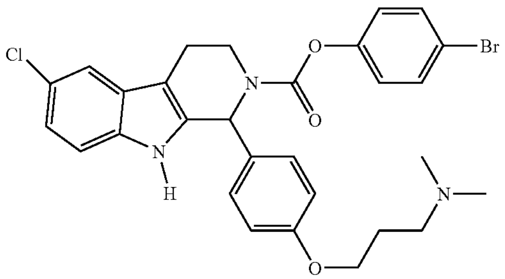
469
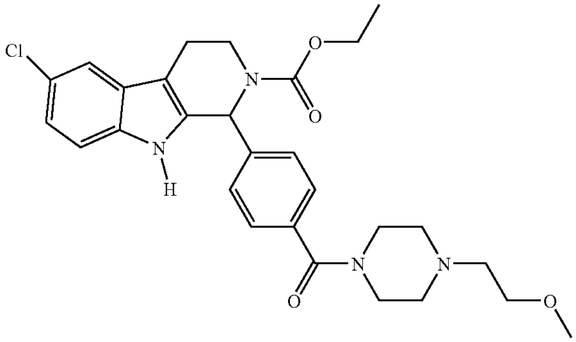
470
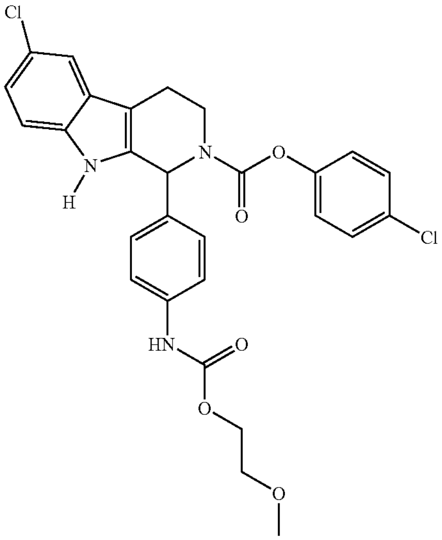
471
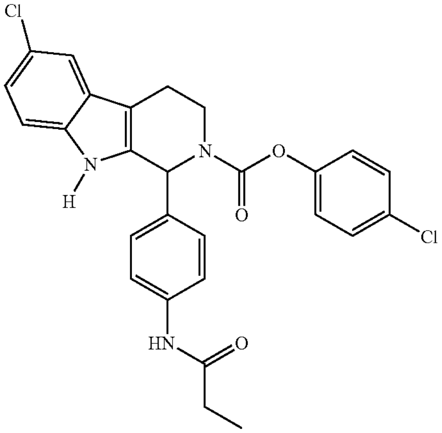
-continued
472
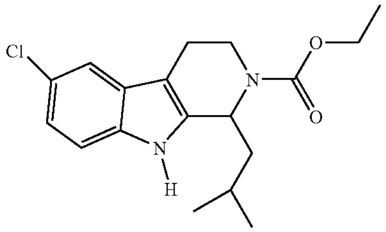
473
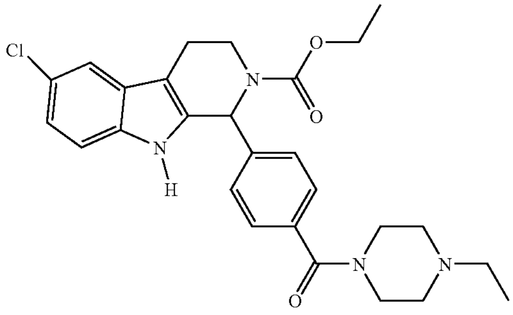
474
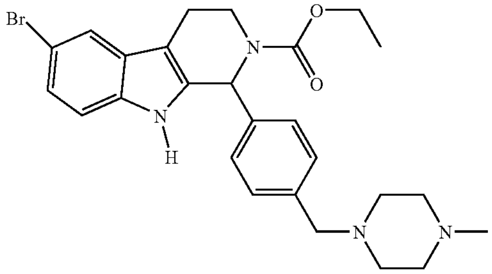
475
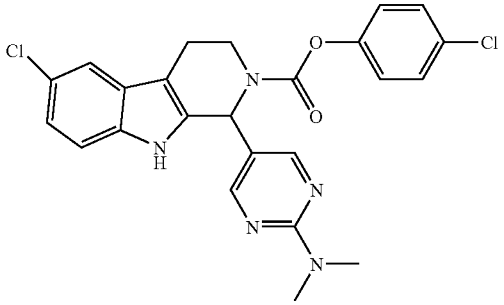
476
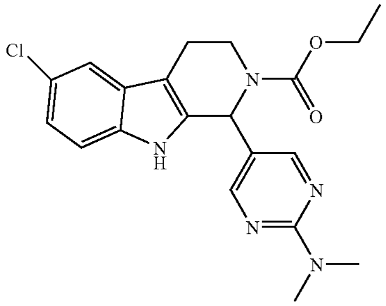

-continued
477
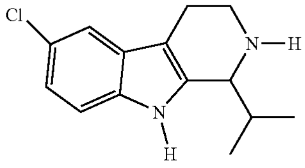
478
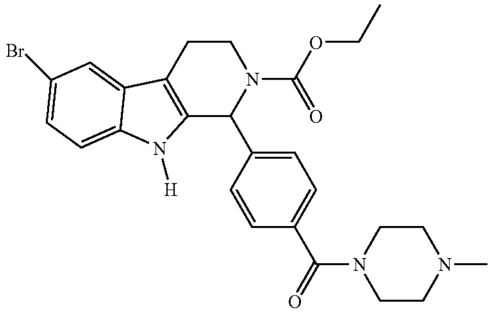
479
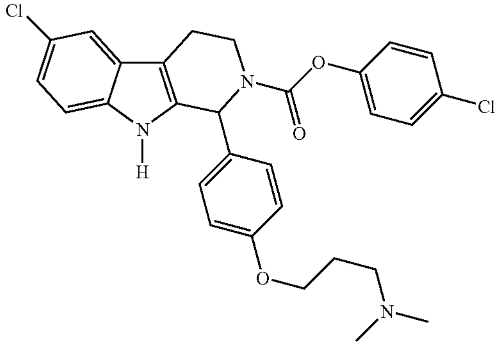
480
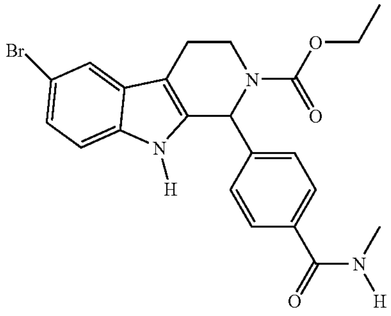
481
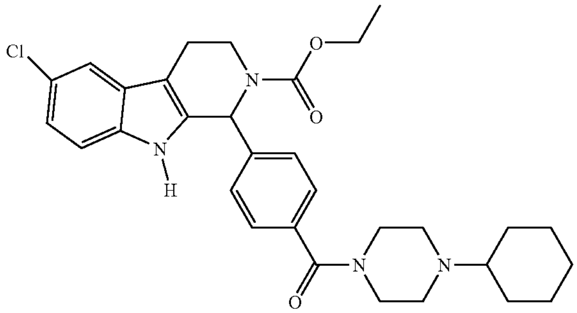
-continued
482
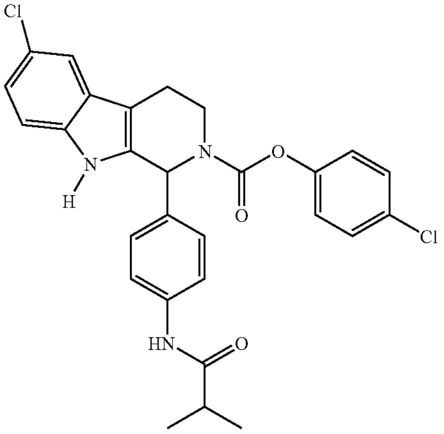
483
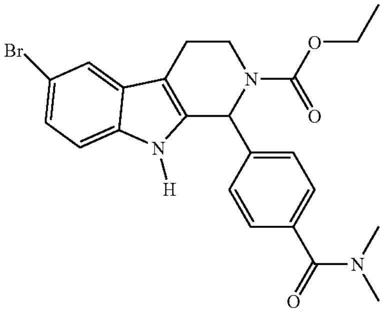
484
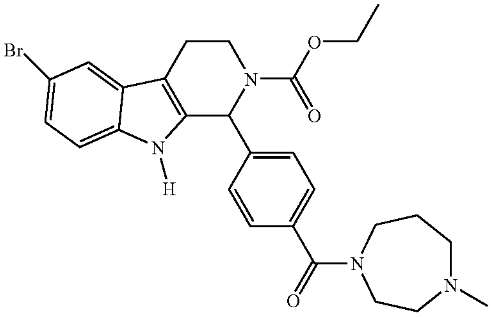
485
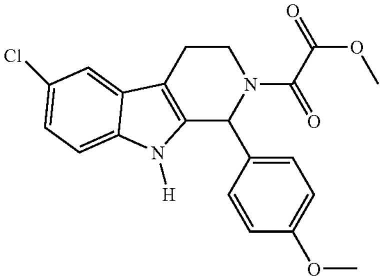
486
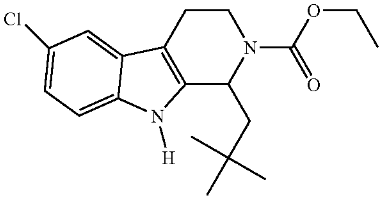

-continued
487
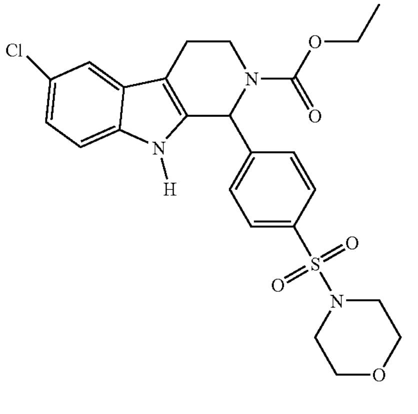
488
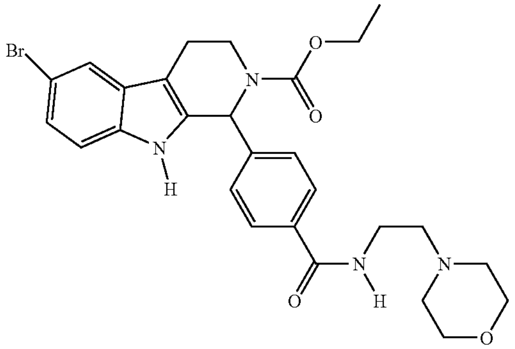
489
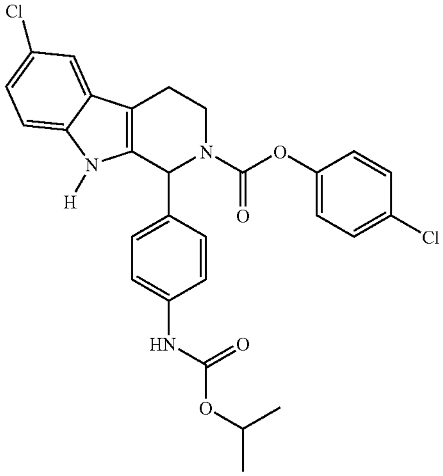
490
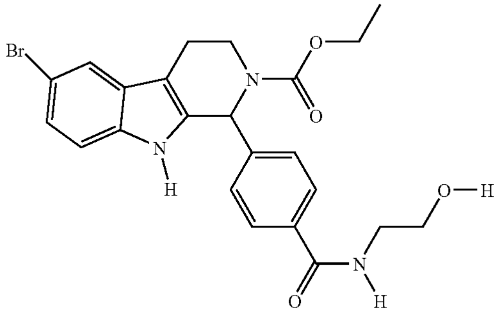
-continued
491
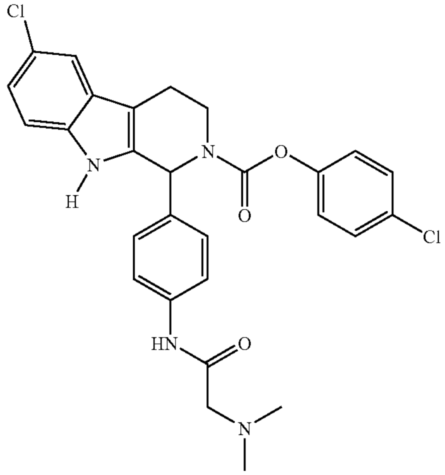
492
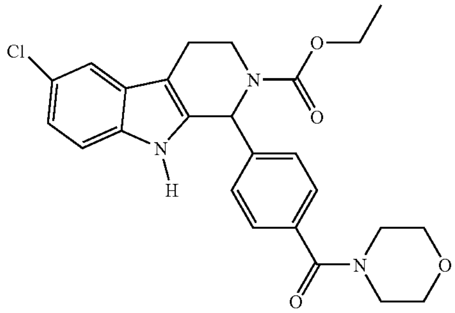
493
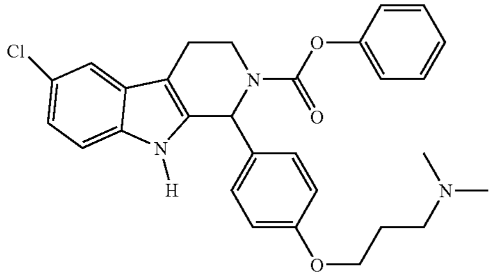
494
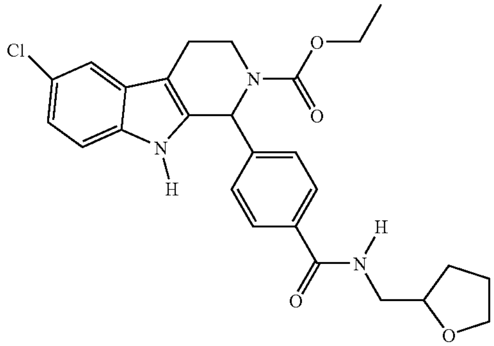

-continued
495
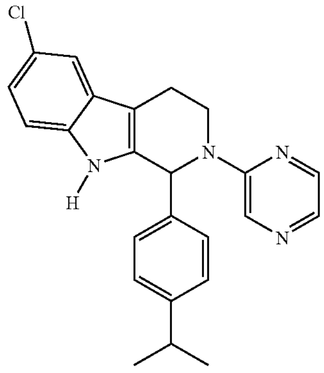
496
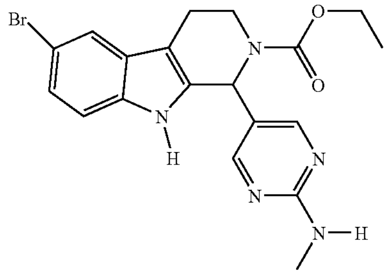
497
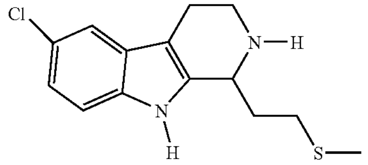
498
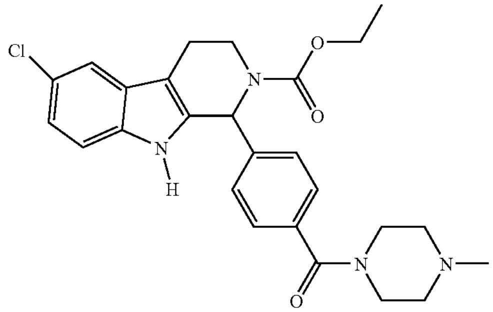
499
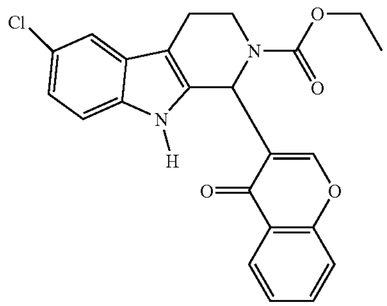
-continued
500
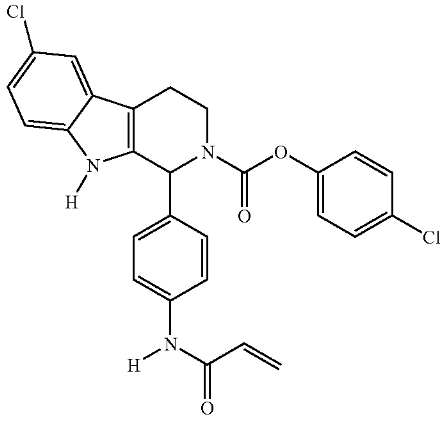
501
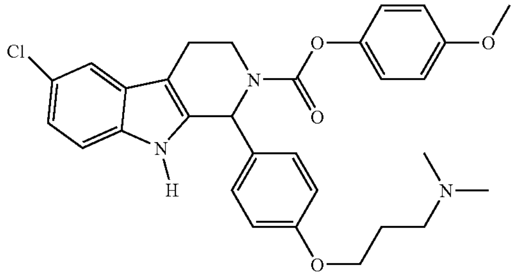
502
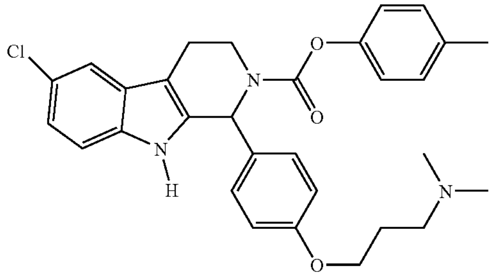
503
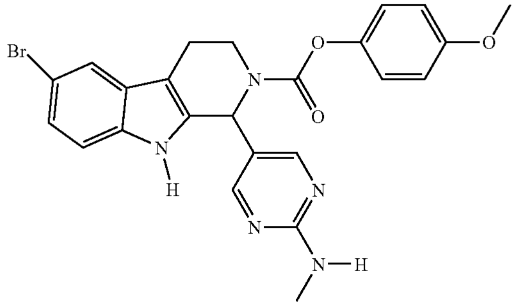
504
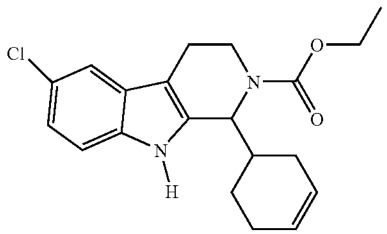

-continued
505
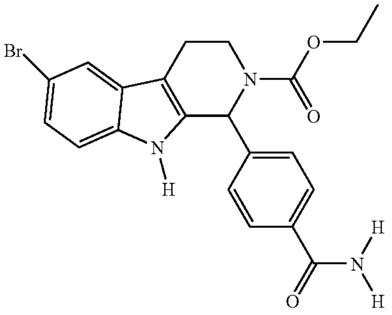
506
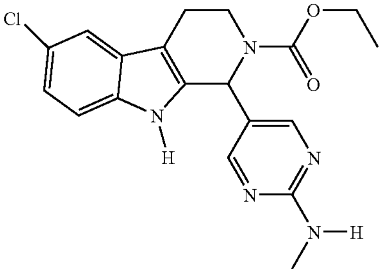
507
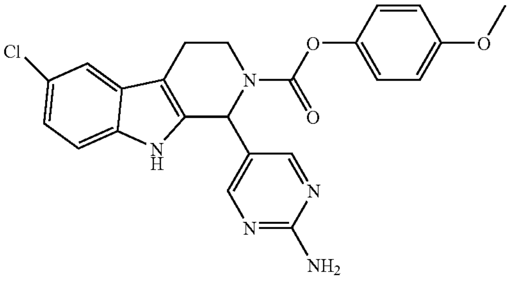
508
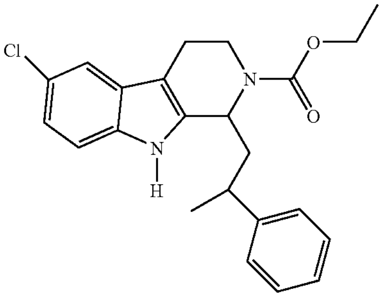
-continued
509
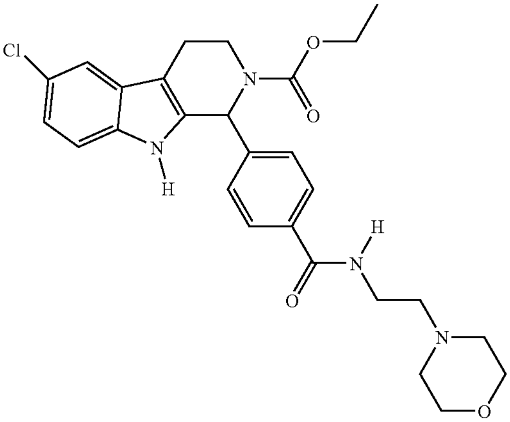
510
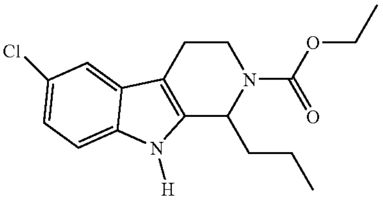
511
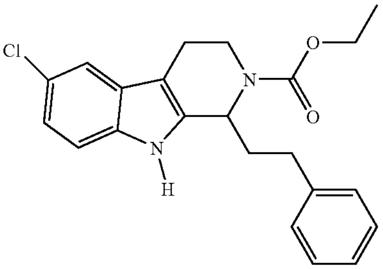
512
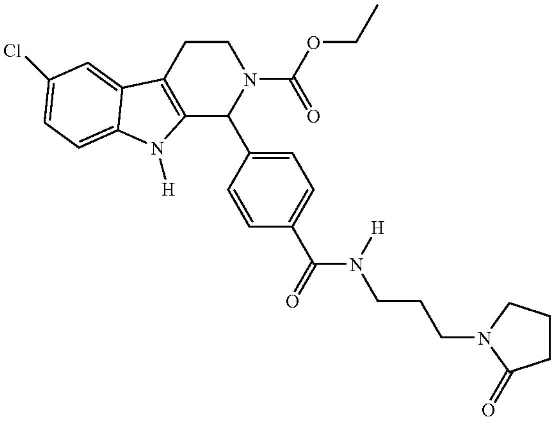
513
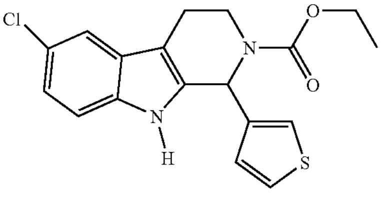

-continued
514
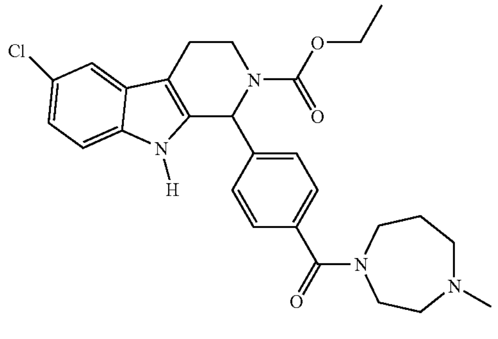
515
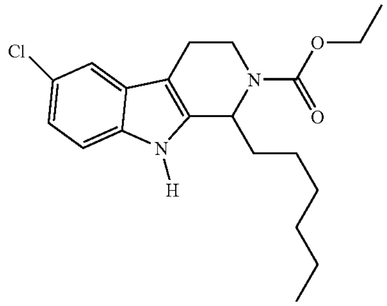
516
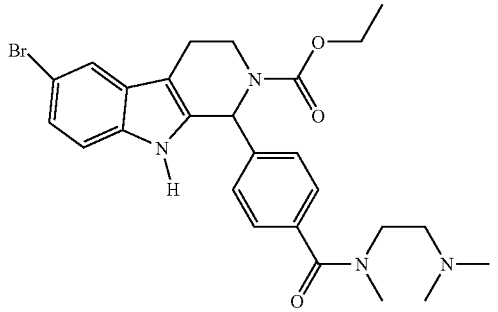
517
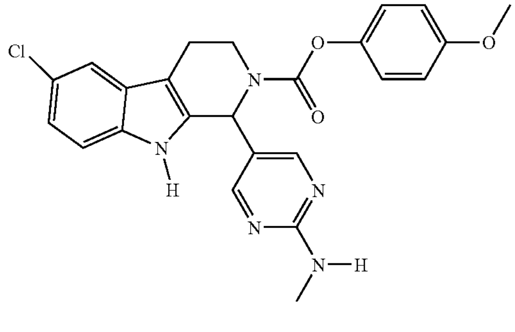
-continued
518
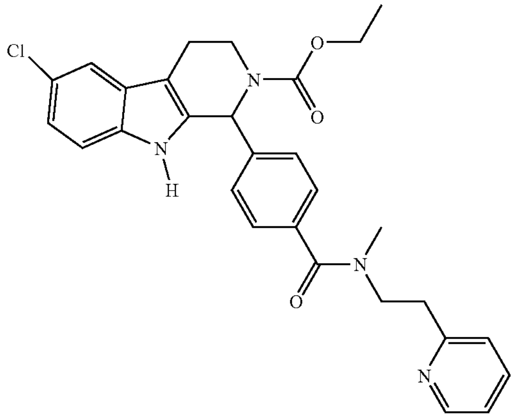
519
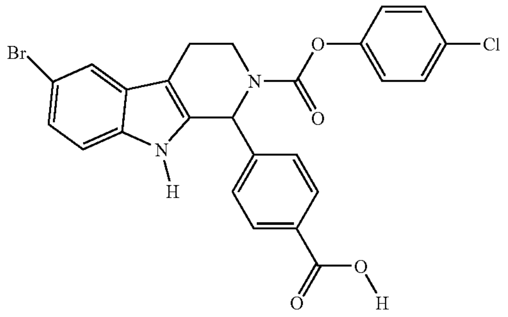
520
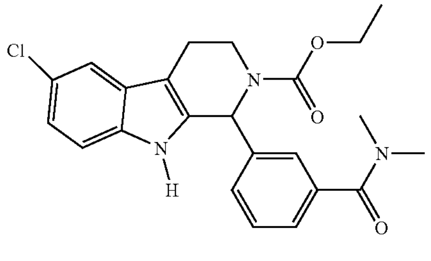
521
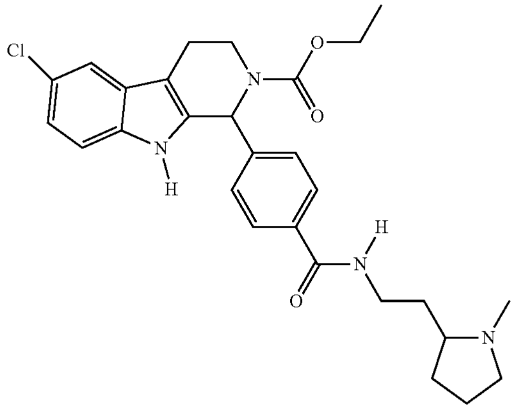

-continued
522
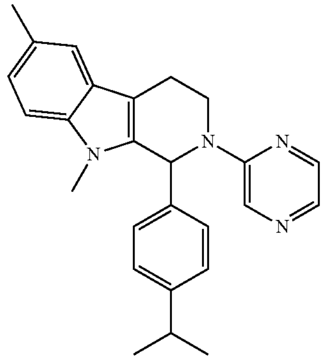
523
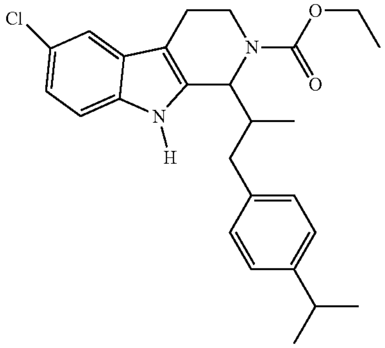
524
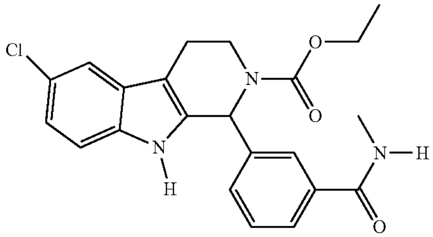
525
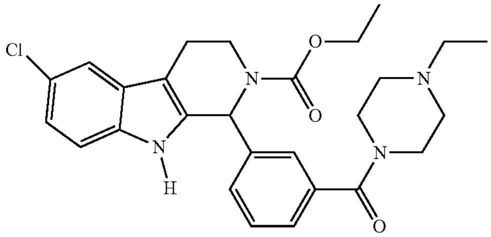
526
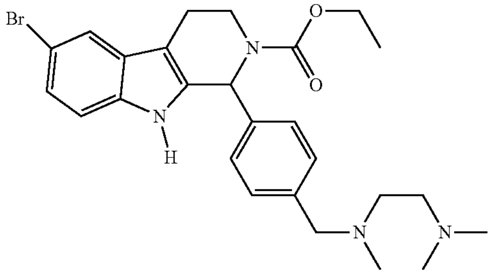
-continued
527
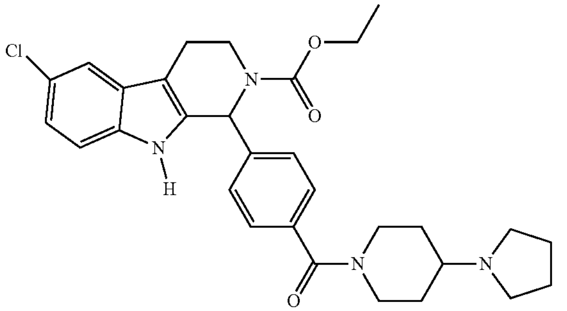
528
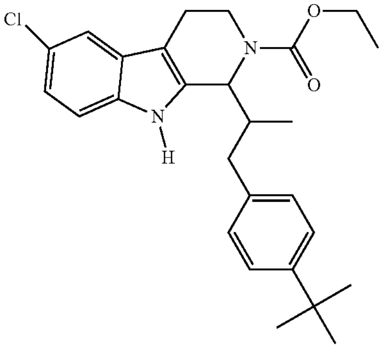
529
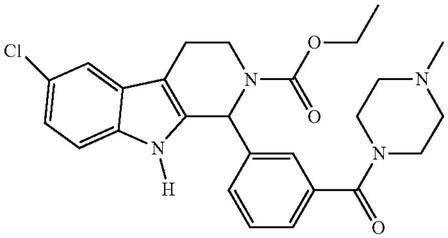
530
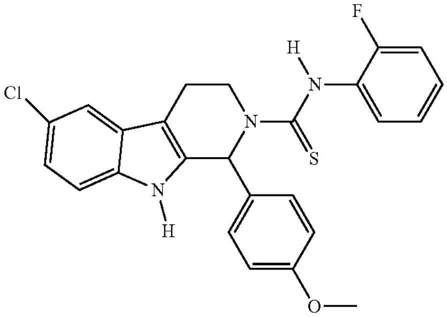
531
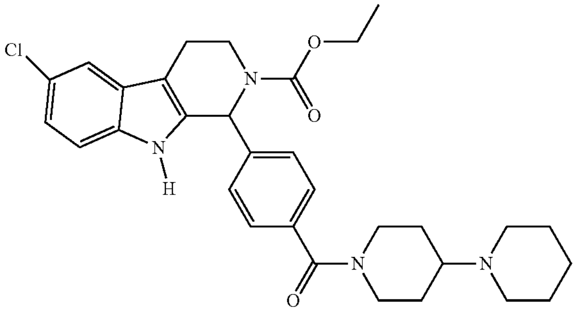

-continued
532
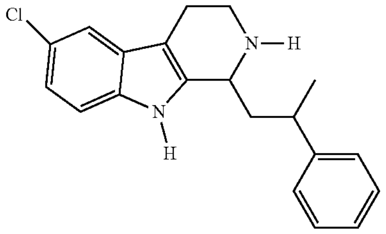
533
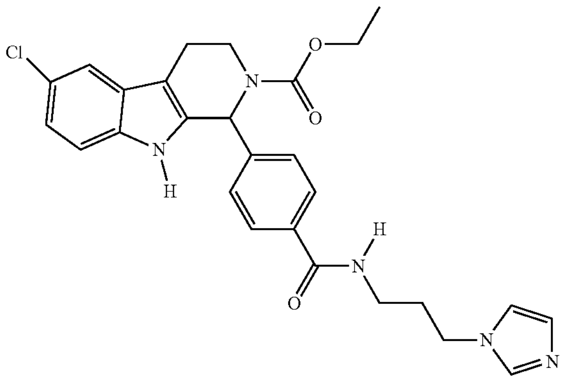
534
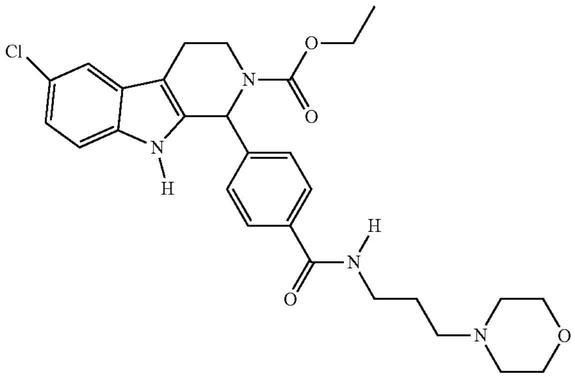
535
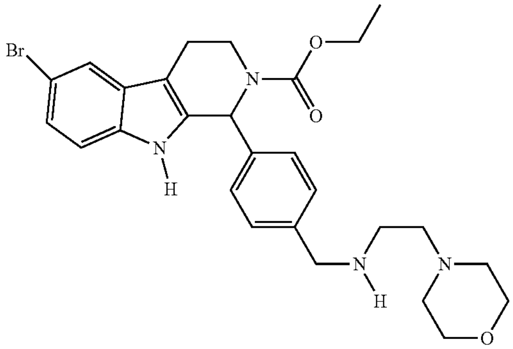
-continued
536
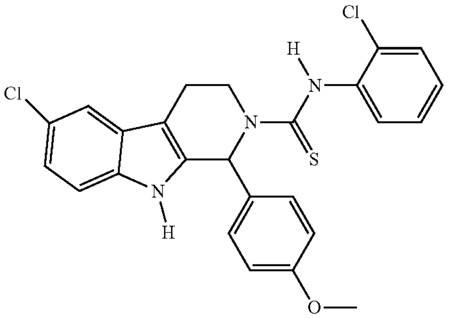
537
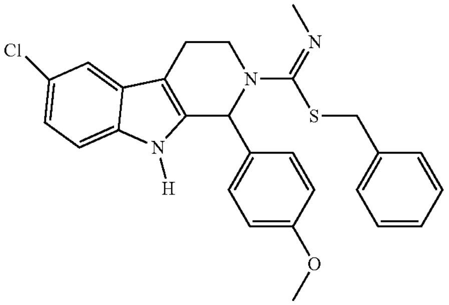
538
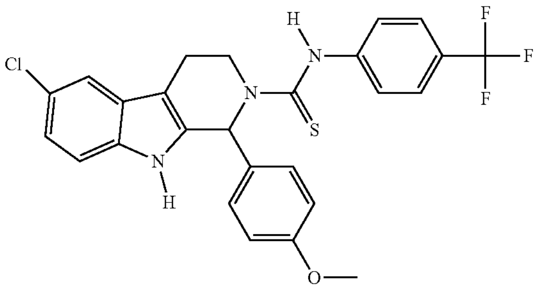
539
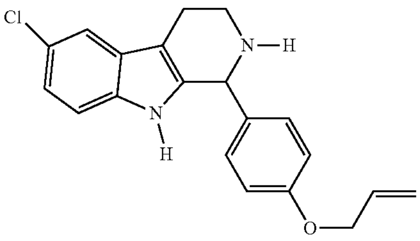
540
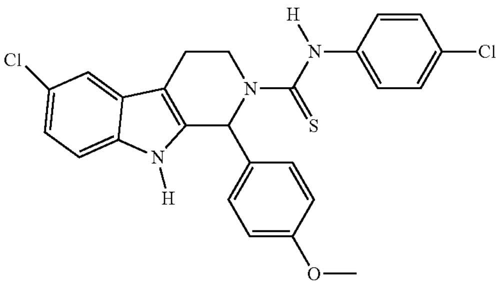

-continued
541
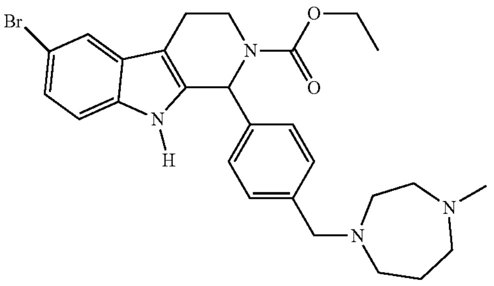
542
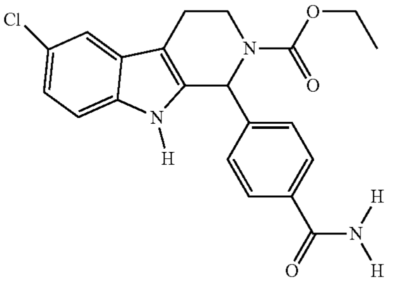
543
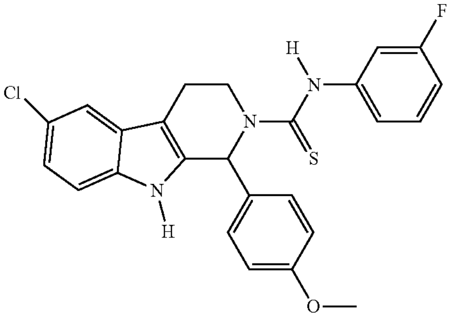
544
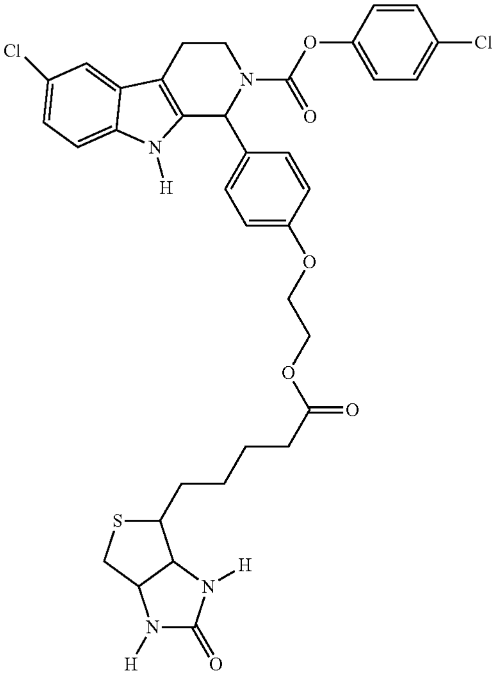
-continued
545
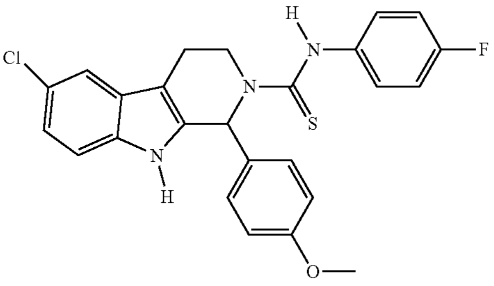
546
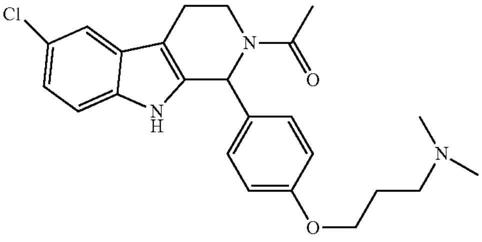
547
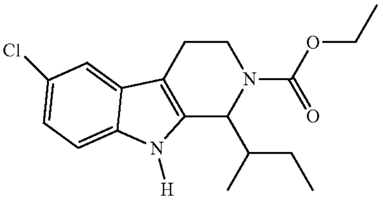
548
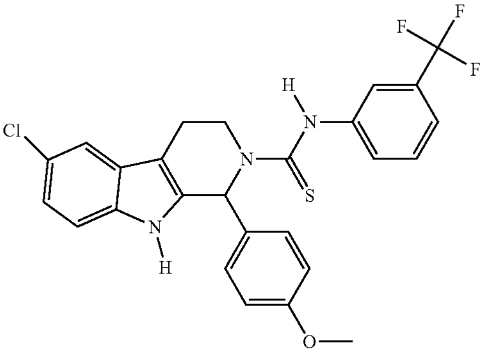
549
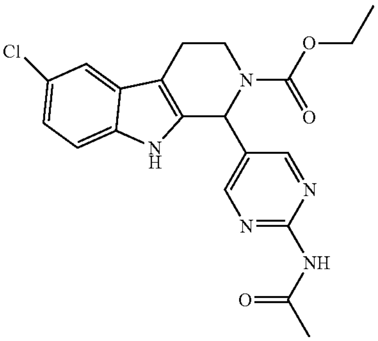

-continued
550
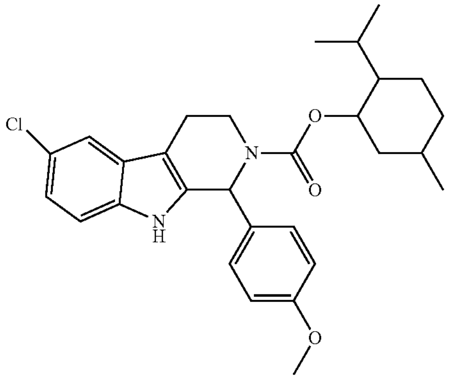
551
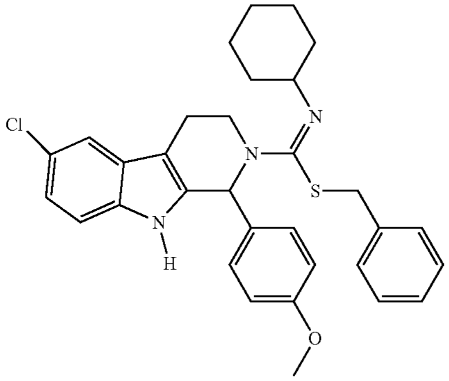
552
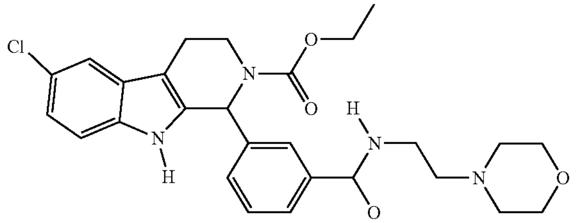
553
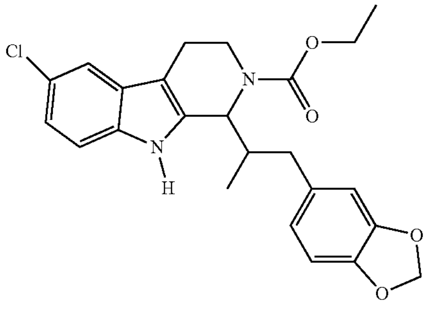
-continued
554
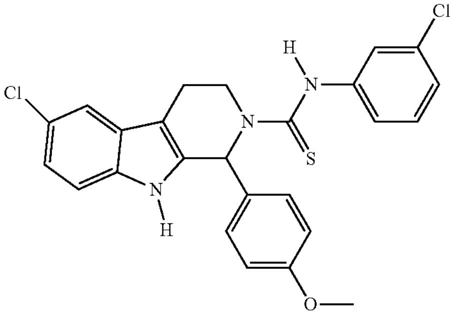
555
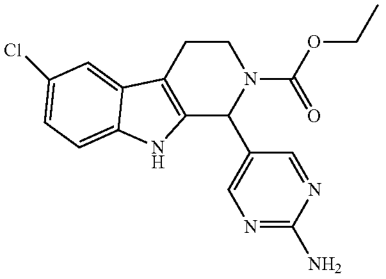
556
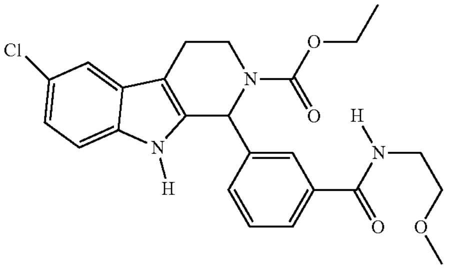
557
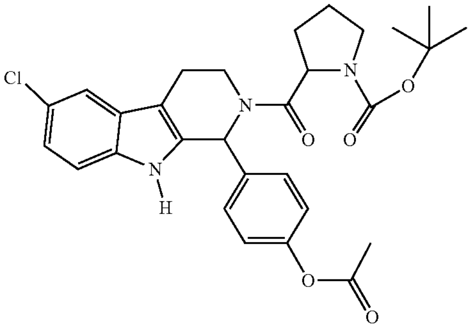
558
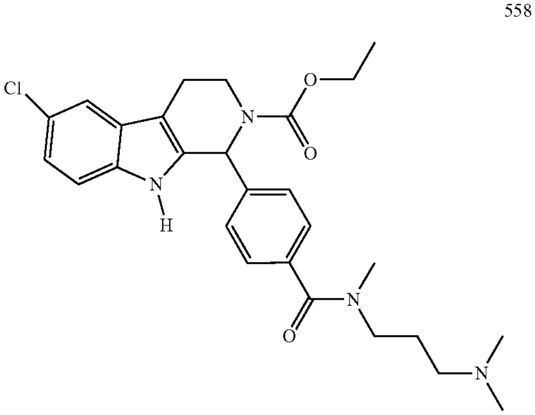

-continued
559
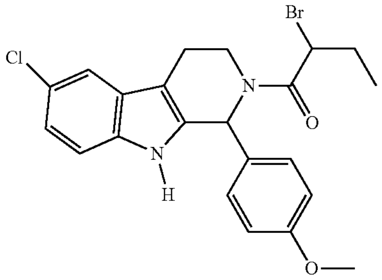
560
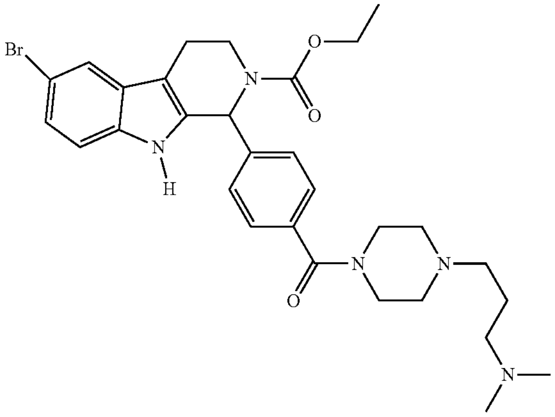
561
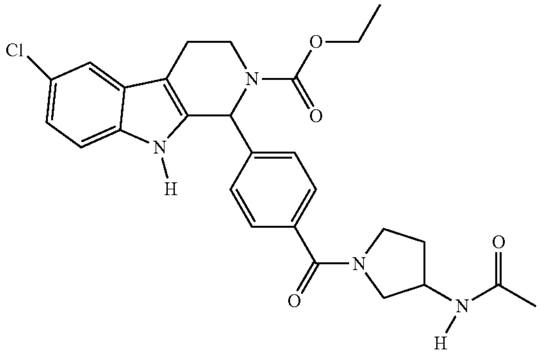
562
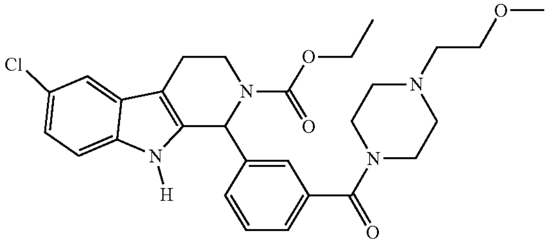
-continued
563
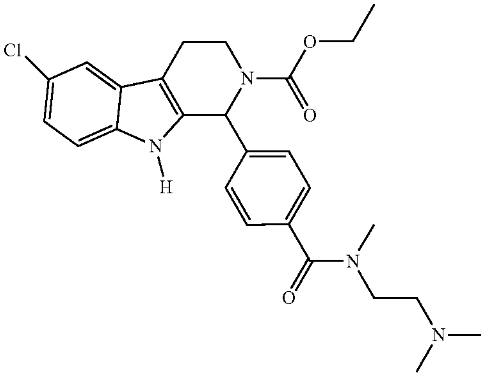
564
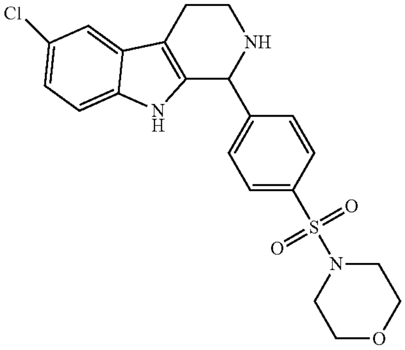
565
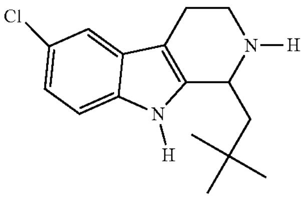
566
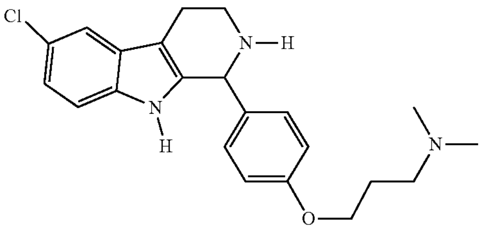
567
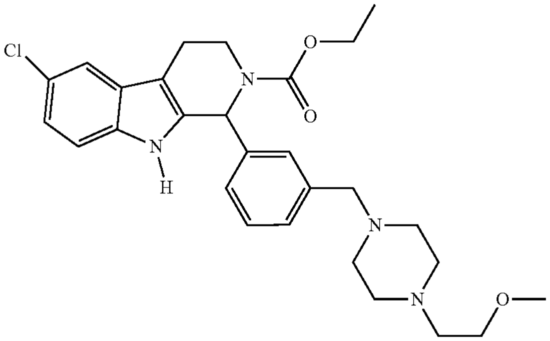

-continued
568
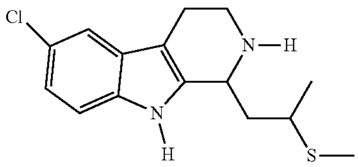
569
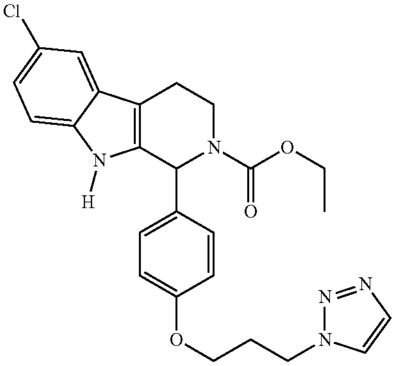
570
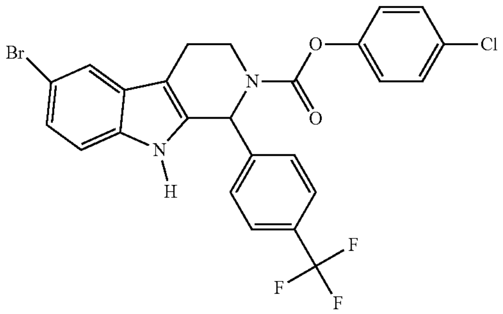
571
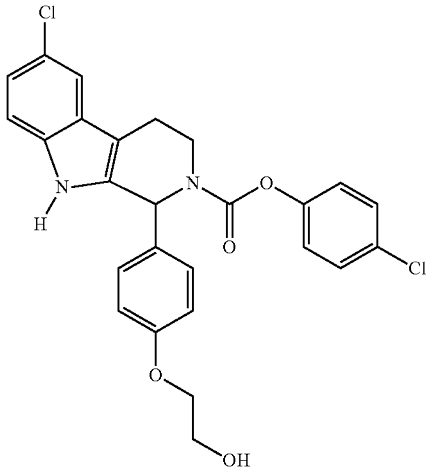
-continued
572
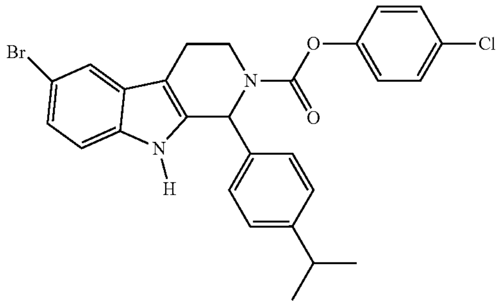
573
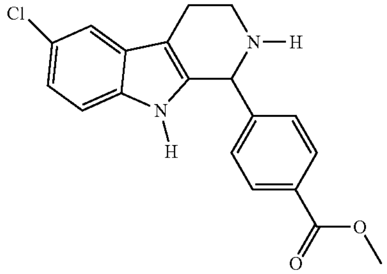
574
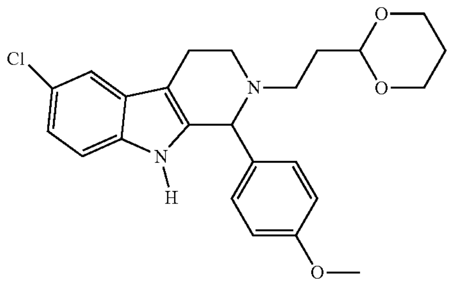
575
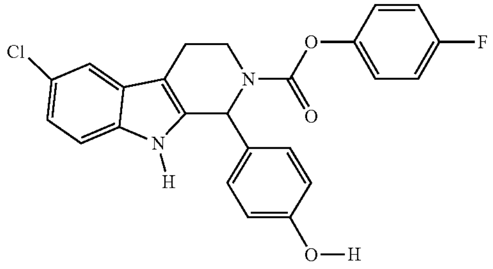
576
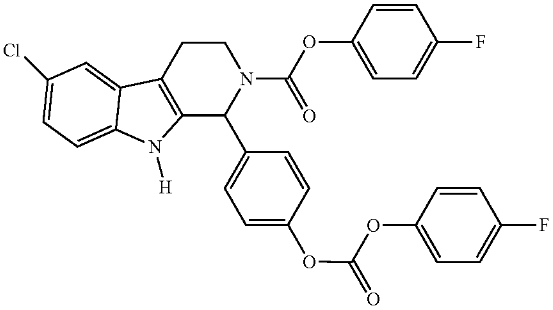

-continued
577
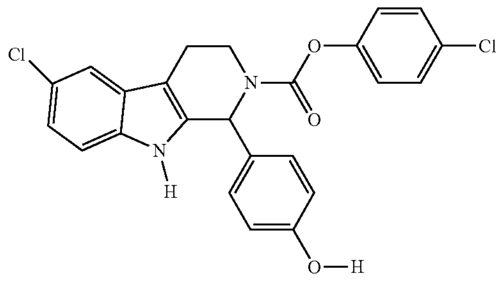
578
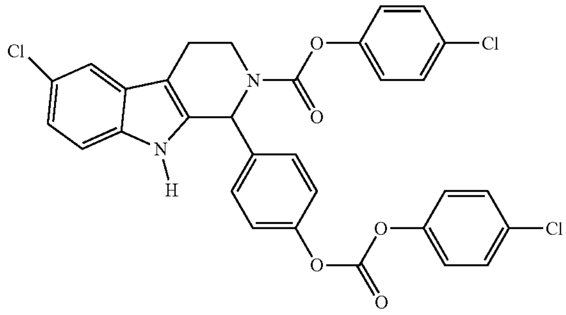
579
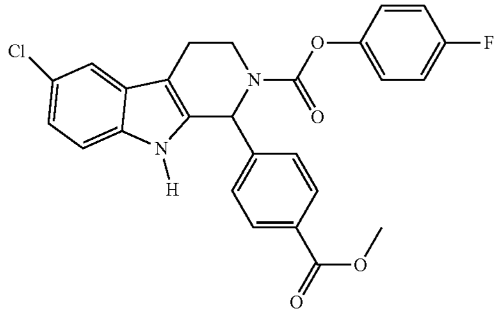
580
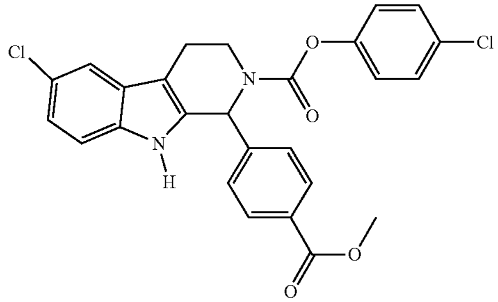
-continued
581
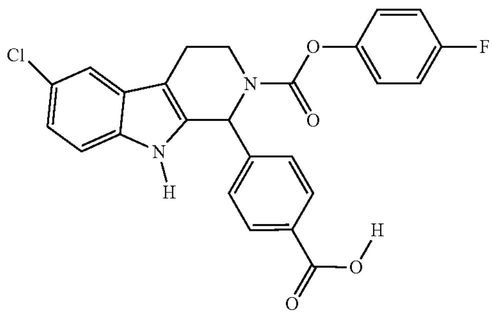
582
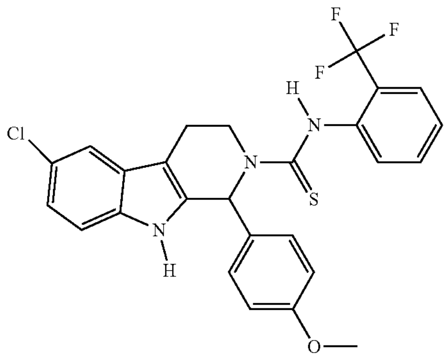
583
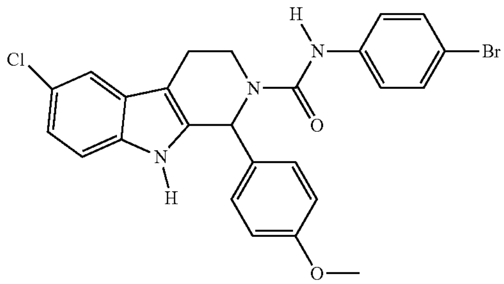
584
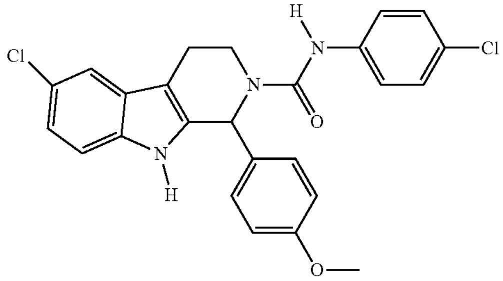

-continued
585
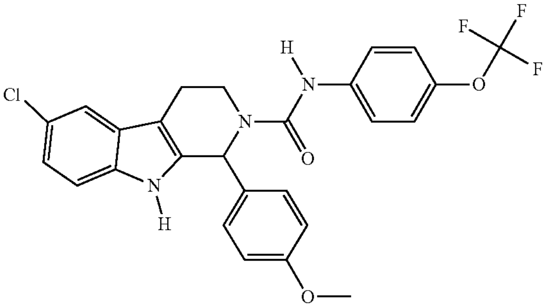
586
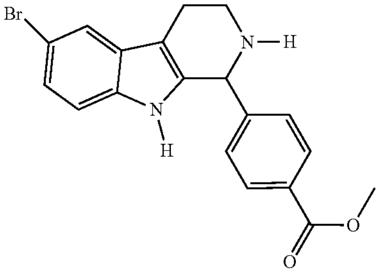
587
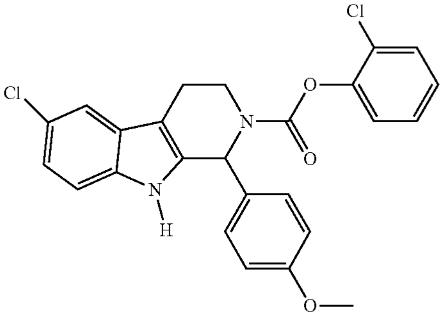
588
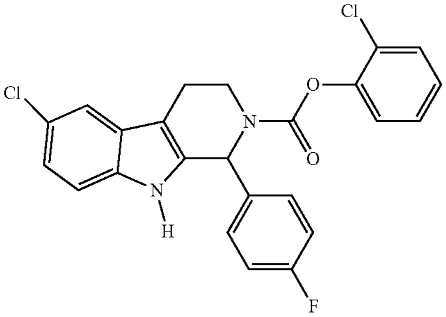
589
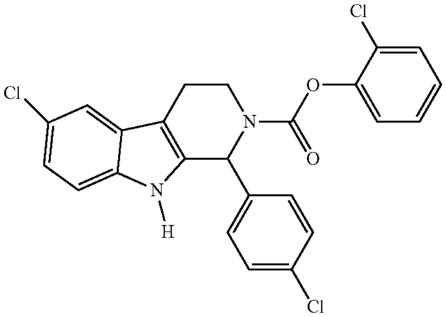
-continued
590
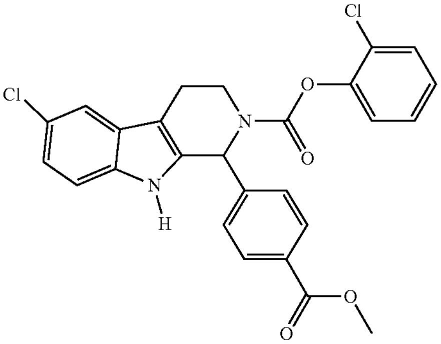
591
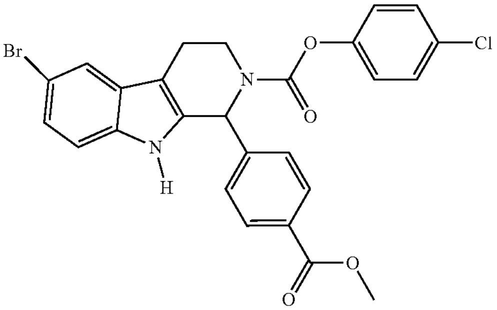
592
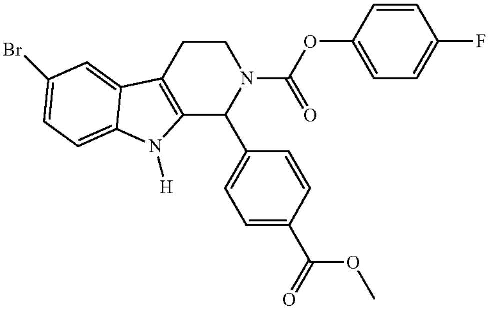
593
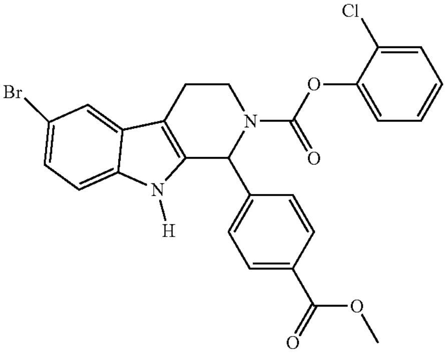

-continued
594
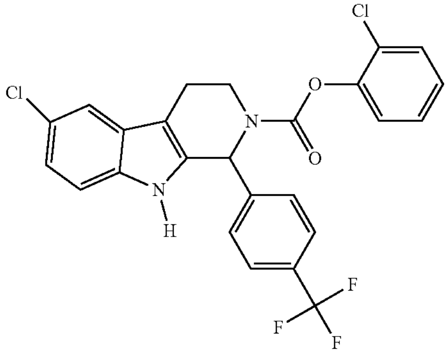
595
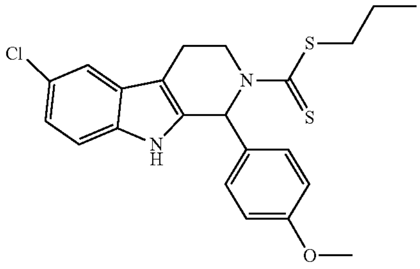
596
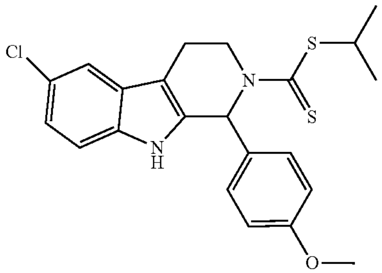
597
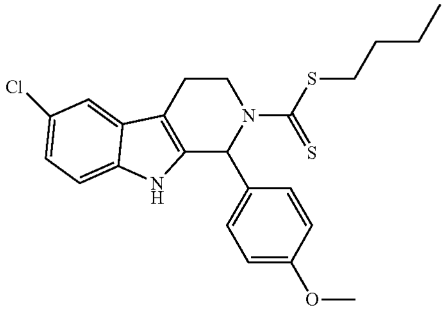
598
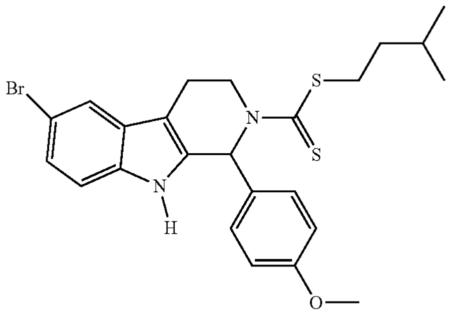
-continued
599
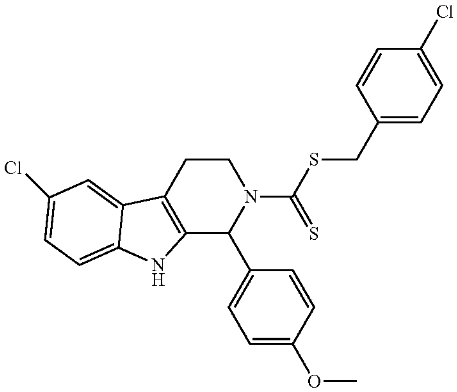
600
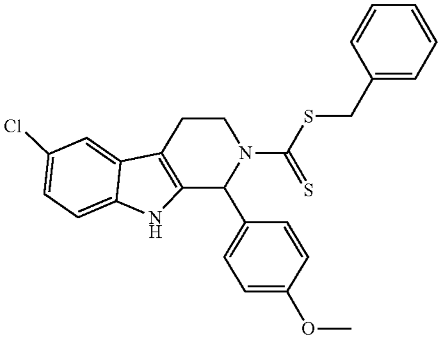
601
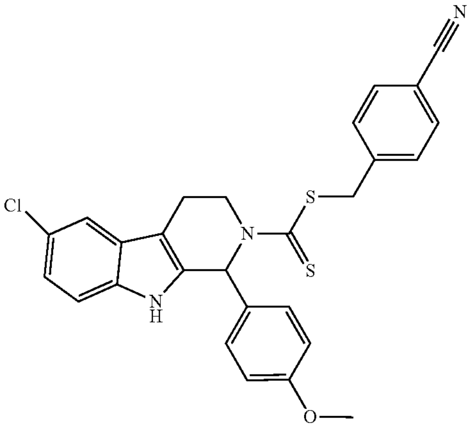
602
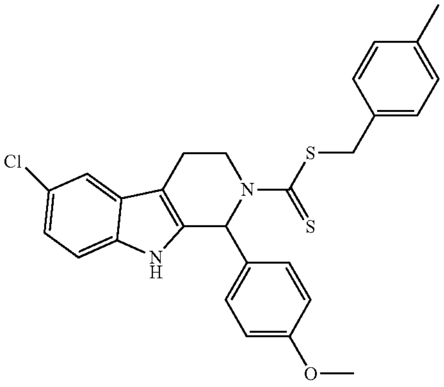

-continued
603
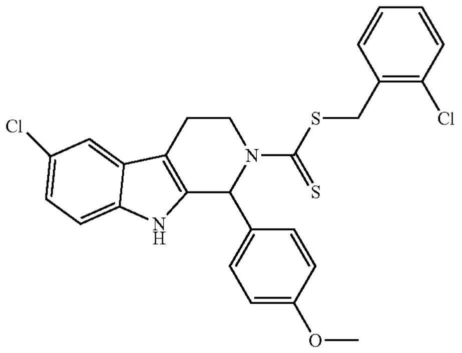
604
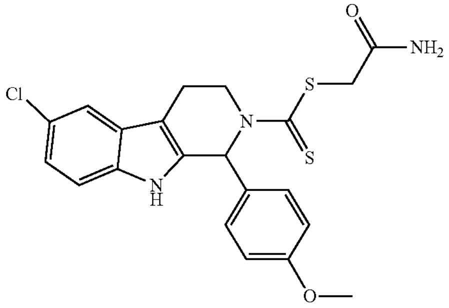
605
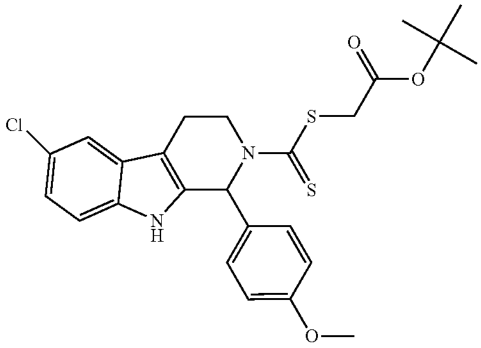
606
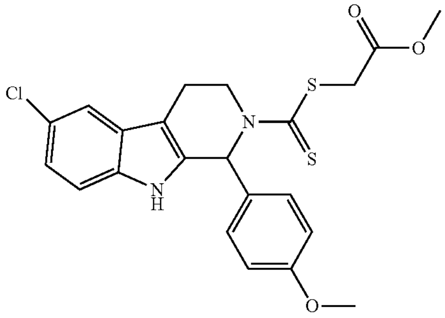
607
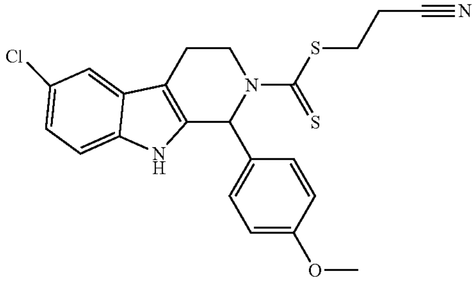
-continued
608
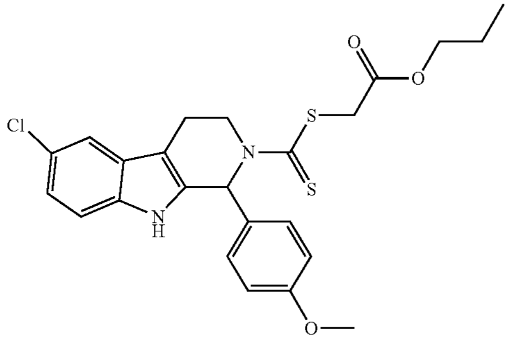
609
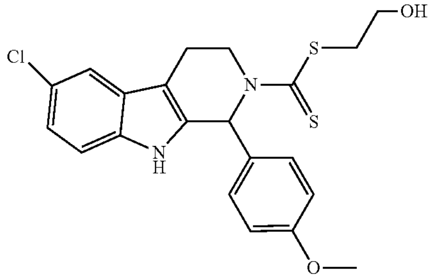
610
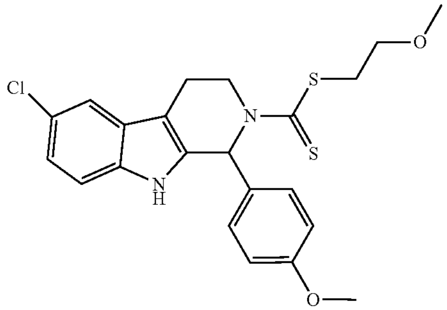
611
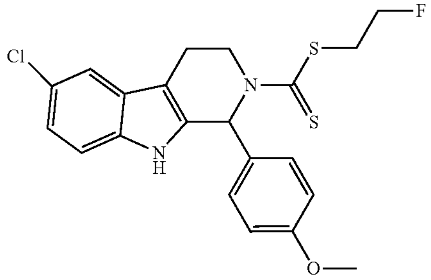
612
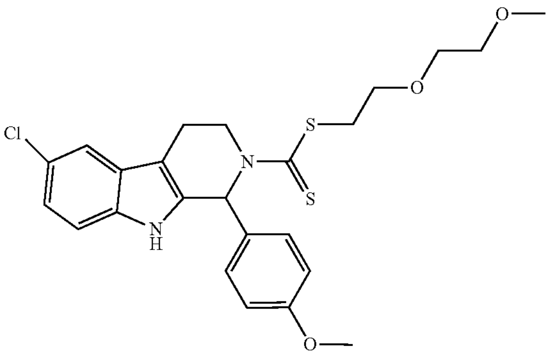

-continued
613
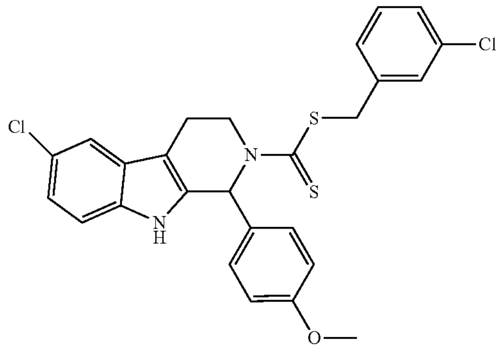
614
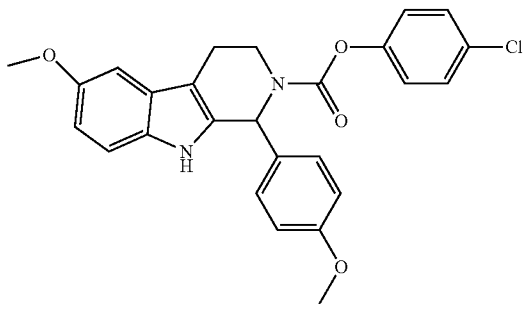
615
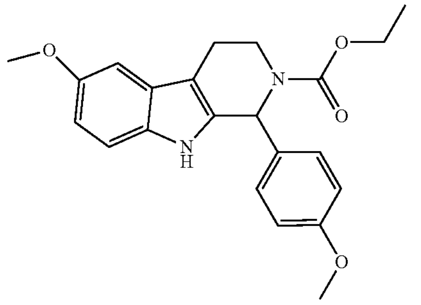
616
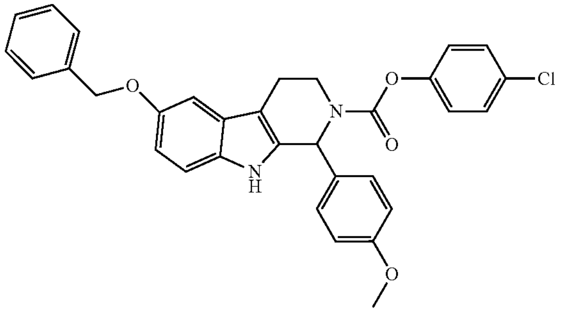
-continued
617
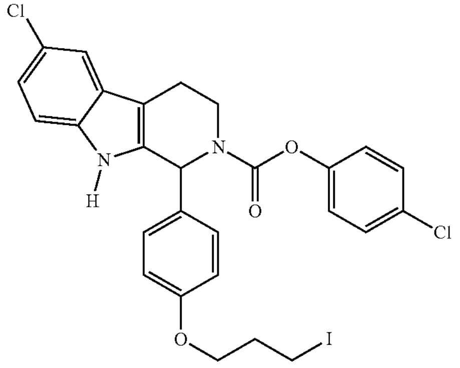
618
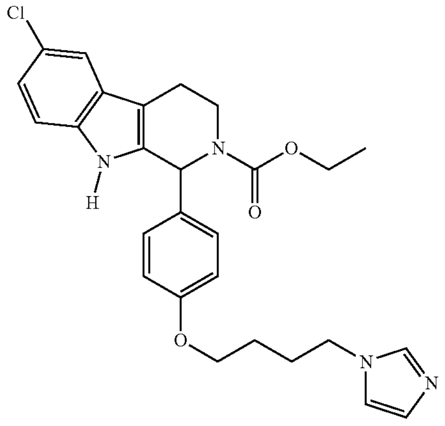
619
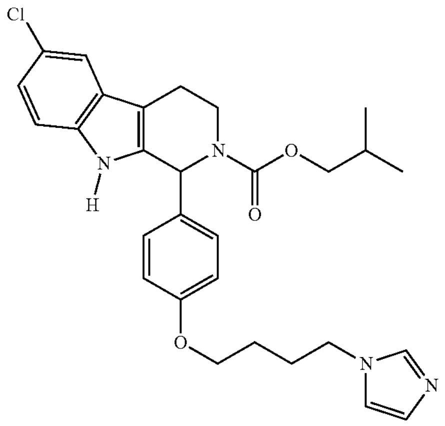
620
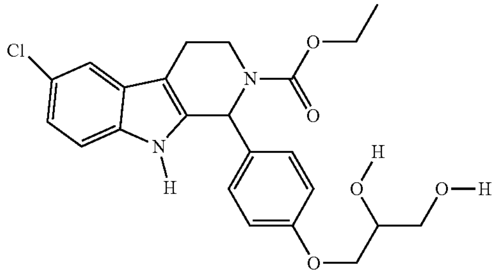

-continued
621
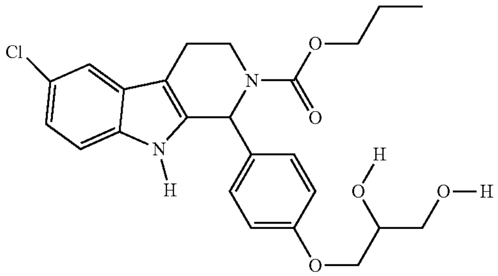
622
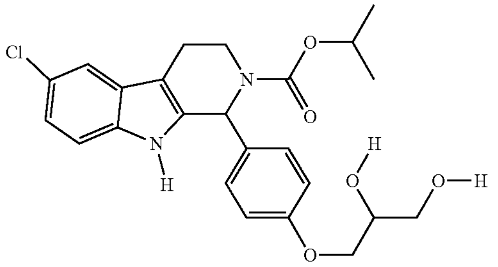
623
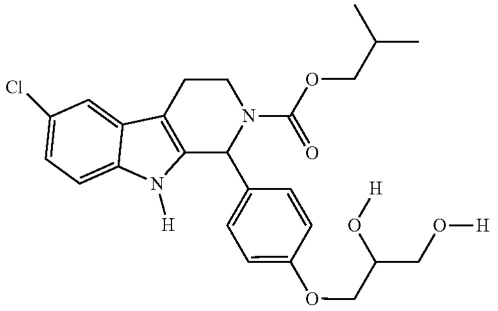
624
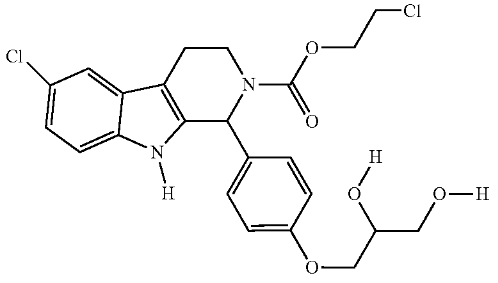
625
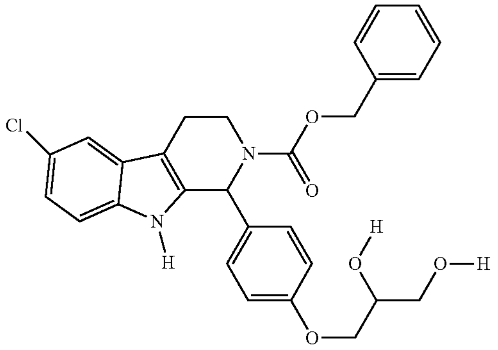
-continued
626
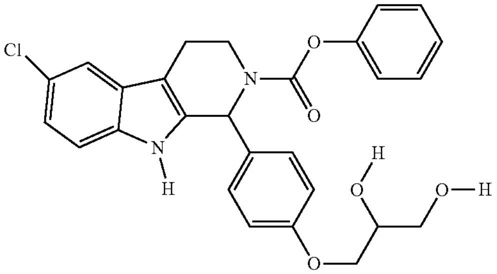
627
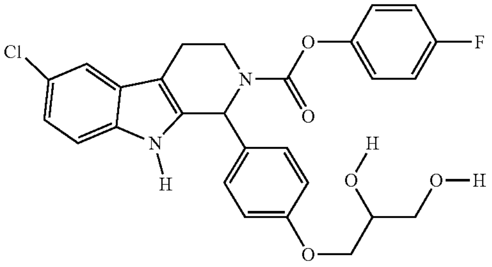
628
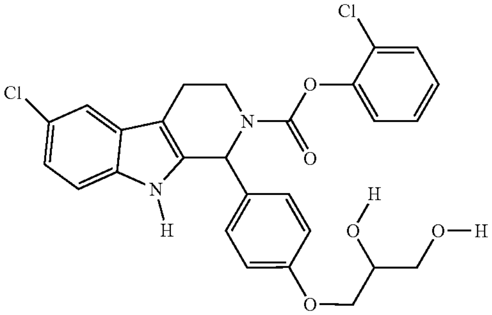
629
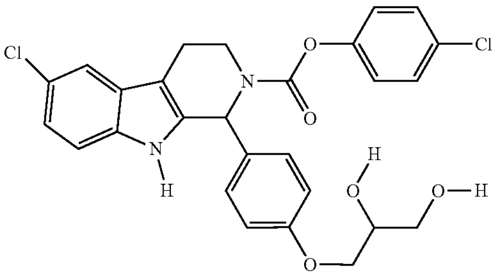
630
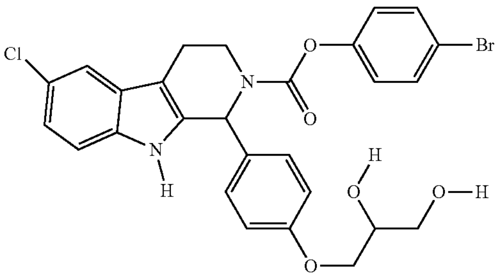

-continued
631
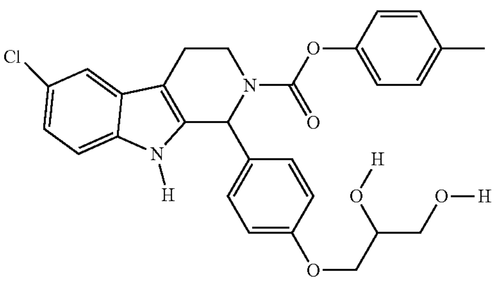
632
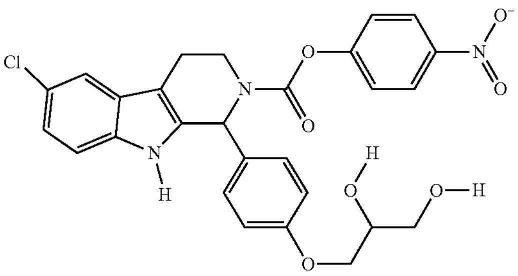
633
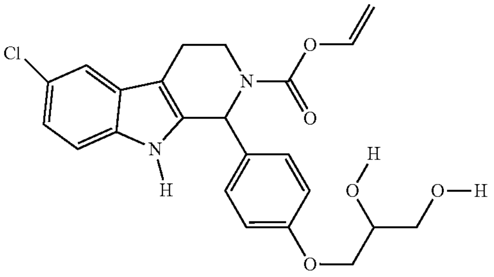
634
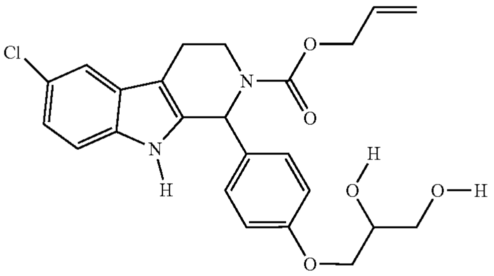
635
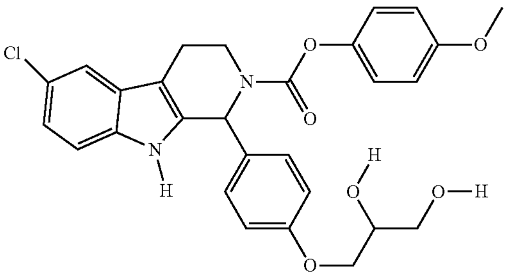
-continued
636
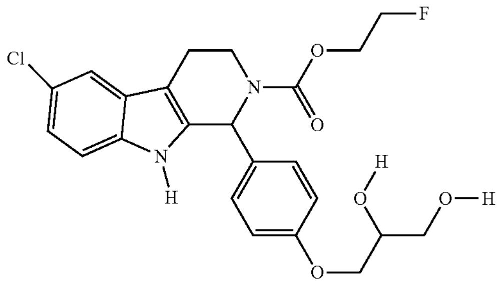
637
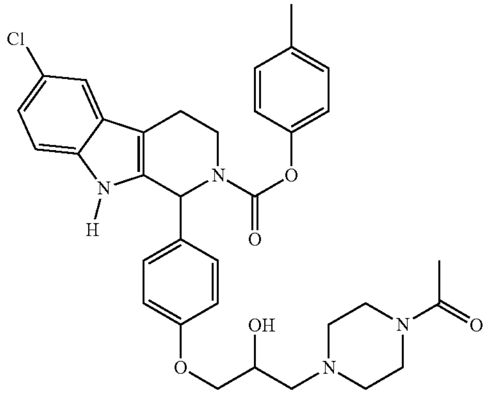
638
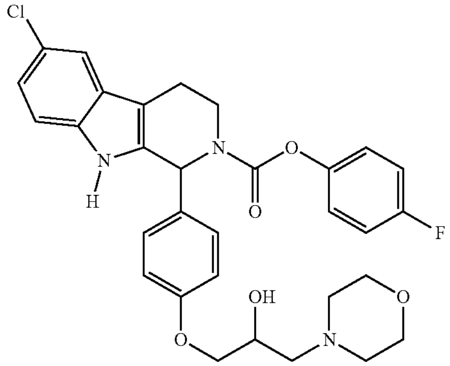
639
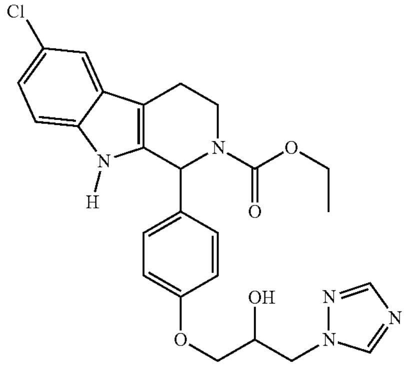

-continued
640
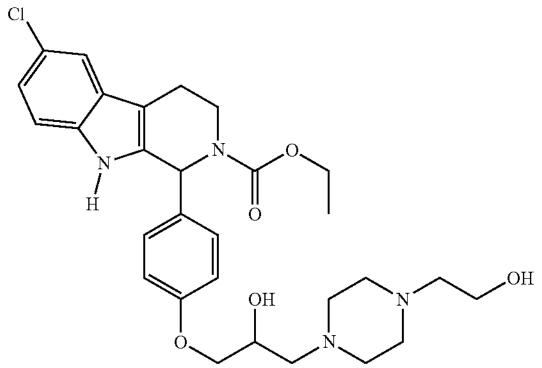
641
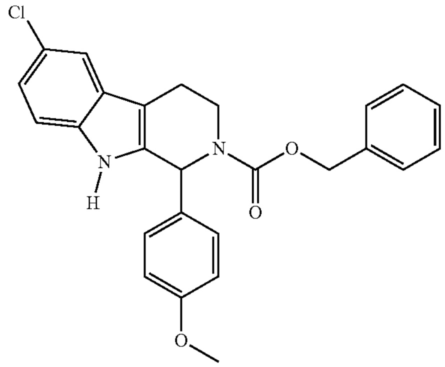
642
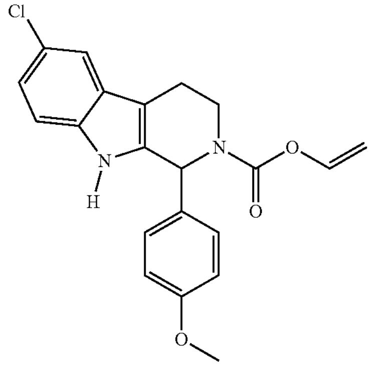
643
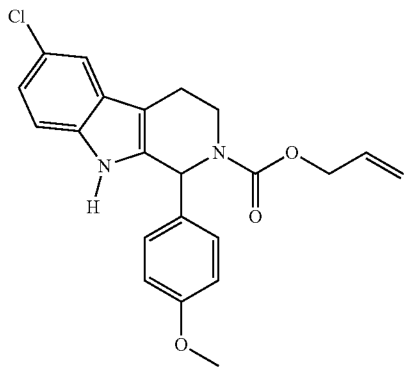
-continued
644
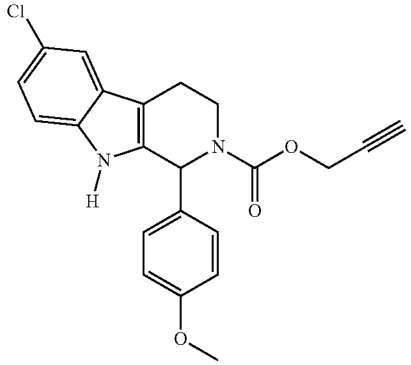
645
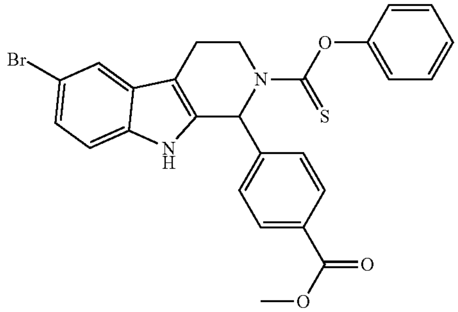
646
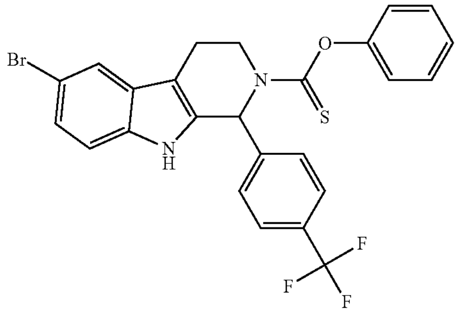
647
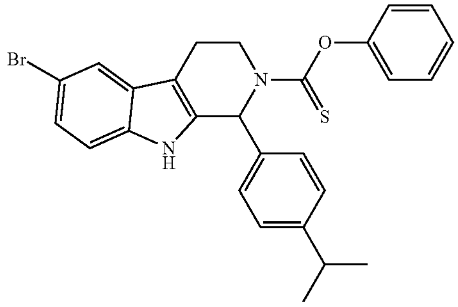
648
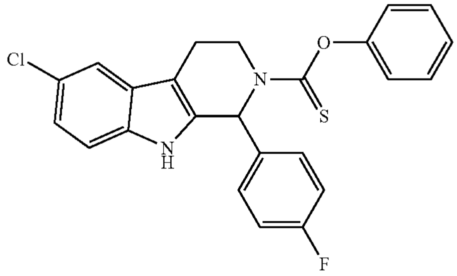

-continued
649
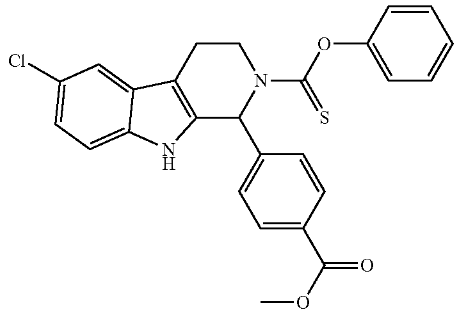
650
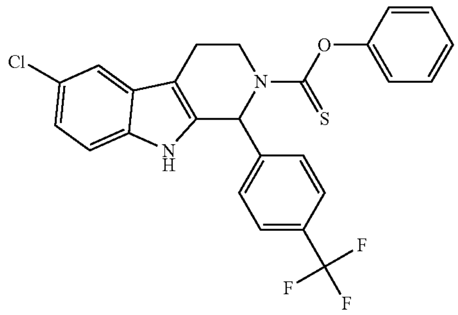
651
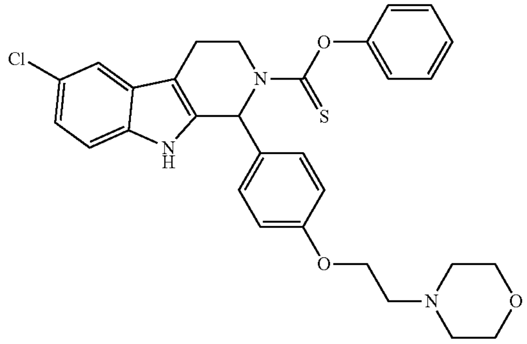
652
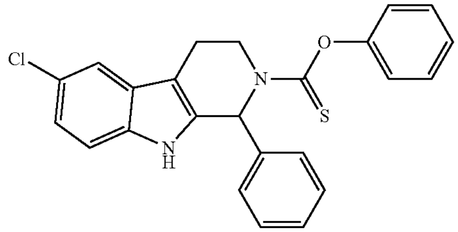
653
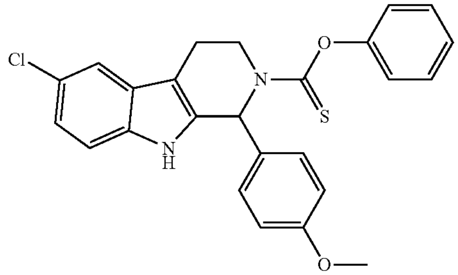
-continued
654
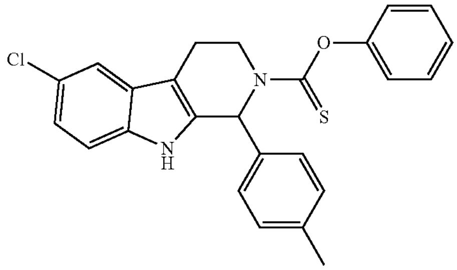
655
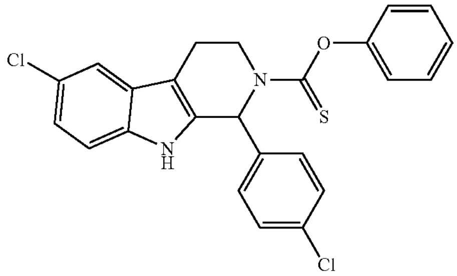
656
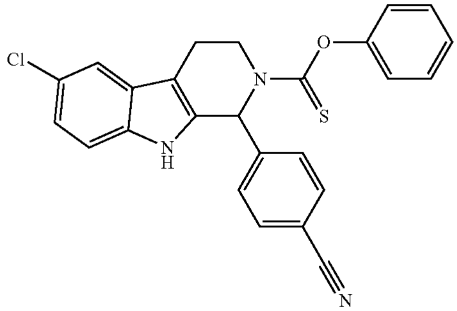
657
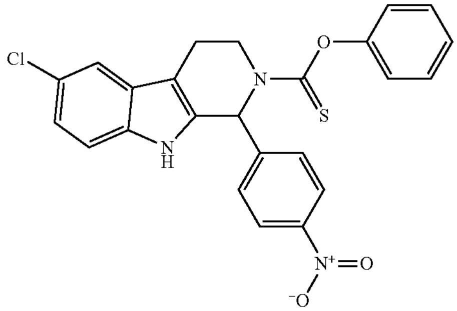
658
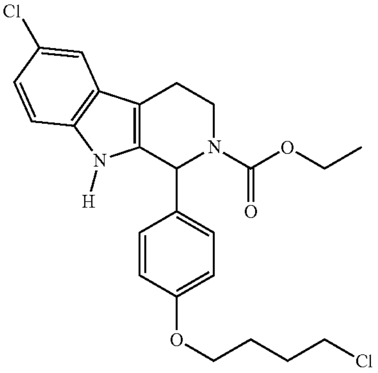

-continued
659
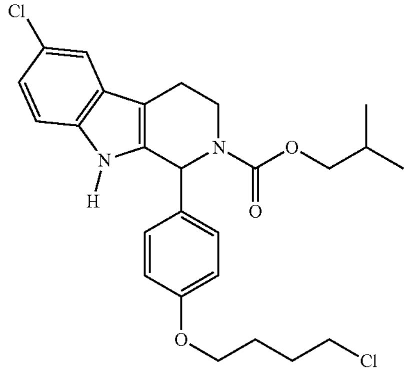
660
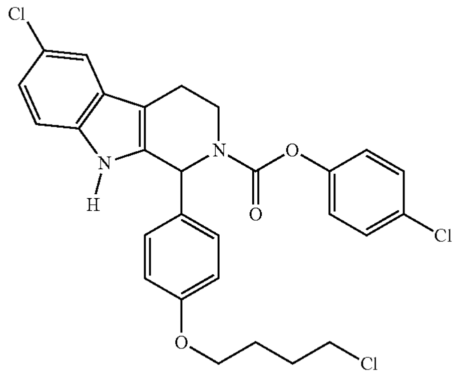
661
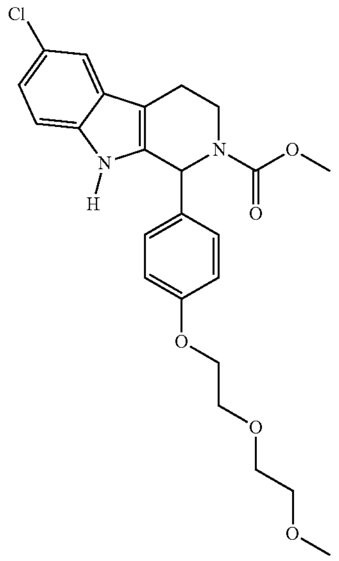
-continued
662
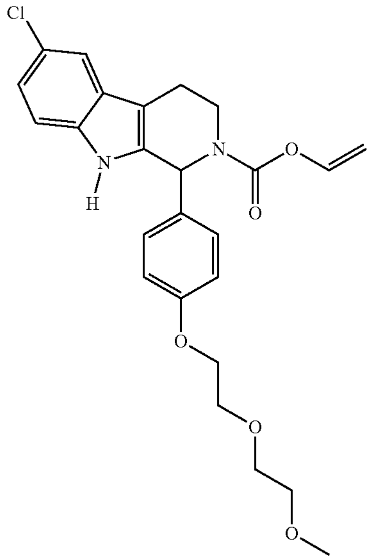
663
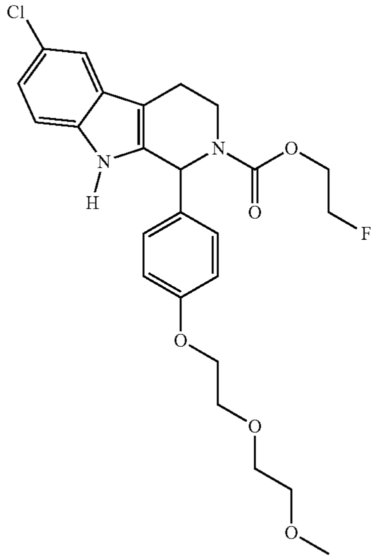
664
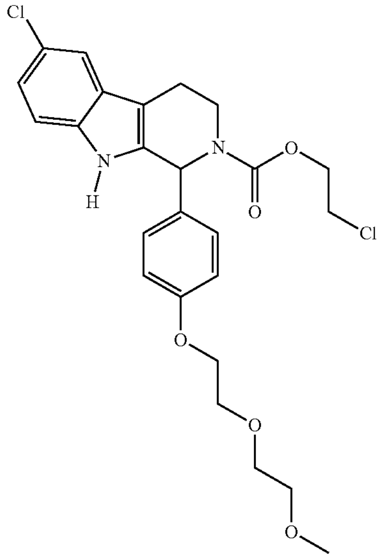

-continued
665
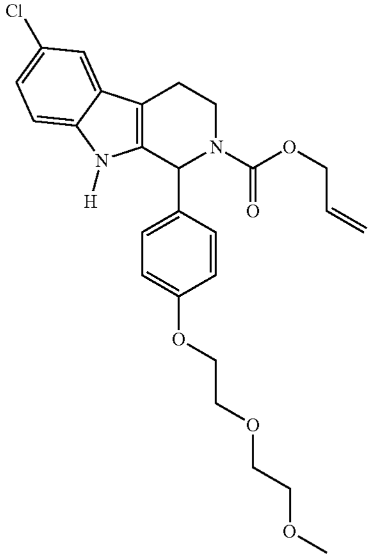
668
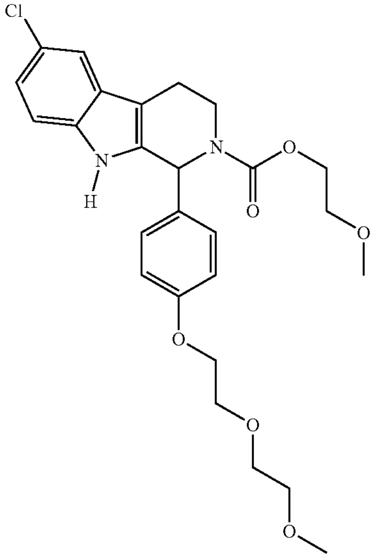
666
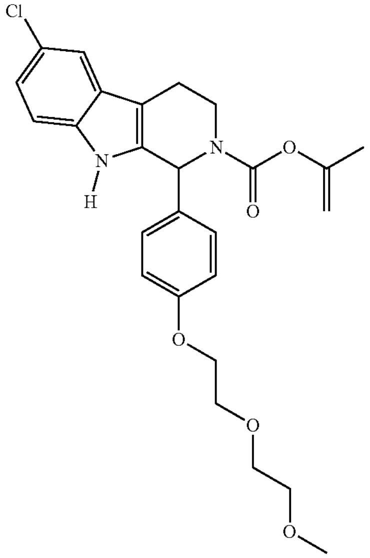
669
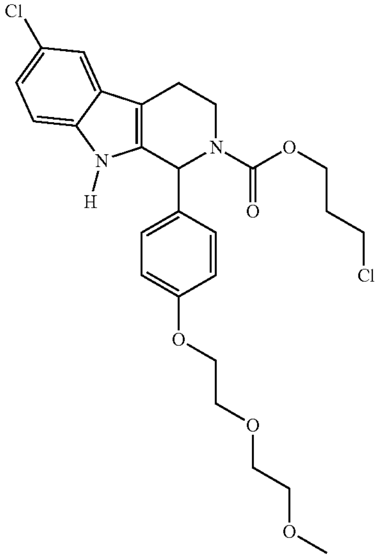
667
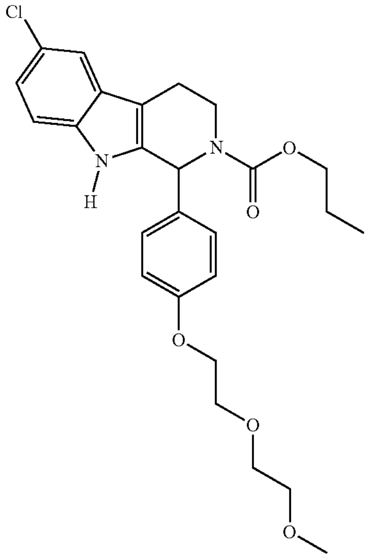
670
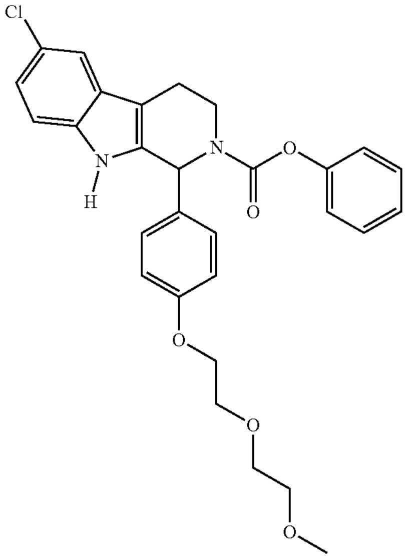

-continued
671
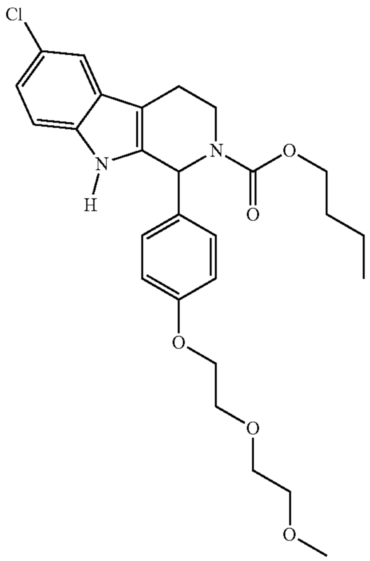
672
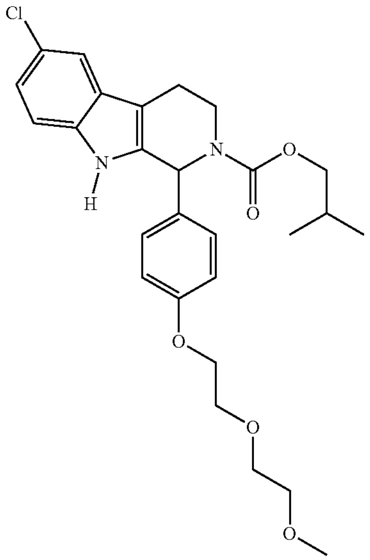
673
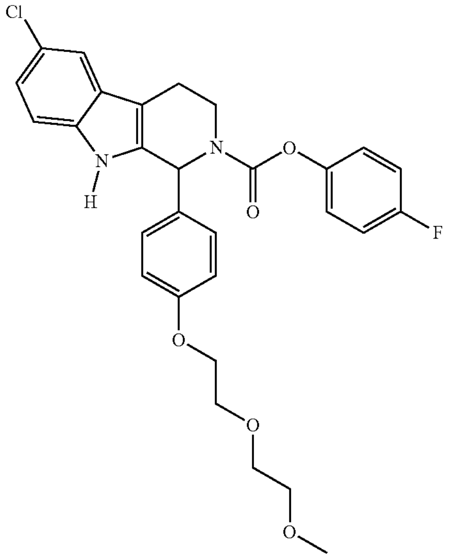
-continued
674
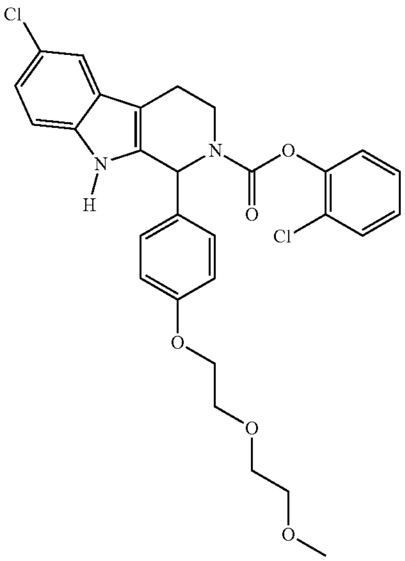
675
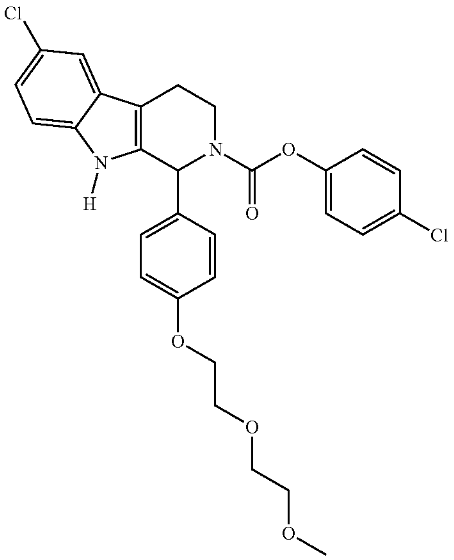
676
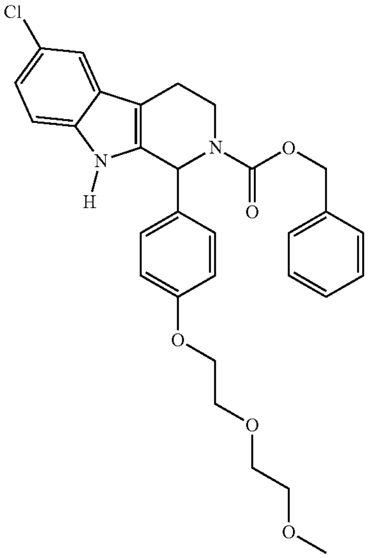

-continued
677
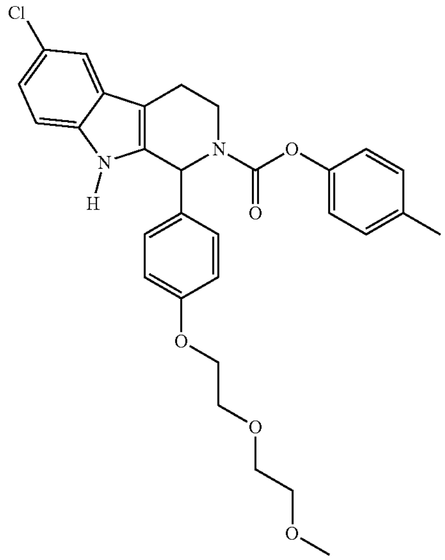
678
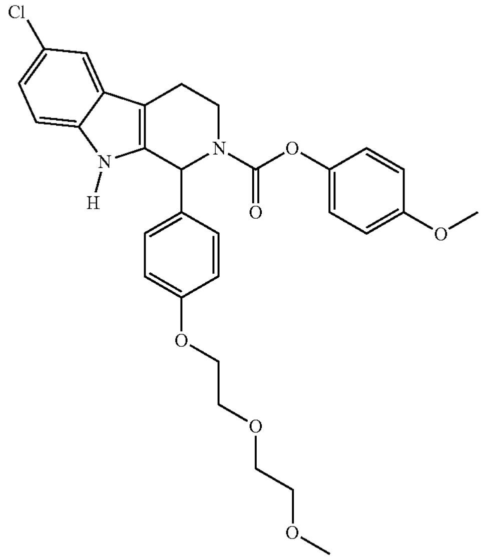
679
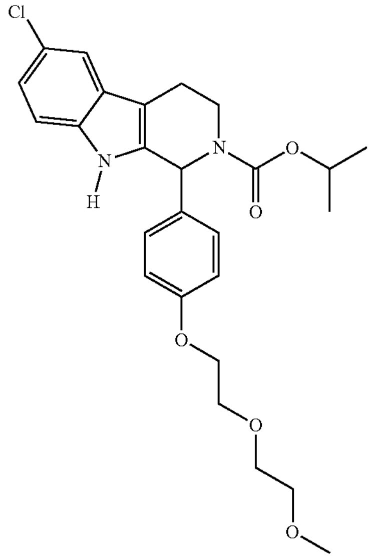
-continued
680
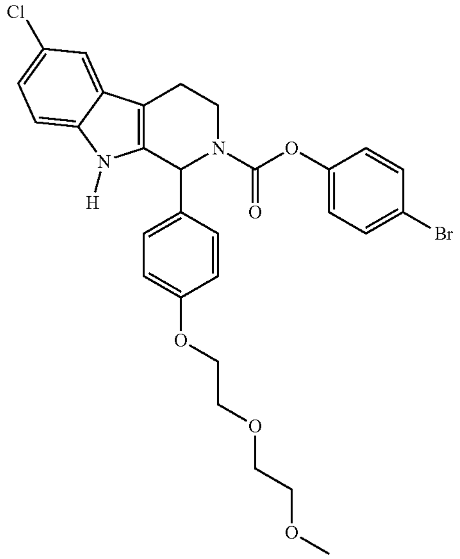
681
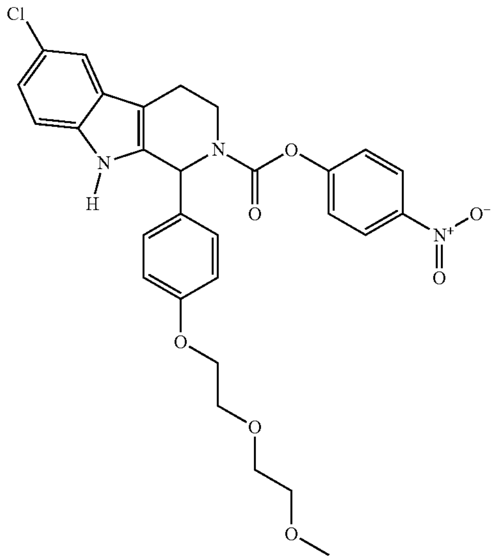
682
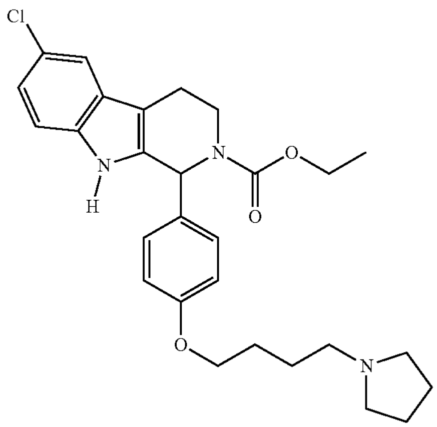

-continued
683
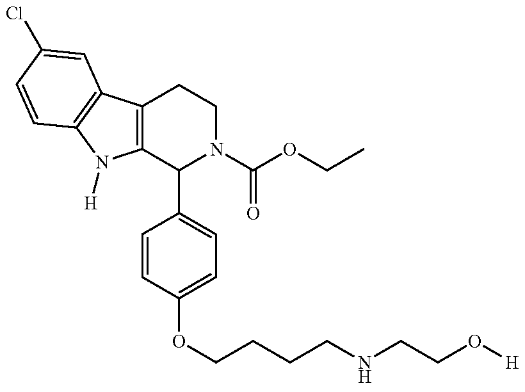
684
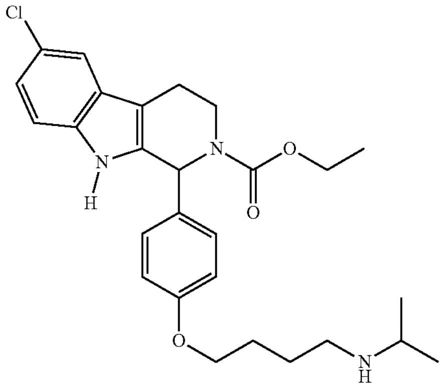
685
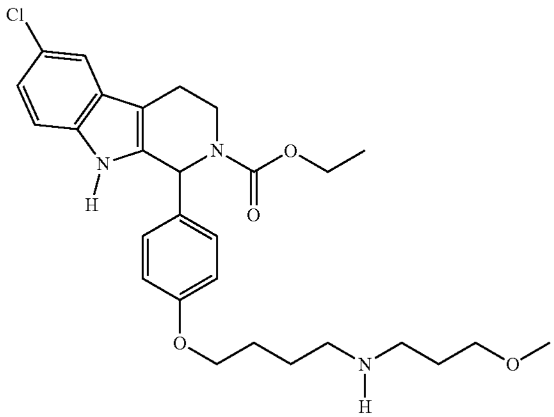
-continued
686
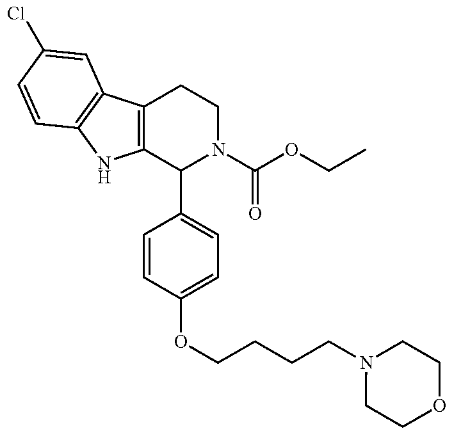
687
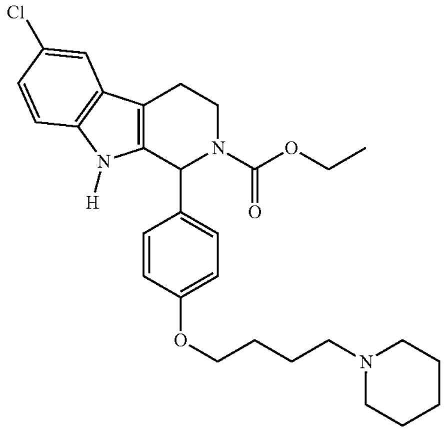
688
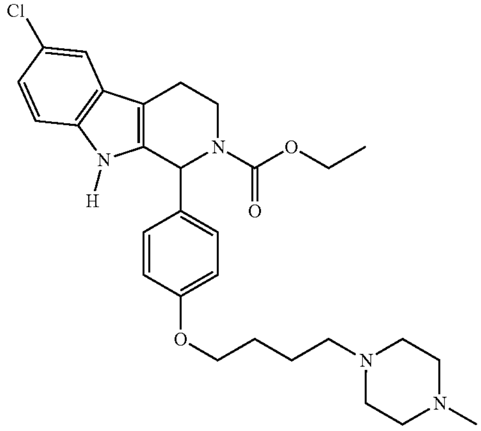

-continued
689
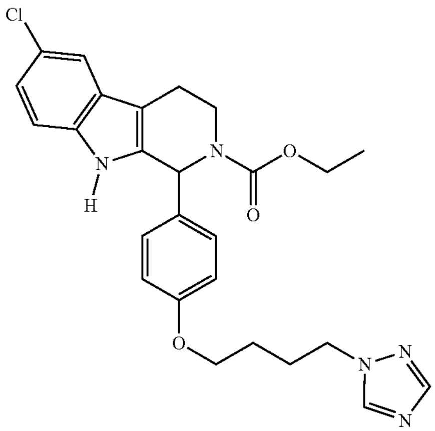
690
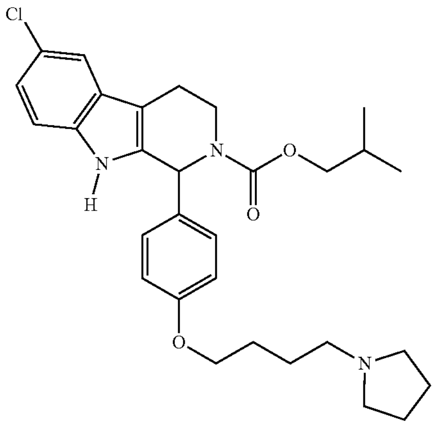
691
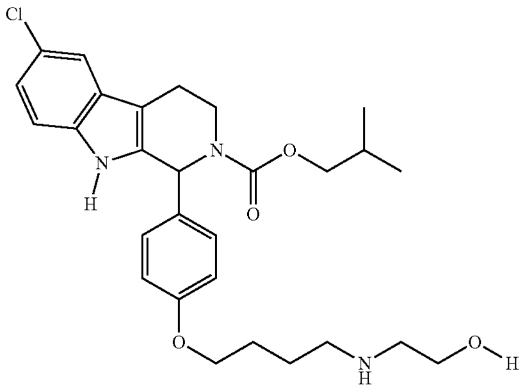
-continued
692
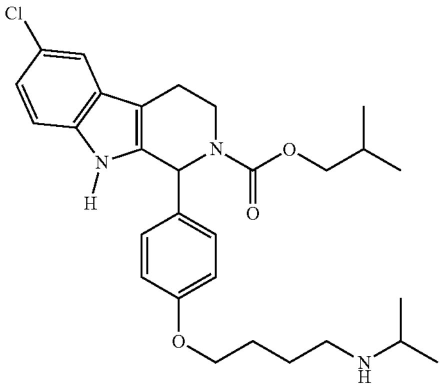
693
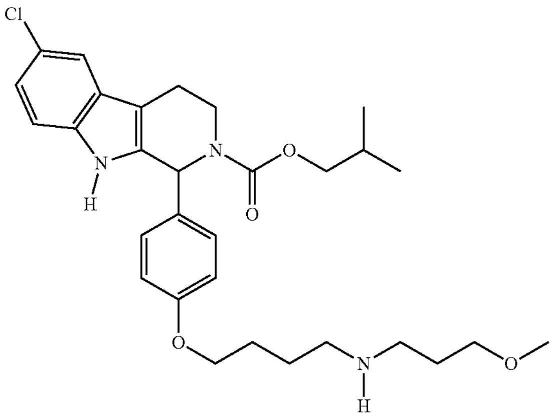
694
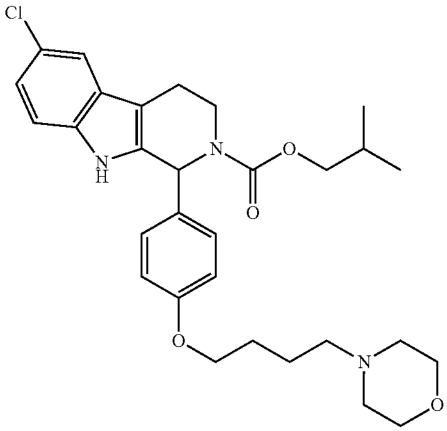

-continued
695
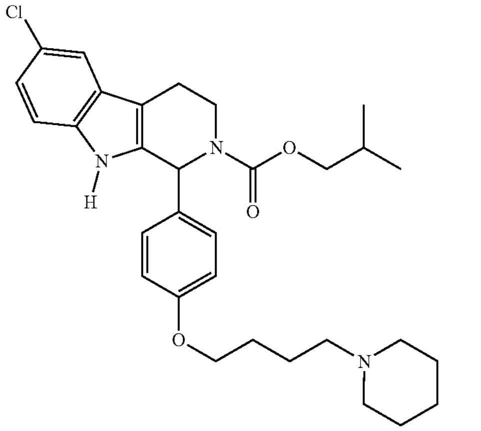
696
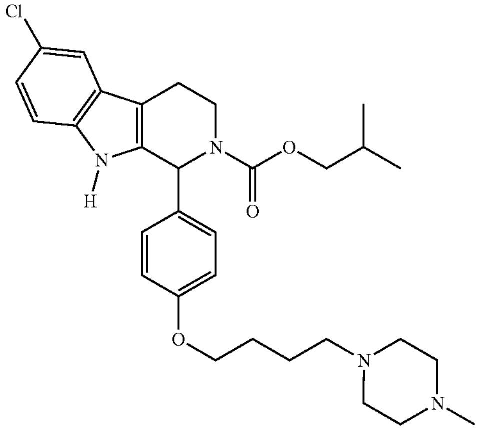
697
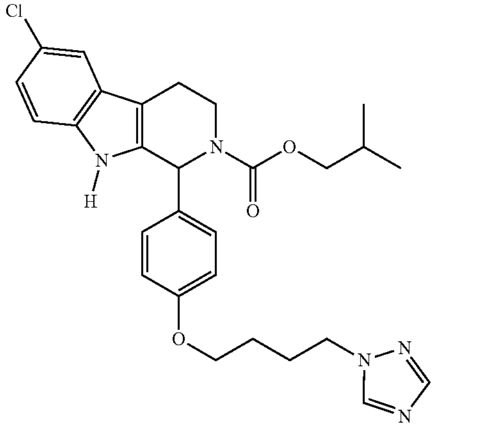
-continued
698
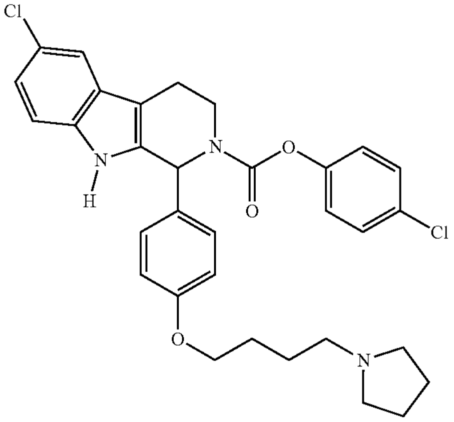
699
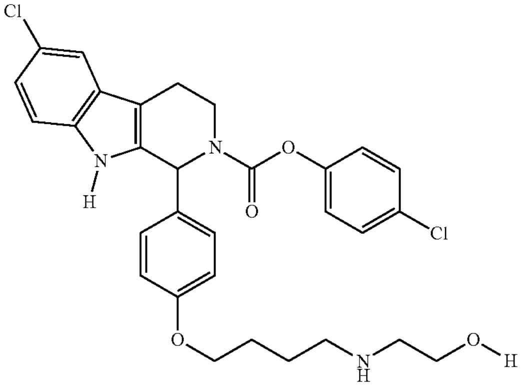
700
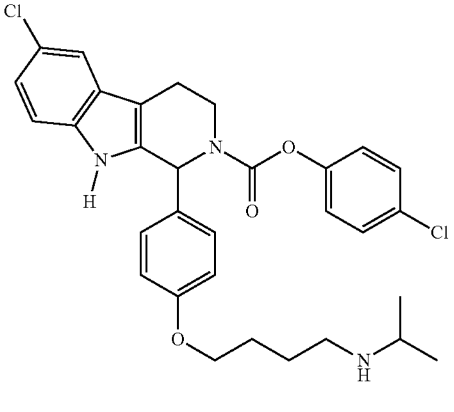

-continued
701
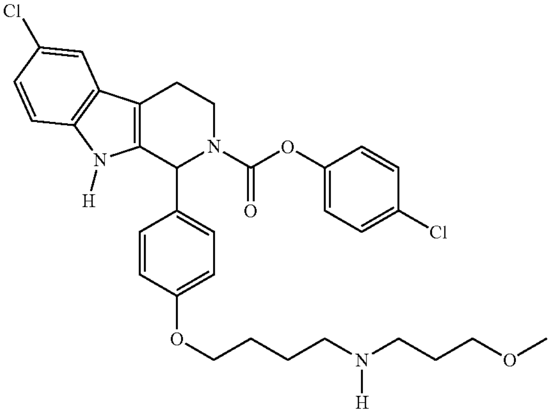
702
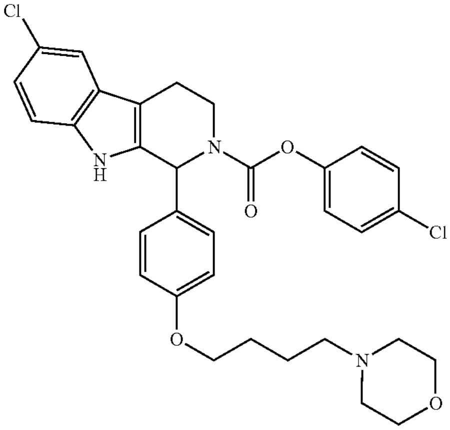
703
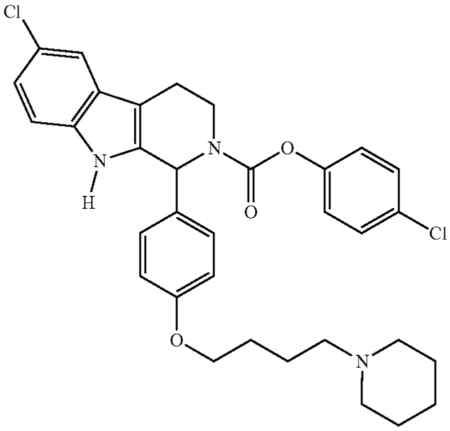
-continued
704
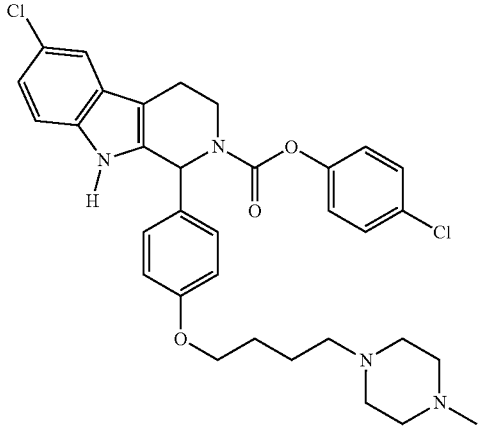
705
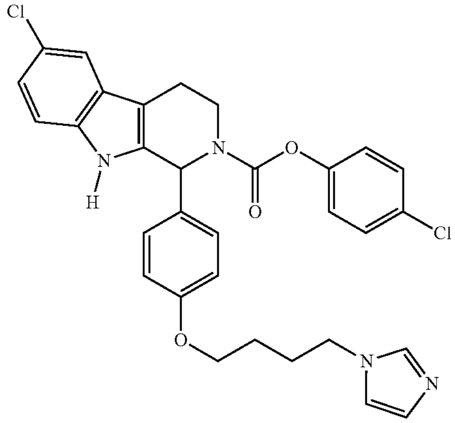
706
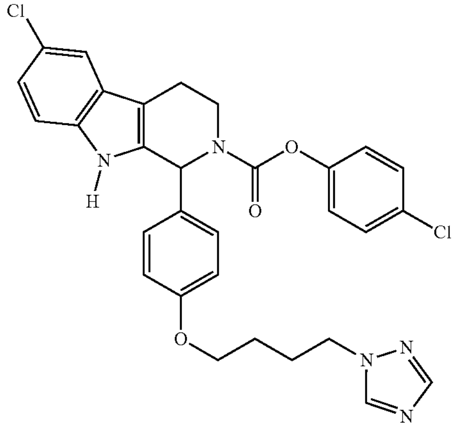

-continued
707
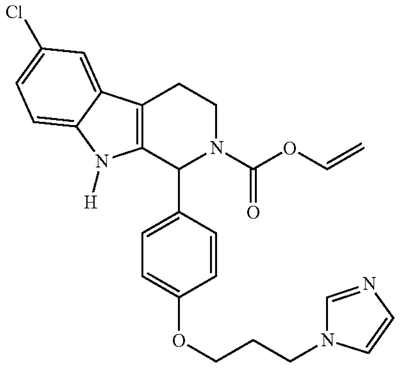
708
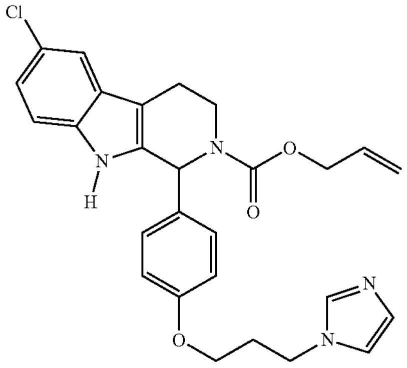
709
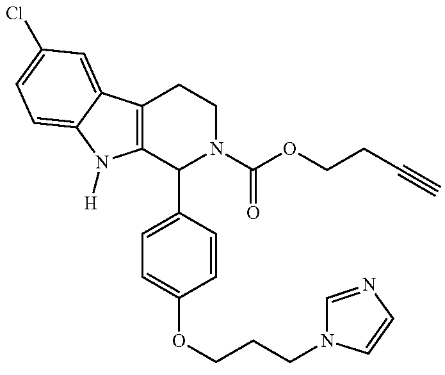
710
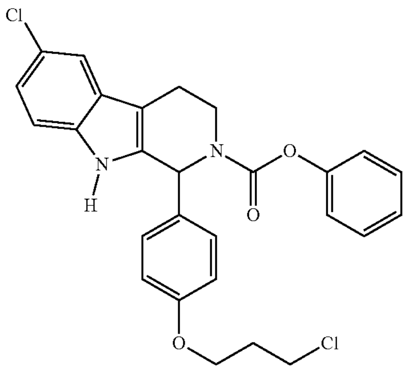
-continued
711
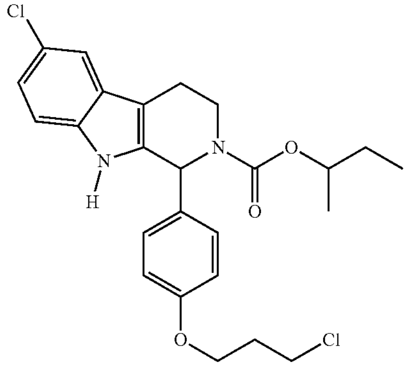
712
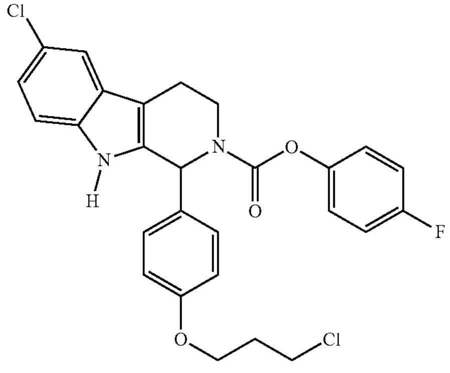
713
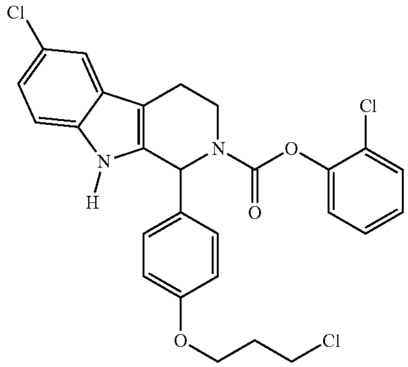
714
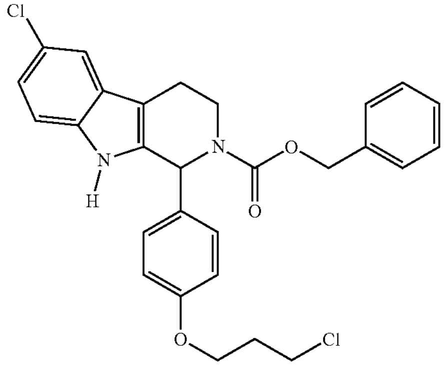

-continued
715
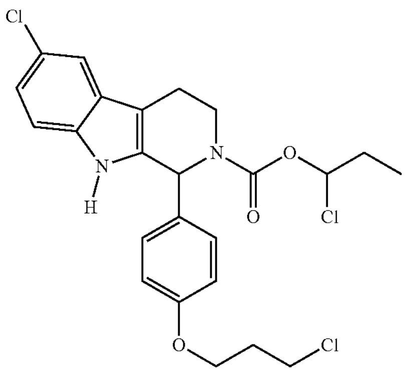
716
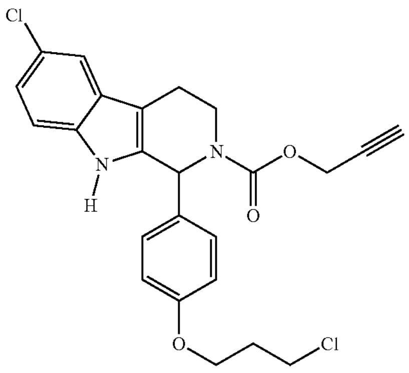
717
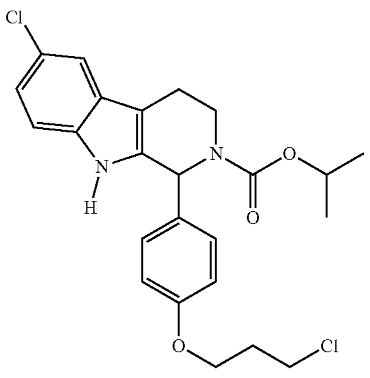
718
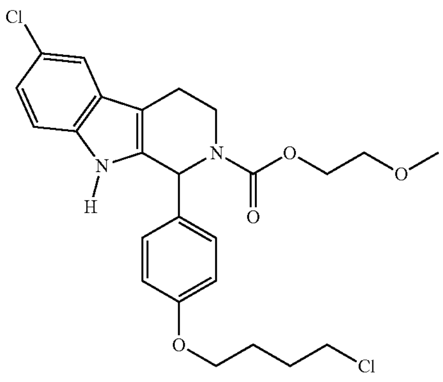
-continued
719
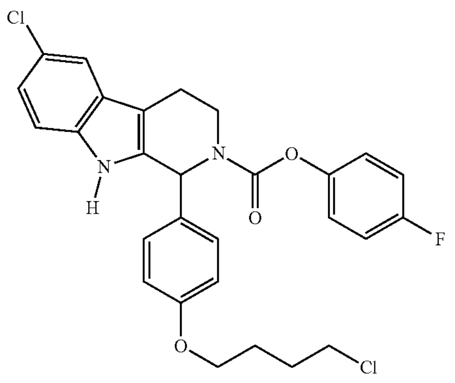
720
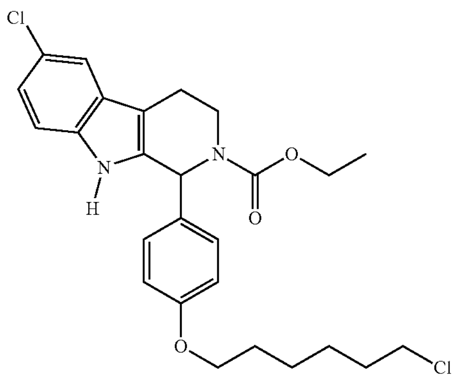
721
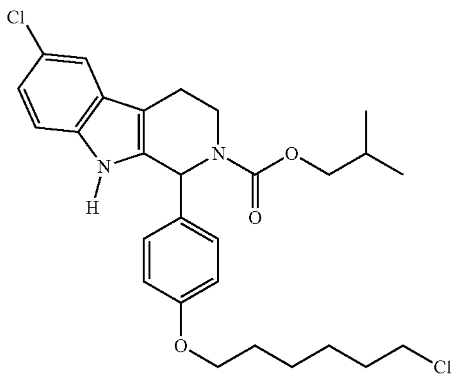
722
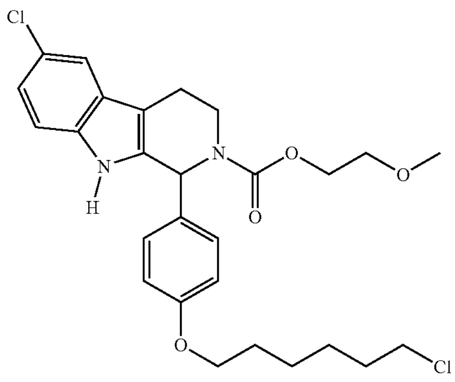

-continued
723
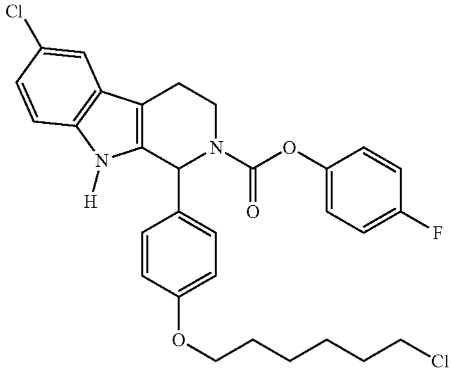
724
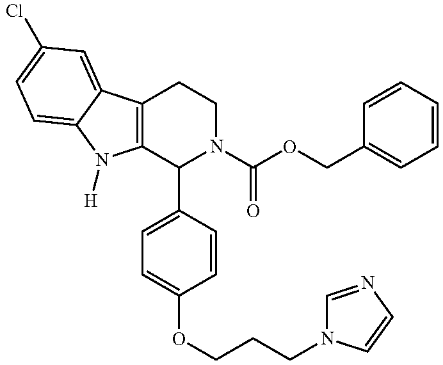
725
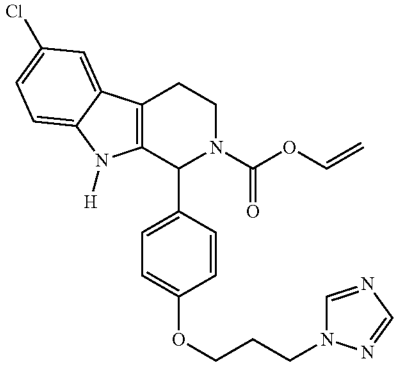
726
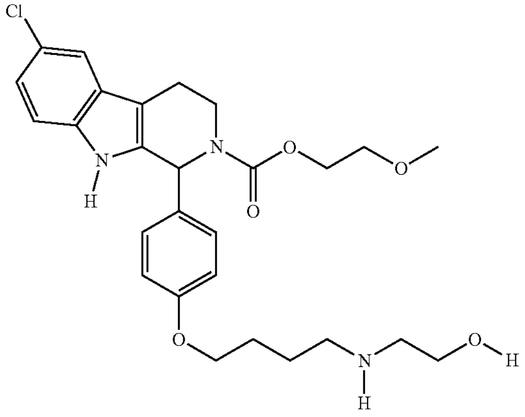
-continued
727
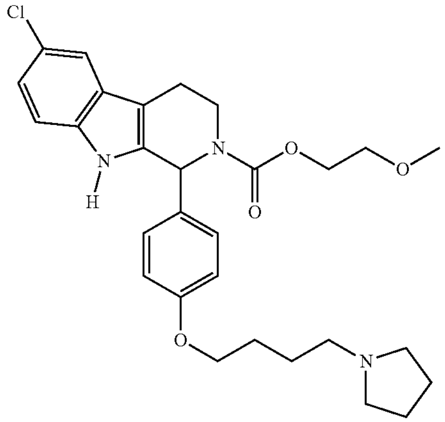
728
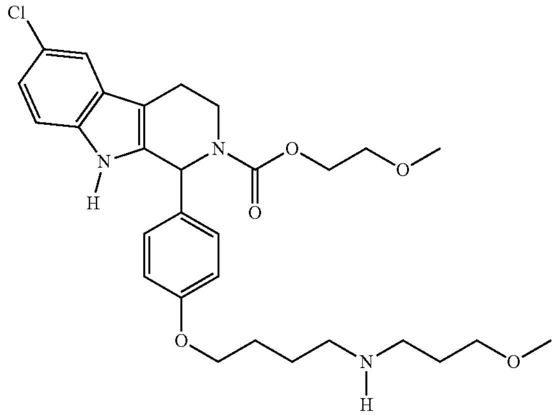
729
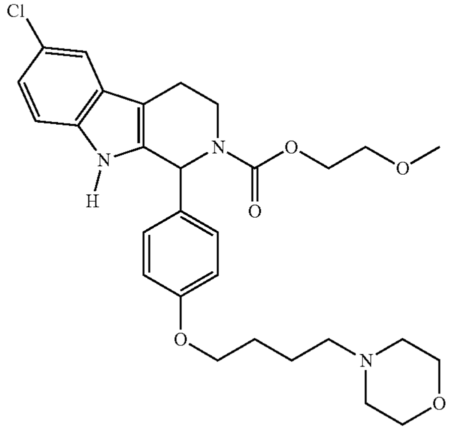

-continued
730
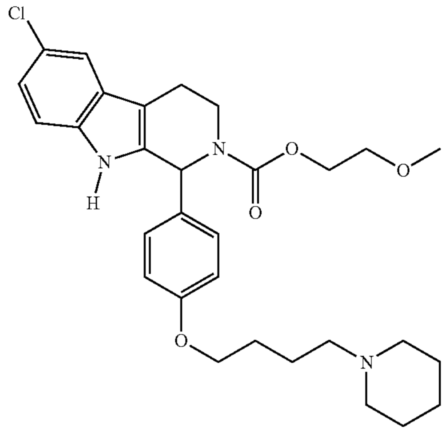
731
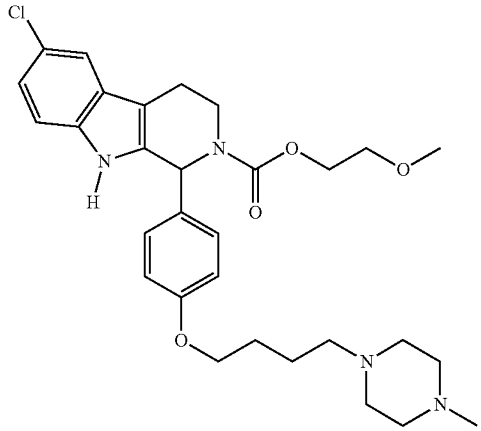
732
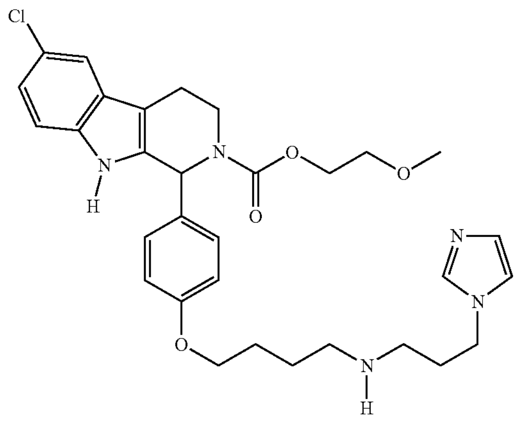
-continued
733
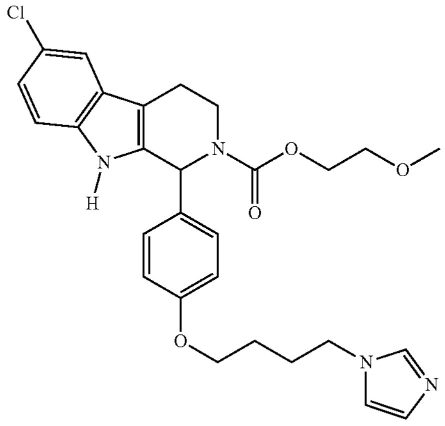
734
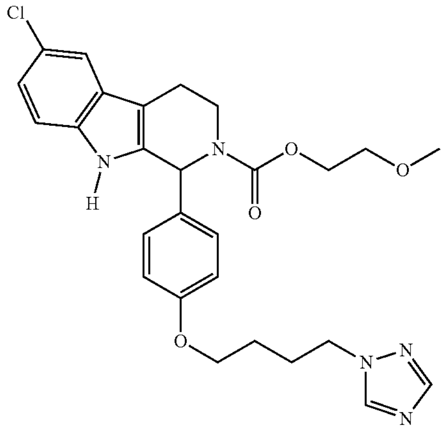
735
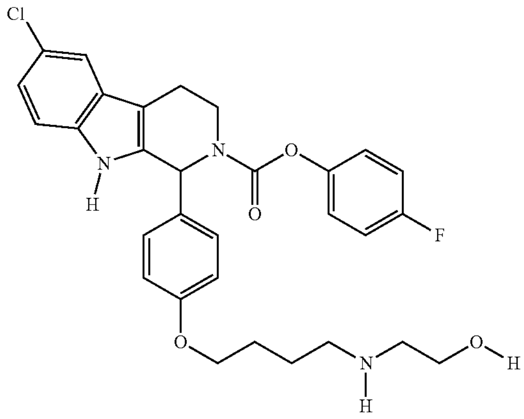

-continued
736
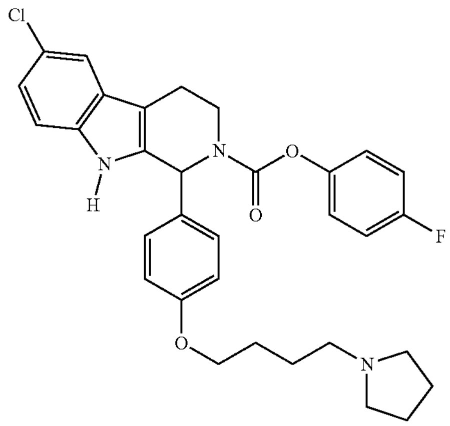
737
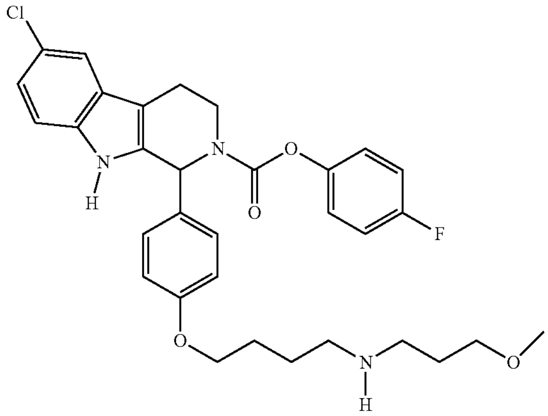
738
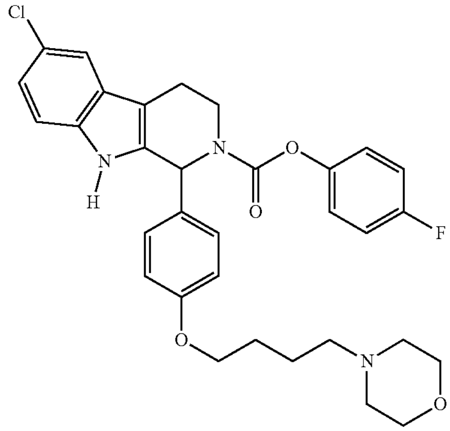
-continued
739
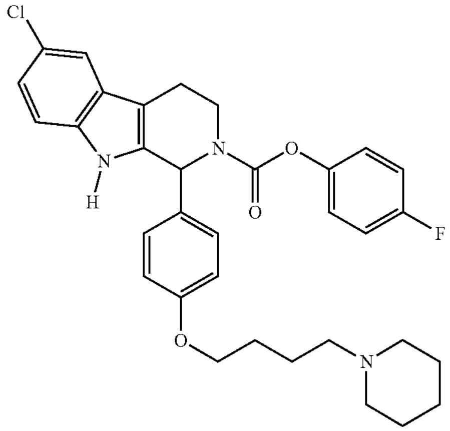
740
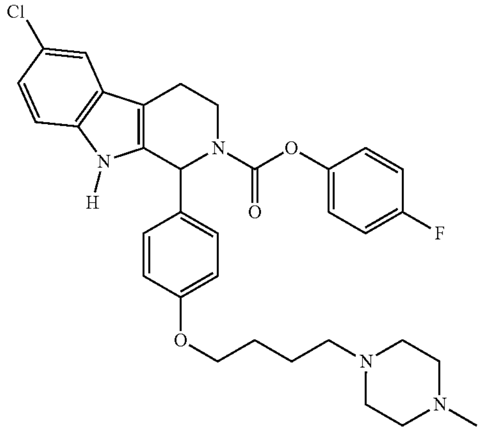
741
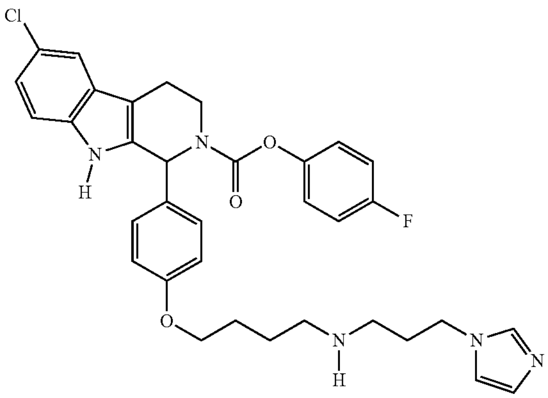

-continued
742
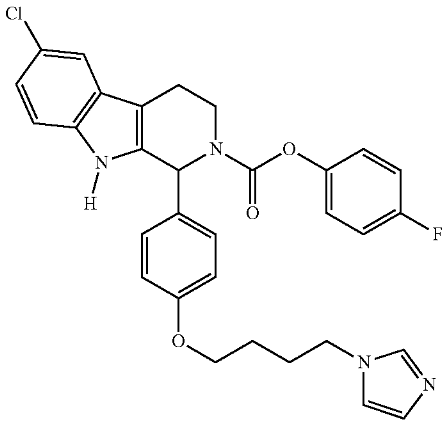
743
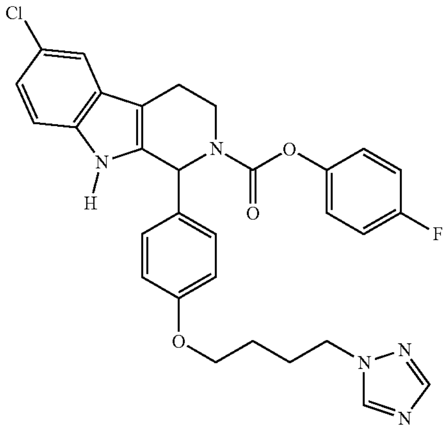
744
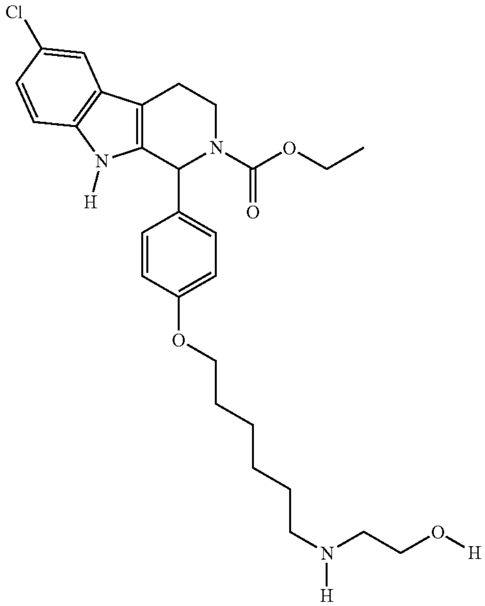
-continued
745
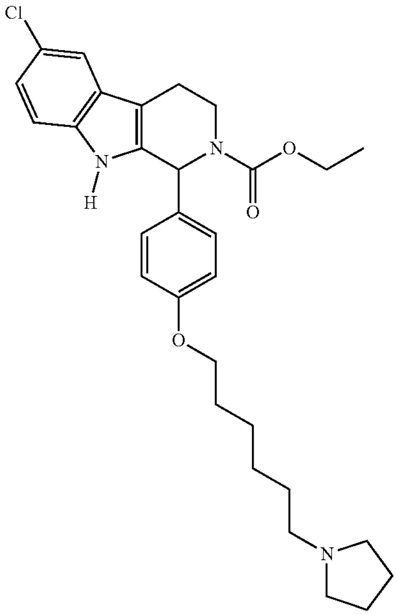
746
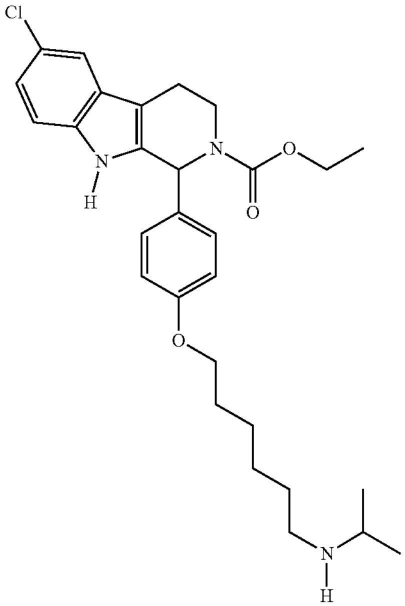

-continued
747
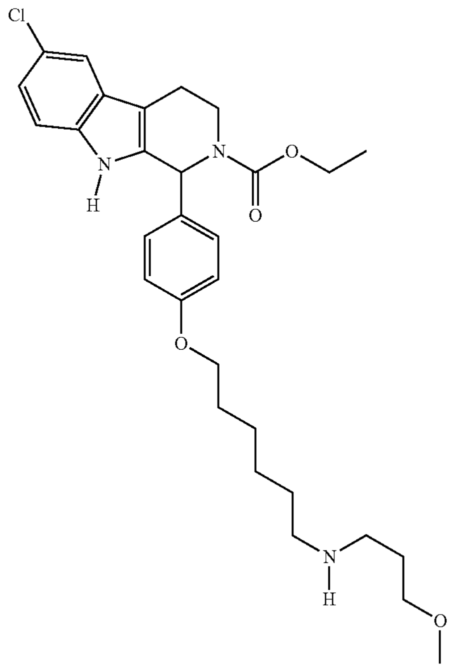
748
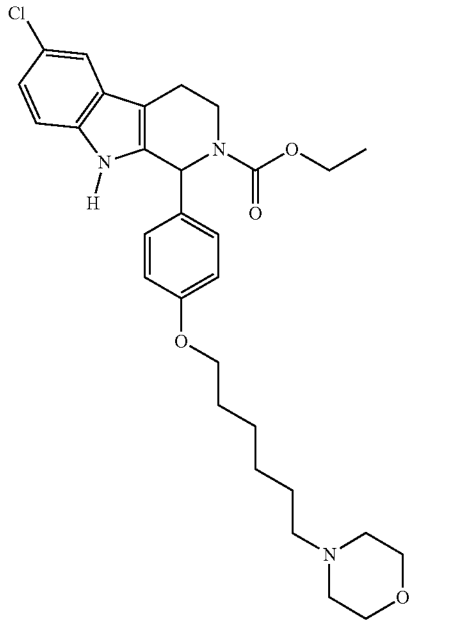
-continued
749
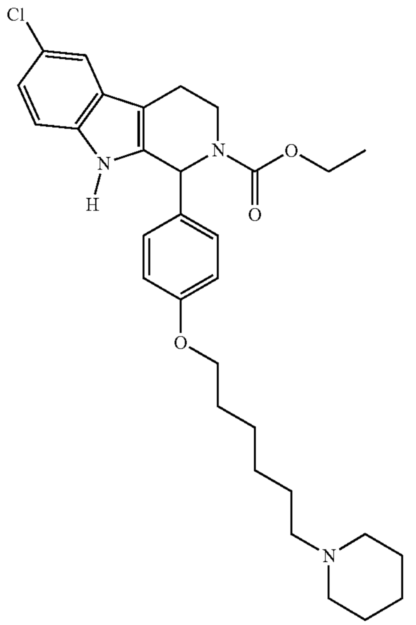
750
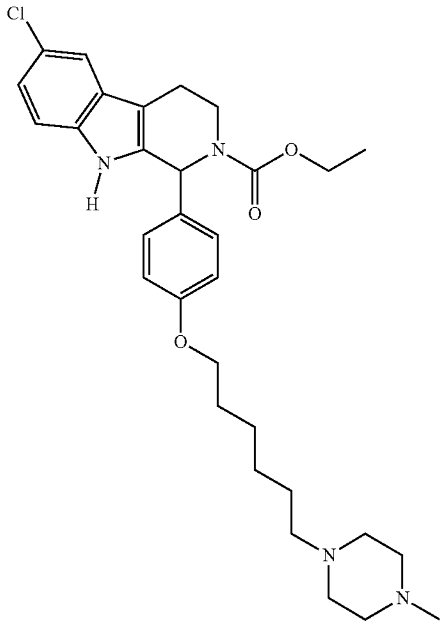

-continued
751
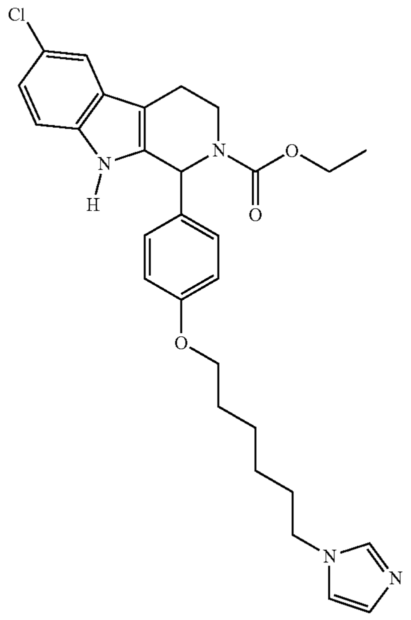
752
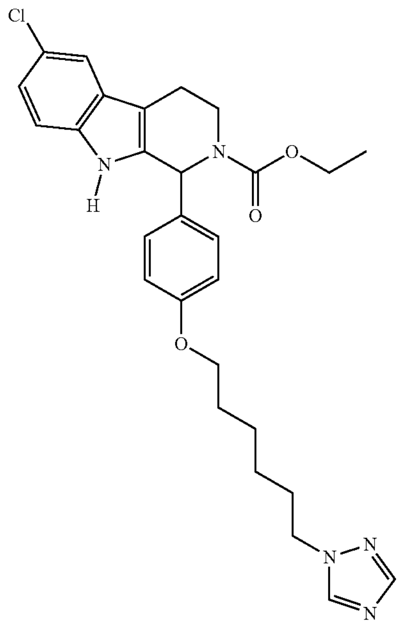
-continued
753
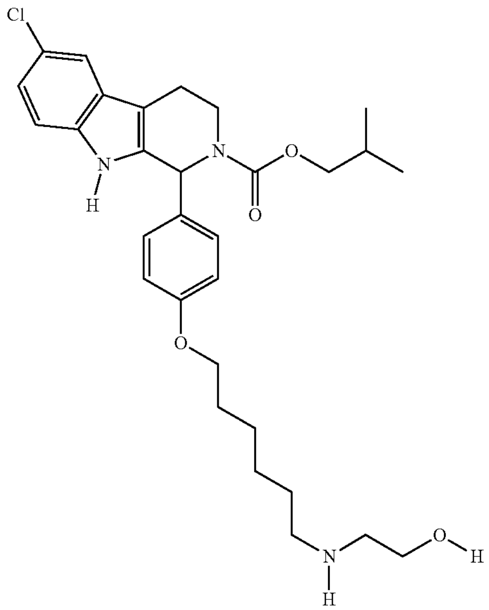
754
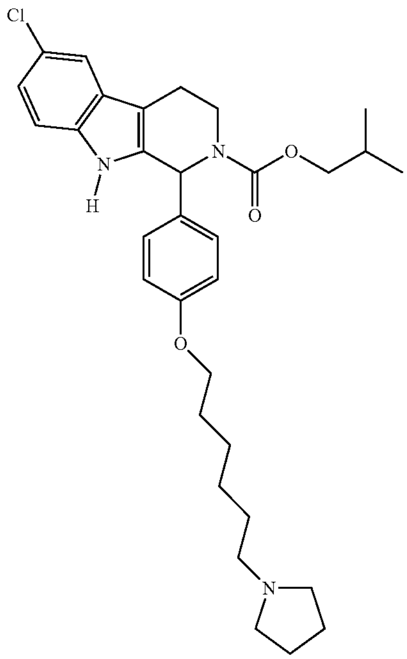

-continued
755
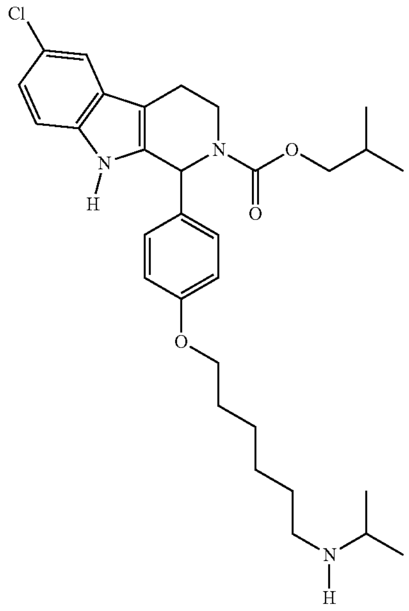
756
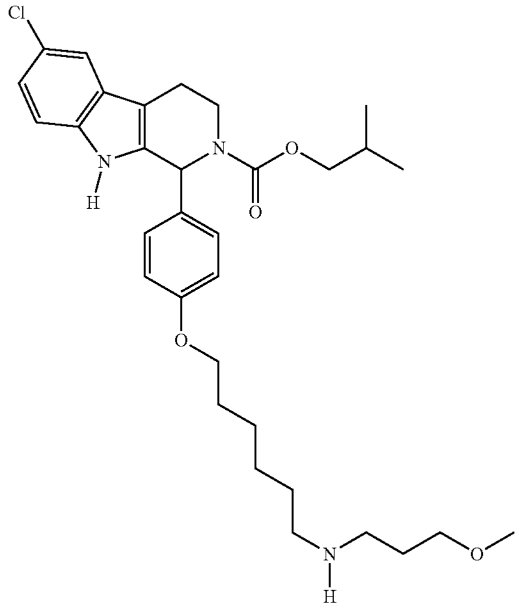
-continued
757
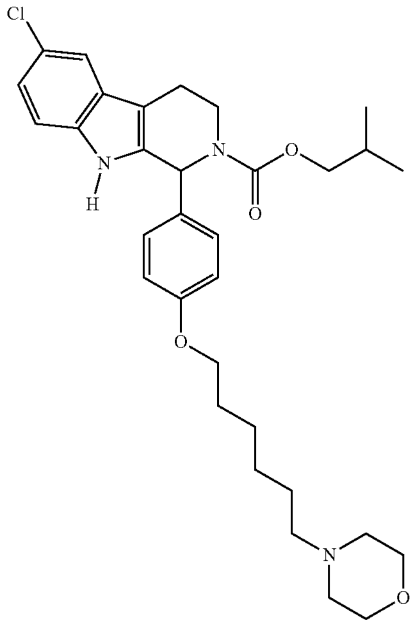
758
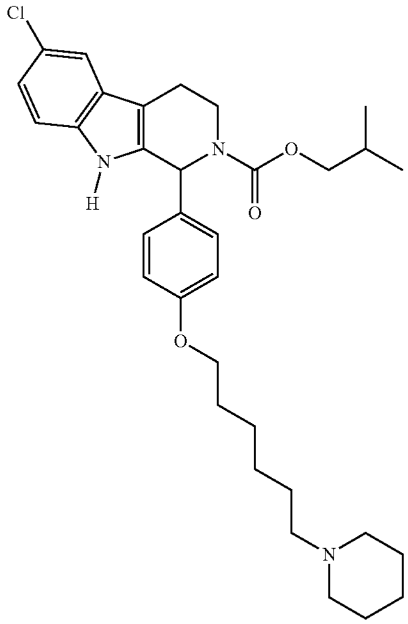

-continued
759
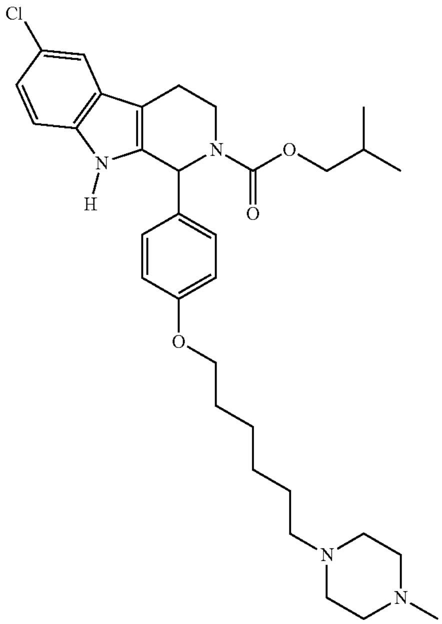
760
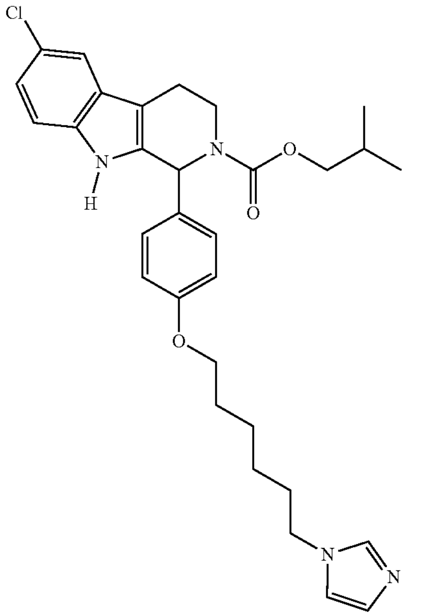
-continued
761
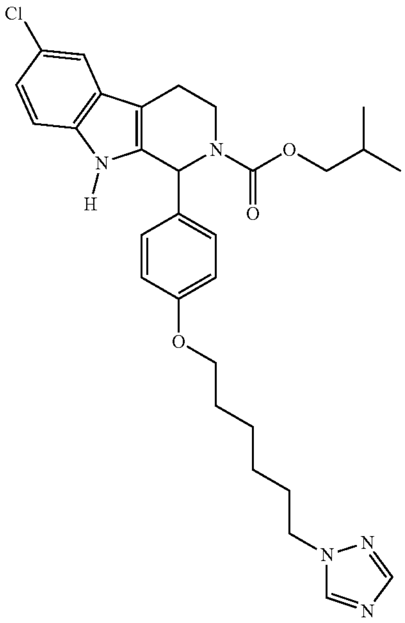
762
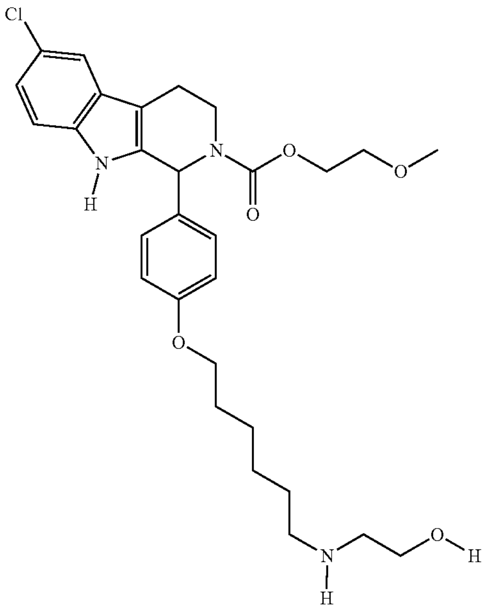

-continued
763
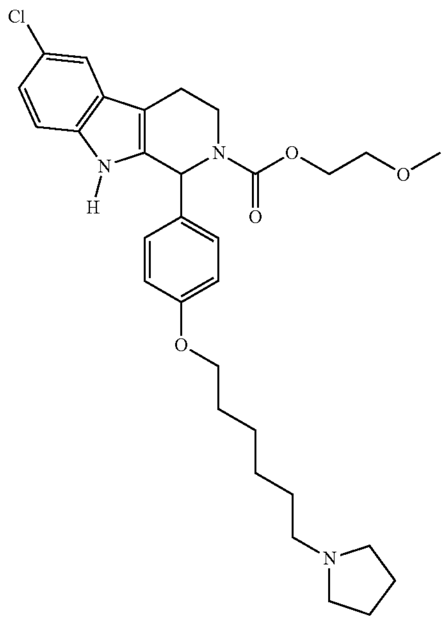
764
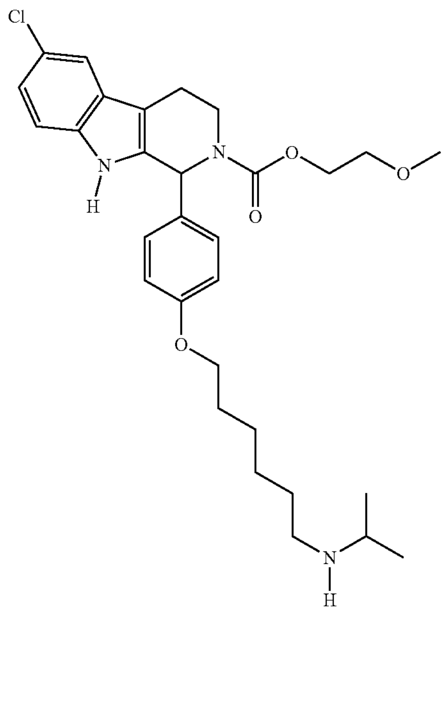
-continued
765
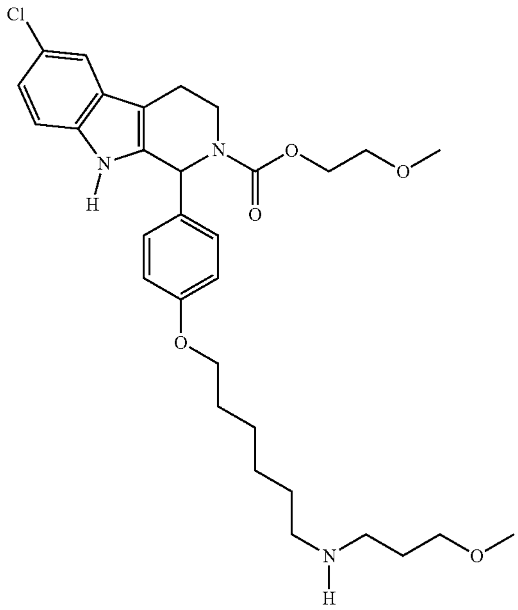
766
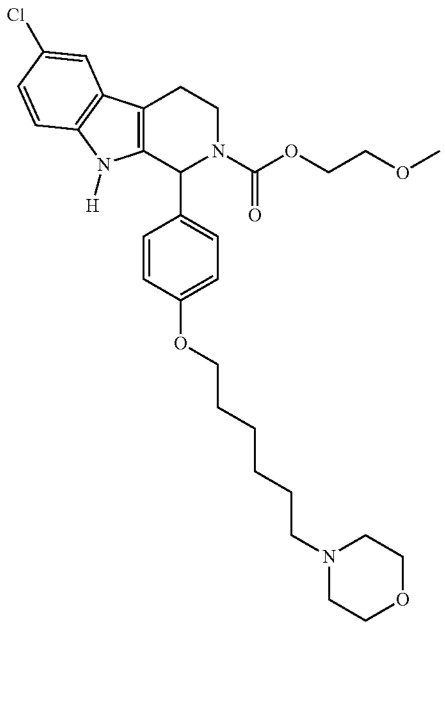

-continued
767
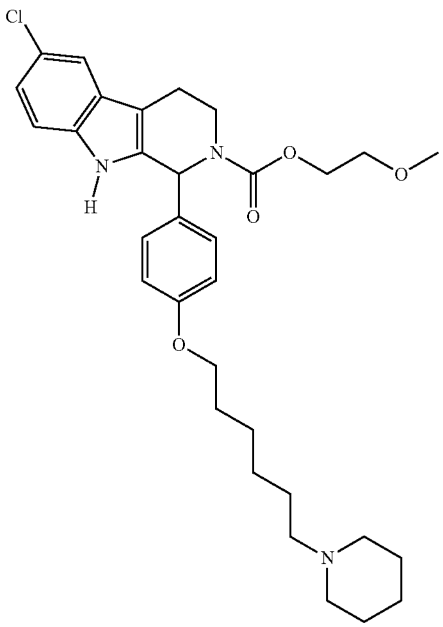
768
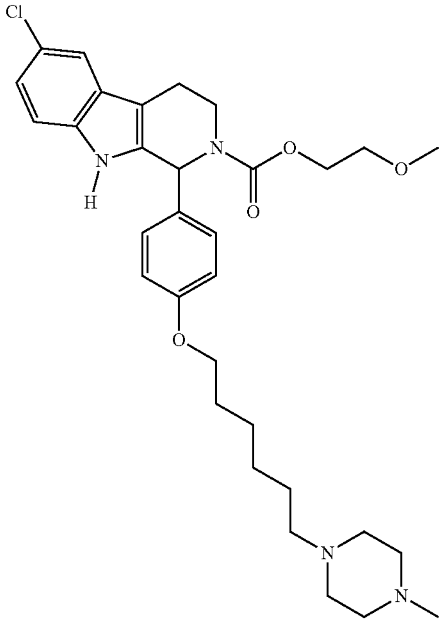
-continued
769
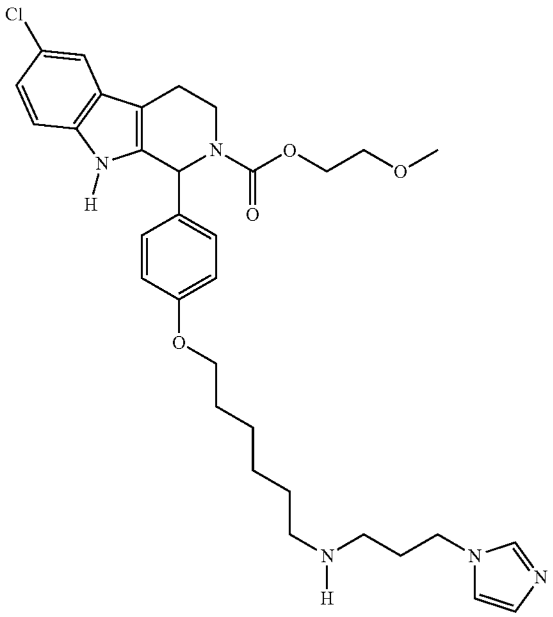
770
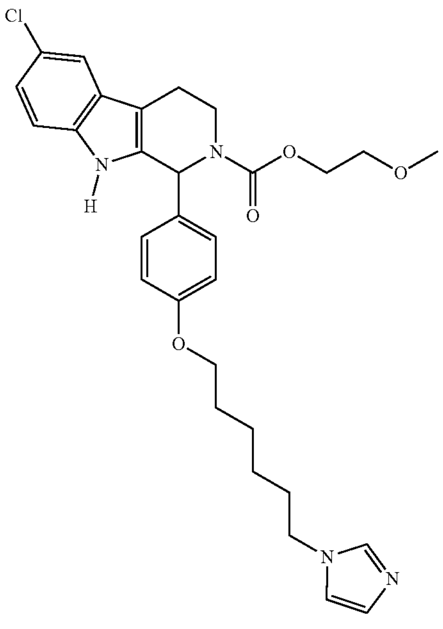

-continued
771
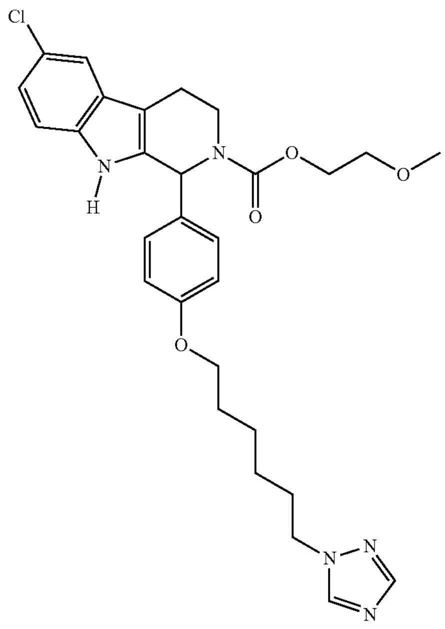
772
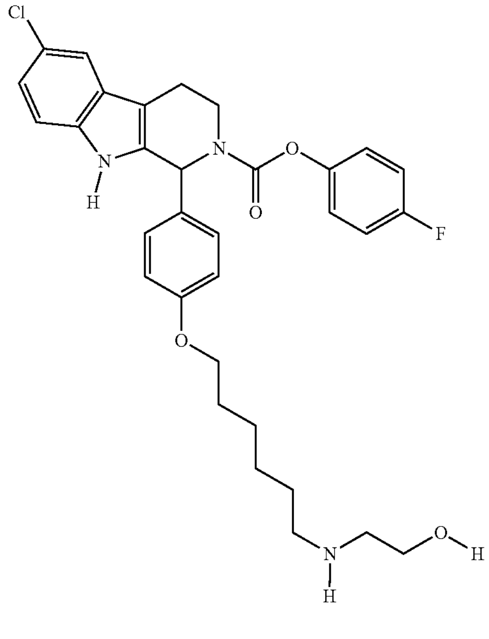
-continued
773
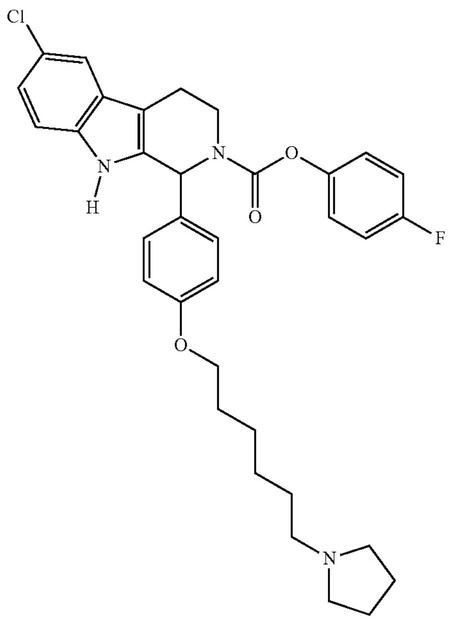
774
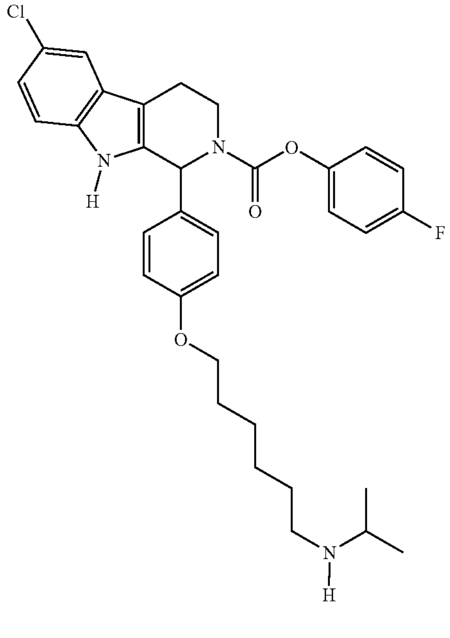

-continued
775
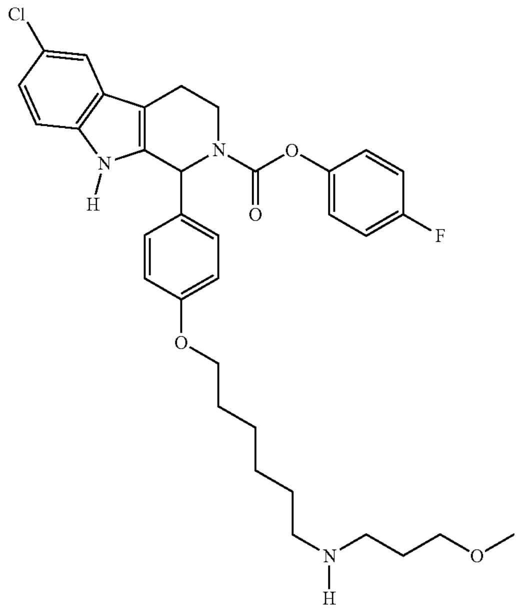
776
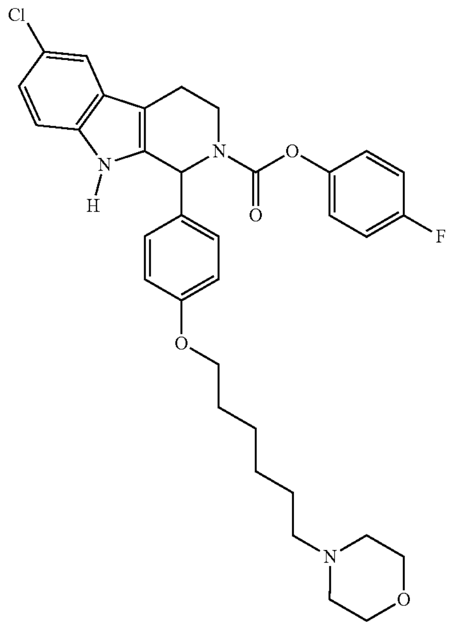
-continued
777
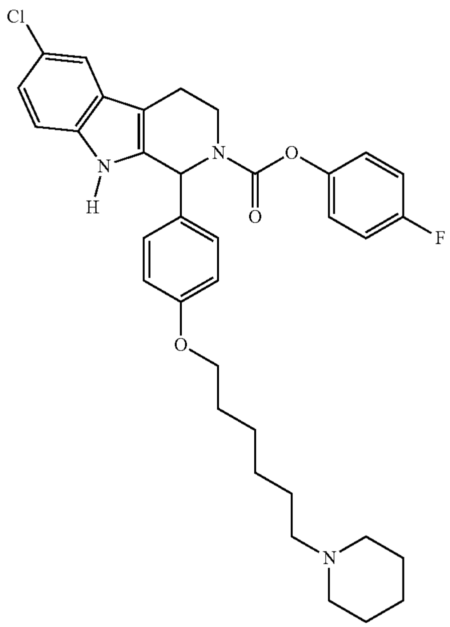
778
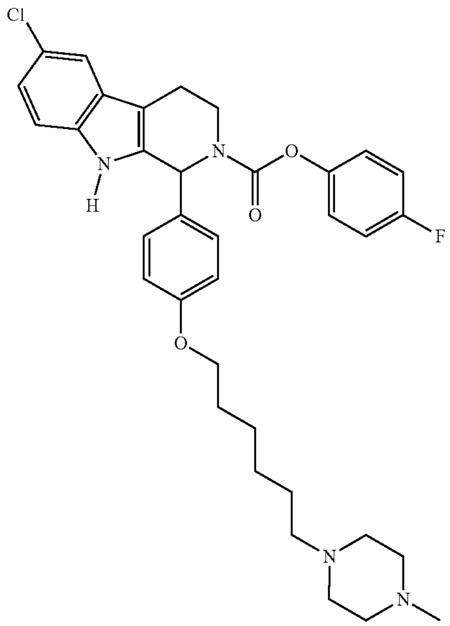

-continued
779
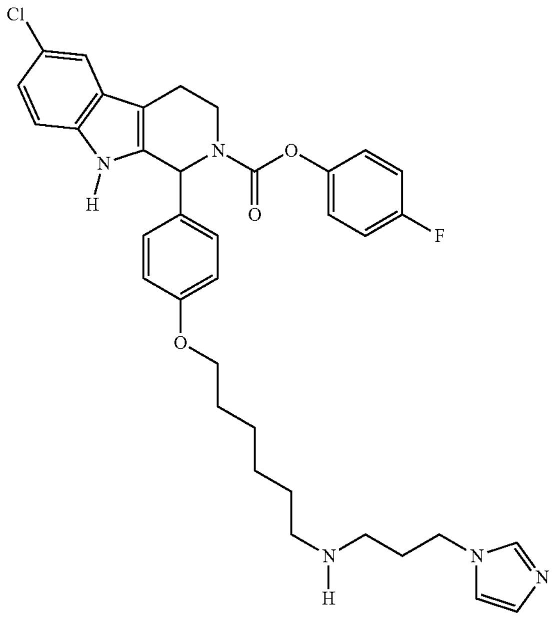
780
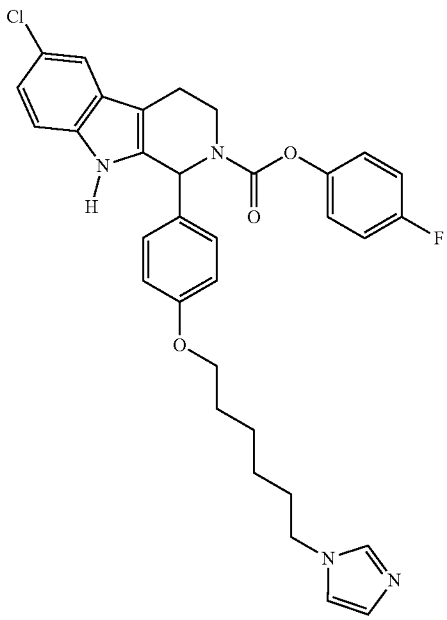
-continued
781
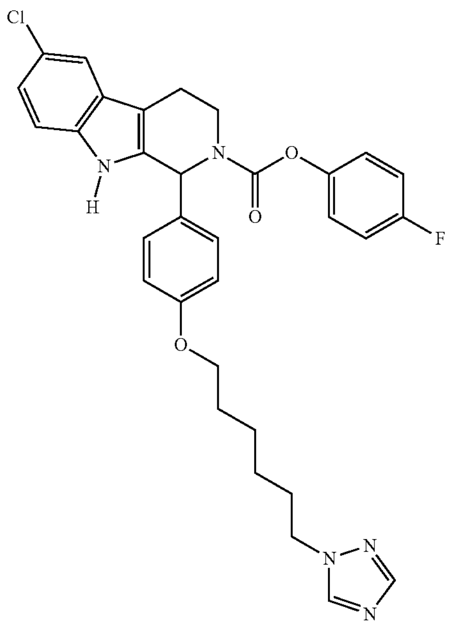
782
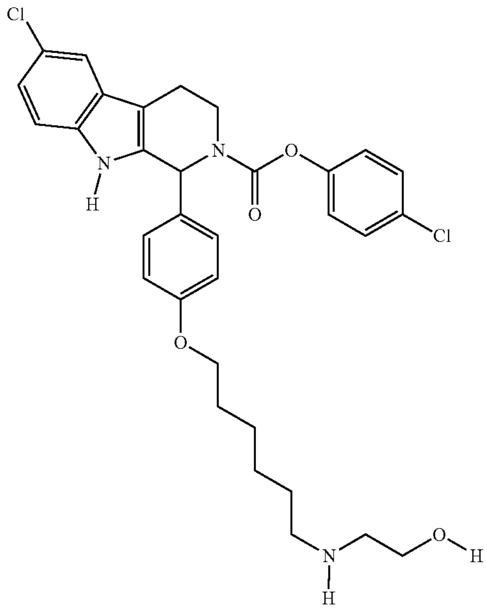

-continued
783
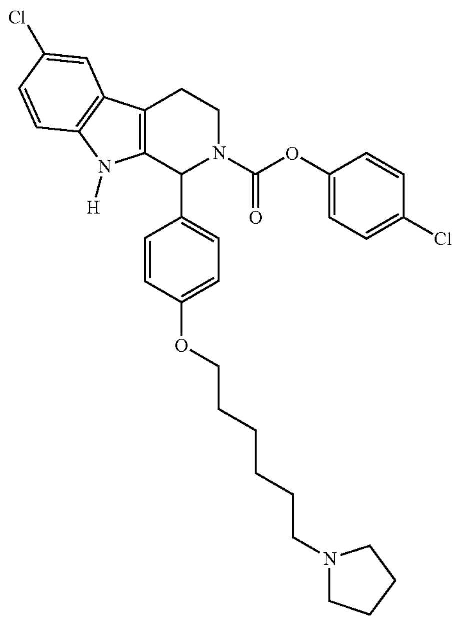
784
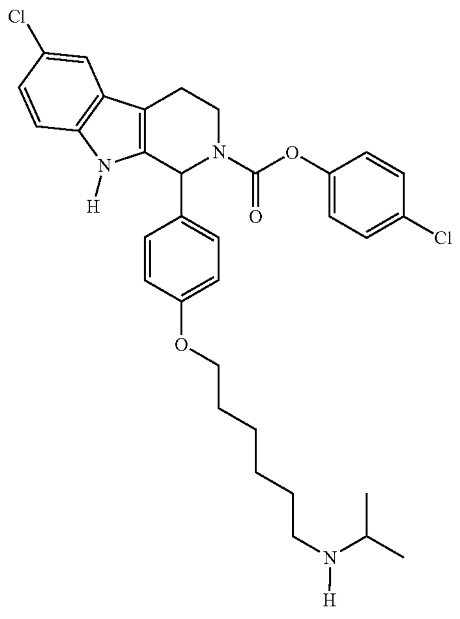
-continued
785
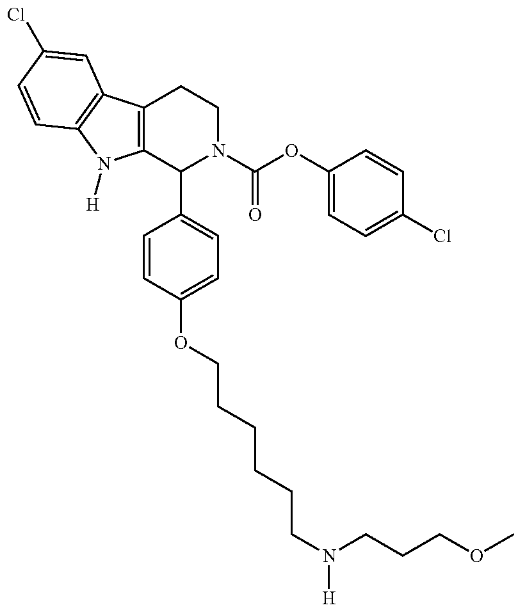
786
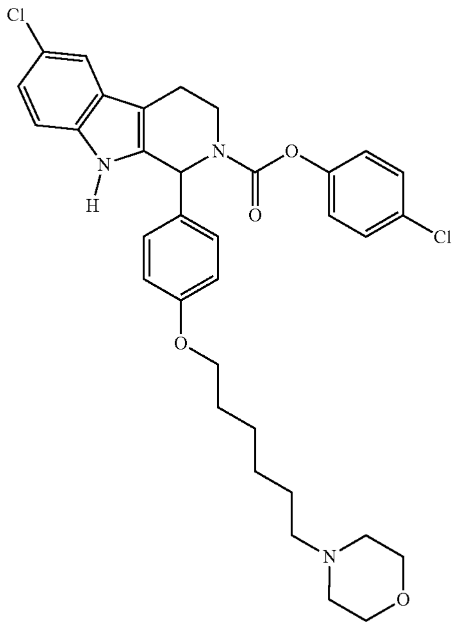

-continued
787
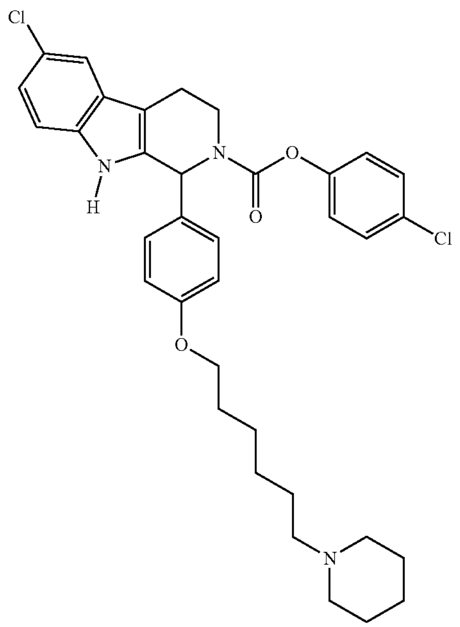
788
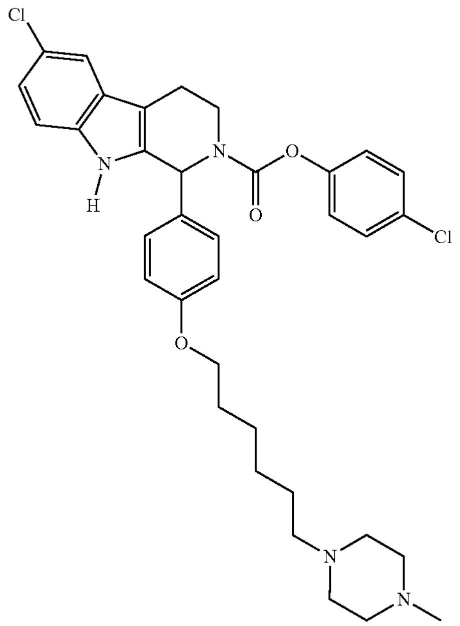
-continued
789
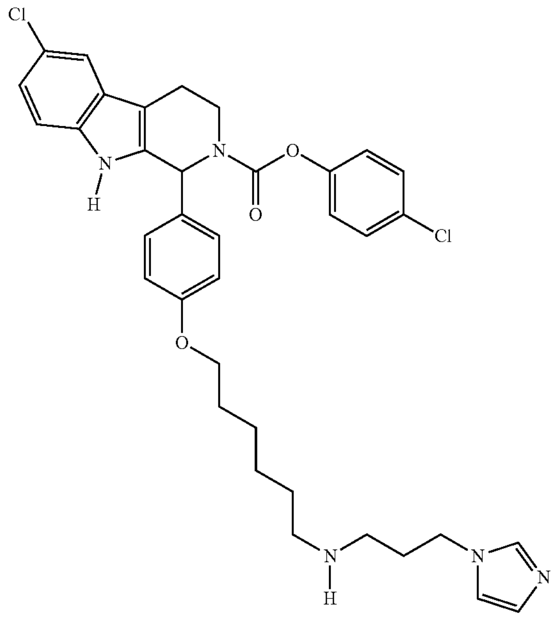
790
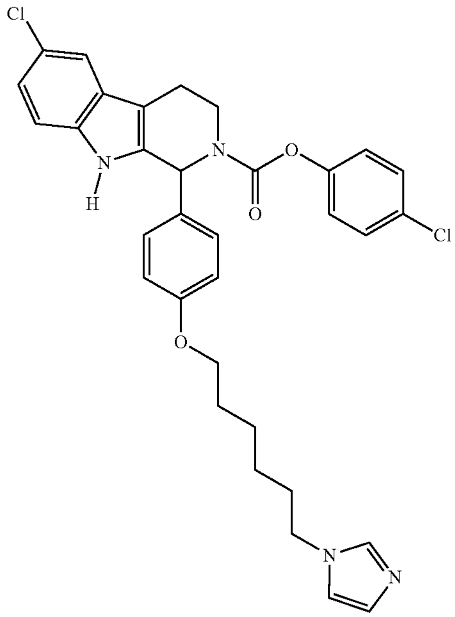

-continued
791
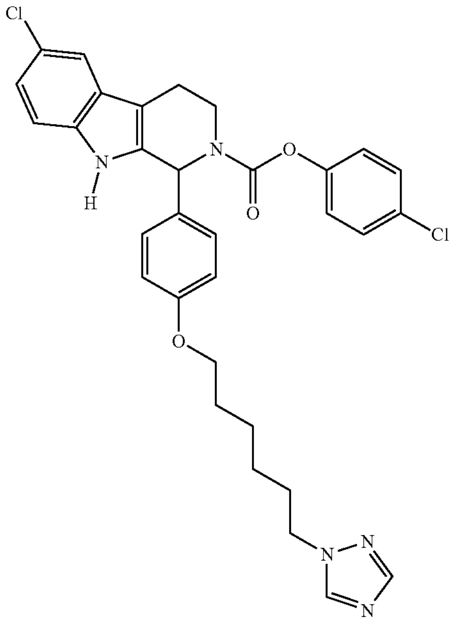
792
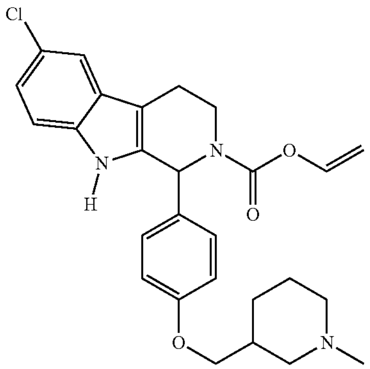
793
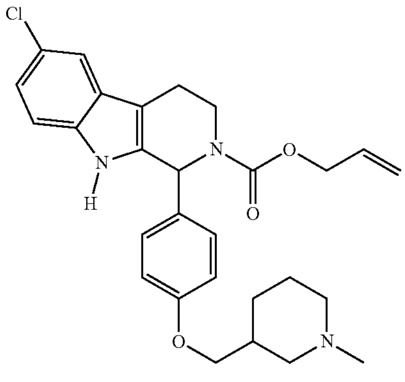
-continued
794
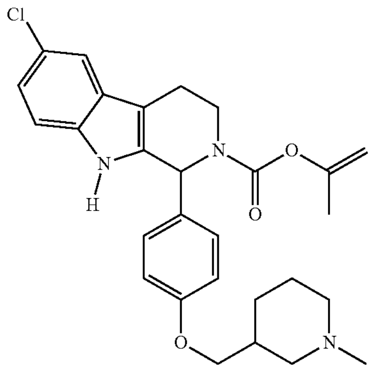
795
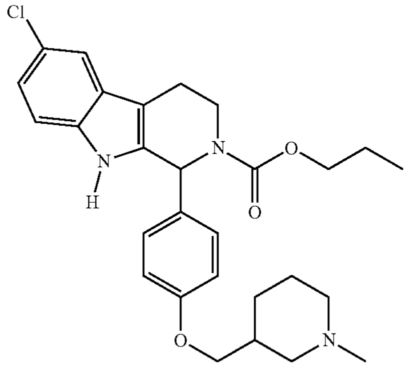
796
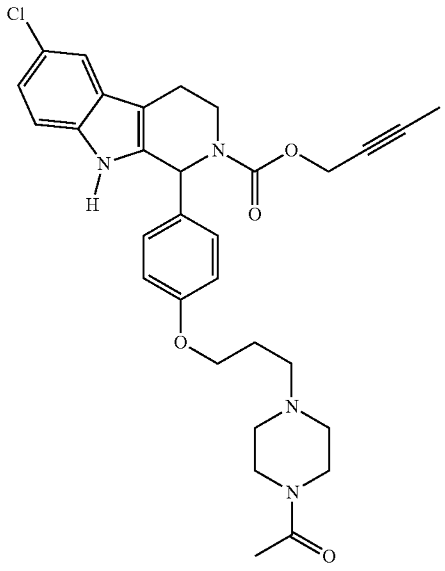

-continued
797
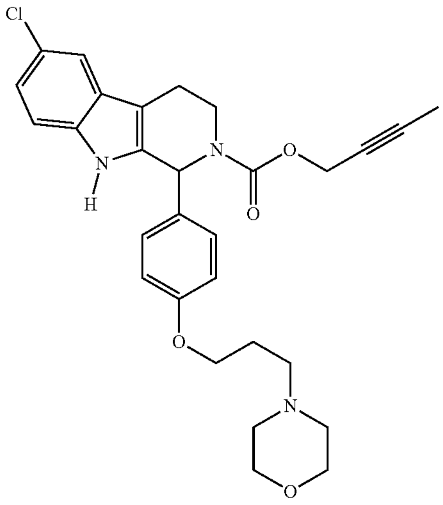
798
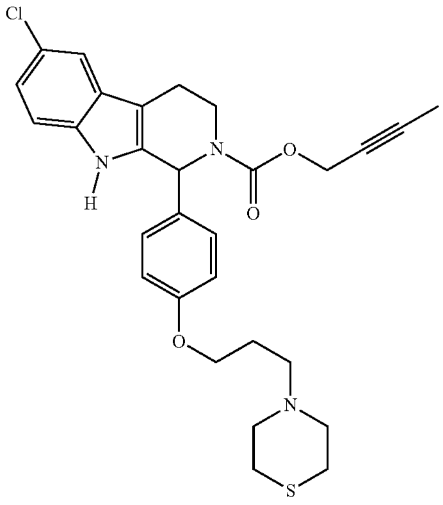
799
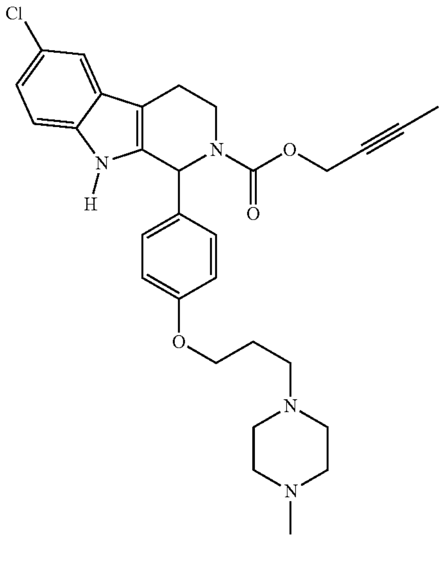
-continued
800
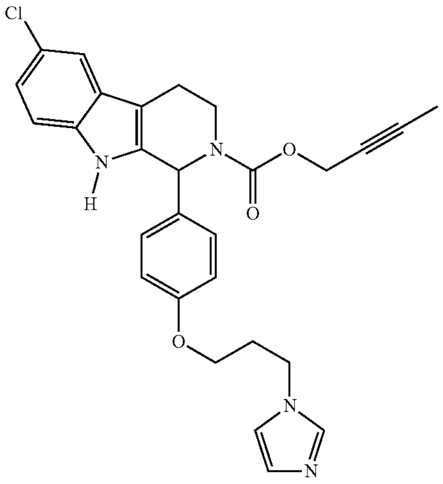
801
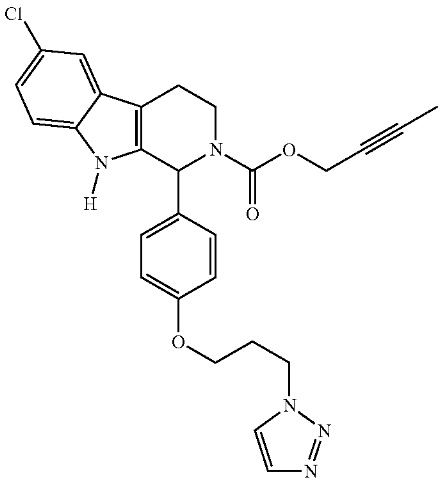
802
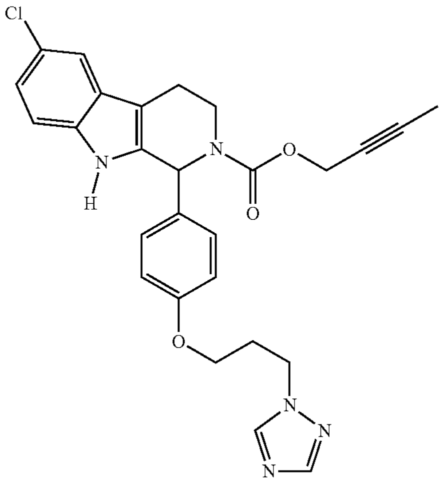

-continued
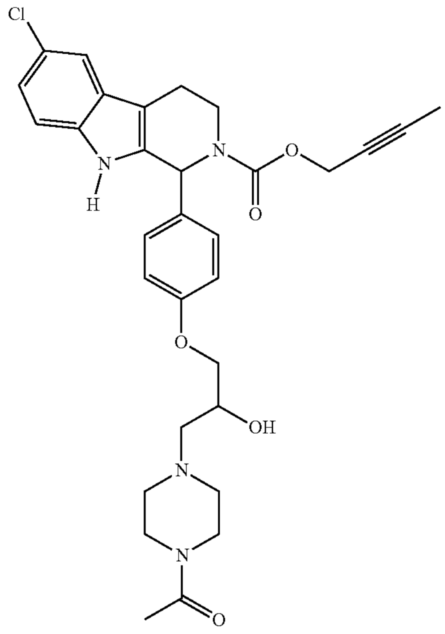
803
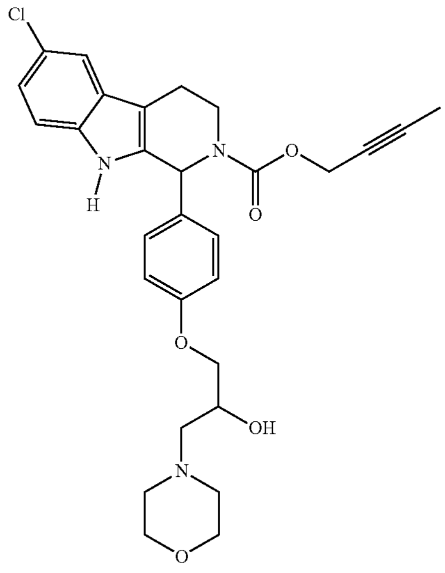
804
-continued
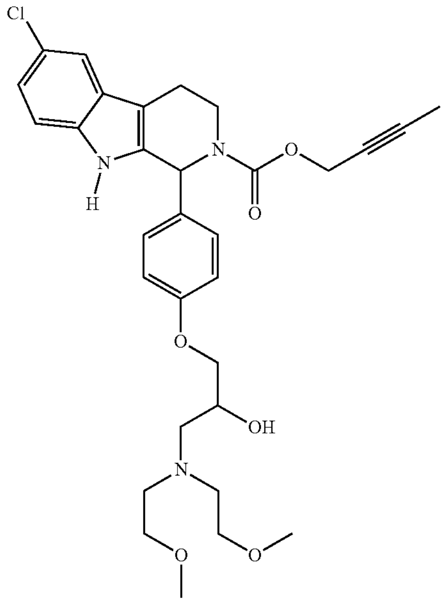
805
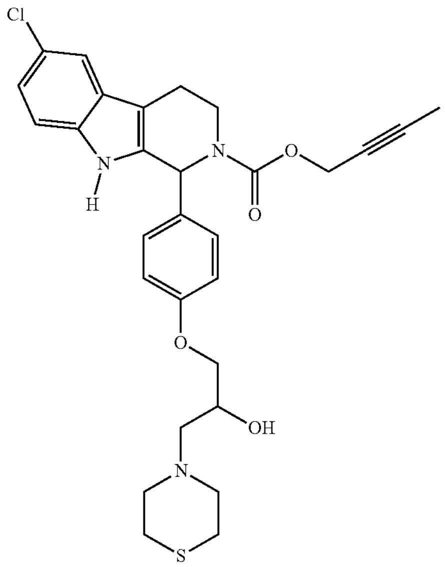
806

-continued
807
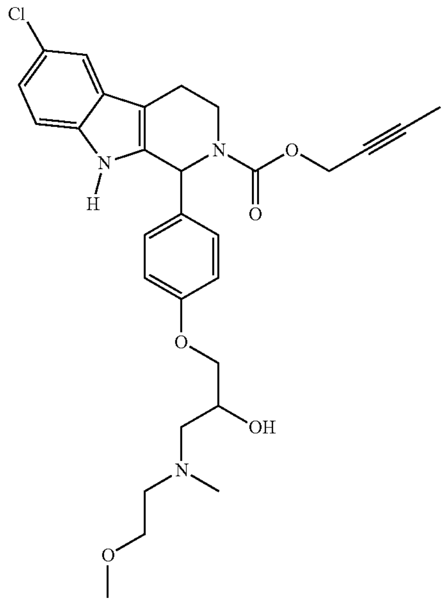
808
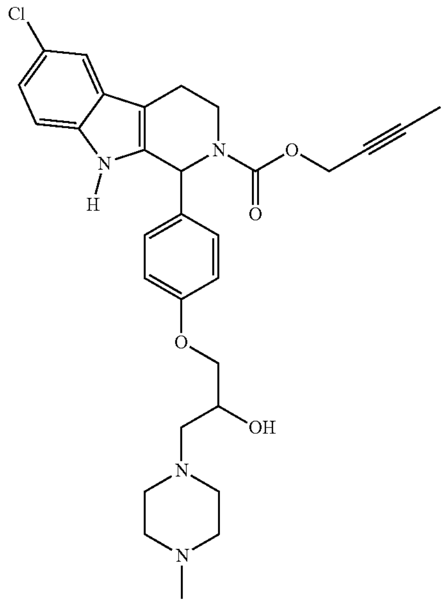
-continued
809
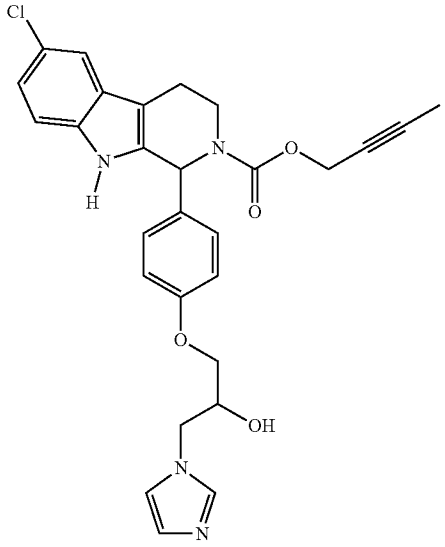
810
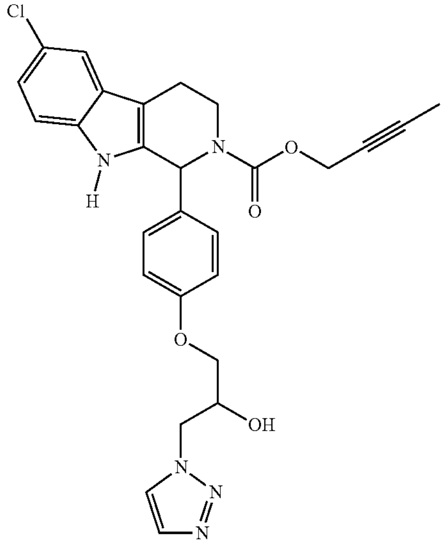
811
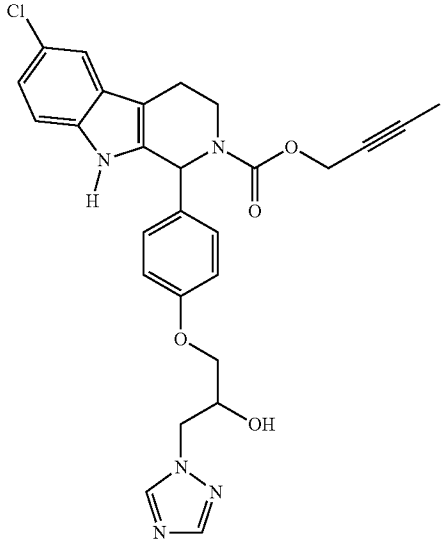

-continued
812
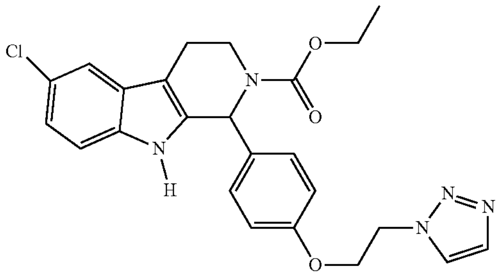
813
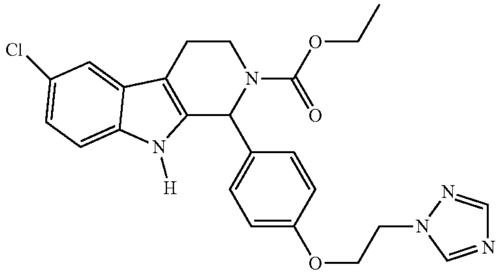
814
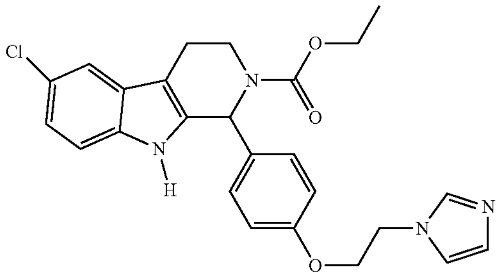
815
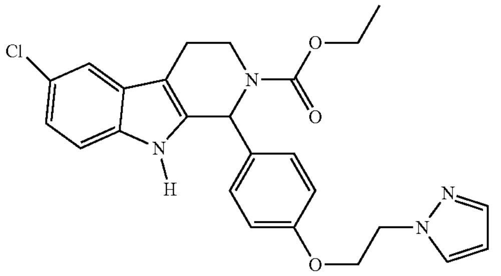
816
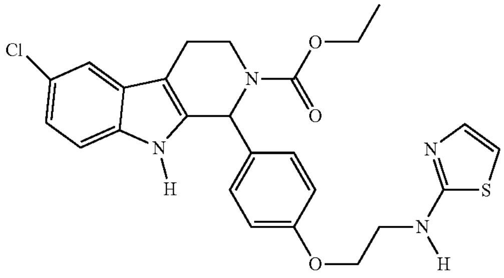
-continued
817
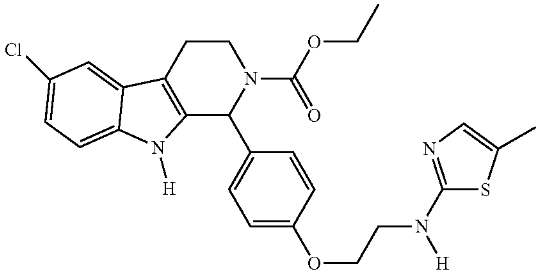
818
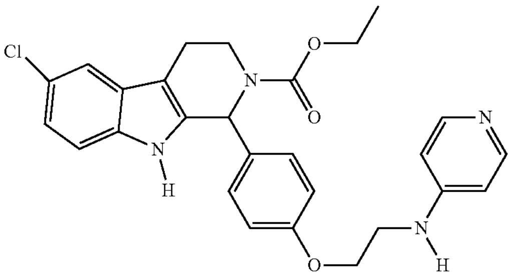
819
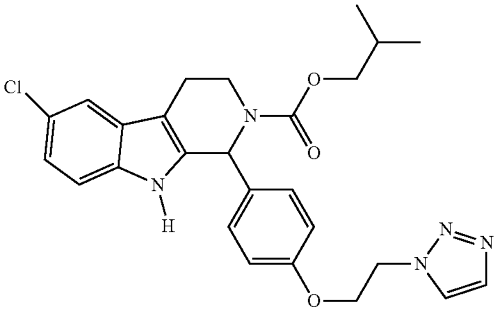
820
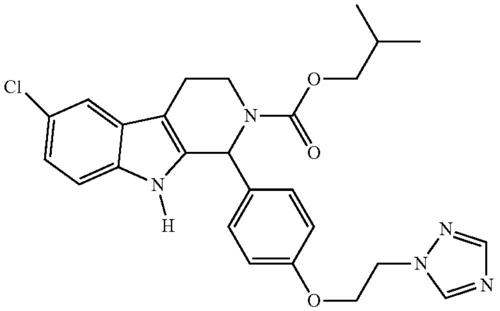
821
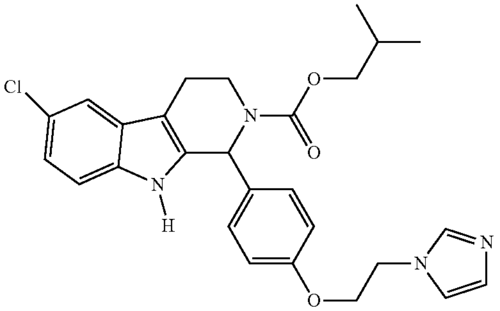

-continued
822
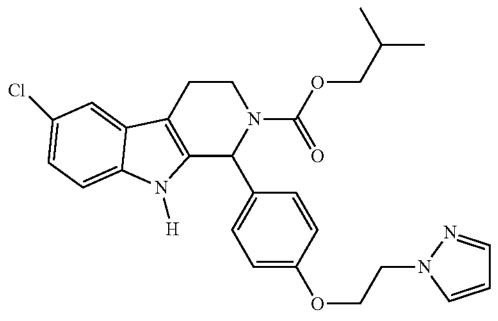
823
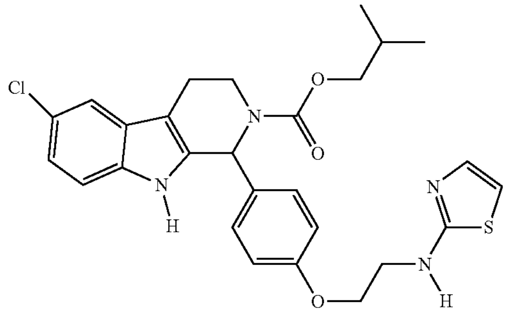
824
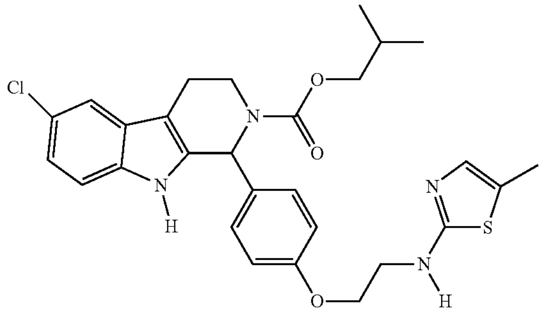
825
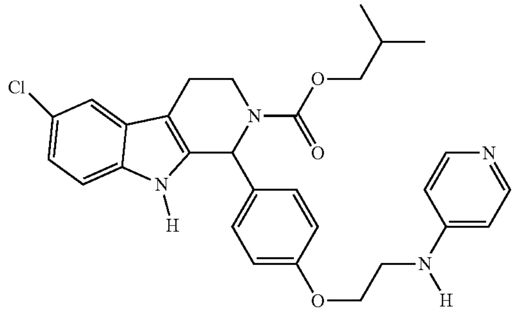
-continued
826
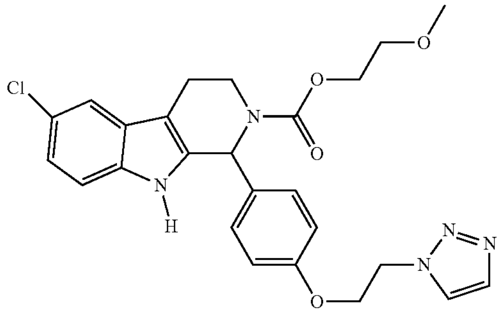
827
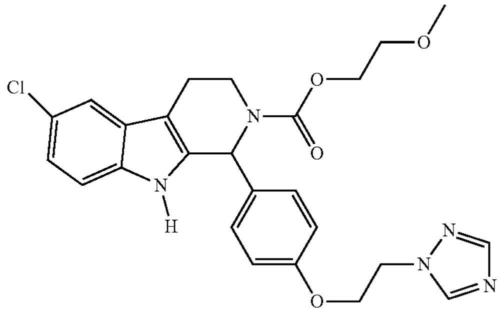
828
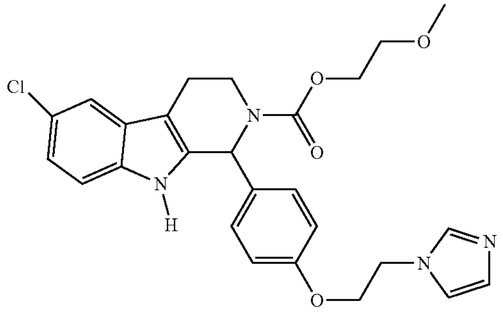
829
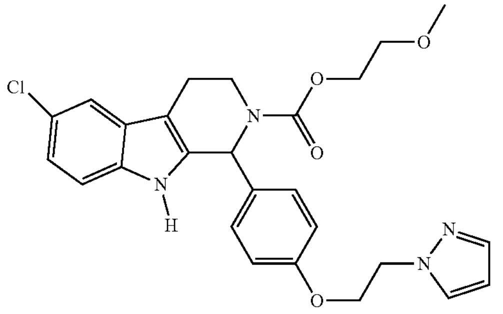

-continued
830
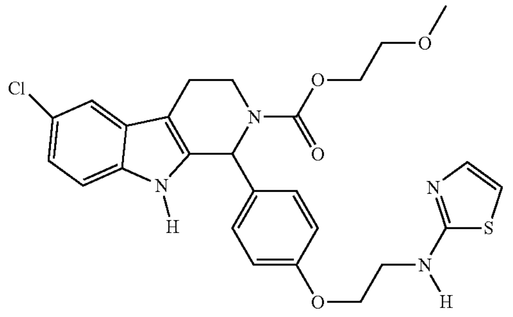
831
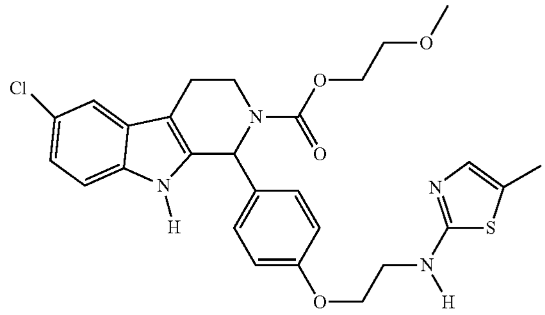
832
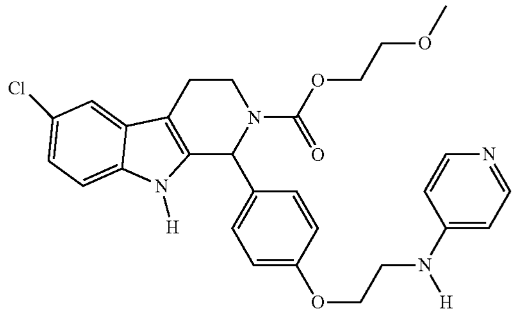
833
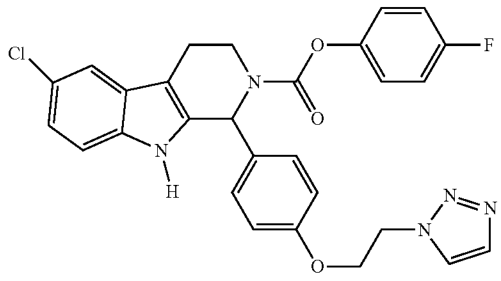
834
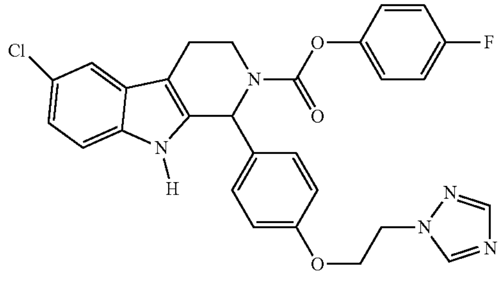
-continued
835
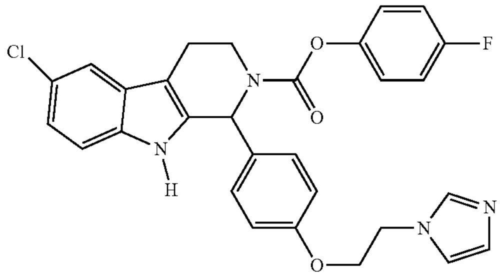
836
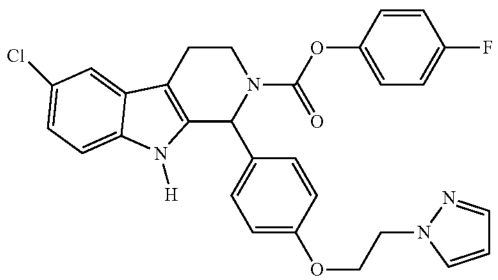
837
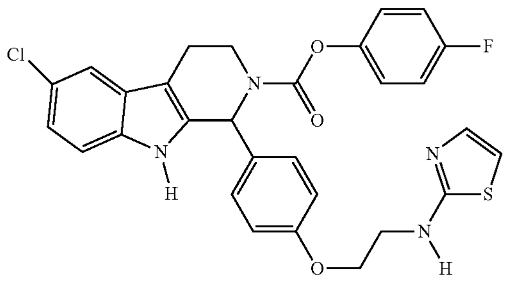
838
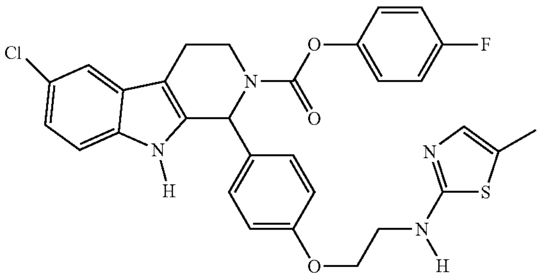
839
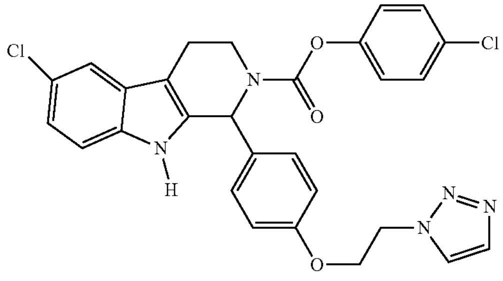

-continued
840
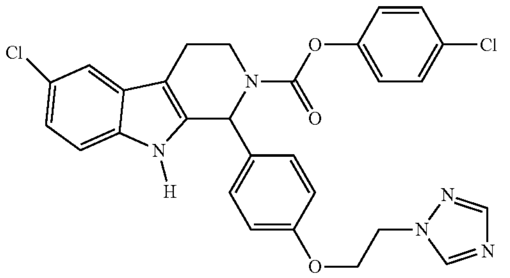
841
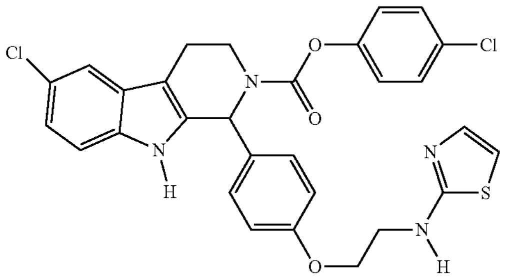
842
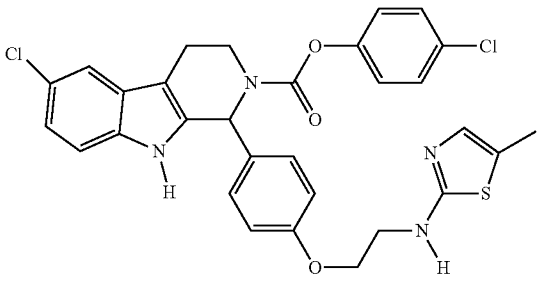
843
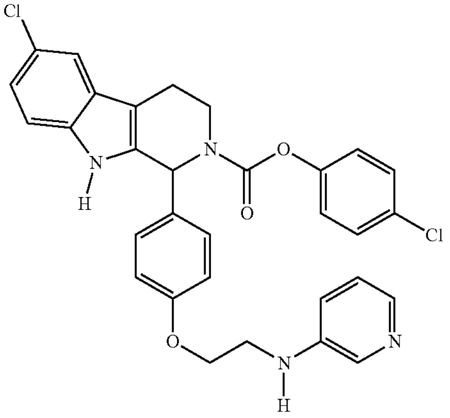
-continued
844
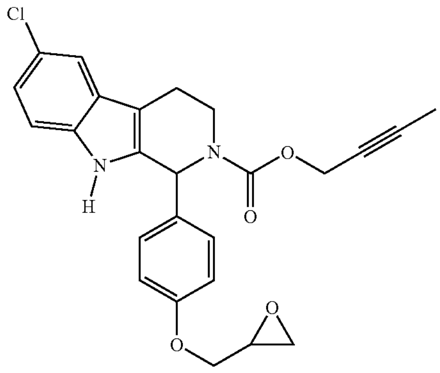
845
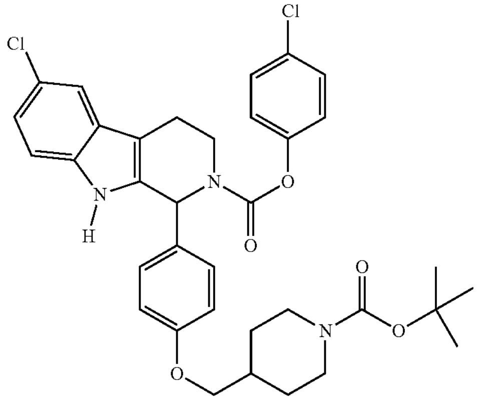
846
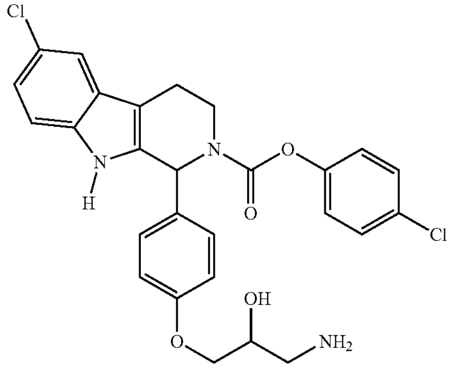
847
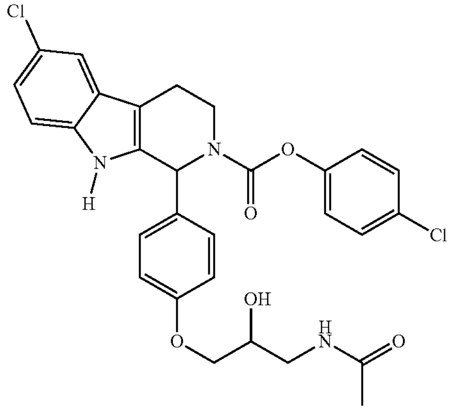

-continued
848
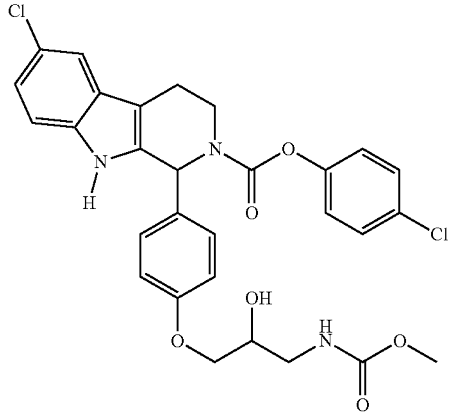
849
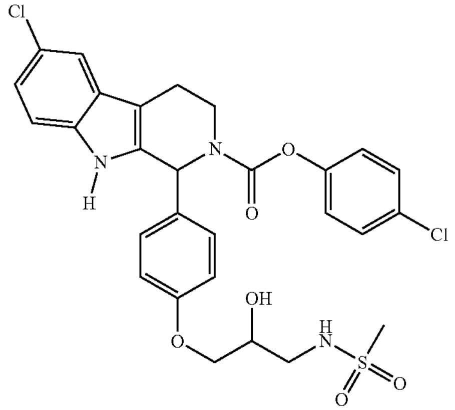
850
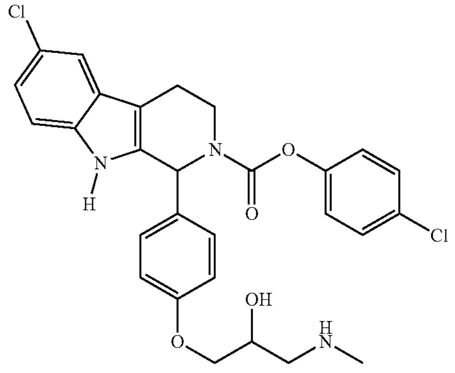
851
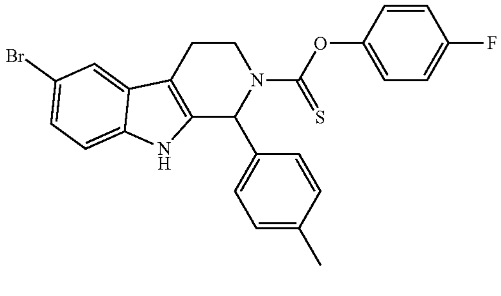
-continued
852
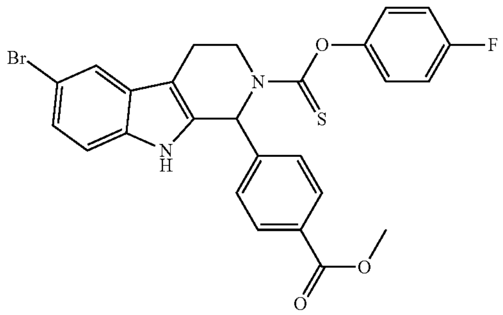
853
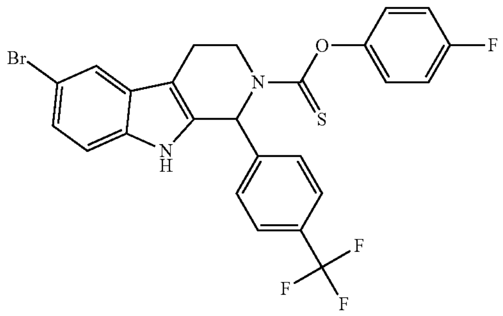
854
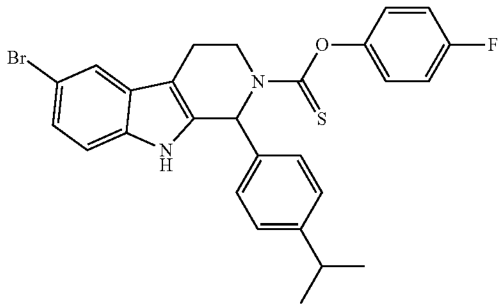
855
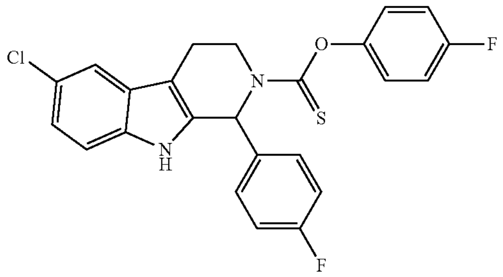

-continued
856
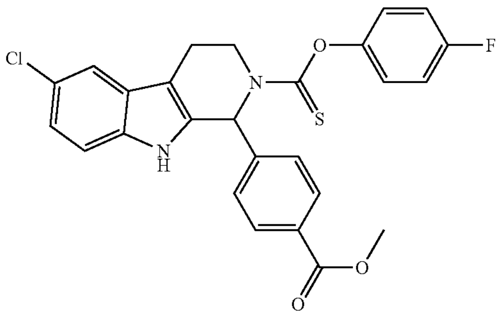
857
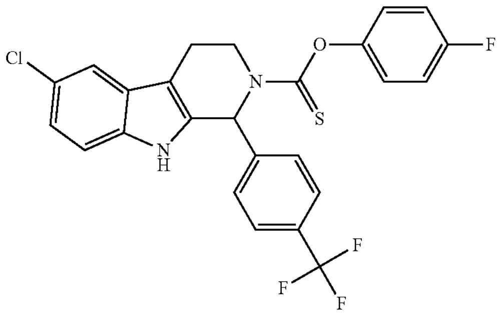
858
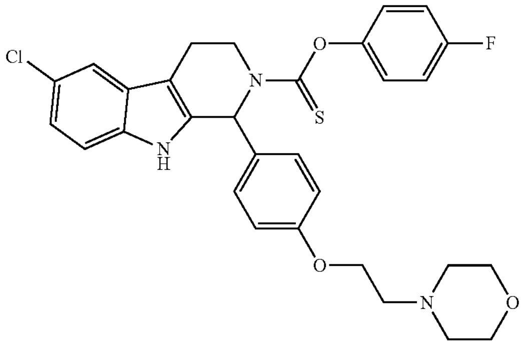
859
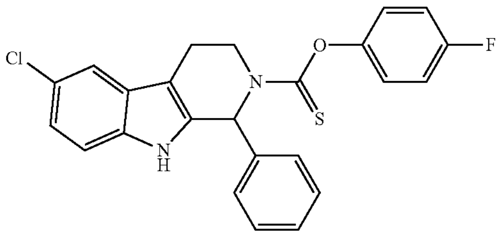
-continued
860
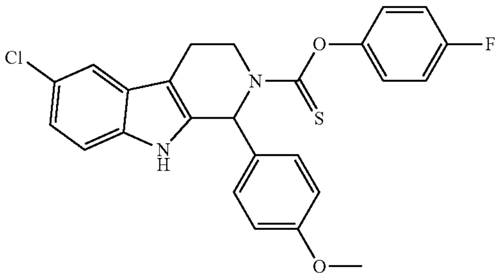
861
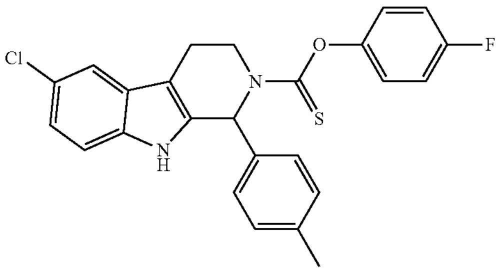
862
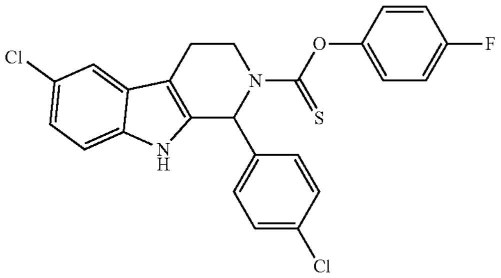
863
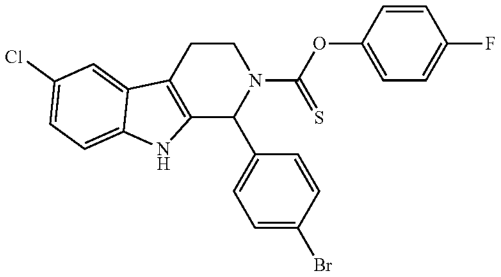
864
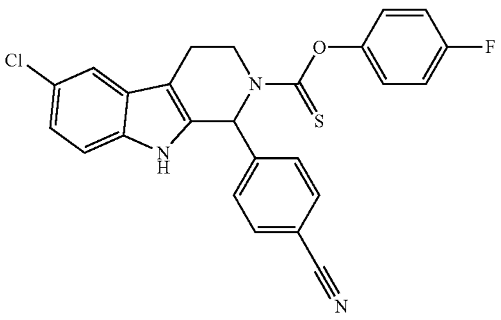

-continued
865
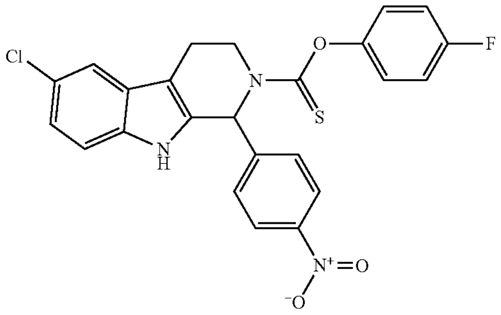
866
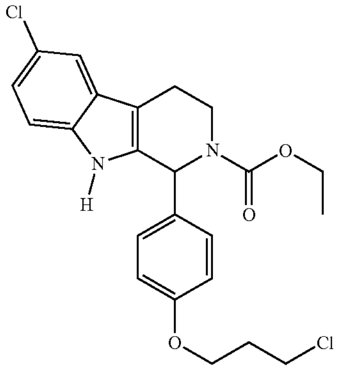
867
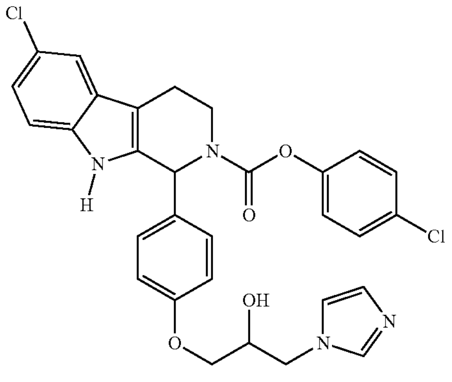
868
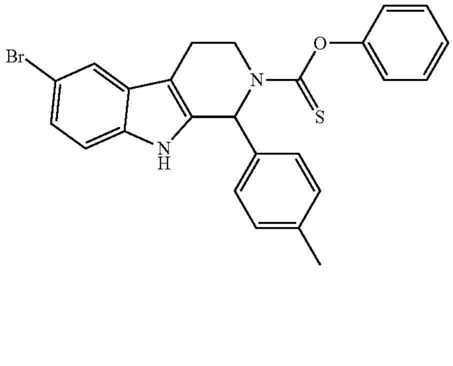
-continued
869
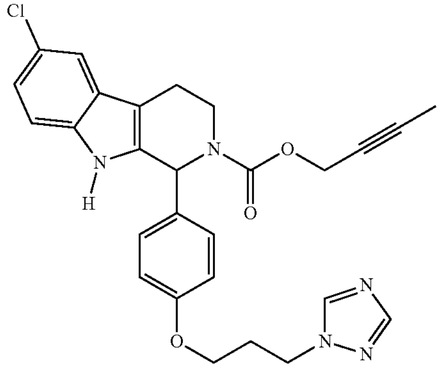
870
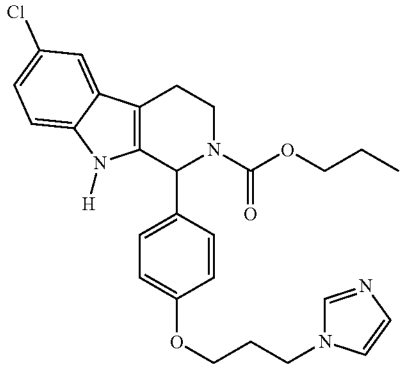
871
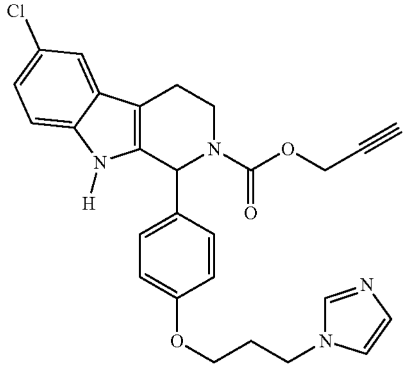
872
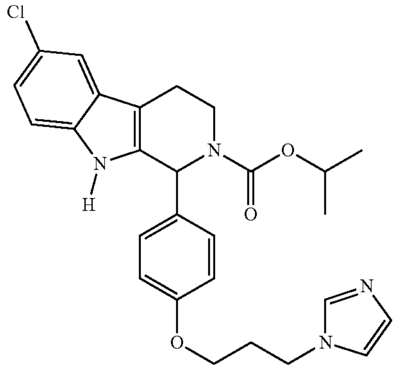

-continued
873
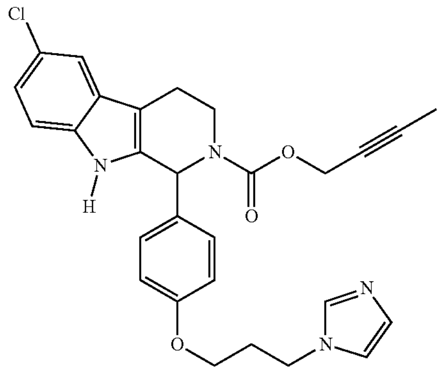
874
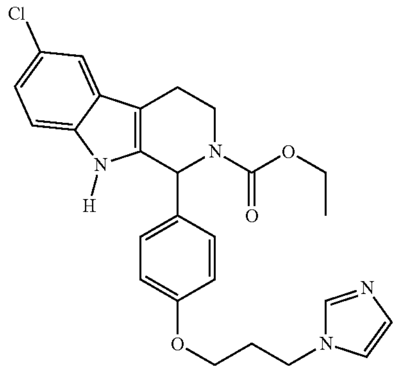
875
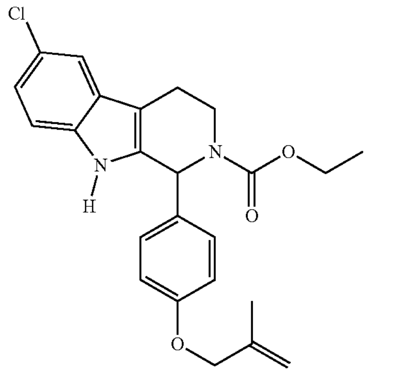
876
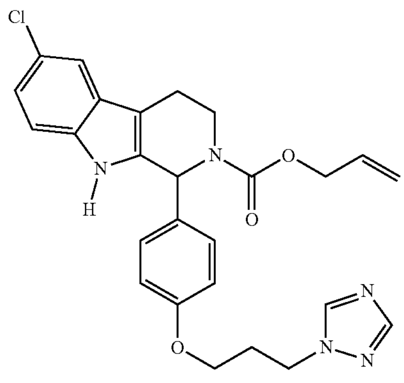
-continued
877
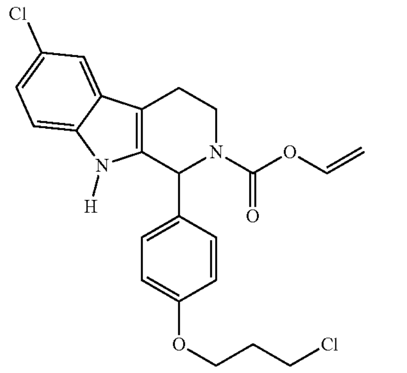
878
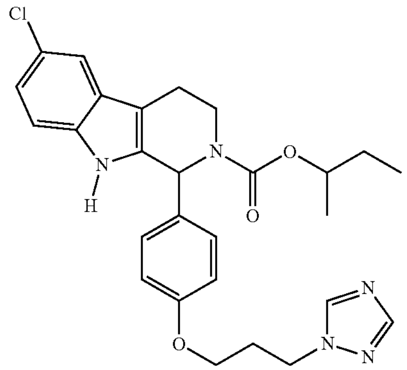
879
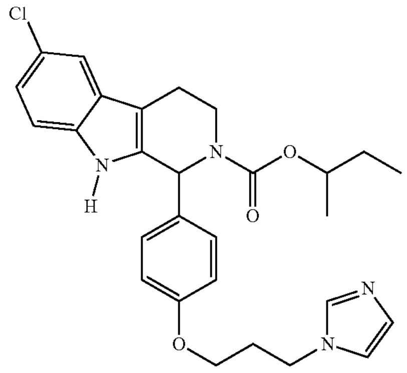
880
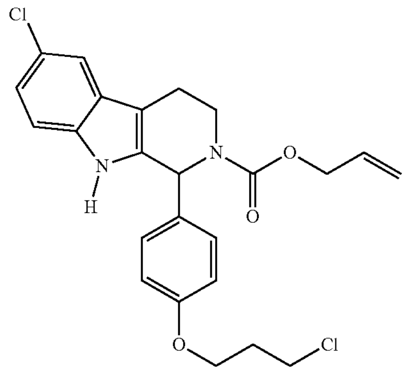

-continued
881
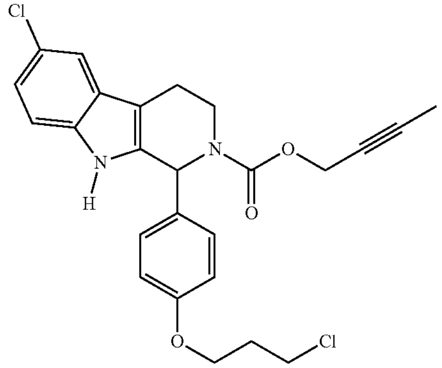
882
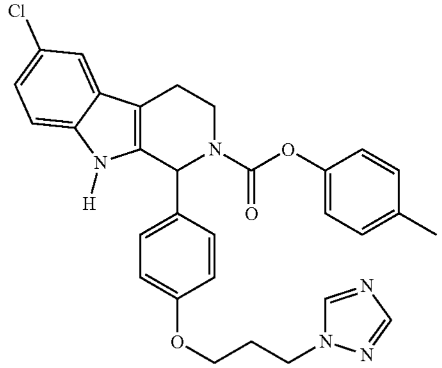
883
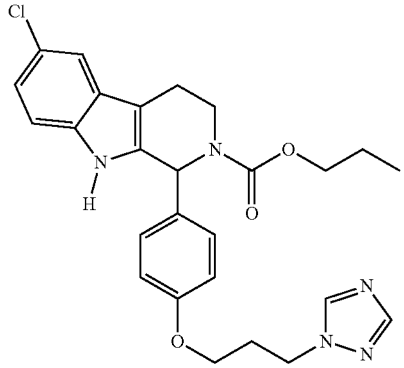
884
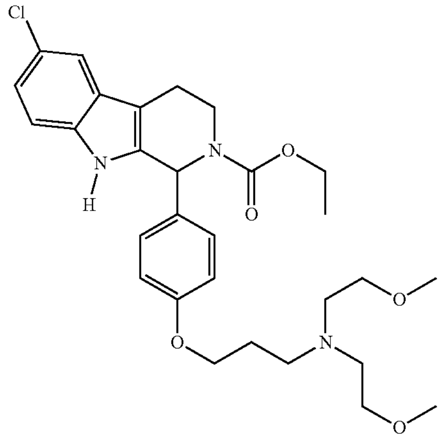
-continued
885
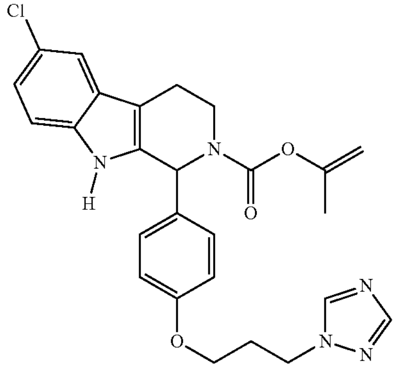
886
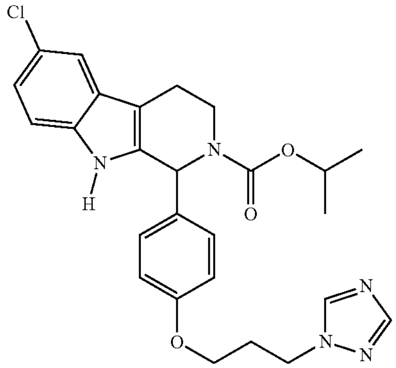
887
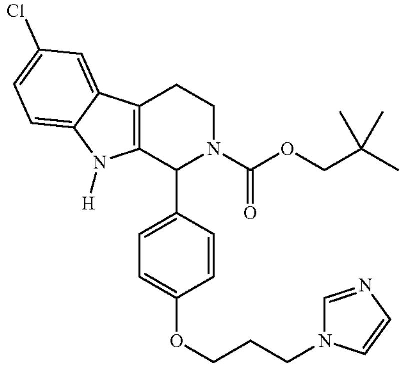
888
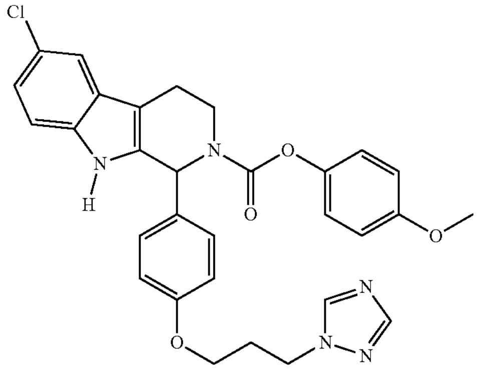

-continued
889
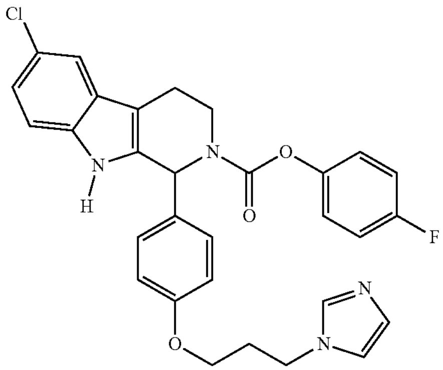
890
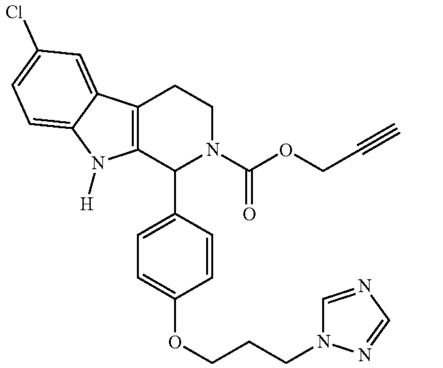
891
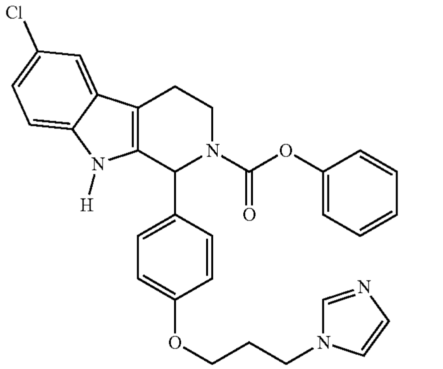
892
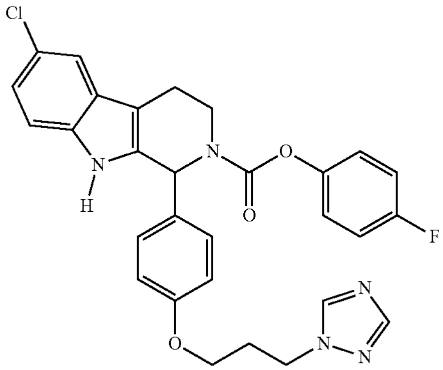
-continued
893
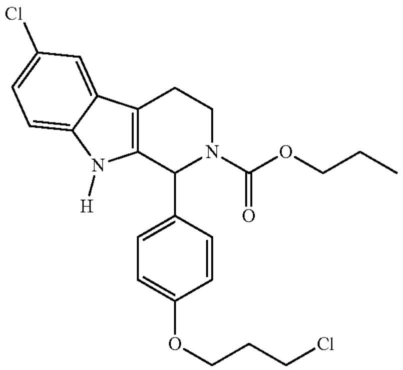
894
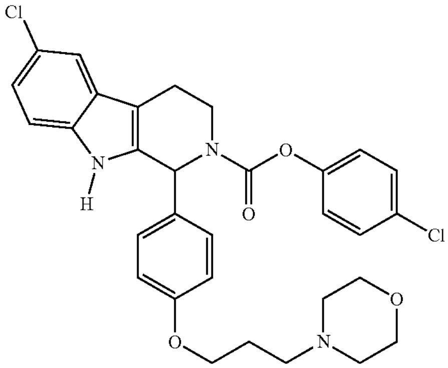
895
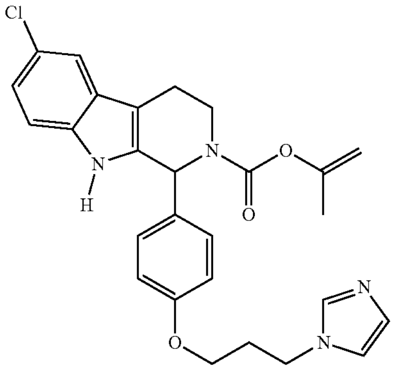
896
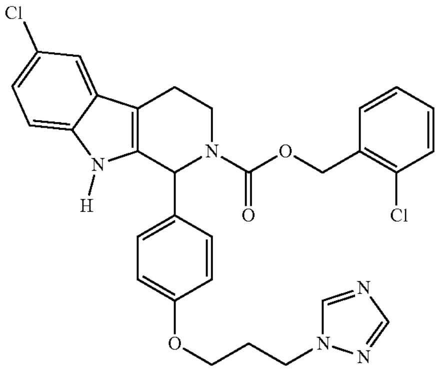

-continued
897
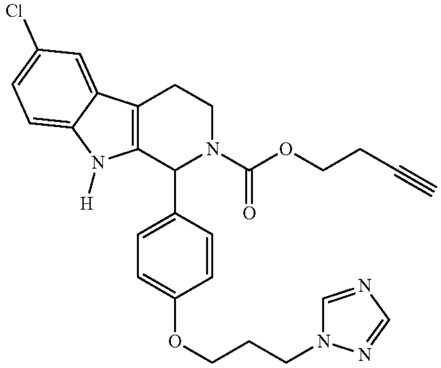
898
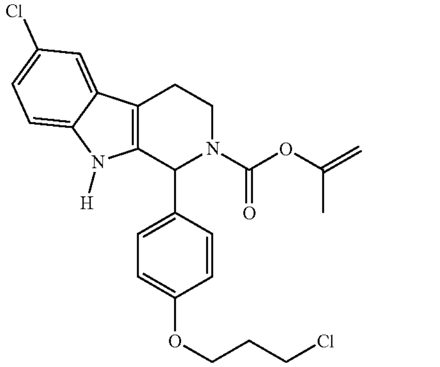
899
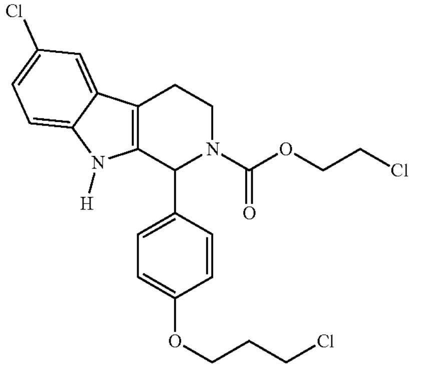
900
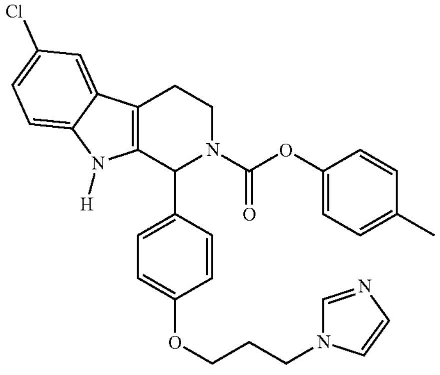
-continued
901
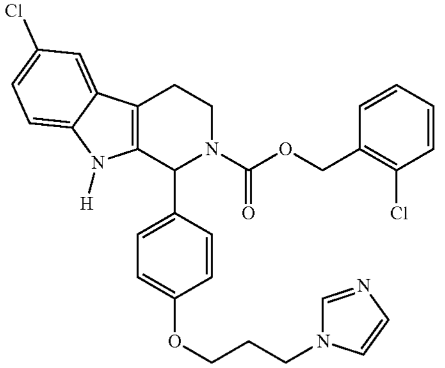
902
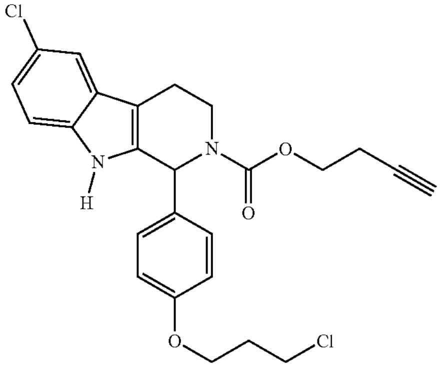
903
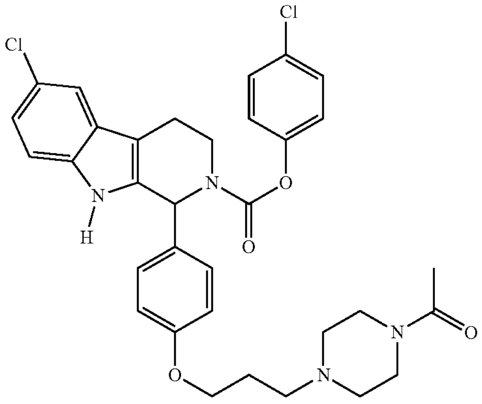
904
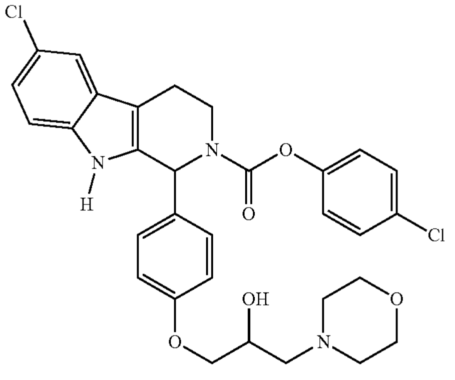

-continued
905
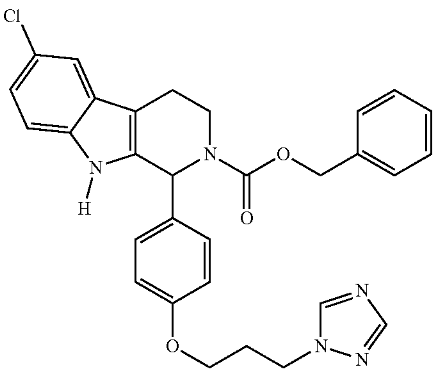
906
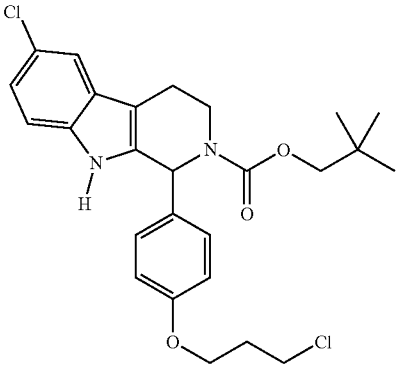
907
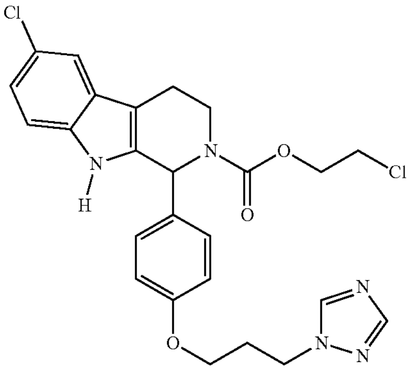
908
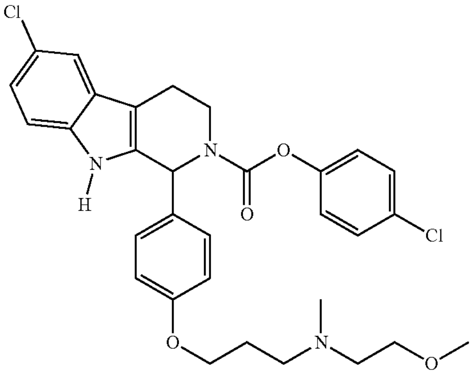
-continued
909
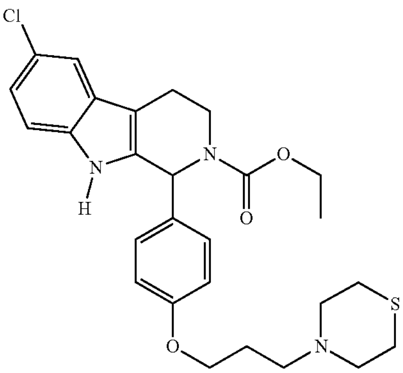
910
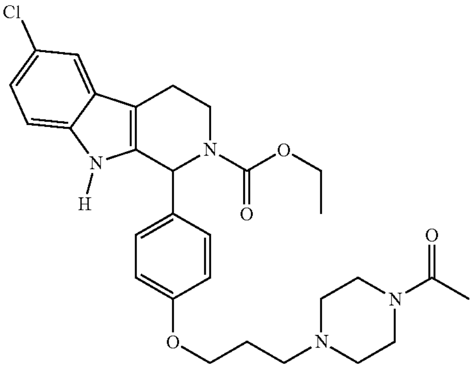
911
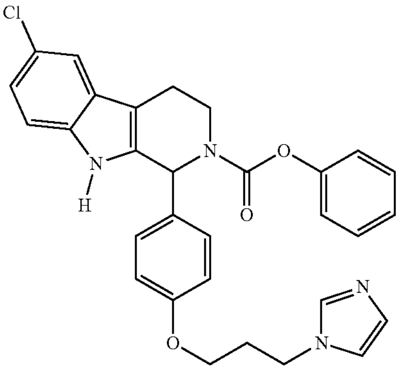
912
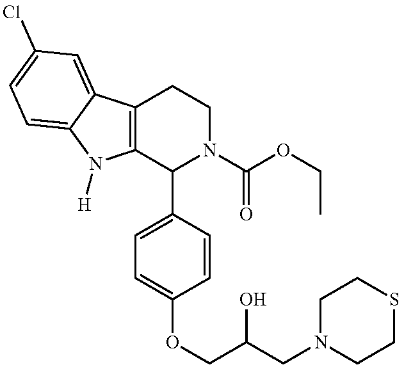

-continued
913
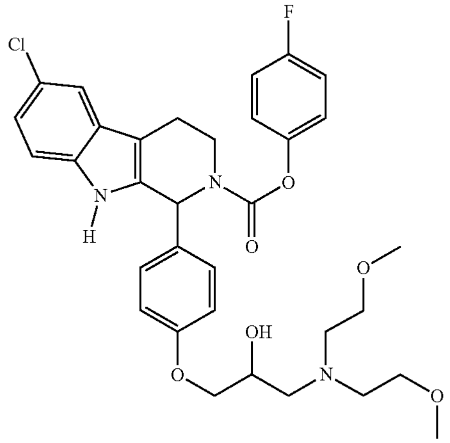
914
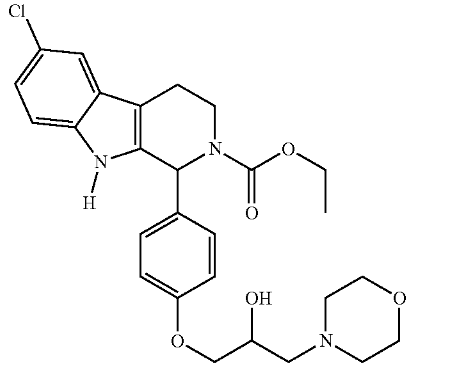
915
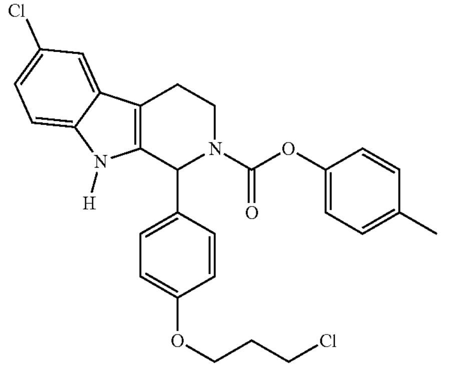
916
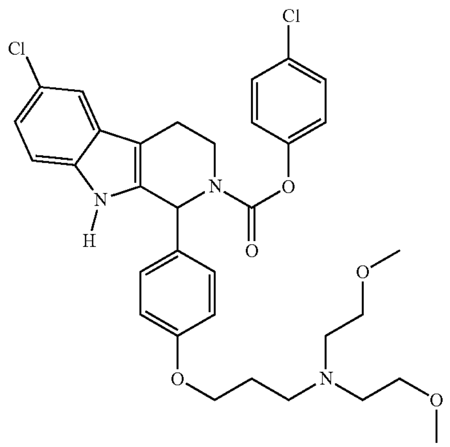
-continued
917
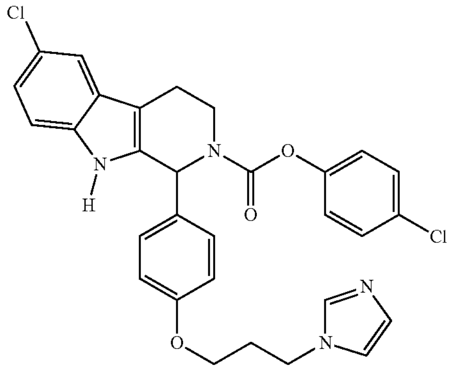
918
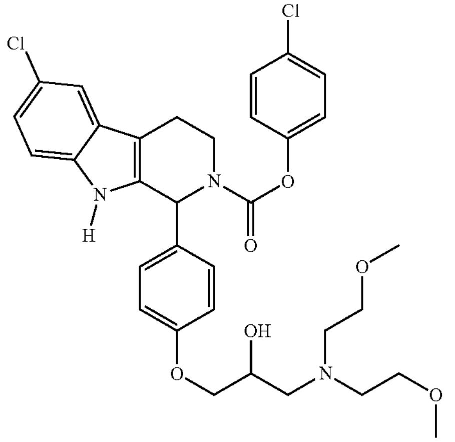
919
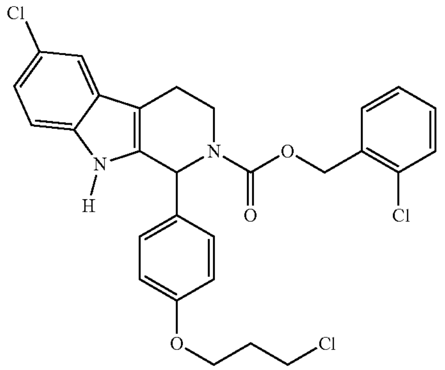
920
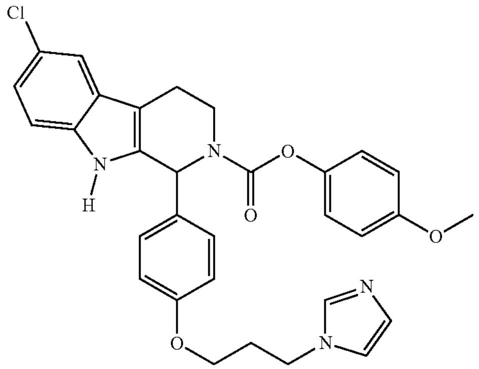

-continued
921
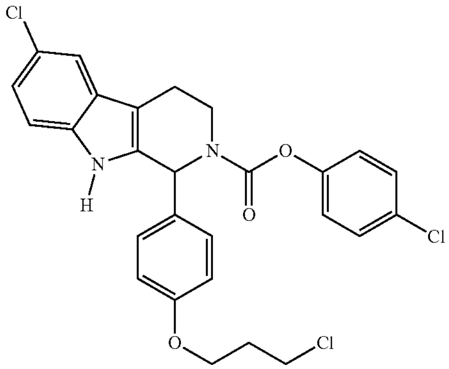
922
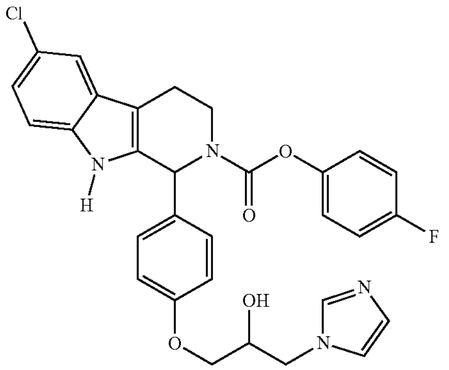
923
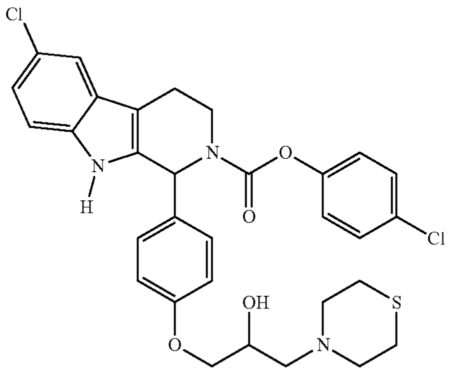
924
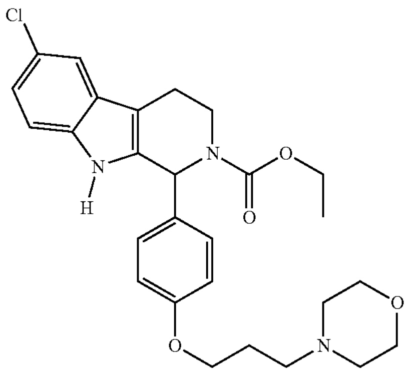
-continued
925
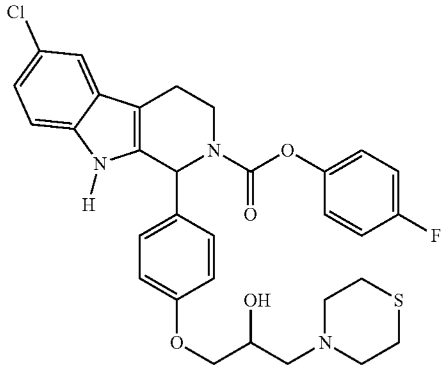
926
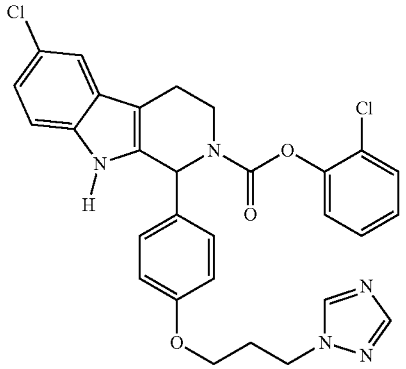
927
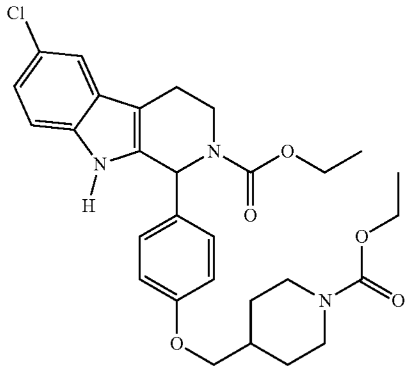
928
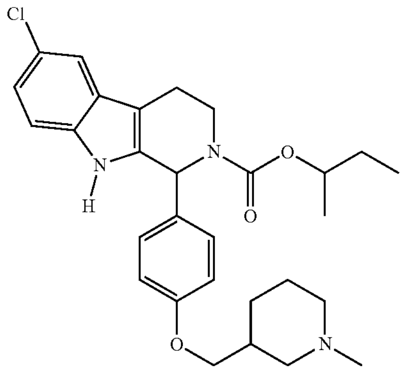

-continued
929
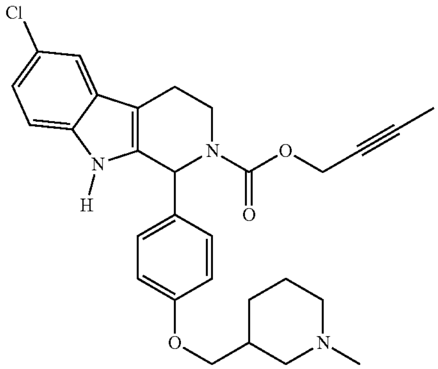
930
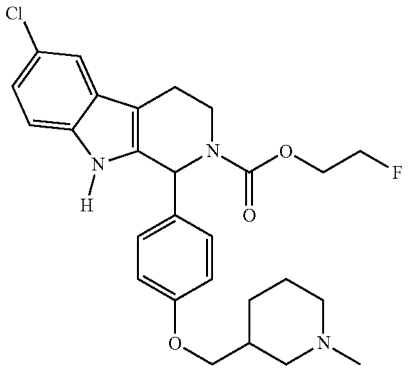
931
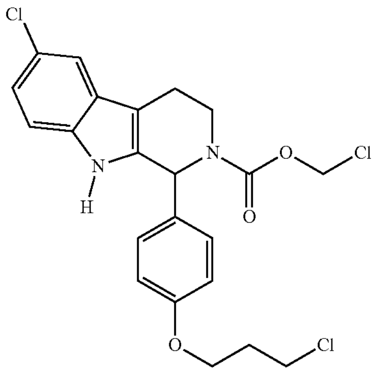
932
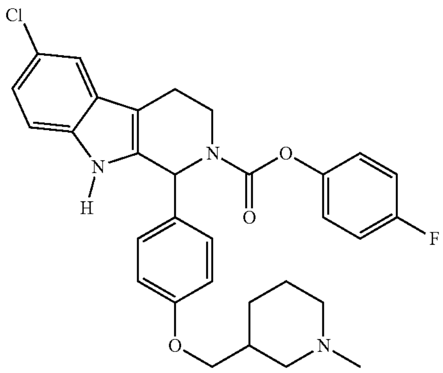
-continued
933
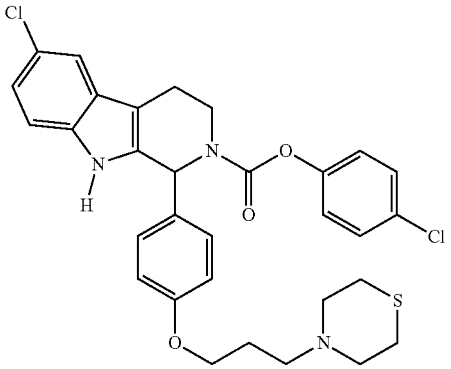
934
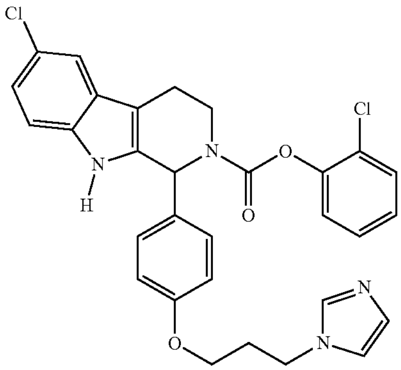
935
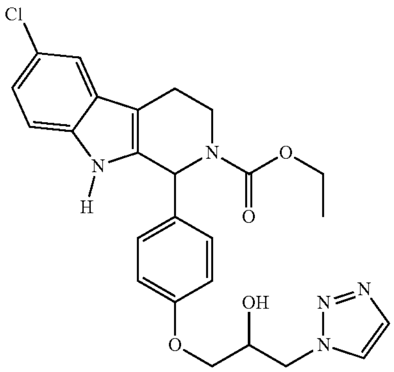
936
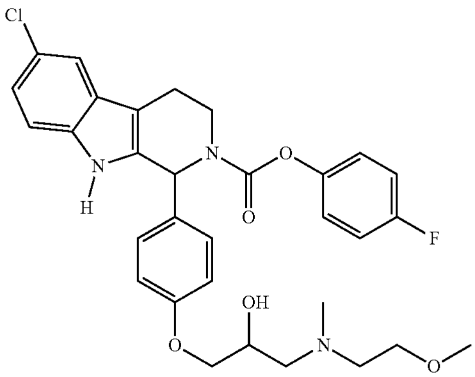

-continued
937
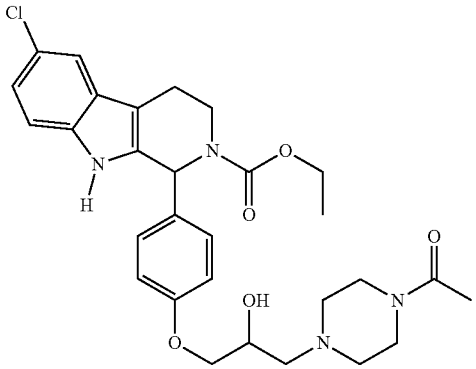
938
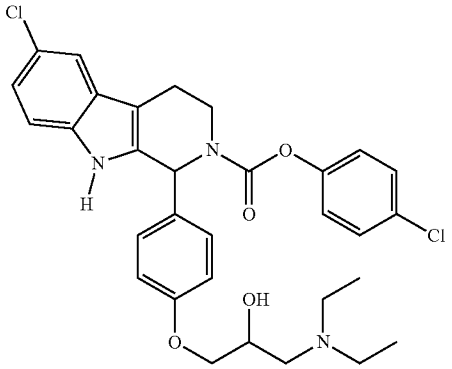
939
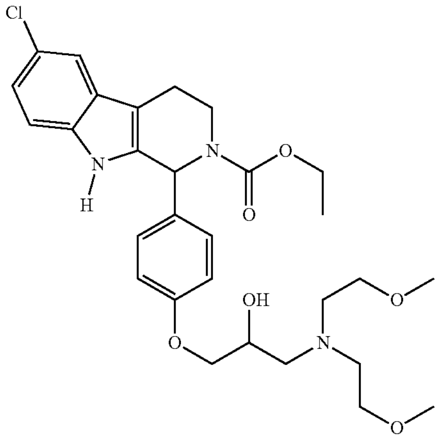
940
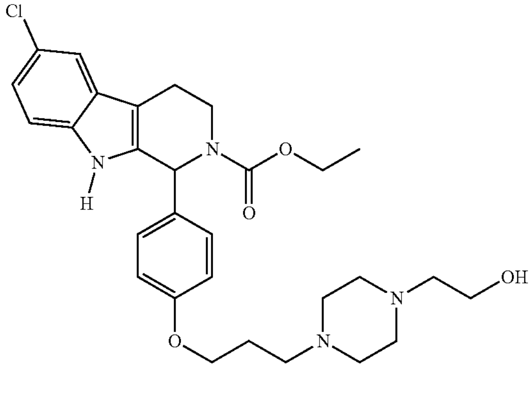
-continued
941
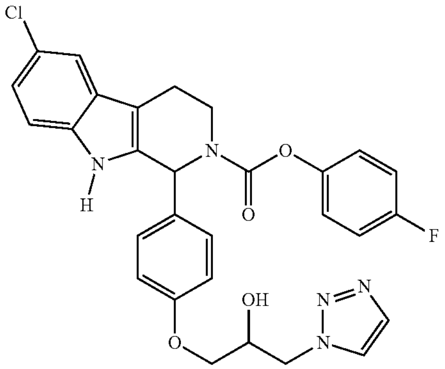
942
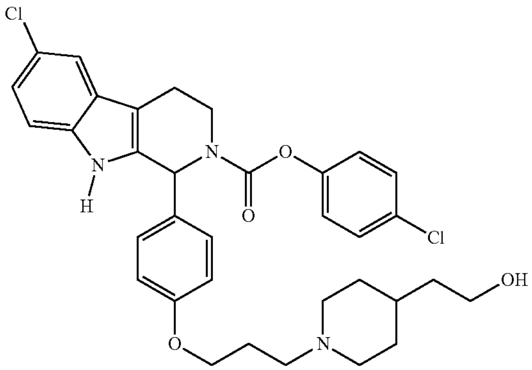
943
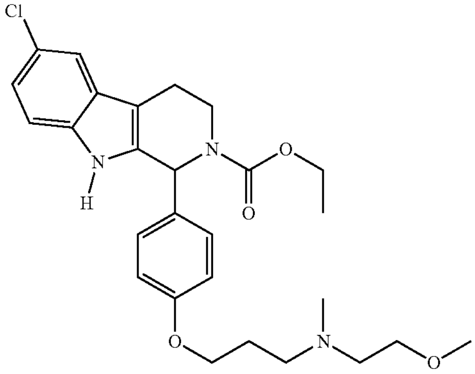
944
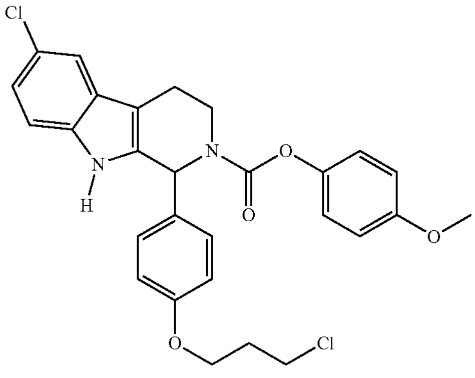

-continued
945
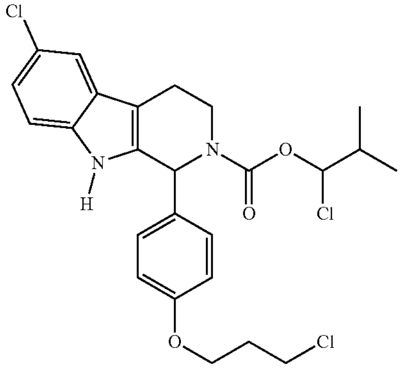
946
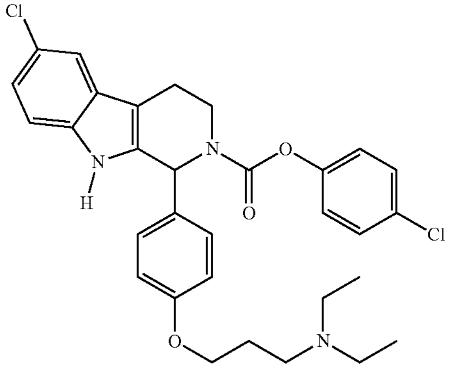
947
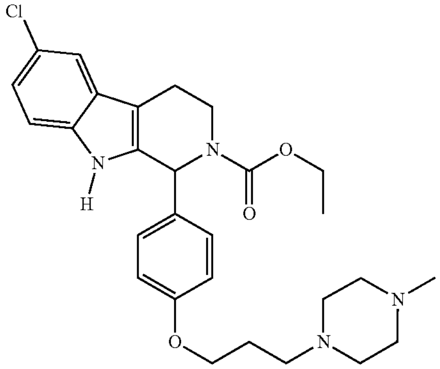
948
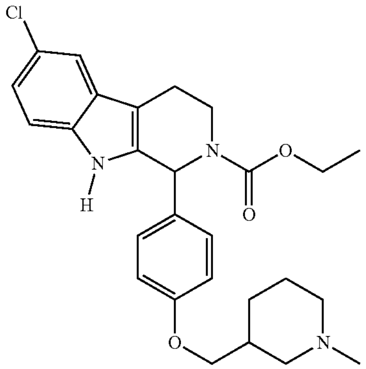
-continued
949
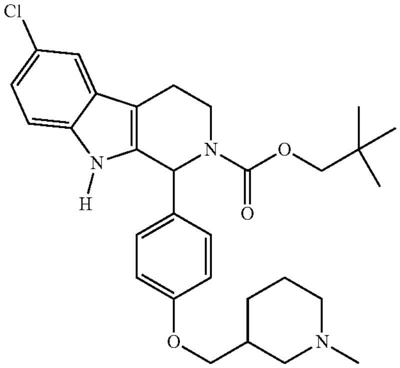
950
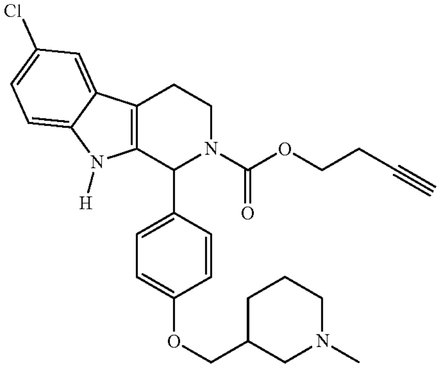
951
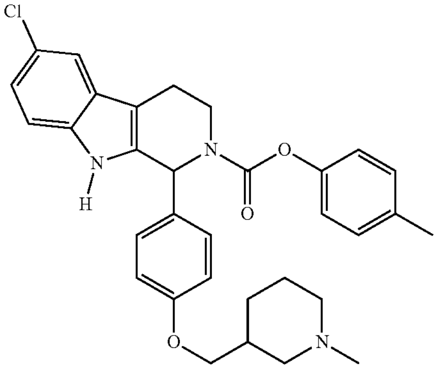
952
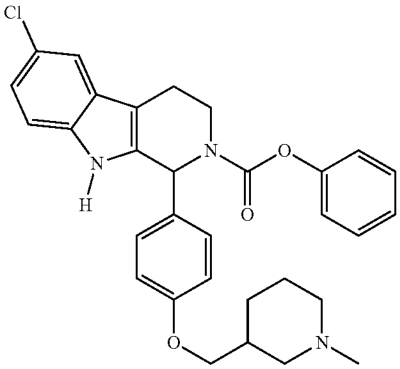

-continued
953
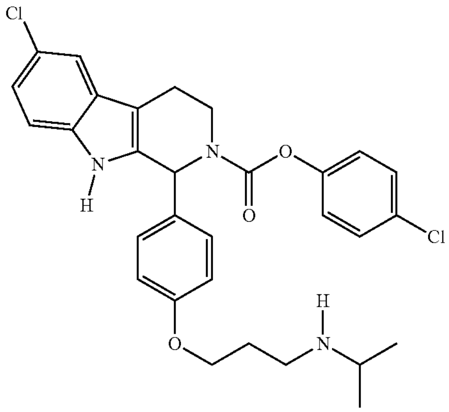
954
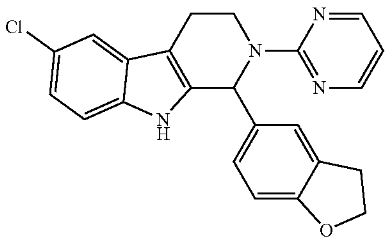
955
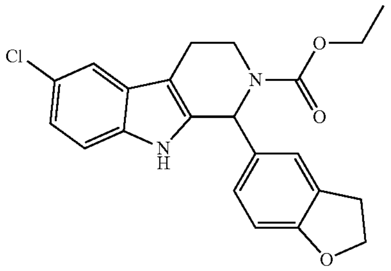
956
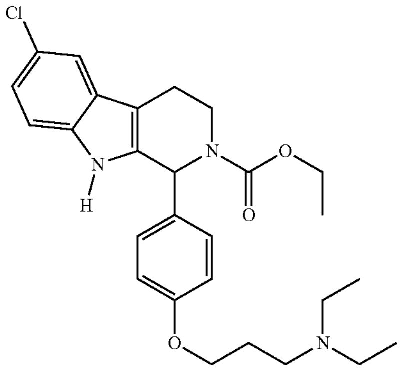
-continued
957
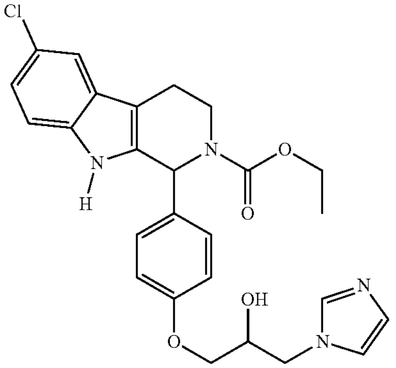
958
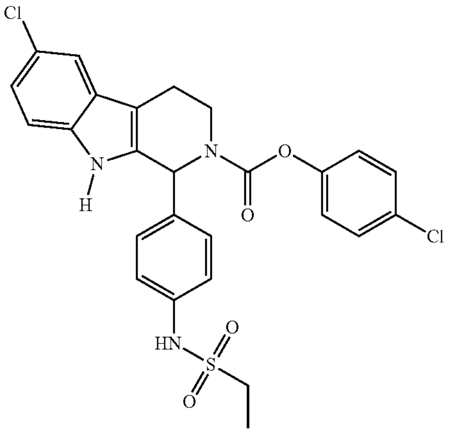
959
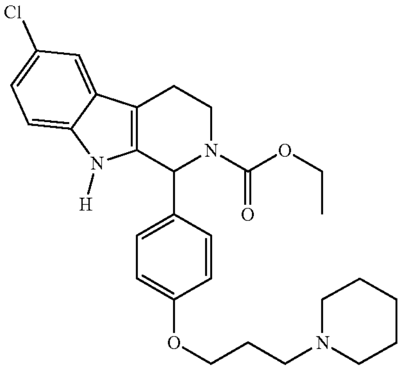
960
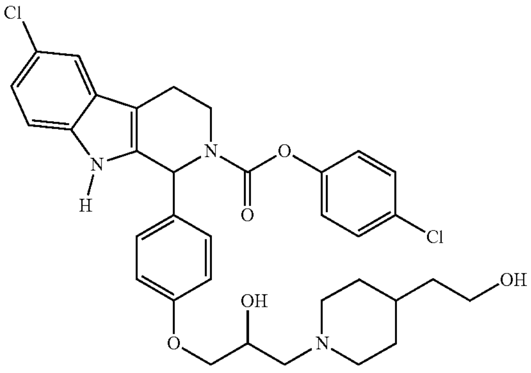

-continued
961
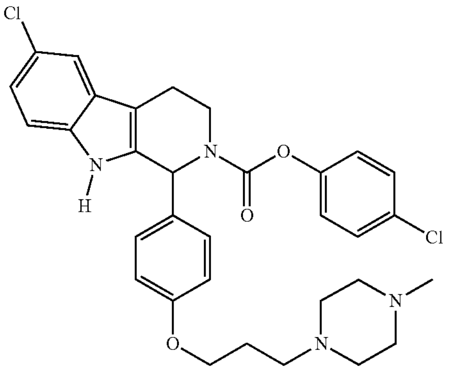
962
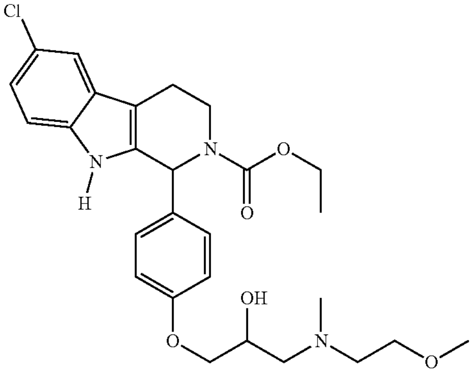
963
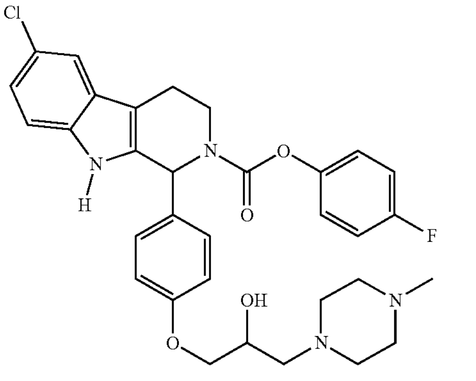
964
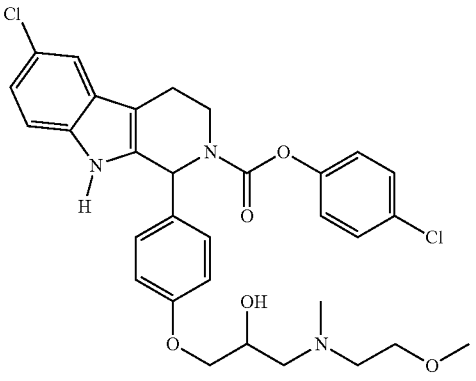
-continued
965
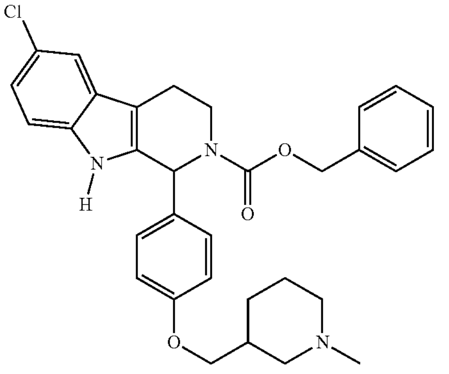
966
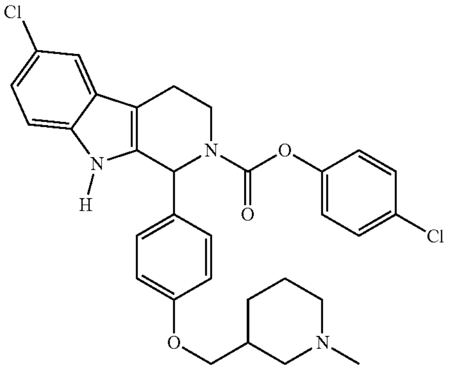
967
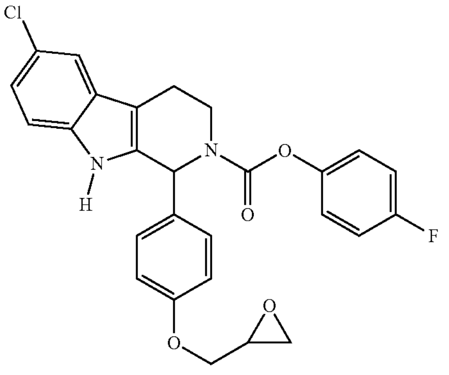
968
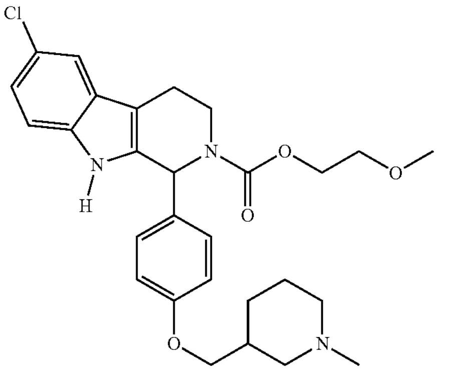

-continued
969
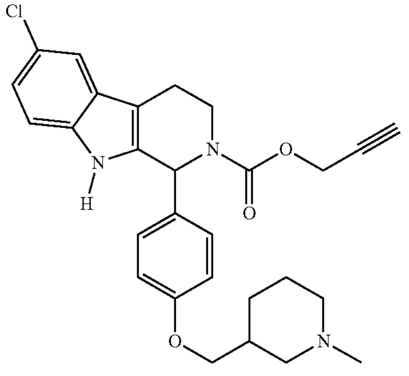
970
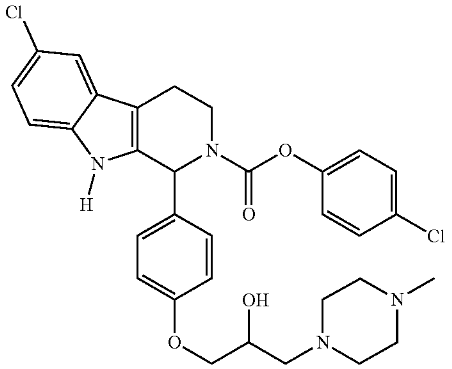
971
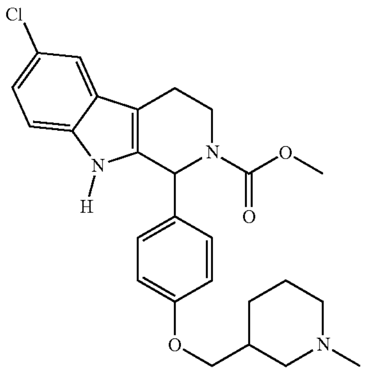
972
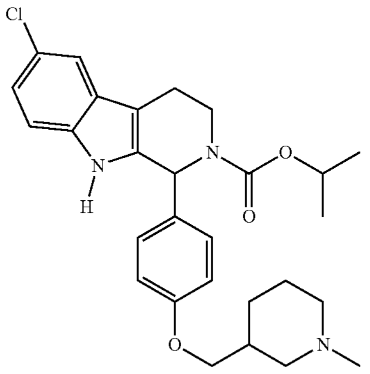
-continued
973
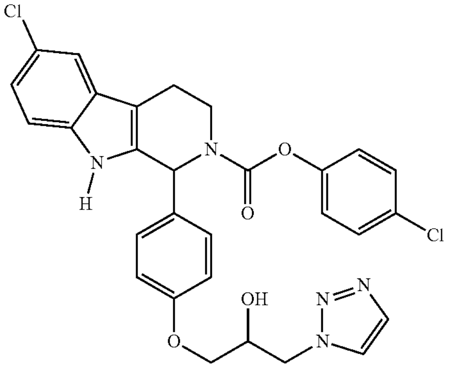
974
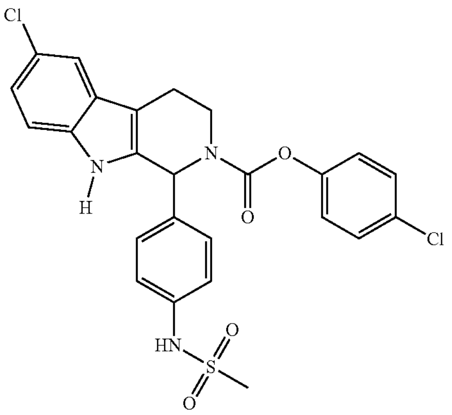
975
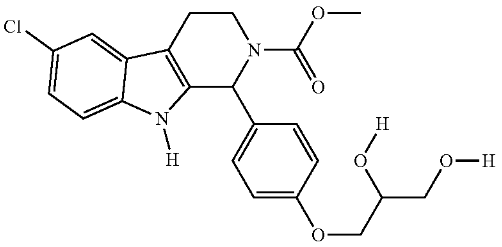
976
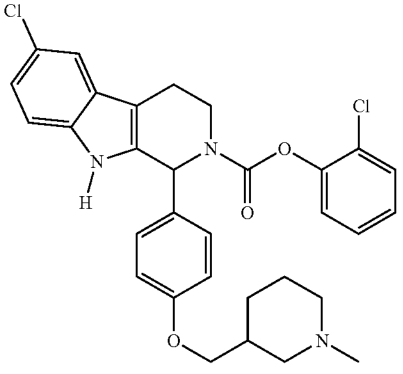

-continued
977
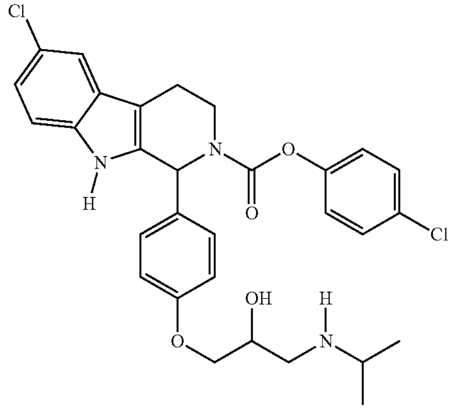
978
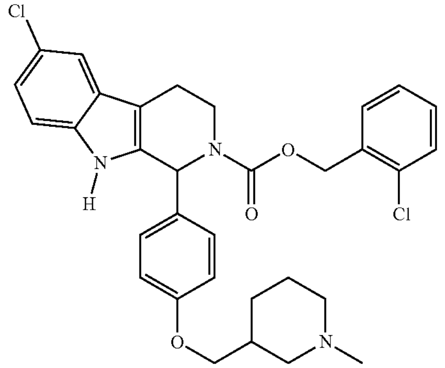
979
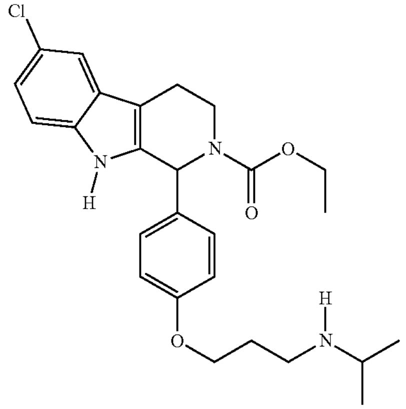
980
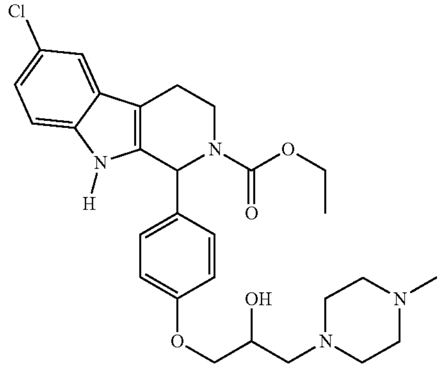
-continued
981
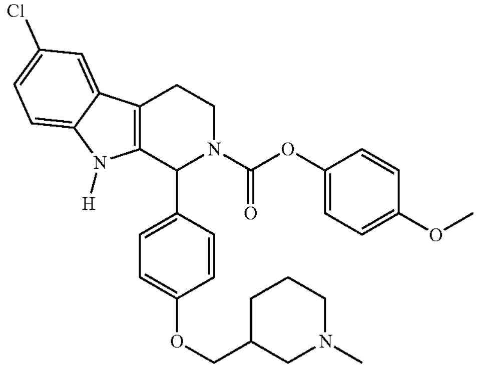
982
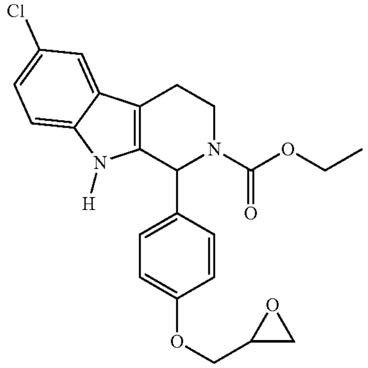
983
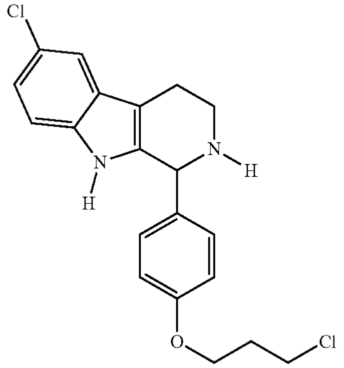
984
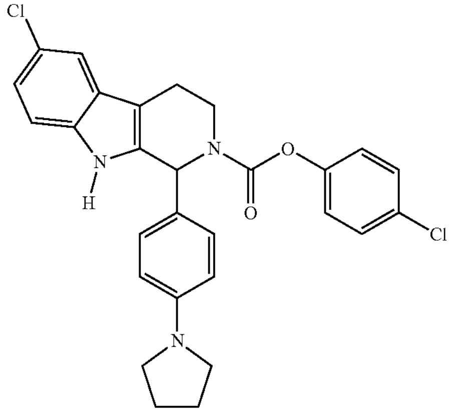

-continued
985
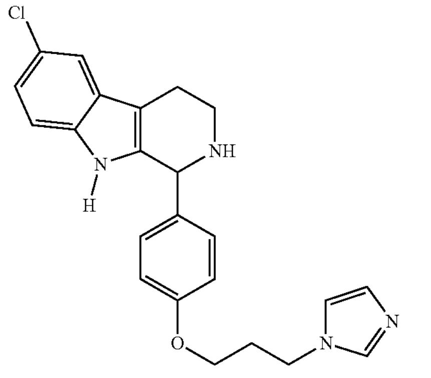
986
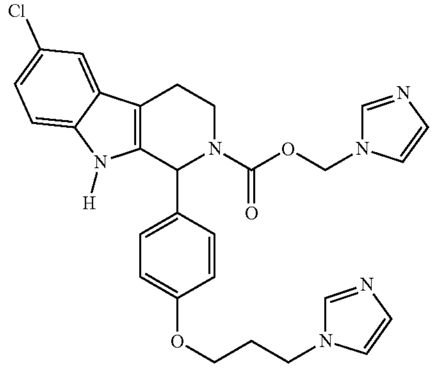
987
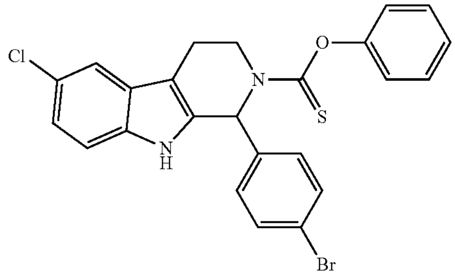
988
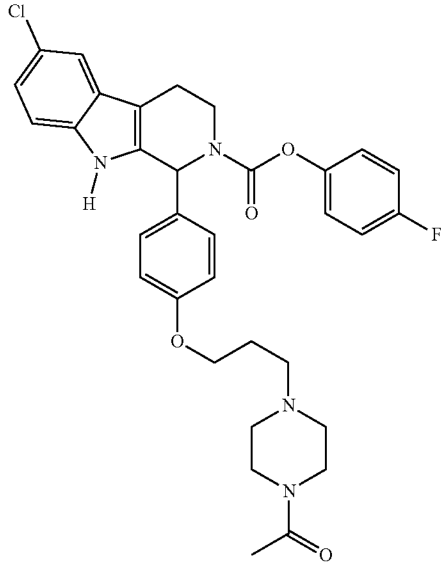
-continued
989
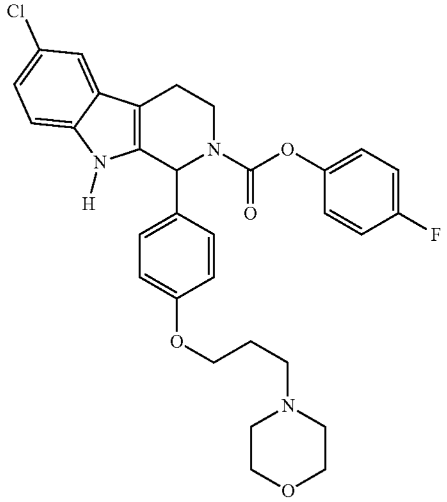
990
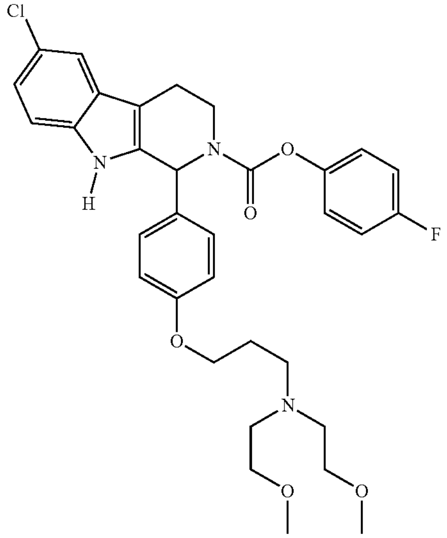
991
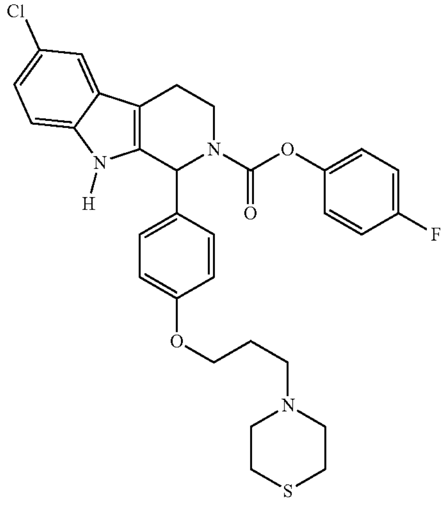

-continued

992

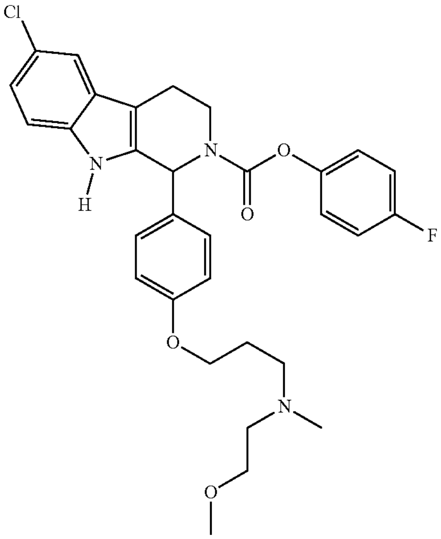

993

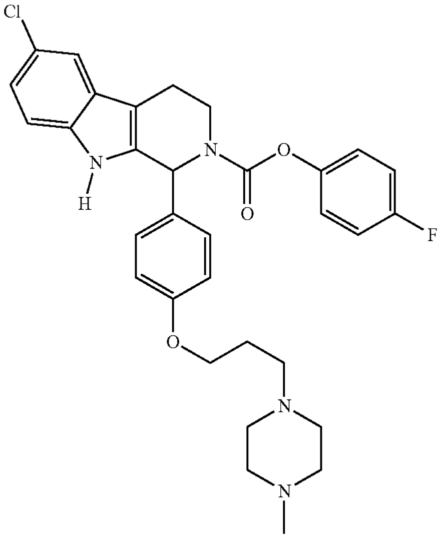

994

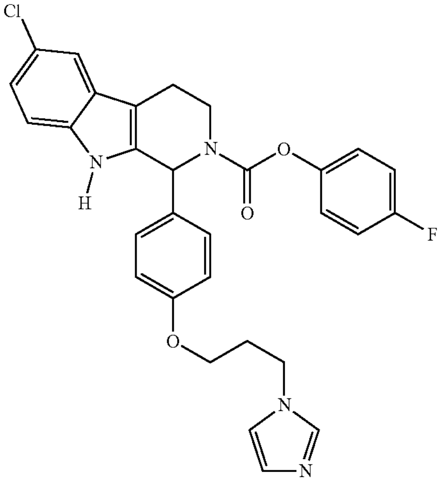

-continued

995

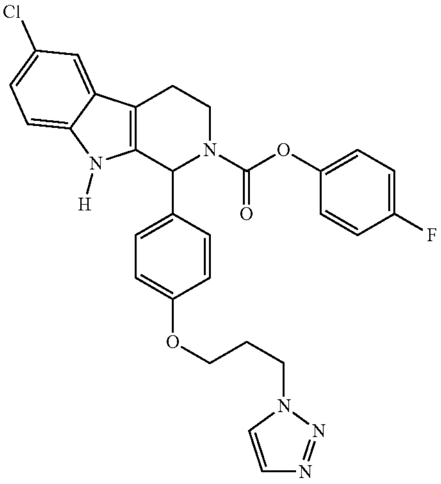

996

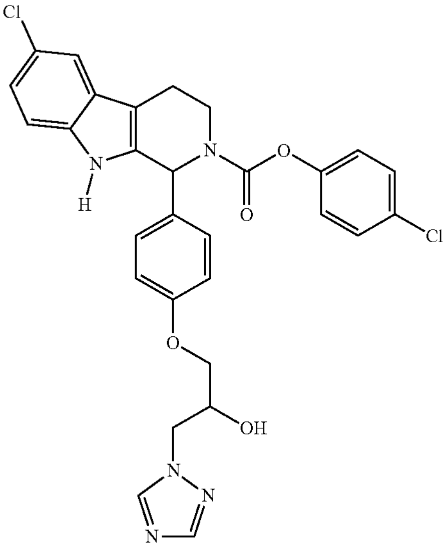

In certain embodiments, preferred compounds include those with an $EC_{50}$ in the VEGF ELISA assay described in Example 5 of less than about 2 uM, more preferably between about 2 uM and about 0.04 uM (200 nM to 40 nM); more preferably from about 0.04 uM to about 0.008 uM to (40 nM to 8 nM); and more preferably less than about 0.008 uM (<8 nM). Particularly preferred compounds are Compound Nos: 2, 4, 5, 7, 8, 10, 11, 12, 17, 23, 25, 81, 102, 112, 140, 328, 329, 330, 331, 332, 355, 816, 817, 818, 823, 824, 825, 830, 831, 832, 837, 838, 841, 842, 843, and regioisomers thereof. In one embodiment, the preferred compounds of the invention form a racemic mixture, and in another embodiment the compounds of the invention are the (R), (S), (R,R), (S,S), (R,S), (S,R) isomer, in an enantiomerically pure composition. More preferably, the compounds of the invention are the (S) isomers, in an enantiomerically pure composition.

The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the following general schemes. More specifically, Scheme I may be used to make compounds of Formula I. Scheme Ia can be used when in conjunction with Scheme I when $R_2$ is a —$CH_2$-furanyl group. Alternatively, for asymmetric synthesis when $R_2$ is hydrogen or hydroxyl, Scheme Ib may be used.

-continued

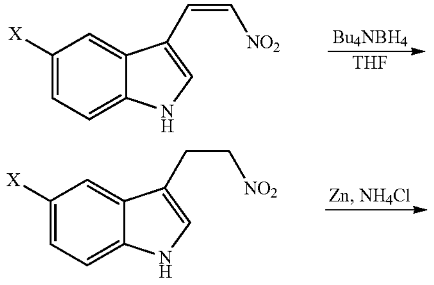

Scheme I

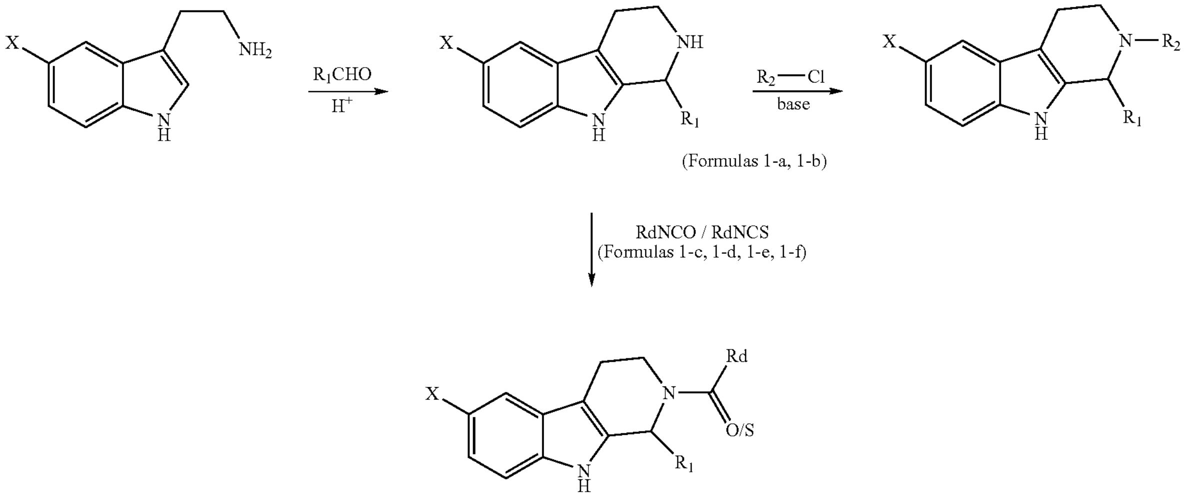

Scheme Ia

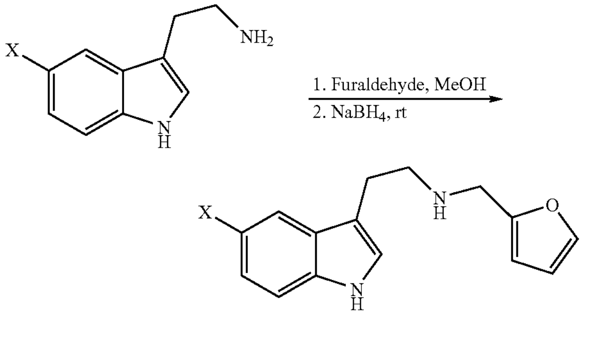

Scheme Ib

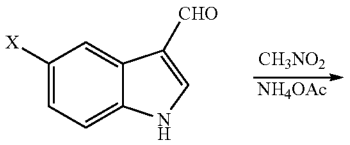

-continued

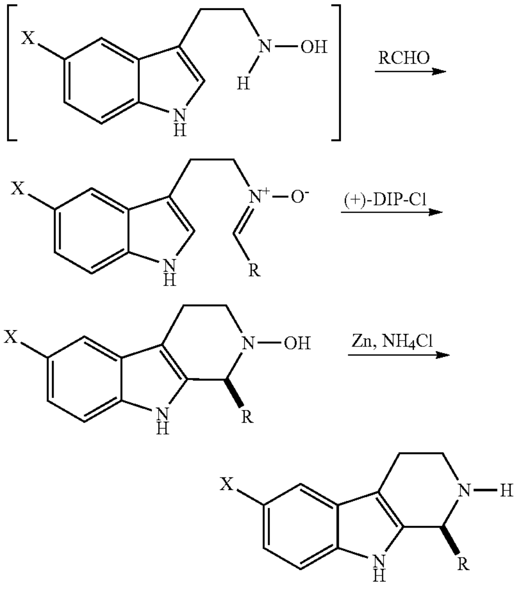

Scheme II can be used to prepare compounds of Formula I-h.

Scheme II

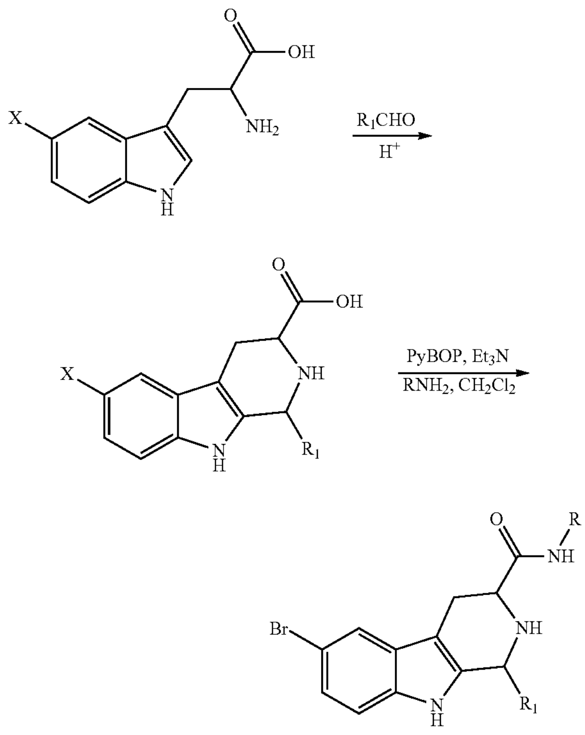

Scheme IIIa or IIIb can be used to prepare compounds of Formula I-i.

Scheme IIIa

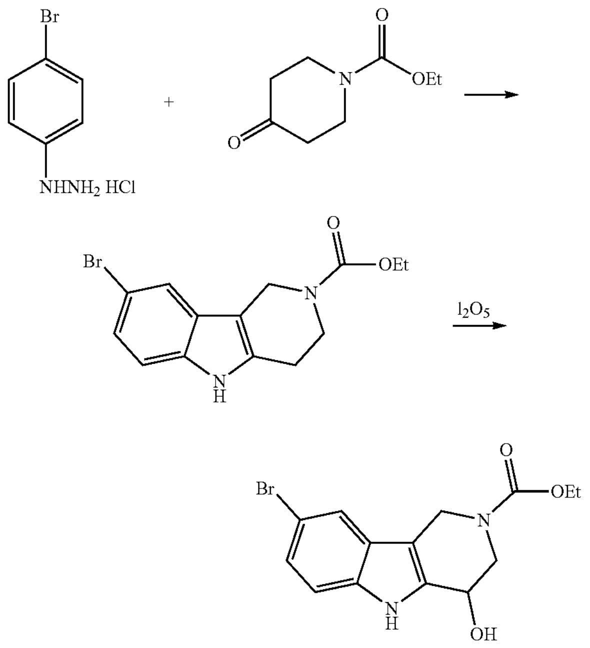

Ref: *Chem. Pharm. Bull.* 1987, 4700.

Scheme IIIb

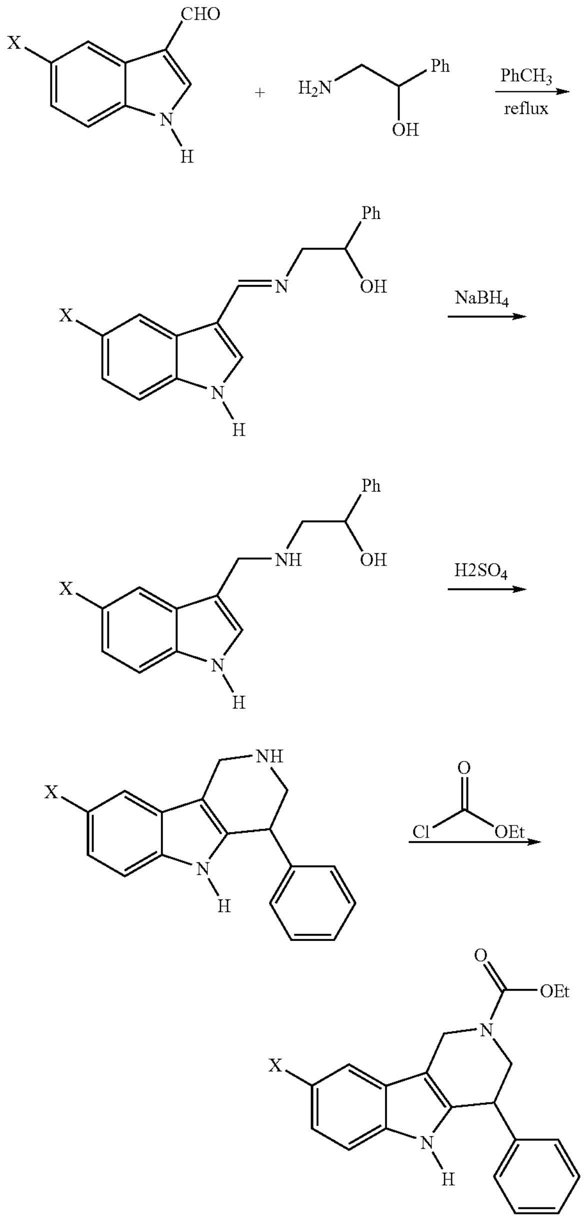

Ref: Magid Abou-Gharbia et al, *J. Med. Chem.* 1987, 30, 1818.

In a preferred embodiment, compounds of the invention may be resolved to enantiomerically pure compositions using any method known in art. By way of example, compounds of the invention may be resolved by direct crystallization of enantiomer mixtures, by diastereomer salt formation of enantiomers, by the formation of diasteriomers and separation, or by enzymatic resolution.

In a preferred embodiment, compounds of the invention may be resolved through crystallization using, e.g., N-acetyl-L-phenylalanine to obtain the (S) isomer, or N-acetyl-D-phenylalanine to obtain the (R) isomer, in a manner similar to that illustrated in Scheme IV.

Scheme IV

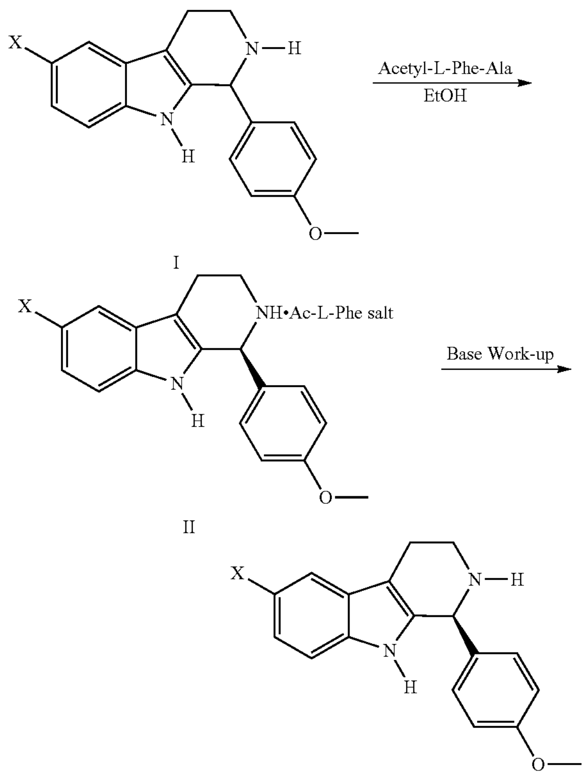

I

II

S-isomer
III

In certain embodiments, exemplary methods of Scheme I for preparing preferred compounds of Formula I involve the formation of free amine Pictet-Spengler reaction products/intermediates, as described below in Procedure-I.

Procedure-I

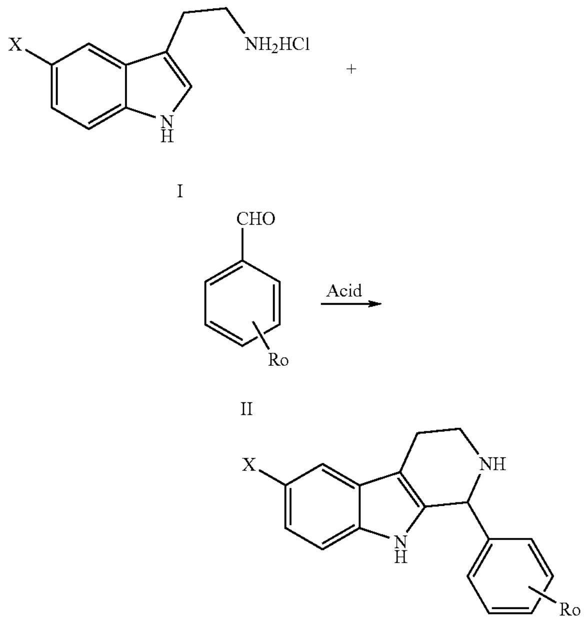

I

II

III

In one embodiment, Procedure-I may involve adding a desired Aldehyde (II) to a suspension of 5-substituted tryptamine. HCl (I) in 0.1N sulfuric acid. The solution may then be stirred at about 110° C.-120° C. in a closed reaction vessel until the reaction is sufficient to complete, e.g., for about 15 minutes to about 20 hours. After completion of the reaction, the reaction mixture may be cooled to room temperature and the precipitated salt may be filtered. The filtered residue may then be washed with ether, EtOAc or a mixture of DUM and DMF and dried to give the product (III) as acid salt. Alternatively, a desired Aldehyde (II) may be added to a suspension of 5-substituted tryptamine.HCl (I) in acetic acid and refluxed until the reaction is sufficiently complete, e.g., for about 15 minutes to about 20 hours. After completion of the reaction, the reaction mixture may be cooled to room temperature and the acid salt may be filtered. The filtered residue may then be washed with acetic acid followed by DCM and dried to give the product (III) as acid salt. The free amine (III) may be obtained by extraction with EtOAc and washing with aqueous ammonium hydroxide or 1M aq. sodium hydroxide.

The free amine, or its salt, may then be used to form other preferred compounds of Formula I, such as carbamate analogs (Formula I-c, Procedure-II), amide analogs, including N-acetyl analogs (Formula I-c, Procedure-IIIa and Procedure-IIIb), urea and thiourea analogs (Formula I-e and I-f, Procedure-IV and Procedure-V respectively), sulfoxide analogs (Formula I-g, Procedure-VI), and pyrimidine analogs (Procedure-VII).

More particularly, Procedure-II may be used to synthesize carbamate analogs of free amines (III), or their salts.

Procedure-II

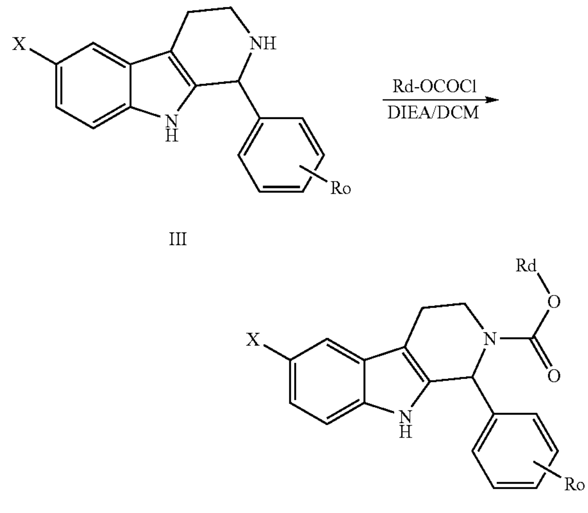

III

IV

In accordance with Procedure-II, diisopropylethylamine (DIEA) may be added to the free amine (III), or its acid salt in dichloromethane (DCM), followed by slow addition of substituted chloroformate. The reaction mixture may be stirred at room temperature for about 1 to 20 hours. The solvent may then be evaporated and the crude product may either be purified by HPLC or silica gel column chromatography.

Procedure-IIIa may be used to synthesize amide analogs of free amine (III), or their salts.

Procedure-IIIa

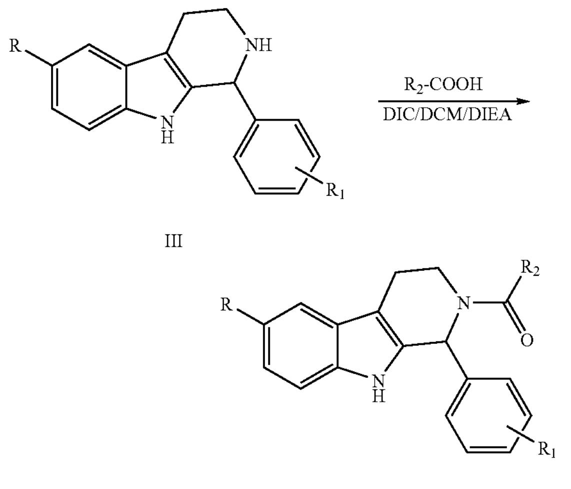

III

X

In accordance with Procedure-IIIa, a 15 min pre-stirred mixture of an $R_2$-acid and diisopropyl carbodiimide (DIC) may be added to the free amine (III), or its acid salt in DCM and DIEA. The reaction mixture may be stirring for about 1 h. The solvents may then be evaporated and the crude product purified by HPLC.

Alternatively, Procedure-IIIb may be used to synthesize N-acetyl analogs of free amines (III), or their salts.

Procedure-IIIb

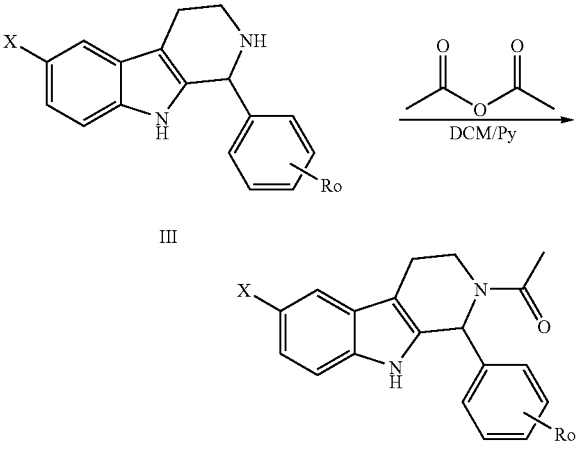

III

V

In accordance with Procedure-IIIb, pyridine may be added to the free amine (III), or its acid salt in DCM, followed by acetic anhydride. The reaction mixture may be stirred at room temperature for about 8 to 20 hours. The solvents may then be evaporated and the crude product was purified by HPLC.

Procedure-IV may be used to synthesize urea analogs of free amines (III), or their salts.

Procedure-IV

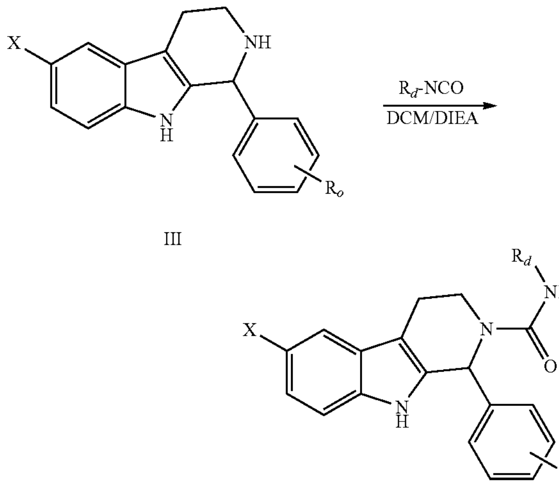

III

VI

In accordance with Procedure-IV, DIEA and $R_2$-isocyanate may be added to the free amine (III), or its acid salt in DCM. The reaction mixture may be refluxed for about 1.5 h. The solvents may then be evaporated and the crude product purified by HPLC.

Procedure-V may be used to synthesize thiourea analogs of free amines (III), or their salts.

Procedure-V

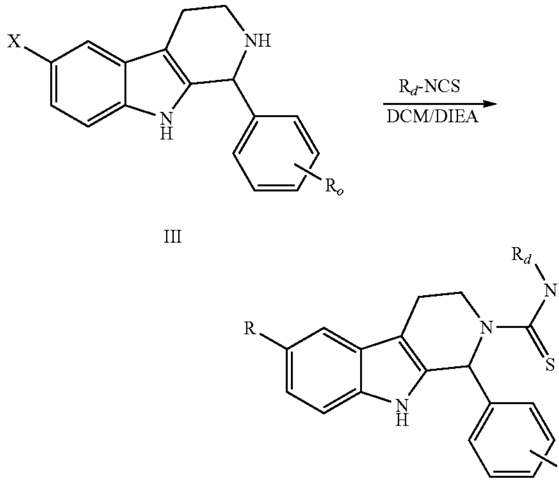

III

VIII

In accordance with Procedure-V, DIEA and $R_2$-isothiocyanate may be added to the free amine (III), or its acid salt in DCM. The reaction mixture may be refluxed for about 12 h. The solvents may then be evaporated and the crude product purified by HPLC.

Procedure-VI may be used to synthesize sulfonyl analogs of free amines (III), or their salts.

Procedure-VI

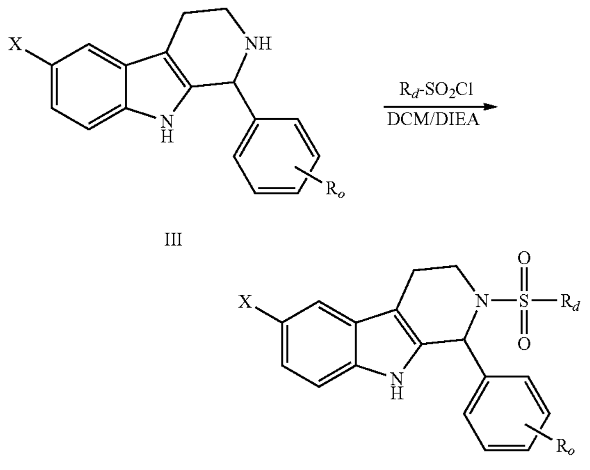

III

IX

In accordance with Procedure-VI, DIEA and $R_2$-sulfonylchloride may be added to the free amine (III), or its acid salt in DCM. The reaction mixture may be stirred at room temperature for about 12 h. The solvents may then be evaporated and the crude product purified by HPLC. Procedure-VII may be used to synthesize pyrimidine analogs of free amines (III), or their salts.

Procedure VII

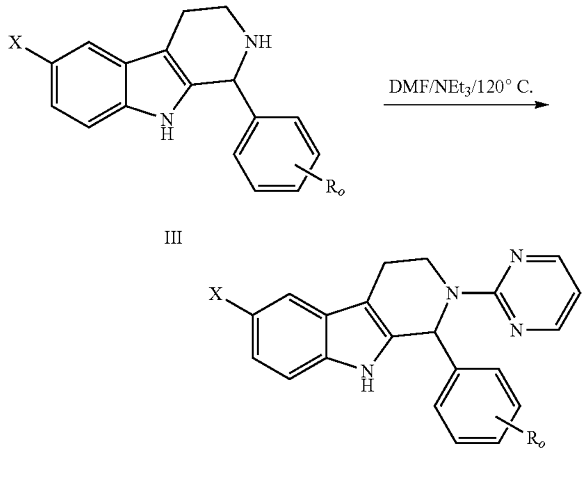

III

VII

In accordance with Procedure-VII, triethylamine and 2-bromopyrimidine in N,N-dimethylformamide (DMF) may be added to the free amine (III), or its acid salt in DCM. The reaction mixture may be heated to about 120° C. for about 12 h. The solvents may then be evaporated and the crude product purified by HPLC.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

In yet another embodiment, methods for treating cancer, diabetic retinopathy, rheumatoid arthritis, psoriasis, atherosclerosis, chronic inflammation, other chronic inflammation-related diseases and disorders, obesity, or exudative macular degeneration are provided comprising administering a therapeutically effective amount of at least one compound of the invention to a subject in need thereof.

In yet a further embodiment, the cancers which can be treated by administering a therapeutically effective amount of at least one compound of the invention to a subject in need thereof include solid tumor cancers. Solid tumor cancers that can be treated by the present invention include solid tumor carcinomas and solid tumor sarcomas. Solid tumor carcinomas include, but are not limited to, pediatric solid tumors, such as Wilms tumor and neuroblastoma, and carcinomas of the epidermis, such as malignant melanomas, as well as lung cancers, cervical cancers, colon cancers and renal cancers. Solid tumor sarcomas include, but are not limited to, fibrosarcomas. The methods of treating cancer can further include the administration of one or more additional agents useful for treating cancer.

In yet another embodiment of the invention, methods for treating a solid tumor cancer by slowing tumorigenesis at a pre-vascular stage are provided, comprising administering a therapeutically effective amount of at least one compound of the invention to a subject in need thereof, either alone or together with one or more additional agents useful for treating cancer.

In another embodiment of the invention, methods for treating a solid tumor cancer by inhibiting VEGF mRNA translation are provided, comprising administering a therapeutically effective amount of at least one compound of the invention to a subject in need thereof, either alone or together with one or more additional agents useful for treating cancer.

In yet another embodiment of the invention methods for treating a solid tumor cancer by reducing tumor VEGF levels are provided, comprising administering a therapeutically effective amount of at least one compound of the invention to a subject in need thereof, either alone or together with one or more additional agents useful for treating cancer.

In yet a further embodiment of the invention, methods for treating a solid tumor cancer by reducing perivascularly sequestered or intratumoral VEGF are provided, comprising administering a therapeutically effective amount of at least one compound of the invention to a subject in need thereof, either alone or together with one or more additional agents useful for treating cancer. In this aspect, reduced perivascularly sequestered VEGF is an in situ comparison of perivascular VEGF in tumors treated with the compound of the invention and tumors not treated with the compound of the invention. In a preferred aspect, reduced perivascularly sequestered VEGF is compared with levels of perivascular VEGF in tumors treated with antibodies to VEGF.

Without intending to be limited by theory, it is believed that the methods of the present invention act through a combination of mechanisms that modulate the activity of VEGF. In this embodiment of the invention, methods for inhibiting VEGF mRNA translation are provided, comprising administering a therapeutically effective amount of at least one compound of the invention to a subject in need thereof. In a preferred aspect, VEGF mRNA translation is inhibited by greater than 10%, 25%, 50%, 75%, 80%, or 90% compared with an untreated tumor or cell.

In another embodiment of the invention, methods for slowing tumorigenesis at a pre-vascular stage are provided, comprising administering a therapeutically effective amount of at least one compound of the invention to a subject in need thereof, either alone or together with one or more additional cancer agents. The pre-vascular stage of tumorigenesis is clinically known as "carcinoma in situ" and tumors at this stage are characterized by their reliance on nearby blood vessels for oxygen and diffusion of nutrients, due to the tumors absence of its own vascular infrastructure. So, by slowing tumorigenesis at a pre-vascular stage, one is preventing or slowing the development of a vascular infrastructure in the tumor. In this embodiment of the invention, whether tumorigenesis has been slowed at the pre-vascular stage is determined by identifying to what extent the tumor has developed a vascular infrastructure. In a preferred aspect, treated tumor growth is prevented or slowed, as compared to the untreated tumors, by 90%, 80%, 70%, 60%, 50%, 40%, 30%, 20% or 10%.

In yet a further embodiment of the invention, methods for reducing perivascularly sequestered or intratumoral VEGF are provided, comprising administering a therapeutically effective amount of at least one compound of the invention to a subject in need thereof.

In yet an additional embodiment of the invention, methods of diagnosing cancer by measuring tumor and/or plasma levels of VEGF are provided. Tumor levels of VEGF can be measured using biopsy tissue, where plasma VEGF levels can be measured by taking blood. In humans, different tumors secrete different levels of VEGF. Standard ELISA procedures can be used to measure the amount of VEGF in the tumor or plasma. See, for example, Verheul, H. M. W. et al. (2000) Platelet and coagulation activation with vascular endothelial growth factor generation in soft tissue sarcomas. *Clin. Cancer Res.* 6:166. For tumors that do not secrete large amounts of VEGF into the plasma, the tumor VEGF concentration can be determined to diagnose the tumor progression. For tumors that do secrete large amount of VEGF into the plasma, plasma VEGF concentration can be determined to diagnose the tumor progression. After most known cancer treatments, VEGF levels are not affected, and therefore the plasma or tumor levels of VEGF do not predict efficacy of the treatment (i.e., progression of the cancer). Compounds of the present invention can affect VEGF levels, both in the plasma and tumor, and therefore measuring VEGF levels is an accurate way to monitor and/or predict the progression of the cancer (i.e., the efficacy of the treatment) when the methods of the present invention are used for treating cancer.

In yet another embodiment of the invention, methods for reducing tumor or plasma VEGF levels are provided, comprising administering a therapeutically effective amount of at least one compound of the invention to a subject in need thereof. In this embodiment, VEGF levels can be measured in a tumor not treated with the compounds of the present invention and the VEGF levels compared to the VEGF levels measured in a tumor treated with the compounds of the present invention, thereby showing that by treatment of tumors with the compounds of the present invention VEGF levels are reduced.

In yet another embodiment of the invention, methods for treating a solid tumor cancer are provided, comprising (a) measuring plasma VEGF levels, tumor VEGF levels, or both, and administering a therapeutically effective amount of at least one compound of the invention to a subject in need thereof. In an embodiment, VEGF concentration is measured to determine whether treatment with a compound of the present invention should be undertaken. In this aspect, treatment with a compound of the present invention is preferred and more effective as the VEGF levels increase.

In yet a further embodiment of the invention, methods for treating a solid tumor cancer are provided, comprising administering a therapeutically effective amount of at least one compound of the invention to a subject in need thereof, together with one or more additional cancer agents.

In preferred embodiments, the methods of the invention comprise administering a therapeutically effective amount of at least one compound of the invention, wherein the compound is an (S) isomer.

According to the methods of the invention, the compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "VEGF-inhibiting amount", "anti-angiogenic amount", and "therapeutically effective amount", as used herein, refer to an amount of a pharmaceutical agent to treat, ameliorate, or prevent the identified disease or condition, or to exhibit a detectable therapeutic or inhibitory affect. The affect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 μg/mL to approximately 100 μg/mL, preferably from approximately 5 μg/mL to approximately 50 μg/mL, more preferably from approximately 5 μg/mL to approximately 10 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDAM; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium steerages, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin, and even more preferably from 2.5% to 10% hydroxypropyl-β-cyclodextrin. The amount of solubility enhancer employed will depend on the amount of the compound of the present invention in the composition.

F. Combination Therapy

It is also possible to combine any compound of the present invention with one or more other active ingredients or agents useful in the treatment of cancer, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the VEGF-inhibiting and/or anti-angiogenesis activity of the compounds of the invention.

More specifically, for methods involving the treatment of cancer, agents known in the art to be useful for treating cancer are provided. Such agents include, but are not limited to, radiation therapy, agents that cause DNA damage, agents that reduce the concentration or effect of a growth factor, agents that inhibit angiogenesis, paclitaxel, fluorouracil, CPT-11, a tyrosine kinase inhibitor, a COX-2 inhibitor, thalidomide, gemcitabine, squalamine, endostatin, angiostatin, AE-941, lenalidomide, medi-522, 2-methoxyestradiol, carboxyamidotriazole, combretastatin A4 phosphate, SU6668, SU11248, BMS-275291, COL-3, cilengitide, IMC-1121B, vatalanib, LY317615, VEGF Trap, ZD6474, halofuginone, hydrobromide, celecoxib, interferon alpha, interleukin-12, and antibodies capable of binding VEGF or a VEGF receptor, such as bevacizumab. VEGF receptors include VEGF receptor 1, VEGF receptor 2, and VEGF receptor 3. In another embodiment, the compounds of the present invention are used in combination with an agent that blocks the activity of a VEGF receptor. In yet another embodiment, the compounds of the present invention can be used in combination with agents that can block the VEGF signaling pathway. Treatment only with a factor that can block VEGF signaling may cause an increase in VEGF concentration. In such a case, including a compound of the present invention in the treatment protocol can prevent the subsequent increase in VEGF levels. Similarly, use of the compounds of the present invention in combination with an antibody is highly preferred. Antibodies are relatively large and may not cross tight barriers, allowing secreted VEGF to remain in areas such as the perivascular space. Post-transcriptional control of VEGF expression can prevent the tumor from retaining as much VEGF in the perivascular space, in the extracellular matrix, or in other spaces and vessels that have a physical barrier to antibodies.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Using the schemes and procedures described above in Section B, one may prepare certain compounds of the invention as follows. Other preferred compounds of the invention, such as those in Table 5 below, may be similarly prepared.

Example 1A

Compounds of Formula I, Scheme I

Certain compounds of Formula I may be prepared according to Scheme I using free amine products/intermediates, or their salts prepared in accordance with Procedure I. By way of example, certain free amines (III), or their salts are prepared using Procedure I. Table 4 illustrates certain free amines (III) or their salts, Intermediates 1-11.

TABLE 4

| Intermediate | R - of Free Amine (III) | $R_1$ - of Free Amine (III) |
|---|---|---|
| 1 | Cl | 4-OMe |
| 2 | Cl | 2,3-difluoro |
| 3 | Cl | 4-Cl |
| 4 | Cl | 4-CN |
| 5 | Cl | 4-F |
| 6 | Cl | 4-iPr |
| 7 | Br | 4-Cl |
| 8 | Br | 4-Me |
| 9 | Br | 4-iPr |
| 10 | Br | 3-Cl |
| 11 | Br | 4-OMe |
| 12 | Cl | 4-(2-morpholine-4-yl-ethoxy) |

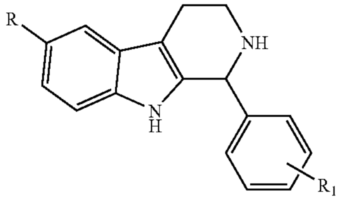

(III)

Intermediate-1:

This intermediate is prepared using Procedure-I with 5-chlorotryptamine.HCl (5.8 g, 25 mmol), p-anisaldehyde (6.13 mL, 50 mmol) and 0.1N sulfuric acid (60 mL) to give the title compound as an acid salt (6.1 g, 59%). ES-MS: 313 $(M+H)^+$. Alternatively, this intermediate is prepared using Procedure-1B with 5-chlorotryptamine.HCl (20 g, 86.5 mmol), p-anisaldehyde (15.9 mL, 130 mmol) and acetic acid (250 mL) to give the title compound as an acid salt (25.8 g, 79%). ES-MS: 313 $(M+H)^+$.

Intermediate-2:

This intermediate is prepared using Procedure-I with 5-chlorotryptamine.HCl (116 mg, 0.5 mmol), 2,3-difluoro benzaldehyde (109 μL, 1 mmol) and 0.1N sulfuric acid (2 mL) to give the title compound as an acid salt (158 mg, 75%). ES-MS: 319 $(M+H)^+$ Intermediate-3:

This intermediate is prepared using Procedure-I with 5-chlorotryptamine.HCl (462 mg, 2 mmol), 4-chloro benzaldehyde (562 mg, 4 mmol) and 0.1N sulfuric acid (8 mL) to give the title compound as an acid salt (825 mg, 99%). ES-MS: 317 $(M+H)^+$ Intermediate-4:

This intermediate is prepared using Procedure-I with 5-chlorotryptamine.HCl (462 mg, 2 mmol), 4-cyano benzaldehyde (525 mg, 4 mmol) and 0.1N sulfuric acid (8 mL) to give the title compound as an acid salt (810 mg, 100%). ES-MS: 308 $(M+H)^+$ Intermediate-5:

This intermediate is prepared using Procedure-I with 5-chlorotryptamine.HCl (374 mg, 1.5 mmol), 4-fluoro benzaldehyde (322 μL, 3 mmol) and 0.1N sulfuric acid (4 mL) to give the title compound as an acid salt (250 mg, 42%). ES-MS: 301 $(M+H)^+$ Intermediate-6:

This intermediate is prepared using Procedure-I with 5-chlorotryptamine.HCl (1.15 g, 5 mmol), 4-isopropyl benzaldehyde (1.516 mL, 10 mmol) and 0.1N sulfuric acid (12 mL) to give the title compound as an acid salt (628 mg, 30%). ES-MS: 325 $(M+H)^+$ Intermediate-7:

This intermediate is prepared using Procedure-I with 5-bromotryptamine.HCl (551 mg, 2 mmol), 4-chloro benzaldehyde (562 mg, 4 mmol) and 0.1N sulfuric acid (8 mL) to give the title compound as an acid salt (330 mg, 36%). ES-MS: 363 $(M+H)^+$ Intermediate-8:

This intermediate is prepared using Procedure-I with 5-bromotryptamine.HCl (551 mg, 2 mmol), p-tolualdehyde (471 μL, 4 mmol) and 0.1N sulfuric acid (8 mL) to give the title compound as hydrogen sulfate salt (257 mg, 29%). ES-MS: 341 $(M+H)^+$. Alternatively, this intermediate is prepared using Procedure-1B with 5-bromotryptamine.HCl (10 g, 36.3 mmol), p-tolualdehyde (6.41 mL, 54.5 mmol) and acetic acid (120 mL) to give the title compound as acetate salt (14.5 g, 100%). ES-MS: 341 $(M+H)^+$ Intermediate-9 (Compound 112):

This product/intermediate is prepared using Procedure-I with 5-bromotryptamine.HCl (551 mg, 2 mmol), 4-isopropyl benzaldehyde (606 μL, 4 mmol) and 0.1N sulfuric acid (8 mL) to give the title compound as hydrogen sulfate salt (329 mg, 35%). ES-MS: 369 $(M+H)^+$. Alternatively, this intermediate is prepared using Procedure-1B with 5-bromotryptamine.HCl (10 g, 36.3 mmol), 4-isopropyl benzaldehyde (8.24 mL, 54.5 mmol) and acetic acid (120 mL) to give the title compound as acetate salt (13 g, 77%). ES-MS: 369 $(M+H)^+$ Intermediate-10:

This intermediate is prepared using Procedure-I with 5-bromotryptamine.HCl (551 mg, 2 mmol), 3-chloro benzaldehyde (453 μL, 4 mmol) and 0.1N sulfuric acid (8 mL) to give the title compound as an acid salt (662 mg, 72%). ES-MS: 361 $(M+H)^+$ Intermediate-11:

This intermediate is prepared using Procedure-I with 5-bromotryptamine.HCl (551 mg, 2 mmol), p-anisaldehyde (491 μL, 4 mmol) and 0.1N sulfuric acid (8 mL) to give the title compound as an acid salt (611 mg, 67%). ES-MS: 357 $(M+H)^+$ Intermediate-12:

The 4-(2-Morpholin-4-yl-ethoxy)-benzaldehyde reaction intermediate is prepared by combining 4-hydroxybenzaldehyde (1.2 g, 10.0 mmol), 4-(2-chloroethyl)-morpholine hydrochloride (2.0 g, 11.0 mmol), potassium carbonate (4.1 g, 30.0 mmol), and potassium iodide (170 mg, 1 mmol) in 100 ml of acetone and heating to reflux with stirring. After all the 4-hydroxybenzaldehyde is consumed (48 hours by LC/MS), the solids are filtered and the solvent is removed in vacuo. The yield is 4.1 g.

Then Intermediate 12 is prepared in accordance with Procedure-IB. Thus, 5-Chlorotryptamine hydrochloride (231 mg, 1.0 mmol) is combined with 4-(2-Morpholin-4-yl-ethoxy)-benzaldehyde (565 mg, ~1.2 mmol) in 3 mL of glacial acetic acid. The suspension is heated to about 120° C. for 10 minutes with constant cooling and a max power of 300 W using the CEM Explorer microwave system. Acetonitrile (2 mL) is added to the cooled reaction mixture, and the solid is filtered and washed with 1 mL of acetonitrile to produce the acetic acid salt of Intermediate 12 (6-Chloro-1-[4-(2-morpholin-4-yl-ethoxy)-phenyl]-2,3,4,9-tetrahydro-1H-β-carboline) (179 mg, 34%).

Intermediates 1-12 may then be used to prepare compounds of the invention according to Procedures II through VII as follows.

Compound 2:

This product is prepared by Procedure-II using the Intermediate-1 (3 g, 9.6 mmol), ethyl chloroformate (1.37 mL, 14.4 mmol) and DIEA (2.5 mL, 14.4 mmol) in dichloromethane (70 mL) to give the title compound as white powder (1.56 g, 42%). ES-MS: 385 $(M+H)^+$.

Compound 4:

This product is prepared by Procedure-II using the Intermediate-7 (72 mg, 0.2 mmol), ethyl chloroformate (29 μL, 0.3 mmol) and DIEA (52 μL, 0.3 mmol) in dichloromethane (2 mL) to give the title compound as white powder (37 mg, 43%). ES-MS: 435 $(M+H)^+$.

Compound 5:

This product is prepared by the Procedure-II using the Intermediate-2 (50 mg, 0.16 mmol), ethyl chloroformate (23 μL, 0.24 mmol) and DIEA (42 μL, 0.24 mmol) in dichloromethane (2 mL) to give the title compound as white powder (25 mg, 41%). ES-MS: 391 $(M+H)^+$.

Compound 7:

This product is prepared by the Procedure-II using the Intermediate-9 (74 mg, 0.2 mmol), ethyl chloroformate (29 μL, 0.3 mmol) and DIEA (52 μL, 0.3 mmol) in dichloromethane (2 mL) to give the title compound as white powder (34 mg, 38%). ES-MS: 441 $(M+H)^+$.

Compound 8:

This product is prepared by the Procedure-II using the Intermediate-8 (72 mg, 0.2 mmol), ethyl chloroformate (29 μL, 0.3 mmol) and DIEA (52 μL, 0.3 mmol) in dichloromethane (2 mL) to give the title compound as white powder (39 mg, 47%). ES-MS: 413 $(M+H)^+$.

Compound 10:

This product is prepared by the Procedure-II using the Intermediate-I acetate (10.5 g, 28.2 mmol), 4-chlorophenyl chloroformate (4.74 mL, 33.8 mmol) and DIEA (9.8 mL, 56.4 mmol) in dichloromethane (300 mL) to give the title compound as white powder (10.2 g, 78%). ES-MS: 467 $(M+H)^+$.

Compound 11:

This product is prepared by the Procedure-II using the Intermediate-3 (63 mg, 0.2 mmol), ethyl chloroformate (29

μL, 0.3 mmol) and DIEA (52 μL, 0.3 mmol) in dichloromethane (2 mL) to give the title compound as white powder (31 mg, 40%). ES-MS: 389 $(M+H)^+$.

Compound 12:

This product is prepared by the Procedure-II using the Intermediate-4 (31 mg, 0.1 mmol), 2-chloroethyl chloroformate (16 μL, 0.15 mmol) and DIEA (26 μL, 0.15 mmol) in dichloromethane (2 mL) to give the title compound as white powder (22 mg, 53%). ES-MS: 414 $(M+H)^+$.

Compound 17:

This product is prepared by the Procedure-II using the Intermediate-I (47 mg, 0.15 mmol), 4-methylphenyl chloroformate (33 μL, 0.23 mmol) and DIEA (39 μL, 0.23 mmol) in dichloromethane (2 mL) to give the title compound as white powder (34 mg, 51%). ES-MS: 447 $(M+H)^+$.

Compound 23:

This product is prepared by the Procedure-II using the Intermediate-5 (30 mg, 0.1 mmol), ethyl chloroformate (14 μL, 0.15 mmol) and DIEA (26 μL, 0.15 mmol) in dichloromethane (2 mL) to give the title compound as white powder (21 mg, 56%). ES-MS: 373 $(M+H)^+$.

Compound 25:

This product is prepared by the Procedure-VII using the Intermediate-9 (74 mg, 0.2 mmol), 2-bromopyrimidine (48 mg, 0.3 mmol) and triethylamine (42 μL, 0.3 mmol) in DMF (2 mL) to give the title compound (42 mg, 47%). ES-MS: 447 $(M+H)^+$.

Compound 102:

This product is prepared by the Procedure-IIIb using the Intermediate-9 (74 mg, 0.2 mmol), acetic anhydride (47 μL, 0.5 mmol) and pyridine (41 μL, 0.5 mmol) in dichloromethane (2 mL) to give the title compound as white powder (31 mg, 38%). ES-MS: 411 $(M+H)^+$.

Compound 140:

This product is prepared by the Procedure-IV using the Intermediate-10 (72 mg, 0.2 mmol), cyclohexyl isocyanate (26 μL, 0.2 mmol) and DIEA (37 μL, 0.21 mmol) in dichloromethane (2 mL) to give the title compound as white powder (51 mg, 53%). ES-MS: 486 $(M+H)^+$.

Compound 166:

This product is prepared by the Procedure-IIIa using its free amine intermediate (141 mg, 0.5 mmol), Boc-L-Alanine (105 mg, 0.6 mmol), DIC (94 μL, 0.6 mmol), DIEA (105 μL, 0.6 mmol) and dichloromethane (4 mL) to give the title compound (105 mg, 46%). ES-MS: 420 $(M+H)^+$.

Compound 225:

This product is prepared by the Procedure-VI using its free amine intermediate (78 mg, 0.2 mmol), methyl sulfonylchloride (16 μL, 0.2 mmol) and DIEA (37 μL, 0.21 mmol) and dichloromethane (2 mL) to give the title compound (32 mg, 34%). ES-MS: 461 $(M+H)^+$.

Compound 242:

This product is prepared by the Procedure-V using its free amine intermediate (59 mg, 0.2 mmol), cyclohexyl isothiocyanate (29 μL, 0.2 mmol), DIEA (35 μL, 0.2 mmol) and dichloromethane (4 mL) to give the title compound (52 mg, 60%). ES-MS: 438 $(M+H)^+$.

Compound 279:

This product is prepared by generating Intermediate 12 (6-Chloro-1-[4-(2-morpholin-4-yl-ethoxy)-phenyl]-2,3,4,9-tetrahydro-1H-β-carboline) using Procedure-I. Intermediate 12 is then used to generate Compound 279 (6-Chloro-1-[4-(2-morpholin-4-yl-ethoxy)-phenyl]-1,3,4,9-tetrahydro-b-carboline-2-carboxylic acid ethyl ester) using Procedure-II.

In accordance with Procedure-II, Intermediate 12 (82 mg, 0.20 mmol), ethyl chloroformate (24 mg, 21 μL, 0.22 mmol), and diisopropylethylamine (175 μL, 1.00 mmol) are dissolved in methylene chloride (2 mL) and stirred at room temperature for 15 minutes to form Compound 279. The solvent is removed under a stream of nitrogen. The crude mixture is purified by preparative reversed phase HPLC on a C-18 column using a gradient of acetonitrile in water buffered with 0.2% trifluoroacetic acid (TFA). The TFA salt of Compound 279 (3.7 mg, 3%) is isolated as a yellow solid. The same procedure may be applied for other carbamate formation reactions according to Procedure-II.

Compound 320:

This product/intermediate is prepared using Procedure-I with 5-benzyloxy tryptamine.HCl (100 mg, 0.33 mmol), pyridine-3-carboxaldehyde (62 μL, 0.66 mmol) and 0.1N sulfuric acid (2 mL) to give the title compound as dihydrogen sulfate salt (64 mg, 55%). ES-MS: 356 $(M+H)^+$ Compound 329:

This product is prepared by the Procedure-VII using the Intermediate-11 (71 mg, 0.2 mmol), 2-bromopyrimidine (48 mg, 0.3 mmol) and triethylamine (42 μL, 0.3 mmol) in DMF (2 mL) to give the title compound (41 mg, 49%). ES-MS: 434 $(M+H)^+$.

Compound 330:

This product is prepared by the Procedure-II using the Intermediate-6 (65 mg, 0.2 mmol), 2-fluoroethyl chloroformate (38 μL, 0.3 mmol) and DIEA (70 μL, 0.4 mmol) in dichloromethane (2 mL) to give the title compound as white powder (34 mg, 41%). ES-MS: 415 $(M+H)^+$.

Compound 332:

This product is prepared by the Procedure-II using the Intermediate-7 (36 mg, 0.1 mmol), 4-methoxyphenyl chloroformate (22 μL, 0.15 mmol) and DIEA (26 μL, 0.15 mmol) in dichloromethane (2 mL) to give the title compound as white powder (41 mg, 81%). ES-MS: 511 $(M+H)^+$.

Example 1B

Certain Starting Materials, Scheme Ia

Scheme Ia can be used when in conjunction with Scheme I (above) to generate starting materials when $R_2$ is a —$CH_2$-furanyl group, as follows.

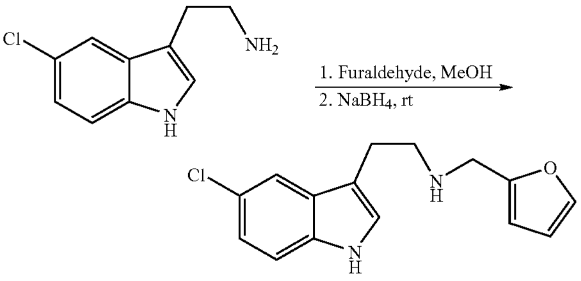

2-furaldehyde (0.05 mL, 1.1 eq) is added to a solution of 5-chlorotryptamine (114 mg, 0.586 mmol) in 2 mL of MeOH. The reaction mixture is stirred at room temperature for about 1 hour. $NaBH_4$ (110 mg, 5 eq) is added slowly. The reaction mixture is stirred at room temperature for about 30 min. MeOH is evaporated and the residue is partitioned between water and methylene chloride. The organic layer is separated and dried over $K_2CO_3$. The collected organic layer is concentrated to give 134.9 mg of viscous oil (84%).

Example 1C

Compounds of Formula I, Scheme Ib

Alternatively, certain compounds of Formula I may be prepared according to Scheme Ib as follows.

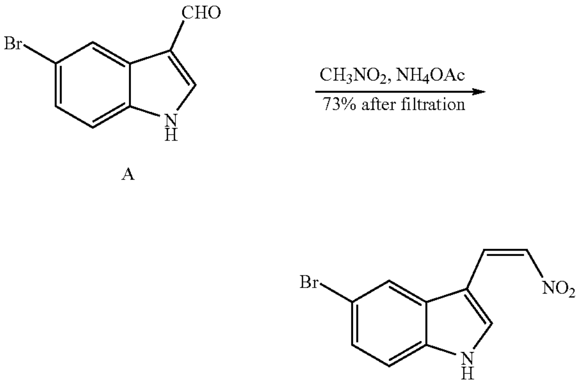

A

B

A suspension of reaction material A (8.05 g, 35.9 mmol) and $CH_3COONH_4$ (4.15 g, 1.5 eq) in 60 mL of $CH_3NO_2$ is refluxed in oil bath at about 110° C. After about 30 minutes, the reaction mixture is cooled with ice-bath. The precipitated solid is filtered and washed with water (3×100 mL), followed by hexane (2×50 mL) to give crude indole product B. The collected solid is dried under vacuum at about 40° C. for about 30 min to give 6.97 g of brown solid (73%).

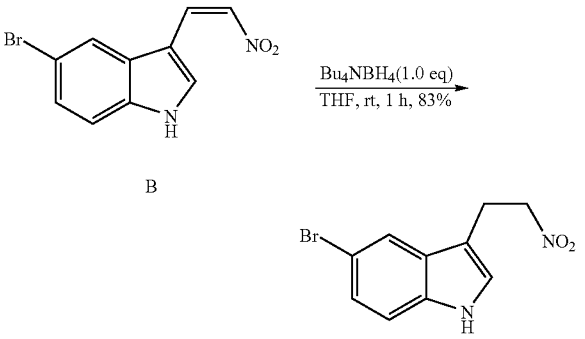

B

C

A solution of indole product B (12.32 g, 46.1 mmol) in THF (130 mL) is then treated with a solution of tetrabutylammonium borohydride (11.9 g, 1 eq) in 75 mL of THF slowly for about 60 minutes at about −5° C. The reaction is stirred at room temperature for about 1 hour and diluted with dichloromethane (200 mL). The organic layer is washed with water twice and brine. The combined organic layers are dried and evaporated under vacuum. The residue is purified on silica gel to give 10.28 g of solid C (83%).

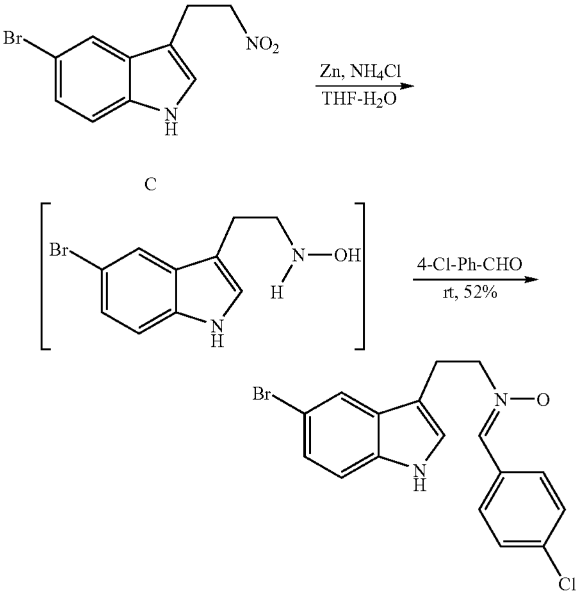

C

D

Ammonium chloride (9.9 mL of aqueous solution (100 mg/mL), 2 eq) and Zn (725 mg, 1.2 eq) are then added to a solution of indole product C (2.49 g, 9.24 mmol) in 161 mL of THF. The reaction mixture is stirred at room temperature for about 10 min and Zn (725 mg, 1.2 eq) is then added. After about 30 min, additional Zn (967 mg, 1.6 eq) is added and stirred for about 2 hours, followed by the addition of further Zn (845 mg, 1.4 eq). After stirring at room temperature for about 15 min, Zn is filtered off and the residue is concentrated and dissolved in THF. The resulting solution is then treated with p-chlorobenzaldehyde (0.7 eq) and stirred at room temperature for about 15 hours. The reaction mixture is concentrated under vacuum and purified on silica gel to give 953.5 mg of the desired nitrone product D.

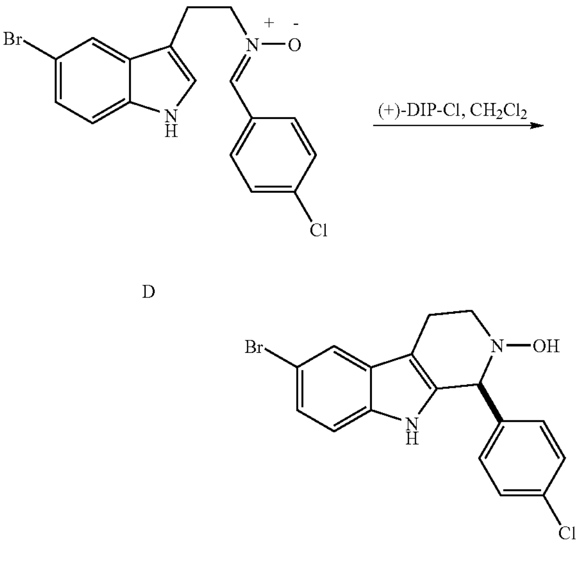

D

E (+)-DIP-Cl (6.93 mL, 2 eq, 85.8 mg/mL in $CH_2Cl_2$) is then added to a solution of nitrone product D (350 mg, 0.93 mmol)

in 60 mL of dichloromethane. The reaction mixture is stirred at about −78° C. for about 10 days and quenched with a mixture of 10% $NaHCO_3$ (7 mL) and 10 mL of water. The aqueous layer is extracted with dichloromethane three times. Combined organic layers are concentrated and purified on silica gel to give the desired hydroxylamine product E (>98% ee).

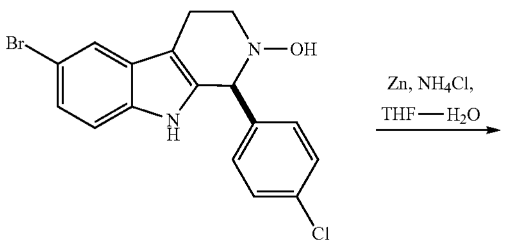

E

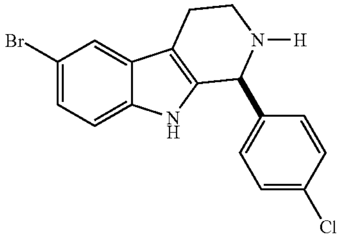

F

Water (11.5 mL), $NH_4Cl$ (2.5 mL, 5 eq) and Zn (908 mg, 15 eq) are then added to a solution of hydroxylamine product E (0.927 mmol) in THF (28 mL). The reaction mixture is stirred at room temperature for about 1 day. Additional THF (10 mL), $NH_4Cl$ (5 mL, 10 eq) and Zn (1.8 g, 30 eq) are then added and stirred for about another 21 hours. Again, THF (10 mL), NH4Cl (5 mL, 10 eq) and Zn (1.8 g, 30 eq) are added and stirred for about another 20 hours. The reaction mixture is then filtered through celite and washed with MC. The collected dichloromethane layer is washed with water and brine. The organic layer is dried and concentrated to give a boron complex of beta-carboline. This product is dissolved in 20 mL of THF. This solution is loaded into prepacked cation exchange resin (preconditioned with MeOH and THF) and washed with THF. The combined THF solution is concentrated to give 390 mg of free amine. The solid is then washed with ether and hexane consecutively to yield 130 mg of the enantiomerically pure compound F.

Example 1D

Compounds of Formula I, Scheme II

Compounds of Formula I-h may be prepared according to Scheme II as follows.

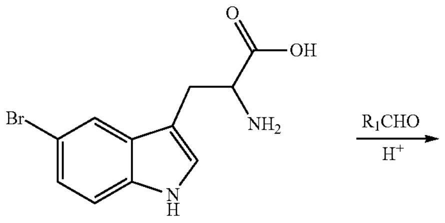

A

-continued

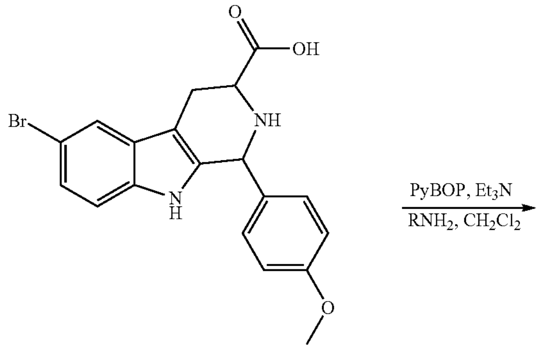

B

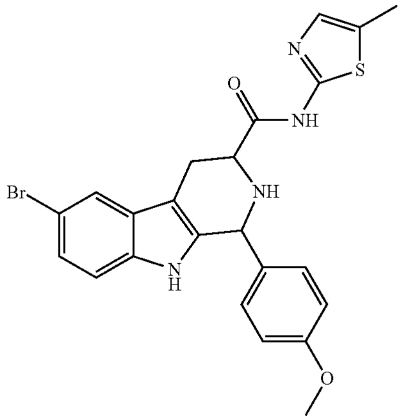

C p-anisaldehyde (2.16 g, 15.9 mmol, 1.93 mL) is added to a suspension of 5-Bromotryptophan A (3 g, 10.6 mmol) in 100 mL of Acetic acid at room temperature. The reaction mixture is then heated to reflux at about 125° C. in silicon oil bath and maintained at that temperature for about 3 hours 20 minutes. The resultant solution is concentrated under vacuum. The residue is triturated with dichloromethane, diethyl ether and hexane to yield a powdery brown solid. The acetic salts of the intermediate product B is collected and washed with hexane three times.

The intermediate product B is suspended (70 mg, 0.174 mmol) in 2 mL of dichloromethane, and triethylamine (52.8 mg, 0.522 mmol), 5-methyl-2-aminothiazole (37.6 mg, 0.26 mmol) and PyBOP (135.8 mg, 0.26 mmol) is added to the suspension. The reaction mixture is stirred at room temperature for about 6 hour and quenched with sat. $NaHCO_3$ solution. The aqueous layer is extracted with dichloromethane. The combined organic layers are dried over $K_2CO_3$ and concentrated. Purification on silica gel with 40% ethyl acetate in hexane yields 8.1 mg of the desired amide C. LCMS $[MH^+]$ 498, Rt=2.54.

Example 1E

Compounds of Formula I, Scheme III

Compounds of Formula I-i may be prepared according to Scheme III as follows.

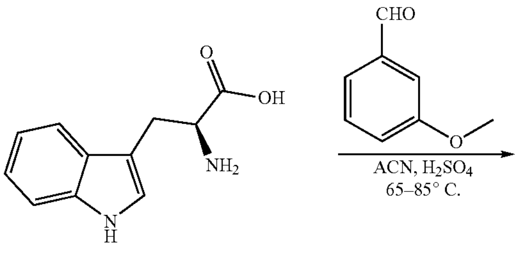

A

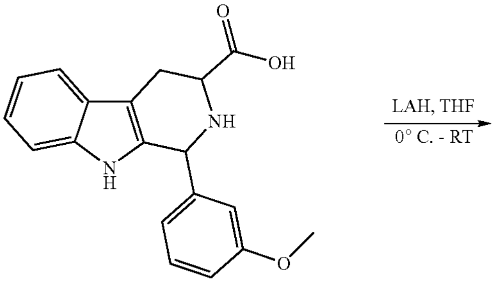

B

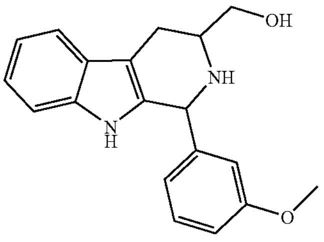

C

Tryptophan A (1.0 g, 5.0 mmol) and 3-methoxybenzaldehyde (670 μL, 5.5 mmol) are suspended/dissolved in acetonitrile (100 mL) and concentrated sulfuric acid (100 μL) is added. The reaction is heated to reflux until all the aldehyde was consumed (overnight). The solvent was removed in vacuo and the residue was dissolved in 5 mL of ethanol. The product was precipitated out with ether, filtered, and washed with 10 mL of ether. The desired β-carboline product/intermediate B (1-(3-Methoxy-phenyl)-2,3,4,9-tetrahydro-1H-β-carboline-3-carboxylic acid) is isolated as a beige solid (1.2 g, 76%). LC/MS RT=2.33 min. M/Z+323, 100%.

The β-carboline product/intermediate B (200 mg, 0.62 mmol) is then dissolved in 5 mL of dry THF and cooled to about 0° C. Lithium aluminum hydride (LAH) solution (1.2 mL, 1.0M in ether, 1.2 mmol) is added to the cooled reaction mixture under nitrogen. After the addition is complete (about 10 minutes), the reaction is allowed to warm to room temperature for about 4 hours. The reaction mixture is then cooled back to 0° C., and saturated sodium sulfate solution (750 μL) is added and the mixture stirred for about 5 minutes at 0° C. The reaction mixture is then filtered and washed with THF (100 mL). The solvent is removed in vacuo, and the crude product purified by preparative HPLC. The product C ([1-(3-Methoxy-phenyl)-2,3,4,9-tetrahydro-1H-b-carbolin-3-yl]-methanol) is isolated as a white solid (106 mg, 55%). LC/MS RT=2.25 min. M/Z+309, 100%.

Example 1F

Chemical Resolution of Compounds of the Invention

Compounds of the invention may optionally be chemical resolved to enantiomerically pure compositions, preferably enantiomerically pure (S) isomer compositions as follows.

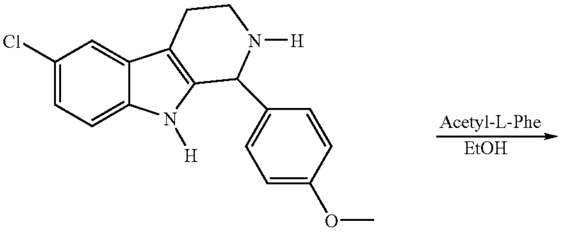

A

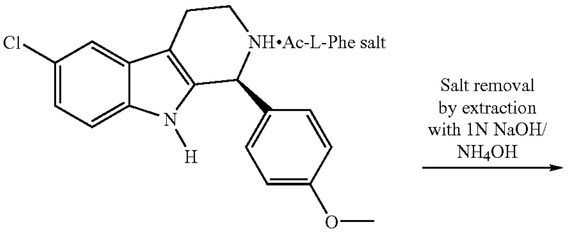

B

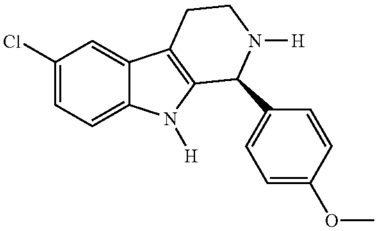

S-isomer
C

The racemic amine A (18.21 g, 58.2 mmol) is mixed with N-acetyl-L-phenylalanine (12.05 g, 58.2 mmol) in EtOH (1.28 L) and refluxed to get a clear solution. The solution is then allowed to cool to room temperature. After overnight standing, the precipitated solid is filtered and washed with EtOH (200 mL) to give the salt B (16.4 g). The salt B is taken in EtOAc (500 mL) and washed with aqueous 1N NaOH (300 mL×2) or $NH_4OH$ (200 mL×2), dried and evaporated to give the S-isomer of the free amine C (7.4 g). The R-isomer is prepared by similar procedure using N-acetyl-D-phenylalanine.

Example 1G

Further Exemplary Compounds of the Invention

By way of further non-limiting example, the following compounds (Table 5) may be prepared by similar methodology to that described above, as will be recognized by one of skill in the art.

TABLE 5
| Compound | NMR | Mass Spec (LCMS) | Reten. Time (min) |
|---|---|---|---|
| 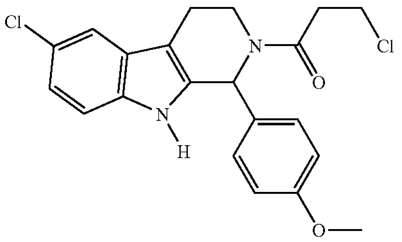 367 | (CDCl3, 400 MHz), δ 8.16 (s, 1H), 7.48 (s, 1H), 7.22 (d, J=8.8 Hz, 1H), 7.19 (d, J=8.8 Hz, 2H), 7.13 (d, J=8.8 Hz, 1H), 6.94 (s, 1H), 6.80 (d, J=8.8 Hz, 2H), 3.92-3.91 (m, 1H), 3.86 (t, J=7.2 Hz, 2H), 3.77 (s, 3H), 3.46-3.39 (m, 1H), 3.11-3.09 (m, 1H), 2.91-2.83 (m, 3H) | 402.8 | 4.37 |
| 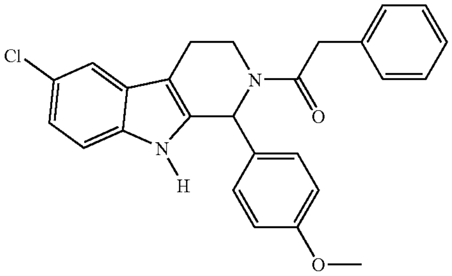 368 | (CDCl3, 400 MHz), δ 8.29 (s, 1H), 7.47-7.09 (m, 10H), 6.98 (s, 1H), 6.77 (d, J=8.8 Hz, 2H), 3.93 (dd, J=13.6 Hz and 4.8 Hz, 1H), 3.82-3.80 (m, 2H), 3.77 (s, 3H), 3.38-3.30 (m, 1H), 2.69-2.65 (m, 1H), 2.53-2.45 (m, 1H) | 430.9 | 4.79 |
| 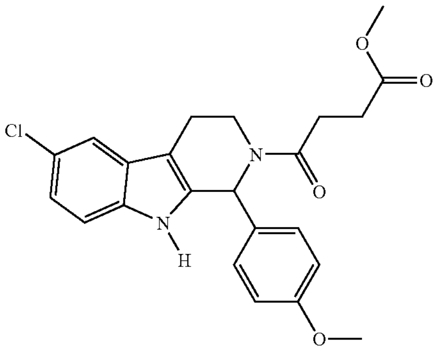 369 | (CDCl3, 400 MHz), δ 8.21 (s, 1H), 7.46 (s, 1H), 7.22 (d, J=8.4 Hz, 1H), 7.17 (d, J=8.4 Hz, 2H), 7.12 (dd, J=8.4 Hz and 2.0 Hz, 1H), 6.92 (s, 1H), 6.77 (d, J=8.4 Hz, 2H), 3.94 (dd, J=13.2 Hz and 4.4 Hz, 1H), 3.76 (s, 3H), 3.65 (s, 3H), 3.43-3.35 (m, 1H), 2.87-2.62 (m, 6H) | 427.0 | 4.06 |
| 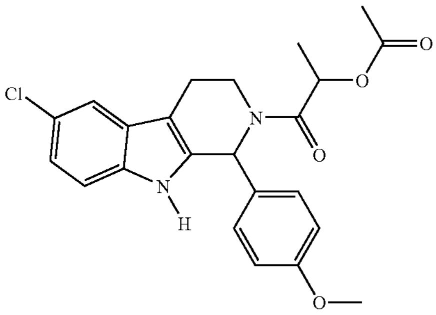 370 | (CDCl3, 400 MHz), δ 8.23, 8.12 (s, 1H), 7.48, 7.42 (d, J=1.6 Hz, 1.2 Hz, 1H), 7.22-7.10 (m, 4H), 6.94, 6.88 (s, 1H), 6.79 (d, J=8.8 Hz, 2H), 5.48-5.45 (m, 1H), 3.96-3.80 (m, 1H), 3.77 (s, 3H), 3.47-3.36 (m, 1H), 3.08-2.77 (m, 2H), 2.14, 2.09 (s, 3H), 1.48, 1.41 (d, J=6.8 Hz, 6.4 Hz, 3H) | 427.0 | 3.99 |

TABLE 5-continued
| Compound | NMR | Mass Spec (LCMS) | Reten. Time (min) |
|---|---|---|---|
| 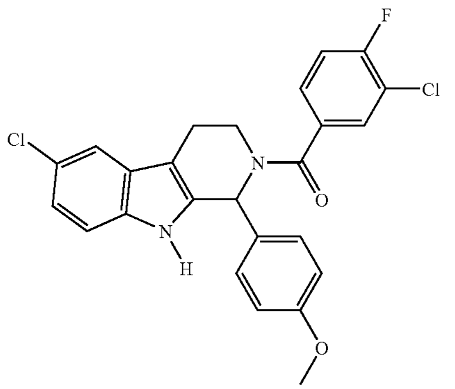 371 | (CDCl3, 400 MHz), δ 7.87 (s, 1H), 7.51 (s, 1H), 7.47 (dd, J=6.8 Hz and 1.6 Hz, 1H), 7.30-7.15 (m, 6H), 6.98 (b, 1H), 6.76 (d, J=8.8 Hz, 2H), 3.80 (s, 3H), 3.77-3.74 (m, 1H), 3.49-3.39 (m, 1H), 2.93-2.82 (m, 2H) | 469.0 | 5.27 |
| 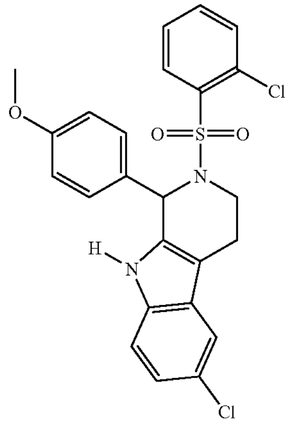 372 | (CDCl3, 400 MHz), δ 8.07 (dd, J=7.6 Hz and 1.2 Hz, 1H), 7.74 (s, 1H), 7.45-7.32 (m, 4H), 7.18 (d, J=8.4 Hz, 1H), 7.12 (dd, J=8.8 Hz and 2.0 Hz, 1H), 7.07 (d, J=8.4 Hz, 2H), 6.76 (d, J=8.8 Hz, 2H), 6.35 (s, 1H), 3.97 (dd, J=14.8 Hz and 5.2 Hz, 1H), 3.77 (s, 3H), 3.49-3.41 (m, 1H), 2.67 (dd, J=15.6 Hz and 3.2 Hz, 1H), 2.57-2.53 (m, 1H) | 486.9 | 4.96 |
| 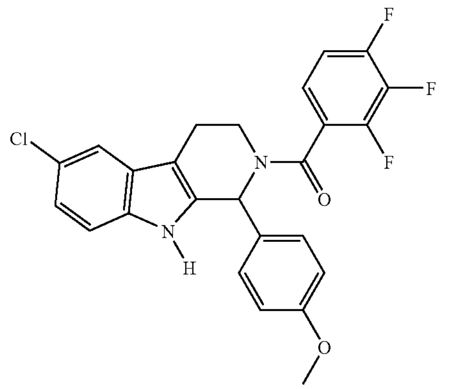 373 | (CDCl3, 400 MHz), δ 7.95 (s, 1H), 7.48 (s, 1H), 7.30 (d, J=8.4 Hz, 2H), 7.23 (d, J=8.8 Hz, 1H), 7.16 (dd, J=8.8 Hz and 1.6 Hz, 1H), 7.05 (b, 3H), 6.86 (d, J=8.4 Hz, 2H), 3.80 (s, 3H), 3.61 (dd, J=13.6 Hz and 5.2 Hz, 1H), 3.52-3.44 (m, 1H), 2.91-2.88 (m, 1H), 2.78 (dd, J=15.2 Hz and 3.2 Hz, 1H) | 470.8 | 5.01 |

TABLE 5-continued
| Compound | NMR | Mass Spec (LCMS) | Reten. Time (min) |
|---|---|---|---|
| 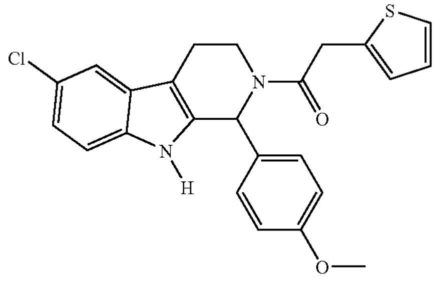 374 | (CDCl3, 400 MHz), δ 8.09 (s, 1H), 7.45 (s, 1H), 7.21-7.17 (m, 4H), 7.12 (d, J=8.8 Hz, 1H), 6.98 (s, 1H), 6.91 (d, J=4 Hz, 1H), 6.80 (s, 1H), 6.79 (d, J=8.4 Hz, 2H), 3.99 (s, 2H), 3.96 (d, J=4.4 Hz, 1H), 3.77 (s, 3H), 3.43-3.38 (m, 1H), 2.77-2.63 (m, 2H) | 436.9 | 4.66 |
| 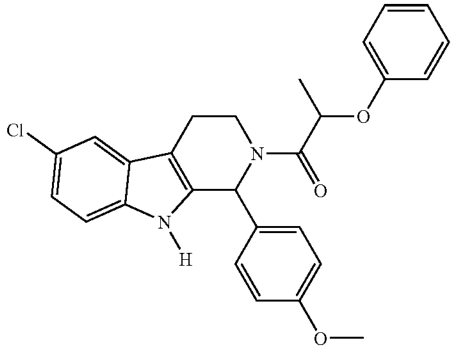 375 | (CDCl3, 400 MHz), δ 8.19, 8.16 (s, 1H), 7.48, 8.42 (s, 1H), 7.24-7.09 (m, 6H), 6.94 (t, J=7.8 Hz, 2H), 6.85 (t, J=8.2 Hz, 2H), 6.77 (d, J=8.4 Hz, 1H), 6.72 (d, J=8.4 Hz, 1H), 5.09-4.98 (m, 1H), 4.39-4.17 (m, 1H), 3.77, 3.75 (s, 3H), 3.41-3.28 (m, 1H), 3.02-2.65 (m, 2H), 1.61-1.59 (m, 3H) | 461 | 4.92 |
| 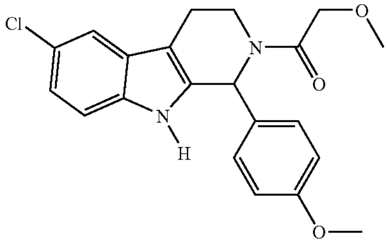 376 | (CDCl3, 400 MHz), δ 8.39 (s, 1H), 7.48 (s, 1H), 7.23 (d, J=8.4 Hz, 1H), 7.19 (d, J=8.4 Hz, 2H), 7.13 (dd, J=8.8 Hz and 1.6 Hz, 1H), 6.89 (s, 1H), 6.77 (d, J=8.4 Hz, 2H), 4.17 (q, J=12.8 Hz, 2H), 3.88 (d, J=10 Hz, 1H), 3.75 (s, 3H), 3.41 (s, 3H), 3.38-3.34 (m, 1H), 2.95-2.81 (m, 2H) | 385 | 3.79 |
| 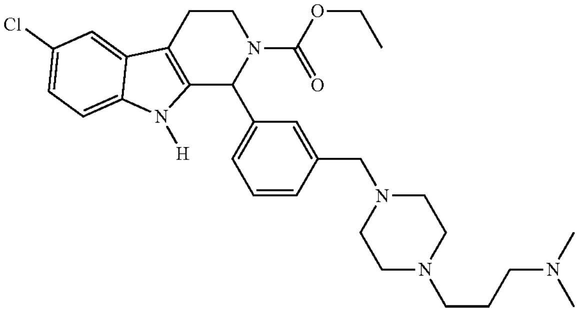 389 | (CD3OD, 400 MHz), δ 7.48-7.46 (m, 4H), 7.35 (b, 1H), 7.23 (d, J=8.8 Hz, 1H), 7.07 (dd, J=8.8 Hz and 2.0 Hz, 1H), 6.46 (b, 1H), 4.35-4.14 (m, 5H), 3.52-3.47 (m, 2H), 3.22-3.19 (m, 7H), 2.98-2.93 (m, 3H), 2.89 (s, 6H), 2.67-2.63 (m, 5H), 2.06-1.96 (m, 2H), 1.31 (t, J=7.2 Hz, 3H) | 538.3 | 4.29 |

TABLE 5-continued

| Compound | NMR | Mass Spec (LCMS) | Reten. Time (min) |
|---|---|---|---|
| 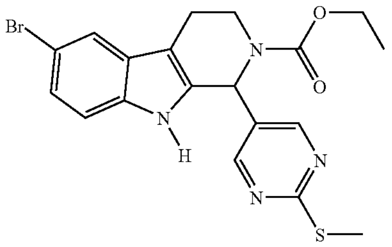 393 | (DMSO, 400 MHz), δ 11.00 (s, 1H), 8.47 (s, 2H), 7.67 (s, 1H), 7.26 (d, J=8.4 Hz, 1H), 7.19 (dd, J=8.8 Hz and 2.0 Hz, 1H), 6.26 (b, 1H), 4.25 (b, 1H), 4.11 (t, J=6.8 Hz, 2H), 3.22-3.17 (m, 1H), 2.86-2.81 (m, 1H), 2.77-2.66 (m, 1H), 2.50 (b, 3H), 1.21 (t, J=6.8 Hz, 3H) | 447.1 | 6.55 |
| 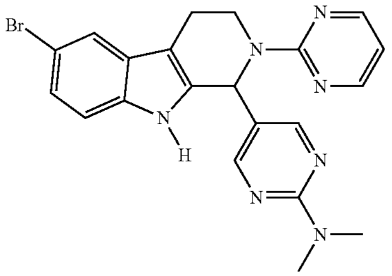 394 | (CD3OD, 400 MHz), δ 8.43-8.41 (m, 4H), 7.63 (d, J=1.2 Hz, 1H), 7.22 (d, J=8.8 Hz, 1H), 7.19 (dd, J=8.4 Hz and 1.6 Hz, 1H), 7.04 (s, 1H), 6.67 (t, J=4.8 Hz, 1H), 5.01 (dd, J=14.0 Hz and 3.6 Hz, 1H), 3.29-3.26 (m, 1H), 3.21 (s, 6H), 2.91-2.86 (m, 2H) | 450.1 | 5.48 |
| 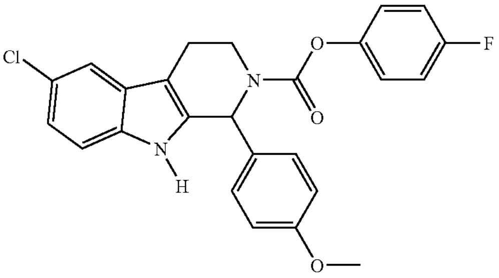 410 | (DMSO, 400 MHz), δ 11.15, 11.05 (b, 1H), 7.53 (d, J=1.6 Hz, 1H), 7.29 (d, J=8.8 Hz, 1H), 7.20-7.18 (m, 6H), 7.06 (dd, J=8.8 Hz and 2 Hz, 1H), 6.93 (d, J=7.2 Hz, 2H), 6.45-6.37 (m, 1H), 4.30 (b, 1H), 3.72 (s, 3H), 3.18 (b, 1H), 2.82 (b, 2H) | 451.3 | 3.99 |
| 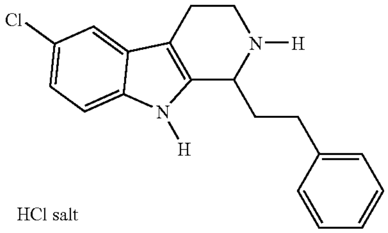 HCl salt 416 | (CD3OD, 400 MHz), δ 10.98 (b, 1H), 7.49 (d, J=2.0 Hz, 1H), 7.34-7.30 (m, 5H), 7.25-7.21 (m, 1H), 7.13 (dd, J=8.8 Hz and 2.0 Hz, 1H), 4.81-4.79 (m, 1H), 3.82-3.76 (m, 1H), 3.54-3.49 (m, 1H), 3.11-3.07 (m, 2H), 2.91-2.87 (m, 2H), 2.59-2.55 (m, 1H), 2.24-2.20 (m, 1H) | 311.1 | 4.39 |
| 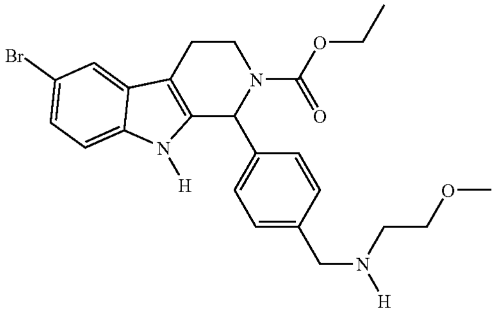 420 | (CD3OD, 400 MHz), δ 7.61 (s, 1H), 7.46 (d, J=8.0 Hz, 2H), 7.38 (d, J=8.0 Hz, 2H), 7.19 (s, 2H), 6.47 (s, 1H), 4.32-4.19 (m, 5H), 3.62 (t, J=3.9 Hz, 2H), 3.42 (s, 1H), 3.19-3.10 (m, 3H), 2.29-2.76 (m, 2H), 1.30 (s, 3H) | 486.6 | 3.45 |

TABLE 5-continued
| Compound | NMR | Mass Spec (LCMS) | Reten. Time (min) |
|---|---|---|---|
| 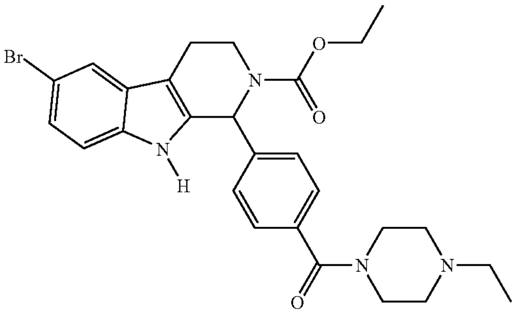 425 | (CD3OD, 400 MHz), δ 7.63 (s, 1H), 7.49 (d, J=8.4 Hz, 2H), 7.42 (d, J=8.4 Hz, 2H), 7.19 (s, 2H), 6.49 (b, 1H), 4.34-4.19 (m, 4H), 3.60 (b, 4H), 3.29-3.17 (m, 6H), 2.89-2.75 (m, 2H), 1.36 (t, J=7.2 Hz, 3H), 1.30 (b, 3H) | 539.2 | 3.11 |
| 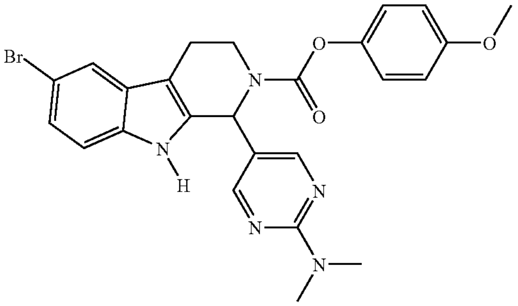 431 | (CDCl3, 400 MHz), δ 8.56 (b, 1H), 8.40 (b, 2H), 7.68 (s, 1H), 7.28 (d, J=2.0 Hz, 1H), 7.14 (d, J=8.4 Hz, 1H), 7.00 (d, J=9.2 Hz, 2H), 6.80 (d, J=8.4 Hz, 2H), 6.48-6.38 (m, 1H), 4.55-4.52 (m, 1H), 3.81-3.74 (m, 4H), 3.24 (s, 6H), 3.00-2.91 (m, 1H), 2.88-2.84 (m, 1H) | 522.2 | 5.05 |
| 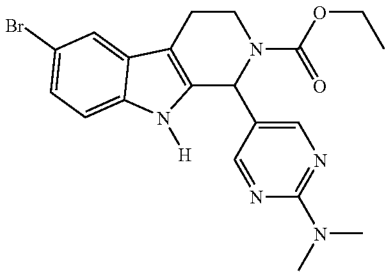 435 | (DMSO, 400 MHz), δ 11.00 (s, 1H), 8.14 (s, 2H), 7.64 (s, 1H), 7.23 (d, J=8.4 Hz, 1H), 7.18 (d, J=8.8 Hz, 1H), 6.14 (s, 1H), 4.23 (b, 1H), 4.11-4.08 (m, 2H), 3.14-3.10 (m, 1H), 3.08 (s, 6H), 2.81-2.77 (m, 1H), 2.70-2.66 (m, 1H), 1.21 (t, J=6.8 Hz, 3H) | 444.3 | 3.95 |
| 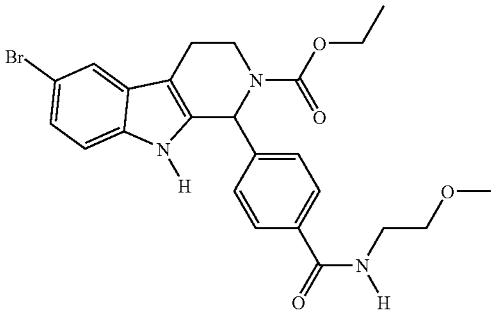 438 | (CD3OD, 400 MHz), δ 7.79 (d, J=8.4 Hz, 2H), 7.63 (s, 1H), 7.37 (d, J=8.4 Hz, 2H), 7.20 (s, 2H), 6.51 (b, 1H), 4.32-4.22 (m, 3H), 3.54 (s, 3H), 3.36 (s, 2H), 3.30 (s, 2H), 3.21-3.11 (m, 1H), 2.90-2.77 (m, 2H), 1.32 (s, 3H) | 500.1 | 4.35 |

TABLE 5-continued
| Compound | NMR | Mass Spec (LCMS) | Reten. Time (min) |
|---|---|---|---|
| 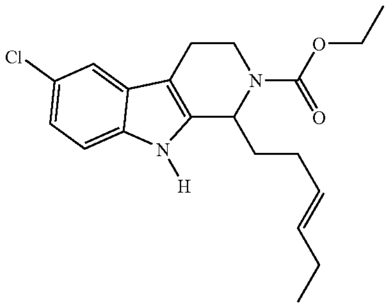 439 | (CDCl3, 400 MHz), δ 7.98, 7.81 (s, 1H), 7.42 (s, 1H), 7.21 (d, J=8.4 Hz, 1H), 7.11 (d, J=8.4 Hz, 1H), 5.40-5.23 (m, 3H), 4.55-4.35 (m, 1H), 4.20-4.11 (m, 2H), 3.24-3.13 (m, 1H), 2.79-2.63 (m, 2H), 2.22 (d, J=6.8 Hz, 2H), 2.08 (b, 2H), 1.89-1.81 (m, 2H), 1.30 (b, 3H), 0.97 (b, 3H) | 361.2 | 5.95 |
| 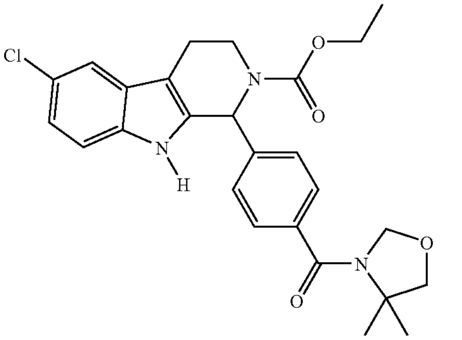 441 | (CD3OD, 400 MHz), δ 7.47 (d, J=1.6 Hz, 1H), 7.43 (d, J=7.6 Hz, 2H), 7.37 (d, J=8.0 Hz, 2H), 7.24 (d, J=8.8 Hz, 1H), 7.06 (dd, J=8.4 Hz and 1.6 Hz, 1H), 6.49 (b, 1H), 4.35-4.21 (m, 3H), 3.83 (s, 4H), 3.19-3.10 (m, 1H), 2.90-2.79 (m, 2H), 1.57 (b, 6H), 1.32 (s, 3H) | 482.1 | 5.11 |
| 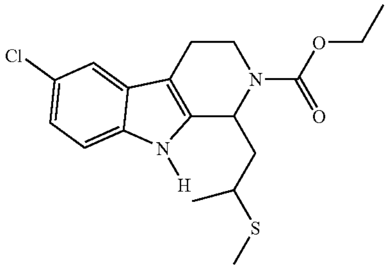 442 | (CDCl3, 400 MHz), δ 8.48-8.09 (m, 1H), 7.44-7.42 (m, 1H), 7.24 (t, J=9 Hz, 1H), 7.11-7.09 (m, 1H), 5.59-5.40 (m, 1H), 4.54-4.34 (m, 1H), 4.21-4.18 (m, 2H), 3.23-3.13 (m, 1H), 2.87-2.81 (m, 2H), 2.76-263 (m, 1H), 2.17 (s, 3H), 2.12-1.90 (m, 2H), 1.42-1.24 (m, 6H) | 367.1 | 2.92 |
| 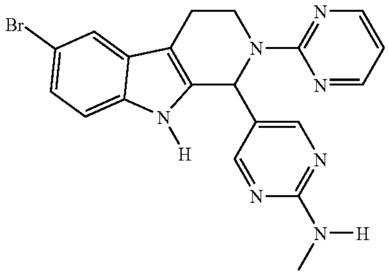 443 | (CD3OD, 400 MHz), δ 8.62 (d, J=4.4 Hz, 2H), 8.59 (s, 2H), 7.84 (s, 1H), 7.43-7.39 (m, 2H), 7.24 (s, 1H), 6.88 (t, J=8.0 Hz, 1H), 5.24-5.20 (m, 1H), 3.47-3.44 (m, 1H), 3.16 (s, 3H), 3.11-3.05 (m, 2H) | 436.2 | 5.25 |

TABLE 5-continued
| Compound | NMR | Mass Spec (LCMS) | Reten. Time (min) |
|---|---|---|---|
| 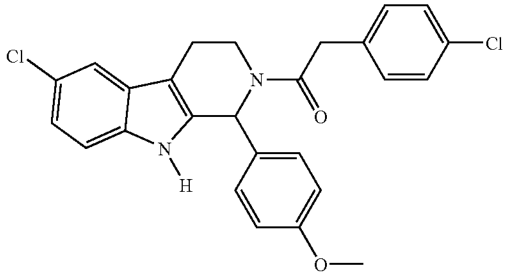 447 | (CDCl3, 400 MHz), δ 8.12 (s, 1H), 7.45 (s, 1H), 7.26 (d, J=8 Hz, 2H), 7.18 (d, J=8.8 Hz, 2H), 7.14-7.12 (m, 4H), 6.97 (s, 1H), 6.78 (d, J=8.8 Hz, 2H), 3.89 (dd, J=14 Hz and 1.2 Hz, 1H), 3.80-3.78 (m, 5H), 3.41-3.33 (m, 1H), 2.73 (dd, J=15.2 Hz and 3.2 Hz, 1H), 2.64-2.60 (m, 1H) | 464.9 | 5.11 |
| 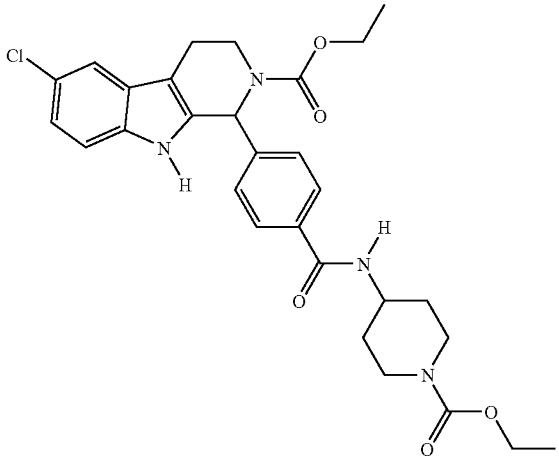 453 | (CD3OD, 400 MHz), δ 7.78 (d, J=8.0 Hz, 2H), 7.47 (d, J=1.6 Hz, 1H), 7.37 (d, J=8.0 Hz, 2H), 7.24 (d, J=8.4 Hz, 1H), 7.06 (dd, J=8.8 Hz and 1.6 Hz, 1H), 6.49 (b, 1H), 4.31-4.05 (m, 8H), 3.20-3.11 (m, 1H), 3.00-2.77 (m, 4H), 1.94-1.90 (m, 2H), 1.54-1.45 (m, 2H), 1.31 (b, 3H), 1.25 (t, J=7.2 Hz, 3H) | 553.1 | 6.13 |
| 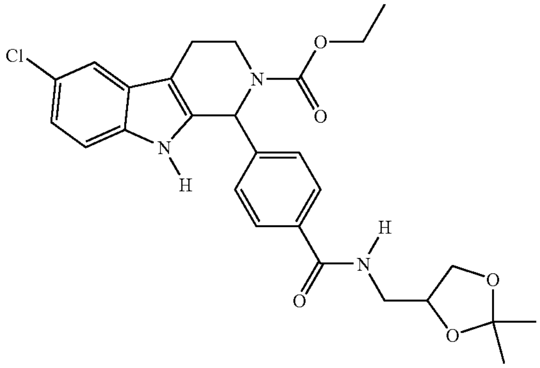 461 | (CD3OD, 400 MHz), δ 7.80 (d, J=8.0 Hz, 2H), 7.48 (d, J=1.6 Hz, 1H), 7.38 (d, J=8.4 Hz, 2H), 7.25 (d, J=8.8 Hz, 1H), 7.07 (dd, J=8.4 Hz and 1.6 Hz, 1H), 6.49 (b, 1H), 4.31-4.21 (m, 4H), 4.06 (t, J=8.4 Hz, 1H), 3.74 (t, J=8.0 Hz, 1H), 3.51 (d, J=5.2 Hz, 2H), 3.21-3.11 (m, 1H), 2.90-2.79 (m, 2H), 2.26 (s, 1H), 1.39 (s, 3H), 1.32 (s, 6H) | 454.3 | 5.98 |

TABLE 5-continued
| Compound | NMR | Mass Spec (LCMS) | Reten. Time (min) |
|---|---|---|---|
| 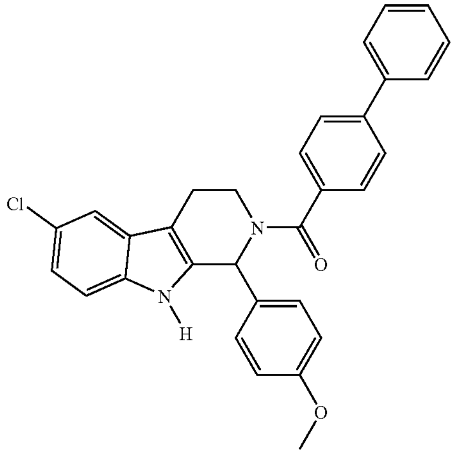 464 | (CDCl3, 400 MHz), δ 8.29 (b, 1H), 7.64 (d, J=8.0 Hz, 2H), 7.61 (d, J=7.2 Hz, 2H), 7.50-7.45 (m, 5H), 7.39 (d, J=7.6 Hz, 1H), 7.33 (d, J=7.6 Hz, 2H), 7.19 (d, J=8.8 Hz, 1H), 7.14 (dd, J=8.4 Hz and 1.6 Hz, 1H), 7.08 (s, 1H), 6.84 (d, J=8 Hz, 2H), 3.87 (d, J=9.2 Hz, 1H), 3.79 (s, 3H), 3.45-3.40 (m, 1H), 2.96-2.94 (m, 1H), 2.80-2.76 (m, 1H) | 493.0 | 5.71 |
| 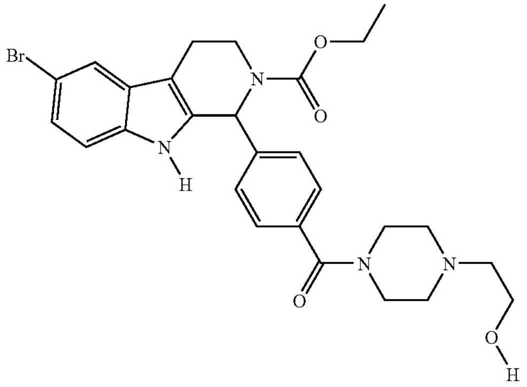 466 | (CD3OD, 400 MHz), δ 7.63 (s, 1H), 7.48 (d, J=8.4 Hz, 2H), 7.42 (d, J=8.0 Hz, 2H), 7.20 (s, 2H), 6.49 (b, 1H), 4.33-4.22 (b, 3H), 3.89 (t, J=5.2 Hz, 2H), 3.50 (b, 4H), 3.21-3.11 (m, 2H), 2.91-2.78 (m, 2H), 1.31 (s, 3H) | 555.2 | 3.14 |
| 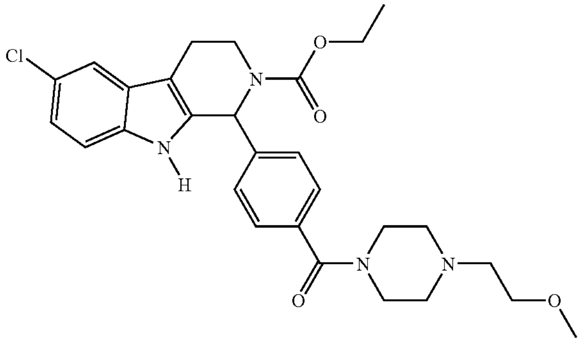 469 | (CD3OD, 400 MHz), δ 7.47 (d, J=2.0 Hz, 1H), 7.39 (s, 4H), 7.23 (d, J=8.8 Hz, 1H), 7.06 (dd, J=8.4 Hz and 2.0 Hz, 1H), 6.49 (b, 1H), 4.35-4.21 (m, 3H), 3.75 (b, 2H), 3.53 (t, J=5.4 Hz, 2H), 3.44 (b, 2H), 3.26-3.30 (m, 4H), 3.22-3.13 (m, 1H), 2.89-2.78 (m, 2H), 2.60 (t, J=5.4 Hz, 4H), 2.46 (b, 2H), 1.32 (s, 3H) | 525.2 | 5.07 |
| 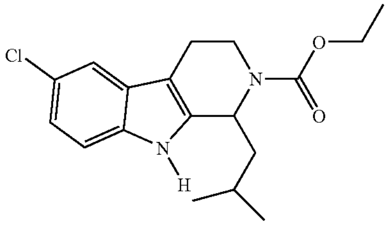 472 | (CDCl3, 400 MHz), δ 7.80, 7.75 (s 1H), 7.43, 7.41 (s, 1H), 7.21 (d, J=8.4 Hz, 1H), 7.10 (d, J=8.0 Hz, 1H), 5.43, 5.27 (d, J=7.2 Hz, 1H), 4.51-4.30 (m, 1H), 4.21-4.10 (m, 2H), 3.18 (q, J=12.8 Hz, 1H), 2.82-2.76 (m, 1H), 2.64-2.61 (m, 1H), 1.82-1.76 (m, 2H), 1.55-1.53 (m, 1H), 1.29-1.24 (m, 3H), 1.08 (b, 3H), 0.98 (d, J=6.8 Hz, 3H) | 335.3 | 5.52 |

TABLE 5-continued
| Compound | NMR | Mass Spec (LCMS) | Reten. Time (min) |
|---|---|---|---|
| 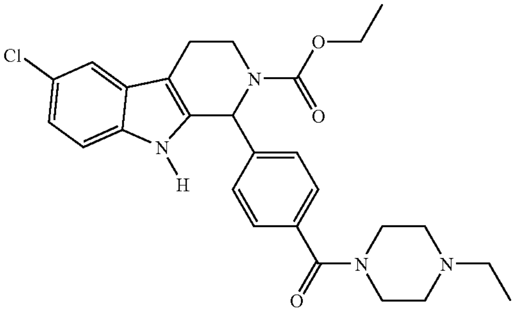 473 | (CD3OD, 400 MHz), δ 7.47 (d, J=2.0 Hz, 1H), 7.39 (s, 4H), 7.23 (d, J=8.8 Hz, 1H), 7.05 (dd, J=8.4 Hz and 2.0 Hz, 1H), 6.49 (b, 1H), 4.32-4.20 (m, 3H), 3.76 (b, 2H), 3.46 (b, 2H), 3.21-3.13 (m, 1H), 2.90-2.78 (m, 2H), 2.54 (b, 2H), 2.49-2.43 (m, 4H), 1.32 (b, 3H), 1.10 (t, J=7.2 Hz, 3H) | 495.3 | 4.68 |
| 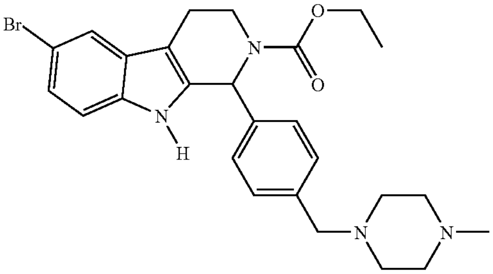 474 | ((CD3OD, 400 MHz), δ 7.61 (s, 1H), 7.44 (d, J=8.0 Hz, 2H), 7.35 (d, J=8.0 Hz, 2H), 7.20-7.16 (m, 2H), 6.45 (b, 1H), 4.28-4.14 (m, 3H), 4.11 (s, 2H), 3.47 (s, 4H), 3.26 (s, 4H), 3.19-3.12 (m, 1H), 2.91 (s, 3H), 2.88-2.79 (m, 2H), 1.30 (s, 3H) | 511.2 | 4.99 |
| 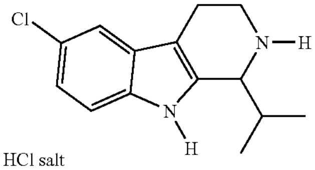 HCl salt 477 | (CD3OD, 400 MHz) δ 7.48 (d, J=1.6 Hz, 1H), 7.34 (d, J=8.4 Hz, 1H), 7.12 (dd, J=8.8 Hz and 2.0 Hz, 1H), 4.68 (s, 1H), 3.77-3.72 (m, 1H), 3.47-3.44 (m, 1H), 3.10-3.03 (m, 2H), 2.65-2.61 (m, 1H), 1.25 (d, J=7.2 Hz, 3H), 0.96 (d, J=7.2 Hz, 3H) | 249.1 | 3.67 |
| 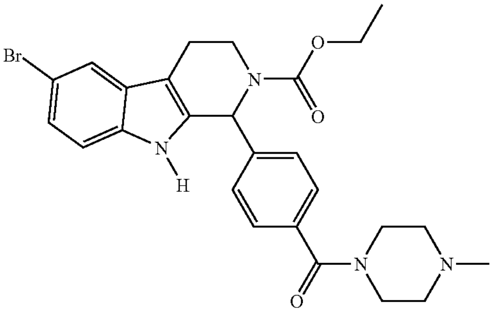 474 | CD3OD, 400 MHz), δ 7.63 (s, 1H), 7.48 (d, J=8.0 Hz, 2H), 7.42 (d, J=8.0 Hz, 2H), 7.20 (s, 2H), 6.49 (b, 1H), 4.32-4.21 (m, 3H), 3.50 (b, 4H), 3.21-3.15 (m, 3H), 2.92 (s, 3H), 2.90-2.73 (m, 2H), 1.32 (s, 3H) | 525.1 | 3.25 |
| 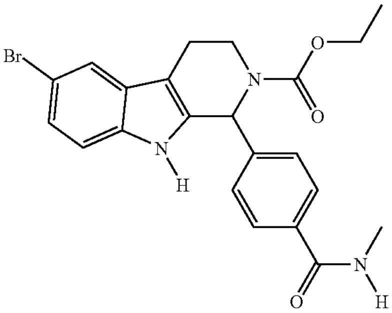 480 | (CD3OD, 400 MHz), δ 7.78 (d, J=8.0 Hz, 2H), 7.63 (s, 1H), 7.37 (d, J=8.4 Hz, 2H), 7.20 (s, 2H), 6.49 (b, 1H), 4.31-4.22 (m, 3H), 3.19-3.11 (m, 1H), 2.90 (s, 3H), 2.86-2.77 (m, 2H), 1.32 (s, 3H) | 456.1 | 4.26 |

TABLE 5-continued
| Compound | NMR | Mass Spec (LCMS) | Reten. Time (min) |
|---|---|---|---|
| 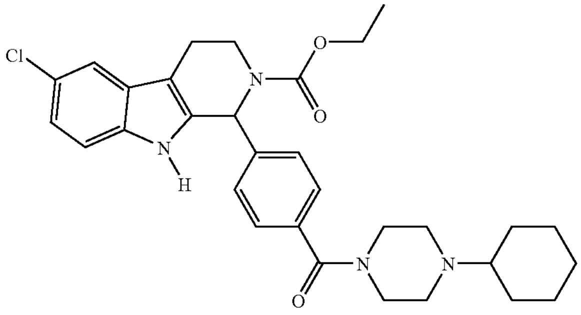 481 | (CD3OD, 400 MHz), δ 7.48 (d, J=2 Hz, 1H), 7.41-7.36 (m, 4H), 7.23 (d, J=8.4 Hz, 1H), 7.06 (dd, J=8.8 Hz and 2.0 Hz, 1H), 6.49 (b, 1H), 4.35-4.21 (m, 3H), 3.64 (b, 2H), 3.45 (b, 2H), 3.20-3.11 (m, 1H), 2.92-2.78 (m, 2H), 2.68 (b, 2H), 2.55 (b, 2H), 1.92-1.80 (m, 4H), 1.66-1.62 (m, 1H), 1.32-1.22 (m, 8H) | 549.3 | 5.29 |
| 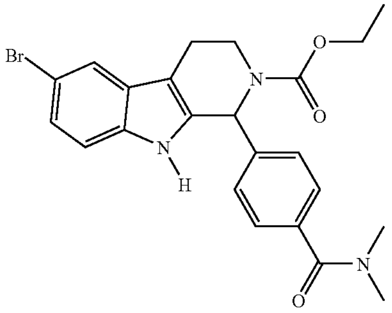 483 | (CD3OD, 400 MHz), δ 7.63 (s, 1H), 7.41 (d, J=8.4 Hz, 2H), 7.37 (d, J=8.0 Hz, 2H), 7.19 (s, 2H), 6.49 (b, 1H), 4.35-4.22 (m, 3H), 3.22-3.13 (m, 1H), 3.08 (s, 3H), 2.98 (s, 3H), 2.89-2.77 (m, 2H), 1.32 (s, 3H) | 470.1 | 4.46 |
| 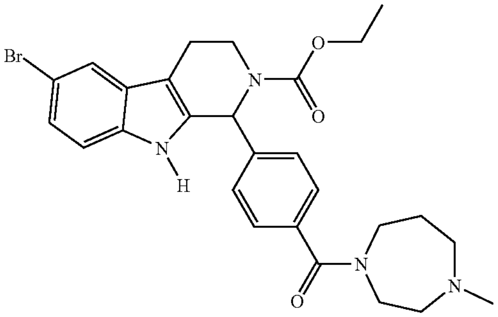 484 | (CD3OD, 400 MHz), δ 7.63 (s, 1H), 7.48 (d, J=7.2 Hz, 2H), 7.40 (d, J=8.0 Hz, 2H), 7.20 (s, 2H), 6.49 (b, 1H), 4.35-4.22 (m, 4H), 3.82-3.50 (m, 6H), 3.45 (b, 1H), 3.21-3.11 (m, 1H), 3.00-2.78 (m, 5H), 2.25-2.15 (m, 2H), 1.32 (s, 3H) | 539.2 | 3.02 |
| 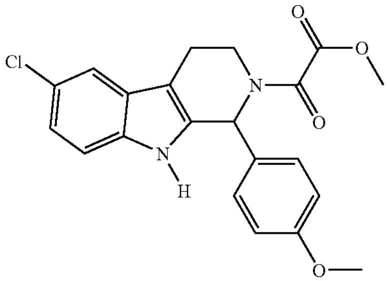 485 | (CDCl3, 400 MHz), δ 8.06 7.98 (s, 1H), 7.50, 7.49 (s, 1H), 7.22 (d, J=6.0 Hz, 1H), 7.21 (d, J=6.4 Hz, 2H), 7.15 (dd, J=8.8 Hz and 1.6 Hz, 1H), 6.81 (d, J=8.4 Hz, 2H), 6.77 (s, 1H), 3.91 (s, 3H), 3.77 (s, 3H), 3.72 (d, J=5.2 Hz, 1H), 3.51-3.43 (m, 1H), 3.02-2.96 (m, 1H), 2.86-2.81 (m, 1H) | 398.9 | 4.18 |

TABLE 5-continued
| Compound | NMR | Mass Spec (LCMS) | Reten. Time (min) |
|---|---|---|---|
| 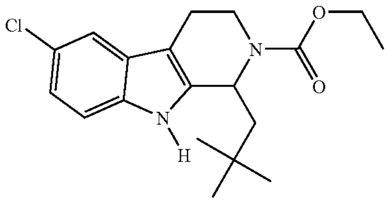 486 | (CDCl3, 400 MHz), δ 7.77, 7.70 (s, 1H), 7.42, 7.39 (s, 1H), 7.20 (dd, J=8.4 Hz and 1.6 Hz, 1H), 7.09 (d, J=8.0 Hz, 1H), 5.52-5.36 (m, 1H), 4.44-4.17 (m, 3H), 3.28-3.20 (m, 1H), 2.88-2.77 (m, 1H), 2.60 (d, J=15.2 Hz, 1H), 2.05-1.88 (m, 1H), 1.58-1.54 (m, 1H), 1.30-1.26 (m, 3H), 1.04 (d, J=2 Hz, 9H) | 349.1 | 6.03 |
| 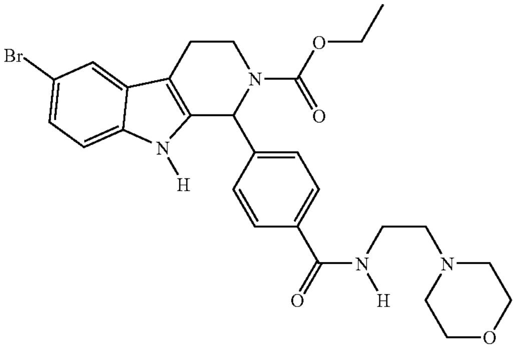 488 | (CD3OD, 400 MHz), δ 7.85 (d, J=8.0 Hz, 2H), 7.64 (s, 1H), 7.41 (d, J=8.4 Hz, 2H), 7.20 (s, 2H), 6.52 (b, 1H), 4.33-4.22 (b, 3H), 4.07 (b, 2H), 3.77 (t, J=5.6 Hz, 4H), 3.65 (b, 2H), 3.39 (t, J=5.6 Hz, 2H), 3.21-3.11 (m, 3H), 2.91-2.78 (m, 2H), 1.32 (s, 3H) | 555.2 | 3.34 |
| 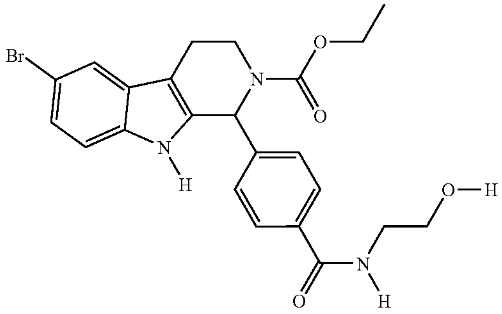 490 | (CD3OD, 400 MHz), δ 7.81 (d, J=8.4 Hz, 2H), 7.63 (s, 1H), 7.37 (d, J=8.0 Hz, 2H), 7.20 (s, 2H), 6.51 (b, 1H), 4.32-4.22 (m, 3H), 3.69 (t, J=5.8 Hz, 2H), 3.48 (t, J=5.6 Hz, 2H), 3.21-3.11 (m, 1H), 2.90-2.77 (m, 2H), 1.32 (s, 3H) | 486.1 | 3.80 |
| 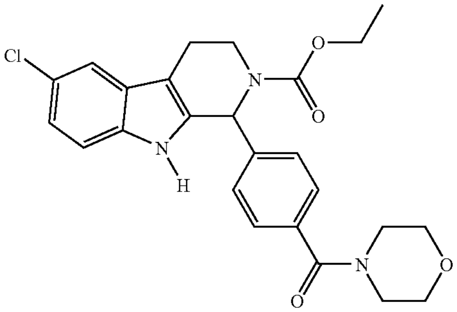 492 | (CD3OD, 400 MHz), δ 7.47 (s, 1H), 7.41-7.38 (m, 4H), 7.23 (d, J=8.8 Hz, 1H), 7.06 (dd, J=8.8 Hz and 1.6 Hz, 1H), 6.49 (b, 1H), 4.35-4.21 (m, 3H), 3.73-3.62 (m, 6H), 3.44 (b, 2H), 3.19-3.10 (m, 1H), 2.91-2.78 (m, 2H), 1.32 (b, 3H) | 468 | 5.52 |

TABLE 5-continued
| Compound | NMR | Mass Spec (LCMS) | Reten. Time (min) |
|---|---|---|---|
| 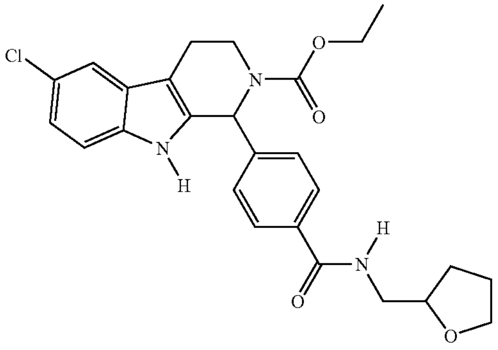 494 | (DMSO, 400 MHz), δ 11.19 (b, 1H), 8.49 (b, 1H), 7.81 (d, J=8.0 Hz, 2H), 7.51 (d, J=1.6 Hz, 1H), 7.30 (d, J=8.4 Hz, 2H), 7.29 (d, J=14.0 Hz, 1H), 7.07 (dd, J=8.4 Hz and 1.6 Hz, 1H), 6.39 (b, 1H), 4.21-4.16 (m, 3H), 3.93 (t, J=6.4 Hz, 1H), 3.74 (q, J=6.8 Hz, 1H), 3.59 (q, J=6.8 Hz, 1H), 3.28 (s, 2H), 3.08-3.01 (m, 1H), 2.81-2.70 (m, 2H), 1.91-1.79 (m, 3H), 1.59-1.52 (m, 1H), 1.21 (s, 3H) | 482.2 | 5.74 |
| 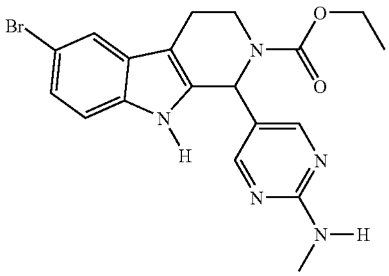 496 | (CD3OD, 400 MHz), δ 11.05 (s, 1H), 8.09 (s, 2H), 7.64 (s, 1H), 7.32 (b, 1H), 7.24 (d, J=8.4 Hz, 1H), 7.17 (dd, J=8.8 Hz and 2.0 Hz, 1H), 6.24 (s, 1H), 4.22 (b, 1H), 4.12-4.09 (m, 2H), 3.15-3.09 (m, 1H), 2.83-2.65 (m, 5H), 1.21 (t, J=6.8 Hz, 3H) | 430.2 | 3.65 |
| 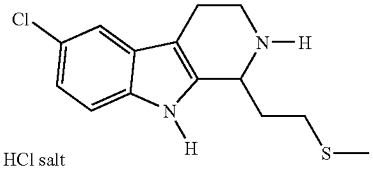 HCl salt 497 | (CD3OD, 400 MHz), δ 7.49 (d, J=1.6 Hz, 1H), 7.34 (d, J=8.8 Hz, 1H), 7.13 (dd, J=8.8 Hz and 2.0 Hz, 1H), 3.77-3.72 (m, 1H), 3.52-3.45 (m, 1H), 3.15-3.01 (m, 2H), 2.80-2.74 (m, 2H), 2.60-2.52 (m, 1H), 2.27-2.20 (m, 4H) | 281.0 | 3.84 |
| 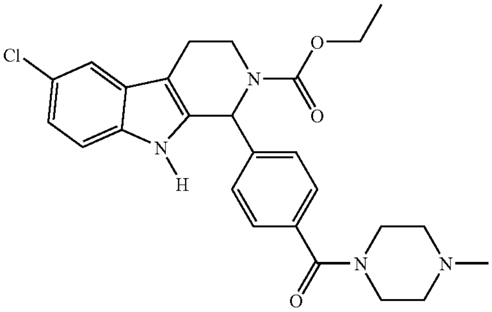 498 | (CDCl3, 400 MHz), δ 8.35 (b, 1H), 7.51 (s, 1H), 7.32-7.26 (m, 4H), 7.20 (d, J=8.4 Hz, 1H), 7.13 (dd, J=8.8 Hz and 2.4 Hz, 1H), 6.39 (b, 1H), 4.25-4.21 (m, 2H), 3.80 (b, 2H), 3.47 (b, 2H), 3.16-3.10 (m, 1H), 2.96-2.88 (m, 3H), 2.79-2.75 (m, 1H), 2.54-2.36 (m, 6H), 1.32 (s, 3H) | 481.4 | 4.81 |

TABLE 5-continued
| Compound | NMR | Mass Spec (LCMS) | Reten. Time (min) |
|---|---|---|---|
| 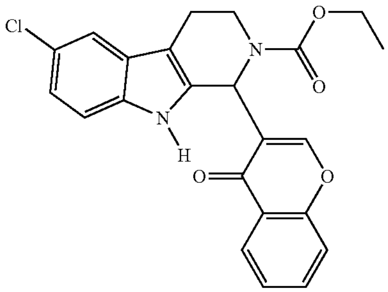 499 | (DMSO, 400 MHz), δ 10.86 (s, 1H), 8.17 (s, 1H), 8.03 (d, J=7.6 Hz, 1H), 7.81 (t, J=8.0 Hz, 1H), 7.65 (d, J=8.4 Hz, 1H), 7.50 (b, 2H), 7.26 (d, J=8.4 Hz, 1H), 7.02 (d, J=8.8 Hz, 1H), 6.24 (s, 1H), 4.35 (b, 1H), 4.09-4.05 (m, 2H), 3.61-3.49 (m, 1H), 2.78-2.65 (m, 2H), 1.45 (t, J=6.8 Hz, 3H) | 423.3 | 5.15 |
| 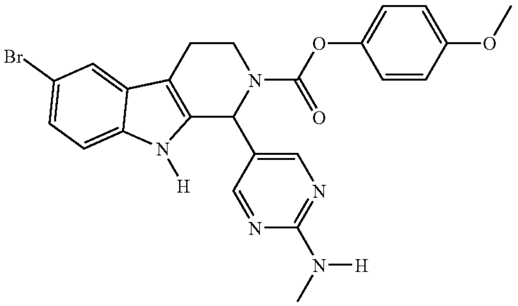 503 | (CD3OD, 400 MHz), δ 8.33 (s, 2H), 7.67 (s, 1H), 7.23 (s, 2H), 7.05 (d, J=8.4 Hz, 2H), 6.91 (d, J=8.8 Hz, 2H), 6.54-6.38 (m, 1H), 4.52 (b, 1H), 3.78 (s, 3H), 3.36-3.34 (m, 1H), 2.99 (s, 3H), 2.92-2.88 (m, 2H) | 508.2 | 5.72 |
| 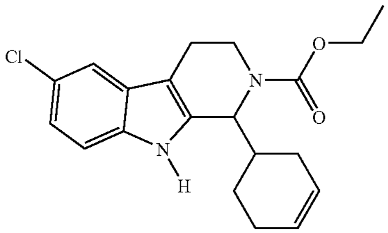 504 | (CDCl3, 400 MHz), δ 7.88-7.77 (m, 1H), 7.43 (d, J=8.0 Hz, 1H), 7.23 (d, J=8.8 Hz, 1H), 7.11 (d, J=8.8 Hz 1H), 5.70-7.68 (m, 2H), 5.19-4.97 (m, 1H), 4.60-4.38 (m, 1H), 4.19-4.07 (m, 2H), 2.82-2.80 (m, 1H), 2.68-2.64 (m, 1H), 2.29-1.84 (m, 6H), 1.55-1.46 (m, 1H), 1.36-1.24 (m, 3H) | 359.1 | 5.65 |
| 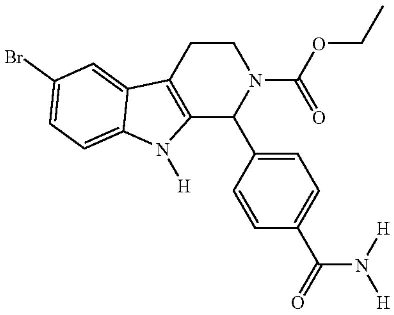 505 | (CD3OD, 400 MHz), δ 7.84 (d, J=8.0 Hz, 2H), 7.63 (s, 1H), 7.38 (d, J=8.0 Hz, 2H), 7.20 (s, 2H), 6.49 (b, 1H), 4.31-4.22 (m, 3H), 3.19-3.11 (m, 1H), 2.89-2.77 (m, 2H), 1.32 (s, 3H) | 442.0 | 4.06 |

TABLE 5-continued
| Compound | NMR | Mass Spec (LCMS) | Reten. Time (min) |
|---|---|---|---|
| 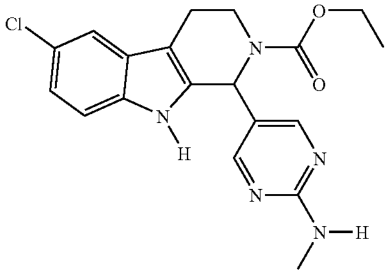 506 | (CD3OD, 400 MHz), δ 8.44 (s, 2H), 7.67 (d, J=2.0 Hz, 1H), 7.44 (d, J=8.8 Hz, 1H), 7.28 (dd, J=8.8 Hz and 2.0 Hz, 1H), 6.52 (s, 1H), 4.58-4.55 (m, 1H), 4.43-4.40 (m, 2H), 3.41-3.31 (m, 1H), 3.15 (s, 3H), 3.03-3.01 (m, 2H), 1.32 (b, 3H) | 386.3 | 5.32 |
| 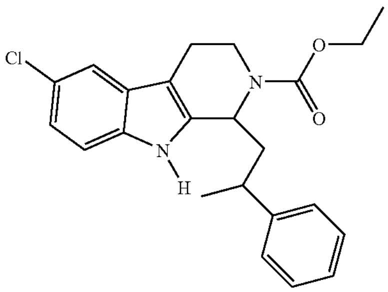 508 | (CDCl3, 400 MHz), δ 7.66 (d, J=24.8 Hz, 1H), 7.39-6.89 (m, 8H), 5.44-5.02 (m, 1H), 4.49-4.10 (m, 3H), 3.23-2.94 (m, 2H), 2.83-2.74 (m, 1H), 2.64-2.58 (m, 1H), 2.26-1.98 (m, 2H), 1.47-1.26 (m, 6H) | 397.1 | 5.97 |
| 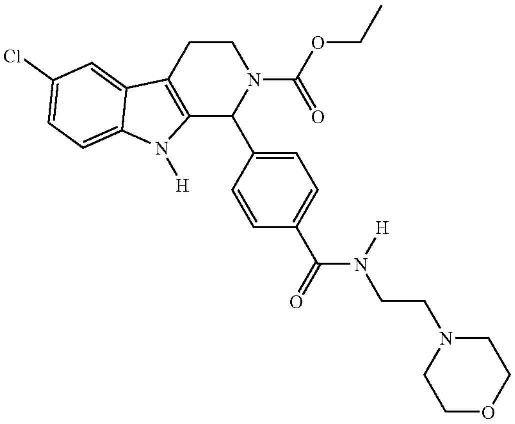 509 | (CD3OD, 400 MHz), δ 7.80 (d, J=8.4 Hz, 2H), 7.47 (d, J=1.6 Hz, 1H), 7.38 (d, J=8.0 Hz, 2H), 7.24 (d, J=8.8 Hz, 1H), 7.07 (dd, J=8.0 Hz and 1.6 Hz, 1H), 6.49 (b, 1H), 4.35-4.21 (m, 3H), 3.69 (t, J=4.6 Hz, 4H), 3.53 (t, J=6.8 Hz, 2H), 3.19-3.10 (m, 1H), 2.90-2.78 (m, 2H), 2.59 (t, J=6.6 Hz, 4H), 2.53 (s, 2H), 1.32 (s, 3H) | 511.4 | 5.05 |
| 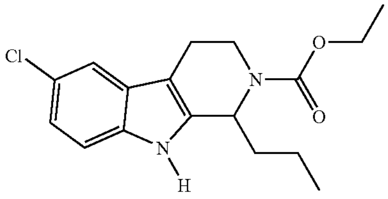 510 | (CDCl3, 400 MHz), δ 8.09, 7.83 (s, 1H), 7.42 (s, 1H), 7.21 (d, J=8.4 Hz, (s, 1H), 7.21 (d, and 1.2 Hz, 1H), 5.33-5.21 (m, 1H), 4.50-4.34 (m, 1H), 4.21-4.10 (m, 2H), 3.19-3.17 (m, 1H), 2.77-2.74 (m, 1H), 2.67-2.61 (m, 1H), 1.81 (s, 2H), 1.52 (s, 2H), 1.29-1.23 (m, 3H), 0.96 (s, 3H) | 321.4 | 5.19 |

TABLE 5-continued
| Compound | NMR | Mass Spec (LCMS) | Reten. Time (min) |
|---|---|---|---|
| 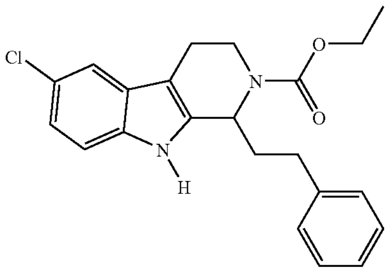 511 | (CDCl3, 400 MHz), δ 7.73-7.52 (m, 1H), 7.47 (s, 1H), 7.42-7.18 (m, 6H), 7.09 (dd, J=8.8 Hz and 2.0 Hz, 1H), 5.41-5.26 (m, 1H), 4.56-4.32 (m, 1H), 4.23-4.10 (m, 2H), 3.21 (b, 1H), 2.85-2.72 (m, 3H), 2.65 (d, J=14.2 Hz, 1H), 2.23-2.10 (m, 2H), 1.38 (b, 3H) | 383.1 | 5.75 |
| 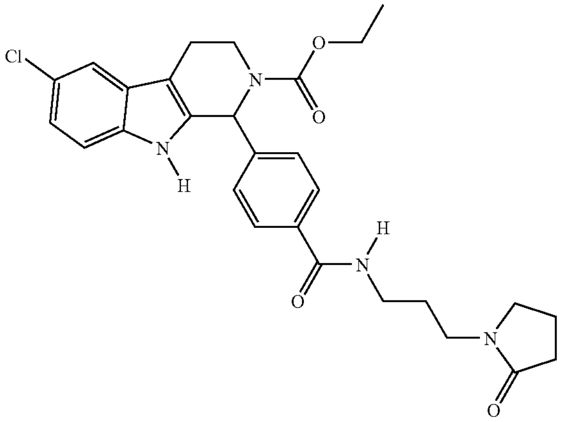 512 | (CD3OD, 400 MHz), δ 7.80 (d, J=8.4 Hz, 2H), 7.47 (d, J=1.6 Hz, 1H), 7.37 (d, J=8.0 Hz, 2H), 7.24 (d, J=8.8 Hz, 1H), 7.06 (dd, J=8.8 Hz and 2.0 Hz, 1H), 6.50 (b, 1H), 4.32-4.21 (m, 3H), 3.47 (t, J=7.2 Hz, 2H), 3.38-3.34 (m, 4H), 3.19-3.10 (m, 1H), 2.89-2.78 (m, 2H), 2.39 (t, J=8.4 Hz, 2H), 2.09-2.00 (m, 2H), 1.86-1.80 (m, 2H), 1.32 (b, 3H) | 523.1 | 5.69 |
| 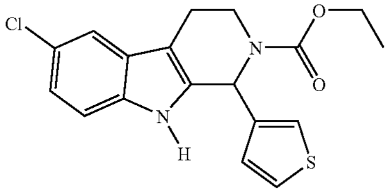 513 | (CDCl3, 400 MHz), δ 7.81 (s, 1H), 7.51 (d, J=6.8 Hz, 1H), 7.29 (dd, J=12.0 Hz and 2.8 Hz, 1H), 7.21 (d, J=8.4 Hz, 1H), 7.13 (dd, J=8.4 Hz and 2.0 Hz, 1H), 7.12-7.08 (m, 1H), 7.07 (s, 1H), 6.50 (b, 1H), 4.49-4.21 (m, 3H), 3.17-3.09 (m, 1H), 2.91-2.85 (m, 1H), 2.77-2.73 (m, 1H), 1.39 (s, 3H) | 361.1 | 5.12 |
| 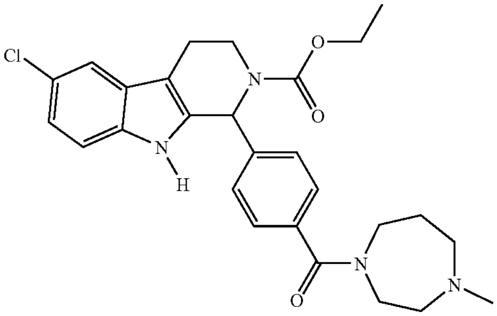 514 | (CD3OD, 400 MHz), δ 7.47 (d, J=2.0 Hz, 1H), 7.46-7.37 (m, 4H), 7.23 (d, J=8.4 Hz, 1H), 7.06 (dd, J=8.8 Hz and 2.0 Hz, 1H), 6.49 (b, 1H), 4.35-4.21 (m, 3H), 3.77-3.69 (m, 2H), 3.55-3.45 (m, 2H), 3.20-3.11 (m, 1H), 2.90-2.78 (m, 3H), 2.67-2.55 (m, 3H), 2.39-2.31 (m, 3H), 2.01-1.95 (m, 1H), 1.82-1.79 (m, 1H), 1.32 (s, 3H) | 495.3 | 4.67 |

TABLE 5-continued
| Compound | NMR | Mass Spec (LCMS) | Reten. Time (min) |
|---|---|---|---|
| 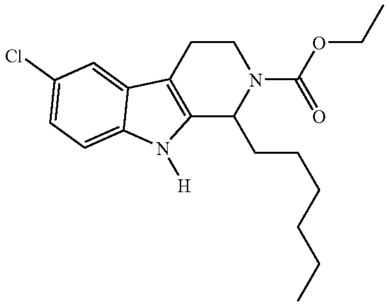 515 | (CDCl3, 400 MHz), δ 7.92, 7.82 (s, 1H), 7.42 (s, 1H), 7.22 (dd, J=8.4 Hz and 1.2 Hz, 1H), 7.10 (d, J=8.8 Hz, 1H), 5.31, 5.19 (s, 1H), 4.52, 4.32 (d, J=10.8 Hz, 1H), 4.20-4.12 (m, 2H), 3.19-3.12 (m, 1H), 2.81-2.62 (m, 2H), 1.81 (d, J=6.8 Hz, 2H), 1.48-22 (m, 12H), 0.88 (s, 3H) | 363.5 | 6.34 |
| 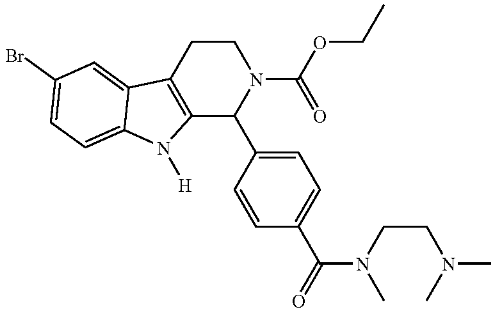 516 | (CD3OD, 400 MHz), δ 7.63 (s, 1H), 7.50 (d, J=8.0 Hz, 2H), 7.40 (d, J=8.0 Hz, 2H), 7.20 (s, 2H), 6.49 (b, 1H), 4.30-4.20 (m, 3H), 3.89 (s, 2H), 3.45 (b, 2H), 3.20-3.10 (m, 1H), 3.03-3.01 (m, 9H), 2.91-2.80 (m, 2H), 1.32 (s, 3H) | 527.1 | 3.16 |
| 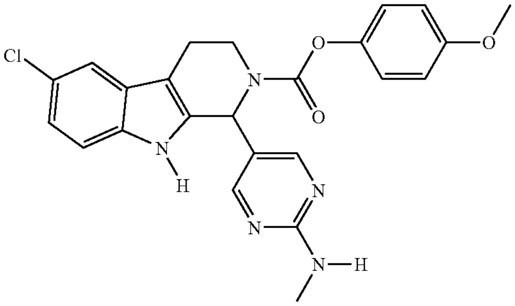 517 | (CD3OD, 400 MHz), δ 8.27 (s, 2H), 7.52 (d, J=2 Hz, 1H), 7.27 (d, J=8.8 Hz, 1H), 7.17 (d, J=8.8 Hz, 1H), 7.10 (dd, J=8.8 Hz and 2.4 Hz, 1H), 7.05 (d, J=8.8 Hz, 2H), 6.95 (d, J=9.2 Hz, 2H), 6.92 (s, 1H), 6.58-6.38 (m, 1H), 4.52 (b, 1H), 3.80 (s, 1H), 3.79 (s, 3H), 3.31-3.30 (m, 1H), 2.95 (s, 3H), 2.92-2.88 (m, 1H) | 464.2 | 5.86 |
| 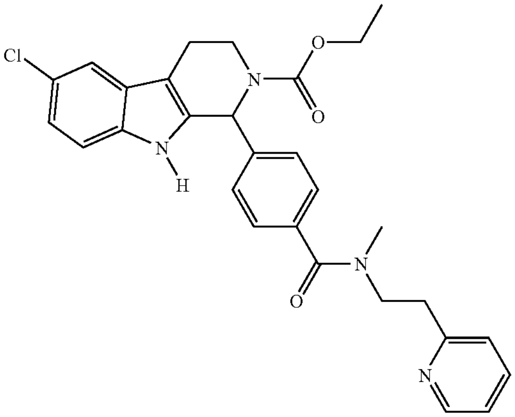 518 | (CD3OD, 400 MHz), δ 8.49, 8.29 (d, J=4.4 Hz, 2.8 Hz, 1H), 7.82, 7.70 (t, J=2.0 Hz, 1H), 7.46 (s, 1H), 7.38-7.23 (m, 5H), 7.15 (d, J=7.6 Hz, 1H), 7.07 (d, J=8.4 Hz, 1H), 6.98 (d, J=6.8 Hz, 1H), 6.46 (b, 1H), 4.35-4.21 (m, 3H), 3.88 (t, J=7.0 Hz, 1H), 3.71-3.67 (m, 1H), 3.20-3.11 (m, 3H), 3.01-2.80 (m, 4H), 1.32 (s, 3H) | 517.6 | 5.03 |

TABLE 5-continued
| Compound | NMR | Mass Spec (LCMS) | Reten. Time (min) |
|---|---|---|---|
| 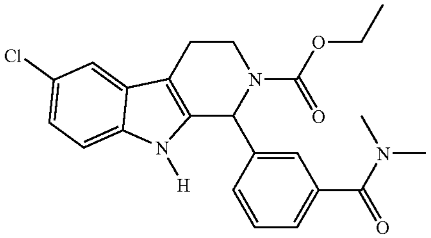 520 | (DMSO, 400 MHz), δ 11.15 (s, 1H), 7.51 (d, J=2.0 Hz, 1H), 7.42 (t, J=7.6 Hz, 1H), 7.35 (d, J=7.6 Hz, 1H), 7.30 (d, J=8.8 Hz, 2H), 7.16 (s, 1H), 7.06 (dd, J=8.4 Hz and 2.0 Hz, 1H), 6.36 (b, 1H), 4.18-4.10 (m, 3H), 3.09-3.00 (m, 1H), 2.91-2.64 (m, 8H), 1.21 (t, J=6.6 Hz, 3H) | 426.2 | 4.29 |
| 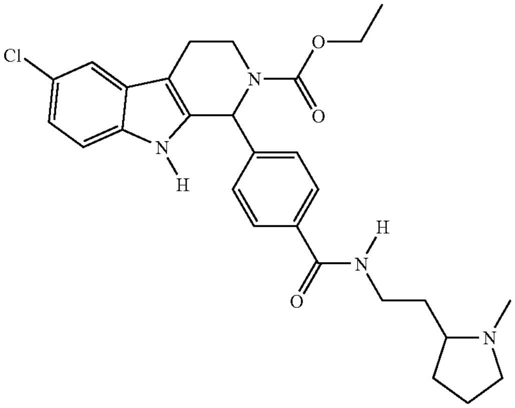 521 | (CD3OD, 400 MHz), δ 7.81 (d, J=8.4 Hz, 2H), 7.47 (d, J=1.6 Hz, 1H), 7.39 (d, J=8.4 Hz, 2H), 7.24 (d, J=8.4 Hz, 1H), 7.07 (dd, J=8.4 Hz and 2.0 Hz, 1H), 6.50 (b, 1H), 4.35-4.29 (m, 3H), 3.70-3.60 (m, 1H), 3.51-3.47 (m, 2H), 3.37-3.29 (m, 1H), 3.19-3.11 (m, 2H), 2.92 (s, 3H), 2.88-2.78 (m, 2H), 2.51-2.41 (m, 1H), 2.29-2.20 (m, 1H), 2.17-2.00 (m, 2H), 1.89-1.78 (m, 2H), 1.32 (s, 3H) | 509.4 | 4.99 |
| 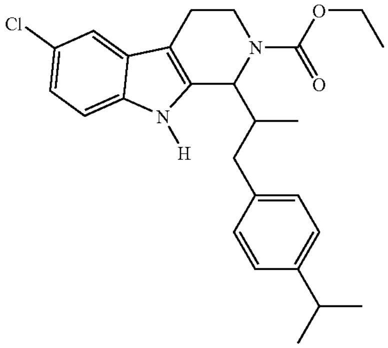 523 | (CDCl3, 400 MHz), δ 7.91, 7.72 (s, 1H), 7.50-7.43 (s, 1H), 7.22-7.06 (m, 6H), 5.28-5.19 (m, 1H), 4.64-4.45 (m, 1H), 4.20 (b, 2H), 3.27-3.10 (m, 2H), 2.91-2.72 (m, 2H), 2.70-2.66 (m, 1H), 2.49-2.28 (m, 2H), 1.38-1.24 (m, 9H), 1.01, 0.96 (d, J=6.8 Hz, 3H) | 439.0 | 6.11 |
| 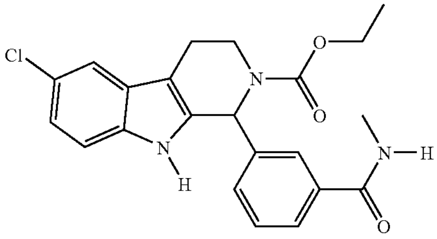 524 | (DMSO, 400 MHz), δ 11.10 (s, 1H), 8.42 (s, 1H), 7.75 (d, J=7.2 Hz, 1H), 7.67 (s, 1H), 7.51 (d, J=1.6 Hz, 1H), 7.43 (t, J=7.2 Hz, 1H), 7.35 (d, J=8.0 Hz, 1H), 7.29 (d, J=8.4 Hz, 1H), 7.06 (dd, J=8.8 Hz and 2.4 Hz, 1H), 6.39 (b, 1H), 4.13-4.09 (m, 3H), 3.10-3.04 (m, 1H), 2.81-2.72 (m, 5H), 1.21 (s, 3H) | 412.1 | 4.13 |

TABLE 5-continued
| Compound | NMR | Mass Spec (LCMS) | Reten. Time (min) |
|---|---|---|---|
| 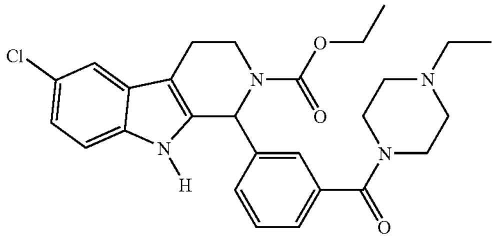 525 | (CD3OD, 400 MHz), δ 7.53-7.46 (m, 4H), 7.29 (b, 1H), 7.25 (d, J=8.8 Hz, 1H), 7.08 (dd, J=8.8 Hz and 2.0 Hz, 1H), 6.49 (b, 1H), 4.34-4.23 (m, 3H), 3.53-3.42 (m, 2H), 3.18-3.12 (m, 5H), 2.91-2.74 (m, 3H), 1.32 (t, J=7.2 Hz, 6H) | 4.95.3 | 3.46 |
| 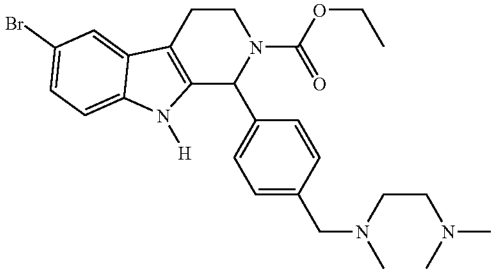 526 | (CD3OD, 400 MHz), δ 7.63 (s, 1H), 7.51 (d, J=8.0 Hz, 2H), 7.41 (d, J=8.4 Hz, 2H), 7.19 (d, J=1.2 Hz, 2H), 6.46 (b, 1H), 4.31 (s, 2H), 4.23-4.20 (m, 3H), 3.62-3.50 (m, 4H), 3.19-3.11 (m, 1H), 2.92 (s, 6H), 2.87-2.81 (m, 2H), 2.76 (s, 3H), 1.31 (s, 3H) | 513.2 | 4.43 |
| 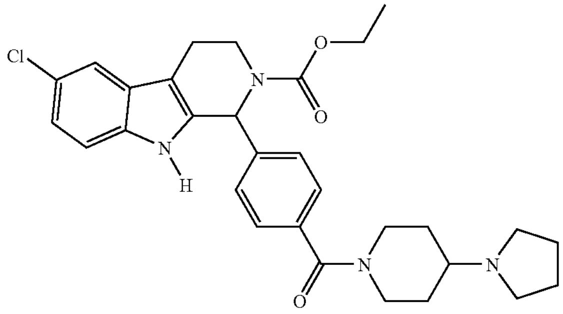 527 | (CD3OD, 400 MHz), δ 7.47 (d, J=2 Hz, 1H), 7.46-7.37 (m, 4H), 7.24 (d, J=8.8 Hz, 1H), 7.07 (d, J=8.8 Hz and 2.0 Hz, 1H), 6.49 (b, 1H), 4.75 (b, 1H), 4.35-4.21 (m, 3H), 3.85 (b, 1H), 3.64 (b, 2H), 3.45-3.37 (m, 1H), 3.19-3.12 (m, 4H), 2.91-2.80 (m, 3H), 2.28-2.00 (m, 6H), 2.12-2.05 (m, 2H), 1.61 (b, 2H), 1.32 (s, 3H) | 535.3 | 4.94 |
| 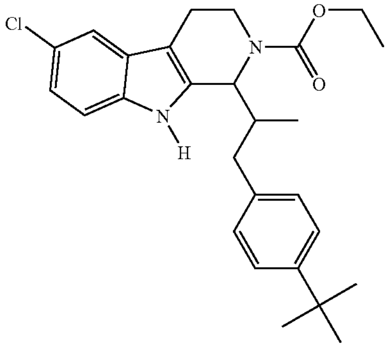 528 | (CDCl3, 400 MHz), δ 7.89-7.69 (m, 1H), 7.43 (b, 1H), 7.33-7.30 (m, 2H), 7.20-7.06 (m, 4H), 5.29-5.19 (m, 1H), 4.64-4.45 (m, 1H), 4.20 (b, 2H), 3.27-3.10 (m, 2H), 2.91-2.72 (m, 2H), 2.70-2.66 (m, 1H), 2.50 (b, 2H), 2.29 (b, 1H), 1.32-1.31 (m, 12H), 1.02, 0.90 (d, J=6.8 Hz, 3H) | 453.0 | 6.30 |

TABLE 5-continued

| Compound | NMR | Mass Spec (LCMS) | Reten. Time (min) |
|---|---|---|---|
| 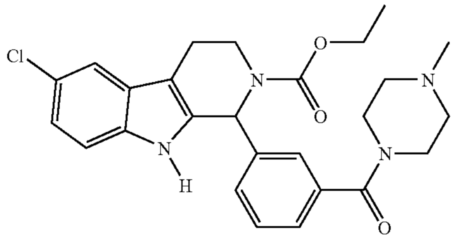 529 | (CD3OD, 400 MHz), δ 7.52-7.45 (m, 4H), 7.31 (b, 1H), 7.25 (d, J=8.4 Hz, 1H), 7.08 (dd, J=8.4 Hz and 2.0 Hz, 1H), 6.48 (b, 1H), 4.34-4.23 (m, 3H), 3.45 (b, 3H), 3.23-3.13 (m, 4H), 2.92-2.80 (m, 5H), 1.32 (s, 3H) | 481.3 | 3.43 |
| 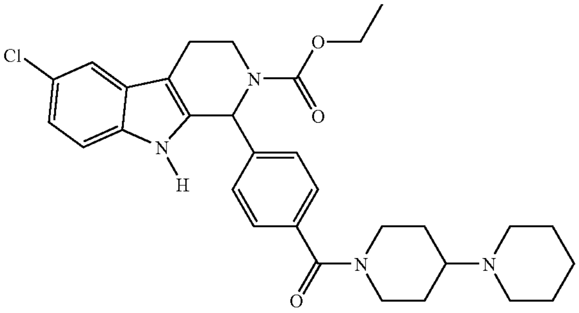 531 | (CD3OD, 400 MHz) δ 7.48 (d, J=1.6 Hz, 1H), 7.43 (d, J=8.4 Hz, 2H), 7.40 (d, J=8.4 Hz, 2H), 7.24 (d, J=8.4 Hz, 1H), 7.07 (dd, J=8.4 Hz and 2.0 Hz, 1H), 6.50 (b, 1H), 4.35-4.29 (m, 3H), 3.90 (b, 1H), 3.52-3.47 (m, 3H), 3.20-3.16 (m, 2H), 3.01 (t, J=12.0 Hz, 2H), 2.91-2.79 (m, 3H), 2.20 (b, 1H), 2.00-1.97 (m, 3H), 1.82-1.71 (m, 6H), 1.56-1.48 (m, 1H), 1.32 (b, 3H) | 549.6 | 5.21 |
| 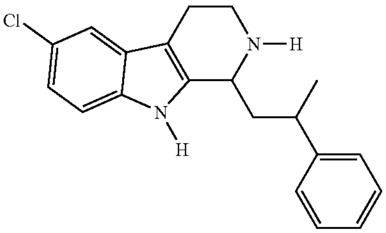 HCl salt 532 | (DMSO, 400 MHz), δ 11.39 (s, 1H), 9.80 (b, 1H), 9.40 (b, 1H), 7.52 (d, J=1.6 Hz, 1H), 7.48 (s, 1H), 7.37-7.31 (m, 4H), 7.25-7.19 (m, 1H), 7.00 (dd, J=8.8 Hz and 2 Hz, 1H), 4.76 (d, J=5.6 Hz, 1H), 3.61-3.53 (m, 1H), 3.25-3.20 (m, 1H), 2.94-2.92 (m, 2H), 2.13-1.97 (m, 1H), 1.35, 1.24 (d, J=6.8 Hz, 3H) | 325.3 | 4.75 |
| 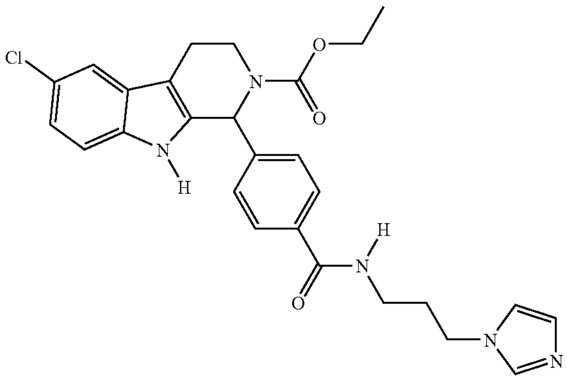 533 | (CD3OD, 400 MHz), δ 8.99 (s, 1H), 7.80 (d, J=8.0 Hz, 2H), 7.71 (d, J=1.2 Hz, 1H), 7.57 (s, 1H), 7.47 (d, J=1.6 Hz, 1H), 7.39 (d, J=8.0 Hz, 2H), 7.24 (d, J=8.4 Hz, 1H), 7.07 (d, J=8.0 Hz, 1H), 6.51 (b, 1H), 4.32 (t, J=4.8 Hz, 3H), 4.23-4.21 (m, 2H), 3.43 (t, J=6.4 Hz, 2H), 3.20-3.11 (m, 1H), 2.91-2.78 (m, 2H), 2.23-2.17 (m, 2H), 1.32 (b, 3H) | 506.2 | 4.96 |

TABLE 5-continued
| Compound | NMR | Mass Spec (LCMS) | Reten. Time (min) |
|---|---|---|---|
| 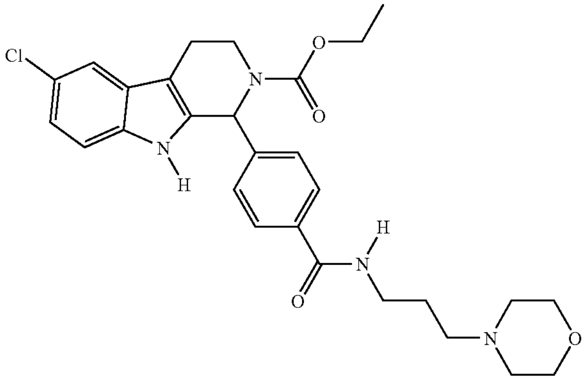 534 | (CD3OD, 400 MHz), δ 7.79 (d, J=8.4 Hz, 2H), 7.48 (s, 1H), 7.38 (d, J=8.0 Hz, 2H), 7.25 (d, J=8.8 Hz, 1H), 7.07 (dd, J=8.4 Hz and 2.0 Hz, 1H), 6.51 (b, 1H), 4.35-4.21 (m, 3H), 3.67 (t, J=4.6 Hz, 4H), 3.41 (q, J=4.8 Hz, 2H), 3.20-3.11 (m, 1H), 2.91-2.79 (m, 2H), 2.62 (s, 1H), 2.46-2.42 (m, 5H), 1.83-1.79 (m, 2H), 1.32 (s, 3H) | 525.2 | 4.76 |
| 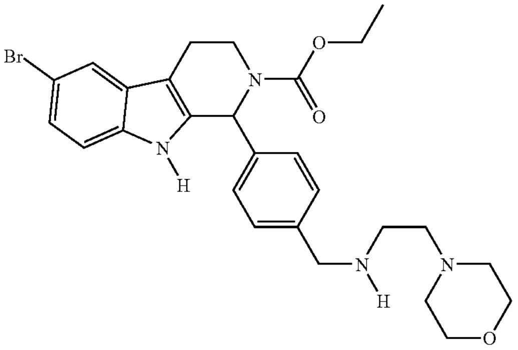 535 | (CD3OD, 400 MHz), δ 7.62 (s, 1H), 7.49 (d, J=8.0 Hz, 2H), 7.39 (d, J=8.4 Hz, 2H), 7.19 (s, 2H), 6.48 (s, 1H), 4.27-4.18 (m, 5H), 3.87 (t, J=4.6 Hz, 4H), 3.47 (t, J=6.8 Hz, 2H), 3.34-3.30 (m, 2H), 3.16-3.12 (m, 5H), 2.89-2.75 (m, 2H), 1.30 (s, 3H) | 541.2 | 3.51 |
| 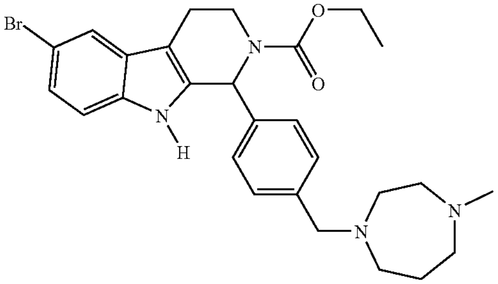 541 | (CD3OD, 400 MHz), δ 7.60 (s, 1H), 7.51 (d, J=8.0 Hz, 2H), 7.40 (d, J=8.0 Hz, 2H), 7.21-7.16 (m, 2H), 6.46 (b, 1H), 4.41 (s, 2H), 4.28-4.19 (m, 3H), 3.79-3.74 (m, 4H), 3.51-3.49 (m, 4H), 3.19-3.11 (m, 1H), 2.95 (s, 3H), 2.88-2.75 (m, 2H), 2.30 (s, 2H), 1.30 (s, 3H) | 525.2 | 4.42 |
| 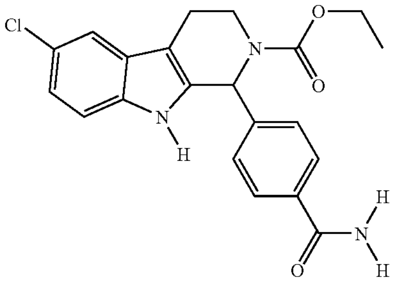 542 | (CD3OD, 400 MHz), δ 7.84 (d, J=8.0 Hz, 2H), 7.47 (d, J=2.0 Hz, 1H), 7.37 (d, J=8.4 Hz, 2H), 7.24 (d, J=8.4 Hz, 1H), 7.06 (dd, J=8.4 Hz and 2.0 Hz, 1H), 6.49 (b, 1H), 4.35-4.16 (m, 3H), 3.21-3.10 (m, 1H), 2.90-2.71 (m, 2H), 1.32 (b, 3H) | 398.1 | 3.95 |

TABLE 5-continued
| Compound | NMR | Mass Spec (LCMS) | Reten. Time (min) |
|---|---|---|---|
| 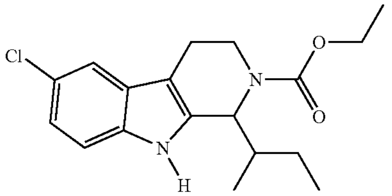 547 | (CDCl3, 400 MHz), δ 7.92-7.77 (m, 1H), 7.42-7.39 (m, 8H), 7.26-7.21 (m, 1H), 7.10 (d, J=8.4 Hz, 1H), 5.16-4.97 (m, 1H), 4.56-4.36 (m, 1H), 4.19-4.11 (m, 2H), 3.27-3.19 (m, 1H), 2.78-2.63 (m, 2H), 1.90 (d, J=5.6 Hz, 1H), 1.74 (b, 1H), 1.49-1.26 (m, 4H), 1.10-0.91 (m, 6H) | 335.2 | 5.45 |
| 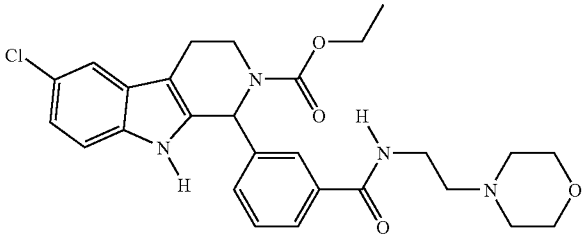 552 | (CD3OD, 400 MHz), δ 7.82 (s, 1H), 7.80 (s, 1H), 7.55-7.48 (m, 3H), 7.23 (d, J=8.4 Hz, 1H), 7.07 (dd, J=8.4 Hz and 2.0 Hz, 1H), 6.49 (b, 1H), 4.33-4.21 (m, 3H), 4.05 (b, 2H), 3.5-3.73 (m, 4H), 3.61 (b, 2H), 3.37 (t, J=5.8 Hz, 2H), 3.25-3.17 (m, 3H), 2.92-2.80 (m, 2H), 1.32 (s, 3H) | 511.3 | 3.56 |
| 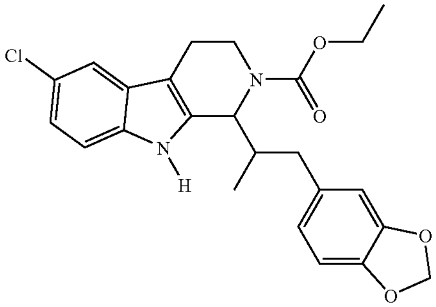 553 | (CDCl3, 400 MHz), δ 8.01, 7.91 (s, 1H), 7.43 (s, 1H), 7.23 (d, J=8.4 Hz, 1H), 7.11 (d, J=7.2 Hz, 1H), 6.71 (d, J=7.6 Hz, 1H), 6.63 (s, 1H), 6.57 (d, J=7.6 Hz, 1H), 5.92 (s, 2H), 5.18-5.07 (m, 1H), 4.63-4.41 (m, 1H), 4.30-4.11 (m, 2H), 3.36-3.31 (m, 1H), 2.91-2.83 (m, 2H), 2.70-2.61 (m, 1H), 2.38-2.15 (m, 2H), 1.38-1.30 (m, 3H), 1.09-1.01 (m, 3H) | 440.9 | 5.75 |
| 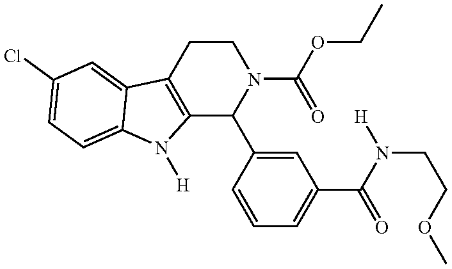 556 | (CD3OD, 400 MHz), δ 7.76 (s, 1H), 7.75 (s, 1H), 7.52-7.43 (m, 2H), 7.23 (d, J=8.4 Hz, 1H), 7.06 (d, J=7.6 Hz, 1H), 6.47 (b, 1H), 4.30-4.21 (m, 3H), 3.52 (s, 4H), 3.33 (s, 3H), 3.26-3.18 (m, 1H), 2.91-2.80 (m, 2H), 1.32 (s, 3H) | 456.1 | 4.21 |

TABLE 5-continued
| Compound | NMR | Mass Spec (LCMS) | Reten. Time (min) |
|---|---|---|---|
| 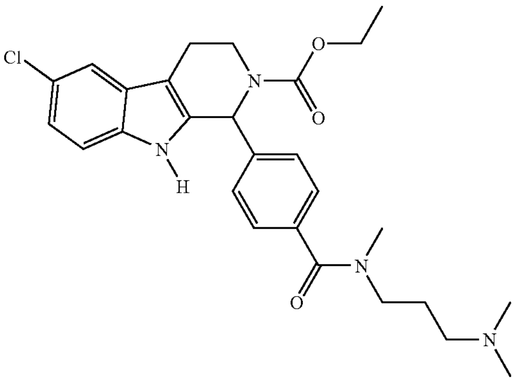 558 | (CD3OD, 400 MHz), δ 7.48 (s, 1H), 7.46 (d, J=8.8 Hz, 2H), 7.40 (d, J=7.6 Hz, 2H), 7.24 (d, J=8.4 Hz, 1H), 7.07 (d, J=8.0 Hz, 1H), 6.49 (b, 1H), 4.35-4.21 (m, 3H), 3.64-3.61 (m, 2H), 3.20-3.11 (m, 3H), 3.01 (s, 3H), 2.93 (s, 5H), 2.89-2.78 (m, 3H), 2.12-2.05 (m, 2H), 1.32 (s, 3H) | 497.2 | 4.69 |
| 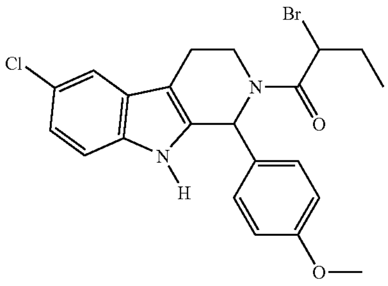 559 | (CDCl3, 400 MHz), δ 8.17, 8.00 (s, 1H), 7.50 (s, 1H), 7.23-7.13 (m, 4H), 6.97, 6.92 (s, 1H), 6.80 (d, J=8.4 Hz, 2H), 4.43, 4.34 (t, J=7.0 Hz, 1H), 4.04-3.98 (m, 1H), 3.77 (s, 3H), 3.47-3.41 (m, 1H), 3.25-2.81 (m, 2H), 2.23-2.06 (m, 2H), 1.02 (t, J=6.2 Hz, 3H) | 460.8 | 4.96 |
| 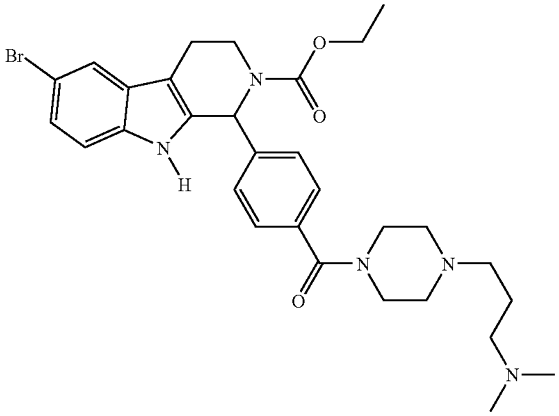 560 | (DMSO, 300 MHz), δ 7.63 (s, 1H), 7.49 (d, J=6.3 Hz, 2H), 7.42 (d, J=6.0 Hz, 2H), 7.20 (s, 2H), 6.49 (s, 1H), 4.32-4.21 (m, 3H), 3.85 (b, 4H), 3.39-3.30 (m, 3H), 3.26-3.15 (m, 5H), 2.92-2.73 (m, 9H), 2.26-2.20 (m, 2H), 1.31 (s, 3H) | 596.3 | 4.45 |

TABLE 5-continued
| Compound | NMR | Mass Spec (LCMS) | Reten. Time (min) |
|---|---|---|---|
| 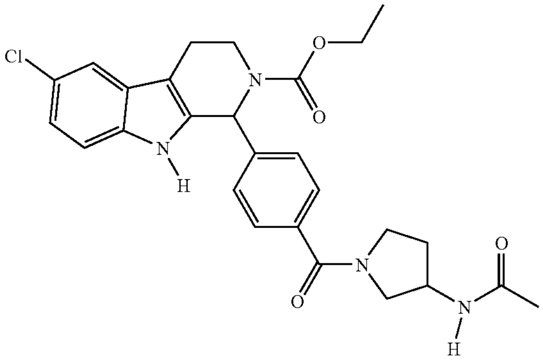 561 | (CD3OD, 400 MHz), δ 7.52 (d, J=8.4 Hz, 2H), 7.47 (s, 1H), 7.39-7.36 (m, 2H), 7.24 (d, J=8.8 Hz, 1H), 7.06 (dd, J=8.4 Hz and 1.6 Hz, 1H), 6.49 (b, 1H), 4.45-4.23 (m, 4H), 3.84-3.45 (m, 4H), 3.20-3.12 (m, 1H), 2.91-2.78 (m, 2H), 2.25-2.10 (m, 1H), 1.98-1.89 (m, 4H), 1.32 (s, 3H) | 509.2 | 5.18 |
| 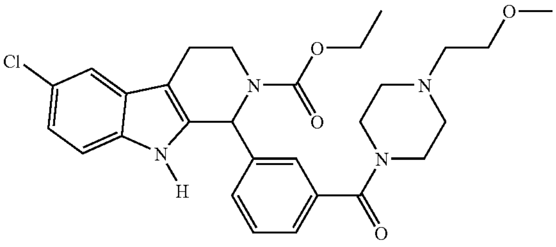 562 | (CD3OD, 400 MHz), δ 7.52-7.45 (m, 4H), 7.32 (b, 1H), 7.25 (d, J=8.4 Hz, 1H), 7.08 (dd, J=8.4 Hz and 1.6 Hz, 1H), 6.49 (b, 1H), 4.34-4.23 (m, 4H), 3.69 (s, 3H), 3.31-3.30 (m, 8H), 3.21-3.12 (m, 3H), 2.91-2.74 (m, 2H), 1.32 (s, 3H) | 525.3 | 3.52 |
| 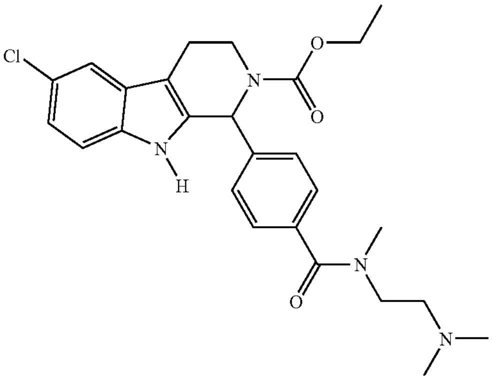 563 | (CD3OD, 400 MHz), δ 7.51-7.48 (m, 3H), 7.40 (d, J=8.0 Hz, 2H), 7.24 (d, J=8.8 Hz, 1H), 7.07 (dd, J=8.4 Hz and 1.2 Hz, 1H), 6.49 (b, 1H), 4.35-4.21 (m, 3H), 3.89 (b, 2H), 3.45 (b, 2H), 3.19-3.10 (m, 1H), 3.05-3.01 (m, 9H), 2.91-2.78 (m, 2H), 1.32 (b, 3H) | 483.1 | 4.96 |
| 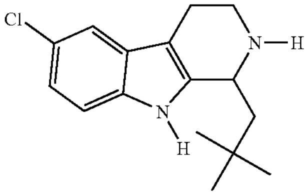 565 | (CD3OD, 400 MHz), δ 7.47 (d, J=1.6 Hz 1H), 7.35 (d, J=8.4 Hz, 1H), 7.12 (dd, J=8.4 Hz and J=2.0 Hz, 1H), 4.87 (s, 1H), 3.75-3.72 (m, 1H), 3.50-3.47 (m, 1H), 3.09-3.03 (m, 2H), 2.22 (dd, J=15.6 Hz and J=2.4 Hz, 1H), 1.84 (dd, J=15.6 Hz and 8.4 Hz, 1H), 1.17 (s, 9H) | 276.9 | 4.00 |

TABLE 5-continued

| Compound | NMR | Mass Spec (LCMS) | Reten. Time (min) |
|---|---|---|---|
| 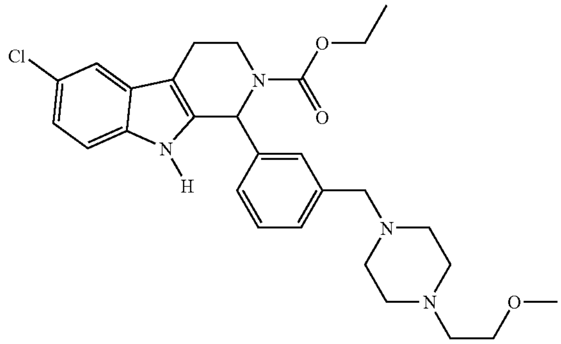 567 | (CD3OD, 400 MHz), δ 7.48 (d, J=1.6 Hz, 1H), 7.41-7.32 (m, 3H), 7.23 (d, J=8.4 Hz, 2H), 7.07 (dd, J=8.4 Hz and 2.0 Hz, 1H), 6.46 (b, 1H), 4.32-4.17 (m, 3H), 3.80 (s, 2H), 3.67 (t, J=5.0 Hz, 2H), 3.39 (s, 3H), 3.30-15 (m, 6H), 2.88-2.83 (m, 6H), 1.32 (s, 3H) | 511.4 | 4.71 |
| 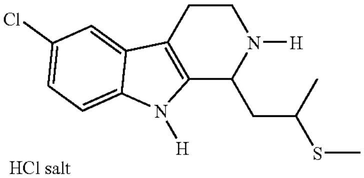 HCl salt 568 | (DMSO, 400 MHz), δ 11.39 (d, J=2.8 Hz, 1H), 9.75 (s, 1H), 9.34 (s, 1H), 7.53 (s, 1H), 7.36 (dd, J=8.4 Hz and 4.0 Hz, 1H), 7.10 (dd, J=8.8 Hz and 2.0 Hz, 1H), 4.82-4.71 (m, 1H), 3.62-3.56 (m, 1H), 3.14 (b, 1H), 3.00-2.83 (m, 2H), 2.35-2.23 (m, 1H), 2.18-1.82 (m, 4H), 1.34 (q, J=6.4 Hz, 3H) | 295.0 | 4.14 |

Example 2

Assay to Evaluate Affect on Hypoxia-Inducible Endogenous VEGF Expression

The ability of the compounds of the invention to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a compound of the invention. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using Cell Titer Glo (Promega) under the same conditions as the ELISA to ensure that the inhibition of VEGF expression was not due to the cytotoxicity. Dose-response curves may be plotted using percentage inhibition versus concentration of the compound, and $EC_{50}$ and $CC_{50}$ values may be generated for each compound with the maximal inhibition set as 100% and the minimal inhibition as 0%.

Preferred compounds of the invention will have an $EC_{50}$ of less than 50, preferably less than 10, more preferably less than 2, even more preferably less than 0.5, and even more preferably less than 0.01.

FIG. 1 shows the ability of a typical compound of the invention, Compound No. 7, to inhibits endogenous VEGF production in tumor cells under hypoxic conditions. The ELISA $EC_{50}$ is 0.0025 μM, while its $CC_{50}$ (50% cytotoxicity) is greater than 0.2 μM. The $EC_{50}$ for a series of preferred compounds of the invention is provided in Table 6.

TABLE 6

| Compound | LCMS [M + H] | LCMS Retention Time (min) | ELISA EC50 μM |
|---|---|---|---|
| 1 | 391.20 | 3.67 | **** |
| 2 | 385.28 | 4.01 | ***** |
| 3 | 479.18 | 4.35 | ***** |
| 4 | 435.23 | 4.28 | ***** |
| 5 | 391.28 | 4.05 | ***** |
| 6 | 425.28 | 4.07 | ***** |
| 7 | 443.28 | 4.61 | ***** |
| # 8 | 415.26 | 4.25 | ***** |
| 9 | 431.25 | 4.07 | ***** |
| # 10 | 467.15 | 4.51 | ***** |
| 11 | 389.24 | 4.24 | ***** |
| 12 | 414.31 | 3.94 | ***** |
| 13 | 411.24 | 4.89 | ***** |
| 14 | 397.22 | 4.57 | ***** |
| 15 | 457.3 | 4.24 | ***** |
| 16 | 435.19 | 4.47 | ***** |
| 17 | 447.14 | 4.44 | ***** |
| 18 | 431.14 | 4.55 | ***** |
| 19 | 437.26 | 4.54 | ***** |
| 20 | 389.24 | 4.22 | ***** |
| 21 | 391.28 | 4.04 | ***** |
| 22 | 425.28 | 4.11 | ***** |
| 23 | 373.23 | 4.04 | ***** |
| 24 | 411.24 | 4.8 | ***** |
| 25 | 449.23 | 4.03 | ***** |
| 26 | 437.15 | 4.52 | ***** |
| 27 | 399.25 | 4.11 | ***** |
| 28 | 399.19 | 4.2 | ***** |
| 29 | 435.09 | 4.14 | ***** |
| 30 | 413.22 | 4.42 | ***** |
| 31 | 423.17 | 4.32 | ***** |
| 32 | 467.25 | 4.26 | ***** |
| 33 | 457.15 | 4.29 | ***** |
| 34 | 383.19 | 4.42 | ***** |
| 35 | 425.28 | 4.14 | ***** |
| 36 | 383.2 | 4.37 | ***** |
| 37 | 423.3 | 4.24 | ***** |
| 38 | 355.24 | 4.07 | ***** |

TABLE 6-continued

| Compound | LCMS [M + H] | LCMS Retention Time (min) | ELISA EC50 μM |
|---|---|---|---|
| 39 | 391.28 | 4.12 | ***** |
| 40 | 403.15 | 4.45 | ***** |
| 41 | 449.11 | 4.59 | ***** |
| 42 | 383.19 | 4.44 | ***** |
| 43 | 371.31 | 3.89 | ***** |
| 44 | 479.18 | 4.35 | ***** |
| 45 | 394.16 | 4.09 | ***** |
| 46 | 421.19 | 4.22 | **** |
| 47 | 449.07 | 4.54 | **** |
| 48 | 403.32 | 4.2 | **** |
| 49 | 403.15 | 4.51 | **** |
| 50 | 405.18 | 3.81 | **** |
| 51 | 373.23 | 4.11 | **** |
| 52 | 355.3 | 4.07 | **** |
| 53 | 375.26 | 3.92 | **** |
| 54 | 435.23 | 4.3 | **** |
| 55 | 425.27 | 4.26 | **** |
| 56 | 414.14 | 4.19 | **** |
| 57 | 399.19 | 4.2 | **** |
| 58 | 469.22 | 4.32 | **** |
| 59 | 444.12 | 4.12 | **** |
| 60 | 433.17 | 4.27 | **** |
| 61 | 419.28 | 4.04 | **** |
| 62 | 409.14 | 4.22 | **** |
| 63 | 435.09 | 4.16 | **** |
| 64 | 435.12 | 4.27 | **** |
| 65 | 387.2 | 3.95 | **** |
| 66 | 414.17 | 4.24 | **** |
| 67 | 429.3 | 4.47 | **** |
| 68 | 359.19 | 3.89 | **** |
| 69 | 449.08 | 4.55 | **** |
| 70 | 375.25 | 4.19 | **** |
| 71 | 394.16 | 4.12 | **** |
| 72 | 403.15 | 4.49 | **** |
| 73 | 381.09 | 3.59 | **** |
| # 74 | 400.15 | 4.05 | **** |
| 75 | 387.22 | 4.29 | **** |
| 76 | 449.26 | 4.3 | **** |
| 77 | 391.28 | 4.19 | **** |
| 78 | 435.12 | 4.24 | **** |
| 79 | 437.19 | 4.49 | **** |
| 80 | 437.2 | 3.84 | **** |
| 81 | 375.03 | 3.57 | **** |
| 82 | 391.28 | 4.05 | **** |
| 83 | 425.28 | 4.16 | **** |
| 84 | 359.22 | 3.95 | **** |
| 85 | 437.15 | 4.44 | **** |
| 86 | 399.19 | 4.22 | **** |
| 87 | 403.15 | 4.44 | **** |
| 88 | 399.19 | 4.17 | **** |
| 89 | 434.07 | 4.04 | **** |
| 90 | 387.23 | 4.26 | **** |
| 91 | 369.27 | 4.17 | **** |
| 92 | 377.29 | 4.04 | **** |
| 93 | 435.23 | 4.29 | **** |
| 94 | 369.17 | 4.24 | **** |
| 95 | 449.06 | 4.51 | **** |
| 96 | 341.27 | 3.89 | **** |
| 97 | 387.19 | 4.2 | **** |
| 98 | 405.18 | 3.79 | **** |
| 99 | 469.22 | 4.29 | **** |
| 100 | 461.32 | 4.61 | **** |
| 101 | 369.17 | 4.26 | **** |
| 102 | 413.28 | 4.02 | **** |
| 103 | 407.1 | 4.05 | **** |
| 104 | 375.27 | 4.11 | **** |
| 105 | 387.21 | 4.19 | **** |
| 106 | 373.18 | 4.04 | **** |
| 107 | 385.28 | 4.02 | **** |
| 108 | 359.16 | 3.92 | **** |
| 109 | 369.34 | 4.16 | **** |
| 110 | 374.24 | 3.07 | **** |
| 111 | 386.19 | 3.89 | **** |
| 112 | 369.27 | 2.63 | **** |
| 113 | 399.13 | 4.01 | **** |
| 114 | 389.3 | 4.05 | **** |

TABLE 6-continued

| Compound | LCMS [M + H] | LCMS Retention Time (min) | ELISA EC50 μM |
|---|---|---|---|
| 115 | 435.13 | 4.14 | **** |
| 116 | 407.16 | 4.09 | **** |
| 117 | 419.28 | 4.05 | **** |
| 118 | 366.29 | 3.79 | **** |
| 119 | 521.19 | 4.16 | **** |
| 120 | 380.31 | 3.92 | **** |
| 121 | 403.32 | 4.27 | **** |
| 122 | 383.31 | 4.37 | **** |
| 123 | 319.2 | 2.19 | **** |
| 124 | 351.14 | 2.53 | *** |
| 125 | 409.3 | 4.14 | *** |
| 126 | 423.3 | 3.95 | *** |
| 127 | 371.31 | 3.9 | *** |
| 128 | 371.31 | 3.62 | *** |
| 129 | 449.13 | 3.81 | *** |
| 130 | 401.23 | 3.56 | *** |
| 131 | 385.22 | 3.74 | *** |
| 132 | 363.06 | 2.31 | *** |
| 133 | 385.15 | 3.86 | *** |
| 134 | 377.3 | 4.04 | *** |
| 135 | 397.15 | 2.42 | *** |
| 136 | 443.33 | 4.11 | *** |
| 137 | 361.07 | 2.53 | *** |
| 138 | 345.07 | 3.15 | *** |
| 139 | 400.27 | 4.01 | *** |
| 140 | 488.23 | 4.36 | *** |
| 141 | 425.21 | 4.37 | *** |
| 142 | 462.15 | 4.11 | *** |
| 143 | 369.23 | 3.74 | *** |
| 144 | 415.33 | 3.84 | *** |
| 145 | 361.3 | 4.39 | *** |
| 146 | 400.21 | 3.81 | *** |
| 147 | 438.21 | 3.97 | *** |
| 148 | 469.01 | 4.42 | *** |
| 149 | 425.25 | 4.24 | *** |
| 150 | 504.2 | 4.68 | *** |
| 151 | 397.01 | 2.44 | *** |
| 152 | 369.21 | 3.59 | *** |
| 153 | 372.21 | 2.36 | *** |
| 154 | 377.29 | 3.97 | *** |
| 155 | 363.11 | 2.32 | *** |
| 156 | 341.21 | 2.46 | *** |
| 157 | 407.14 | 1.78 | *** |
| 158 | 428.11 | 3.85 | *** |
| 159 | 351.13 | 2.47 | *** |
| 160 | 450.15 | 3.95 | *** |
| 161 | 363.05 | 2.32 | *** |
| 162 | 325.26 | 2.66 | *** |
| 163 | 319.2 | 2.24 | *** |
| 164 | 462.19 | 3.87 | *** |
| 165 | 371.31 | 3.65 | *** |
| 166 | 354.28 (−Boc) | 3.95 | *** |
| 167 | 432.16 | 3.87 | *** |
| 168 | 351.08 | 2.4 | *** |
| 169 | 385.35 | 4.09 | *** |
| 170 | 351.07 | 2.51 | *** |
| 171 | 363.09 | 2.68 | ** |
| 172 | 384.21 | 3.52 | ** |
| 173 | 319.2 | 2.24 | ** |
| 174 | N/A | 2.38 | ** |
| 175 | 443.33 | 4.09 | ** |
| 176 | 417.30 | 2.77 | ** |
| 177 | 398.17 | 3.67 | ** |
| 178 | 363.11 | 2.31 | ** |
| 179 | 450.14 | 3.89 | ** |
| 180 | 421.19 | 2.65 | ** |
| 181 | 363.15 | 2.46 | ** |
| 182 | 419.14 | 4.14 | ** |
| 183 | 389.29 | 4.14 | ** |
| 184 | 431.27 | 4.1 | ** |
| 185 | 328.02 | 2.41 | ** |
| 186 | 462.19 | 3.81 | ** |
| 187 | 443.28 | 3.99 | ** |
| 188 | 446.19 | 3.81 | ** |
| 189 | 405.19 | 3.8 | ** |

TABLE 6-continued

| Compound | LCMS [M + H] | LCMS Retention Time (min) | ELISA EC50 µM |
|---|---|---|---|
| 190 | 317.16 | 2.7 | ** |
| 191 | 369.23 | 3.89 | ** |
| 192 | 495.28 | 4.89 | ** |
| 193 | 297.2 | 2.53 | ** |
| 194 | 319.21 | 2.19 | ** |
| 195 | 494.25 | 2.79 | ** |
| 196 | 419.22 | 4.09 | ** |
| 197 | 317.16 | 2.41 | ** |
| 198 | 317.08 | 2.53 | ** |
| 199 | 448.24 | 3.95 | ** |
| 200 | 363.09 | 2.45 | ** |
| 201 | 365.09 | 2.36 | ** |
| 202 | 464.2 | 4.32 | ** |
| 203 | 301.18 | 2.27 | ** |
| 204 | 429.23 | 3.57 | ** |
| 205 | 301.15 | 2.27 | ** |
| 206 | 476.3 | 4.33 | ** |
| 207 | 395.17 | 2.55 | ** |
| 208 | 367.36 | 2.72 | ** |
| 209 | 353.33 | 3.97 | ** |
| 210 | 313.21 | 2.33 | ** |
| 211 | 415.26 | 4.07 | ** |
| 212 | 389.2 | 2.88 | ** |
| 213 | 407.1 | 2.46 | ** |
| 214 | 357.07 | 2.48 | ** |
| 215 | 319.23 | 2.24 | ** |
| 216 | 283.1 | 2.41 | ** |
| 217 | 418.17 | 3.62 | ** |
| 218 | 435.23 | 3.77 | ** |
| 220 | 308.23 | 2.37 | ** |
| 221 | 460.29 | 4.05 | ** |
| 222 | 365.11 | 2.52 | ** |
| 223 | 441.02 | 2.6 | ** |
| 224 | 341.27 | 2.6 | ** |
| 225 | 467.25 | 4.18 | ** |
| 226 | 369.34 | 4.01 | ** |
| 227 | 327.16 | 2.26 | ** |
| 228 | 369.34 | 2.64 | ** |
| 229 | 373.29 | 4.04 | * |
| 230 | 401.23 | 3.2 | * |
| 231 | 313.12 | 2.43 | * |
| 232 | 433.25 | 2.73 | * |
| 233 | 430.38 (−Boc) | 4.34 | * |
| 234 | 351.17 | 2.4 | * |
| 235 | 351.25 | 3.79 | * |
| 236 | 379.35 | 2.74 | * |
| 237 | 439.11 | 4.41 | * |
| 238 | 479.24 | 3.77 | * |
| 239 | 328.16 | 2.35 | * |
| 240 | 307.27 | 3.87 | * |
| 241 | 523.19 | 3.7 | * |
| 242 | 438.27 | 4.14 | * |
| 243 | 323.20 | 3.49 | * |
| 244 | 512 | 2.27 | * |
| 245 | 485 | 2.62 | * |
| 246 | 498 | 2.54 | * |
| 247 | 471 | 2.36 | * |
| 248 | 283.23 | 2.24 | * |
| 249 | 339.17 | 3.07 | * |
| 250 | 355.30 | 3.57 | * |
| 251 | 297.26 | 2.26 | * |
| 252 | 341.21 | 2.44 | * |
| 253 | 301.27 | 2.29 | * |
| 254 | 301.25 | 2.27 | * |
| 255 | 281.31 | 2.2 | * |
| 256 | 345.2 | 2.26 | * |
| 257 | 335.21 | 2.34 | * |
| 258 | 459.27 | 3.72 | * |
| 259 | 479.24 | 3.52 | * |
| 260 | 287.26 | 2.36 | * |
| 261 | 287.26 | 2.56 | * |
| 262 | 380.24 | 3.92 | * |
| 263 | 503.50 | 3.20 | * |
| 264 | 369.36 | 2.52 | * |
| 265 | 355.26 | 2.54 | * |
| 266 | 355.26 | 2.42 | * |
| 267 | 370.22 | 3.61 | * |
| 268 | 355.26 | 2.42 | * |
| 269 | 355.27 | 2.37 | * |
| 270 | 370.23 | 3.19 | * |
| 271 | 369.34 | 2.62 | * |
| 272 | 374.31 | 2.90 | * |
| 273 | 492.25 | 2.76 | * |
| 274 | 451.30 | 3.17 | * |
| 275 | 374.31 | 2.61 | * |
| 276 | 374.31 | 2.72 | * |
| 277 | 349.28 | 1.5 | * |
| 278 | 457.28 | 4.11 | * |
| 279 | | | ***** |
| 280 | 407.10 | 3.92 | * |
| 281 | 508.15 | 4.74 | * |
| 282 | 507.08 | 4.42 | * |
| 283 | 422.32 | 3.86 | * |
| 284 | 373.29 | 4.01 | * |
| 285 | 385.24 | 2.25 | * |
| 286 | 297.2 | 2.52 | * |
| 287 | 289.22 | 2.48 | * |
| 288 | 461.26 | 2.57 | * |
| 289 | 380.29 | 3.82 | * |
| 290 | 396.27 | 3.60 | * |
| 291 | 299.17 | 2.43 | * |
| 292 | 385.18 | 2.6 | * |
| 293 | 413.22 | 3.8 | * |
| 294 | 340.25 | 2.27 | * |
| 295 | 404.34 | 3.84 | * |
| 296 | 299.17 | 2.23 | * |
| 297 | 326.24 | 2.4 | * |
| 298 | 235.13 | 2.18 | * |
| 299 | 351.16 | 2.62 | * |
| 300 | 401 | 2.57 | * |
| 301 | 313.21 | 2.35 | * |
| 302 | 398.28 | 3.74 | * |
| 303 | 355.22 | 2.58 | * |
| 304 | 440.32 | 4.09 | * |
| 305 | 341.08 | 2.48 | * |
| 306 | 364.3 | 3.65 | * |
| 307 | 350.32 | 3.35 | * |
| 308 | 432.27 | 3.92 | * |
| 309 | 474.26 | 3.02 | **** |
| 310 | 289.03 | 2.35 | * |
| 311 | 345.19 | 2.58 | * |
| 312 | 420.28 | 4.12 | * |
| 313 | 279.28 | 2.18 | * |
| 314 | 293.24 | 2.20 | * |
| 315 | 297.26 | 2.17 | * |
| 316 | 472.26 | 3.85 | * |
| 317 | 428.25 | 3.95 | * |
| 318 | 309 | 2.25 | * |
| 319 | 284.09 | 2.1 | * |
| 320 | 356.21 | 2.37 | * |
| 321 | 279.2 | 2.1 | * |
| 322 | 279.2 | 1.76 | * |
| 323 | 309.23 | 1.82 | * |
| 324 | 280.19 | 1.76 | * |
| 325 | 279.2 | 1.76 | * |
| 326 | 263.17 | 1.93 | * |
| 327 | 343.18 | 2.33 | * |
| 328 | ~0.005 | 4.16 | * |
| 329 | 0.0036 | 4.26 | * |
| 330 | 0.0047 | 4.24 | * |
| 331 | ~0.010 | 2.94 | * |
| # 332 | ~0.010 | 4 | * |
| 333 | 410.27 | 3.64 | ** |
| 334 | 426.24 | 3.39 | * |
| 335 | 466.23 | 4.64 | *** |
| 336 | 438.31 | 4.31 | ** |
| 337 | 454.24 | 4.63 | *** |
| 338 | 474.32 | 4.33 | ** |
| 339 | 412.3 | 3.83 | * |
| 340 | 446.33 | 4.49 | * |
| 341 | 447.26 | 4.25 | *** |

TABLE 6-continued

| Compound | LCMS [M + H] | LCMS Retention Time (min) | ELISA EC50 μM |
|---|---|---|---|
| 342 | 371.31 | 3.88 | *** |
| 343 | 371.31 | 3.61 | * |
| 344 | 459.31 | 4.91 | **** |
| 345 | 383.35 | 4.44 | **** |
| 346 | 587 | 4.04 | **** |
| 347 | 451.16 | 3.93 | ***** |
| 348 | 479.28 | 4.13 | ***** |
| 349 | 481.21 | 3.74 | **** |
| 350 | 462.17 | 3.66 | ***** |
| 351 | 471.17 | 3.93 | **** |
| 352 | 403.29 | 3.98 | **** |
| 353 | 497.16 | 3.94 | ***** |
| 354 | 525.2 | 4.19 | ***** |
| 355 | 511.21 | 3.81 | ***** |
| 356 | 490.3 | 3.93 | ** |
| 357 | 534.23 | 3.93 | *** |
| 358 | 433.2 | 3.45 | *** |
| 359 | 511.25 | 3.64 | *** |
| 360 | 516 | 3.82 | **** |
| 361 | 474.26 | 3.02 | **** |
| 362 | 427 | 4.2 | ***** |
| 363 | 412.4 | 1.80 | * |
| 364 | 484.3 | 2.49 | ***** |
| 365 | 457.3 | 4.06 | *** |
| 366 | 553.3 | 4.42 | * |
| 367 | 402.8 | 4.37 | **** |
| 368 | 430.9 | 4.79 | ** |
| 369 | 427.0 | 4.06 | ** |
| 370 | 427.0 | 3.99 | ***** |
| 371 | 469.0 | 5.27 | *** |
| 372 | 486.9 | 4.96 | * |
| 373 | 470.8 | 5.01 | *** |
| 374 | 436.9 | 4.66 | *** |
| 375 | 461 | 4.92 | ** |
| 376 | 385 | 3.79 | ** |
| 377 | n/d | n/d | * |
| 378 | n/d | n/d | * |
| 379 | n/d | n/d | * |
| 380 | n/d | n/d | * |
| 381 | n/d | n/d | * |
| 382 | n/d | n/d | * |
| 383 | 417.2 | 4.93 | ***** |
| 384 | 403.22 | 4.65 | ***** |
| 385 | 509.51 | 2.57 | **** |
| 386 | 465.26 | 2.52 | ***** |
| 387 | 465.26 | 2.52 | ***** |
| 388 | 495.4 | 3.94 | ***** |
| 389 | 538.3 | 4.29 | ***** |
| 390 | 480.5 | 3.23 | ***** |
| 391 | 562.55 | 3.63 | ***** |
| 392 | 443.4 | 3.88 | ***** |
| 393 | 447.1 | 6.55 | ***** |
| 394 | 450.1 | 5.48 | ***** |
| 395 | 481.32 | 3.51 | ***** |
| 396 | 411.3 | 3.99 | ***** |
| 397 | 535.3 | 4.29 | ***** |
| 398 | 481.3 | 4.23 | ***** |
| 399 | 429.3 | 3.81 | ***** |
| 400 | 493.3 | 4.43 | ***** |
| 401 | 451.3 | 3.99 | ***** |
| 402 | 494.4 | 3.71 | ***** |
| 403 | 479.3 | 4.23 | ***** |
| 404 | 473.6 | 3.78 | ***** |
| 405 | 551.17 | 4.58 | ***** |
| 406 | 425.4 | 4.13 | ***** |
| 407 | 457.4 | 4.04 | ***** |
| 408 | 425.4 | 4.09 | ***** |
| 409 | 477.4 | 4.18 | ***** |
| 410 | 451.3 | 3.99 | ***** |
| 411 | 443.4 | 3.86 | ***** |
| 412 | 473.4 | 4.23 | ***** |
| 413 | 459.3 | 4.16 | ***** |
| 414 | 439.4 | 4.31 | ***** |
| 415 | 637.64 | 2.82 | ***** |
| 416 | 311.1 | 4.39 | ***** |
| 417 | 562.47 | 4.15 | ***** |
| 418 | 511.3 | 4.13 | ***** |
| 419 | 491.4 | 3.98 | ***** |
| 420 | 486.6 | 3.45 | ***** |
| 421 | 553.30 | 4.05 | ***** |
| 422 | 359.29 | 4.17 | ***** |
| 423 | 447.4 | 3.56 | ***** |
| 424 | 594.2 [M − H] | 4.58 | ***** |
| 425 | 539.2 | 3.11 | ***** |
| 426 | 535.27 | 4.29 | ***** |
| 427 | 554.3 | 4.45 | ***** |
| 428 | 563.55 | 4.64 | ***** |
| 429 | 564.42 | 2.77 | ***** |
| 430 | 431.3 | 3.41 | ***** |
| 431 | 522.2 | 5.05 | ***** |
| 432 | 489.4 | 4.14 | ***** |
| 433 | 578.44 | 2.82 | ***** |
| 434 | 467.18 | 4.11 | ***** |
| 435 | 444.3 | 3.95 | ***** |
| 436 | 477.4 | 3.93 | ***** |
| 437 | 543.4 | 3.92 | ***** |
| 438 | 500.1 | 4.35 | ***** |
| 439 | 361.2 | 5.95 | ***** |
| 440 | 536.43 | 3.95 | ***** |
| 441 | 482.1 | 5.11 | **** |
| 442 | 367.1 | 2.92 | **** |
| 443 | 436.2 | 5.25 | **** |
| 444 | 455.28 | 3.73 | **** |
| 445 | 478 | 3.67 | **** |
| 446 | 383.3 | 4.10 | **** |
| 447 | 464.9 | 5.11 | **** |
| 448 | 501.27 | 3.65 | **** |
| 449 | 482.24 | 2.62 | **** |
| 450 | 587 | 4.04 | **** |
| 451 | 644.3 [M − H] | 4.80 | **** |
| 452 | 439.3 | 3.56 | **** |
| 453 | 553.1 | 6.13 | **** |
| 454 | 579.3 | 2.75 | **** |
| 455 | 583 | 3.84 | **** |
| 456 | 474.3 | 2.44 | **** |
| 457 | 455 | 3.4 | **** |
| 458 | 456.3 | 2.51 | **** |
| 459 | 470.3 | 2.61 | **** |
| 460 | 509.30 | 4.16 | **** |
| 461 | 454.3 | 5.98 | **** |
| 462 | 580.56 | 2.85 | **** |
| 463 | 495.44 | 4.13 | **** |
| 464 | 493.0 | 5.71 | **** |
| 465 | 507.4 | 3.98 | **** |
| 466 | 555.2 | 3.14 | **** |
| 467 | 524.2 | 4.02 | **** |
| 468 | 582.2 | 2.81 | **** |
| 469 | 525.2 | 5.07 | **** |
| 470 | 554.3 | 3.90 | **** |
| 471 | 620.18 | 3.85 | **** |
| 472 | 335.3 | 5.52 | **** |
| 473 | 495.3 | 4.68 | *** |
| 474 | 511.2 | 4.99 | *** |
| 475 | 483 | 3.87 | *** |
| 476 | 400 | 3.45 | *** |
| 477 | 249.1 | 3.67 | *** |
| 478 | 525.1 | 3.25 | *** |
| 479 | 538.3 | 2.76 | *** |
| 480 | 456.1 | 4.26 | *** |
| 481 | 549.3 | 5.29 | *** |
| 482 | 522.3 | 3.95 | *** |
| 483 | 470.1 | 4.46 | *** |
| 484 | 539.2 | 3.02 | *** |
| 485 | 398.9 | 4.18 | *** |
| 486 | 349.1 | 6.03 | *** |
| 487 | 505 | 3.66 | *** |
| 488 | 555.2 | 3.34 | *** |
| 489 | 538.3 | 4.15 | *** |
| 490 | 486.1 | 3.80 | *** |
| 491 | 537.31 | 2.64 | *** |

TABLE 6-continued

| Compound | LCMS [M + H] | LCMS Retention Time (min) | ELISA EC50 μM |
|---|---|---|---|
| 492 | 468 | 5.52 | *** |
| 493 | 504.3 | 2.68 | *** |
| 494 | 482.2 | 5.74 | *** |
| 495 | 403.3 | 4.16 | *** |
| 496 | 430.2 | 3.65 | *** |
| 497 | 281.0 | 3.84 | *** |
| 498 | 481.4 | 4.81 | *** |
| 499 | 423.3 | 5.15 | *** |
| 500 | 506.29 | 3.85 | *** |
| 501 | 534.3 | 2.68 | *** |
| 502 | 518.3 | 2.76 | *** |
| 503 | 508.2 | 5.72 | *** |
| 504 | 359.1 | 5.65 | *** |
| 505 | 442.0 | 4.06 | *** |
| 506 | 386.3 | 5.32 | *** |
| 507 | 450 | 3.19 | *** |
| 508 | 397.1 | 5.97 | *** |
| 509 | 511.4 | 5.05 | *** |
| 510 | 321.4 | 5.19 | *** |
| 511 | 383.1 | 5.75 | *** |
| 512 | 523.1 | 5.69 | *** |
| 513 | 361.1 | 5.12 | *** |
| 514 | 495.3 | 4.67 | *** |
| 515 | 363.5 | 6.34 | ** |
| 516 | 527.1 | 3.16 | ** |
| 517 | 464.2 | 5.86 | ** |
| 518 | 517.6 | 5.03 | ** |
| 519 | 527.2 | 3.88 | ** |
| 520 | 426.2 | 4.29 | ** |
| 521 | 509.4 | 4.99 | ** |
| 522 | 383.3 | 4.10 | ** |
| 523 | 439.0 | 6.11 | ** |
| 524 | 412.1 | 4.13 | ** |
| 525 | 4.95.3 | 3.46 | ** |
| 526 | 513.2 | 4.43 | ** |
| 527 | 535.3 | 4.94 | ** |
| 528 | 453.0 | 6.30 | ** |
| 529 | 481.3 | 3.43 | ** |
| 530 | 466.28 | 3.21 | ** |
| 531 | 549.6 | 5.21 | ** |
| 532 | 325.3 | 4.75 | ** |
| 533 | 506.2 | 4.96 | ** |
| 534 | 525.2 | 4.76 | ** |
| 535 | 541.2 | 3.51 | ** |
| 536 | 482.29 | 3.29 | ** |
| 537 | 476.3 | 2.51 | ** |
| 538 | 516.37 | 3.49 | ** |
| 539 | 337.3 [M − H] | 2.14 | ** |
| 540 | 428.28 | 3.43 | ** |
| 541 | 525.2 | 4.42 | ** |
| 542 | 398.1 | 3.95 | ** |
| 543 | 466.34 | 3.29 | ** |
| 544 | 723.58 | 3.92 | ***** |
| 545 | 466.31 | 3.28 | ** |
| 546 | 426.3 | 2.26 | ** |
| 547 | 335.2 | 5.45 | ** |
| 548 | 516.37 | 3.46 | ** |
| 549 | 414 | 2.89 | ** |
| 550 | 496 | 4.58 | ** |
| 551 | 544.5 | 2.78 | ** |
| 552 | 511.3 | 3.56 | ** |
| 553 | 440.9 | 5.75 | ** |
| 554 | 482.32 | 3.41 | ** |
| 555 | 372 | 2.89 | ** |
| 556 | 456.1 | 4.21 | ** |
| 557 | 538.4 | 3.71 | ** |
| 558 | 497.2 | 4.69 | ** |
| 559 | 460.8 | 4.96 | ** |
| 560 | 596.3 | 4.45 | * |
| 561 | 509.2 | 5.18 | * |
| 562 | 525.3 | 3.52 | * |
| 563 | 483.1 | 4.96 | * |
| 564 | 432 | 2.18 | * |
| 565 | 276.9 | 4.00 | * |
| 566 | 384.4 | 1.73 | * |

TABLE 6-continued

| Compound | LCMS [M + H] | LCMS Retention Time (min) | ELISA EC50 μM |
|---|---|---|---|
| 567 | 511.4 | 4.71 | * |
| 568 | 295.0 | 4.14 | * |
| 569 | 480.21 | 3.50 | ***** |
| 570 | 549.22 | 4.59 | ***** |
| 571 | 497.13 | 3.50 | ** |
| 572 | 525.29 | 4.14 | ***** |
| 573 | 341.34 | 2.14 | **** |
| 574 | 427.37 | 2.23 | * |
| 575 | 437.33 | 3.16 | ** |
| 576 | 575.43 | 3.71 | *** |
| 577 | 453.28 | 3.34 | *** |
| 578 | 610.45 | 3.94 | *** |
| 579 | 481.32 | 3.51 | ***** |
| 580 | 495.29 | 3.64 | ***** |
| 581 | 465.43 | 3.64 | * |
| 582 | 516.34 | 3.31 | * |
| 583 | 512.26 | 3.39 | *** |
| 584 | 466.37 | 3.34 | *** |
| 585 | 516.33 | 3.46 | *** |
| 586 | 387.27 | 2.13 | ***** |
| 587 | 467.29 | 3.66 | *** |
| 588 | 455.26 | 3.69 | *** |
| 589 | 471.3 | 3.83 | *** |
| 590 | 495.31 | 3.64 | **** |
| 591 | 541.35 | 3.73 | ***** |
| 592 | 523.42 | 3.58 | ***** |
| 593 | 541.38 | 3.69 | **** |
| 594 | 505.38 | 3.83 | *** |
| 595 | 431.21 | 4.01 | **** |
| 596 | 431.24 | 3.99 | ***** |
| 597 | 445.24 | 4.19 | ***** |
| 598 | 459.24 | 4.36 | ***** |
| 599 | 513.17 | 4.19 | **** |
| 600 | 479.23 | 3.99 | ***** |
| 601 | 504.21 | 3.79 | **** |
| 602 | 493.2 | 4.18 | **** |
| 603 | 513.16 | 4.19 | **** |
| 604 | 446.18 | 2.86 | * |
| 605 | 503.23 | 3.84 | ***** |
| 606 | 461.19 | 3.46 | *** |
| 607 | 442.25 | 3.46 | *** |
| 608 | 489.2 | 3.72 | *** |
| 609 | 433.27 | 3.98 | ** |
| 610 | n/d | n/d | **** |
| 611 | n/d | n/d | ** |
| 612 | 491.23 | 3.56 | *** |
| 613 | 513.14 | 4.18 | **** |
| 614 | 463 | 3.88 | ** |
| 615 | 381 | 3.48 | *** |
| 616 | 540 | 4.17 | ** |
| 617 | 621.57 | 4.13 | **** |
| 618 | 493.6 | 2.63 | ***** |
| 619 | 521.6 | 2.80 | ***** |
| 620 | 445.5 | 3.23 | **** |
| 621 | 459.5 | 3.40 | ***** |
| 622 | 459.5 | 3.38 | ***** |
| 623 | 473.5 | 3.57 | ***** |
| 624 | 479.5 | 3.28 | **** |
| 625 | 507.6 | 3.53 | ***** |
| 626 | 493.6 | 3.48 | **** |
| 627 | 511.6 | 3.53 | ***** |
| 628 | 527.4 | 3.62 | *** |
| 629 | 527.5 | 3.72 | ***** |
| 630 | 573.5 | 3.75 | ***** |
| 631 | 507.6 | 3.65 | ***** |
| 632 | 538.6 | 3.53 | **** |
| 633 | 443.5 | 3.32 | ***** |
| 634 | 457.6 | 3.30 | ***** |
| 635 | 523.6 | 3.47 | **** |
| 636 | 463.6 | 3.12 | ***** |
| 637 | 621.62 | 2.77 | ***** |
| 638 | 580.56 | 2.80 | ***** |
| 639 | 496.54 | 3.28 | ***** |
| 640 | 552.64 | 2.48 | **** |
| 641 | 445.55 | 4.13 | ***** |
| 642 | 381.49 | 3.97 | ***** |

TABLE 6-continued

| Compound | LCMS [M + H] | LCMS Retention Time (min) | ELISA EC50 μM |
|---|---|---|---|
| 643 | 397.47 | 3.95 | ***** |
| 644 | 395.45 | 3.78 | ***** |
| 645 | 521.15 | 4.17 | ***** |
| 646 | 531.11 | 4.58 | **** |
| 647 | 505.18 | 4.7 | ***** |
| 648 | 437.19 | 4.15 | **** |
| 649 | 477.21 | 4.1 | ***** |
| 650 | 487.18 | 4.3 | **** |
| 651 | 548.3 | 2.53 | **** |
| 652 | 419.23 | 4.15 | **** |
| 653 | 449.24 | 4.12 | **** |
| 654 | 433.26 | 4.3 | ***** |
| 655 | 453.19 | 4.33 | **** |
| 656 | 444.17 | 4.02 | ***** |
| 657 | 464.22 | 4.08 | ***** |
| 658 | 461.6 | 4.30 | ***** |
| 659 | 489.7 | 4.78 | ***** |
| 660 | 543.7 | 4.92 | ***** |
| 661 | 459.5 | 3.63 | ***** |
| 662 | 471.5 | 3.87 | ***** |
| 663 | 491.6 | 3.63 | ***** |
| 664 | 507.6 | 3.80 | ***** |
| 665 | 485.6 | 3.85 | **** |
| 666 | 485.6 | 3.83 | ***** |
| 667 | 486.6 | 3.95 | ***** |
| 668 | 503.6 | 3.58 | ***** |
| 669 | 521.6 | 3.88 | ***** |
| 670 | 521.6 | 4.02 | ***** |
| 671 | 501.6 | 4.13 | ***** |
| 672 | 501.6 | 4.10 | ***** |
| 673 | 539.6 | 4.02 | |
| 674 | 555.6 | 4.13 | **** |
| 675 | 555.6 | 4.22 | **** |
| 676 | 535.6 | 4.05 | **** |
| 677 | 535.6 | 4.15 | **** |
| 678 | 551.6 | 3.98 | *** |
| 679 | 487.6 | 3.93 | **** |
| 680 | 599.5 | 4.27 | ***** |
| 681 | 566.6 | 4.02 | **** |
| 682 | 496.5 | 2.13 | ** |
| 683 | 486.5 | 2.03 | *** |
| 684 | 484.6 | 2.67 | *** |
| 685 | 514.6 | 2.15 | *** |
| 686 | 512.6 | 2.12 | **** |
| 687 | 510.6 | 2.13 | *** |
| 688 | 525.6 | 1.85 | *** |
| 689 | 494.5 | 3.12 | *** |
| 690 | 524.6 | 2.32 | *** |
| 691 | 514.6 | 2.23 | *** |
| 692 | 512.6 | 2.35 | *** |
| 693 | 542.6 | 2.35 | **** |
| 694 | 540.6 | 2.27 | **** |
| 695 | 538.6 | 2.35 | **** |
| 696 | 553.6 | 2.07 | *** |
| 697 | 522.6 | 3.95 | ***** |
| 698 | 578.5 | 2.43 | **** |
| 699 | 568.5 | 2.35 | **** |
| 700 | 566.6 | 2.45 | **** |
| 701 | 596.6 | 2.47 | **** |
| 702 | 594.6 | 2.43 | **** |
| 703 | 592.6 | 2.48 | **** |
| 704 | 607.6 | 2.20 | *** |
| 705 | 575.5 | 2.47 | **** |
| 706 | 576.5 | 3.58 | ***** |
| 707 | 477.51 | 2.77 | ***** |
| 708 | 491.53 | 2.73 | ***** |
| 709 | 503.55 | 2.68 | ***** |
| 710 | 495.45 | 4.42 | ***** |
| 711 | 475.51 | 4.62 | ***** |
| 712 | 513.50 | 4.42 | ***** |
| 713 | 529.46 | 4.62 | **** |
| 714 | 509.51 | 4.43 | ***** |
| 715 | 482.46 | 4.28 | ***** |
| 716 | 457.47 | 4.05 | **** |
| 717 | 459.59 | 4.33 | ***** |
| 718 | 491.5 | 4.10 | ***** |

TABLE 6-continued

| Compound | LCMS [M + H] | LCMS Retention Time (min) | ELISA EC50 μM |
|---|---|---|---|
| 719 | 527.5 | 4.47 | ***** |
| 720 | 489.5 | 4.75 | ***** |
| 721 | 517.5 | 4.26 | ***** |
| 722 | 519.5 | 3.84 | ***** |
| 723 | 555.4 | 4.09 (non polar) | ***** |
| 724 | 541.54 | 2.90 | ***** |
| 725 | 478.47 | 3.58 | ***** |
| 726 | 516.5 | 2.67 | ** |
| 727 | 526.5 | 2.78 | **** |
| 728 | 544.5 | 2.80 | *** |
| 729 | 542.5 | 2.72 | ***** |
| 730 | 540.5 | 2.83 | **** |
| 731 | 555.6 | 2.43 | *** |
| 732 | 580.6 | 2.40 | *** |
| 733 | 523.5 | 2.78 | ***** |
| 734 | 524.5 | 3.40 | ***** |
| 735 | 552.5 | 2.98 | ***** |
| 736 | 562.5 | 3.15 | ***** |
| 737 | 580.6 | 3.17 | **** |
| 738 | 578.5 | 3.02 | ***** |
| 739 | 576.6 | 3.17 | ***** |
| 740 | 591.6 | 2.75 | *** |
| 741 | 616.5 | 2.62 | *** |
| 742 | 559.5 | 3.13 | ***** |
| 743 | 560.5 | 3.83 | ***** |
| 744 | 514.6 | 2.80 | ***** |
| 745 | 524.6 | 2.92 | ***** |
| 746 | 512.5 | 2.93 | ***** |
| 747 | 542.6 | 2.93 | ***** |
| 748 | 540.5 | 2.85 | ***** |
| 749 | 538.6 | 2.93 | ***** |
| 750 | 553.6 | 2.55 | ***** |
| 751 | 521.5 | 2.92 | **** |
| 752 | 522.5 | 3.87 | ***** |
| 753 | 542.6 | 2.98 | **** |
| 754 | 552.6 | n/d | ***** |
| 755 | 540.6 | 3.17 | **** |
| 756 | 570.6 | 3.17 | **** |
| 757 | 568.6 | 3.07 | ***** |
| 758 | 566.6 | 3.17 | *** |
| 759 | 581.6 | 2.78 | *** |
| 760 | 549.6 | 3.13 | ***** |
| 761 | 550.5 | 4.17 | ***** |
| 762 | 544.5 | 2.68 | **** |
| 763 | 554.5 | 2.77 | ***** |
| 764 | 542.6 | 2.78 | **** |
| 765 | 572.5 | 2.75 | **** |
| 766 | 570.6 | 2.70 | ***** |
| 767 | 568.6 | 2.82 | **** |
| 768 | 583.6 | 2.47 | **** |
| 769 | 608.6 | 2.38 | *** |
| 770 | 551.5 | 2.73 | ***** |
| 771 | 552.5 | 3.65 | ***** |
| 772 | 580.5 | 3.03 | ***** |
| 773 | 590.6 | 3.12 | ***** |
| 774 | 578.5 | 3.12 | **** |
| 775 | 608.6 | 3.05 | ***** |
| 776 | 606.5 | 3.05 | ***** |
| 777 | 604.6 | 3.12 | ***** |
| 778 | 619.6 | 2.77 | ***** |
| 779 | 644.5 | 2.63 | *** |
| 780 | 587.5 | 3.10 | ***** |
| 781 | 588.5 | 4.05 | ***** |
| 782 | 596.5 | 3.10 | ***** |
| 783 | 606.5 | 3.18 | ***** |
| 784 | 594.5 | 3.27 | ***** |
| 785 | 624.5 | 3.22 | ***** |
| 786 | 622.5 | 3.12 | ***** |
| 787 | 620.5 | 3.20 | ***** |
| 788 | 635.6 | 2.85 | **** |
| 789 | 660.5 | 2.68 | *** |
| 790 | 603.5 | 3.22 | ***** |
| 791 | 604.5 | 4.25 | ***** |
| 792 | 480.50 | 2.98 | ***** |
| 793 | 494.50 | 2.97 | **** |

TABLE 6-continued

| Compound | LCMS [M + H] | LCMS Retention Time (min) | ELISA EC50 μM |
|---|---|---|---|
| 794 | 494.50 | 2.97 | *** |
| 795 | 496.48 | 2.97 | **** |
| 796 | 563.50 | 2.41 | **** |
| 797 | 522.48 | 2.50 | ***** |
| 798 | 538.48 | 2.92 | ***** |
| 799 | 535.49 | 2.35 | *** |
| 800 | 503.40 | 2.52 | **** |
| 801 | 504.43 | 3.42 | ***** |
| 802 | 504.42 | 3.37 | ***** |
| 803 | 579.48 | 2.42 | **** |
| 804 | 538.48 | 2.43 | ***** |
| 805 | 584.50 | 2.52 | ***** |
| 806 | 554.40 | 2.47 | ***** |
| 807 | 540.47 | 2.50 | ***** |
| 808 | 551.48 | 2.33 | **** |
| 809 | 516.45 | 2.47 | ***** |
| 810 | 520.40 | 3.21 | ***** |
| 811 | 520.40 | 3.12 | ***** |
| 812 | 466.4 | 3.27 | ***** |
| 813 | 466.4 | 3.18 | ***** |
| 814 | 465.4 | 2.38 | ***** |
| 815 | 465.4 | 3.45 | ***** |
| # 816 | 497.4 | 2.70 | ***** |
| # 817 | 511.4 | 2.62 | ***** |
| # 818 | 491.4 | 2.43 | **** |
| 819 | 494.4 | 3.53 | ***** |
| 820 | 494.4 | 3.47 | **** |
| 821 | 493.4 | 2.55 | **** |
| 822 | 493.4 | 3.73 | ***** |
| # 823 | 525.4 | 2.95 | ***** |
| # 824 | 539.4 | 2.83 | ***** |
| # 825 | 519.4 | 2.58 | * |
| 826 | 496.4 | 3.07 | *** |
| 827 | 496.4 | 2.98 | **** |
| 828 | 495.4 | 2.32 | *** |
| 829 | 495.4 | 3.28 | *** |
| # 830 | 527.4 | 2.53 | ***** |
| # 831 | 541.4 | 2.50 | ***** |
| # 832 | 521.4 | 2.35 | |
| 833 | 532.4 | 3.50 | *** |
| 834 | 532.4 | 3.42 | **** |
| 835 | 531.4 | 2.57 | *** |
| 836 | 531.4 | 3.67 | **** |
| # 837 | 563.4 | 2.93 | ***** |
| # 838 | 577.4 | 2.82 | ***** |
| 839 | 548.3 | 3.63 | **** |
| 840 | 548.3 | 3.58 | **** |
| # 841 | 579.3 | 3.08 | ***** |
| # 842 | 593.3 | 2.95 | ***** |
| # 843 | 573.4 | 2.75 | ***** |
| 844 | 451.91 | 3.58 | *** |
| 845 | 648.48 | 4.45 | *** |
| 846 | 526.45 | 2.57 | *** |
| 847 | 568.37 | 3.40 | **** |
| 848 | 585.30 | 3.57 | ***** |
| 849 | 604.37 | 3.52 | **** |
| 850 | 540.39 | 2.60 | *** |
| 851 | 495.06 | 4.37 | ***** |
| 852 | 539.08 | 4.17 | ***** |
| 853 | 549.09 | 4.38 | ***** |
| 854 | 523.17 | 4.73 | ***** |
| 855 | 455.19 | 4.15 | **** |
| 856 | 495.18 | 4.10 | ***** |
| 857 | 505.16 | 4.30 | ***** |
| 858 | 566.3 | 2.57 | ***** |
| 859 | 437.22 | 4.15 | ***** |
| 860 | 467.2 | 4.13 | ***** |
| 861 | 451.12 | 4.10 | **** |
| 862 | 471.17 | 4.32 | ***** |
| 863 | 514.55 | 4.38 | ***** |
| 864 | 462.28 | 4.00 | **** |
| 865 | 482.13 | 4.08 | **** |
| 866 | 447.37 | 4.04 | ***** |
| 867 | 577.43 | 2.85 | **** |
| 868 | 477.14 | 4.37 | ***** |
| 869 | 504.53 | 3.62 | ***** |

TABLE 6-continued

| Compound | LCMS [M + H] | LCMS Retention Time (min) | ELISA EC50 μM |
|---|---|---|---|
| 870 | 493.55 | 2.80 | ***** |
| 871 | 489.54 | 2.72 | ***** |
| 872 | 493.55 | 2.80 | ***** |
| 873 | 503.54 | 2.73 | ***** |
| 874 | 479.2 | 2.74 | ***** |
| 875 | 425.52 | 4.27 | ***** |
| 876 | 492.52 | 3.57 | ***** |
| 877 | 489.54 | 2.72 | ***** |
| 878 | 508.55 | 3.82 | ***** |
| 879 | 507.55 | 2.90 | ***** |
| 880 | 459.49 | 4.24 | ***** |
| 881 | 471.45 | 4.22 | ***** |
| 882 | 542.51 | 3.87 | ***** |
| 883 | 494.50 | 3.67 | ***** |
| 884 | 544.27 | 2.79 | ***** |
| 885 | 490.54 | 3.54 | ***** |
| 886 | 494.57 | 3.68 | ***** |
| 887 | 521.62 | 2.93 | ***** |
| 888 | 558.54 | 3.70 | ***** |
| 889 | 545.55 | 2.93 | ***** |
| 890 | 490.49 | 3.48 | ***** |
| 891 | 528.49 | 3.69 | ***** |
| 892 | 546.50 | 3.75 | ***** |
| 893 | 461.49 | 4.36 | ***** |
| 894 | 580.47 | 2.72 | ***** |
| 895 | 491.51 | 2.77 | ***** |
| 896 | 576.49 | 4.00 | ***** |
| 897 | 504.51 | 3.52 | ***** |
| 898 | 457.53 | 4.25 | ***** |
| 899 | 481.37 | 4.17 | ***** |
| 900 | 541.55 | 3.00 | ***** |
| 901 | 575.54 | 2.98 | ***** |
| 902 | 471.49 | 4.12 | ***** |
| 903 | 621.39 | 2.72 | ***** |
| 904 | 596.54 | 2.85 | ***** |
| 905 | 542.54 | 3.78 | ***** |
| 906 | 489.53 | 4.82 | ***** |
| 907 | 514.47 | 3.54 | ***** |
| 908 | 582.43 | 2.79 | ***** |
| 909 | 514.21 | 2.75 | ***** |
| 910 | 539.45 | 3.97 | ***** |
| 911 | 527.54 | 2.88 | ***** |
| 912 | 530.53 | 2.67 | ***** |
| 913 | 626.6 | 2.88 | ***** |
| 914 | 514.55 | 2.60 | ***** |
| 915 | 509.56 | 4.63 | ***** |
| 916 | 626.40 | 2.82 | ***** |
| 917 | 561.46 | 2.95 | ***** |
| 918 | 642.56 | 2.85 | ***** |
| 919 | 543.45 | 4.82 | ***** |
| 920 | 557.57 | 2.87 | ***** |
| 921 | 527.39 | 4.52 | ***** |
| 922 | 561.53 | 2.85 | ***** |
| 923 | 612.51 | 2.92 | ***** |
| 924 | 498.20 | 2.71 | ***** |
| 925 | 596.54 | 2.88 | ***** |
| 926 | 5.62 | 3.85 | ***** |
| 927 | 540.65 | 4.25 | ***** |
| 928 | 510.52 | 3.10 | ***** |
| 929 | 506.46 | 2.95 | ***** |
| 930 | 500.48 | 2.83 | ***** |
| 931 | 467.39 | 4.17 | ***** |
| 932 | 548.49 | 3.17 | ***** |
| 933 | 596.37 | 2.79 | ***** |
| 934 | 561.53 | 2.95 | ***** |
| 935 | 496.54 | 3.37 | ***** |
| 936 | 582.6 | 2.83 | ***** |
| 937 | 555.61 | 2.55 | ***** |
| 938 | 582.53 | 2.85 | ***** |
| 939 | 560.63 | 2.68 | ***** |
| 940 | 541.43 | 2.45 | ***** |
| 941 | 562.55 | 3.63 | ***** |
| 942 | 623.35 | 2.73 | **** |
| 943 | 499 | 2.72 | **** |
| 944 | 525.56 | 4.36 | **** |
| 945 | 509.43 | 4.73 | **** |

TABLE 6-continued

| Compound | LCMS [M + H] | LCMS Retention Time (min) | ELISA EC50 μM |
|---|---|---|---|
| 946 | 566.53 | 2.77 | **** |
| 947 | 510 | 2.44 | **** |
| 948 | 482.47 | 2.88 | **** |
| 949 | 524.55 | 3.22 | **** |
| 950 | 506.46 | 2.87 | **** |
| 951 | 544.53 | 3.27 | **** |
| 952 | 530.53 | 3.12 | **** |
| 953 | 552.46 | 2.90 | **** |
| 954 | 403 | 4.11 | **** |
| 955 | 397 | 3.9 | **** |
| 956 | 484.55 | 2.42 | **** |
| 957 | 495.52 | 2.62 | **** |
| 958 | 542.36 | 3.84 | **** |
| 959 | 496.24 | 2.81 | **** |
| 960 | 639.57 | 2.70 | **** |
| 961 | 593.52 | 2.64 | **** |
| 962 | 516.59 | 2.65 | **** |
| 963 | 593.61 | 2.72 | **** |
| 964 | 598.55 | 2.83 | **** |
| 965 | 544.53 | 3.15 | **** |
| 966 | 564.45 | 3.32 | **** |
| 967 | 491.57 | 4.00 | **** |
| 968 | 512.51 | 2.73 | **** |
| 969 | 492.46 | 2.90 | **** |
| 970 | 609.54 | 2.72 | **** |
| 971 | 468.46 | 2.78 | **** |
| 972 | 496.47 | 3.02 | **** |
| 973 | 578.47 | 3.80 | **** |
| 974 | 528.34 | 3.79 | *** |
| 975 | 431.5 | 3.10 | *** |
| 976 | 564.46 | 3.23 | *** |
| 977 | 568.53 | 2.85 | *** |
| 978 | 578.45 | 3.30 | *** |
| 979 | 470.55 | 2.45 | *** |
| 980 | 527.61 | 2.50 | *** |
| 981 | 560.51 | 3.12 | *** |
| 982 | 425.60 | 3.78 | *** |
| 983 | 375.37 | 2.27 | *** |
| 984 | 506.19 | 3.97 | ** |
| 985 | 407.31 | 1.82 | * |
| 986 | 531.56 | 2.17 | * |
| 987 | 497.1 | 4.4 | ***** |
| 988 | 605.62 | 2.52 | ***** |
| 989 | 564.61 | 2.55 | ***** |
| 990 | 610.62 | 2.67 | ***** |
| 991 | 580.58 | 2.60 | *** |
| 992 | 566.61 | 2.60 | *** |
| 993 | 577.61 | 2.45 | ***** |
| 994 | 545.54 | 2.57 | ***** |
| 995 | 546.57 | 3.53 | ***** |
| 996 | 578.46 | 3.71 | ***** |

(S) Isomer prepared and tested.
Wherein:
1 star, >1 uM (1000 nM)
2 stars, 0.2 to 1 uM (200 nM to 1000 nM)
3 stars, 0.04 uM to 0.2 uM (40 nM to 200 nM)
4 stars, 0.008 uM to 0.04 uM (8 nM to 40 nM)
5 stars, <0.008 uM (<8 nM)

Example 3

Compounds of the Invention Inhibit VEGF Expression and Tumor Growth, and Inhibits Angiogenesis, in an In Vivo Tumor Growth PD Model Compounds of the invention also show activity in the following pharmacodynamic model that assesses tumor VEGF levels. Briefly, HT1080 cells (a human fibrosarcoma cell line) may be implanted subcutaneously in nude mice. After seven days, mice may be administrated compounds orally at a desired dosage range, e.g., 200 mg/kg/day, for seven days. The tumors may then be excised from mice, weighed and homogenized in Tris-HCl buffer containing proteinase inhibitors. Moulder et al., *Cancer Res.* 61(24):8887-95 (2001). Tumor VEGF levels are subsequently measured using a human VEGF ELISA kit (R&D System). Protein concentrations of the homogenates are measured with a Bio-Rad Protein assay kit and tumor VEGF levels are normalized to the protein concentrations.

Figure 2:
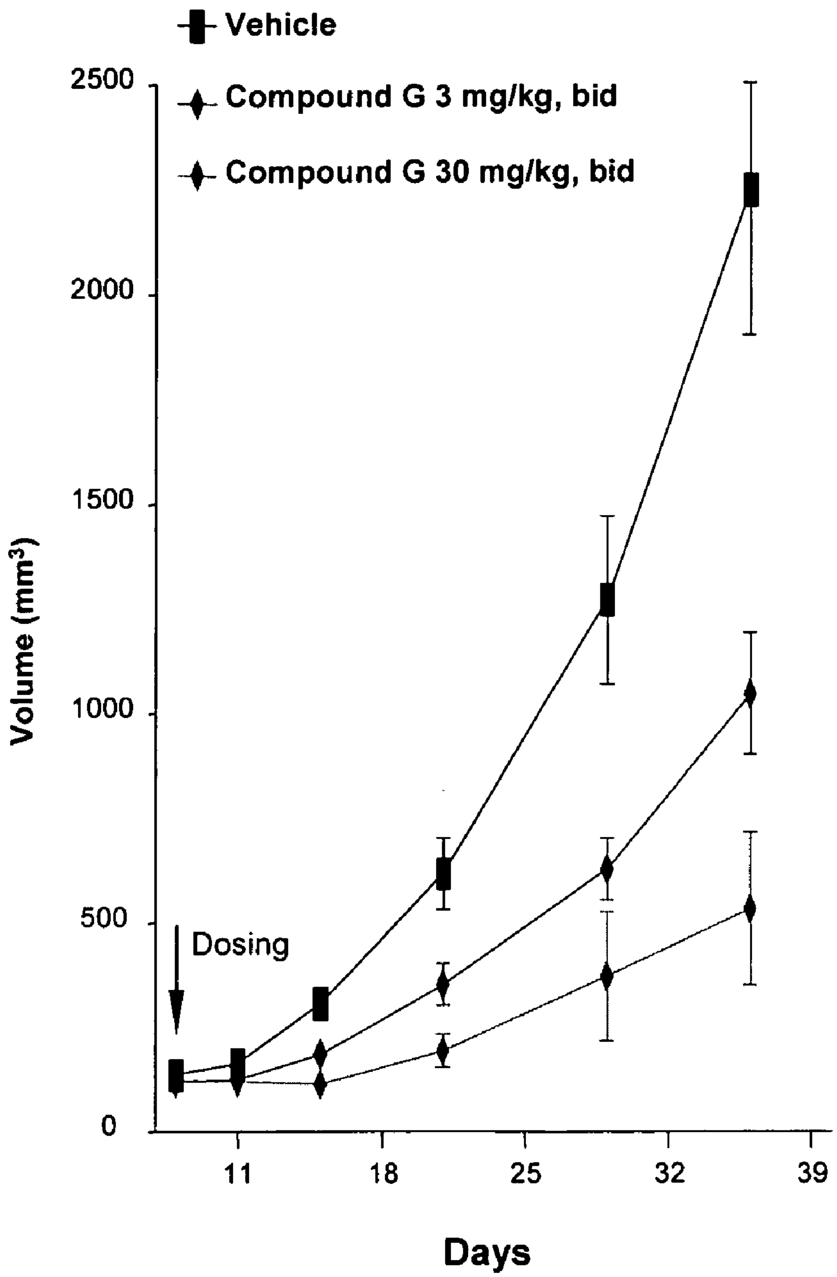
FIG. 2.
Figure 3:
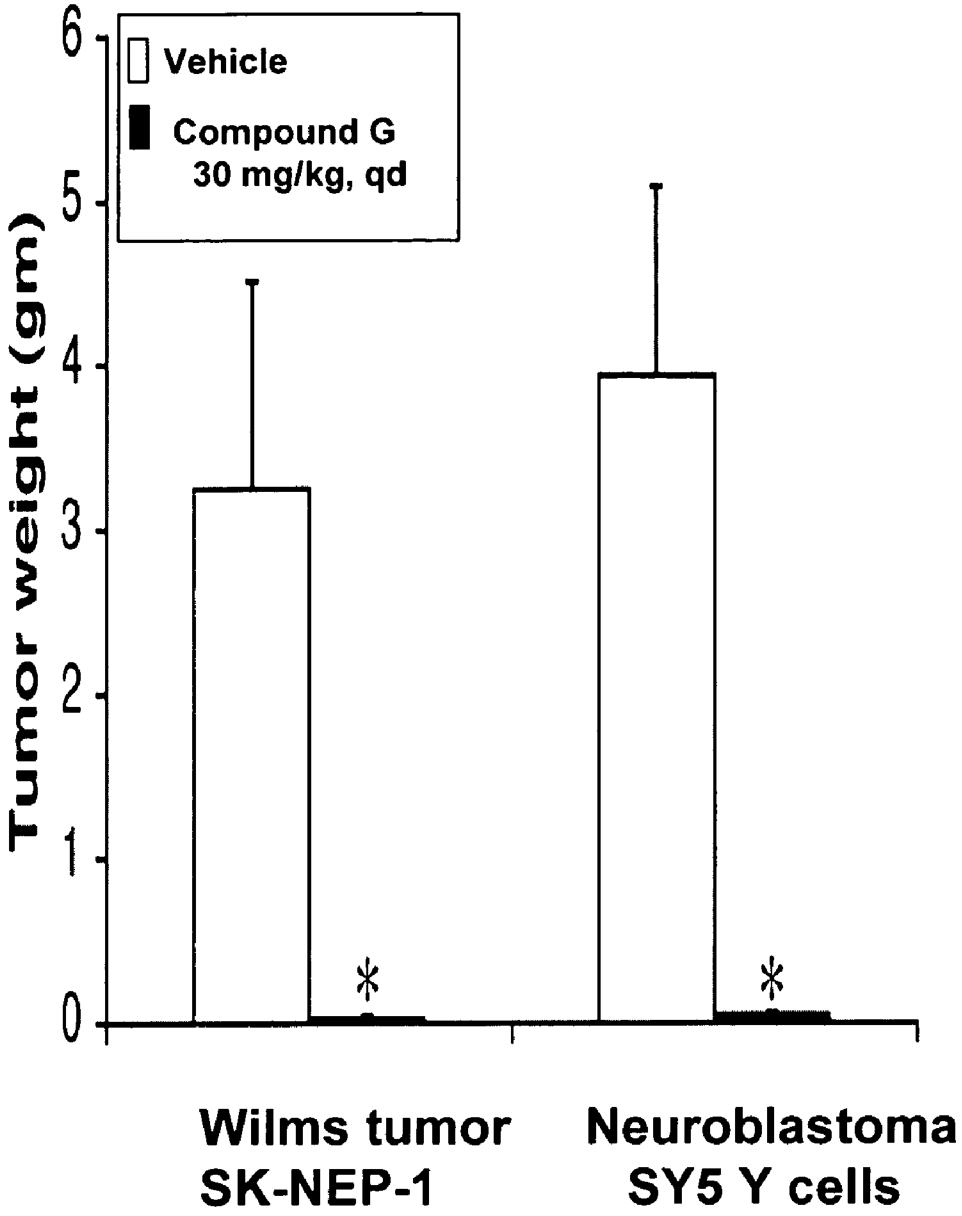
FIG. 3.
Figure 4:
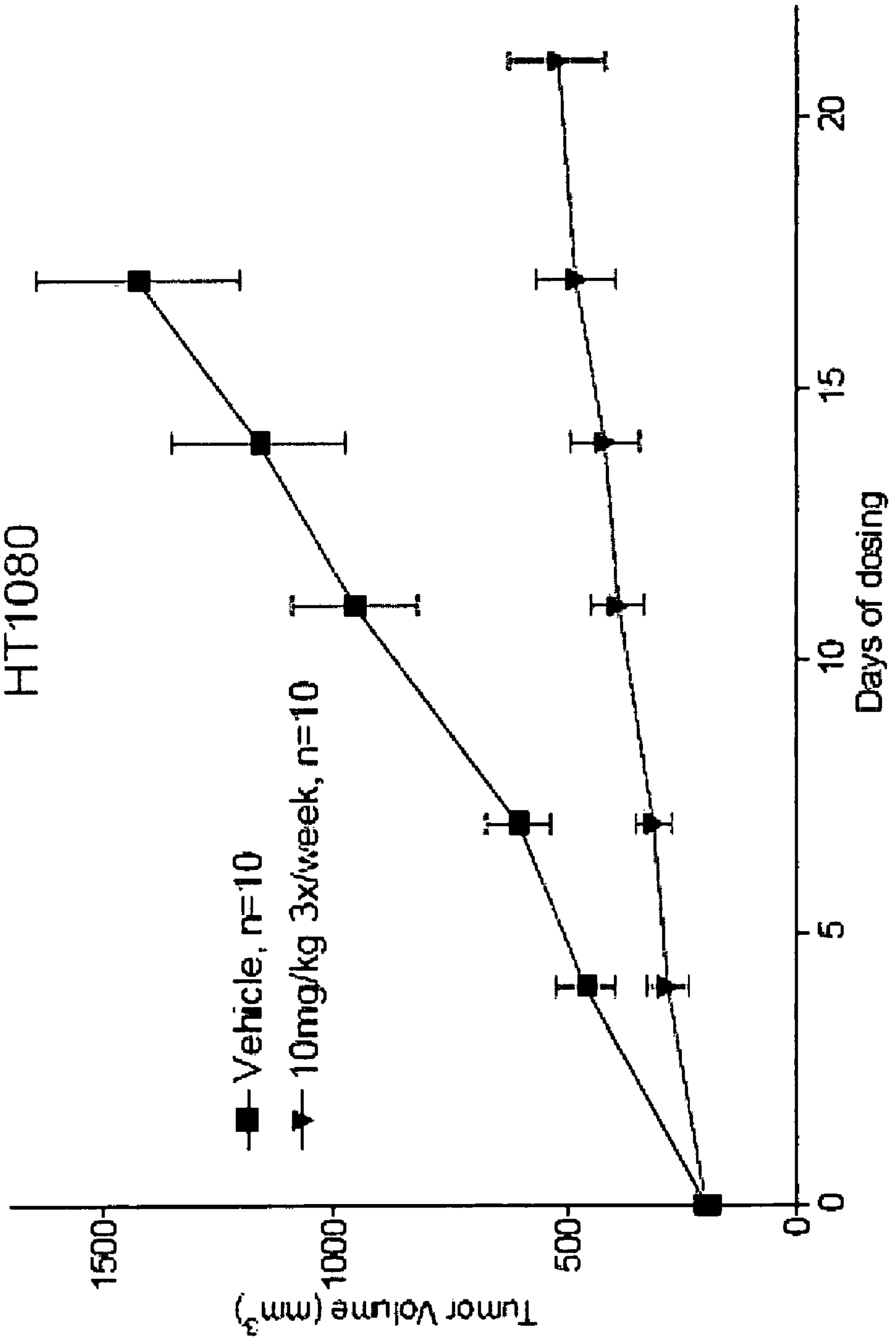
FIG. 4.
Figure 5:
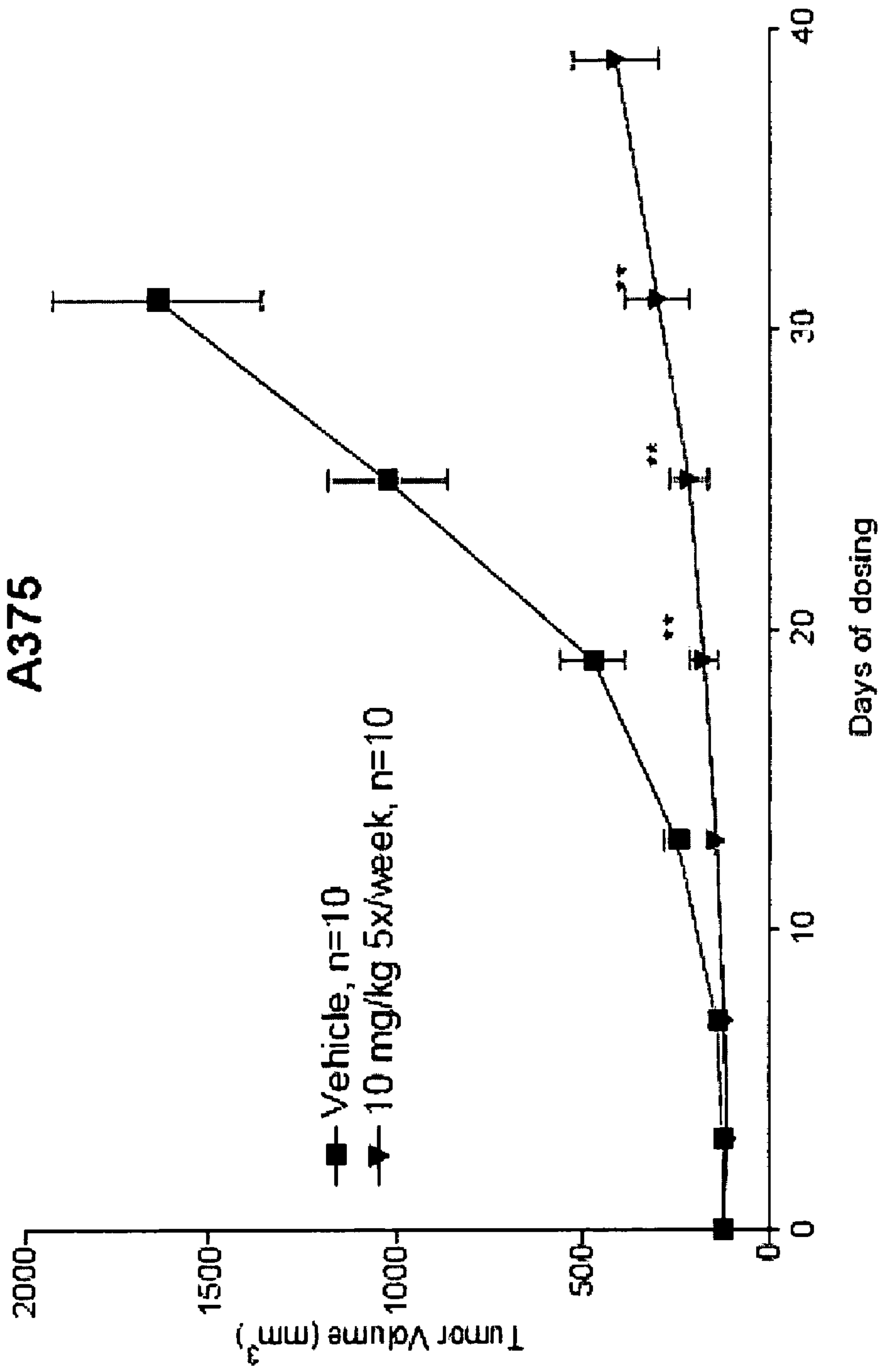
FIG. 5.
Figure 6:
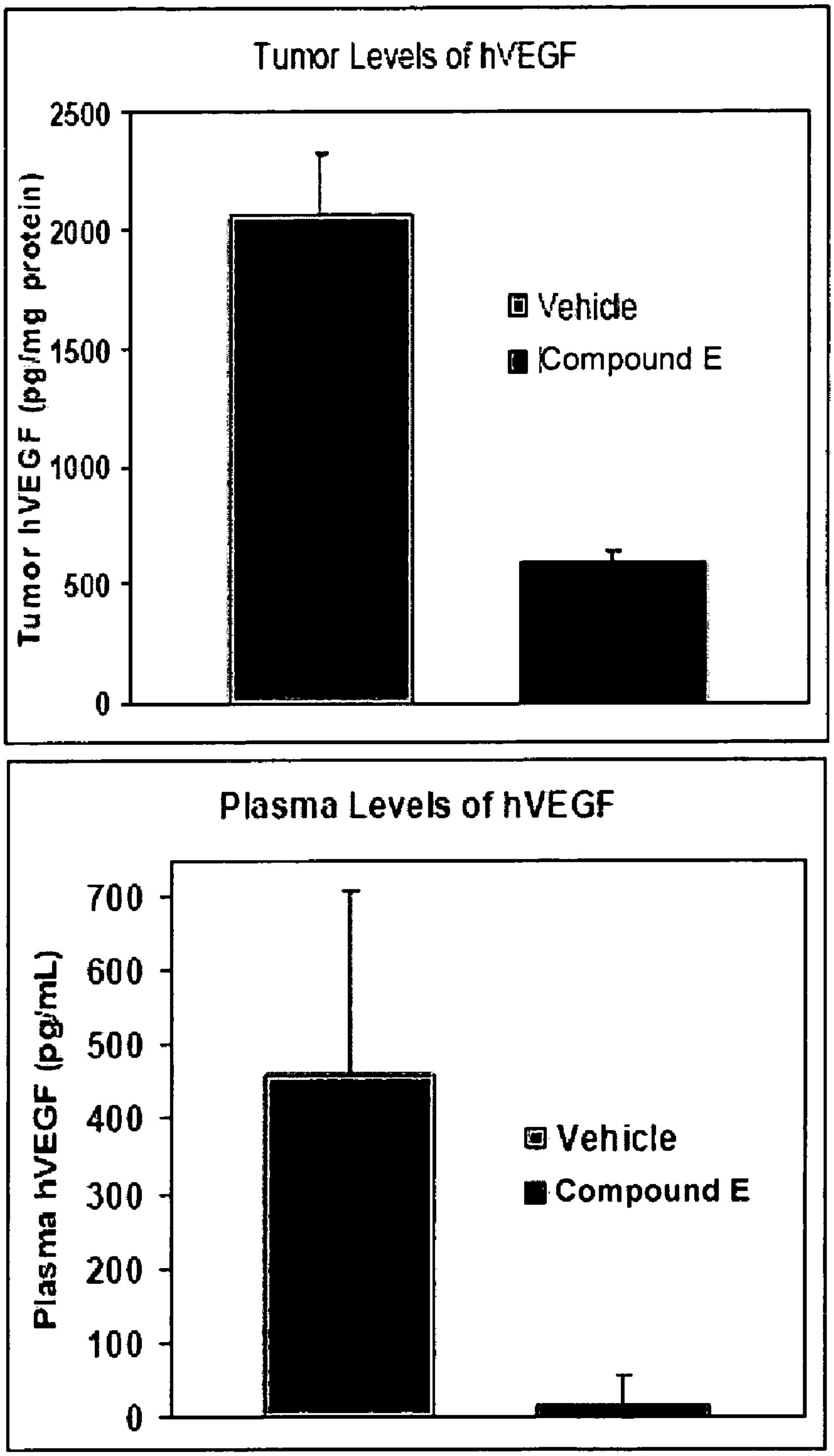
FIG. 6.
Figure 7:
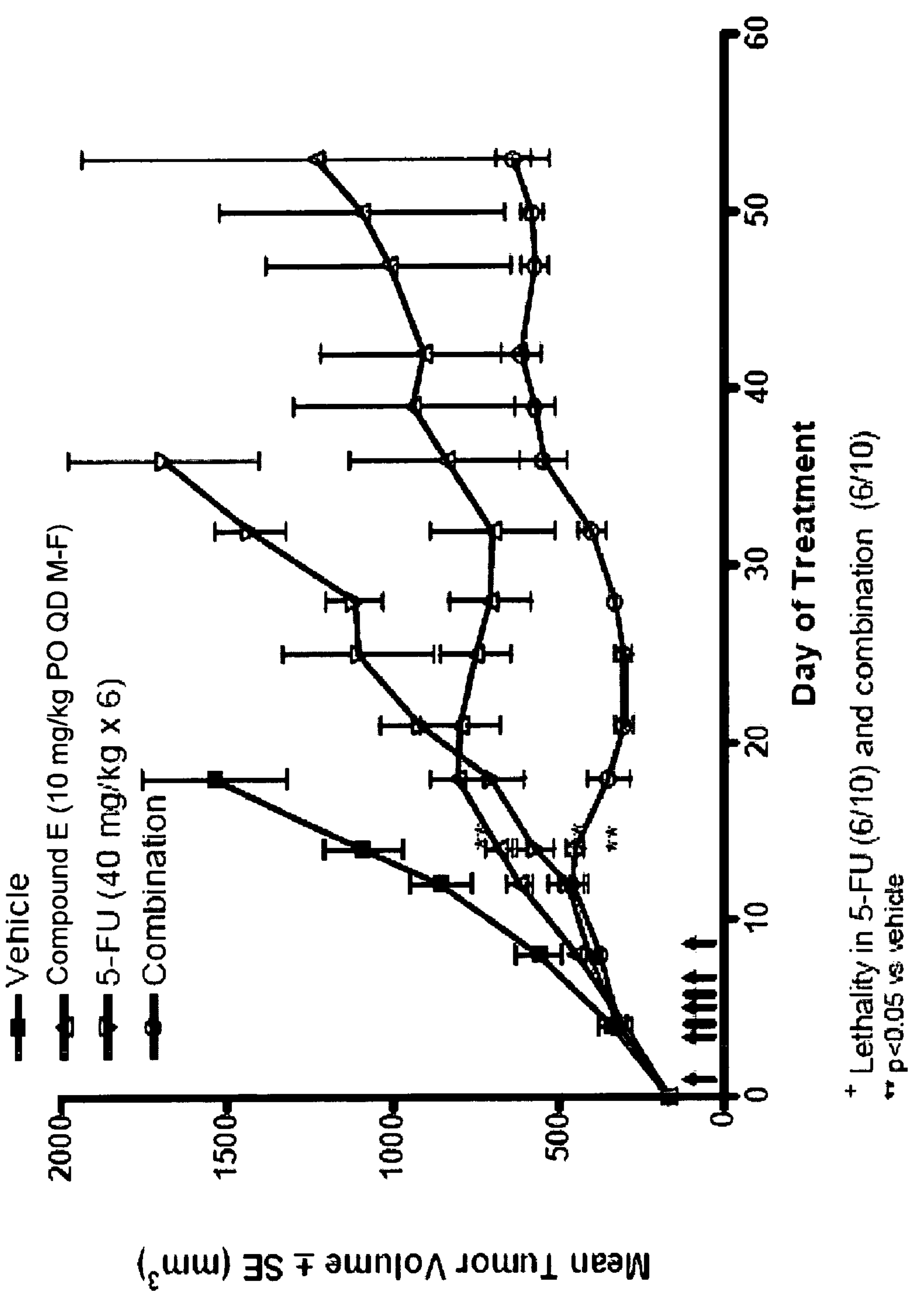
FIG. 7.
Figure 8:
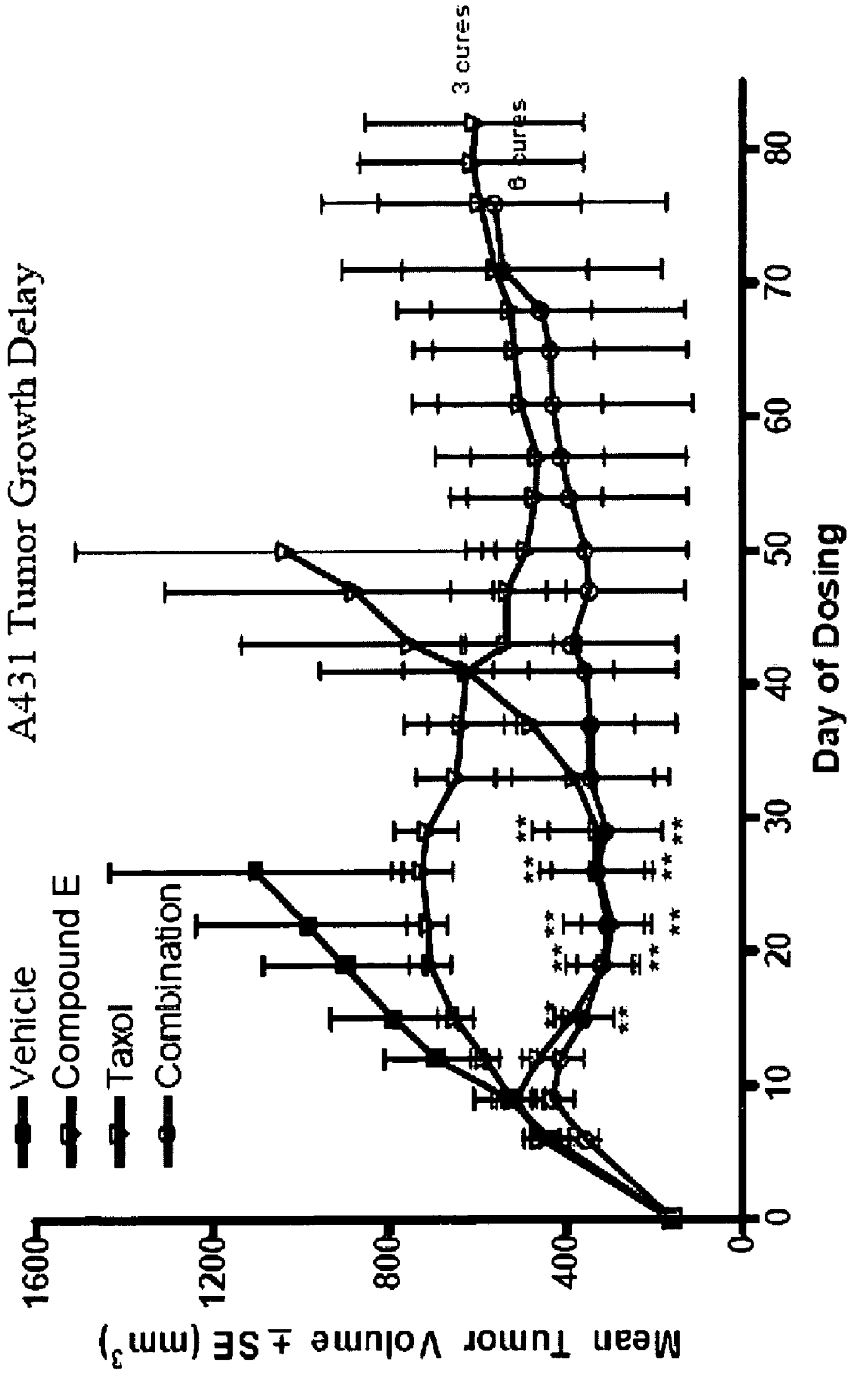
FIG. 8.
Figure 9:
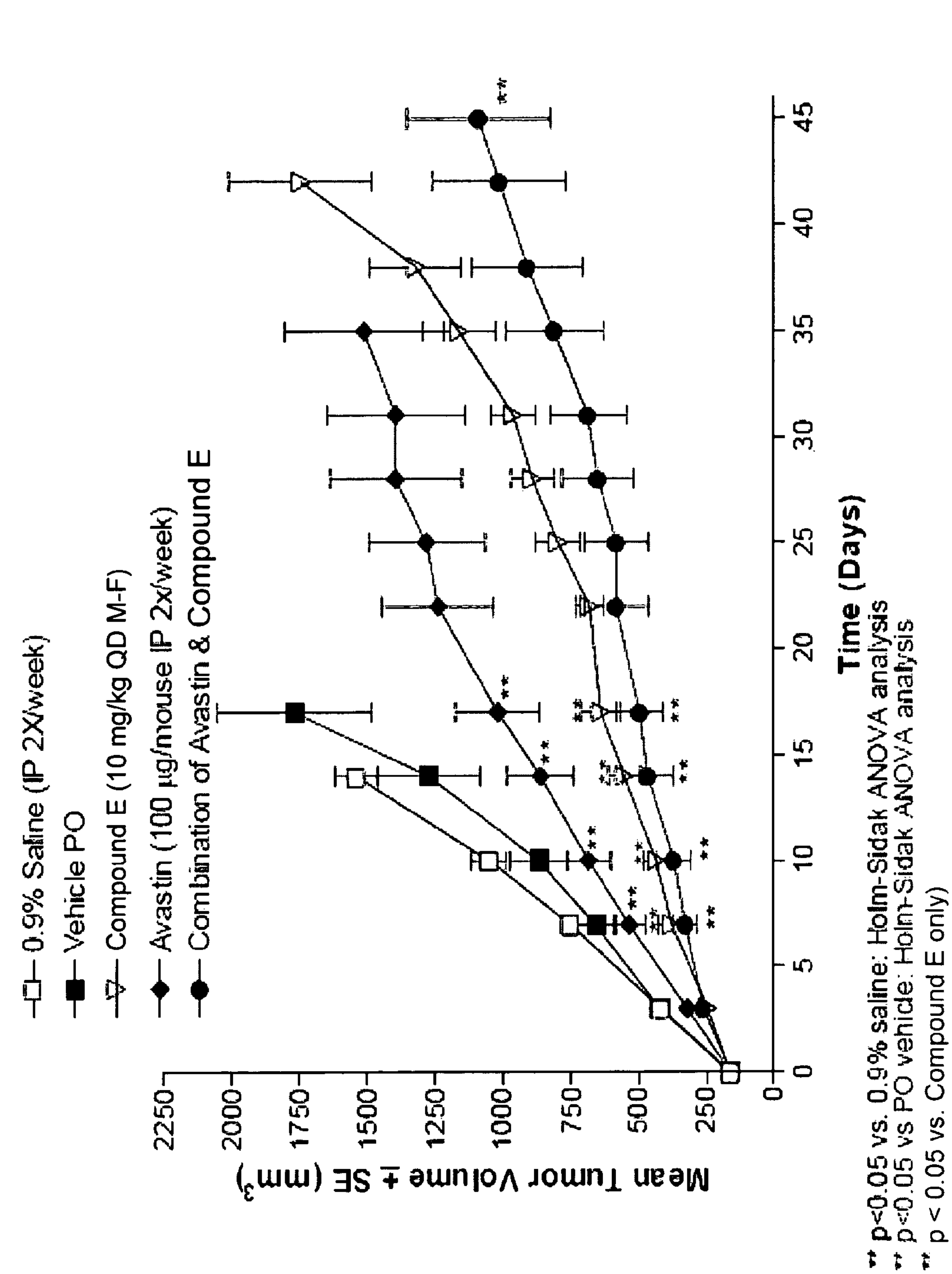
FIG. 9.
Figure 10:
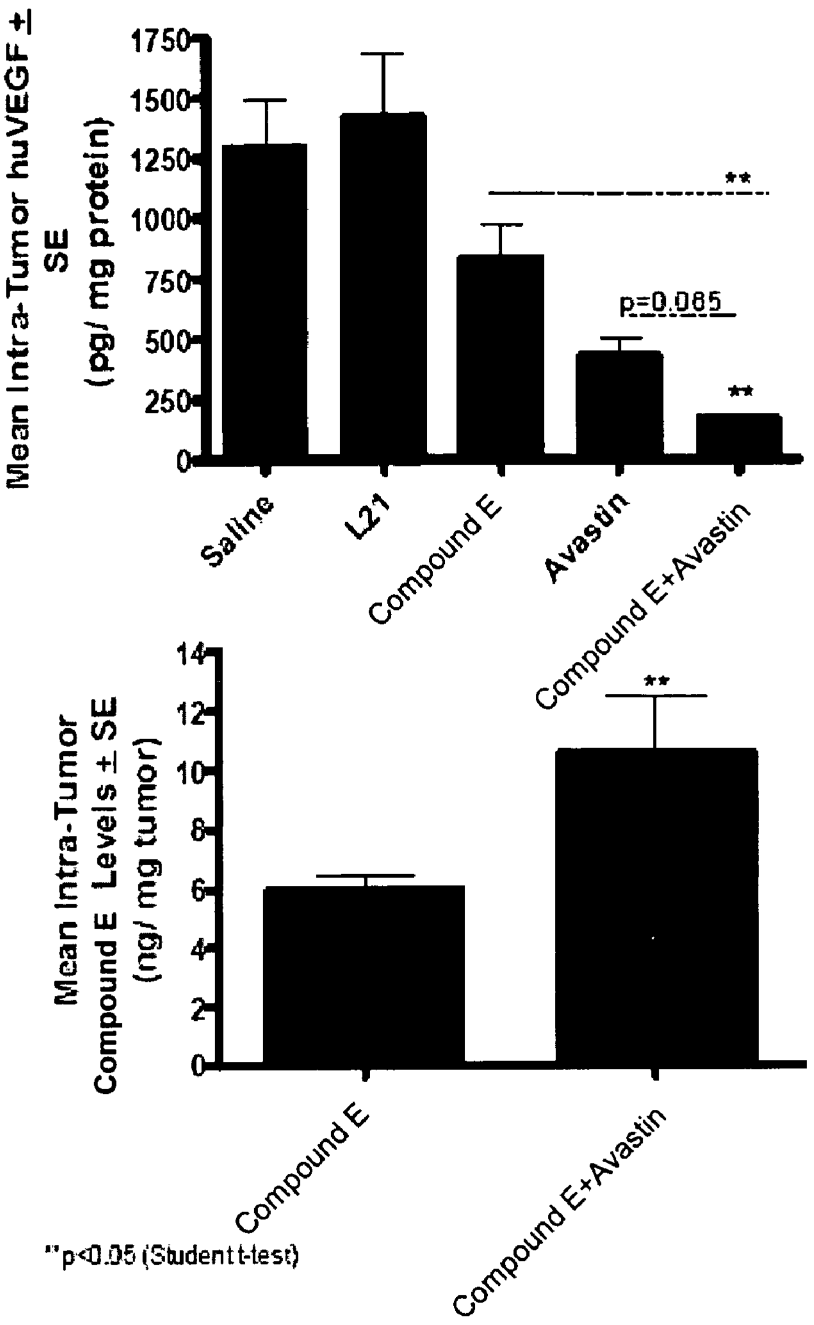
FIG. 10.

Preferred compounds of the invention, when used for one week on a 100 $mm^3$ tumor, will generally inhibit tumor growth by at least 50%, as compared to the vehicle-treated control groups. In similarly conducted experiments, compounds of the invention are shown to reduce lung cancer tumor growth (at a dosage of 3 mg/kg, twice a day, or 30 mg/kg, twice a day) (FIG. 2), Wilms and neuroblastoma tumor growth (at a dosage of 30 mg/kg, once a day) (FIG. 3), fibrosarcoma tumor growth (at a dosage of 10 mg/kg 3×/week) (FIG. 4), and human skin malignant melanoma (at a dosage of 10 mg/kg 5×/week) (FIG. 5) as compared to vehicle. Furthermore, the compounds of the invention are shown to reduce VEGF plasma and tumor levels in fibrosarcoma tumors as compared to vehicle (at a dosage of 10 mg/kg 3×/week) (FIG. 6). The compounds of the invention also inhibit tumor growth when administered together with other cancer agents, such as 5-FU (fluorouracil) in a colon cancer tumor (FIG. 7), taxol (paclitaxel) in a human cervical carcinoma (FIG. 8), and Avastin (bevacizumab) (FIG. 9). Furthermore, as shown in FIG. 10, the compounds of the invention also reduce tumor and plasma VEGF levels when administered together with another cancer agent (such as Avastin).

Figure 11:
FIG. 11.

The tumors excised from the mice can also be used in immunochemistry experiments to determine levels of angiogenesis. As seen in FIG. 11, when antibodies to Collagen IV are used, angiogenesis is shown to be inhibited by the administration of a compound of the invention in Wilms tumor (SK-NEP-1) and neuroblastoma (SY5Y and NGP) tumors.

Example 4

Compounds of the Invention Do Not Affect VEGF mRNA Levels

Human solid tumor cells are treated with various concentrations of a compound of the present invention or a control under hypoxic conditions. Actinomycin D blocks transcription and is used as a control. Total RNA is isolated using the RNeasy kit (Qiagen, Inc., Valencia, Calif., USA) or an acid-guanidinium thiocyanate-phenol-chloroform based method (See Chomczynski, P. and Sacchi, N., Anal. Biochem. 162: 156 (1987), hereby incorporated by reference).

Figure 12:
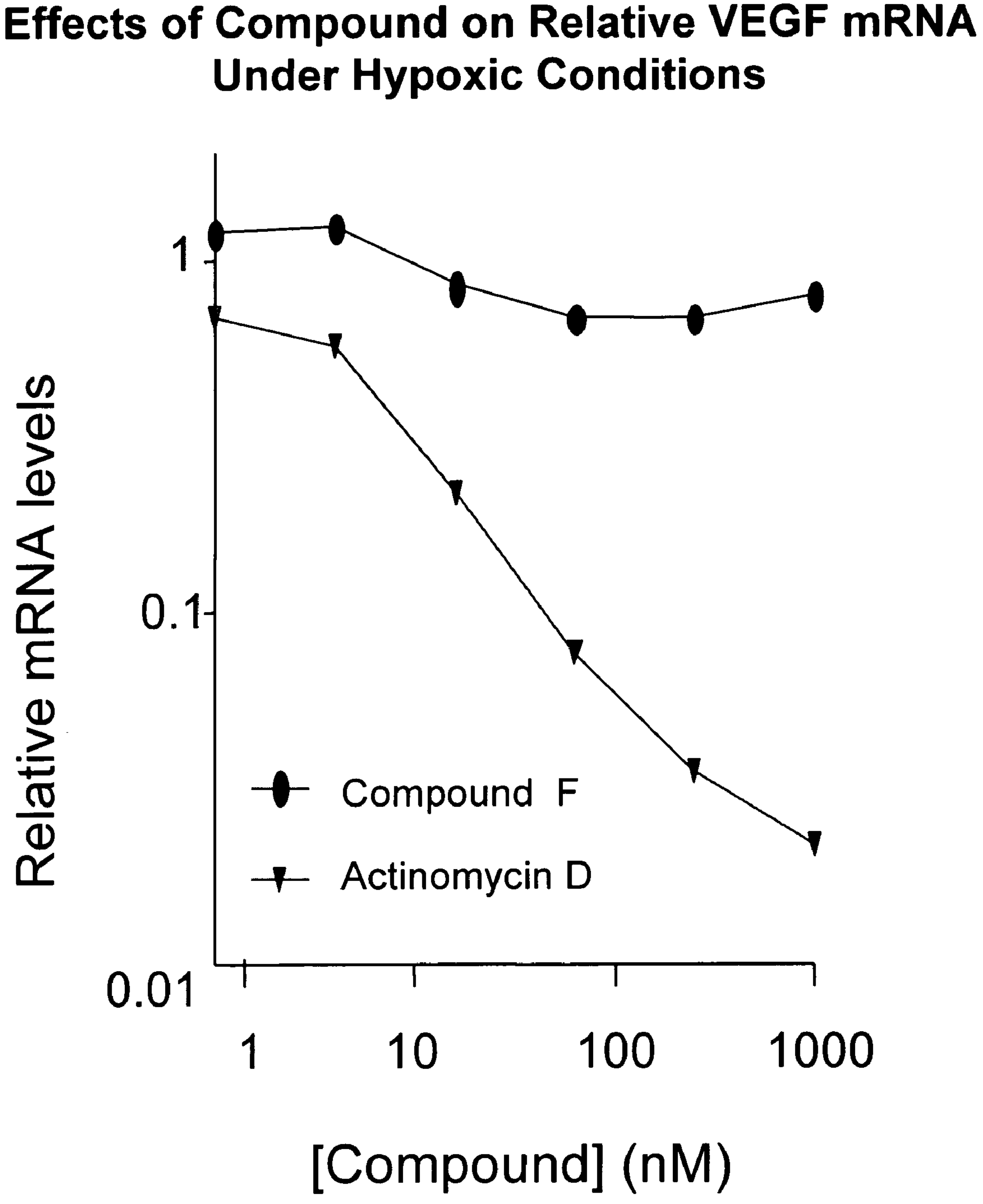
FIG. 12.

Concentration of total RNA can be determined using the RiboGreen® fluorescent dye (Molecular Probes, Inc., Eugene, Oreg., USA) with the VersaFluor Fluorometer System (BioRad, Hercules, Calif., USA). Quality and integrity of total RNA can be assessed on 1% formaldehyde-agarose gels. First-strand cDNA was synthesized using 1 μg of total RNA (DNase-treated) in a 20 μl reverse transcriptase reaction mixture (Leclerc G J, Barredo J C, Clin. Cancer Res. 2001, 7:942-951, which is hereby incorporated by reference). A region of the VEGF mRNA is amplified using PCR primers. The cDNA amplified fragment (approximately 300 basepairs) is cloned into a vector such as the pCR2.1-TOPO vector (Invitrogen, Carlsbad, Calif., USA) to generate a plasmid. Serial ten-fold dilutions (104 to 109 molecules) of this plasmid are used as a reference molecule for standard curve calculation. All Real-Time PCR reactions are performed in a 25 μl mixture containing 1/20 volume of cDNA preparation (1 μl), 1×SYBR Green buffer (PE Applied Biosystems, Foster City, Calif., USA), 4 mM MgCl2, 0.2 μM of each VEGF primer used above, 0.2 mM dNTPs mix and 0.025 Unit of AmpliTaq Gold® thermostable DNA polymerase (Applied Biosystems, Foster City, Calif., USA). Real-Time quantitations are performed using the BIO-RAD iCycler iQ system (BioRad, Hercules, Calif., USA). The fluorescence threshold value can be calculated using the iCycle iQ system software. Using similar methodologies, the data shown in FIG. 12 was obtained, and shows that a compound of the present invention does not affect VEGF mRNA levels

Example 5

Compounds of the Invention Do Not Affect the Activity of PDE5

The compounds of the invention are tested to assess their affect on phosphodiesterase 5 (PDE5) activity. The affect on PDE5 activity is determined using the High-Efficiency Fluorescence Polarization Assay (HEFP) kit from Molecular Devices. The HEFP assay measures the activity of PDE-5 by using fluorescein-labeled derivatives of cGMP as a substrate. When hydrolyzed by PDE-5, fluorescein-labeled cGMP derivatives are able to bind to a binding reagent. The cGMP substrate:binding reagent complex results in a highly polarized fluorescent state.

Figure 13:
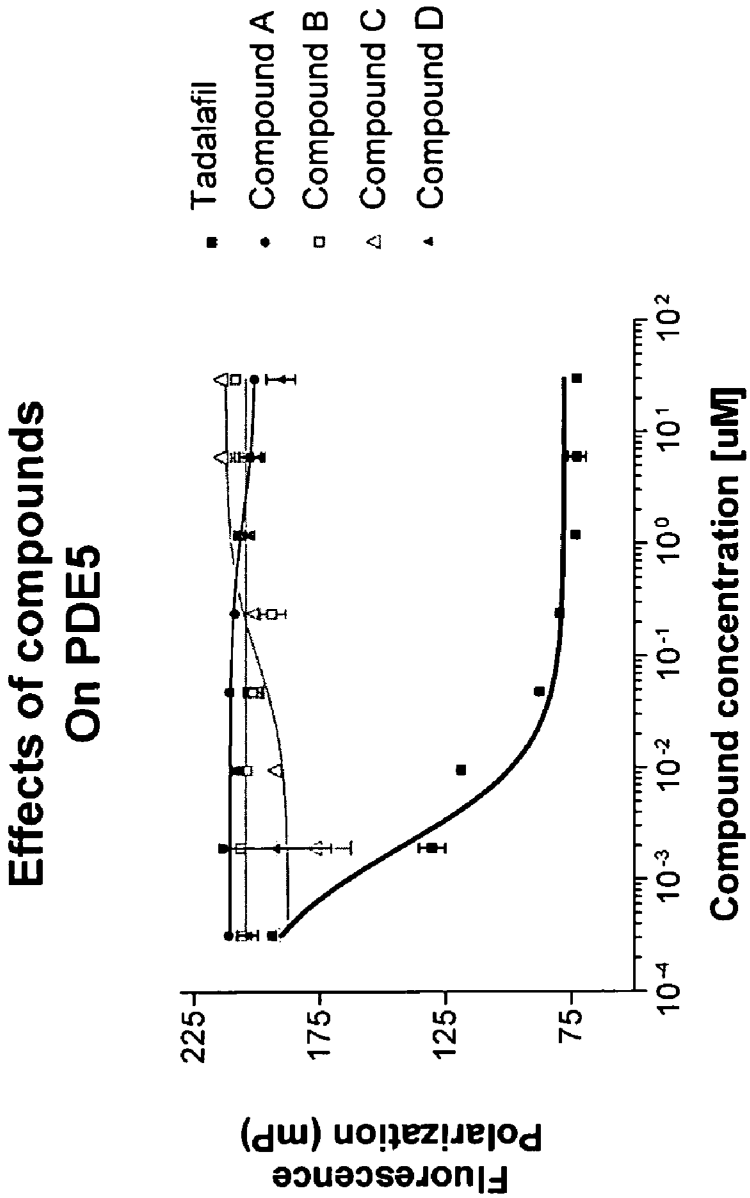
FIG. 13.

FIG. 13 shows the results of the compounds of the invention on PDE-5 activity. After combining recombinant PDE5 (CalBioChem) and the cGMP substrate, the mixture is incubated at room temperature for 45 minutes in the presence or absence of compounds or a positive control (Tadalafil). The reaction is stopped upon addition of the binding reagent. Fluorescence polarization is determined on a Viewlux using a setting recommended by the manufacturer. As is evident from FIG. 13, the compounds of the invention do not inhibit the activity of PDE-5 in comparison to the positive control.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed is:

1. A method for treating a solid tumor cancer comprising administering a therapeutically effective amount of a compound of Formula (IV):

(IV)

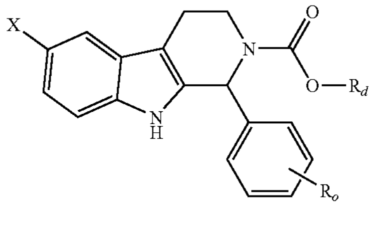

or a pharmaceutically acceptable salt, racemate or stereoisomer of said compound, to a subject in need thereof; wherein X is hydrogen; $C_1$ to $C_6$ alkyl optionally substituted with one or more halogen substituents; hydroxyl halogen or $C_1$ to $C_5$ alkoxy optionally substituted with phenyl;

$R_o$ is hydrogen; halogen; cyano; nitro; sulfonyl substituted with $C_1$ to $C_6$ alkyl or morpholinyl; amino optionally substituted with $C_1$ to $C_6$ alkyl, —C(O)—$R_b$, —C(O)O—$R_b$, alkylsulfonyl, morpholinyl or tetrahydropyranyl; $C_1$ to $C_6$ alkyl optionally substituted with one or more substituents independently selected from hydroxyl, halogen or amino; —C(O)—$R_n$; or —O$R_a$;

$R_a$ is hydrogen; $C_2$ to $C_8$ alkenyl; —C(O)O—$R_b$; —C(O)—NH—$R_b$; $C_1$ to $C_8$ alkyl optionally substituted with one or more substituents independently selected from hydroxyl, halogen, $C_1$ to $C_4$ alkoxy, amino, alkylamino, dialkylamino, acetamide, —C(O)—$R_b$, —C(O)O—$R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene or tetrazole;

wherein amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

wherein alkylamino and dialkylamino are each optionally substituted on alkyl with hydroxyl, $C_1$ to $C_4$ alkoxy, imidazole, pyrazole, pyrrole or tetrazole; and, wherein morpholinyl, thiomorpholinyl, pyrrolidinyl, piperidinyl, piperazinyl and oxiranyl are each optionally substituted with —C(O)—$R_n$, —C(O)O—$R_n$ or $C_1$ to $C_4$ alkyl, wherein $C_1$ to $C_4$ alkyl is optionally substituted with hydroxyl;

$R_b$ is hydroxyl; amino; alkylamino optionally substituted on alkyl with hydroxyl, amino, alkylamino or $C_1$ to $C_4$ alkoxy; a $C_1$ to $C_4$ alkoxy; $C_2$ to $C_8$ alkenyl; $C_2$ to $C_8$ alkynyl; aryl optionally substituted with one or more substituents independently selected from halogen and $C_1$ to $C_4$ alkoxy; furan; or $C_1$ to $C_8$ alkyl optionally substituted with one or more substituents independently selected from $C_1$ to $C_4$ alkoxy, aryl, amino, morpholinyl, piperidinyl or piperazinyl;

$R_d$ is phenyl substituted with one or more substituents independently selected from hydrogen, halogen, nitro, $C_1$ to $C_6$ alkyl, —C(O)O—$R_e$, and —O$R_e$;

$R_e$ is hydrogen; $C_1$ to $C_6$ alkyl optionally substituted with one or more substituents independently selected from halogen and alkoxy; or phenyl optionally substituted with one or more substituents independently selected from halogen or alkoxy; and $R_n$ is a hydroxyl, $C_1$ to $C_4$ alkoxy, amino or $C_1$ to $C_6$ alkyl, wherein the compound inhibits VEGF production in a HT1080 solid tumor grown in a nude mouse, inhibits HT1080 solid tumor growth in a nude mouse or inhibits angiogenesis in a HT1080 solid tumor grown in a nude mouse.

2. The method of claim 1, wherein said compound is selected from the group consisting of:

10
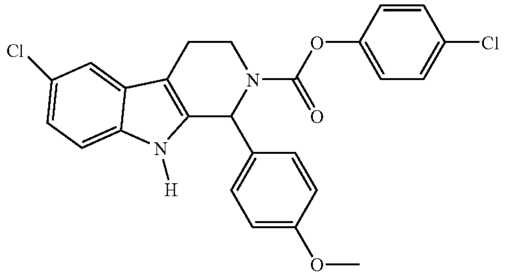
17
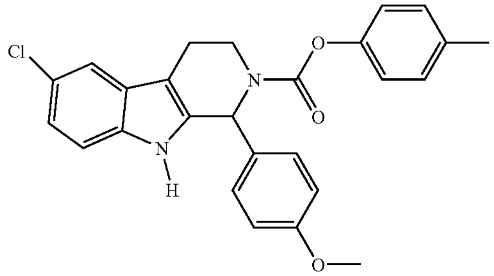
60
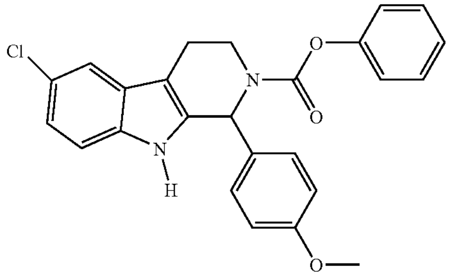
76
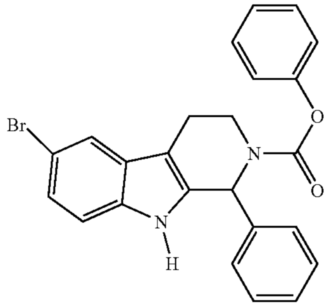
121
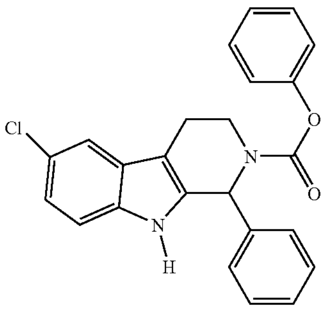
-continued
192
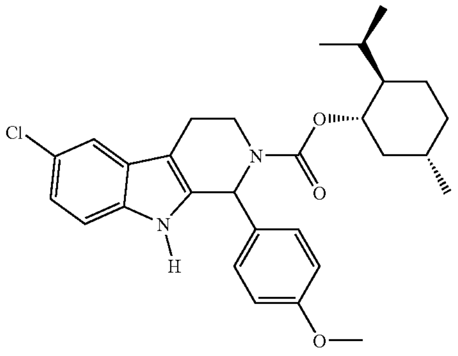
331
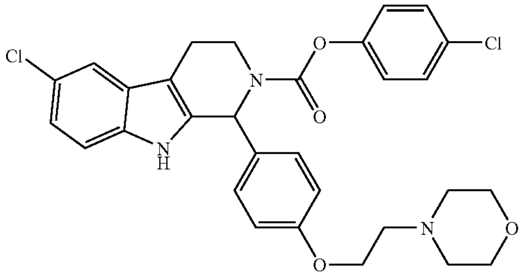
332
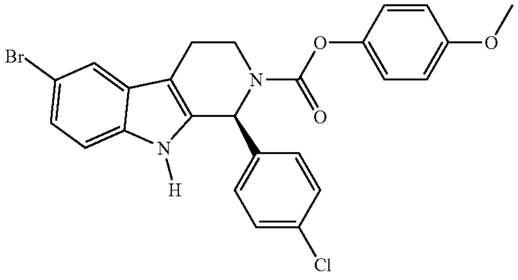
341
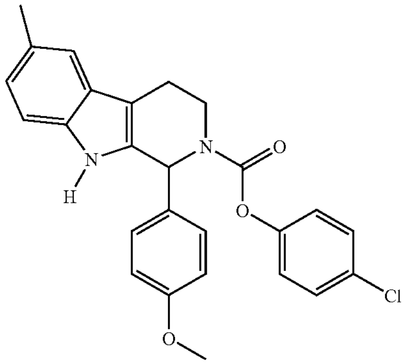

-continued
344
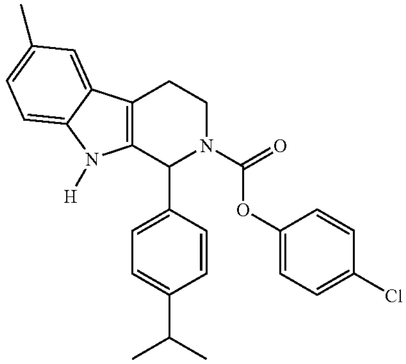
346
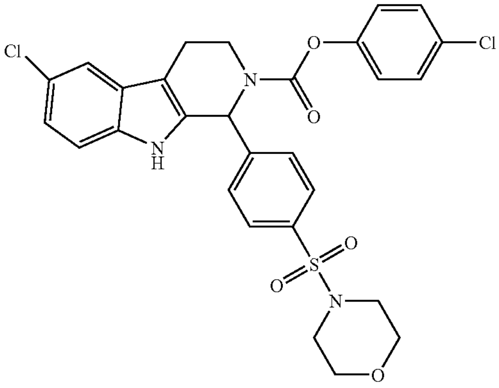
347
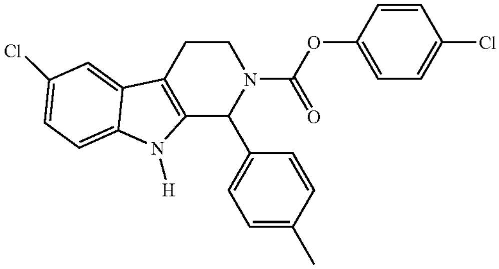
348
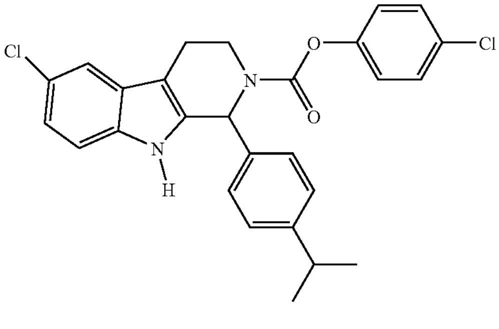
-continued
350
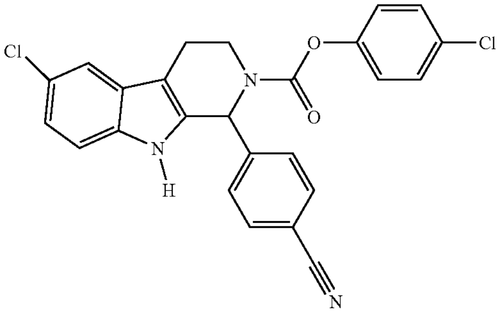
351
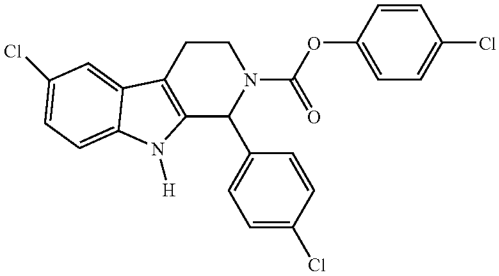
353
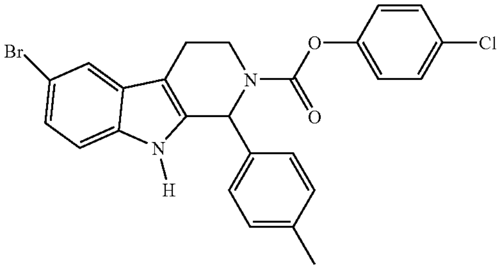
354
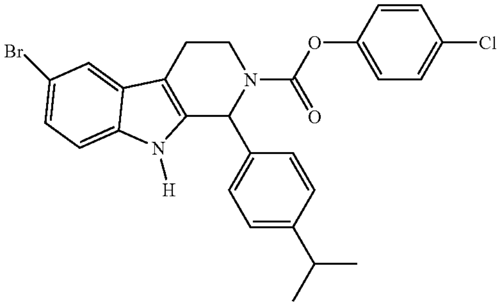
355
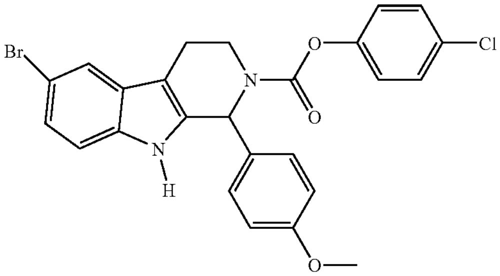

-continued
359
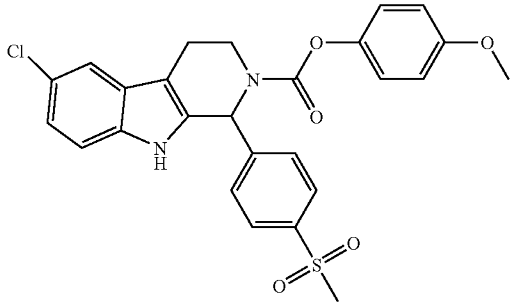
360
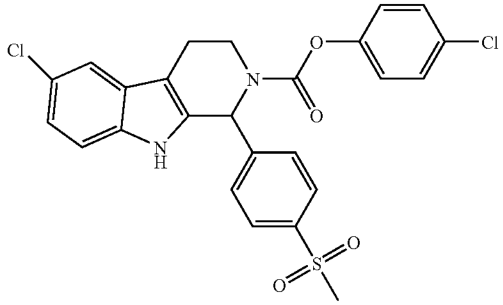
366
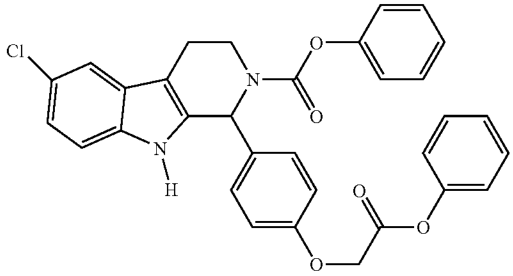
388
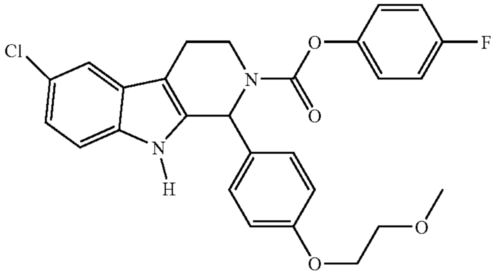
391
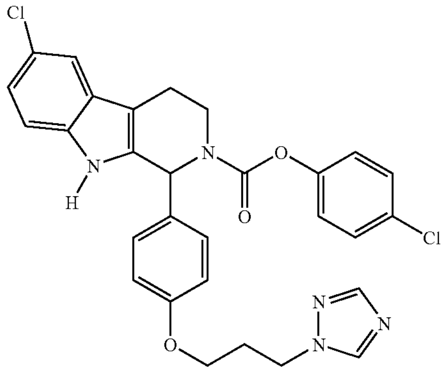
-continued
395
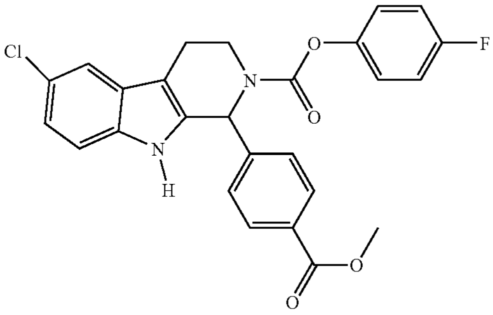
397
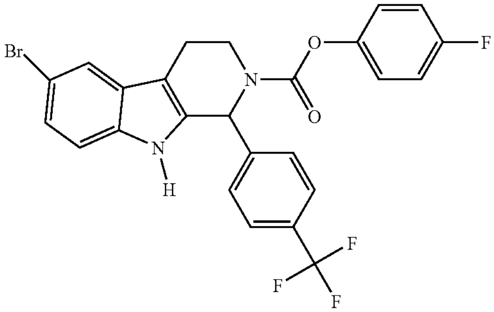
398
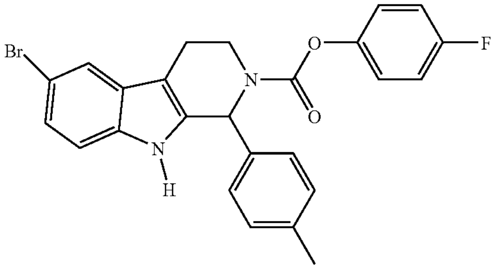
400
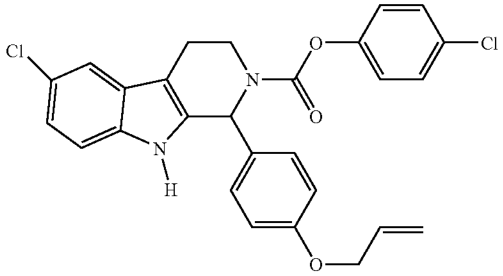
401
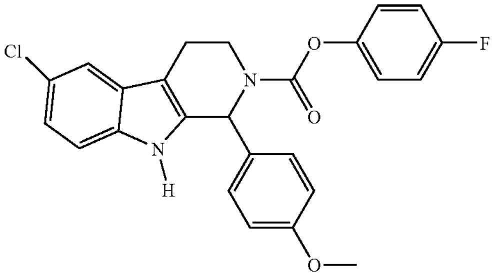

-continued
403
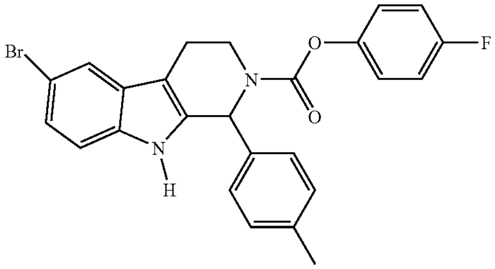
405
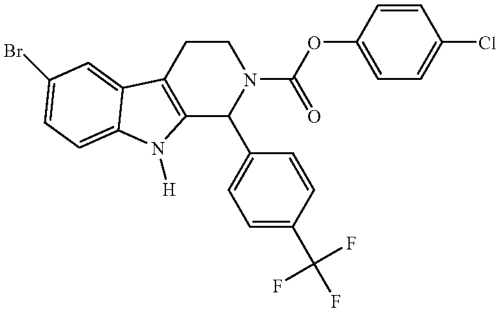
409
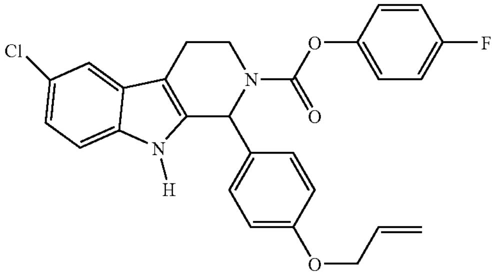
410
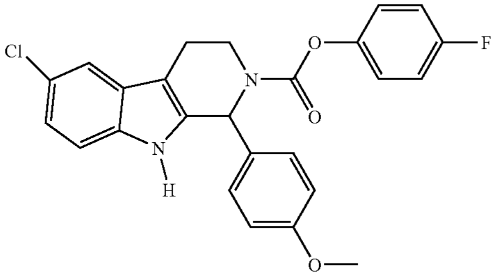
413
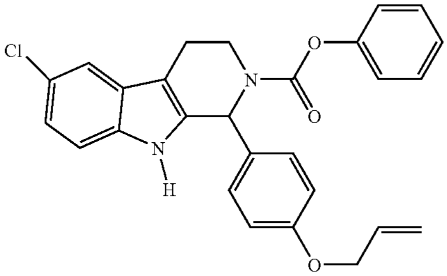
-continued
415
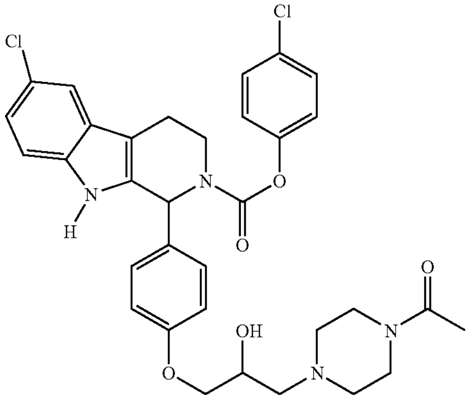
417
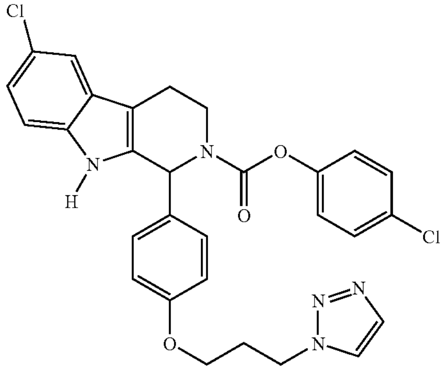
418
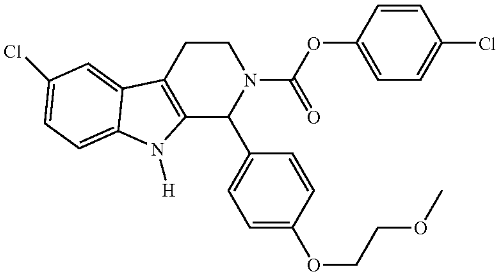
421
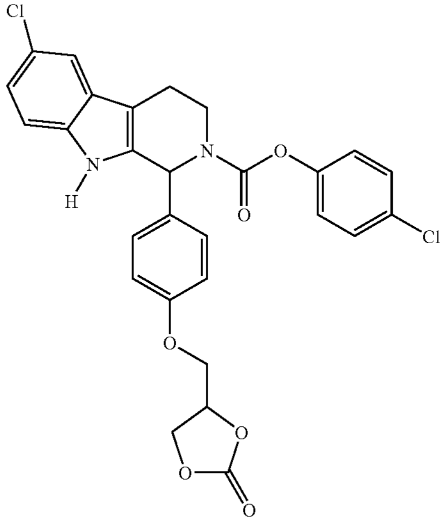

-continued
422
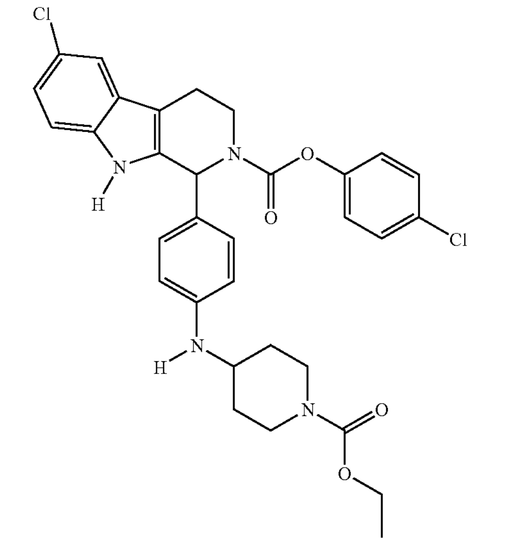
426
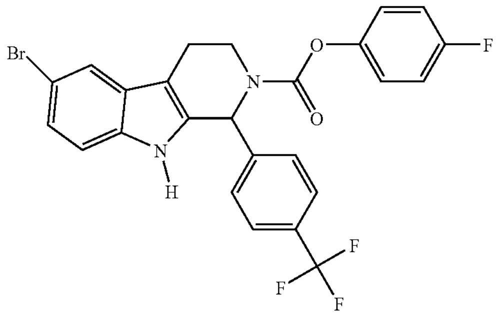
427
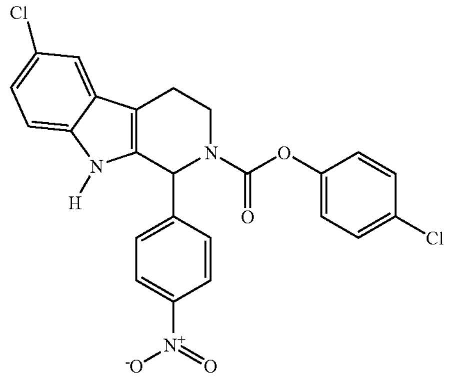
428
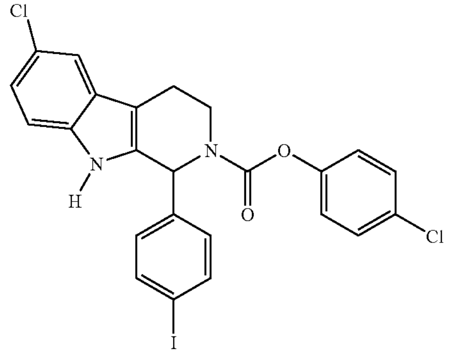
-continued
429
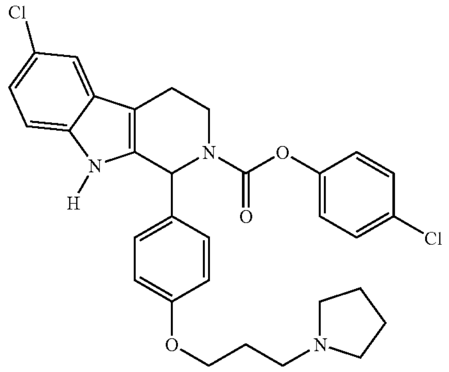
432
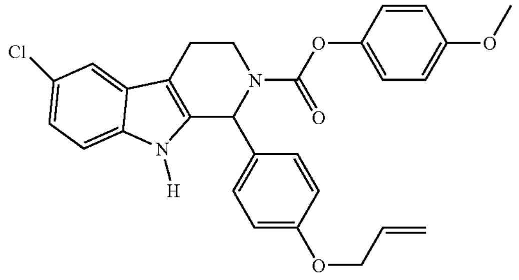
433
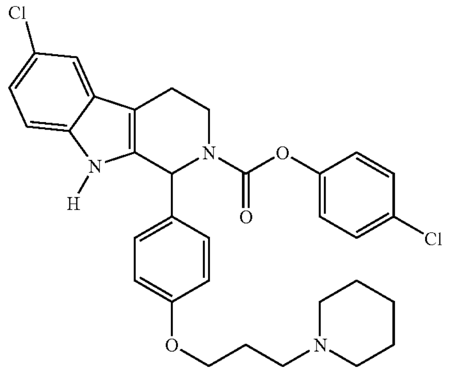
436
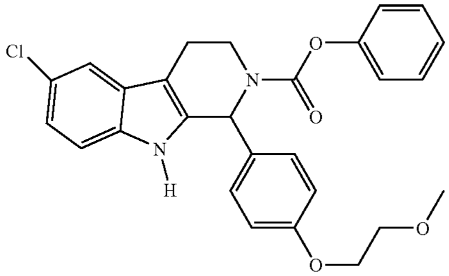

-continued
437
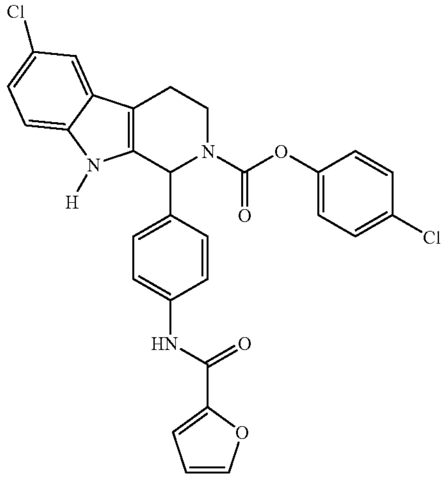
440
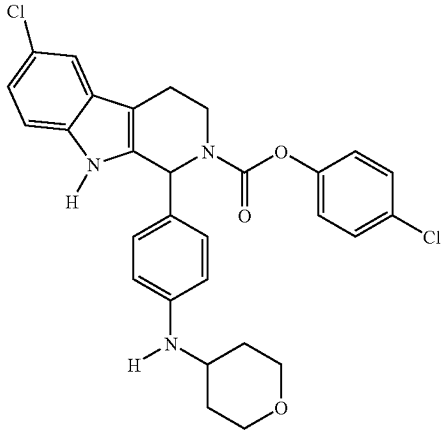
444
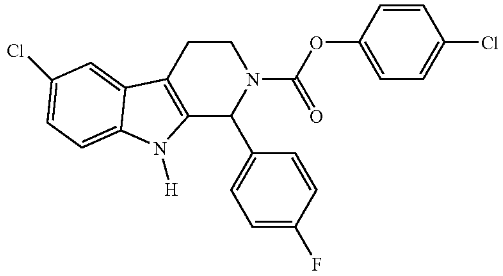
446
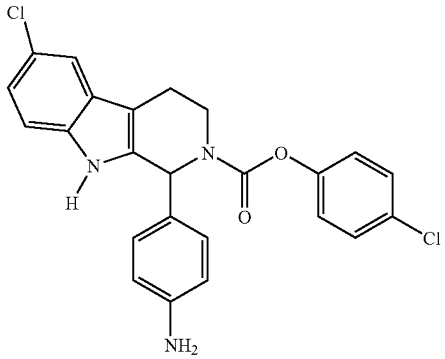
-continued
448
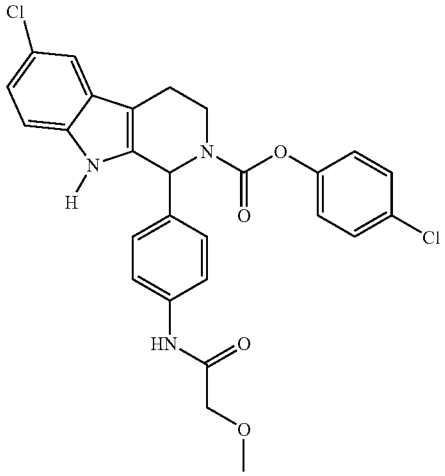
450
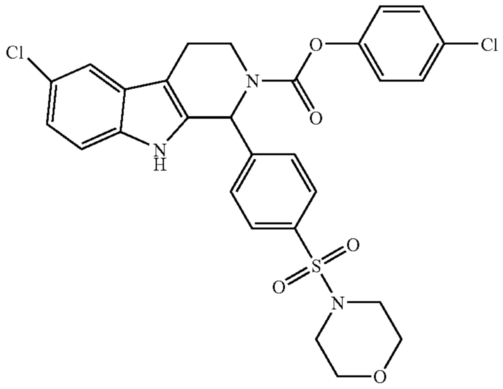
452
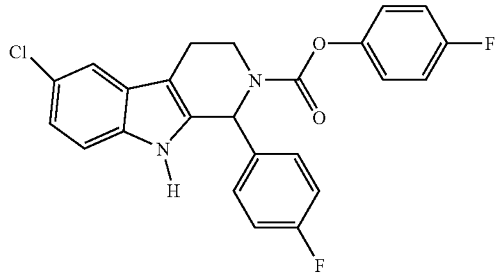

-continued
454
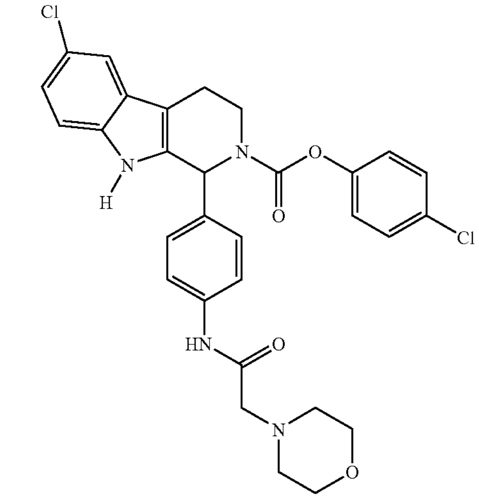
455
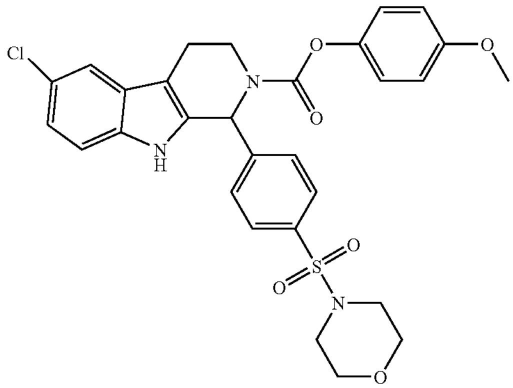
460
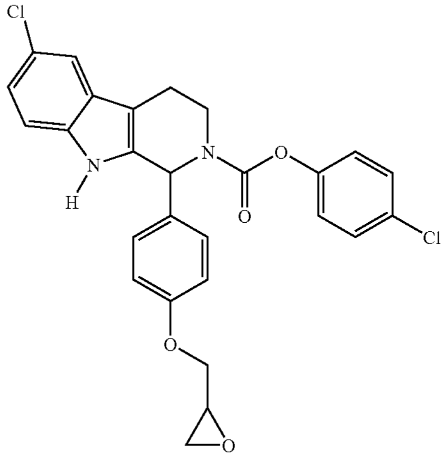
-continued
462
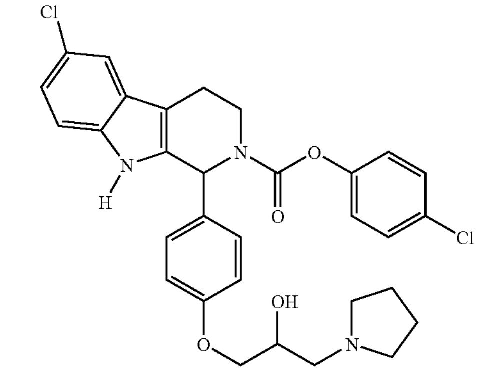
463
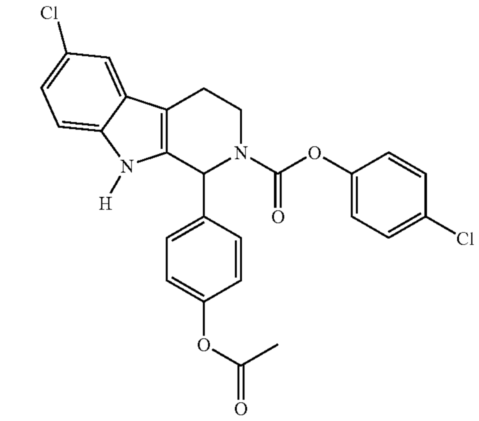
465
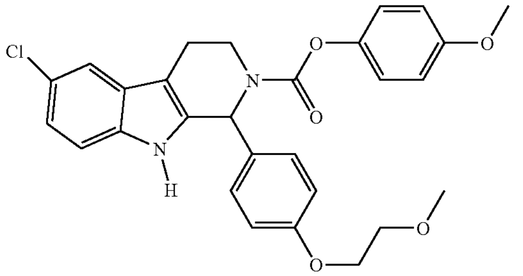
467
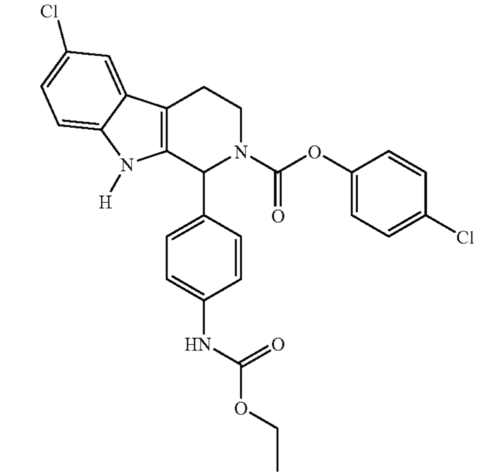

-continued
468
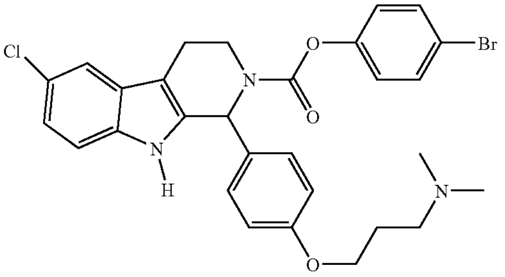
470
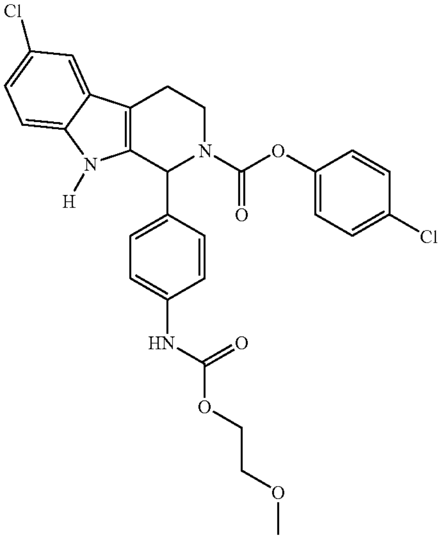
471
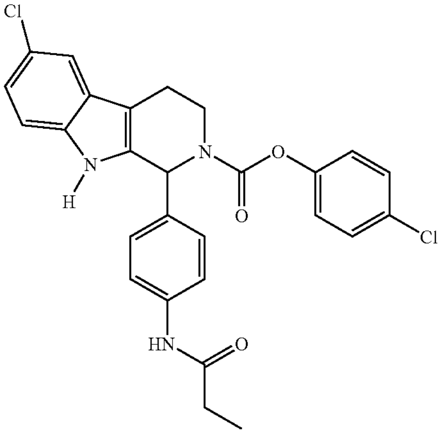
479
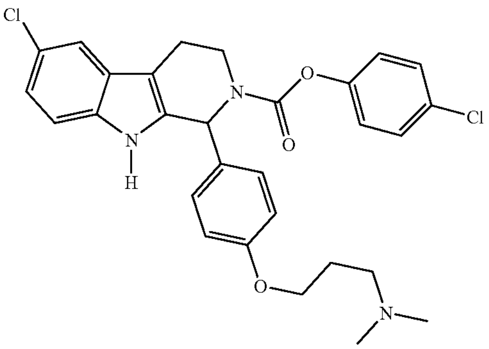
-continued
482
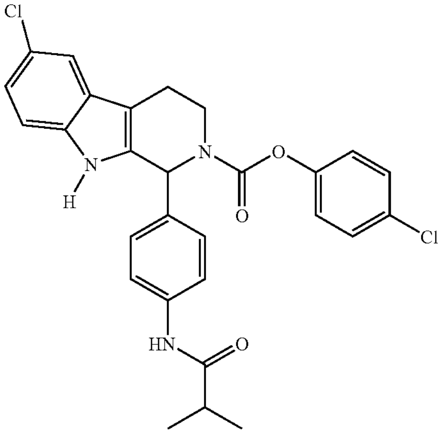
489
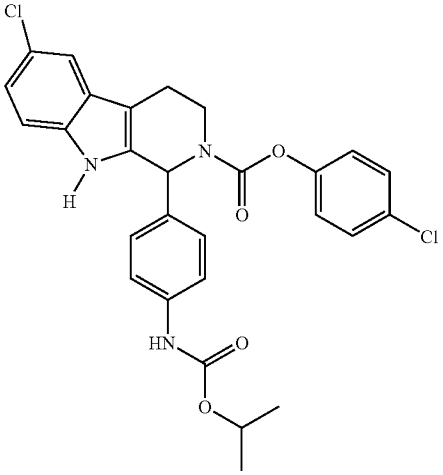
491
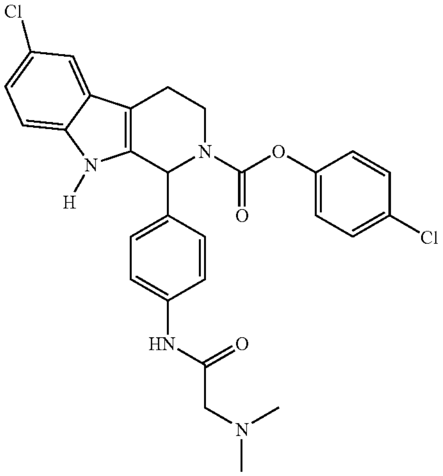

-continued
493
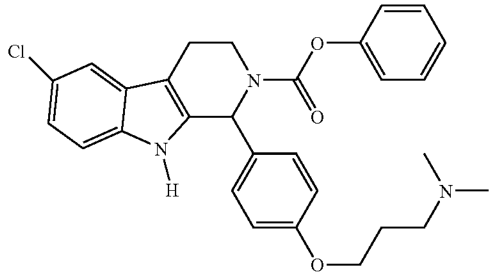
500
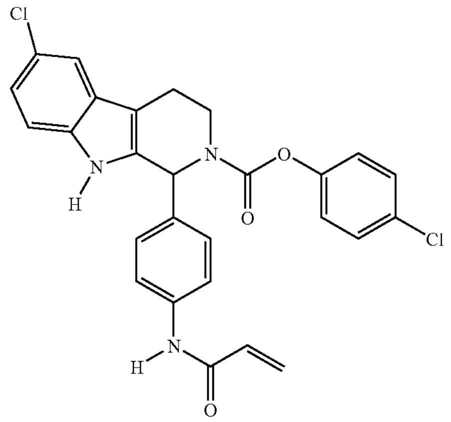
501
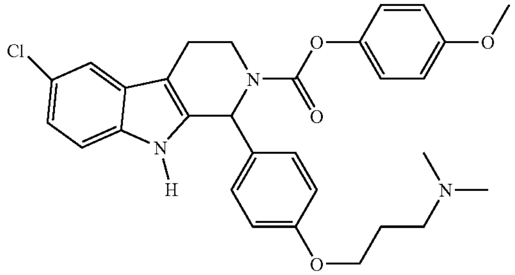
502
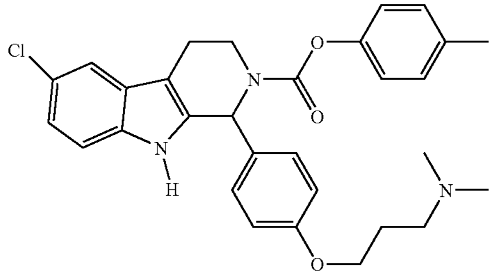
519
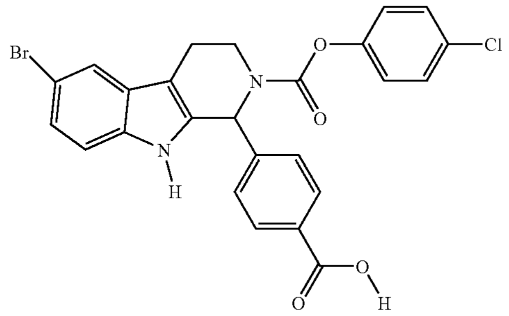
-continued
544
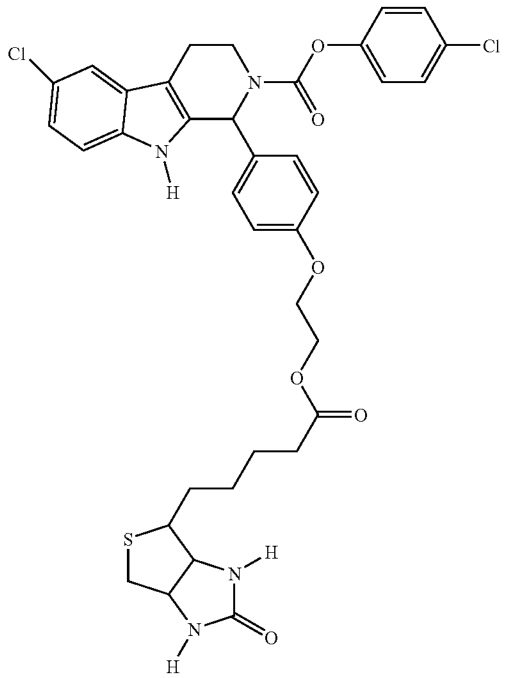
570
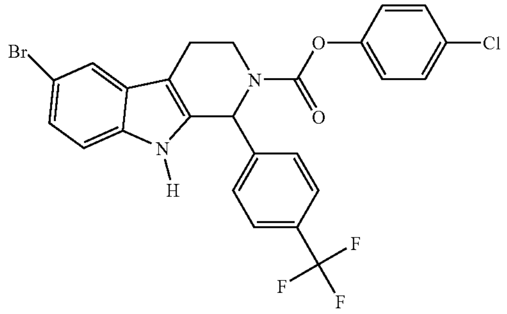
571
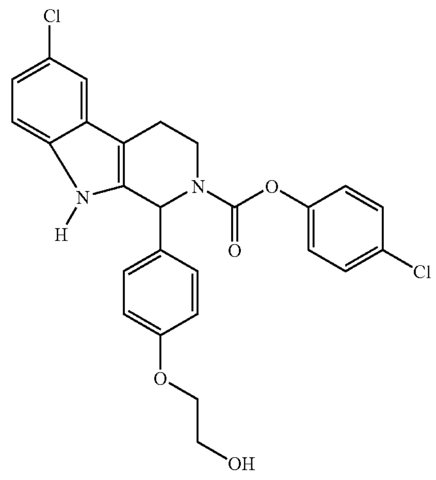

-continued
572
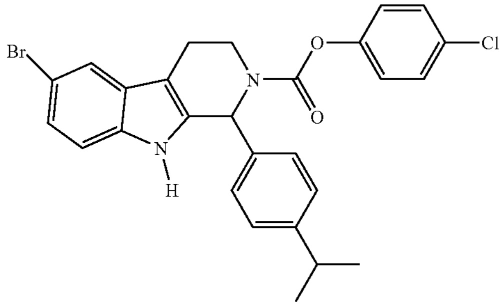
575
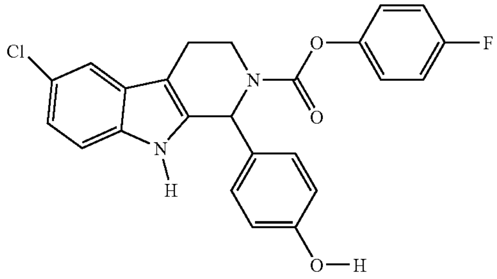
576
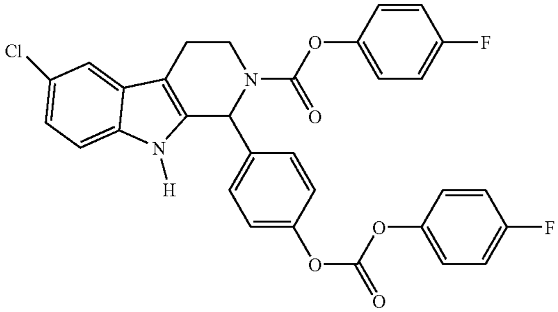
577
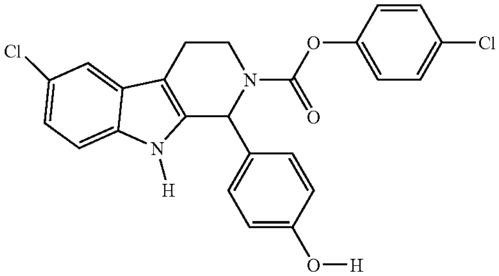
578
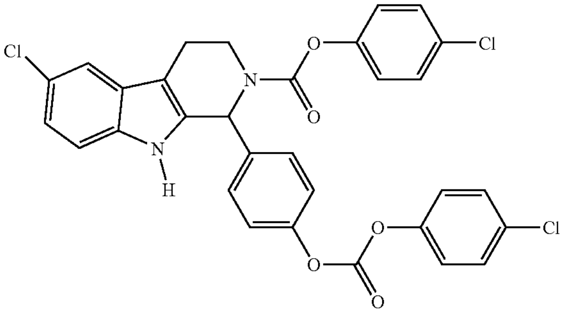
-continued
579
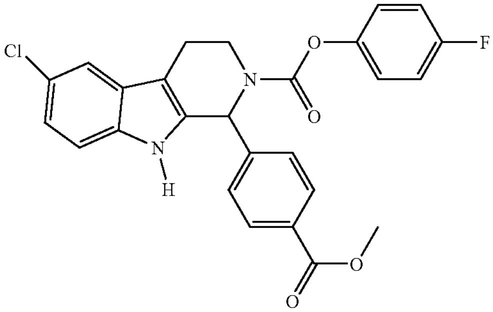
580
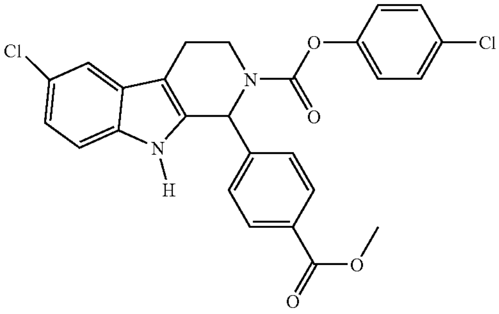
581
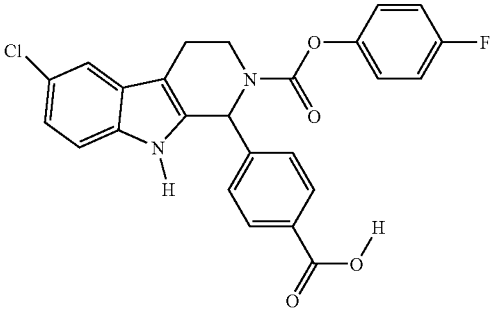
587
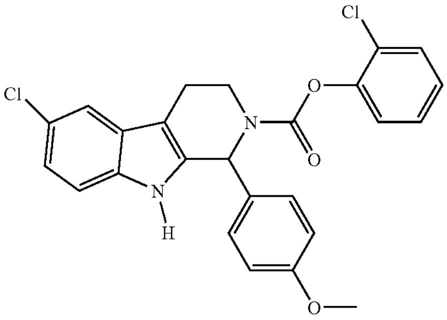
588
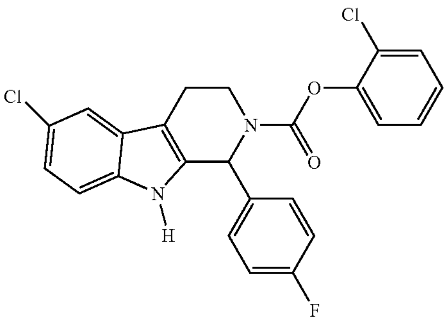

-continued
589
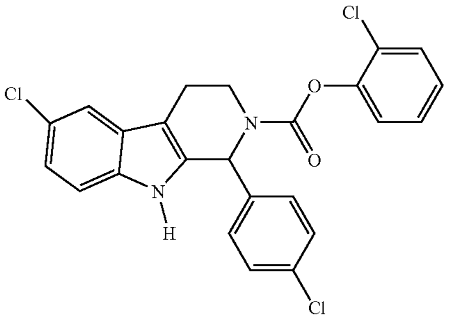
590
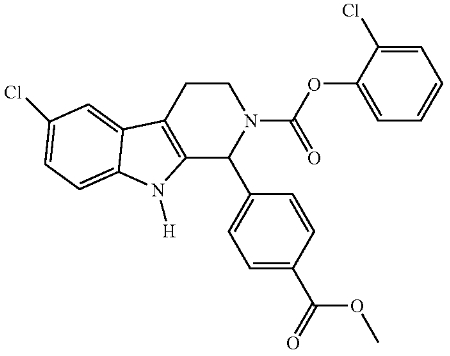
591
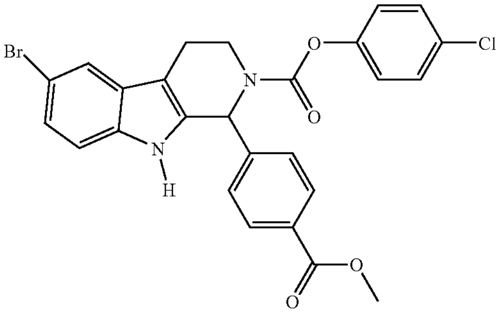
592
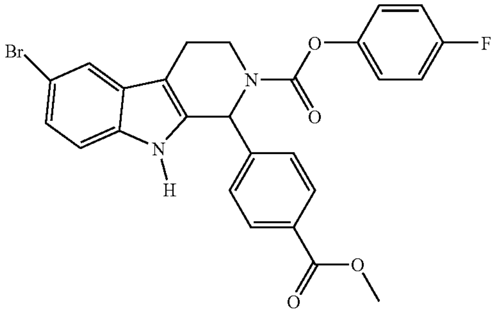
-continued
593
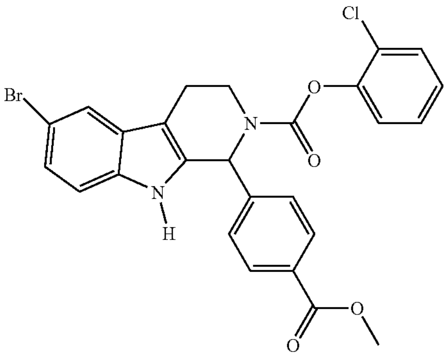
594
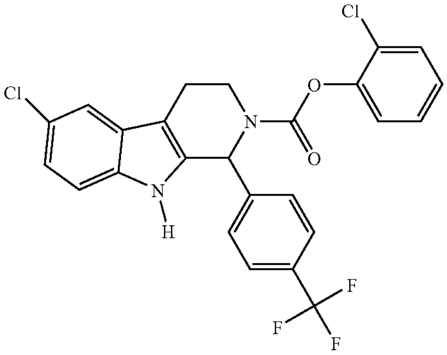
614
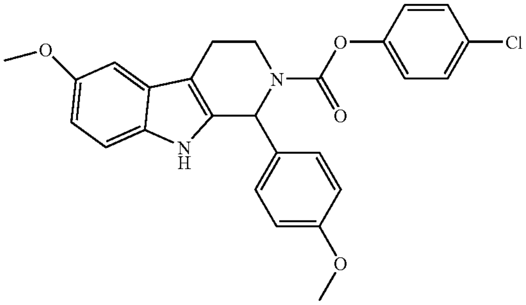
616
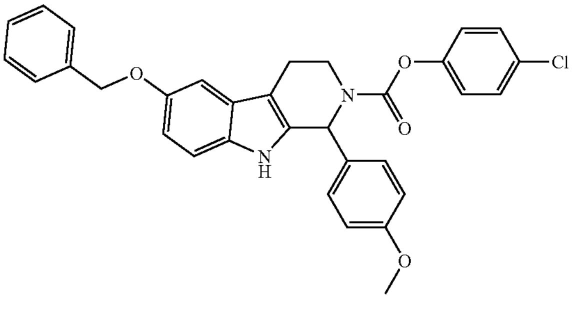

-continued
617
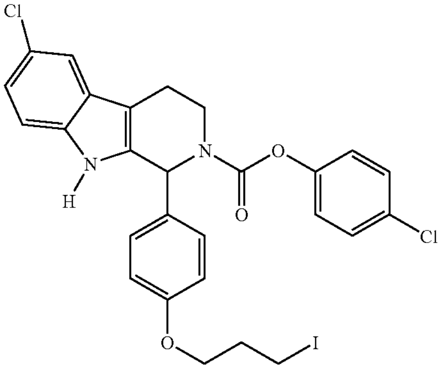
626
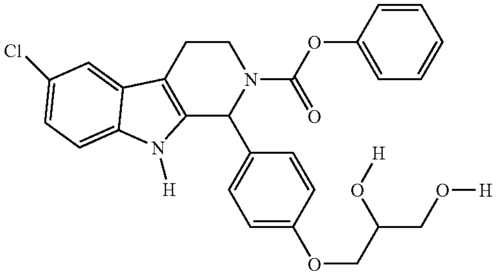
627
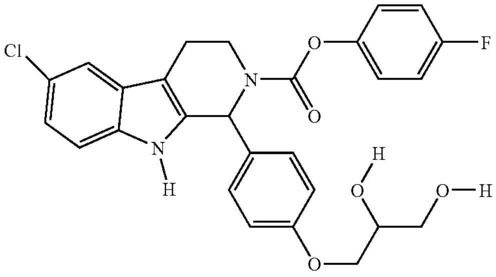
628
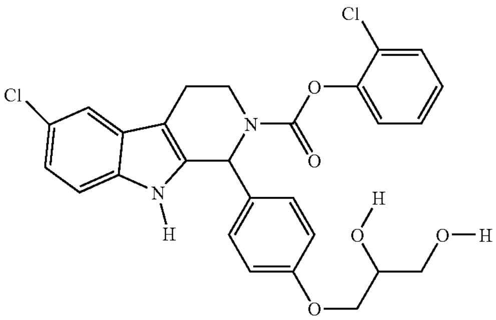
629
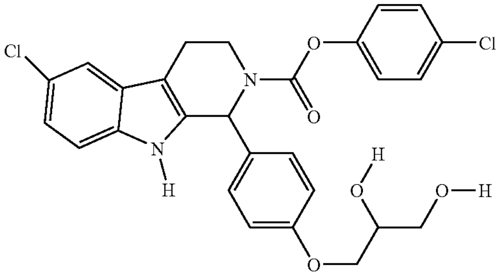
-continued
630
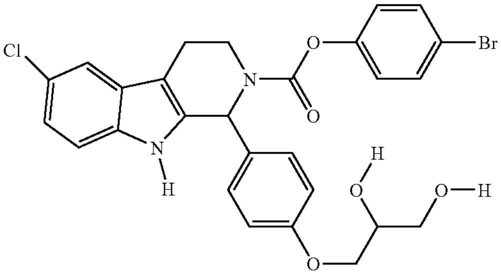
631
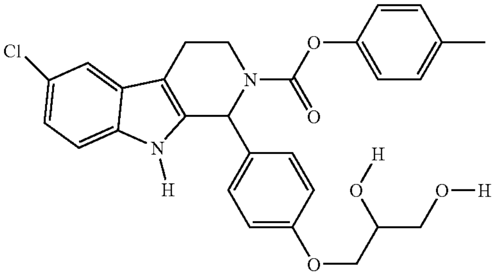
632
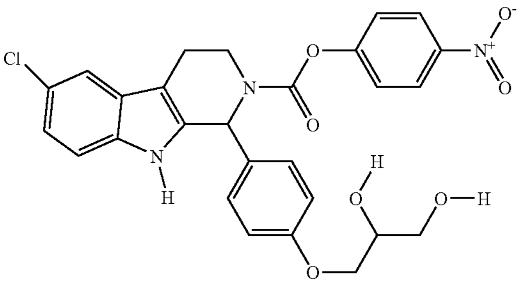
635
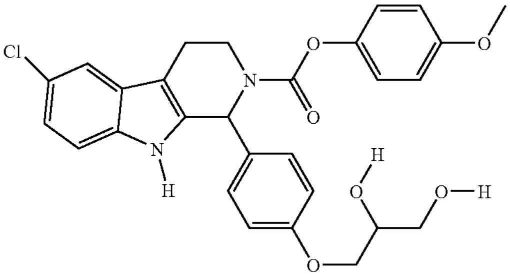

-continued
637
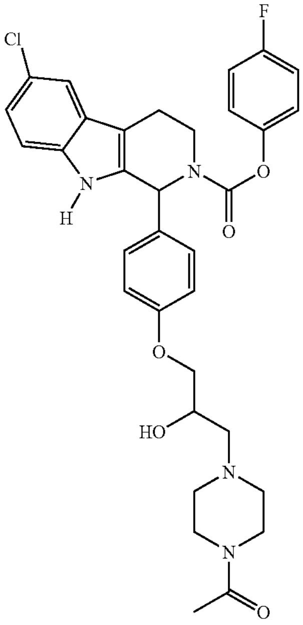
638
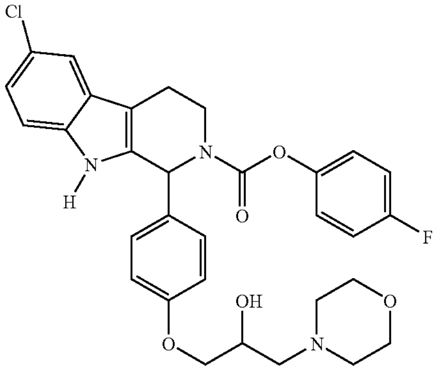
660
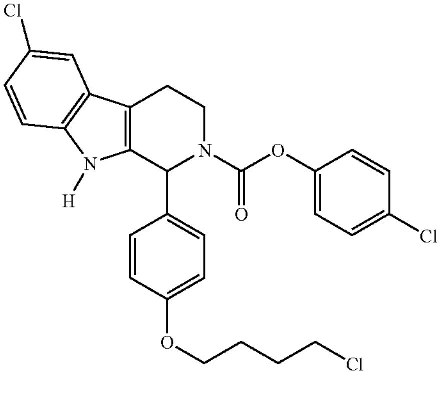
-continued
670
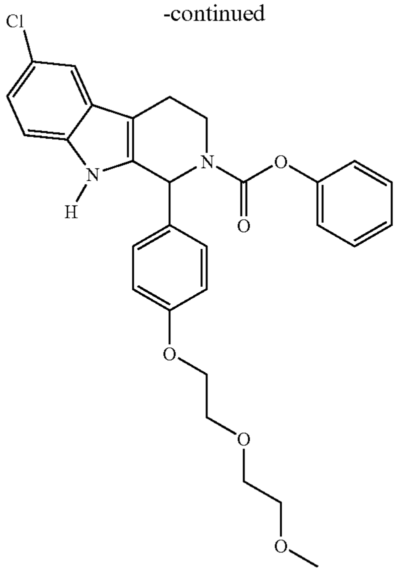
673
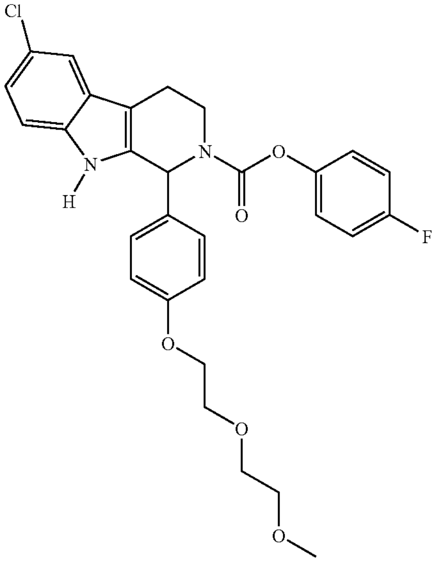
674
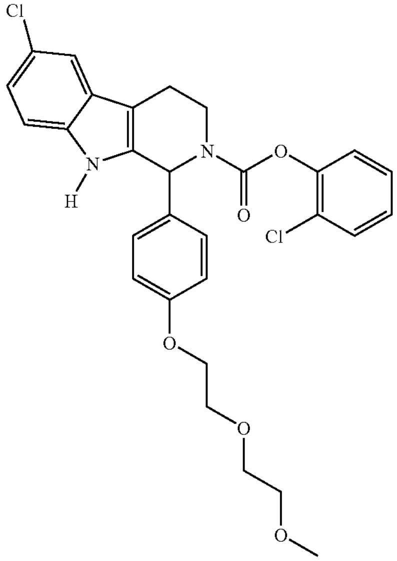

-continued
675
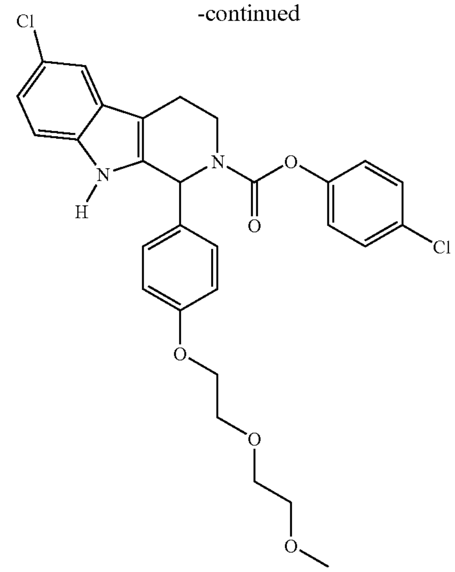
677
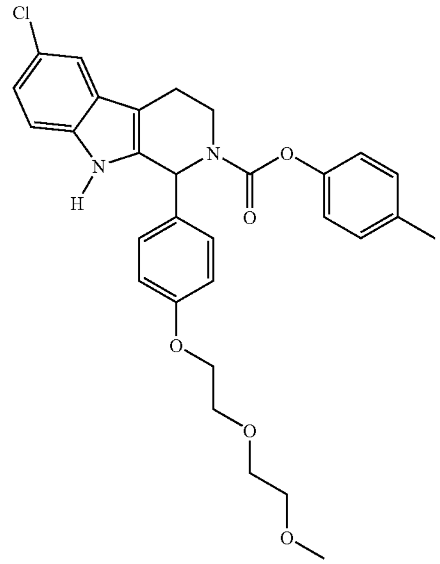
678
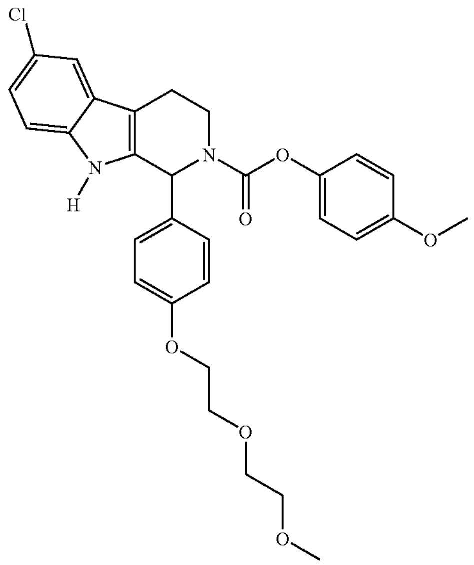
-continued
680
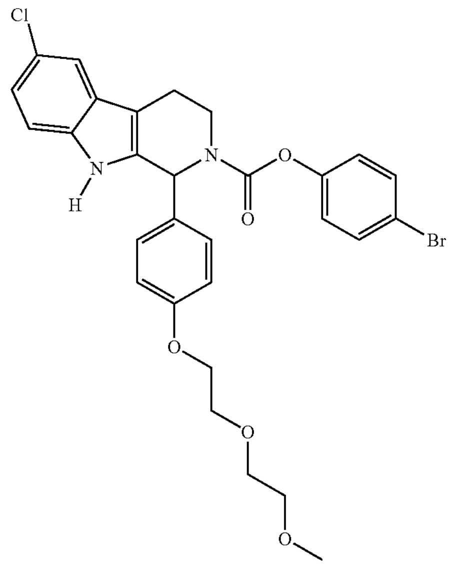
681
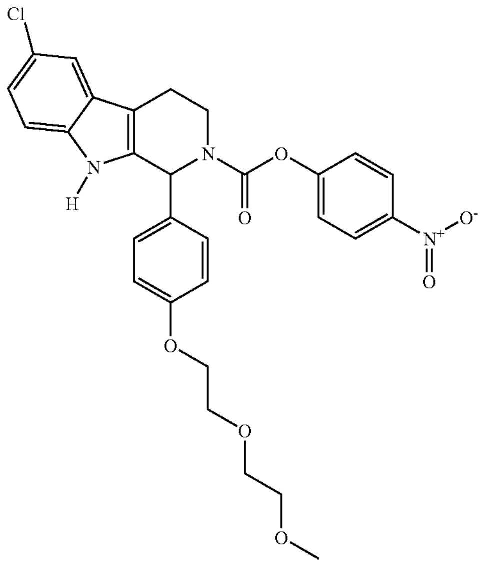
698
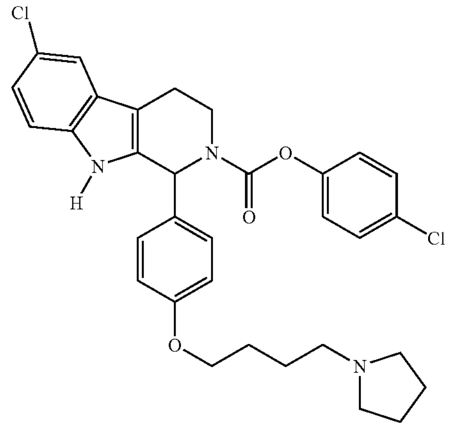

-continued
699
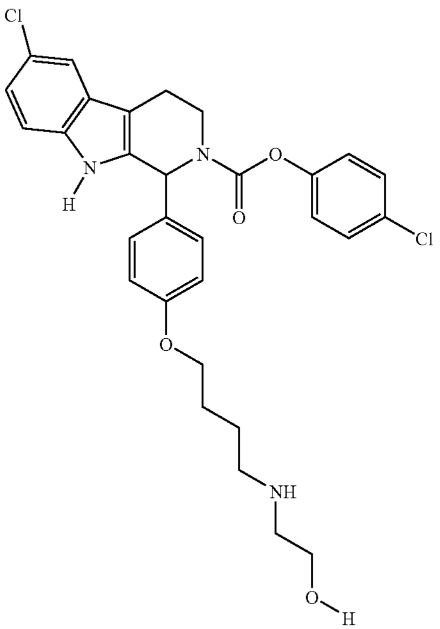
700
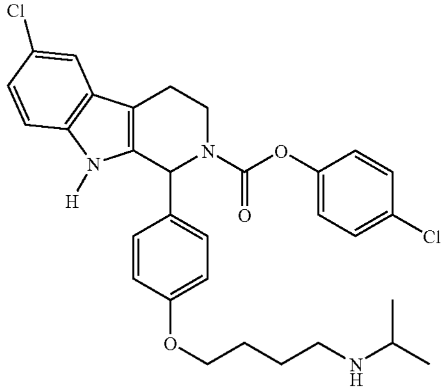
701
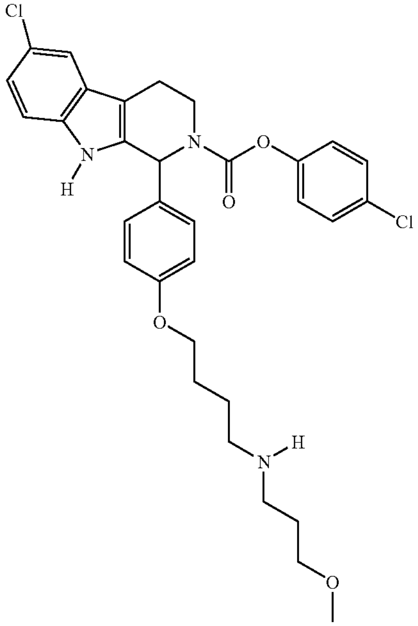
-continued
702
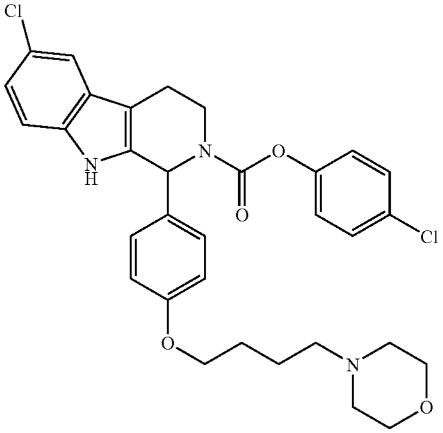
703
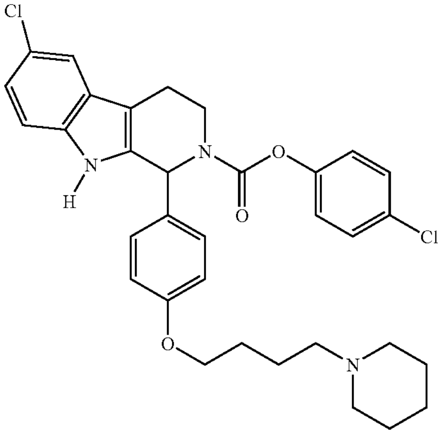
704
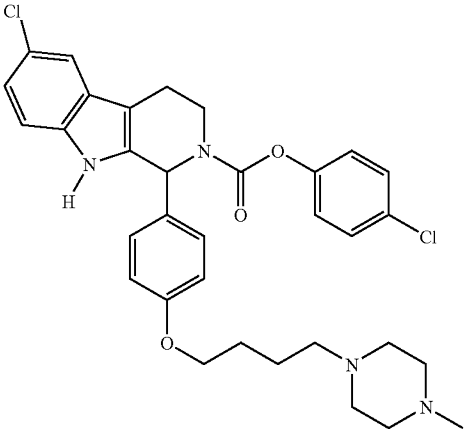

-continued
705
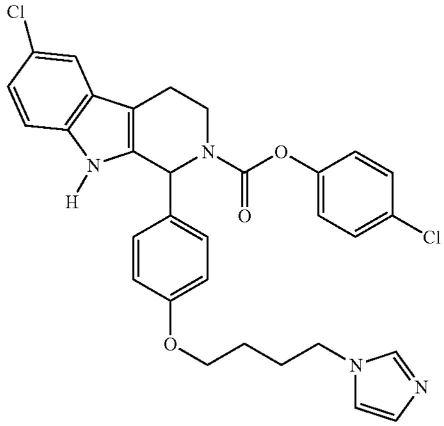
706
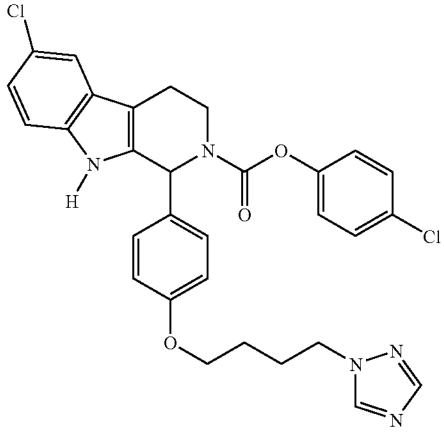
710
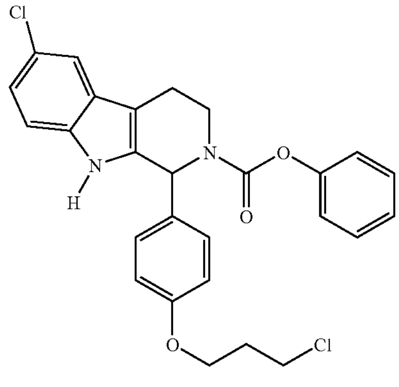
712
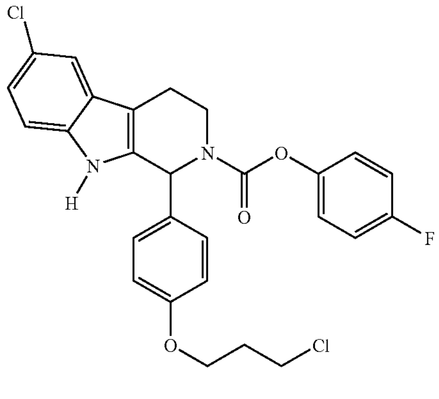
-continued
713
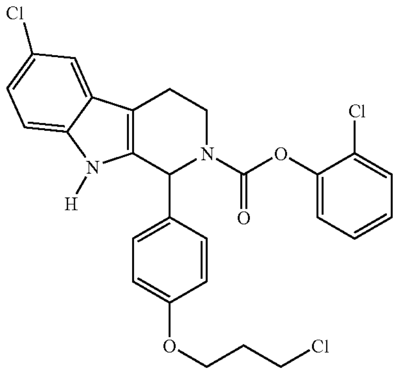
719
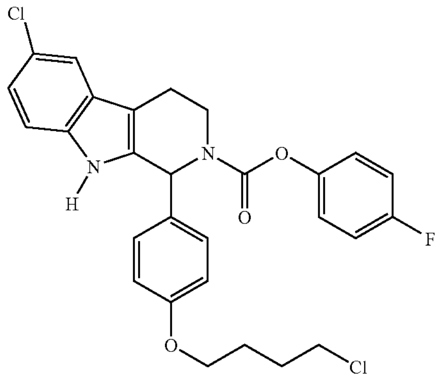
723
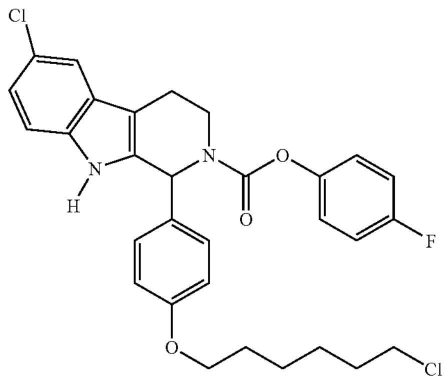

-continued
735
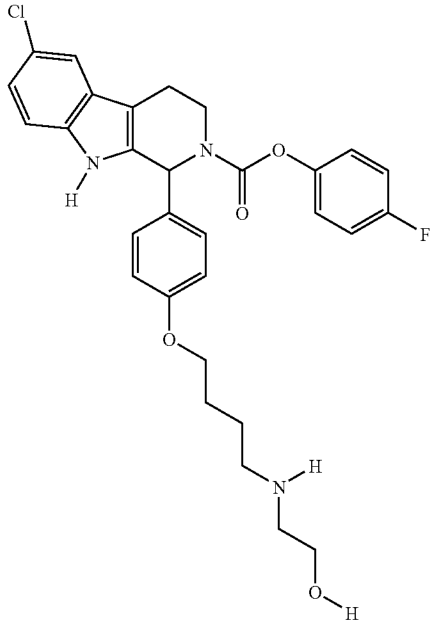
736
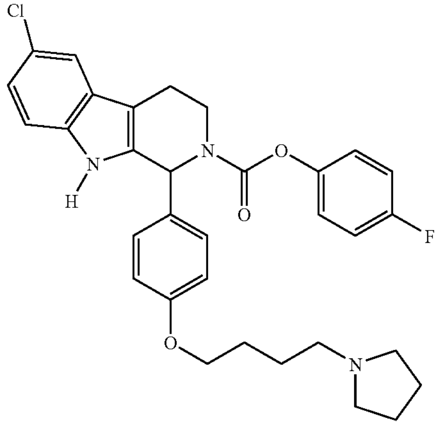
737
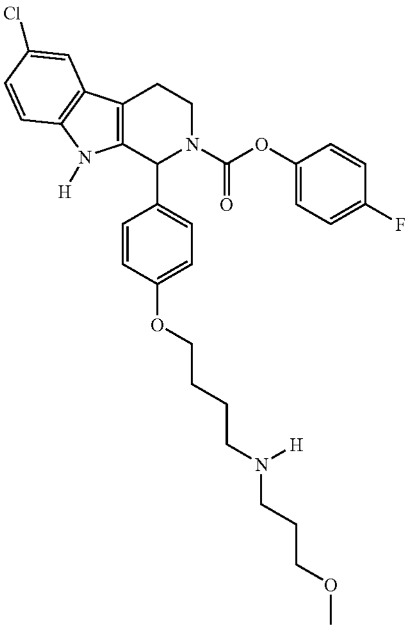
-continued
738
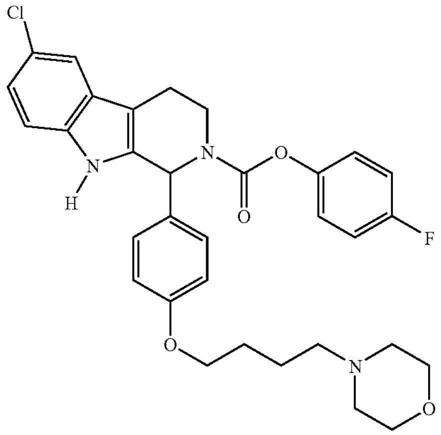
739
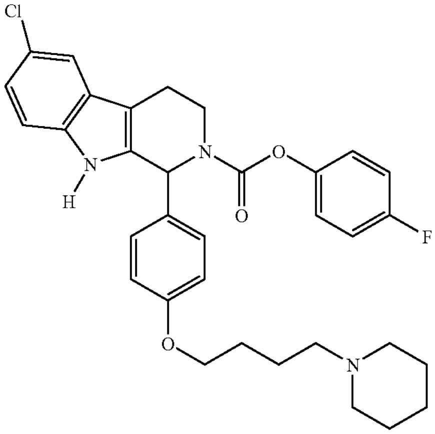
740
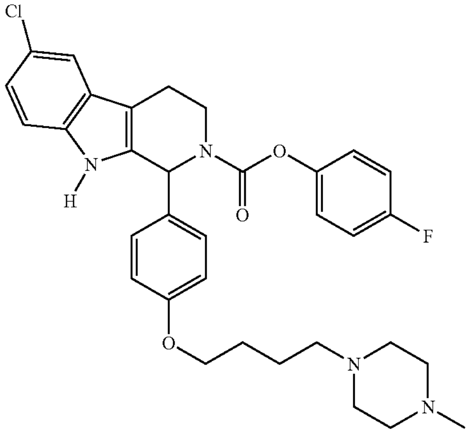

-continued
741
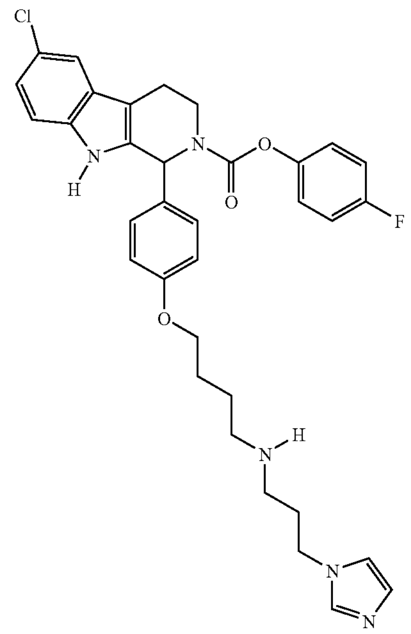
742
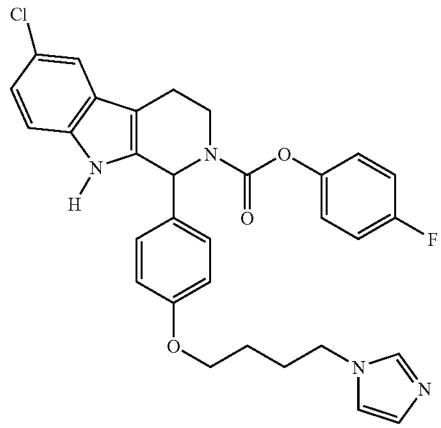
743
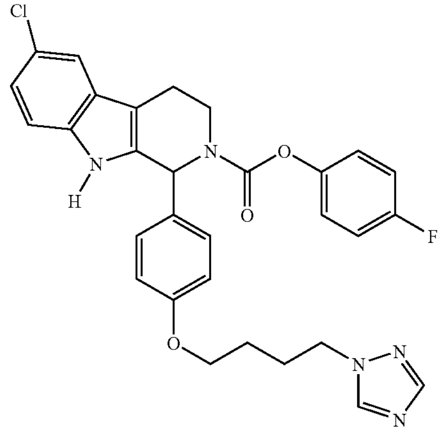
-continued
772
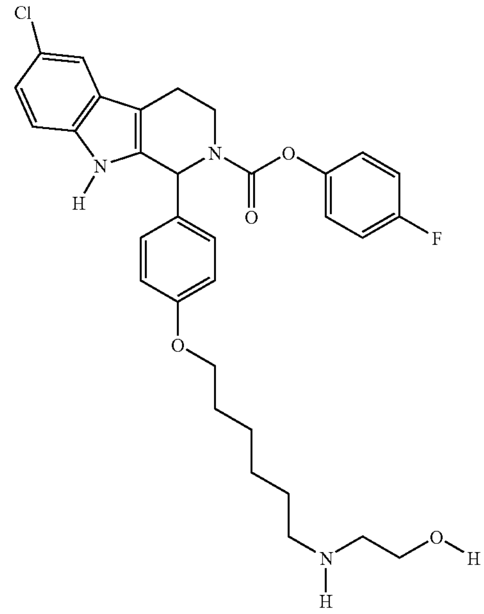
773
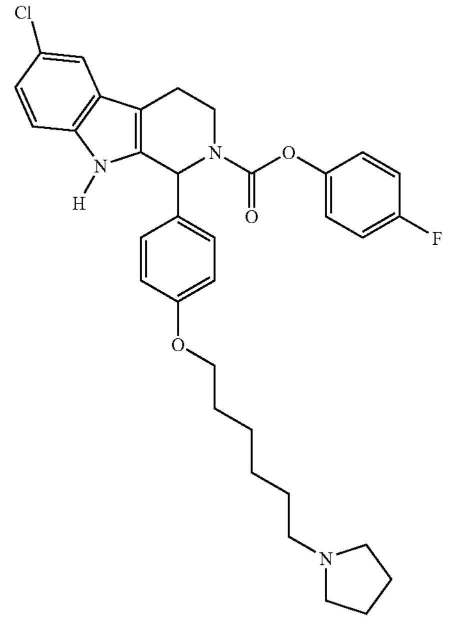

-continued
774
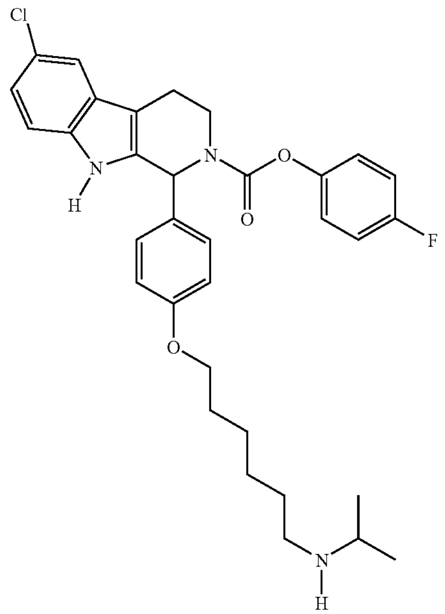
775
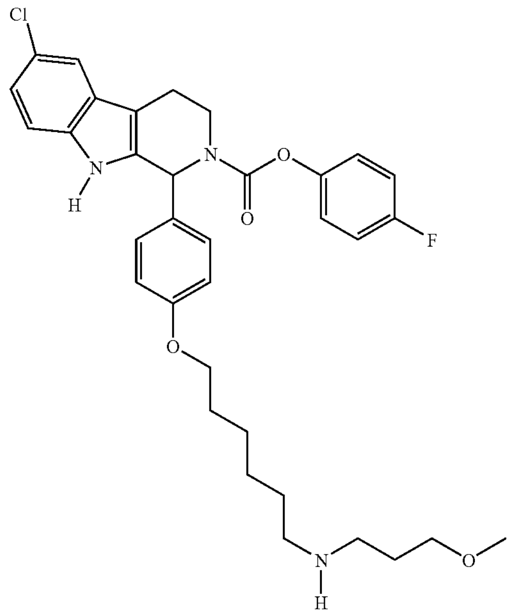
-continued
776
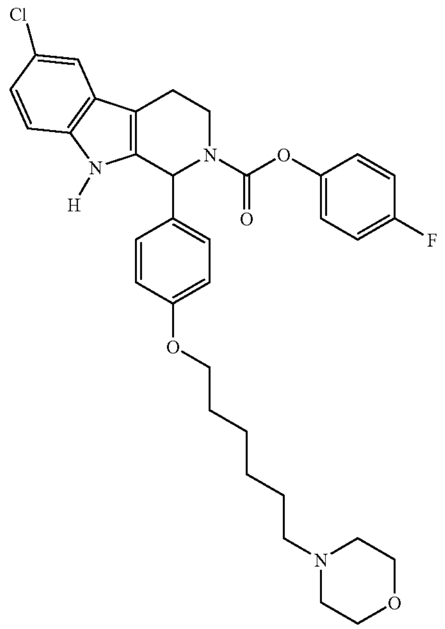
777
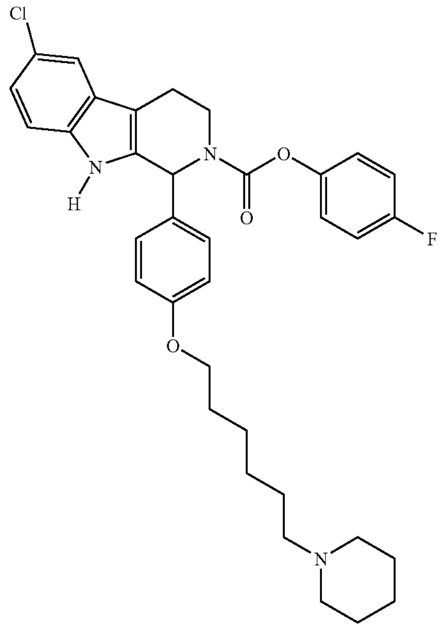

-continued
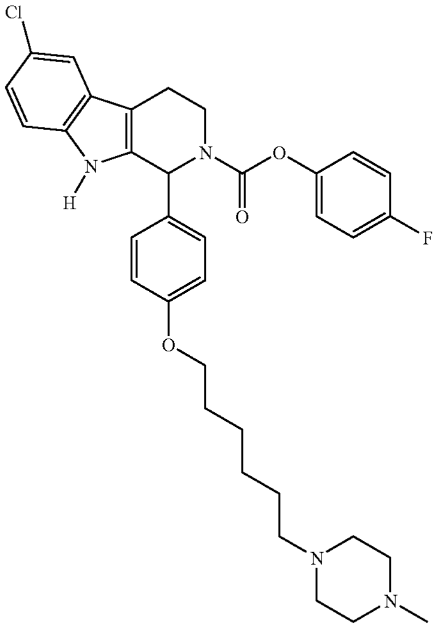
778
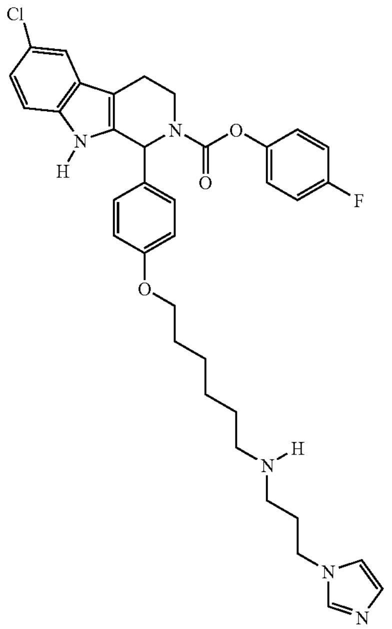
779
-continued
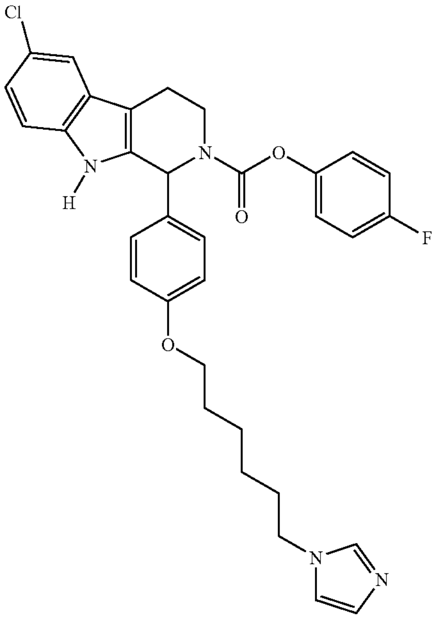
780
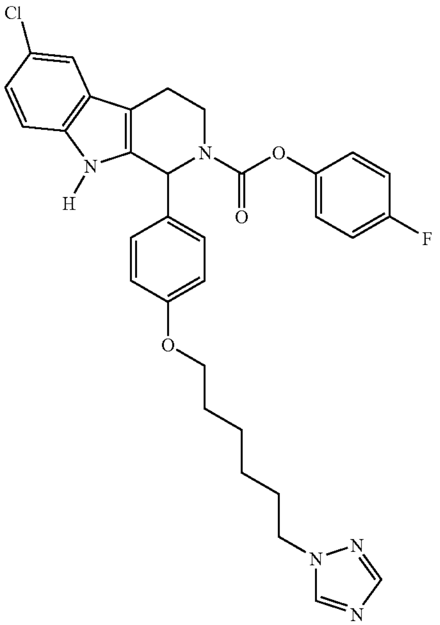
781

-continued
782
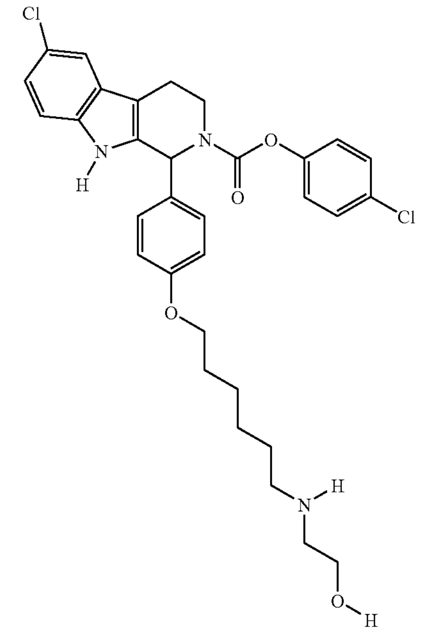
783
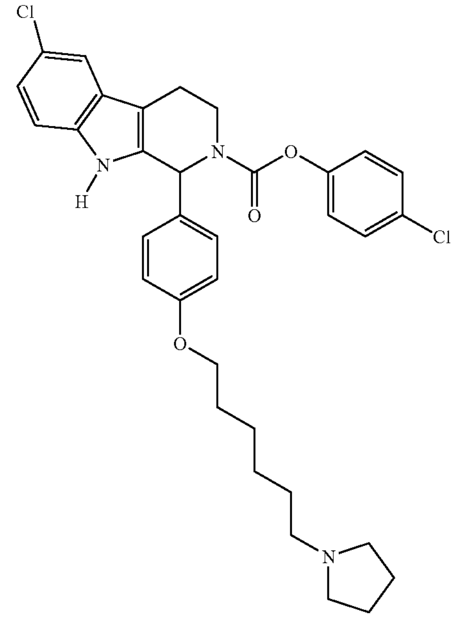
-continued
784
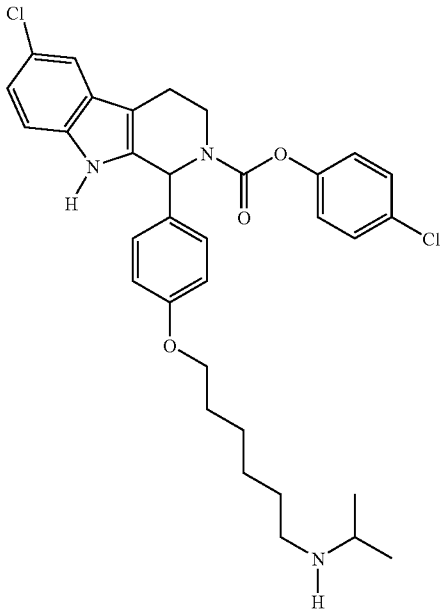
785
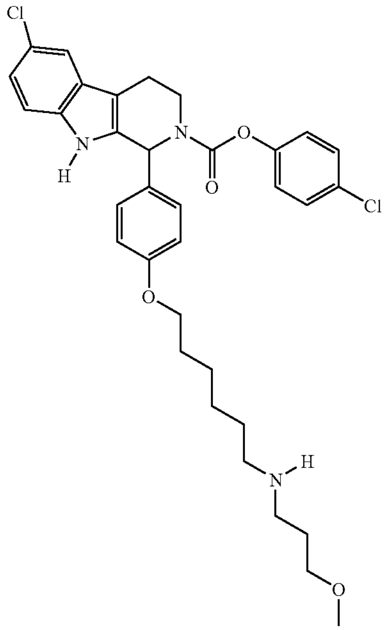

-continued
786
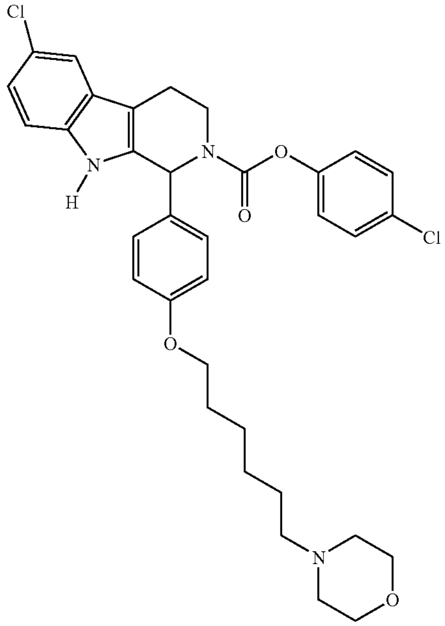
787
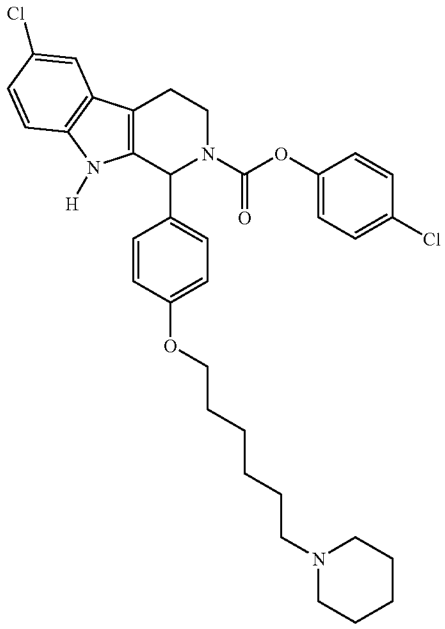
-continued
788
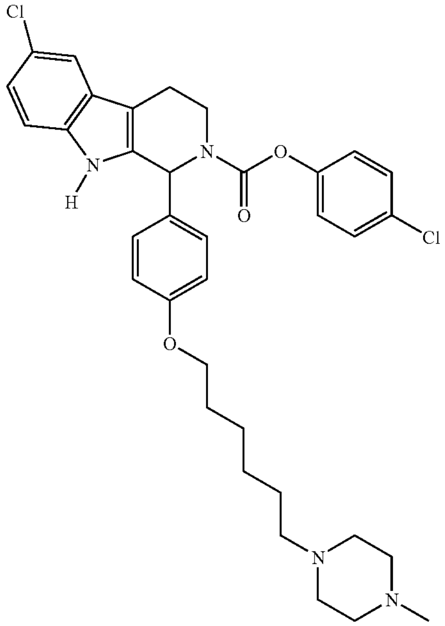
789
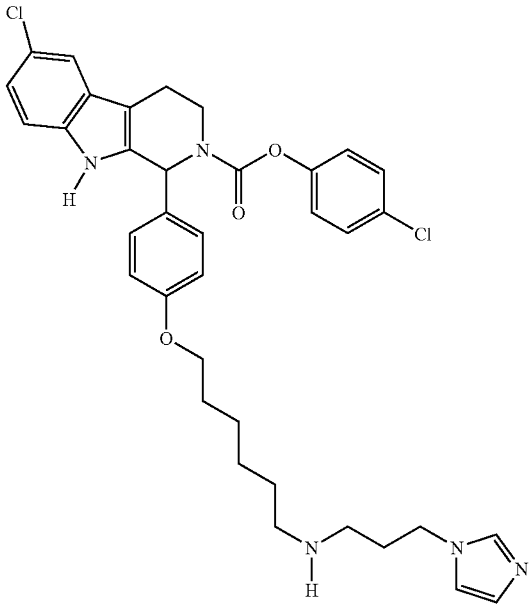

-continued
790
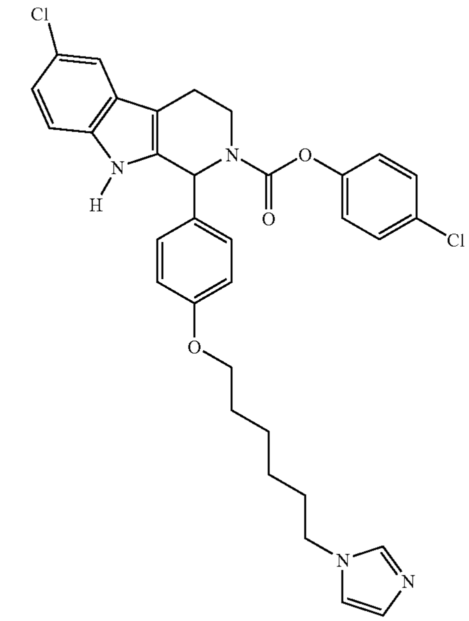
791
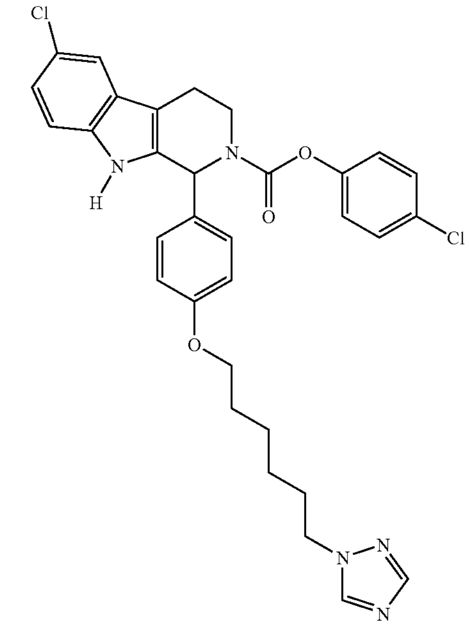
833
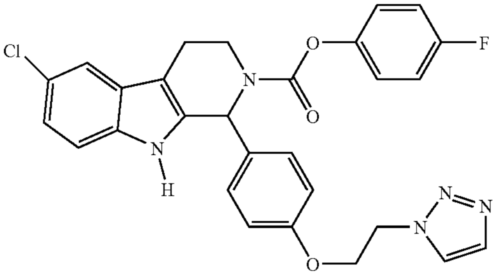
-continued
834
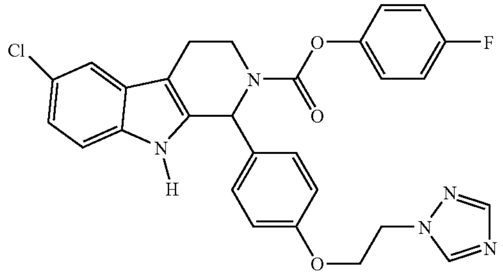
835
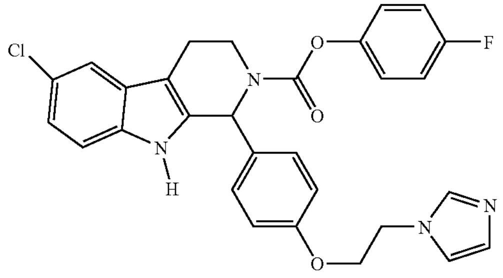
836
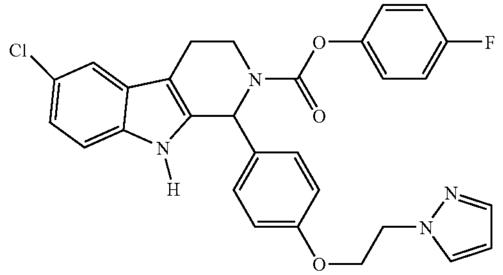
837
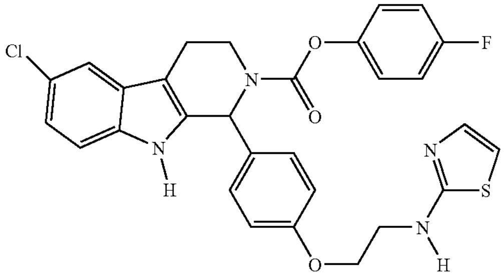
838
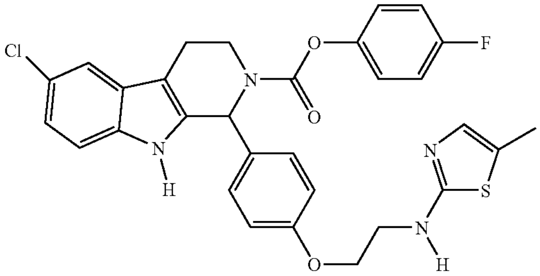

-continued
839
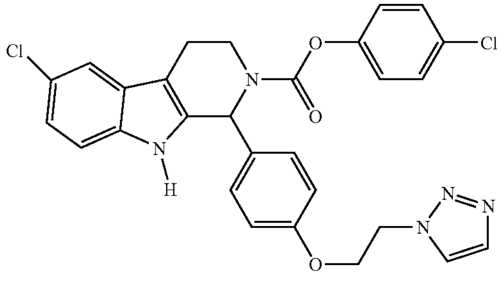
840
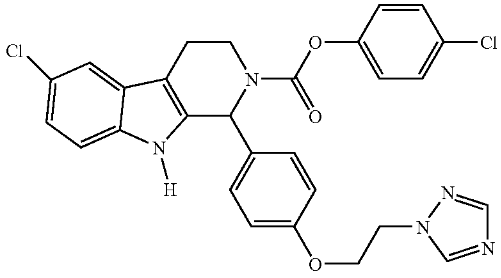
841
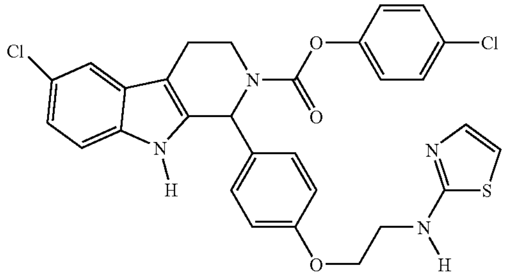
842
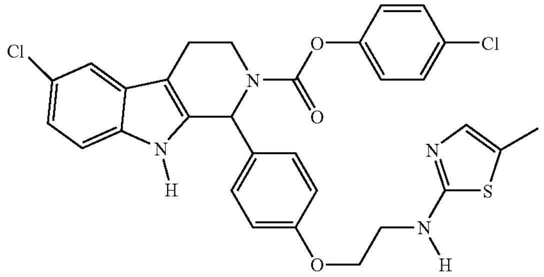
843
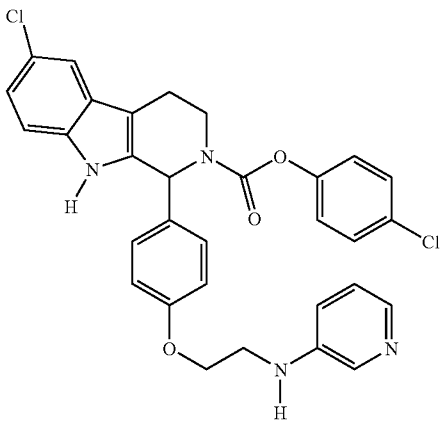
-continued
845
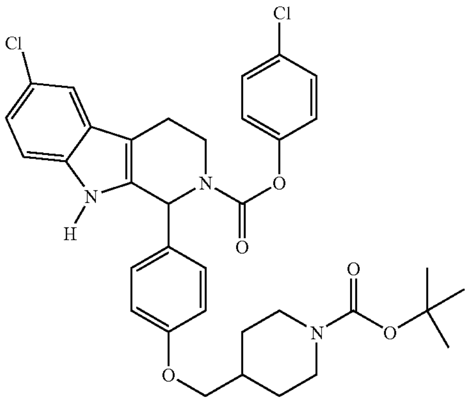
846
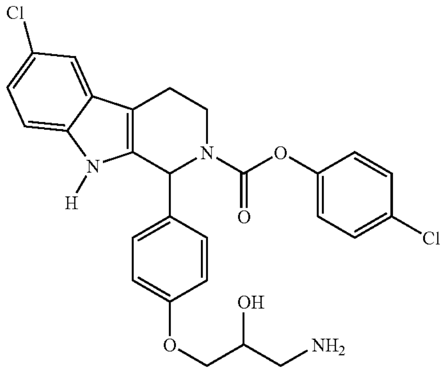
847
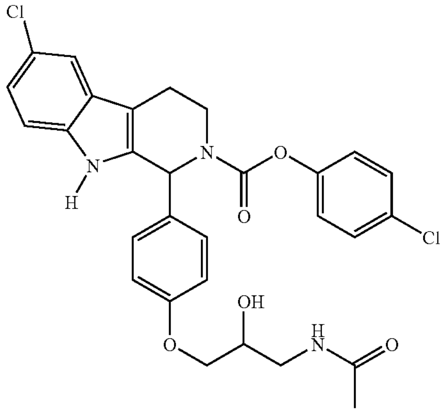
848
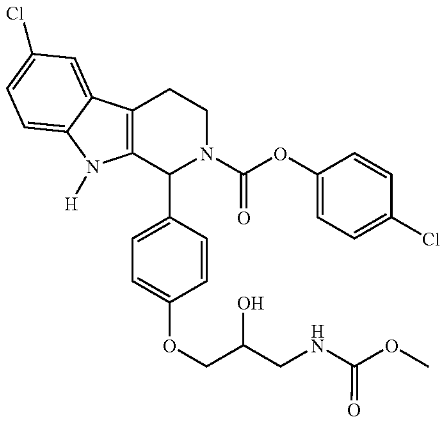

-continued
849
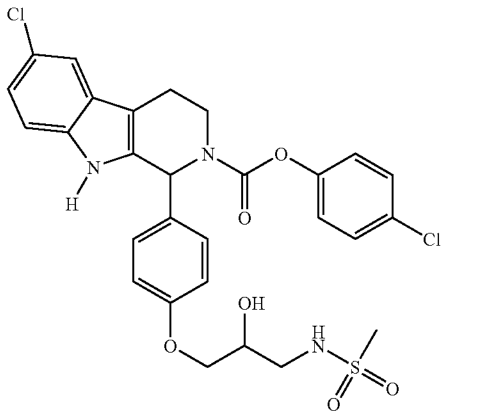
850
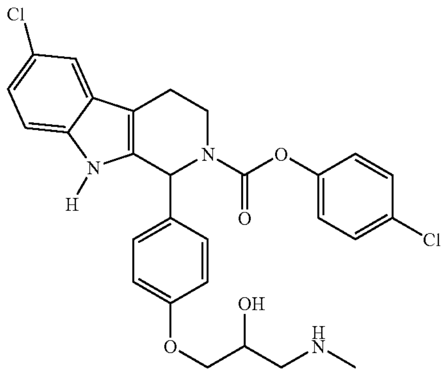
867
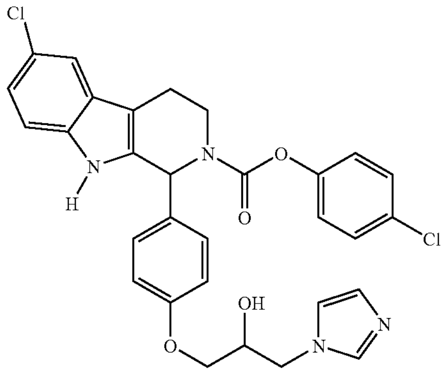
882
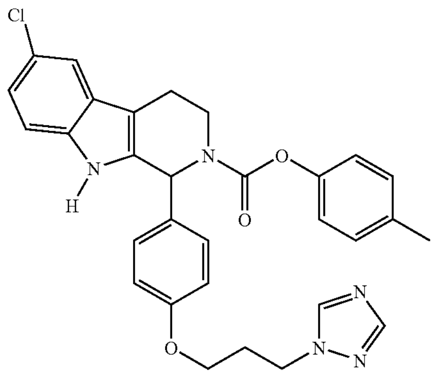
-continued
888
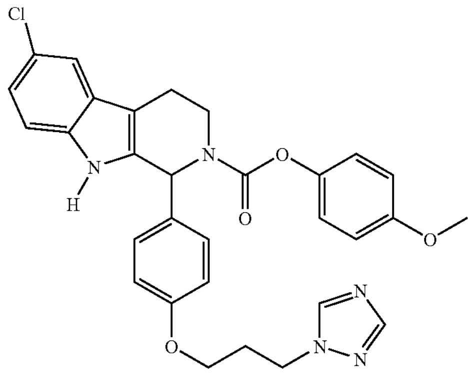
889
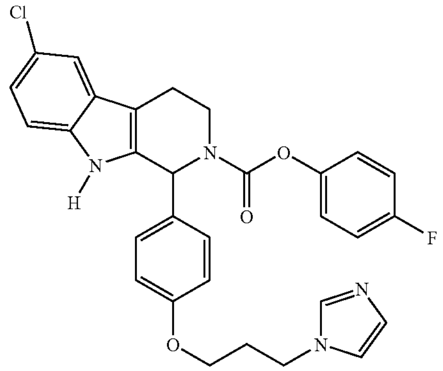
891
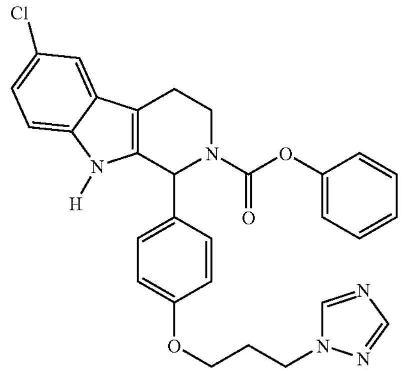
892
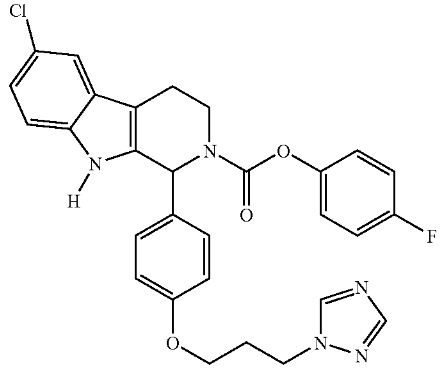

-continued
894
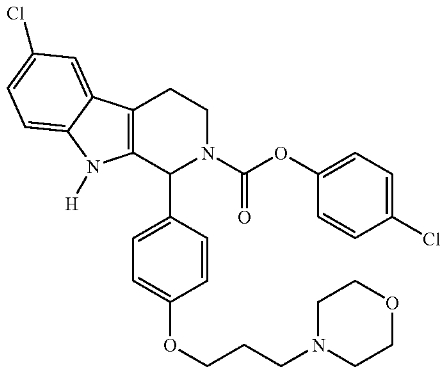
900
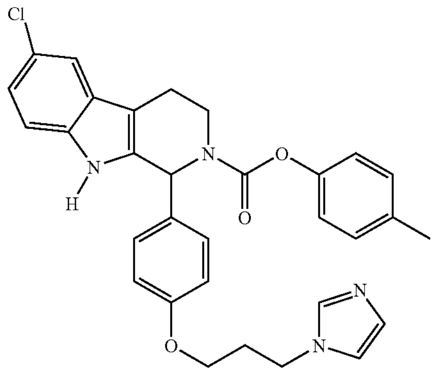
903
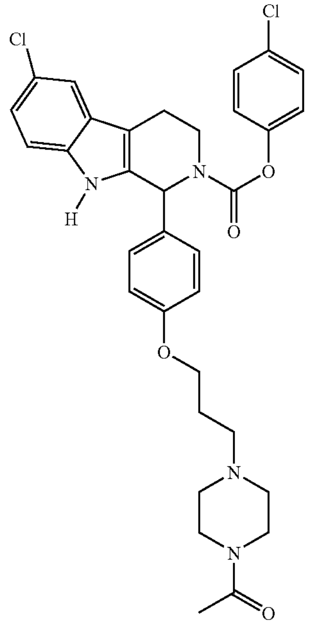
-continued
904
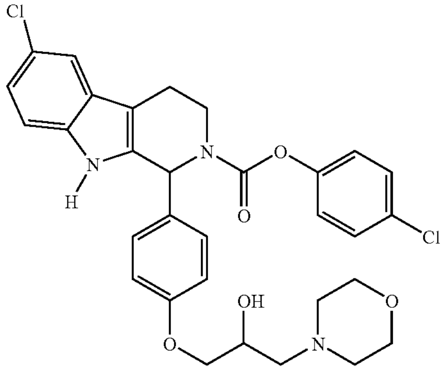
908
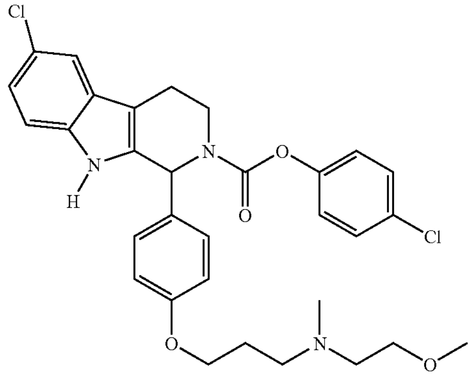
911
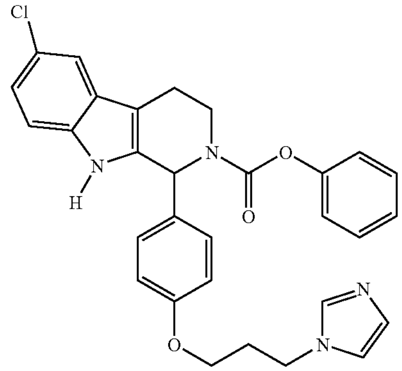
913
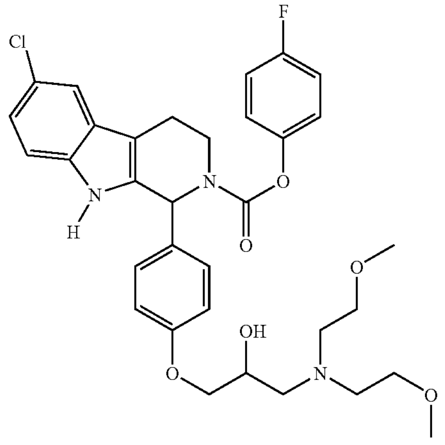

-continued
915
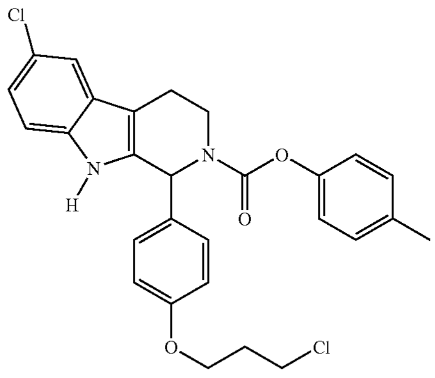
916
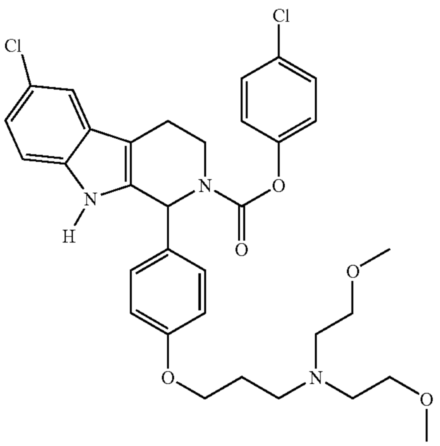
917
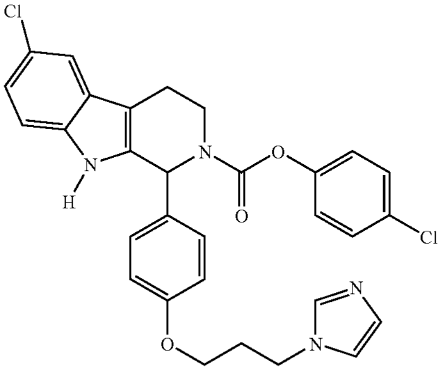
918
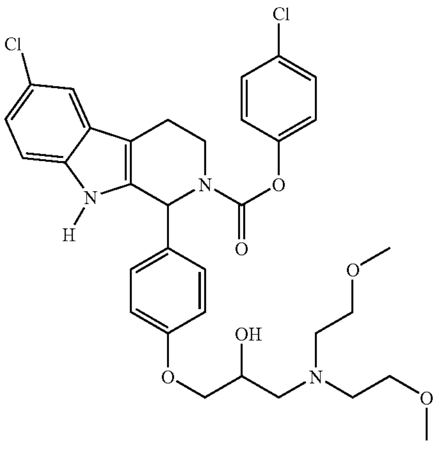
-continued
920
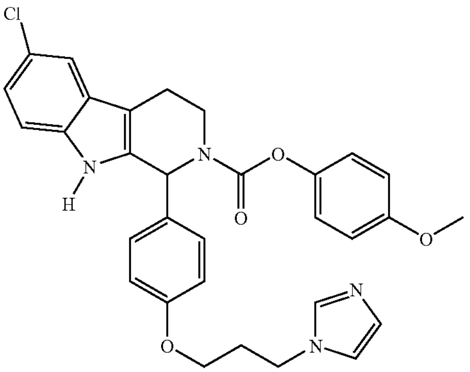
921
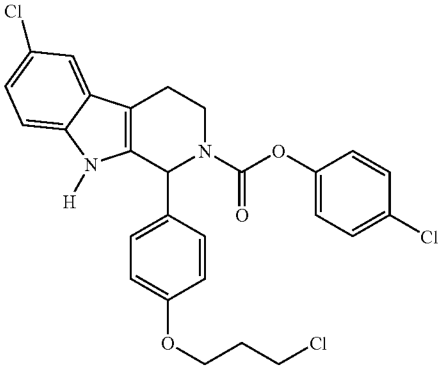
922
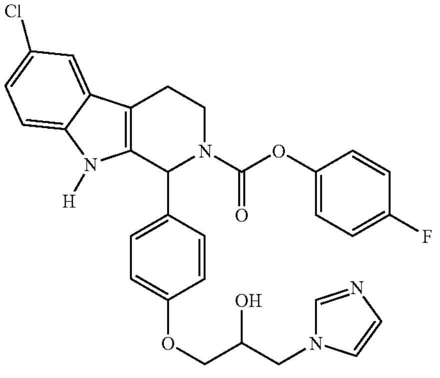
923
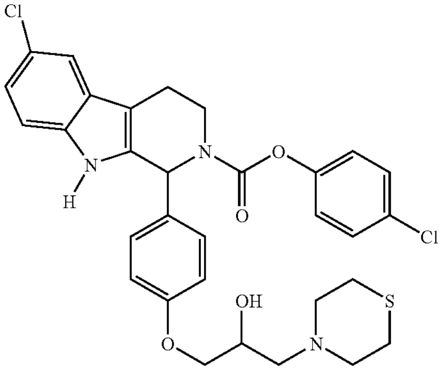

-continued
925
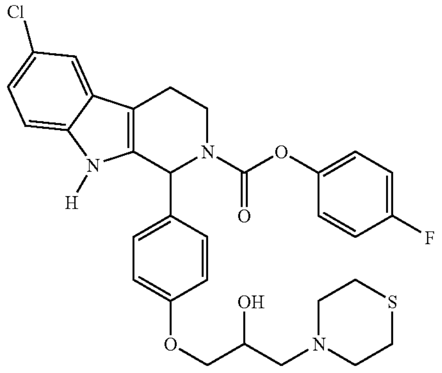
926
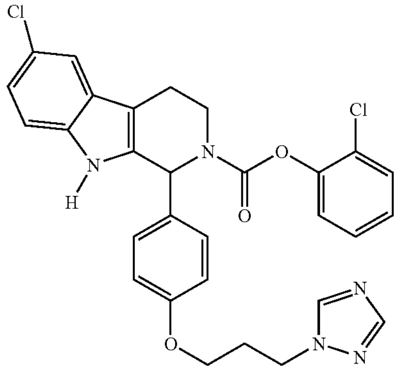
932
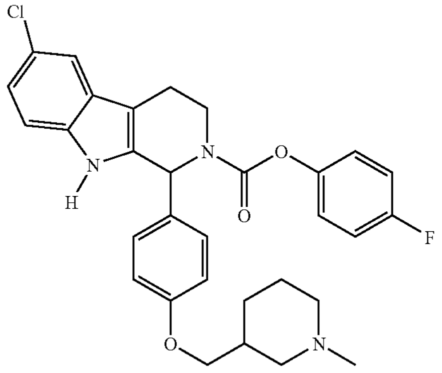
933
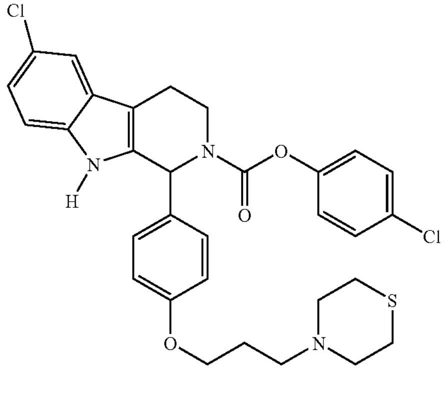
-continued
934
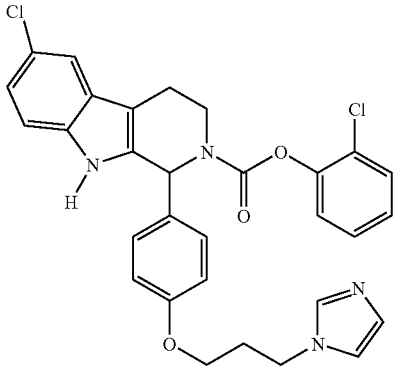
936
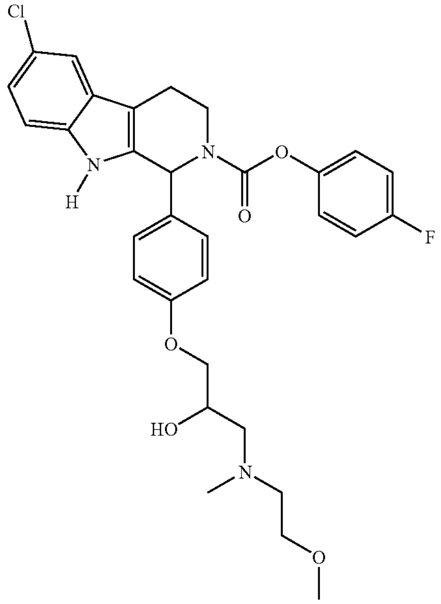
938
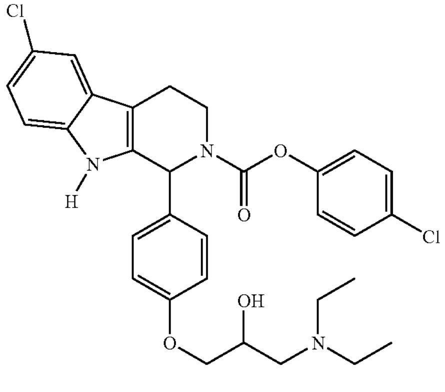

-continued
941
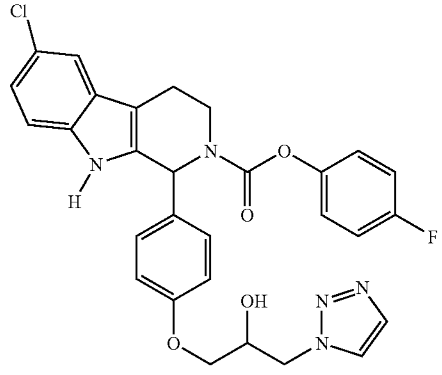
942
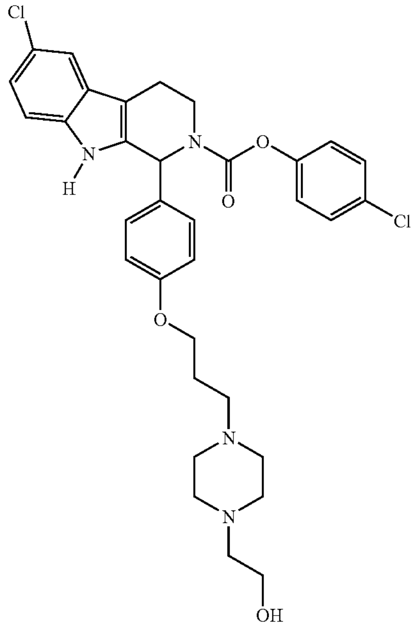
944
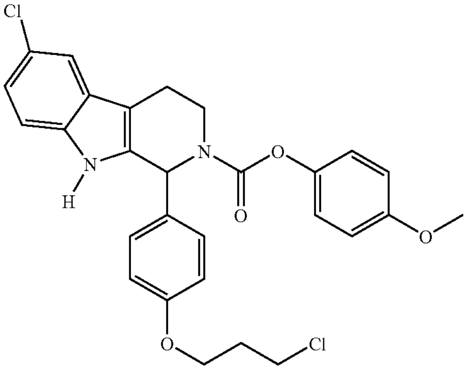
-continued
946
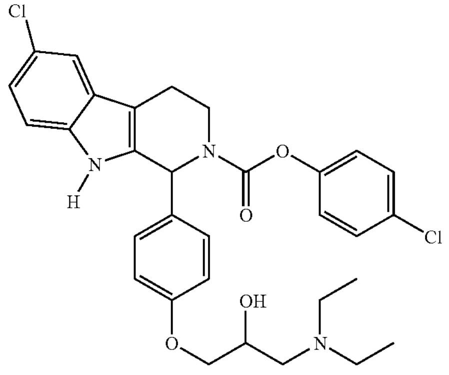
951
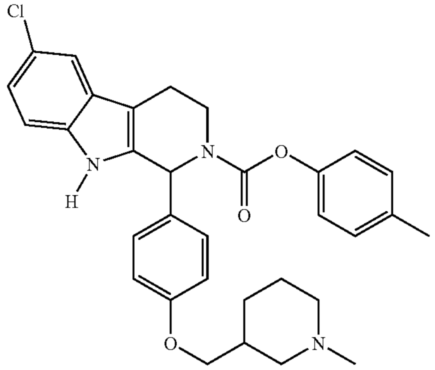
952
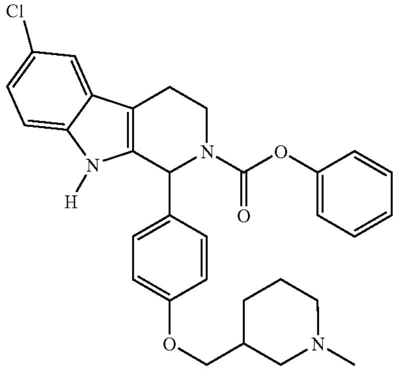
953
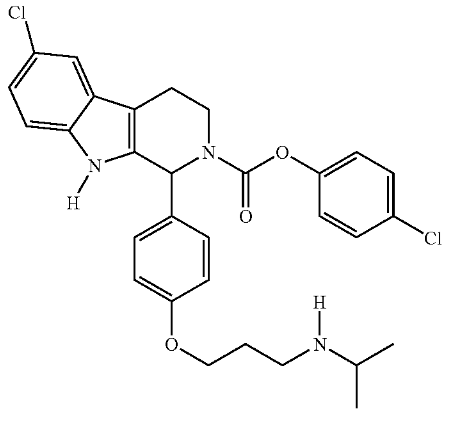

-continued
958
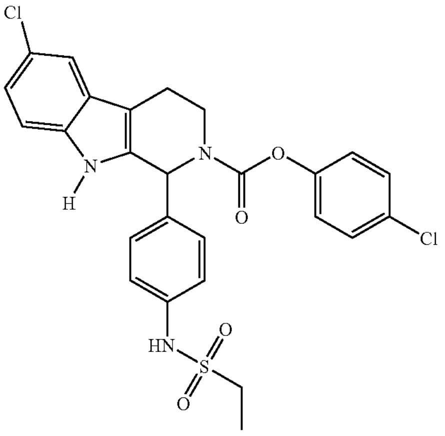
960
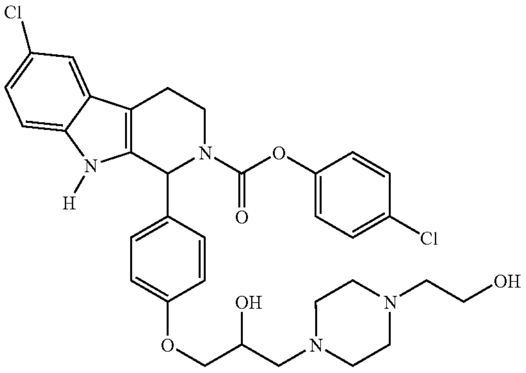
961
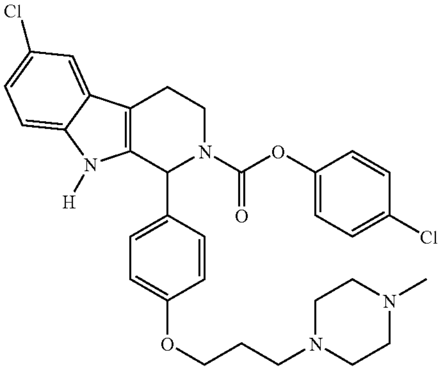
963
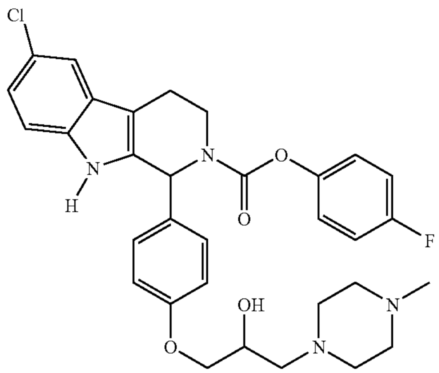
-continued
964
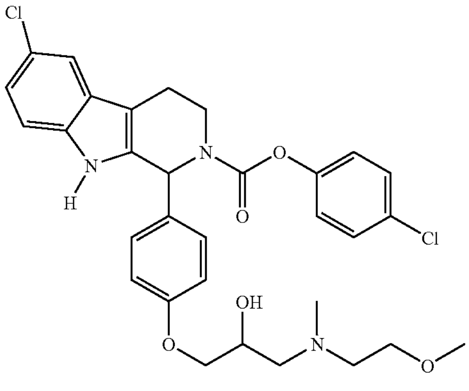
966
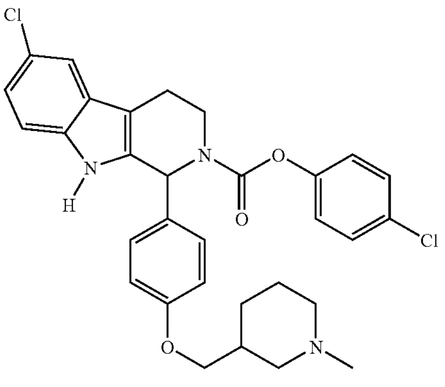
967
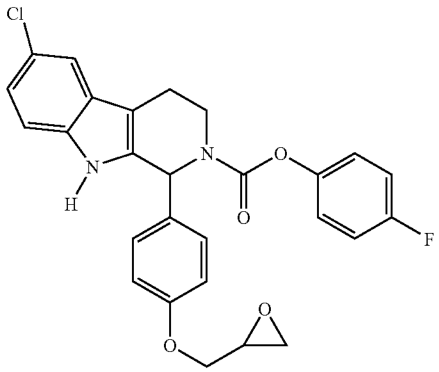
970
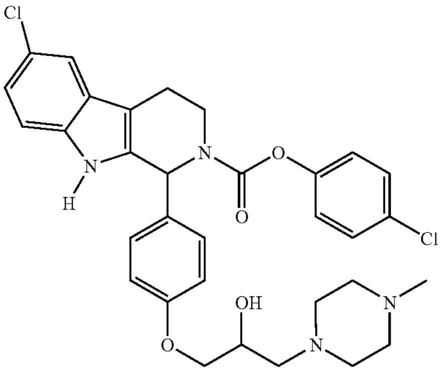

-continued
973
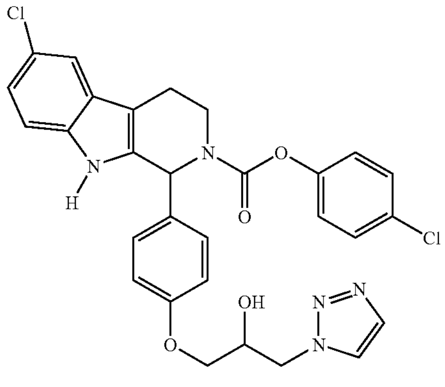
974
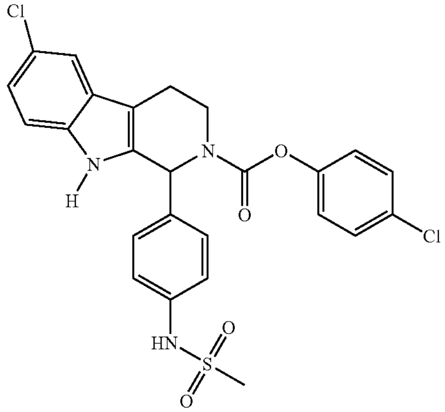
976
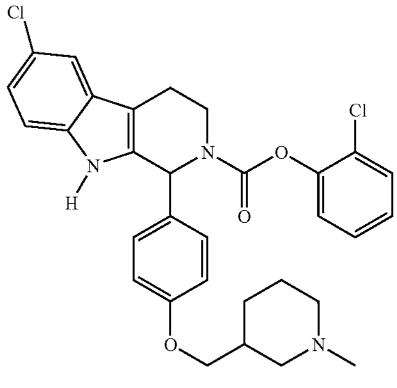
977
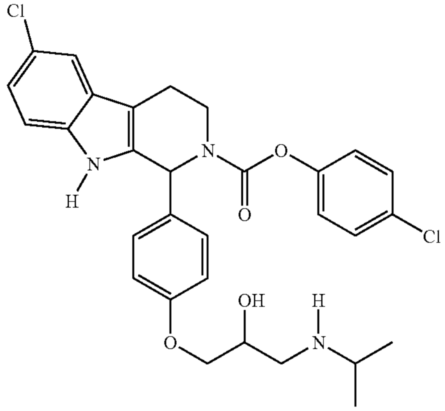
-continued
981
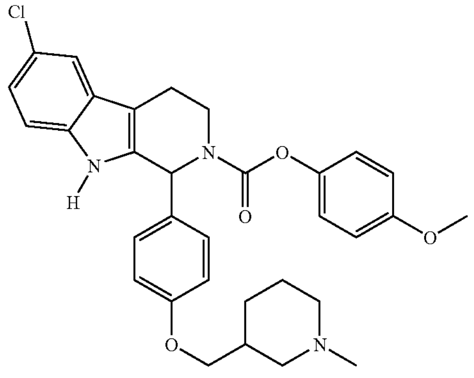
984
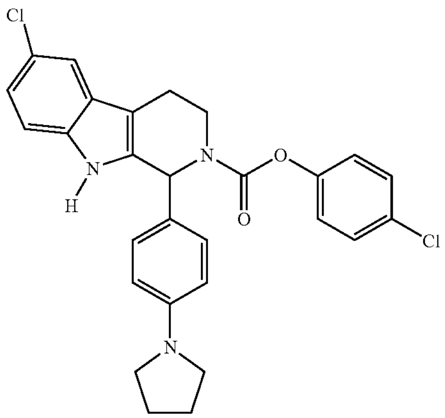
988
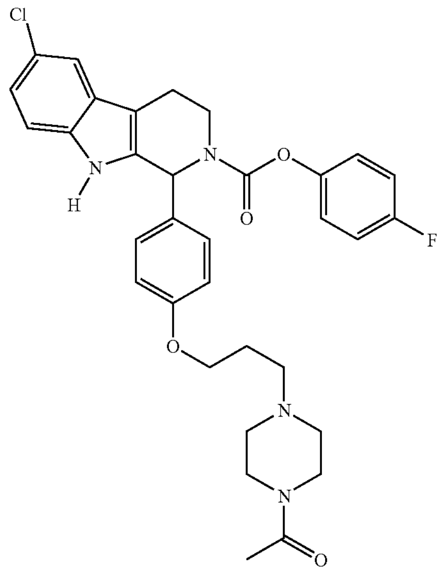

-continued
989
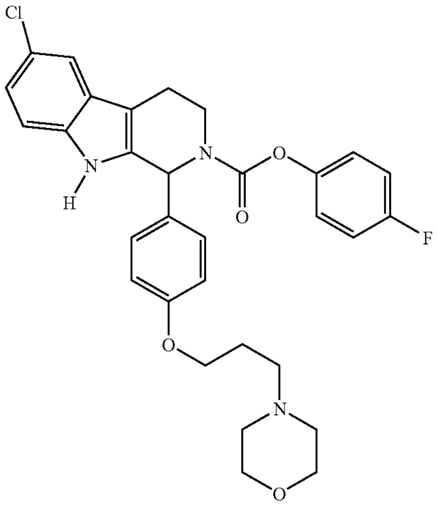
990
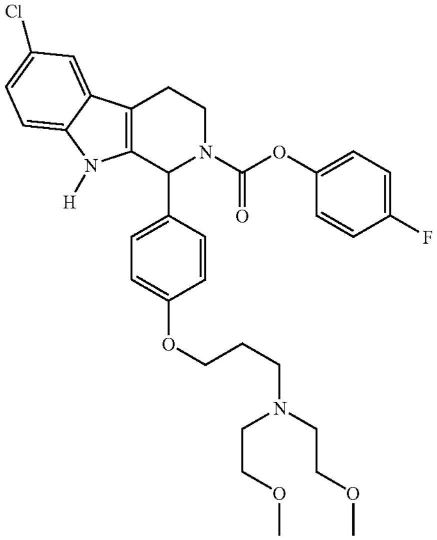
991
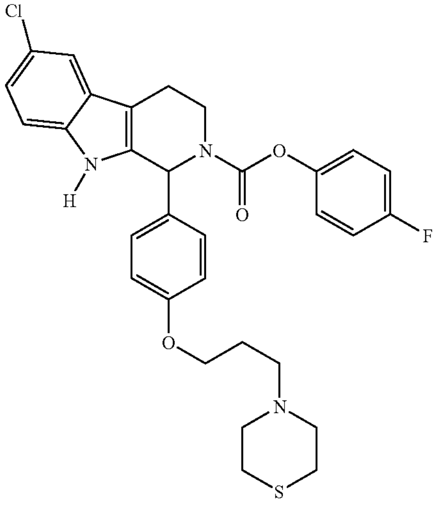
-continued
992
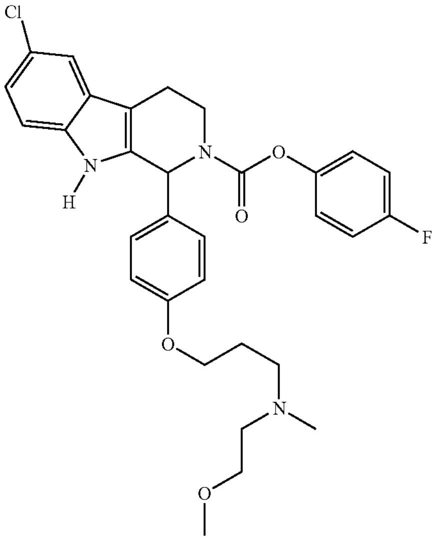
993
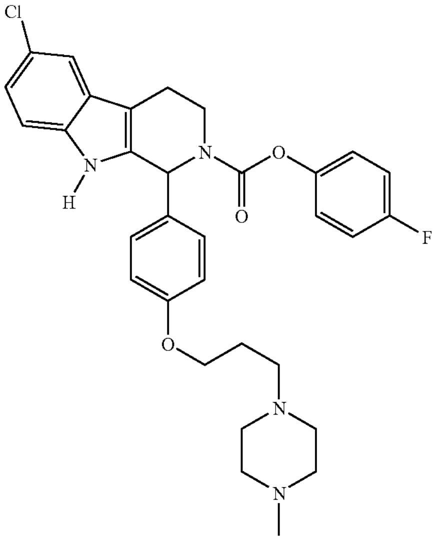
994
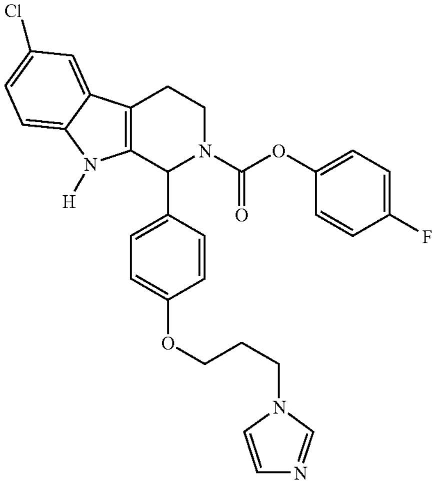

-continued

995

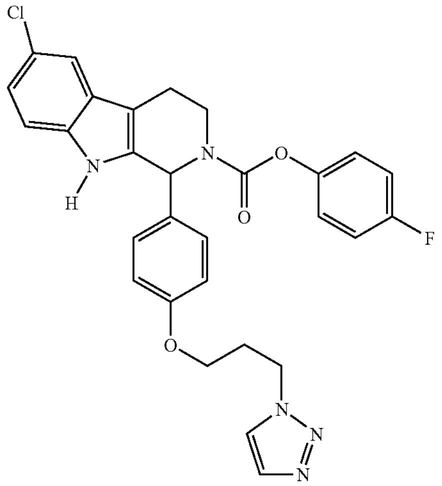

996

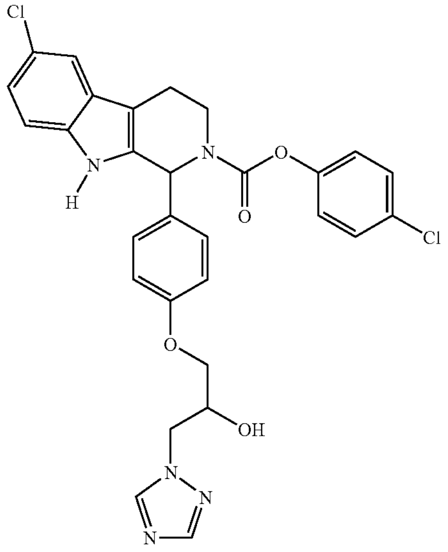

or a pharmaceutically acceptable salt, racemate or stereoisomer thereof.

3. The method of claim 1, where said compound has a chiral carbon at the point of attachment of the $R_o$ substituted phenyl on the compound of Formula (IV) and said compound is an (S) isomer at said chiral carbon.

4. The method of claim 1, wherein said compound is administered simultaneously or sequentially with one or more additional agents useful in the treatment of cancer.

5. The method of claim 4, wherein said one or more additional agents useful in the treatment of cancer is selected from the group consisting of paclitaxel, fluorouracil, irinotecan, thalidomide, gemcitabine, squalamine, endostatin, angiostatin, neovastat, lenalidomide, vitaxin, 2-methoxyestradiol, carboxyamidotriazole, combretastatin A4 phosphate, 5-[1,2-Dihydro-2-oxo-3H-indol-3-ylidene)methyl]-2,4-dimethyl-1H-pyrrole-3-propanoic acid, sunitinib malate, rebimastat, metastat, cilengitide, ramucirumab, vatalanib, vandetanib, halofuginone, hydrobromide, celecoxib, interferon alpha, interleukin-12, and bevacizumab.

6. The method of claim 4, wherein said one or more additional agents are selected from bevacizumab, paclitaxel and fluorouracil.

7. The method of claim 1, wherein the solid tumor cancer is selected from a group consisting of a solid tumor carcinoma, a pediatric solid tumor, a Wilms tumor, a neuroblastoma, a carcinoma of the epidermis, a malignant melanoma, a cervical carcinoma, a cervical cancer, a colon carcinoma, a colon cancer, a lung carcinoma, a lung cancer, a renal carcinoma, and a solid tumor sarcoma.

8. The method of claim 1 or 2, wherein the compound has an $EC_{50}$ of less than 50 nM for inhibiting hypoxia-induced VEGF expression in cultured HeLa cells.

9. The method of claim 1 or 2, wherein the compound inhibits VEGF production in a HT1080 solid tumor grown in a nude mouse.

10. The method of claim 1 or 2, wherein the compound inhibits HT1080 solid tumor growth in a nude mouse.

11. The method of claim 1 or 2, wherein the compound inhibits angiogenesis in a HT1080 solid tumor grown in a nude mouse.

12. The method of claim 2, wherein said compound has a carboline scaffold and at a chiral carbon of said scaffold, said compound is an (S) enantiomer.

* * * * *

UNITED STATES PATENT AND TRADEMARK OFFICE

CERTIFICATE OF CORRECTION

PATENT NO. : 7,767,689 B2
APPLICATION NO. : 11/107783
DATED : August 3, 2010
INVENTOR(S) : Moon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1273 days.

Signed and Sealed this
Twentieth Day of March, 2012

David J. Kappos
*Director of the United States Patent and Trademark Office*